(12) United States Patent
Bazzana et al.

(10) Patent No.: US 9,109,196 B2
(45) Date of Patent: Aug. 18, 2015

(54) PROCESSES AND SYSTEMS FOR THE PRODUCTION OF FERMENTATION PRODUCTS

(71) Applicant: BUTAMAX ADVANCED BIOFUELS LLC, Wilmington, DE (US)

(72) Inventors: Stephane Francois Bazzana, Wilmington, DE (US); Adam Bernfeld, Newark, DE (US); Keith H. Burlew, Middletown, DE (US); James Timothy Cronin, Townsend, DE (US); Michael Charles Grady, Oaklyn, NJ (US); Brian Michael Roesch, Middletown, DE (US); Joseph J. Zaher, Newark, DE (US); Raymond Richard Zolandz, Wilmington, DE (US)

(73) Assignee: Butamax Advanced Biofuels LLC, Wilmington, DE (US)

( * ) Notice: Subject to any disclaimer, the term of this patent is extended or adjusted under 35 U.S.C. 154(b) by 0 days.

(21) Appl. No.: 14/024,722

(22) Filed: Sep. 12, 2013

(65) Prior Publication Data
US 2014/0073021 A1     Mar. 13, 2014

Related U.S. Application Data

(63) Continuation-in-part of application No. 13/828,353, filed on Mar. 14, 2013.

(60) Provisional application No. 61/699,976, filed on Sep. 12, 2012, provisional application No. 61/712,385, filed on Oct. 11, 2012.

(51) Int. Cl.
*C12M 1/00* (2006.01)
*C12P 7/06* (2006.01)

(52) U.S. Cl.
CPC ............... *C12M 43/02* (2013.01); *C12M 21/12* (2013.01); *C12P 7/06* (2013.01); *C12P 7/065* (2013.01)

(58) Field of Classification Search
CPC .................................. C12P 7/065; C12P 7/06
USPC .................................. 435/161, 160, 158, 159
See application file for complete search history.

(56) References Cited

U.S. PATENT DOCUMENTS

| | | | |
|---|---|---|---|
| 2,374,379 A | 4/1945 | Rittmeister | |
| 2,461,936 A | 2/1949 | Strohmaier et al. | |
| 3,193,586 A | 7/1965 | Rittmeister | |
| 4,865,973 A | 9/1989 | Kollerup et al. | |
| 5,110,319 A | 5/1992 | Turpin et al. | |
| 7,360,724 B2 | 4/2008 | Willey et al. | |
| 7,541,173 B2 | 6/2009 | Bramucci et al. | |
| 7,851,188 B2 | 12/2010 | Donaldson et al. | |
| 8,373,008 B2 | 2/2013 | Grady et al. | |
| 8,373,009 B2 | 2/2013 | Grady et al. | |
| 8,409,834 B2 | 4/2013 | Burlew et al. | |
| 8,426,173 B2 | 4/2013 | Bramucci et al. | |
| 8,426,174 B2 | 4/2013 | Bramucci et al. | |
| 8,460,439 B2 | 6/2013 | Parten | |
| 8,476,047 B2 | 7/2013 | Burlew et al. | |
| 8,557,540 B2 | 10/2013 | Burlew et al. | |
| 8,563,788 B2 | 10/2013 | Grady et al. | |
| 8,569,552 B2 | 10/2013 | Grady et al. | |
| 8,574,406 B2 | 11/2013 | Grady et al. | |
| 8,617,861 B2 | 12/2013 | Grady et al. | |
| 8,628,643 B2 | 1/2014 | Grady et al. | |
| 8,697,404 B2 | 4/2014 | Anton et al. | |
| 8,759,044 B2 | 6/2014 | DiCosimo et al. | |
| 8,765,425 B2 | 7/2014 | DiCosimo et al. | |
| 8,828,695 B2 | 9/2014 | Grady et al. | |
| 2008/0274526 A1 | 11/2008 | Bramucci et al. | |
| 2009/0171129 A1 | 7/2009 | Evanko et al. | |
| 2009/0305370 A1 | 12/2009 | Grady et al. | |
| 2010/0143995 A1 | 6/2010 | Erdner-Tindall et al. | |
| 2011/0097773 A1 | 4/2011 | Grady et al. | |
| 2011/0136193 A1 | 6/2011 | Grady et al. | |
| 2011/0162953 A1 | 7/2011 | Xu et al. | |
| 2011/0162954 A1 | 7/2011 | Xu et al. | |
| 2011/0294179 A1 | 12/2011 | Grady et al. | |
| 2011/0312044 A1 | 12/2011 | Anton et al. | |
| 2011/0312053 A1 | 12/2011 | Burlew et al. | |
| 2011/0315541 A1 | 12/2011 | Xu | |
| 2012/0156738 A1 | 6/2012 | Anton et al. | |
| 2012/0208246 A1 | 8/2012 | Anton et al. | |
| 2012/0323047 A1 | 12/2012 | Dauner et al. | |
| 2013/0164795 A1 | 6/2013 | Lowe et al. | |
| 2013/0217060 A1 | 8/2013 | Bramucci et al. | |
| 2013/0224728 A1 | 8/2013 | Bramucci et al. | |
| 2013/0236935 A1 | 9/2013 | Burlew et al. | |
| 2013/0252297 A1 | 9/2013 | Parten | |
| 2013/0295661 A1 | 11/2013 | Roesch et al. | |

(Continued)

FOREIGN PATENT DOCUMENTS

| | | |
|---|---|---|
| FR | 1061101 | 4/1954 |
| FR | 1061102 | 4/1954 |

(Continued)

OTHER PUBLICATIONS

U.S. Appl. No. 13/156,830, filed Jun. 9, 2011, (Butamax).
U.S. Appl. No. 13/162,868, filed Jun. 17, 2011, (Butamax).
U.S. Appl. No. 13/326,511, filed Dec. 15, 2011, (Butamax).
U.S. Appl. No. 14/203,809, filed Mar. 11, 2014, (Butamax).
U.S. Appl. No. 14/211,342, filed Mar. 14, 2014, (Butamax).
U.S. Appl. No. 14/213,274, filed Mar. 14, 2014, (Butamax).
U.S. Appl. No. 14/275,432, filed May 12, 2014, (Butamax).
U.S. Appl. No. 14/317,249, filed Jun. 27, 2014, (Butamax).
U.S. Appl. No. 14/320,681, filed Jul. 1, 2014, (Butamax).
U.S. Appl. No. 14/363,360, filed Jun. 6, 2014, (Butamax).
Badugu, et al., Development and Application of an Excitation Ratiometric Optical pH Sensor for Bioprocess Monitoring, Biotechnol. Prog. 24:1393-1401, 2008.
Branco, et al., Survival rate of wine-related yeasts during alcoholic fermentation assessed by direct live/dead staining combined with fluorescence in situ hybridization, Intl. J. Food Microbiol. 158:49-57, 2012.

(Continued)

*Primary Examiner* — Elvis O Price

(57) ABSTRACT

The present invention relates to the production of fermentation products such as alcohols including ethanol and butanol, and processes employing in situ product removal methods.

17 Claims, 34 Drawing Sheets

(56) References Cited

U.S. PATENT DOCUMENTS

| | | |
|---|---|---|
| 2013/0309738 A1 | 11/2013 | Barr et al. |
| 2014/0018581 A1 | 1/2014 | Grady et al. |
| 2014/0024064 A1 | 1/2014 | Burlew et al. |
| 2014/0080189 A1 | 3/2014 | Grady et al. |
| 2014/0093931 A1 | 4/2014 | Dauner et al. |
| 2014/0094630 A1 | 4/2014 | Anton et al. |
| 2014/0099688 A1 | 4/2014 | Grady et al. |
| 2014/0106419 A1 | 4/2014 | Bazzana et al. |
| 2014/0142352 A1 | 5/2014 | Dauner et al. |
| 2014/0162344 A1 | 6/2014 | DiCosimo et al. |
| 2014/0178529 A1 | 6/2014 | Anton et al. |
| 2014/0234929 A1 | 8/2014 | Barr et al. |

FOREIGN PATENT DOCUMENTS

| | | |
|---|---|---|
| GB | 1064317 | 4/1967 |
| JP | 61192291 | 8/1986 |
| JP | 62022593 | 1/1987 |
| WO | WO 2008143704 | 11/2008 |
| WO | WO 2009/086391 | 7/2009 |
| WO | WO 2009/149270 | 12/2009 |
| WO | WO 2010/119339 | 10/2010 |
| WO | WO 2011/008927 | 1/2011 |
| WO | WO 2011/159967 | 12/2011 |
| WO | WO 2013/166458 | 11/2013 |

OTHER PUBLICATIONS

Bryant, et al., Monitoring real-time enzymatic hydrolysis of Distillers Dried Grains with Solubles (DDGS) by dielectric spectroscopy following hydrothermal pre-treatment by steam explosion, Bioresource Technol. 128:765-768, 2013.

Buratti, et al., Monitoring of alcoholic fermentation using near infrared and mid infrared spectroscopies combined with electronic nose and electronic tongue, Analytica Chimica Acta 697:67-74, 2011.

Cevera, et al., Application of Near-Infrared Spectroscopy for Monitoring and Control of Cell Culture and Fermentation, Biotechnol. Prog. 25:1561-1581, 2009.

Chun, et al., Drop Size and Hold-up in Countercurrent Extraction with Supercritical CO2 in a Spray Column, Ind. Eng. Chem. Res. 39:4673-4677, 2000.

Dahod, Dissolved Carbon Dioxide Measurement and Its Correlation with Operating Parameters in Fermentation Processes, Biotechnol. Prog. 9:655-660, 1993.

Davidson, et al., Using Computational Fluid Dynamics Software to Estimate Circulation Time Distributions in Bioreactors, Biotechnol. Prog. 19:1480-1486, 2003.

Gray, et al., Real-Time Monitoring of High-Gravity Corn Mash Fermentation Using In Situ Raman Spectroscopy, Biotechnol. Bioeng., Wiley Online Library, DOI 10.1002/bit.24849, 2013.

Hierro, et al. Monitoring of *Saccharomyces* and *Hanseniaspora* populations during alcoholic fermentation by real-time quantitative PCR, FEMS Yeast Res. 7:1340-1349, 2007.

Junker, et al., Feasibility of an in situ measurement device for bubble size and distribution, Bioprocess Biosyst. Eng., 30:313-326, 2007.

Kornmann, et al., Methodology for Real-Time, Multianalyte Monitoring of Fermentations Using an In-Situ Mid-Infrared Sensor, DOI: 10.1002/bit.10618, 2003.

Mariano, et al., Optimization Strategies Based on Sequential Quadratic Programming Applied for a Fermentation Process for Butanol Production, Appl. Biochem. Biotechnol. 159:366-381, 2009.

Mas, et al., On-Line Size Measurement of Yeast Aggregates Using Image Analysis, Biotechnol. Bioeng. 76:91-98, 2001.

Massanet-Nicolau, et al., Use of real time gas production data for more accurate comparison of continuous single-stage and two-stage fermentation, Bioresource Technology 129:561-567, 2013.

Schucker, Recovery of Dilute Organics Using Liquid-Liquid Extraction, Merrick & Company, Oct. 6, 2010.

Nyiri, et al., On-Line Measurement of Gas-Exchange Conditions in Fermentation Processes, Biotechnol. Bioeng. 17:1663-1678, 1975.

Olsvik, et al., Rheology of Filamentous Fermentations, Biotech. Adv. 12:1-39, 1994.

Stamixco, 2-Component Resin Mixing Technology Plastic Disposable & Metal Static Mixers for Mixing Viscous Materials, Product Bulletin, 2K-3.0, Jun. 11, 2008.

Picque, et al., New Instrument for On-Line Viscosity Measurement of Fermentation Media, Biotechnol. Bioeng.31:19-23, 1988.

Pouliot, et al., KLa Evaluation during the course of fermentation using data reconciliation techniques, Bioprocess Eng. 23:565-573, 2000.

Rudnitskaya, et al., Sensor systems, electronic tongues and electronic noses, for the monitoring of biotechnological processes J. Ind. Microbiol. Biotechnol. 35:443-451, 2008.

Saucedo, et al., Experimental Optimization of a Real Time Fed-Batch Fermentation Process Using Markov Decision Process, Biotechnol. Bioeng.55:317-327, 1997.

Tibayrenc, et al., On-line monitoring of dielectrical properties of yeast cells during a stress-model alcoholic fermentation, Process Biochem. DOI:10.1016/j.procbio.2010.08.007, 2010.

Tsui, et al., Membrane processing of xanthophylls in ethanol extracts of corn, J. Food Eng. 83:590-595, 2007.

Veale, et al., An On-Line Approach to Monitor Ethanol Fermentation Using FTIR Spectroscopy, Biotechnol. Prog. 23:494-500, 2007.

Yardley, et al., On-line, real-time measurements of cellular biomass using dielectric spectroscopy, Biotechnol. Genetic Eng. Rev. 17:3-35, 2000.

Groot, et al., Butanol recovery from fermentation by liquid-liquid extraction and membrane solvent extraction, Bioprocess Eng. 5:203-216, 1990.

Wang, et al., Enhanced Alcohol Production Through On-line Extraction, Biotechnol. Bioeng. Symp. 11:555-565, 1981.

Minier, et al., Ethanol Production by Extractive Fermentation, Biotechnol. Bioeng. 24:1565-1579, 1982.

Matsumura, et al., Application of solvent extraction to ethanol fermentation, Appl. Microbiol. Biotechnol. 20:371,-377 1984.

Taya, et al., Monitoring and control for Extractive Fermentation of *Clostridium acetobutylicum*, J. Ferment. Technol. 63:181-187, 1985.

Honda, et al., Ethanol fermentation associated with solvent extraction using immobilized growing cells of *Saccharomyces cerevisiae* and its lactose-fermentable fusant, J. Chem. Eng. Jpn. 19:268-273, 1986.

Wayman, et al., Production of acetone-butanol by extractive fermentation using dibutylphtalate, J. Ferment .Technol. 65:295-300, 1987.

Eckert, et al., Continuous acetone-butanol production with direct product removal, Appl. Microbiol. Biotechnol. 27:221-228, 1987.

Bar, et al., Effect of interphase mixing on a water-organic solvent two-liquid phase microbial system: ethanol fermentation, J. Chem. Tech. Biotechnol. 43:49-62, 1988.

Roffler, et al., In situ extractive fermentation of acetone and butanol, Biotechnol. Bioeng. 31:135-143, 1988.

Eiterman, et al., In situ extraction versus the use of an external column in fermentation, Appl. Microbiol. Biotechnol. 30:614-618, 1989.

Daugulis, et al., Continuous fermentation of high-strength glucose feeds to ethanol, Biotechnol. Lett. 16:637-642, 1994.

Weilnhammer, et al., Continuous fermentation with product recovery by in-situ extraction, Chem. Eng. Technol. 17:365-373, 1994.

Gyamerah, et al., Production of ethanol by continuous fermentation and liquid-liquid extraction, J. Chem. Tech. Biotechnol. 66:145-152, 1996.

Roffler, et al. in Extractive Bioconversions ed by Bo Mattiasson and Olle Holst (Marcel Dekker, NY, 1991) pp. 133-172.

Roffler, Steve Ronald, Ph. D., "Extractive fermentation-lactic acid and acetone/butanol production", University of California, Berkeley 1986, pp. 1-289.

Davison, et al., Continuous Direct Solvent Extraction of Butanol in a Fermenting Fluidized-Bed Bioreactor with Immobilized *Clostridium acetobutylicum*Appl. Biochem. Biotechnol. 39-40, pp. 415-426, 1993.

Ezeji, et al., Bioproduction of butanol from biomass: from genes to bioreactorsCurr. Opin. Biotechnol. 18:220-7, 2007.

Jeon, et al., Membrane-assisted extractive butanol fermentation, Ann. NY Acad. Sci. 506:536-42, 1987.

Steen, et al., Metabolic engineering of *Saccharomyces cerevisiae* for the production of n-butanol, Microb. Cell Fact., 7:36; doi:10.1186/1475-2859-7-361-8, 2008.

(56) References Cited

OTHER PUBLICATIONS

Ramey et al., Production of Butyric Acid and Butanol from Biomass, Final Report, 2004, pp. 1-103.

Ishizaki, et al., Extractive acetone-butanol-ethanol fermentation using methylated crude palm oil as extractant in batch culture of *Clostridium saccharoperbutylacetonicum* N1-4 (ATCC 13564), J. Biosci. Bioeng. 87:352-356, 1999.

Atsumi, et al., Non-fermentative pathways for synthesis of branched-chain higher alcohols as biofuels, Nature 451:86-90, 2008.

Mitchell, et al., Mixed solvent systems for recovery of ethanol from dilute aqueous solution by liquid-liquid extraction, Biotech. Bioeng., 30:348-351, 1987.

Bruce, et al., Extractive fermentation by *Zymomonas mobilis* and the use of solvent mixtures, Biotechnol. Lett. 14:71-76, 1992.

Jones, et al., Ethanol production from lactose by extractive fermentation, Biotechnol. Lett. 15:871-876, 1993.

Qureshi, et al., Continuous production of acetone-butanol-ethanol using immobilized cells of *Clostridium acetobutylicum* and integration with product removal by liquid-liquid extraction, J. Ferment. Bioeng. 80:185-189, 1995.

Offeman, et al., Extraction of ethanol with higher alcohol solvents and their toxicity to yeast, Separation and Purification Technology 63:444-451, 2008.

Daugulis, Integrated fermentation and recovery process, Curr. Opin. Biotechnol. 5:192-195, 1994.

Oliveira, et al., Production and Extractive Biocatalysis of Ethanol Using Microencapsulated Yeast Cells and Lipase System, J. Chem. Technol. Biotechnol. 52:219-225, 1991.

Oliveira, et al., Immobilization of *Saccharomyces cerevisiae* Cells and *Rhizomucor miehi* Lipase for the Production and Extractive Biocatalysis of Ethanol, Bioprocess Eng. 16:349-353, 1997.

Oliveira, et al., Effect of extraction and Enzymatic Esterification of Ethanol on Glucose Consumption by Two *Saccharomyces cerevisiae* strains: a comparative study, J. Chem. Technol. Biotechnol. 76:285-290, 2001.

Oliveira, et al., Improvement of Alcoholic Fermentations by Simultaneous Extraction and Enzymatic Esterification of Ethanol, J. Mol. Catal. B: Enzym 5:29-33, 1998.

Klm, et al., Extractive Recovery of Products from Fermentation Broths, Biotechnol. Bioprocess Eng. 4:1-11, 1999.

Barros, et al., Integration of Enzyme Catalysis in an Extraction Fermentation Process, Studies in Organic Chemistry 29, 1986.

International Search Report and Written Opinion in co-pending PCT/US2013/059340, dated Feb. 18, 2014.

Baffle Tray

Sieve Tray

Packed

PROCESSES AND SYSTEMS FOR THE PRODUCTION OF FERMENTATION PRODUCTS

This application is a continuation-in-part of U.S. patent application Ser. No. 13/828,353, filed on Mar. 14, 2013, which claims the benefit of U.S. Provisional Application No. 61/699,976, filed on Sep. 12, 2012; and this application claims the benefit of U.S. Provisional Application No. 61/712,385, filed on Oct. 11, 2012; the entire contents of each are herein incorporated by reference.

The Sequence Listing associated with this application is filed in electronic form via EFS-Web and hereby incorporated by reference into the specification in its entirety.

FIELD OF THE INVENTION

The present invention relates to the production of fermentation products such as alcohols including ethanol and butanol, and processes employing in situ product removal methods.

BACKGROUND OF THE INVENTION

A number of chemicals and consumer products may be produced utilizing fermentation as the manufacturing process. For example, alcohols such as ethanol and butanol have a variety of industrial and scientific applications such as fuels, reagents, and solvents. Butanol is an important industrial chemical with a variety of applications including use as a fuel additive, as a feedstock chemical in the plastics industry, and as a food-grade extractant in the food and flavor industry. The production of butanol or butanol isomers from materials such as plant-derived materials could minimize the use of petrochemicals and would represent an advance in the art. Furthermore, production of chemicals and fuels using plant-derived materials or other biomass sources would provide eco-friendly and sustainable alternatives to petrochemical processes.

Techniques such as genetic engineering and metabolic engineering may be utilized to modify a microorganism to produce a certain product from plant-derived materials or other sources of biomass. However, in the production of butanol, for example, some microorganisms that produce butanol in high yields also have low butanol toxicity thresholds. Removal of butanol from the fermentation as it is being produced is a means to manage these low butanol toxicity thresholds. Thus, there is a continuing need to develop efficient methods and systems for producing butanol in high yields despite the low butanol toxicity thresholds of the butanol-producing microorganisms.

In situ product removal (ISPR) (also referred to as extractive fermentation) can be used to remove butanol or other fermentation products from the fermentation as it is produced, thereby allowing the microorganism to produce butanol at high yields. One ISPR method for removing fermentative alcohol that has been described in the art is liquid-liquid extraction (see, e.g., U.S. Patent Application Publication No. 2009/0305370). In general, with regard to butanol fermentation, the fermentation broth which includes the microorganism is contacted with an extractant at a time before the butanol concentration reaches, for example, a toxic level. Butanol partitions into the extractant decreasing the concentration of butanol in the fermentation broth containing the microorganism, thereby limiting the exposure of the microorganism to the inhibitory butanol.

In order to be technically and economically viable, liquid-liquid extraction requires contact between the extractant and the fermentation broth for efficient mass transfer of the alcohol into the extractant; phase separation of the extractant from the fermentation broth (during and/or after fermentation); efficient recovery and recycle of the extractant; and minimal decrease of the partition coefficient of the extractant over long-term operation. Extractant can become contaminated over time with each recycle, for example, by the build-up of lipids present in the biomass used as feedstock for fermentation, and this contamination can lead to a concomitant reduction in the partition coefficient of the extractant.

In addition, the presence of undissolved solids during extractive fermentation can negatively affect the efficiency of alcohol production. For example, the presence of the undissolved solids may lower the mass transfer coefficient, impede phase separation, result in the accumulation of oil from the undissolved solids in the extractant leading to reduced extraction efficiency over time, slow the disengagement of extractant drops from the fermentation broth, result in a lower fermentation vessel volume efficiency, and increase the loss of extractant because it becomes trapped in the solids and ultimately removed as Dried Distillers' Grains with Solubles (DDGS).

Thus, there is a continuing need for alternative extractive fermentation processes that reduce the toxic effect of the fermentative alcohol such as butanol on the microorganism, and which can also reduce the degradation of the partition coefficient of an extractant. The present invention satisfies the needs described herein and provides methods, processes, and systems for the fermentative production of alcohols such as ethanol and butanol.

SUMMARY OF THE INVENTION

The present invention is directed to a method for recovering a fermentation product from a fermentation broth comprising providing a fermentation broth comprising a microorganism, wherein the microorganism produces fermentation product in a fermentor; contacting the fermentation broth with at least one extractant; and recovering the fermentation product. In some embodiments, the contacting of the fermentation broth with at least one extractant occurs in the fermentor, an external unit, or both. In some embodiments, the external unit is an extractor. In some embodiments, the extractor is selected from siphon, decanter, centrifuge, gravity settler, phase splitter, mixer-settler, column extractor, centrifugal extractor, agitated extractor, hydrocyclone, spray tower, and combinations thereof. In some embodiments, the extractant is selected from $C_7$ to $C_{22}$ fatty alcohols, $C_7$ to $C_{22}$ fatty acids, esters of $C_7$ to $C_{22}$ fatty acids, $C_7$ to $C_{22}$ fatty aldehydes, $C_7$ to $C_{22}$ fatty amides, and mixtures thereof. In some embodiments, the extractant is selected from oleyl alcohol, behenyl alcohol, cetyl alcohol, lauryl alcohol, myristyl alcohol, stearyl alcohol, oleic acid, lauric acid, linoleic acid, linolenic acid, myristic acid, stearic acid, octanoic acid, decanoic acid, undecanoic acid, methyl myristate, methyl oleate, 1-nonanol, 1-decanol, 2-undecanol, 1-nonanal, 1-undecanol, undecanal, lauric aldehyde, 2-methylundecanal, oleamide, linoleamide, palmitamide, stearylamide, 2-ethyl-1-hexanol, 2-hexyl-1-decanol, 2-octyl-1-dodecanol, and mixtures thereof. In some embodiments, a hydrophilic solute is added to the fermentation broth. In some embodiments, the hydrophilic solute is selected from polyhydroxlated compounds, polycarboxylic acids, polyol compounds, ionic salts, and mixtures thereof. In some embodiments, the contacting of the fermentation broth with at least one extractant occurs in two or more external units. In some embodiments, the contacting of the fermentation broth with at least one extractant occurs in two or more fermentors. In some embodiments, the fermentors comprise internals or devices to improve phase separation. In some embodiments, the internals or devices are selected from coalescers, baffles, perforated plates, wells, lamella separators, cones, and combinations thereof. In some embodiments, real-time measurements are used to monitor extraction of the fermentation product. In some embodiments, extraction of the fermentation product is monitored by real-time measurements of phase separation. In some embodiments, phase separation is monitored by measuring rate of phase separation, extractant droplet size, and/or composition of fermentation broth. In some embodiments, phase separation is monitored by conductivity measurements, dielectric measurements, viscoelastic measurements, and/or ultrasonic measurements. In some embodiments, providing a fermentation broth comprising a microorganism occurs in two or more fermentors. In some embodiments, the fermentation product may be a product alcohol. In some embodiments, the product alcohol is selected from ethanol, propanol, butanol, pentanol, hexanol, and fusel alcohols. In some embodiments, the microorganism comprises a butanol biosynthetic pathway. In some embodiments, the butanol biosynthetic pathway is a 1-butanol biosynthetic pathway, a 2-butanol biosynthetic pathway, an isobutanol biosynthetic pathway, or a 2-butanone pathway. In some embodiments, the microorganism is a recombinant microorganism. In some embodiments, the method further comprises the steps of providing a feedstock slurry comprising fermentable carbon source, undissolved solids, oil, and water; separating the feedstock slurry forming three streams: (i) an aqueous solution comprising fermentable carbon source, (ii) a wet cake comprising solids, and (iii) oil; and adding the aqueous solution to the fermentation broth. In some embodiments, the oil is hydrolyzed to form fatty acids. In some embodiments, the fermentation broth is contacted with the fatty acids. In some embodiments, the oil is hydrolyzed by an enzyme. In some embodiments, the enzyme is one or more lipases or phospholipases. In some embodiments, the feedstock slurry is generated by hydrolysis of feedstock. In some embodiments, feedstock is selected from rye, wheat, corn, cane, barley, cellulosic or lignocellulosic material, and combinations thereof. In some embodiments, the feedstock slurry is separated by decanter bowl centrifugation, three-phase centrifugation, disk stack centrifugation, filtering centrifugation, decanter centrifugation, filtration, membrane filtration, microfiltration, vacuum filtration, beltfilter, pressure filtration, filtration using a screen, screen separation, grating, porous grating, flotation, hydrocyclone, filter press, screwpress, gravity settler, vortex separator, or combination thereof. In some embodiments, separating the feedstock is a single step process. In some embodiments, the wet cake is combined with the aqueous solution. In some embodiments, the method further comprises contacting the aqueous solution with a catalyst converting oil in the aqueous solution to fatty acids. In some embodiments, the aqueous solution and fatty acids are added to the fermentation broth. In some embodiments, the catalyst is deactivated.

The present invention is also directed to a system comprising one or more fermentors comprising: an inlet for receiving feedstock slurry; and an outlet for discharging fermentation broth comprising fermentation product; and one or more extractors comprising: a first inlet for receiving the fermentation broth; a second inlet for receiving extractant; a first outlet for discharging a lean fermentation broth; and a second outlet for discharging a rich extractant. In some embodiments, the system further comprises one or more liquefaction units; one or more separation means; and optionally one or more wash systems. In some embodiments, the separation means is selected from decanter bowl centrifugation, three-phase centrifugation, disk stack centrifugation, filtering centrifugation, decanter centrifugation, filtration, vacuum filtration, belt filter, pressure filtration, membrane filtration, microfiltration, filtration using a screen, screen separation, grating, porous grating, flotation, hydrocyclone, filter press, screwpress, gravity settler, vortex separator, and combinations thereof. In some embodiments, the system also comprises on-line measurement devices. In some embodiments, the on-line measurement devices are selected from particle size analyzers, Fourier transform infrared spectroscopes, near-infrared spectroscopes, Raman spectroscopes, high pressure liquid chromatography, viscometers, densitometers, tensiometers, droplet size analyzers, pH meters, dissolved oxygen probes, and combinations thereof.

DESCRIPTION OF THE DRAWINGS

The accompanying drawings, which are incorporated herein and form a part of the specification, illustrate the present invention and, together with the description, further serve to explain the principles of the invention and to enable a person skilled in the pertinent art to make and use the invention.

DESCRIPTION OF THE INVENTION

Figure 1:
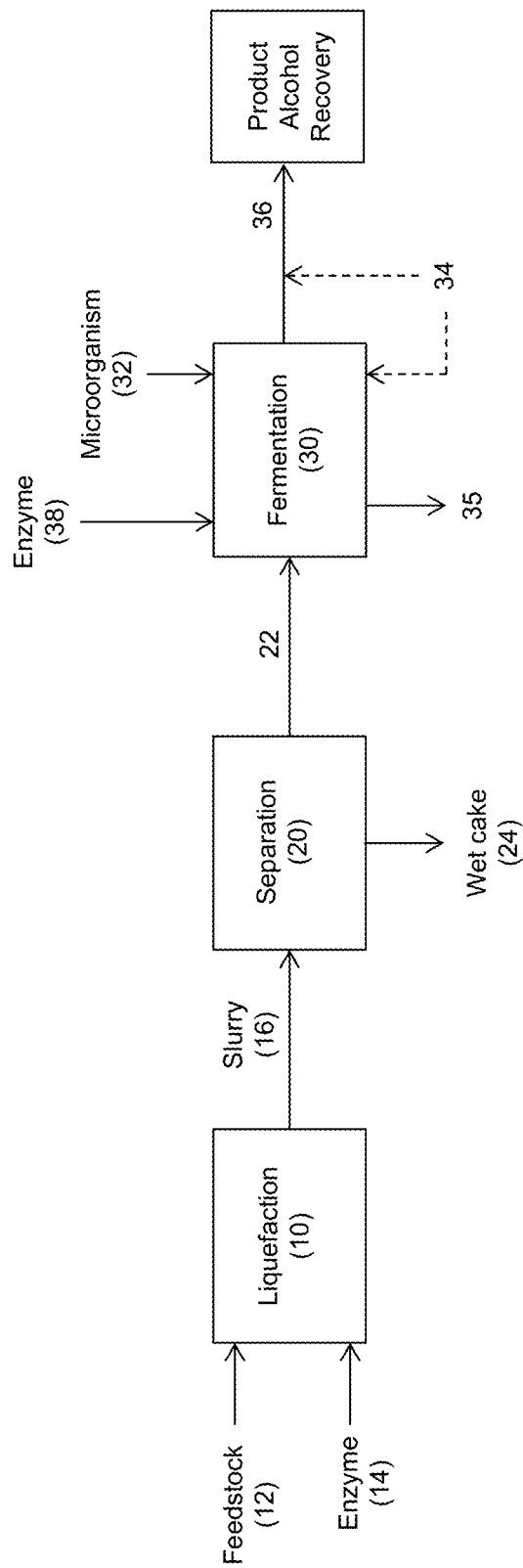
FIG. 1 schematically illustrates an exemplary process and system of the present invention, in which undissolved solids are removed via separation after liquefaction and before fermentation.

Unless defined otherwise, all technical and scientific terms used herein have the same meaning as commonly understood by one of ordinary skill in the art to which this invention belongs. In case of conflict, the present application including the definitions will control. Also, unless otherwise required by context, singular terms shall include pluralities and plural terms shall include the singular. All publications, patents, and other references mentioned herein are incorporated by reference in their entireties for all purposes.

In order to further define this invention, the following terms and definitions are herein provided.

As used herein, the terms "comprises," "comprising," "includes," "including," "has," "having," "contains," or "containing," or any other variation thereof, will be understood to imply the inclusion of a stated integer or group of integers but not the exclusion of any other integer or group of integers. For example, a composition, a mixture, a process, a method, an article, or an apparatus that comprises a list of elements is not necessarily limited to only those elements but can include other elements not expressly listed or inherent to such composition, mixture, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of the invention are intended to be nonrestrictive regarding the number of instances, that is, occurrences of the element or component. Therefore, "a" or "an" should be read to include one or at least one, and the singular word form of the element or component also includes the plural unless the number is obviously meant to be singular.

The term "invention" or "present invention" as used herein is a non-limiting term and is not intended to refer to any single embodiment of the invention but encompasses all possible embodiments as described in the application.

As used herein, the term "about" modifying the quantity of an ingredient or reactant of the invention employed refers to variation in the numerical quantity that can occur, for example, through typical measuring and liquid handling procedures used for making concentrates or solutions in the real world; through inadvertent error in these procedures; through differences in the manufacture, source, or purity of the ingredients employed to make the compositions or to carry out the methods; and the like. The term "about" also encompasses amounts that differ due to different equilibrium conditions for a composition resulting from a particular initial mixture. Whether or not modified by the term "about," the claims include equivalents to the quantities. In one embodiment, the term "about" means within 10% of the reported numerical value, alternatively within 5% of the reported numerical value.

"Biomass" as used herein refers to a natural product containing hydrolyzable polysaccharides that provide fermentable sugars and/or starches including any sugar and starch derived from natural resources such as corn, sugar cane, wheat, cellulosic or lignocellulosic material, and materials comprising cellulose, hemicellulose, lignin, starch, oligosaccharides, disaccharides, and/or monosaccharides, and mixtures thereof. Biomass may also comprise additional components such as protein and/or lipids. Biomass may be derived from a single source or biomass may comprise a mixture derived from more than one source. For example, biomass may comprise a mixture of corn cobs and corn stover, or a mixture of grass and leaves. Biomass includes, but is not limited to, bioenergy crops, agricultural residues, municipal solid waste, industrial solid waste, sludge from paper manufacture, yard waste, wood and forestry waste (e.g., forest thinnings). Examples of biomass include, but are not limited to, corn, corn cobs, crop residues such as corn husks, corn stover, grasses, wheat, rye, wheat straw, spelt, triticale, barley, barley straw, oats, hay, rice, rice straw, switchgrass, potato, sweet potato, cassava, Jerusalem artichoke, sugar cane bagasse, sorghum, sugar cane, sugar beet, fodder beet, soy, palm, coconut, rapeseed, safflower, sunflower, millet, eucalyptus, miscanthus, components obtained from milling of grains, trees (e.g., branches, roots, leaves), wood chips, sawdust, shrubs and bushes, vegetables, fruits, flowers, manure, and mixtures thereof. For example, mash, juice, molasses, or hydrolysate may be formed from biomass by any processing known in the art for processing biomass for purposes of fermentation such as milling and liquefaction. For example, cellulosic and/or lignocellulosic biomass may be processed to obtain a hydrolysate containing fermentable sugars by any method known to one skilled in the art, such as low ammonia pretreatment disclosed in U.S. Patent Application Publication No. 2007/0031918, which is herein incorporated by reference. Enzymatic saccharification of cellulosic and/or lignocellulosic biomass typically makes use of an enzyme consortium (e.g., cellulases, xylanases, glucosidases, glucanases, lyases) for breaking down cellulose and hemicellulose to produce a hydrolysate containing sugars including glucose, xylose, and arabinose. Saccharification enzymes suitable for cellulosic and/or lignocellulosic biomass are reviewed in Lynd, et al. (Microbiol. Mol. Biol. Rev. 66:506-577, 2002).

"Fermentable carbon source" or "fermentable carbon substrate" as used herein refers to a carbon source capable of being metabolized by microorganisms. Suitable fermentable carbon sources include, but are not limited to, monosaccharides such as glucose or fructose; disaccharides such as lactose or sucrose; oligosaccharides; polysaccharides such as starch or cellulose; one carbon substrates; and mixtures thereof.

"Fermentable sugar" as used herein refers to one or more sugars capable of being metabolized by the microorganisms disclosed herein for the production of fermentation products.

"Feedstock" as used herein refers to a feed in a fermentation process, the feed containing a fermentable carbon source with or without undissolved solids and oil, and where applicable, the feed containing the fermentable carbon source before or after the fermentable carbon source has been removed from starch or obtained from the breakdown of complex sugars by further processing such as by liquefaction, saccharification, or other process. Feedstock includes or may be derived from biomass. Suitable feedstocks include, but are not limited to, rye, wheat, corn, corn mash, cane, cane mash, barley, cellulosic material, lignocellulosic material, or mixtures thereof. Where reference is made to "feedstock oil," it will be appreciated that the term encompasses the oil produced from a given feedstock.

"Fermentation broth" as used herein refers to a mixture of water, fermentable carbon sources (e.g., sugars), dissolved solids, optionally microorganisms producing fermentation products (e.g., product alcohol), optionally fermentation products (e.g., product alcohol), and other constituents. In some embodiments, fermentation broth refers to the material held in the fermentor in which the fermentation product (e.g., product alcohol) is being made by the metabolism of fermentable carbon sources by the microorganisms. From time to time as used herein, the term "fermentation broth" may be used synonymously with "fermentation medium" or "fermented mixture." In some embodiments, fermentation broth comprising product alcohol may be referred to as fermentation beer or beer.

"Fermentor" or "fermentation vessel" as used herein refers to the unit in which the fermentation reaction is carried out whereby fermentation product (e.g., product alcohol such as ethanol or butanol) is produced from fermentable carbon sources. The term "fermentor" may be used synonymously herein with "fermentation vessel."

"Liquefaction unit" as used herein refers to the unit in which liquefaction is carried out. Liquefaction is the process in which oligosaccharides are released from feedstock. In some embodiments where the feedstock is corn, oligosaccharides are released from the corn starch content during liquefaction.

"Saccharification unit" as used herein refers to the unit in which saccharification (i.e., the breakdown of oligosaccharides into monosaccharides) is carried out. Where fermentation and saccharification occur simultaneously, the saccharification unit and the fermentor may be the same unit.

"Sugar" as used herein refers to oligosaccharides, disaccharides, monosaccharides, and/or mixtures thereof. The term "saccharide" also includes carbohydrates including starches, dextrans, glycogens, cellulose, pentosans, as well as sugars.

As used herein, "saccharification enzyme" refers to one or more enzymes that are capable of hydrolyzing polysaccharides and/or oligosaccharides, for example, alpha-1,4-glucosidic bonds of glycogen or starch. Saccharification enzymes may include enzymes capable of hydrolyzing cellulosic or lignocellulosic materials as well.

"Undissolved solids" as used herein refers to non-fermentable portions of feedstock, for example, germ, fiber, gluten, and any additional components that do not dissolve in aqueous media. For example, the non-fermentable portions of feedstock include the portion of feedstock that remains as solids and can absorb liquid from the fermentation broth.

"Oil" as used herein refers to lipids obtained from plants (e.g., biomass) or animals. Examples of oils include, but are not limited to, tallow, corn, canola, capric/caprylic triglycerides, castor, coconut, cottonseed, fish, jojoba, lard, linseed, neetsfoot, oiticica, palm, peanut, rapeseed, rice, safflower, soya, sunflower, tung, jatropha, and vegetable oil blends.

"Product alcohol" as used herein refers to any alcohol that can be produced by a microorganism in a fermentation process that utilizes biomass as a source of fermentable carbon substrate. Product alcohols include, but are not limited to, $C_1$ to $C_8$ alkyl alcohols. In some embodiments, the product alcohols are $C_2$ to $C_8$ alkyl alcohols. In other embodiments, the product alcohols are $C_2$ to $C_5$ alkyl alcohols. It will be appreciated that $C_1$ to $C_8$ alkyl alcohols include, but are not limited to, methanol, ethanol, propanol, butanol, pentanol, and hexanol. Likewise $C_2$ to $C_8$ alkyl alcohols include, but are not limited to, ethanol, propanol, butanol, pentanol, and hexanol. In some embodiments, product alcohol may also include fusel alcohols (or fusel oils) and glycerol. "Alcohol" is also used herein with reference to a product alcohol.

"Butanol" as used herein refers to the butanol isomers 1-butanol (1-BuOH), 2-butanol (2-BuOH), tert-butanol (t-BuOH), and/or isobutanol (iBuOH, i-BuOH, I-BUOH, iB also known as 2-methyl-1-propanol), either individually or as mixtures thereof. From time to time, when referring to esters of butanol, the terms "butyl esters" and "butanol esters" may be used interchangeably.

"Propanol" as used herein refers to the propanol isomers isopropanol or 1-propanol.

"Pentanol" as used herein refers to the pentanol isomers 1-pentanol, 3-methyl-1-butanol, 2-methyl-1-butanol, 2,2-dimethyl-1-propanol, 3-pentanol, 2-pentanol, 3-methyl-2-butanol, or 2-methyl-2-butanol.

"In Situ Product Removal (ISPR)" as used herein refers to the selective removal of a specific product from a biological process such as fermentation to control the product concentration in the biological process as the product is produced.

"Extractant" as used herein refers to a solvent used to extract a fermentation product (e.g., product alcohol). From time to time as used herein, the term "extractant" may be used synonymously with "solvent."

"Water-immiscible" as used herein refers to a chemical component such as an extractant or solvent, which is incapable of mixing with an aqueous solution such as fermentation broth, in such a manner as to form one liquid phase.

"Carboxylic acid" as used herein refers to any organic compound with the general chemical formula —COOH in which a carbon atom is bonded to an oxygen atom by a double bond to make a carbonyl group (—C=O) and to a hydroxyl group (—OH) by a single bond. A carboxylic acid may be in the form of the protonated carboxylic acid, in the form of a salt of a carboxylic acid (e.g., an ammonium, sodium, or potassium salt), or as a mixture of protonated carboxylic acid and salt of a carboxylic acid. The term carboxylic acid may describe a single chemical species (e.g., oleic acid) or a mixture of carboxylic acids as can be produced, for example, by the hydrolysis of biomass-derived fatty acid esters or triglycerides, diglycerides, monoglycerides, and phospholipids.

"Fatty acid" as used herein refers to a carboxylic acid (e.g., aliphatic monocarboxylic acid) having $C_4$ to $C_{28}$ carbon atoms (most commonly $C_{12}$ to $C_{24}$ carbon atoms), which is either saturated or unsaturated. Fatty acids may also be branched or unbranched. Fatty acids may be derived from, or contained in esterified form, an animal or vegetable fat, oil, or wax. Fatty acids may occur naturally in the form of glycerides in fats and fatty oils or may be obtained by hydrolysis of fats or by synthesis. The term fatty acid may describe a single chemical species or a mixture of fatty acids. In addition, the term fatty acid also encompasses free fatty acids.

"Fatty alcohol" as used herein refers to an alcohol having an aliphatic chain of $C_4$ to $C_{22}$ carbon atoms, which is either saturated or unsaturated.

"Fatty aldehyde" as used herein refers to an aldehyde having an aliphatic chain of $C_4$ to $C_{22}$ carbon atoms, which is either saturated or unsaturated.

"Fatty amide" as used herein refers to an amide having an aliphatic chain of $C_4$ to $C_{22}$ carbon atoms, which is either saturated or unsaturated.

"Fatty ester" as used herein refers to an ester having an aliphatic chain of $C_4$ to $C_{22}$ carbon atoms, which is either saturated or unsaturated.

"Aqueous phase" as used herein refers to the aqueous phase of, for example, a biphasic mixture containing, for example, a liquid phase and a vapor phase, to the aqueous phase of a triphasic mixture containing two liquid phases (e.g., an organic phase and an aqueous phase) and a vapor phase, to the aqueous phase of either a biphasic or triphasic mixture where the aqueous phase contains some amount of suspended solids, or to a quartphasic mixture comprising a vapor phase, an organic phase, an aqueous phase and a solid phase. In some embodiments, a triphasic mixture may comprise a vapor phase, a liquid phase, and a solid phase. In some embodiments, an aqueous phase may be obtained by contacting a fermentation broth with a water-immiscible organic extractant. In an embodiment of a process described herein that includes fermentative extraction, the term "fermentation broth" then may refer to the aqueous phase in biphasic fermentative extraction.

"Organic phase" as used herein refers to the non-aqueous phase of a mixture (e.g., biphasic mixture, triphasic mixture, quartphasic mixture) obtained by contacting a fermentation broth with a water-immiscible organic extractant. From time to time as used herein, the terms "organic phase" may be used synonymously with "extractant phase."

"Effective titer" as used herein refers to the total amount of a particular fermentation product (e.g., product alcohol) produced by fermentation per liter of fermentation broth.

"Portion" as used herein with reference to a process stream refers to any fractional part of the stream which retains the composition of the stream, including the entire stream, as well as any component or components of the stream, including all components of the stream.

The present invention provides processes and methods for producing fermentation products such as product alcohols using fermentation. Other fermentation products that may be produced using the processes and methods described herein include propanediol, butanediol, acetone, acids such as lactic acid, acetic acid, butyric acid, and propionic acid; gases such as hydrogen methane, and carbon dioxide; amino acids; vitamins such as biotin, vitamin $B_2$ (riboflavin), vitamin $B_{12}$ (e.g., cobalamin), ascorbic acid (e.g., vitamin C), vitamin E (e.g., a-tocopherol), and vitamin K (e.g., menaquinone); antibiotics such as erythromycin, penicillin, streptomycin, and tetracycline; and other products such as citric acid, invertase, sorbitol, pectinase, and xylitol.

The present invention provides processes and systems for producing a product alcohol by fermentative processes and recovering a product alcohol produced by a fermentative process. As an example of an embodiment of the processes described herein, fermentation may be initiated by introducing feedstock directly into a fermentor. In some embodiments, one or more fermentors may be used in the processes described herein. Suitable feedstocks include, but are not limited to, rye, wheat, corn, corn mash, cane, cane mash, barley, cellulosic material, lignocellulosic material, or mixtures thereof. These feedstocks may be processed using methods such as dry milling or wet milling. In some embodiments, prior to the introduction to the fermentor, the feedstock may be liquefied to create feedstock slurry which may comprise undissolved solids, a fermentable carbon source (e.g., sugar), and oil. Liquefaction of the feedstock may be accomplished by any known liquefying processes including, but not limited to, acid process, enzyme process (e.g., alpha-amylase), acid-enzyme process, or combinations thereof. In some embodiments, liquefaction may take place in a liquefaction unit.

If the feedstock slurry is fed directly to the fermentor, the undissolved solids and/or oil may interfere with efficient removal and recovery of a product alcohol. In particular, when liquid-liquid extraction is utilized to extract a product alcohol from the fermentation broth, the presence of the undissolved solids (e.g., particulates) may cause system inefficiencies including, but not limited to, decreasing the mass transfer rate of the product alcohol to the extractant by interfering with the contact between the extractant and the fermentation broth; creating or promoting an emulsion in the fermentor and thereby interfering with phase separation of the extractant and the fermentation broth; reducing the efficiency of recovering and recycling the extractant because at least a portion of the extractant and product alcohol becomes "trapped" in the solids which may be removed as Distillers' Dried Grains with Solubles (DDGS); lowering fermentor volume efficiency because there are solids taking up volume in the fermentor and because there is a slower disengagement of the extractant from the fermentation broth; and shortening the life cycle of the extractant by contamination with oil. These effects may result in higher capital and operating costs. In addition, extractant "trapped" in the DDGS may detract from the DDGS value and qualification for sale as animal feed. Thus, in order to avoid and/or minimize these problems, at least a portion of the undissolved solids may be removed from the feedstock slurry prior to the addition of the feedstock slurry to the fermentor. Extraction activity and efficiency of product alcohol production may be increased when extraction is performed on a fermentation broth where the undissolved solids have been removed.

Processes and systems to process feedstock generating a feedstock slurry and to separate feedstock slurry generating an aqueous phase comprising fermentable carbon source and a solid phase (e.g., wet cake) are described herein with reference to the Figures. As shown in FIG. 1, in some embodiments, the system includes liquefaction 10 configured to liquefy feedstock to create a feedstock slurry. For example, feedstock 12 may be introduced to liquefaction 10 (e.g., via an inlet in the liquefaction unit). Feedstock 12 can be any suitable biomass material known in the industry including, but not limited to, barley, oat, rye, sorghum, wheat, triticale, spelt, millet, cane, corn, or combinations thereof that contains a fermentable carbon source such as sugar and/or starch. Water may also be introduced to liquefaction 10.

The process of liquefying feedstock 12 involves hydrolysis of starch in feedstock 12 to water-soluble sugars. Any known liquefying processes, as well as liquefaction unit, utilized by the industry can be used including, but not limited to, an acid process, an enzyme process, or an acid-enzyme process. Such processes can be used alone or in combination. In some embodiments, the enzyme process may be utilized and an appropriate enzyme 14, for example, alpha-amylase, is introduced to liquefaction 10. Examples of alpha-amylases that may be used in the systems and processes of the present invention are described in U.S. Pat. No. 7,541,026; U.S. Patent Application Publication No. 2009/0209026; U.S. Patent Application Publication No. 2009/0238923; U.S. Patent Application Publication No. 2009/0252828; U.S.

Patent Application Publication No. 2009/0314286; U.S. Patent Application Publication No. 2010/02278970; U.S. Patent Application Publication No. 2010/0048446; U.S. Patent Application Publication No. 2010/0021587, the entire contents of each are herein incorporated by reference.

In some embodiments, the enzymes for liquefaction and/or saccharification may be produced by the microorganism. Examples of microorganisms producing such enzymes are described in U.S. Pat. No. 7,498,159; U.S. Patent Application Publication No. 2012/0003701; U.S. Patent Application Publication No. 2012/0129229; PCT International Publication No. WO 2010/096562; and PCT International Publication No. WO 2011/153516, the entire contents of each are herein incorporated by reference. In some embodiments, enzymes for liquefaction and/or saccharification may be expressed by a microorganism that also produces a product alcohol. In some embodiments, enzymes for liquefaction and/or saccharification may be expressed by a microorganism that also expresses a butanol biosynthetic pathway. In some embodiments, the butanol biosynthetic pathway may be 1-butanol biosynthetic pathway, 2-butanol biosynthetic pathway, isobutanol biosynthetic pathway, or 2-butanone biosynthetic pathway.

The process of liquefying feedstock 12 creates feedstock slurry 16 (also referred to as mash or thick mash) that includes fermentable carbon source (e.g., sugar) and undissolved solids. In some embodiments, feedstock slurry 16 may include fermentable carbon source (e.g., sugar), oil, and undissolved solids. The undissolved solids may be non-fermentable portions of feedstock 12. In some embodiments, feedstock 12 may be corn, such as dry milled, unfractionated corn kernels, and feedstock slurry 16 is corn mash slurry. Feedstock slurry 16 may be discharged from an outlet of liquefaction 10, and may be conducted to separation 20.

Separation 20 has an inlet for receiving feedstock slurry 16, and may be configured to remove undissolved solids from feedstock slurry 16. Separation 20 may also be configured to remove oil, and/or oil and undissolved solids. Separation 20 may agitate or spin feedstock slurry 16 to create a liquid phase or aqueous solution 22 and a solid phase or wet cake 24.

Aqueous solution 22 may include sugar, for example, in the form of oligosaccharides, and water. Aqueous solution 22 may comprise at least about 10% by weight oligosaccharides, at least about 20% by weight of oligosaccharides, or at least about 30% by weight of oligosaccharides. Aqueous solution 22 may be discharged from separation 20 via an outlet. In some embodiments, the outlet may be located near the top of separation 20.

Wet cake 24 may include undissolved solids. Wet cake 24 may be discharged from separation 20 via an outlet. In some embodiments, the outlet may be located near the bottom of separation 20. Wet cake 24 may also include a portion of sugar and water. Wet cake 24 may be washed with additional water in separation 20 after aqueous solution 22 has been discharged from separation 20. Alternatively, wet cake 24 may be washed with additional water by additional separation devices. Washing wet cake 24 will recover the sugar (e.g., oligosaccharides) present in the wet cake, and the recovered sugar and water may be recycled to liquefaction 10. After washing, wet cake 24 may be further processed to form Dried Distillers' Grains with Solubles (DDGS) through any suitable known process. The formation of DDGS from wet cake 24 formed in separation 20 has several benefits. Since the undissolved solids do not go to the fermentor, DDGS is not subjected to the conditions of the fermentor. For example, DDGS does not contact the microorganisms present in the fermentor or any other substances that may be present in the fermentor (e.g., extractant and/or product alcohol) and therefore, the microorganism and/or other substances are not trapped in the DDGS. These effects provide benefits to subsequent processing and selling of DDGS, for example, as animal feed.

Separation 20 may be any conventional separation device utilized in the industry, including, for example, centrifuges such as a decanter bowl centrifuge, three-phase centrifuge, disk stack centrifuge, filtering centrifuge, or decanter centrifuge. In some embodiments, removal of the undissolved solids from feedstock slurry 16 may be accomplished by filtration, vacuum filtration, belt filter, pressure filtration, membrane filtration, microfiltration, filtration using a screen, screen separation, grates or grating, porous grating, flotation, hydrocyclone, filter press, screwpress, gravity settler, vortex separator, or any method or device that may be used to separate solids from liquids. In some embodiments, separation 20 is a single step process. In one embodiment, undissolved solids may be removed from feedstock slurry 16 to form two product streams, for example, an aqueous solution of oligosaccharides which contains a lower concentration of solids as compared to feedstock slurry 16 and a wet cake which contains a higher concentration of solids as compared to feedstock slurry 16. In addition, a third stream containing oil may be generated, for example, if three-phase centrifugation is utilized for solids removal from feedstock slurry 16. As such, a number of product streams may be generated by using different separation techniques or combinations thereof.

A three-phase centrifuge may be used for three-phase separation of feedstock slurry such as separation of the feedstock slurry to generate two liquid phases (e.g., aqueous stream and oil stream) and a solid phase (e.g., solids or wet cake) (see, e.g., Flottweg Tricanter®, Flottweg AG, Vilsibiburg, Germany). The two liquid phases may be separated and decanted, for example, from the bowl of the centrifuge via two discharge systems to prevent cross contamination and the solids phase may be removed via a separate discharge system.

In some embodiments using corn as feedstock, a three-phase centrifuge may be used to remove solids and corn oil simultaneously from liquefied corn mash. The solids may be undissolved solids remaining after starch is hydrolyzed to soluble oligosaccharides during liquefaction. The corn oil may be released from the germ of the corn kernel during grinding and/or liquefaction. In some embodiments, the three-phase centrifuge may have one feed stream and three outlet streams. The feed stream may consist of liquefied corn mash produced during liquefaction. The mash may consist of an aqueous solution of oligosaccharides (e.g., liquefied starch); undissolved solids which consist of insoluble, non-starch components from the corn; and corn oil which consists of glycerides and free fatty acids. The three outlet streams from the three-phase centrifuge may be a wet cake which contains most of the undissolved solids from the mash; a heavy centrate stream which contains most of the liquefied starch from the mash; and a light centrate stream which contains most of the corn oil from the mash. The heavy centrate stream may be fed to fermentation. The wet cake may be washed with process recycle water, such as evaporator condensate and/or backset as described herein, to recover soluble starch from the wet cake. The light centrate stream may be sold as a co-product, converted to another co-product, or used in processing such as converting the corn oil to corn oil fatty acids (COFA). In some embodiments, COFA may be used as an extractant.

Referring to FIG. 1, fermentation 30 (or fermentor 30), configured to ferment aqueous solution 22 to produce a product alcohol, has an inlet for receiving aqueous solution 22. Fermentation 30 may be any suitable fermentor known in the art. Fermentation 30 may include fermentation broth. In some embodiments, simultaneous saccharification and fermentation (SSF) may occur inside fermentation 30. Any known saccharification process utilized by the industry may be used including, but not limited to, an acid process, an enzyme process, or an acid-enzyme process. In some embodiments, enzyme 38 (e.g., such as glucoamylase) may be introduced to an inlet in fermentation 30 in order to hydrolyze oligosaccharides in aqueous solution 22 forming monosaccharides. Examples of glucoamylases that may be used in the systems and processes of the present invention are described in U.S. Pat. No. 7,413,887; U.S. Pat. No. 7,723,079; U.S. Patent Application Publication No. 2009/0275080; U.S. Patent Application Publication No. 2010/0267114; U.S. Patent Application Publication No. 2011/0014681; and U.S. Patent Application Publication No. 2011/0020899, the entire contents of each are herein incorporated by reference. In some embodiments, glucoamylase may be expressed by the microorganism. In some embodiments, glucoamylase may be expressed by a microorganism that also produces a product alcohol. In some embodiments, glucoamylase may be expressed by a microorganism that also expresses a butanol biosynthetic pathway. In some embodiments, the butanol biosynthetic pathway may be 1-butanol biosynthetic pathway, 2-butanol biosynthetic pathway, isobutanol biosynthetic pathway, or 2-butanone biosynthetic pathway.

In some embodiments, enzymes such as glucoamylases may be added to liquefaction. The addition of enzymes such as glucoamylases to liquefaction may reduce the viscosity of the feedstock slurry or liquefied mash and may improve separation efficiency. In some embodiments, any enzyme capable of reducing the viscosity of the feedstock slurry may be used (e.g., Viscozyme®, Sigma-Aldrich, St. Louis, Mo.). Viscosity of the feedstock may be measured by any method known in the art (e.g., viscometers, rheometers).

Microorganism 32 may be introduced to fermentation 30. In some embodiments, microorganism 32 may be included in the fermentation broth. In some embodiments, microorganism 32 may be propagated in a separate vessel or tank (e.g., propagation tank). In some embodiments, microorganisms from the propagation tank may be used to inoculate one or more fermentors. In some embodiments, one or more propagation tanks may be used in the processes and systems described herein. In some embodiments, the propagation tank may be about 2% to about 5% the size of the fermentor. In some embodiments, the propagation tank may comprise one or more of the following mash, water, enzymes, nutrients, extractant, and microorganisms. In some embodiments, product alcohol may be produced in the propagation tank.

In some embodiments, microorganism 32 may be bacteria, cyanobacteria, filamentous fungi, or yeast. In some embodiments, microorganism 32 metabolizes the sugar in aqueous solution 22 and produces product alcohol. In some embodiments, microorganism 32 may be a recombinant microorganism. In some embodiments, microorganism 32 may be immobilized, such as by adsorption, covalent bonding, crosslinking, entrapment, and encapsulation. Methods for encapsulating cells are known in the art, for example, as described in U.S. Patent Application Publication No. 2011/0306116, which is incorporated herein by reference.

In some embodiments, in situ product removal (ISPR) may be utilized to remove product alcohol from fermentation 30 as the product alcohol is produced by microorganism 32. In some embodiments, liquid-liquid extraction may be utilized for ISPR. In some embodiments, fermentation 30 may have an inlet for receiving extractant 34. In some embodiments, extractant 34 may be added to the fermentation broth downstream of fermentation 30. Alternative means of additions of extractant 34 to fermentation 30 or downstream of fermentation 30 are represented by the dotted lines. In some embodiments, ISPR may be conducted in a propagation tank. In some embodiments, ISPR may be conducted in the fermentor and the propagation tank. In some embodiments, ISPR may be performed at the initiation (e.g., time 0) of fermentation and/or propagation. By initiating ISPR at the beginning of fermentation and/or propagation, the concentration of product alcohol in the fermentor and propagation tank may be maintained at low levels, and thereby minimize the effects of product alcohol on the microorganism and allowing the microorganism to achieve increased cell mass. In some embodiments, extractant may be added to the propagation tank. In some embodiments, extractant may be added prior to inoculation of the propagation tank. In some embodiments, extractant may be added after inoculation of the propagation tank. In some embodiments, extractant may be added at various time points after inoculation of the propagation tank. In some embodiments, extractant may be added to the fermentor. In some embodiments, extractant may be added prior to inoculation of the fermentor. In some embodiments, extractant may be added after inoculation of the fermentor. In some embodiments, extractant may be added at various time points after inoculation of the fermentor. In some embodiments, extractant may be added to the fermentor and the propagation tank. Examples of liquid-liquid extraction are described herein. Processes for producing and recovering alcohols from fermentation broth using extractive fermentation are described in U.S. Patent Application Publication No. 2009/0305370; U.S. Patent Application Publication No. 2010/0221802; U.S. Patent Application Publication No. 2011/0097773; U.S. Patent Application Publication No. 2011/0312044; U.S. Patent Application Publication No. 2011/0312043; and PCT International Publication No. WO 2011/159998; the entire contents of each are herein incorporated by reference.

Extractant 34 contacts the fermentation broth forming stream 36 comprising, for example, a biphasic mixture (e.g., extractant-rich phase with product alcohol and aqueous phase depleted of product alcohol). In some embodiments, stream 36 may be a quartphasic mixture comprising, for example, a vapor phase, an organic phase, an aqueous phase, and a solid phase. Product alcohol, or a portion thereof, in the fermentation broth is transferred to extractant 34. In some embodiments, stream 36 may be discharged through an outlet in fermentation 30. Product alcohol may be separated from the extractant in stream 36 using conventional techniques.

In some embodiments, fermentor internals or devices may be used to improve phase separation between fermentation broth and extractant. For example, the internal or device may serve as a coalescer to promote phase separation between fermentation broth and extractant and/or act as a physical barrier to improve phase separation. These fermentor internals or devices may also prevent solids from settling in the extractant phase (or layer), promote coalescensce of aqueous droplets that may be entrained in the extractant layer, and promote removal of off-gases (e.g., $CO_2$, air), and thereby minimize disturbance of the extractant phase and/or liquid-liquid interface. Examples of internals or devices that may be used in the processes and systems described herein include, but are not limited to, baffles, perforated plates, deep wells, lamella separators, cones, and the like. In some embodiments, the perforated plate may be a flat horizontal perforated plate. In some embodiments, the cone may be an inverted cone or concentric cone(s). In some embodiments, the internals may be rotating. In some embodiments, the internals or devices may be located at or about the level of the liquid-liquid interface of fermentation broth and extractant. In some embodiments, a coalescing pad may be added and/or exit ports may be relocated to improve coalescence and recovery of the aqueous phase.

In some embodiments prior to ISPR and/or completion of fermentation, stream 35 may be discharged from an outlet in fermentation 30. Discharged stream 35 may include microorganism 32. Microorganism 32 may be separated from stream 35, for example, by centrifugation or membrane filtration. In some embodiments, by removing the microorganism prior to addition of extractant to the fermentation broth, the microorganism is not exposed to the extractant and therefore, not exposed to any negative impact that the extractant may have on the microorganism. In addition, by removing the microorganism upstream of the extraction process, a more aggressive extraction process (e.g., heating or cooling the mixture to enhance separation, using a higher $K_D$ and/or higher selectivity extractant, or an extractant with improved properties but lower biocompatibility) may be employed to recover the product alcohol. In some embodiments, microorganism 32 may be recycled to fermentation 30 which can increase the production rate of product alcohol, thereby resulting in an increase in the efficiency of product alcohol production.

Figure 2:
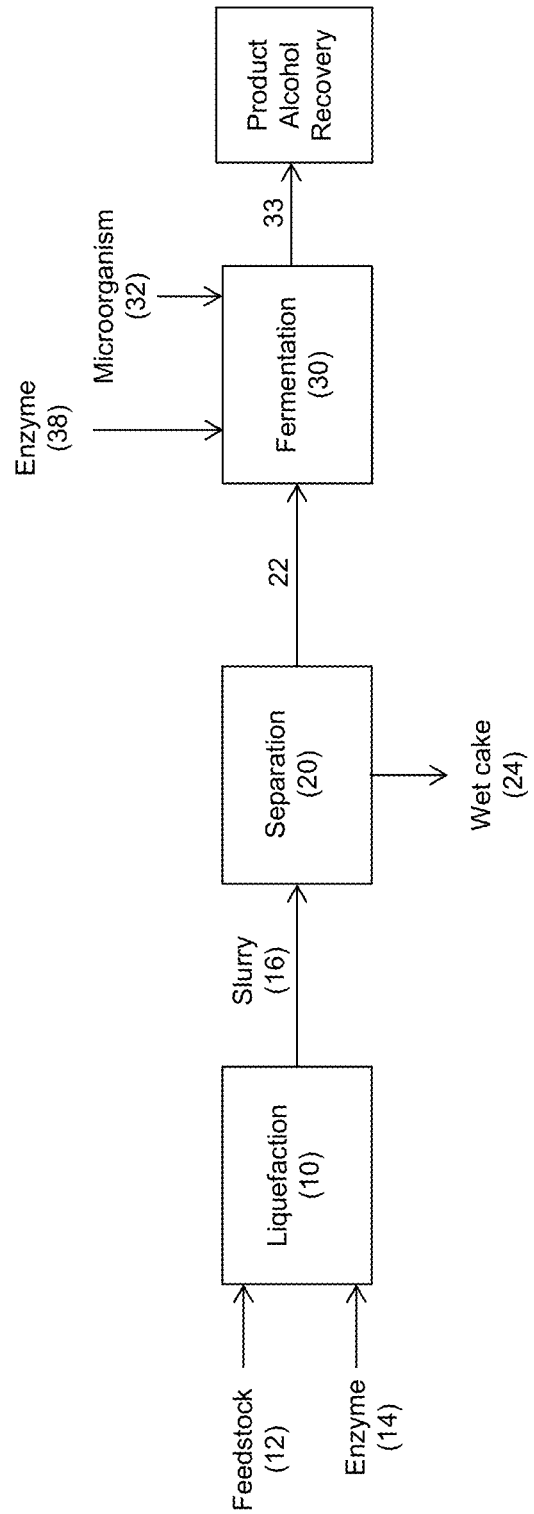
FIG. 2 schematically illustrates an exemplary process and system of the present invention, in which ISPR is conducted downstream of fermentation.

Referring to FIG. 2, in some embodiments, ISPR may be conducted downstream of fermentation 30. In some embodiments, stream 33 including product alcohol and microorganism 32 may be discharged from an outlet in fermentation 30 and conducted downstream, for example, to an extraction column for recovery of product alcohol. In some embodiments, stream 33 may be processed by separating microorganism 32 prior to ISPR. For example, removal of microorganism 32 from stream 33 may be accomplished by centrifugation, filtration, vacuum filtration, belt filter, pressure filtration, membrane filtration, microfiltration, filtration using a screen, screen separation, grates or grating, porous grating, flotation, hydrocyclone, filter press, screwpress, gravity settler, vortex separator, or any method or separation device that may be used to separate solids (e.g., microorganisms) from liquids. Following removal of microorganism 32, stream 33 may be conducted to an extraction column for recovery of product alcohol.

Additional embodiments of the processes and systems described herein are illustrated in FIGS. 3 to 6. FIGS. 3 to 6, including the options for the addition of extractant to the fermentor (e.g., generating stream 36) or extraction conducted downstream of the fermentor (e.g., generating stream 33), are similar to FIGS. 1 and 2, respectively, and therefore will not be described in detail again.

Figure 3:
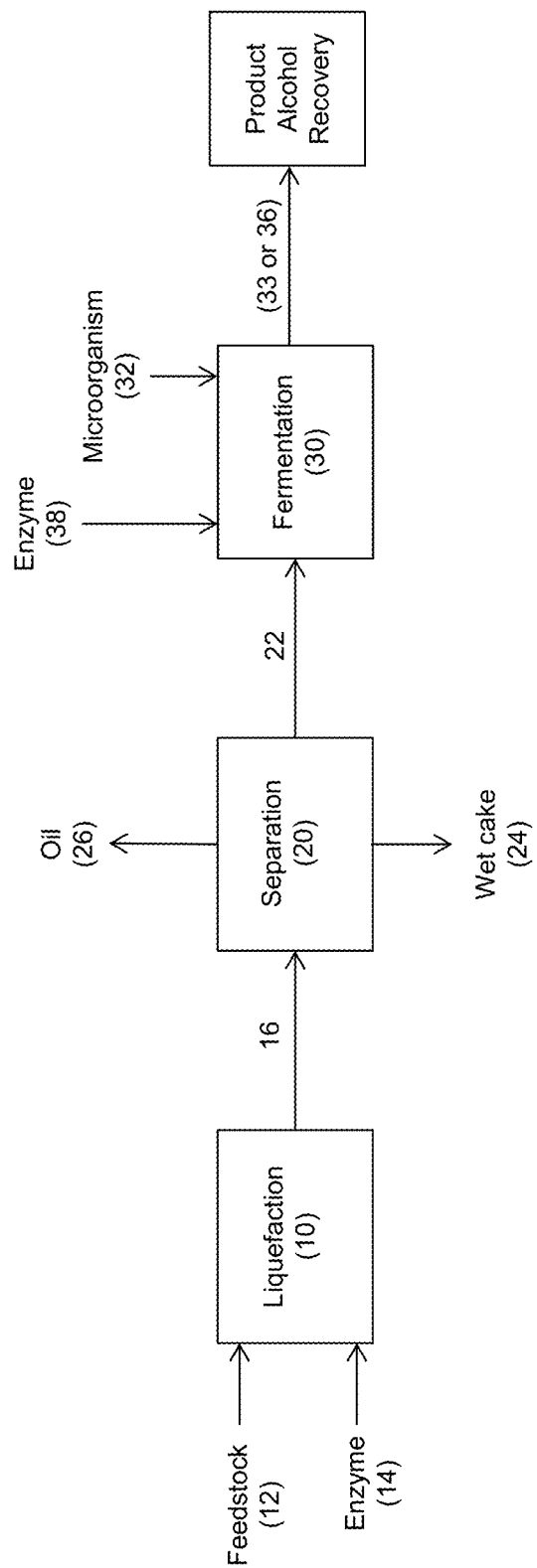
FIG. 3 schematically illustrates another exemplary alternative process and system of the present invention, in which an oil stream is discharged.

Referring to FIG. 3, the systems and processes of the present invention may include discharging oil 26 from an outlet of separation 20. Feedstock slurry 16 may be separated into a first liquid phase or aqueous solution 22 comprising a fermentable sugar, a solid phase or wet cake 24 comprising undissolved solids, and a second liquid phase comprising oil 26 which may exit separation 20. In some embodiments, separation of feedstock slurry 16 into a first liquid phase, a second liquid phase, and a solid phase may occur in a single step. In some embodiments, feedstock 12 is corn and oil 26 is corn oil. Oil 26 may be conducted to a storage tank or any unit that is suitable for oil storage. Any suitable separation device may be used to discharge aqueous solution 22, wet cake 24, and oil 26, for example, a three-phase centrifuge. In some embodiments, a portion of the oil from feedstock 12 such as corn oil when the feedstock is corn, remains in wet cake 24. In some embodiments, when oil 26 is removed via separation 20 from feedstock 12 (e.g., corn), the fermentation broth in fermentation 30 includes a reduced amount of corn oil.

As described herein, in some embodiments, oil may be separated from the feedstock or feedstock slurry and may be stored in an oil storage unit. For example, oil may be separated from the feedstock or feedstock slurry using any suitable means for separation including a three-phase centrifuge or mechanical extraction. To improve the removal of oil from the feedstock or feedstock slurry, oil extraction aids such surfactants, anti-emulsifiers, or flocculents as well as enzymes may be utilized. Examples of oil extraction aids include, but are not limited to, non-polymeric, liquid surfactants; talcum powder; microtalcum powder; salts (NaOH); calcium carbonate; and enzymes such as Pectinex® Ultra SP-L, Celluclast®, and Viscozyme® L (Sigma-Aldrich, St. Louis, Mo.), and NZ 33095 (Novozymes, Franklinton, N.C.).

Figure 4:
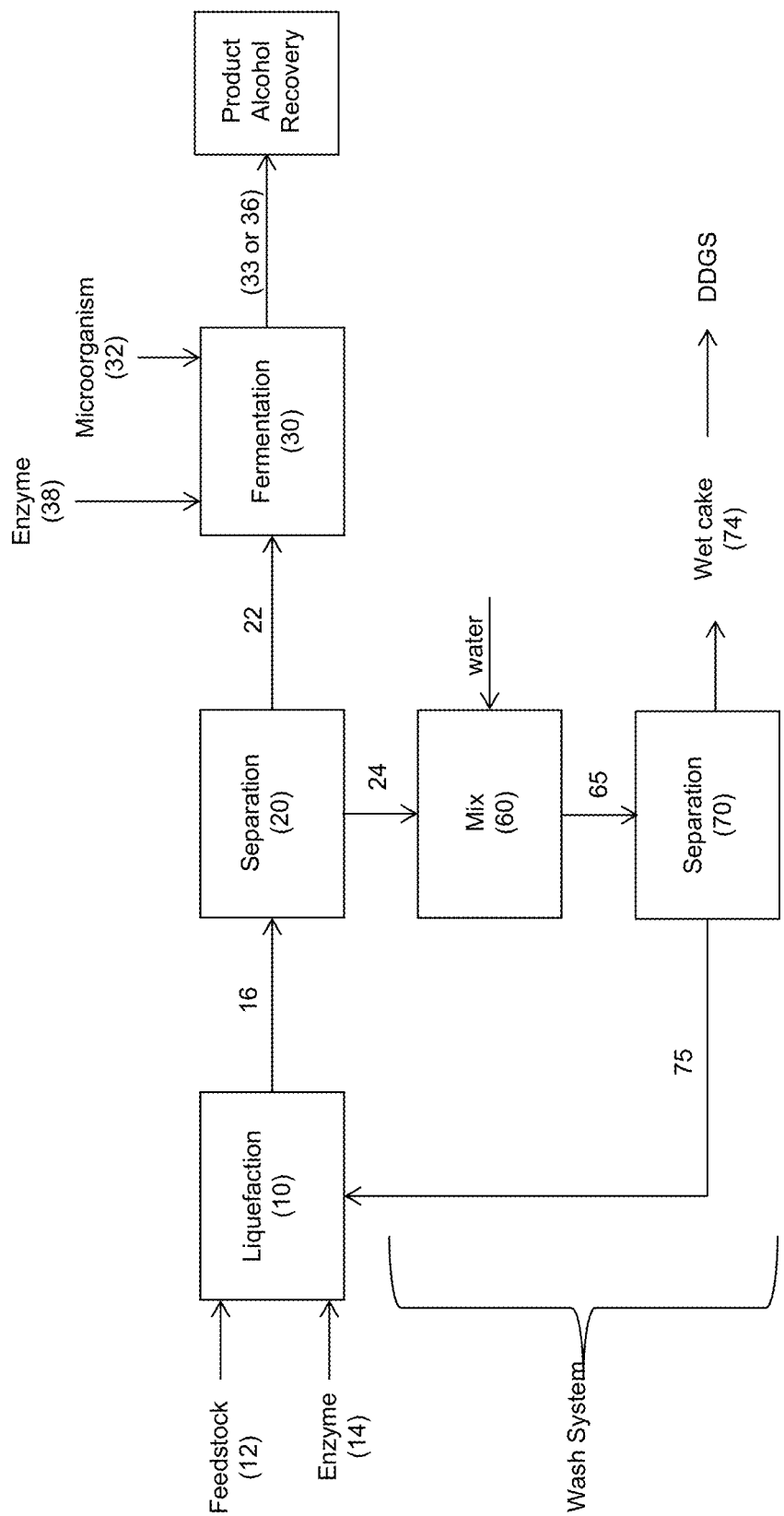
FIG. 4 schematically illustrates another exemplary alternative process and system of the present invention, in which the wet cake is subjected to wash cycles.

As illustrated in FIG. 4, if oil is not discharged separately it may be removed with wet cake 24. When wet cake 24 is removed via separation 20, in some embodiments, a portion of the oil from feedstock 12, such as corn oil when the feedstock is corn, remains in wet cake 24. Wet cake 24 may be conducted to mix 60 and combined with water or other solvents forming wet cake mixture 65. In some embodiments, water may be fresh water, backset, cook water, process water, lutter water, evaporation water, or any water source available in the fermentation processing facility, or any combination thereof. Wet cake mixture 65 may be conducted to separation 70 producing wash centrate 75 comprising fermentable sugars recovered from wet cake 24, and wet cake 74. Wash centrate 75 may be recycled to liquefaction 10.

In some embodiments, separation 70 may be any separation device capable of separating solids and liquids including, for example, decanter bowl centrifugation, three-phase centrifugation, disk stack centrifugation, filtering centrifugation, decanter centrifugation, filtration, vacuum filtration, belt filter, pressure filtration, membrane filtration, filtration using a screen, screen separation, grating, porous grating, flotation, hydrocyclone, filter press, screwpress, gravity settler, vortex separator, or combinations thereof.

In some embodiments, wet cake may be subjected to one or more wash cycles or wash systems. For example, wet cake 74 may be further processed by conducting wet cake 74 to a second wash system. In some embodiments, wet cake 74 may be conducted to a second mix 60' forming wet cake mixture 65'. Wet cake mixture 65' may be conducted to a second separation 70' producing wash centrate 75' and wet cake 74'. Wash centrate 75' may be recycled to liquefaction 10. In some embodiments, wash centrate 75' may be combined with wash centrate 75, and recycled to liquefaction 10. In some embodiments, wet cake 74' may be combined with wet cake 74 for further processing as described herein. In some embodiments, separation 70' may be any separation device capable of separating solids and liquids including, for example, decanter bowl centrifugation, three-phase centrifugation, disk stack centrifugation, filtering centrifugation, decanter centrifugation, filtration, vacuum filtration, belt filter, pressure filtration, membrane filtration, microfiltration, filtration using a screen, screen separation, grating, porous grating, flotation, hydrocyclone, filter press, screwpress, gravity settler, vortex separator, or combination thereof. In some embodiments, the wet cake may be subjected to one, two, three, four, five, or more wash cycles or wash systems.

Wet cake 74 may be combined with syrup and then dried to form DDGS through any suitable known process. The formation of the DDGS from wet cake 74 has several benefits. Since the undissolved solids do not go to the fermentor, the DDGS does not have trapped extractant and/or product alcohol, it is not subjected to the conditions of the fermentor, and it does not contact the microorganisms present in the fermentor. These benefits make it easier to process DDGS, for example, as animal feed.

In some embodiments, a portion of undissolved solids may be conducted to fermentation 30. In some embodiments, this portion of undissolved solids may have smaller particle sizes (e.g., fines). In some embodiments, this portion of undissolved solids may form whole stillage. In some embodiments, this whole stillage may be processed to form thin stillage and a wet cake. In some embodiments, the wet cake formed from whole stillage and wet cake 74 and/or 74' may be combined and further processed to produce DDGS.

As shown in FIG. 4, oil is not discharged separately from the wet cake, but rather oil is included as part of the wet cake and is ultimately present in the DDGS. If corn is utilized as feedstock, corn oil contains triglycerides, diglycerides, monoglycerides, fatty acids, and phospholipids, which provide a source of metabolizable energy for animals. The presence of oil (e.g., corn oil) in the wet cake and ultimately DDGS may provide a desirable animal feed, for example, a high fat content animal feed.

In some embodiments, oil may be separated from wet cake and DDGS and converted to an ISPR extractant for subsequent use in the same or different alcohol fermentation processes. Methods for deriving extractants from biomass are described in U.S. Patent Application Publication No. 2011/0312044; U.S. Patent Application Publication No. 2011/0312043; and U.S. Patent Application Publication No. 2012/0156738; the entire contents of each are herein incorporated by reference. Oil may be separated from wet cake and DDGS using any suitable process including, for example, a solvent extraction process. In one embodiment of the invention, wet cake or DDGS may be added to an extraction unit and washed with a solvent such as hexane to remove oil. Other solvents that may be utilized include, for example, butanol, isohexane, ethanol, petroleum distillates such as petroleum ether, or mixtures thereof. Following oil extraction, wet cake or DDGS may be treated to remove any residual solvent. For example, wet cake or DDGS may be heated to vaporize any residual solvent using any method known in the art. Following solvent removal, wet cake or DDGS may be subjected to a drying process to remove any residual water. The processed wet cake may be used to generate DDGS. The processed DDGS may be used as a feed supplement for animals such as dairy and beef cattle, poultry, swine, livestock, equine, aquaculture, and domestic pets.

In some embodiments, extractant may be used as a means to modify the color of the wet cake. For example, feedstocks such as corn contain pigments (e.g., xanthophylls) which may be used as a coloring agent in food products including animal feeds (e.g., poultry feed). Exposure to extractants can modify these pigments resulting in a wet cake that is, for example, lighter in color. A lighter color wet cake may produce DDGS with a lighter color, which may be a desirable quality for certain animal feeds.

In some embodiments, where corn is used as the feedstock, xanthophylls may be isolated from corn and/or undissolved solids and used as a pigment ingredient in DDGS or animal feed, or as a supplement for pharmaceutical and nutraceutical applications. Methods for isolating xanthophylls include, but are not limited to, chromatography such as size exclusion chromatography, solvent extraction such as ethanol extraction, and enzyme treatment such as alcalase hydrolysis (see, e.g., Tsui, et al., J. Food Eng. 83:590-595, 2007; Li, et al., Food Science 31: 72-77, 2010: U.S. Pat. No. 5,648,564; U.S. Pat. No. 6,169,217; U.S. Pat. No. 6,329,557; U.S. Pat. No. 8,236,929; the entire contents of each are herein incorporated by reference). In some embodiments, xanthophylls may be isolated from corn and/or undissolved solids and added to COFA. In some embodiments, COFA and/or xanthophylls may be used for food, pharmaceutical, and nutraceutical applications.

After extraction from wet cake or DDGS, the resulting oil and solvent mixture may be collected for separation of oil and solvent. In one embodiment, the oil/solvent mixture may be processed by evaporation whereby the solvent is evaporated and may be collected and recycled. The recovered oil may be converted to an ISPR extractant for subsequent use in the same or different alcohol fermentation processes.

Removal of the oil component of the feedstock is advantageous to product alcohol production because oil present in the fermentor can break down into fatty acids and glycerin. Glycerin can accumulate in water and reduce the amount of water that is available for recycling throughout the system. Thus, removal of the oil component of feedstock can increase the efficiency of product alcohol production by increasing the amount of water that can be recycled through the system.

Figure 5:
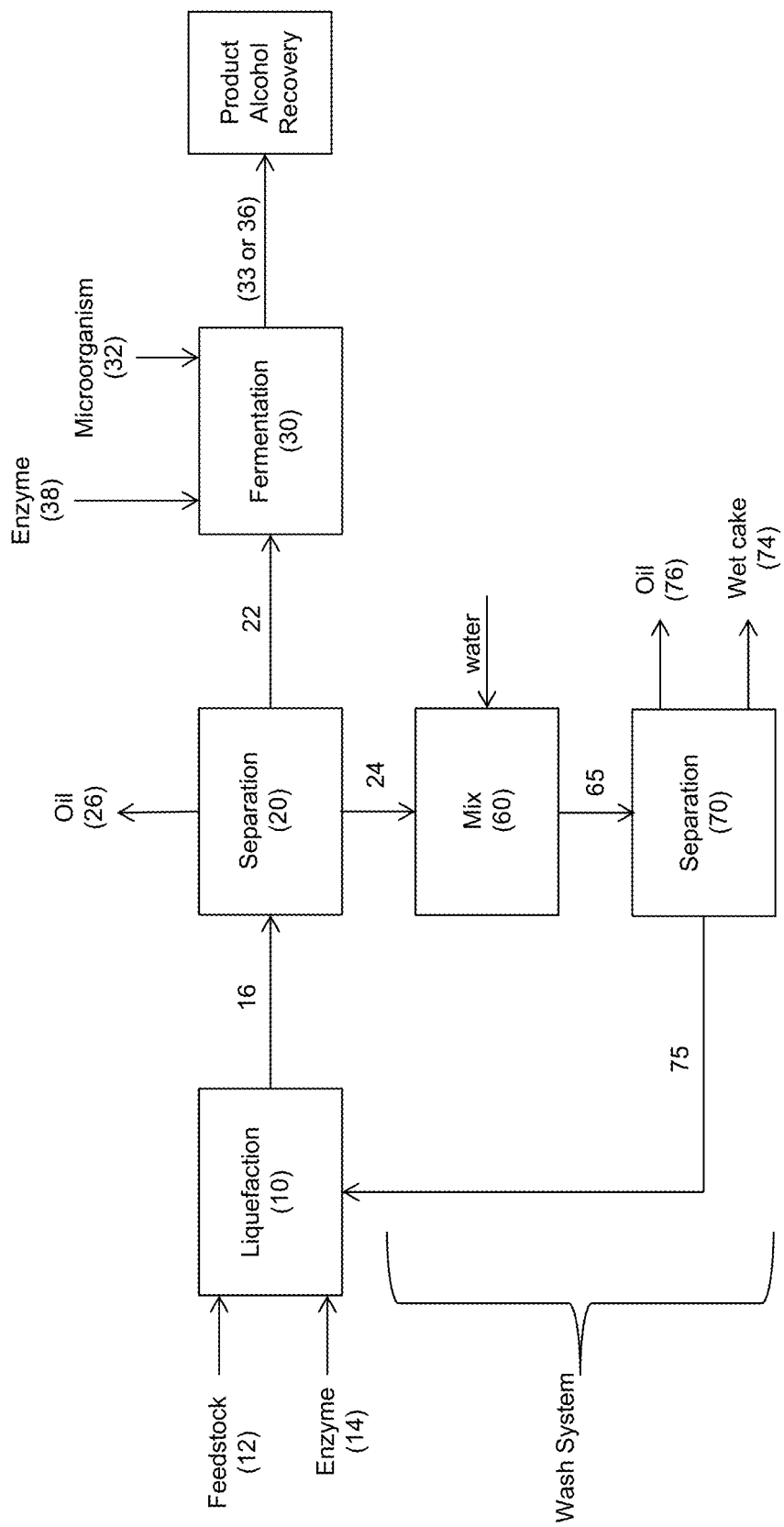
FIG. 5 schematically illustrates another exemplary alternative process and system of the present invention, in which an oil stream is discharged and wet cake is subjected to wash cycles.

Referring to FIG. 5, oil may be removed at various points during the processes described herein. Feedstock slurry 16 may be separated, for example, using a three-phase centrifuge, into a first liquid phase or aqueous solution 22, a second liquid phase comprising oil 26, and a solid phase or wet cake 24. Wet cake 24 may be further processed to recover fermentable sugars and oil. Wet cake 24 may be conducted to mix 60 and combined with water or other solvents forming wet cake mixture 65. In some embodiments, water may be backset, cook water, process water, lutter water, water collected from evaporation, or any water source available in the fermentation processing facility, or any combination thereof. Wet cake mixture 65 may be conducted to separation 70 (e.g., three-phase centrifuge) producing wash centrate 75 comprising fermentable sugars, oil stream 76, and wet cake 74. Wash centrate 75 may be recycled to liquefaction 10.

As described herein, wet cake may be subjected to one or more wash cycles or wash systems. In some embodiments, wet cake 74 may be conducted to a second mix 60' forming wet cake mixture 65'. Wet cake mixture 65' may be conducted to a second separation 70' producing wash centrate 75', oil stream 76' and wet cake 74'. Wash centrate 75' may be recycled to liquefaction 10. In some embodiments, wash centrate 75' may be combined with wash centrate 75, and recycled to liquefaction 10. In some embodiments, wet cake 74' may be combined with wet cake 74 for further processing as described below. In some embodiments, oil stream 76' and oil 26 may be combined and further processed for the generation of extractant that may be used in the fermentation process or oil stream 76' and oil 26 may be combined and further processed for the manufacture of consumer products.

Wet cake 74 may be combined with syrup and then dried to form DDGS utilizing any suitable process. The formation of DDGS from wet cake 74 has several benefits. Since the undissolved solids do not go to the fermentor, the DDGS does not contain extractant and/or product alcohol, it is not subjected to the conditions of the fermentor, and it does not contact the microorganisms present in the fermentor. These benefits make it easier to process DDGS, for example, as animal feed. As described herein, in some embodiments, wet cake 74, 74', and wet cake formed from whole stillage may be combined and further processed to produce DDGS.

Figure 6A:
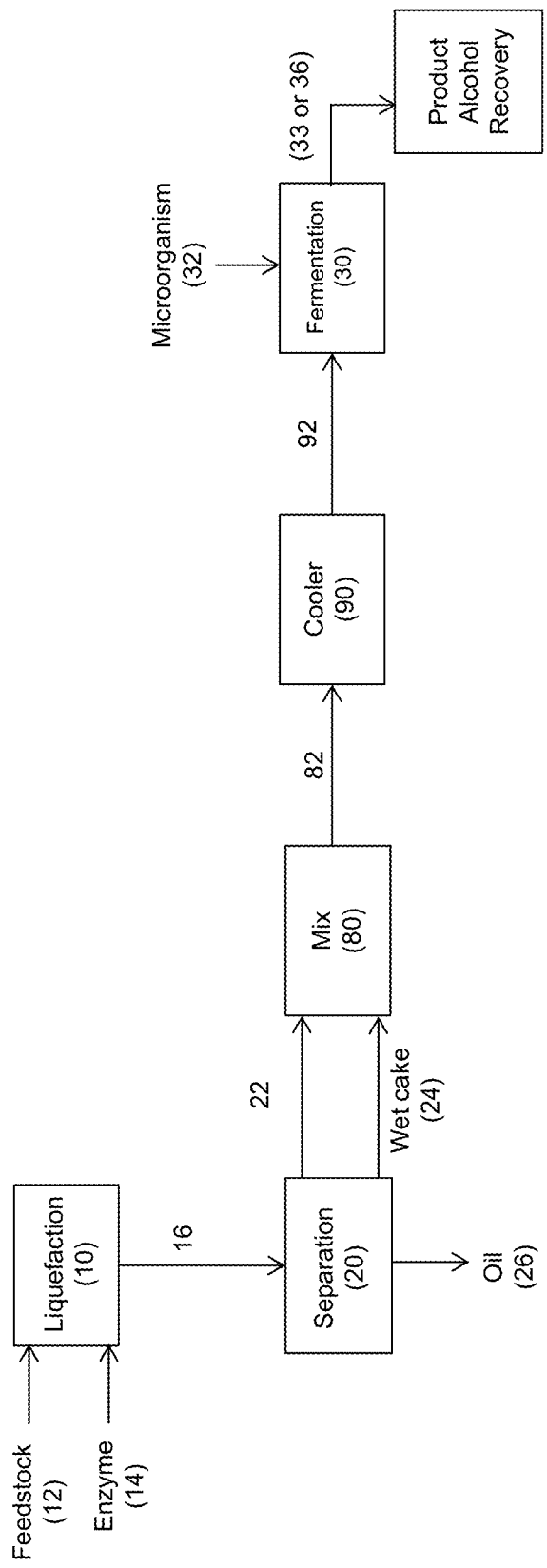
FIGS. 6A and 6B schematically illustrates another exemplary alternative process and system of the present invention, in which the aqueous solution and wet cake are combined and conducted to fermentation (FIG. 6A) and aqueous solution, oil, and wet cake are combined and conducted to fermentation (FIG. 6B).

As illustrated in FIG. 6A, aqueous solution 22 and wet cake 24 may be combined, cooled, and conducted to fermentation 30. Feedstock slurry 16 may be separated, for example, using a three-phase centrifuge, into a first liquid phase or aqueous solution 22, a second liquid phase comprising oil 26, and a solid phase or wet cake 24. In some embodiments, oil 26 may be conducted to a storage tank or any unit that is suitable for oil storage. Aqueous solution 22 and wet cake 24 may be conducted to mix 80 and re-slurried forming aqueous solution/wet cake mixture 82. Mixture 82 may be conducted to cooler 90 producing cooled mixture 92 which may be conducted to fermentation 30. In some embodiments, when oil 26 is removed via separation 20 from feedstock slurry 16, mixtures 82 and 92 include a reduced amount of oil.

Figure 6B:
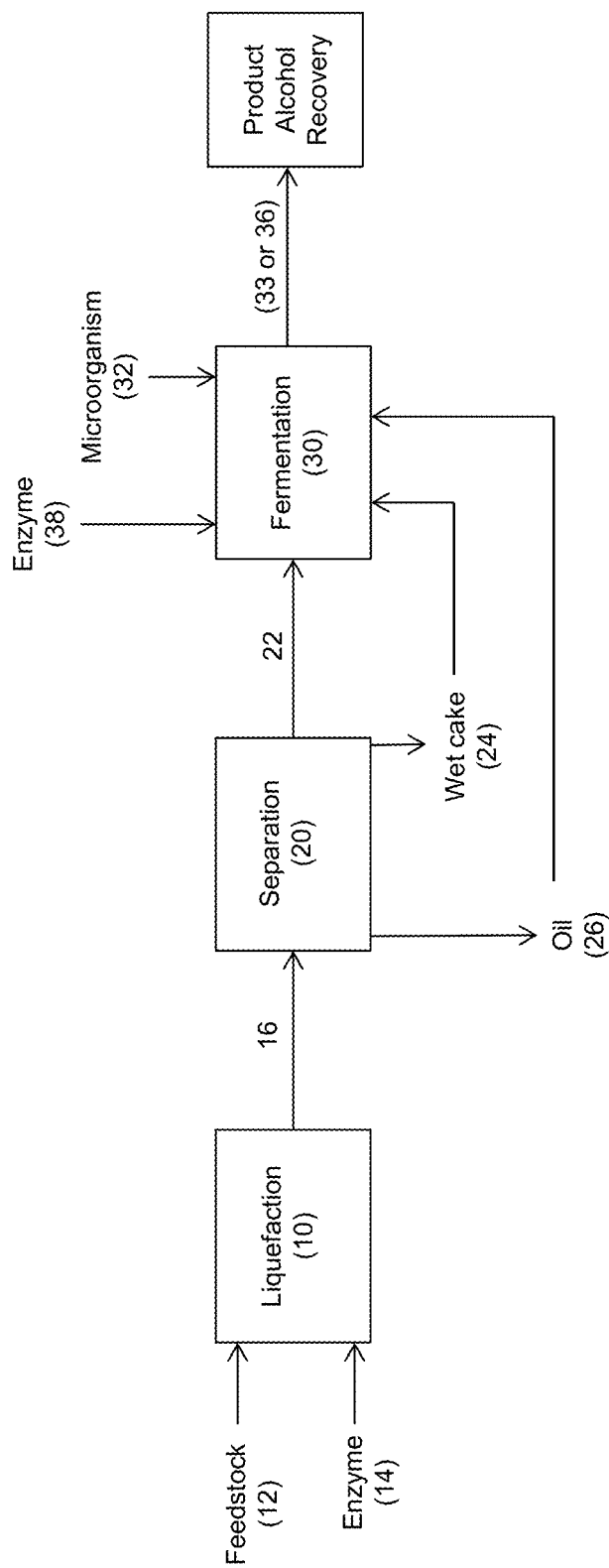

In another embodiment, as illustrated in FIG. 6B, feedstock slurry 16 may be separated using a separation device (e.g., a three-phase centrifuge) to generate a first liquid phase or aqueous solution 22, a second liquid phase comprising oil 26, and a solid phase or wet cake 24. Aqueous solution 22, wet cake 24, and oil 26, or portions thereof, may be conducted to fermentation 30. In some embodiments, aqueous solution 22, wet cake 24, and oil 26, or portions thereof, may be combined, for example, by mixing, forming an aqueous solution, wet cake, and oil mixture, and the mixture may be conducted to fermentation 30. In some embodiments, aqueous solution 22 and wet cake 24 may be combined forming an aqueous solution and wet cake mixture, then oil 26 may be added to the mixture forming an aqueous solution, wet cake, and oil mixture and this mixture may be conducted to fermentation 30. In some embodiments, aqueous solution 22 and wet cake 24 may be combined forming an aqueous solution and wet cake mixture, and this mixture and oil 26, or a portion thereof, may be conducted to fermentation 30 as separate streams.

In additional embodiments of the processes and systems described herein, saccharification may occur in a separate saccharification system. In some embodiments, a saccharification system may be located between liquefaction 10 and separation 20 or between separation 20 and fermentation 30. In some embodiments, liquefaction and/or saccharification may be conducted utilizing raw starch enzymes or low temperature hydrolysis enzymes such as Stargen™ (Genencor International, Palo Alto, Calif.) and BPX™ (Novozymes, Franklinton, N.C.). In some embodiments, feedstock slurry may be subjected to raw starch hydrolysis (also known as cold cooking or cold hydrolysis).

In some embodiments, the systems and processes of the present invention may include a series of two or more separation devices (e.g., centrifuges) for the removal of undissolved solids and/or oil. For example, aqueous solution discharged from a first separation unit may be conducted to an inlet of a second separation unit. The first separation unit and second separation unit may be identical (e.g., two three-phase centrifuges) or may be different (e.g., a three-phase centrifuge and a decanter centrifuge). Separation may be accomplished by a number of means including, but not limited to, decanter bowl centrifugation, three-phase centrifugation, disk stack centrifugation, filtering centrifugation, decanter centrifugation, filtration, vacuum filtration, belt filter, pressure filtration, membrane filtration, filtration using a screen, screen separation, grating, porous grating, flotation, hydrocyclone, filter press, screwpress, gravity settler, vortex separator, or combinations thereof.

The absence or minimization of undissolved solids in the fermentation broth has several benefits. For example, the need for units of operation in the downstream processing may be eliminated, thereby resulting in an increased efficiency for product alcohol production. Also, some or all of the centrifuges used to process whole stillage may be eliminated as a result of less undissolved solids in the fermentation broth exiting the fermentor. Removal of undissolved solids from feedstock slurry may improve the processing productivity of biomass and cost effectiveness. Improved productivity may include increased efficiency of product alcohol production and/or increased extraction activity relative to processes and systems that do not remove undissolved solids prior to fermentation. For additional description of processes and systems for separating undissolved solids from feedstock slurry see, for example, U.S. Patent Application Publication No. 2012/0164302 and PCT International Patent Application No. PCT/US2013/51571, the entire contents of each are herein incorporated by reference.

As described herein, product alcohol may be recovered from fermentation broth using a number of methods including liquid-liquid extraction. In some embodiments of the processes and systems described herein, an extractant may be used to recover product alcohol from fermentation broth. Extractants used herein may have, for example, one or more of the following properties and/or characteristics: (i) biocompatible with the microorganisms, (ii) immiscible with the fermentation broth, (iii) a high partition coefficient (Kp) for the extraction of product alcohol, (iv) a low partition coefficient for the extraction of nutrients and/or water, (v) low viscosity ($\mu$), (vi) high selectivity for product alcohol as compared to, for example, water, (vii) low density ($\rho$) relative to the fermentation broth or a density that is different as compared to the density of the fermentation broth, (viii) a boiling point suitable for downstream processing of the extractant and product alcohol, (ix) a melting point lower than ambient temperature, (x) minimal absorbency in solids, (xi) a low tendency to form emulsions with the fermentation broth, (xii) stability throughout the fermentation process, (xiii) low cost, and (xiv) nonhazardous.

In some embodiments, the extractant may be selected based upon certain properties and/or characteristics as described herein. For example, viscosity of the extractant can influence the mass transfer properties of the system, that is, the efficiency with which the product alcohol may be extracted from the aqueous phase to the extractant phase (i.e., organic phase). The density of the extractant can affect phase separation. In some embodiments, selectivity refers to the relative amounts of product alcohol to water taken up by the extractant. The boiling point can affect the cost and method of product alcohol recovery. For example, in the case where butanol is recovered from the extractant phase by distillation, the boiling point of the extractant should be sufficiently low as to enable separation of butanol while minimizing any thermal degradation or side reactions of the extractant, or the need for deep vacuum in the distillation process.

The extractant may be biocompatible with the microorganism, that is, nontoxic to the microorganism or toxic only to such an extent that the microorganism is impaired to an acceptable level. In some embodiments, biocompatible refers to the measure of the ability of a microorganism to utilize fermentable carbon sources in the presence of an extractant. The extent of biocompatibility of an extractant may be determined, for example, by the glucose utilization rate of the microorganism in the presence of the extractant and product alcohol. In some embodiments, a non-biocompatible extractant refers to an extractant that interferes with the ability of a microorganism to utilize fermentable carbon sources. For example, a non-biocompatible extractant does not permit the microorganism to utilize glucose at a rate greater than about 25%, greater than about 30%, greater than about 35%, greater than about 40%, greater than about 45%, or greater than about 50% of the rate when the extractant is not present.

One skilled in the art may select an extractant to maximize the desired properties and/or characteristics as described herein and to optimize recovery of a product alcohol. One of skill in the art can also appreciate that it may be advantageous to use a mixture of extractants. For example, extractant mixtures may be used to increase the partition coefficient for the product alcohol. Additionally, extractant mixtures may be used to adjust and optimize physical characteristics of the extractant, such as the density, boiling point, and viscosity. For example, the appropriate combination may provide an extractant which has a sufficient partition coefficient for the product alcohol and sufficient biocompatibility to enable its economical use for removing product alcohol from fermentative broth.

In some embodiments, extractants useful in the processes and systems described herein may be organic solvents. In some embodiments, extractants useful in the processes and systems described herein may be water-immiscible organic solvents. In some embodiments, the extractant may be an organic extractant selected from the group consisting of saturated, mono-unsaturated, poly-unsaturated $C_{12}$ to $C_{22}$ fatty alcohols, $C_{12}$ to $C_{22}$ fatty acids, esters of $C_{12}$ to $C_{22}$ fatty acids, $C_{12}$ to $C_{22}$ fatty aldehydes, $C_{12}$ to $C_{22}$ fatty amides, and mixtures thereof. In some embodiments, the extractant may also be an organic extractant selected from the group consisting of saturated, mono-unsaturated, poly-unsaturated $C_4$ to $C_{22}$ fatty alcohols, $C_4$ to $C_{28}$ fatty acids, esters of $C_4$ to $C_{28}$ fatty acids, $C_4$ to $C_{22}$ fatty aldehydes, $C_4$ to $C_{22}$ fatty amides, and mixtures thereof. In some embodiments, the fatty acid may be a $C_4$ to $C_{24}$ fatty acid and/or the ester may be an ester of a $C_4$ to $C_{24}$ fatty acid. In some embodiments, the extractant may be an organic extractant selected from the group consisting of saturated, mono-unsaturated, poly-unsaturated $C_{12}$ to $C_{18}$ fatty alcohols, $C_{12}$ to $C_{18}$ fatty acids, esters of $C_{12}$ to $C_{18}$ fatty acids, $C_{12}$ to $C_{18}$ fatty aldehydes, $C_{12}$ to $C_{18}$ fatty amides, and mixtures thereof. In some embodiments, the extractant may be an organic extractant selected from the group consisting of saturated, mono-unsaturated, poly-unsaturated $C_{14}$ to $C_{18}$ fatty alcohols, $C_{14}$ to $C_{18}$ fatty acids, esters of $C_{14}$ to $C_{18}$ fatty acids, $C_{14}$ to $C_{18}$ fatty aldehydes, $C_{14}$ to $C_{18}$ fatty amides, and mixtures thereof. In some embodiments, the extractant may be an organic extractant selected from the group consisting of saturated, mono-unsaturated, poly-unsaturated $C_{16}$ to $C_{18}$ fatty alcohols, $C_{16}$ to $C_{18}$ fatty acids, esters of $C_{16}$ to $C_{18}$ fatty acids, $C_{16}$ to $C_{18}$ fatty aldehydes, $C_{16}$ to $C_{18}$ fatty amides, and mixtures thereof. In some embodiments, the extractant may comprise carboxylic acids. In some embodiments, the ester of a fatty acid may be the combination of a fatty acid with an alcohol (e.g., fatty ester). In some embodiments, the alcohol may be a product alcohol. In some embodiments, the ester may be methyl ester, ethyl ester, propyl ester, butyl ester, pentyl ester, hexyl ester, or glycerides.

In some embodiments, the extractant may include a first extractant selected from $C_{12}$ to $C_{22}$ fatty alcohols, $C_{12}$ to $C_{22}$ fatty acids, esters of $C_{12}$ to $C_{22}$ fatty acids, $C_{12}$ to $C_{22}$ fatty aldehydes, $C_{12}$ to $C_{22}$ fatty amides, and mixtures thereof; and a second extractant selected from $C_{12}$ to $C_{22}$ fatty alcohols, $C_{12}$ to $C_{22}$ fatty acids, esters of $C_{12}$ to $C_{22}$ fatty acids, $C_{12}$ to $C_{22}$ fatty aldehydes, $C_{12}$ to $C_{22}$ fatty amides, and mixtures thereof. In some embodiments, the extractant may include a first extractant selected from $C_{12}$ to $C_{22}$ fatty alcohols, $C_{12}$ to $C_{22}$ fatty acids, esters of $C_{12}$ to $C_{22}$ fatty acids, and mixtures thereof; and a second extractant selected from $C_{12}$ to $C_{22}$ fatty alcohols, $C_{12}$ to $C_{22}$ fatty acids, esters of $C_{12}$ to $C_{22}$ fatty acids, and mixtures thereof. In some embodiments, the extractant may include a first extractant selected from $C_{12}$ to $C_{18}$ fatty alcohols, $C_{12}$ to $C_{18}$ fatty acids, esters of $C_{12}$ to $C_{18}$ fatty acids, and mixtures thereof; and a second extractant selected from $C_{12}$ to $C_{18}$ fatty alcohols, $C_{12}$ to $C_{18}$ fatty acids, esters of $C_{12}$ to $C_{18}$ fatty acids, and mixtures thereof. In some embodiments, the extractant may include a first extractant selected from $C_{14}$ to $C_{18}$ fatty alcohols, $C_{14}$ to $C_{18}$ fatty acids, esters of $C_{14}$ to $C_{18}$ fatty acids, and mixtures thereof; and a second extractant selected from $C_{14}$ to $C_{18}$ fatty alcohols, $C_{14}$ to $C_{18}$ fatty acids, esters of $C_{14}$ to $C_{18}$ fatty acids, and mixtures thereof. In some embodiments, the extractant may include a first extractant selected from $C_{12}$ to $C_{22}$ fatty alcohols, $C_{12}$ to $C_{22}$ fatty acids, esters of $C_{12}$ to $C_{22}$ fatty acids, $C_{12}$ to $C_{22}$ fatty aldehydes, $C_{12}$ to $C_{22}$ fatty amides, and mixtures thereof; and a second extractant selected from $C_7$ to $C_{11}$ fatty alcohols, $C_7$ to $C_{11}$ fatty acids, esters of $C_7$ to $C_{11}$ fatty acids, $C_7$ to $C_{11}$ fatty aldehydes, and mixtures thereof.

In some embodiments, the extractant may be an organic extractant such as oleyl alcohol, behenyl alcohol, cetyl alcohol, lauryl alcohol (also referred to as 1-dodecanol), myristyl alcohol, stearyl alcohol, oleic acid, lauric acid, linoleic acid, linolenic acid, myristic acid, palmitic acid, stearic acid, octanoic acid, decanoic acid, undecanoic acid, methyl myristate, methyl oleate, 1-nonanol, 1-decanol, 2-undecanol, 1-nonanal, 1-undecanol, undecanal, lauric aldehyde, 2-methylundecanal, oleamide, linoleamide, palmitamide, stearylamide, 2-ethyl-1-hexanol, 2-hexyl-1-decanol, 2-octyl-1-dodecanol, and mixtures thereof. In some embodiments, the extractant may comprise one or more of the following oleic acid, lauric acid, linoleic acid, linolenic acid, myristic acid, palmitic acid, stearic acid, octanoic acid, decanoic acid, and undecanoic acid. In some embodiments, the extractant may comprise one or more of the following oleic acid, linoleic acid, linolenic acid, myristic acid, palmitic acid, and stearic acid. In some embodiments, the extractant may comprise one or more of the following oleic acid, linoleic acid, palmitic acid, and stearic acid. In some embodiments, the extractant may comprise one or more of the following oleic acid, lauric acid, linoleic acid, linolenic acid, myristic acid, palmitic acid, stearic acid, octanoic acid, decanoic acid, and undecanoic acid, and one or more esters of oleic acid, lauric acid, linoleic acid, linolenic acid, myristic acid, palmitic acid, stearic acid, octanoic acid, decanoic acid, and undecanoic acid. In some embodiments, the extractant may comprise one or more of the following oleic acid, linoleic acid, linolenic acid, myristic acid, palmitic acid, and stearic acid, and one or more esters of oleic acid, linoleic acid, linolenic acid, myristic acid, palmitic acid, and stearic acid. In some embodiments, the extractant may comprise one or more of the following oleic acid, linoleic acid, palmitic acid, and stearic acid, and one or more esters of oleic acid, linoleic acid, palmitic acid, and stearic acid. In some embodiments, the extractant may comprise one or more of the following oleyl alcohol, behenyl alcohol, cetyl alcohol, lauryl alcohol, myristyl alcohol, stearyl alcohol. In some embodiments, the extractant may comprise one or more of the following 1-nonanol, 1-decanol, 2-undecanol, 1-nonanal, 1-undecanol, undecanal, 2-ethyl-1-hexanol, 2-hexyl-1-decanol, 2-octyl-1-dodecanol.

In some embodiments, the extractant may be a mixture of biocompatible and non-biocompatible extractants. Examples of mixtures of biocompatible and non-biocompatible extractants include, but are not limited to, oleyl alcohol and nonanol, oleyl alcohol and 1-undecanol, oleyl alcohol and 2-undecanol, oleyl alcohol and 1-nonanal, oleyl alcohol and decanol, and oleyl alcohol and dodecanol. Additional examples of biocompatible and non-biocompatible extractants are described in U.S. Patent Application Publication No. 2009/0305370 and U.S. Patent Application Publication No. 2011/0097773; the entire contents of each herein incorporated by reference. In some embodiments, biocompatible extractants may have high atmospheric boiling points. For example, biocompatible extractants may have atmospheric boiling points greater than the atmospheric boiling point of water.

In some embodiments, a hydrophilic solute may be added to fermentation broth that is contacted with an extractant. The presence of a hydrophilic solute in the aqueous phase may improve phase separation and may increase the fraction of product alcohol that partitions into the organic phase. Examples of a hydrophilic solute may include, but are not limited to, polyhydroxylated compounds, polycarboxylic compounds, polyol compounds, and dissociating ionic salts. Sugars such as glucose, fructose, sucrose, maltose, and oligosaccharides may serve as a hydrophilic solute. Other polyhydroxylated compounds may include glycerol, ethylene glycol, propanediol, polyglycerol, and hydroxylated fullerene. Polycarboxylic compounds may include citric acid, tartaric acid, maleic acid, succinic acid, polyacrylic acid, and sodium, potassium, or ammonium salts thereof. Ionic salts that may be used as a hydrophilic solute in fermentation broth comprise cations that include sodium, potassium, ammonium, magnesium, calcium, and zinc; and anions that include sulfate, phosphate, chloride, and nitrate. The amount of hydrophilic solute in the fermentation broth may be selected by one skilled in the art to maximize the transfer of product alcohol from the aqueous phase (e.g., fermentation broth) to the organic phase (e.g., extractant) while not having a negative impact on the growth and/or productivity of the product alcohol-producing microorganism. High levels of hydrophilic solute may impose osmotic stress and/or toxicity on the microorganism. One skilled in the art may use any number of known methods to determine an optimal amount of hydrophilic solute to minimize the effects of osmotic stress and/or toxicity on the microorganism.

In some embodiments where the product alcohol is butanol, the extractant may be selected for attracting the alkyl portion of butanol and for providing little or no affinity to water. An extractant that offers no hydrogen bonding, for example, to water will absorb the alcohol selectively. In some embodiments, the extractant may comprise an aromatic compound. In some embodiments, the extractant may comprise alkyl substituted benzenes including, but not limited to, cumene, para-cymene (also known as 1-methyl-4-(1-methylethyl)benzene), meta-cymene (also known as 1-methyl-3-(1-methylethyl)benzene), meta-diisopropylbenzene, para-diisopropylbenzene, triethylbenzene, ethyl butyl benzene, and tert-butylstyrene. An advantage of using an alkyl-substituted benzene is the comparatively higher butanol affinity relative to other hydrocarbons. In addition, isopropyl-substituted or isobutyl-substituted benzenes may offer a particular advantage in butanol affinity over other substituted benzenes. Another advantage is the lower viscosity, lower surface tension, lower density, higher thermal stability, and higher chemical stability that aids in phase separability and long-term reuse. In some embodiments, an extractant that attracts the alkyl portion of butanol may be combined with another extractant that offers affinity in the form of hydrogen bonding, for example, to the hydroxyl portion of butanol such that the mixture provides an optimal balance between selectivity and partitioning over water. In some embodiments, an extractant containing butanol may be phase separated from fermentation broth and distilled in a column operating under vacuum. This distillation may operate with reflux in order to maintain a distillate of high purity butanol that contains very little extractant. The bottoms may comprise a portion of the butanol contained in the distillation feed such that the reboiling temperature under vacuum is suitable for delivering heat indirectly from available steam. Distillation may be carried out with a partial condenser where only reflux liquid is condensed, and a vapor distillate of substantially butanol composition may be directed into the bottom of a rectification column that is simultaneously fed a butanol stream decanted from condensed beer column overhead vapor. An advantage of this type of distillation is that the need for a reboiler to purify the decanted butanol stream is eliminated by heat integrating the vapor generated from stripping butanol out of the extractant.

In some embodiments, extractant may be generated from feedstock. For example, oils such as corn oil present in feedstock may be used for the generation of extractant for extractive fermentation. The glycerides in oil may be chemically or enzymatically converted into a reaction product, such as fatty acids and/or fatty esters (e.g., ethyl esters, butyl esters, fusel esters) which may be used as an extractant for the recovery of the product alcohol. Using corn oil as an example, corn oil triglycerides may be reacted with a base such as ammonia hydroxide to obtain fatty amides and glycerol. In some embodiments, oil in the feedstock may be hydrolyzed by a catalyst to generate fatty acids. In some embodiments, at least a portion of the acyl glycerides in oil may be hydrolyzed to carboxylic acid by contacting the oil with catalyst. In some embodiments, the resulting acid/oil composition includes monoglycerides and/or diglycerides from the partial hydrolysis of the acyl glycerides in the oil. In some embodiments, the resulting acid/oil composition includes glycerol, a by-product of acyl glyceride hydrolysis. In some embodiments, the resulting acid/oil composition includes lysophospholipids from the partial hydrolysis of phospholipids in the oil. Methods for deriving extractants from biomass are described in U.S. Patent Application Publication No. 2011/0312044; U.S. Patent Application Publication No. 2011/0312043; and U.S. Patent Application Publication No. 2012/0156738, the entire contents of each are all herein incorporated by reference.

In some embodiments, the conversion of oil (e.g., hydrolysis, transesterification) in the feedstock or feedstock slurry may occur in the fermentor by the addition of a catalyst to the fermentor. For example, a catalyst such as lipase may be added to the fermentor, converting the oil present in the feedstock or feedstock slurry to fatty acids and/or fatty esters. In some embodiments, the conversion of oil in the feedstock or feedstock slurry may occur in a separate unit. For example, the feedstock or feedstock slurry may be conducted to a unit, and a catalyst such as lipase may be added to the unit, converting the oil present in the feedstock or feedstock slurry to fatty acids. As another example, the feedstock or feedstock slurry may be conducted to a unit, and a catalyst such as lipase and an alcohol (e.g., ethanol, butanol, fusel alcohols) may be added to the unit, converting the oil present in the feedstock or feedstock slurry to fatty esters. In some embodiments, the fatty acids and/or fatty esters may be added to the fermentor and may be used as an extractant for the recovery of the product alcohol. In some embodiments, the fatty acids and/or fatty esters may be added to an external extractor or extractant column and may be used as an extractant for the recovery of the product alcohol.

In some embodiments, oil may be separated from feedstock slurry and the oil may be conducted to a unit, and a catalyst such as lipase may be added to the unit, generating a fatty acid stream. The fatty acid stream may be heated to deactivate the lipase and then the fatty acid stream may be conducted to an external extractor or a storage tank. Fatty acids from the storage tank may be conducted to an external extractor for extraction of product alcohol from fermentation broth. In some embodiments, oil separated from feedstock slurry may be stored in a storage tank. A catalyst such as lipase may be added to the storage tank, generating a fatty acid stream. The fatty acid stream may be heated to deactivate the lipase, cooled, and then conducted to an external extractor for extraction of product alcohol from fermentation broth. In some embodiments, oil separated from feedstock slurry may be conducted to a unit, and a catalyst such as lipase may be added to the unit, generating a fatty acid stream. The fatty acid stream may be heated to deactivate the lipase, cooled, and then the fatty acid stream may be conducted to a fermentor.

In some embodiments, the one or more catalysts may be one or more enzymes, for example, hydrolase enzymes. In some embodiments, the one or more catalysts may be one or more enzymes, for example, lipase enzymes. Lipase enzymes may be derived from any source including, for example, *Absidia, Achromobacter, Aeromonas, Alcaligenes, Alternaria, Aspergillus, Achromobacter, Aureobasidium, Bacillus, Beauveria, Brochothrix, Candida, Chromobacter, Coprinus, Fusarium, Geotricum, Hansenula, Humicola, Hyphozyma, Lactobacillus, Metarhizium, Mucor, Nectria, Neurospora, Paecilomyces, Penicillium, Pseudomonas, Rhizoctonia, Rhizomucor, Rhizopus, Rhodosporidium, Rhodotorula, Saccharomyces, Sus, Sporobolomyces, Thermomyces, Thiarosporella, Trichoderma, Verticillium*, and/or *Yarrowia*. In some embodiments, the source of the lipase may be selected from the group consisting of *Absidia blakesleena, Absidia corymbifera, Achromobacter iophagus, Alcaligenes* sp., *Alternaria brassiciola, Aspergillus flavus, Aspergillus niger, Aspergillus tubingensis, Aureobasidium pullulans, Bacillus coagulans, Bacillus pumilus, Bacillus strearothermophilus, Bacillus subtilis, Brochothrix thermosohata, Burkholderia cepacia, Candida cylindracea (Candida rugosa), Candida paralipolytica, Candida antarctica* lipase A, *Candida antarctica* lipase B, *Candida ernobii, Candida deformans, Candida rugosa, Candida parapsilosis, Chromobacter viscosum, Coprinus cinerius, Fusarium heterosporum, Fusarium oxysporum, Fusarium solani, Fusarium solani pisi, Fusarium roseum culmorum, Geotrichum candidum, Geotricum penicillatum, Hansenula anomala, Humicola brevispora, Humicola brevis* var. *thermoidea, Humicola insolens, Lactobacillus curvatus, Rhizopus oryzae, Mucor javanicus, Neurospora crassa, Nectria haematococca, Penicillium cyclopium, Penicillium crustosum, Penicillium expansum, Penicillium roqueforti, Penicillium camembertii, Penicillium* sp. I, *Penicillium* sp. II, *Pseudomonas aeruginosa, Pseudomonas alcaligenes, Pseudomonas cepacia* (syn. *Burkholderia cepacia*), *Pseudomonas fluorescens, Pseudomonas fragi, Pseudomonas maltophilia, Pseudomonas mendocina, Pseudomonas mephitica lipolytica, Pseudomonas alcaligenes, Pseudomonas plantari, Pseudomonas pseudoalcaligenes, Pseudomonas putida, Pseudomonas stutzeri*, and *Pseudomonas wisconsinensis, Rhizoctonia solani, Rhizomucor miehei, Rhizopus arrhizus, Rhizopus delemar, Rhizopus japonicus, Rhizopus microsporus, Rhizopus nodosus, Rhizopus oryzae, Rhodosporidium toruloides, Rhodotorula glutinis, Saccharomyces cerevisiae, Sporobolomyces shibatanus, Sus scrofa, Thermomyces lanuginosus* (formerly *Humicola lanuginose*), *Thiarosporella phaseolina, Trichoderma harzianum, Trichoderma reesei*, and *Yarrowia lipolytica*.

In some embodiments, hydrolase and/or lipase may be expressed by the microorganism. In some embodiments, the microorganism may be engineered to express homologous or heterologous hydrolase and/or lipase. In some embodiments, hydrolase and/or lipase may be expressed by a microorganism that also produces a product alcohol. In some embodiments, hydrolase and/or lipase may be expressed by a microorganism that also expresses a butanol biosynthetic pathway.

In some embodiments, the butanol biosynthetic pathway may be a 1-butanol biosynthetic pathway, 2-butanol biosynthetic pathway, isobutanol biosynthetic pathway, or 2-butanone biosynthetic pathway.

Commercial lipase preparations suitable as a catalyst include, but are not limited to, Lipolase® 100 L, Lipex® 100L, Lipoclean® 2000T, Lipozyme® CALB L, Novozyme® CALA L, and Palatase 20000L, available from Novozymes (Franklinton, N.C.), or lipases from *Pseudomonas fluorescens, Pseudomonas cepacia, Mucor miehei*, hog pancreas, *Candida cylindracea, Candida rugosa, Rhizopus niveus, Candida antarctica, Rhizopus arrhizus* or *Aspergillus* available from Sigma Aldrich (St. Louis, Mo.). In some embodiments, the lipase may be thermostable and/or thermotolerant, and/or solvent tolerant.

In some embodiments, the one or more catalysts may be phospholipases. A phospholipase useful in the present invention may be obtained from a variety of biological sources, for example, but not limited to, filamentous fungal species within the genus *Fusarium*, such as a strain of *Fusarium culmorum, Fusarium heterosporum, Fusarium solani*, or *Fusarium oxysporum*; or a filamentous fungal species within the genus *Aspergillus*, such as a strain of *Aspergillus awamori, Aspergillus foetidus, Aspergillus japonicus, Aspergillus niger* or *Aspergillus oryzae*. Also useful in the present invention are *Thermomyces lanuginosus* phospholipase variants such as the commercial product Lecitase® Ultra (Novozymes A'S, Denmark). One or more phospholipases may be applied as lyophilized powder, immobilized, or in aqueous solution.

In some embodiments, phospholipase may be expressed by the microorganism. In some embodiments, the microorganism may be engineered to express homologous or heterologous phospholipases. In some embodiments, phospholipase may be expressed by a microorganism that also produces a product alcohol. In some embodiments, phospholipase may be expressed by a microorganism that also expresses a butanol biosynthetic pathway. In some embodiments, the butanol biosynthetic pathway may be a 1-butanol biosynthetic pathway, 2-butanol biosynthetic pathway, isobutanol biosynthetic pathway, or 2-butanone biosynthetic pathway.

By-products of fermentation such as isobutyric acid, phenylethanol, 3-methyl-1-butanol, 2-methyl-1-butanol, isobutyraldehyde, acetic acid, ketoisovaleric acid, pyruvic acid, and dihydroxyisovaleric acid may have an inhibitory effect on the microorganism. In some embodiments, these by-products may be modified by esterification. For example, the by-products may be esterified with carboxylic acids, alcohols, fatty acids, or other by-products. In some embodiments, these esterification reactions may be catalyzed by lipases or phospholipases. As an example, lipase present in the fermentation broth may catalyze the esterification of by-products generated during fermentation. Esterification of these by-products may minimize their inhibitory effects on the microorganism.

Figure 7A:
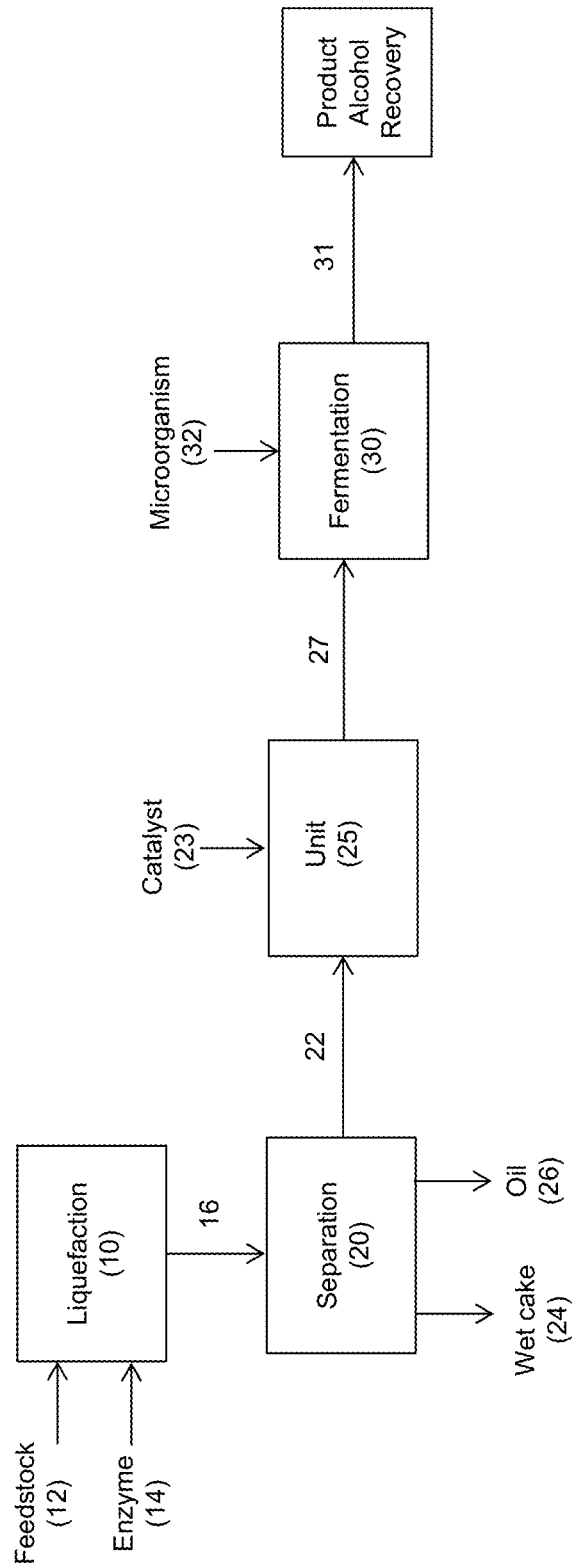
FIGS. 7A-7D schematically illustrates exemplary alternative processes and systems of the present invention, in which the aqueous solution is subjected to conversion (e.g., hydrolysis, transesterification) and/or deactivation.

Referring to FIG. 7A, feedstock 12 may be processed as described in FIGS. 1 to 6, and therefore will not be described in detail. Aqueous solution 22 may then be further treated to remove any residual oil. In some embodiments, aqueous solution 22 may be subjected to centrifugation, decantation, or any other method that may be used for oil removal. In some embodiments, aqueous solution 22 may be conducted to unit 25 (or vessel) and catalyst 23 (e.g., lipase) may be added to unit 25, converting the oil present in aqueous solution 22 to fatty acids, generating stream 27. Stream 27 may then be conducted to fermentation 30 and microorganism 32 may also be added to fermentation 30 for the production of product alcohol. Following fermentation 30, stream 31 comprising product alcohol and fatty acids may be conducted to an external unit, for example, an external extractor or external extraction loop for the recovery of product alcohol.

Figure 7B:
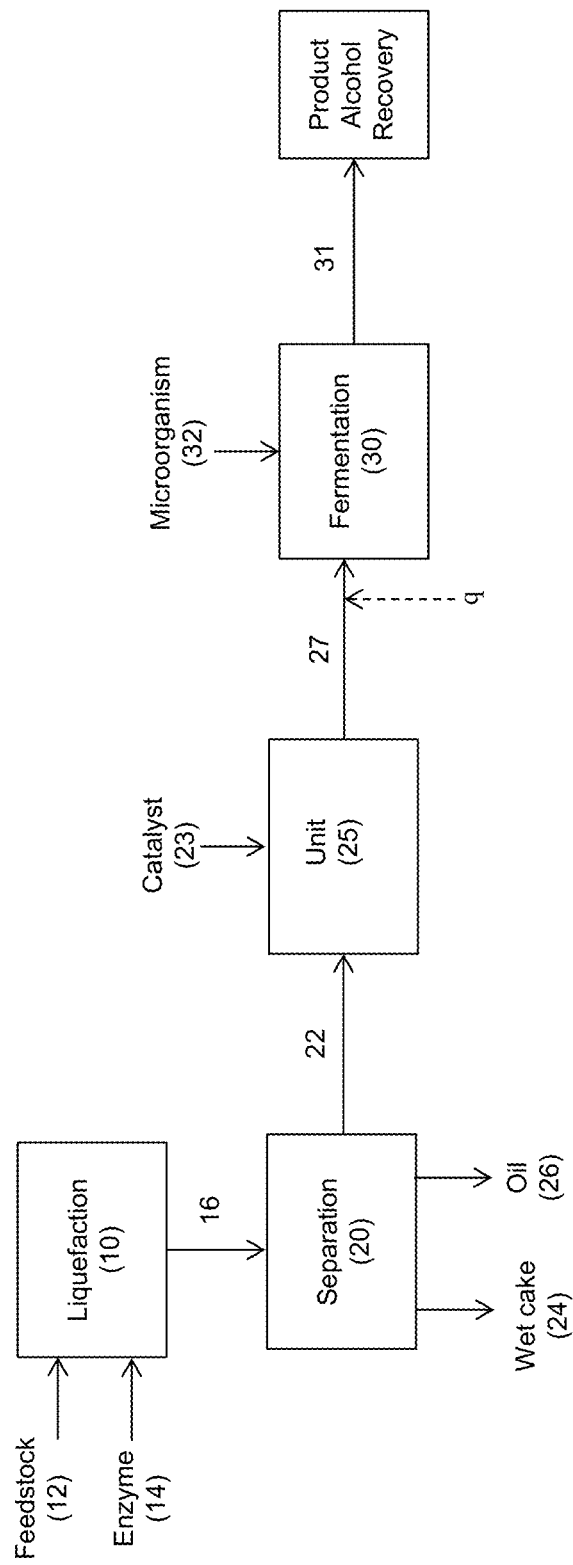
Figure 7C:
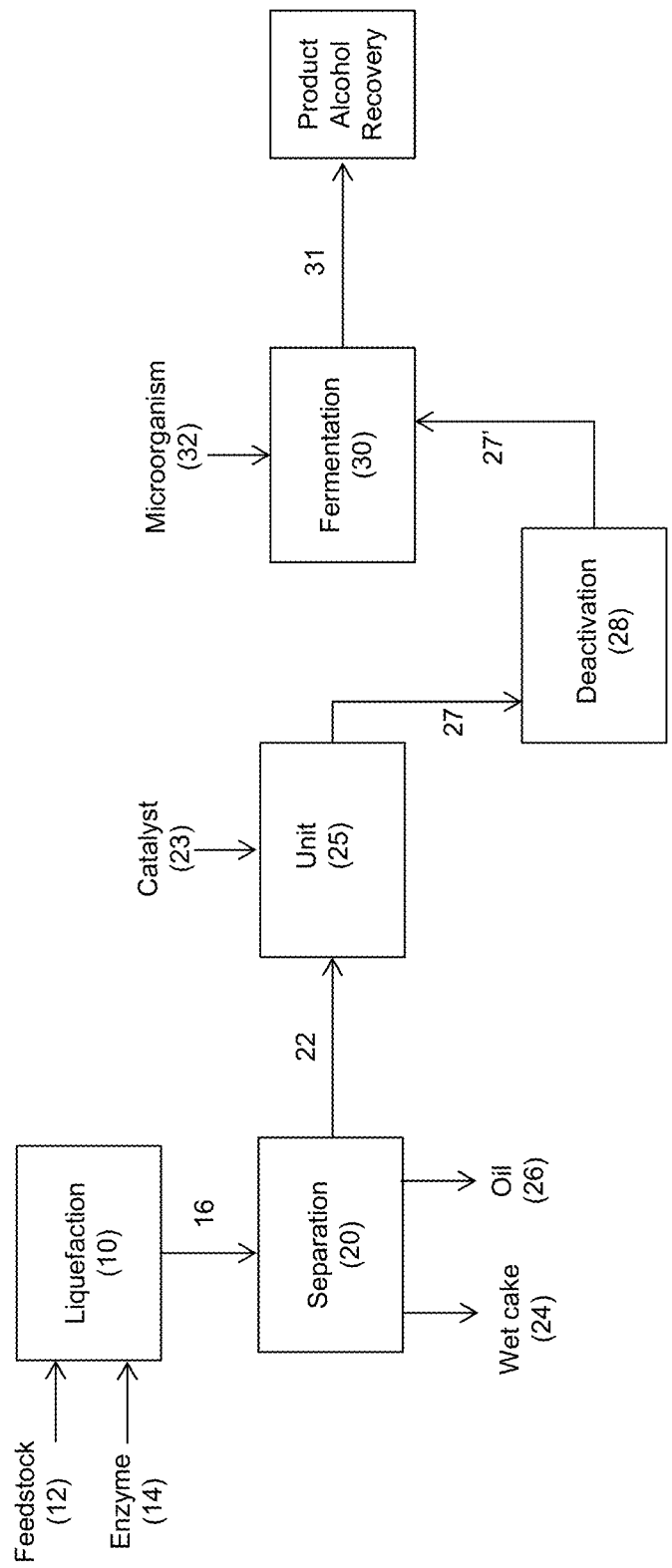

Referring to FIG. 7B, in some embodiments, catalyst 23 may be deactivated, for example, by heating. In some embodiments, stream 27 comprising catalyst 23 may be heated (q) to deactivate catalyst 23 prior to addition to fermentation 30. Referring to FIG. 7C, in some embodiments, deactivation may be conducted in a separate unit, for example, a deactivation unit. In some embodiments, stream 27 may be conducted to deactivation 28. Following deactivation, stream 27' may be conducted to fermentation 30 and microorganism 32 may also be added to fermentation 30 for production of product alcohol.

Removing oil from aqueous solution 22 by converting the oil to fatty acids can result in energy savings for the production plant due to more efficient fermentation, less fouling of the equipment due to the removal of the oil, decreased energy requirements, for example, the energy needed to dry distillers grains, and improved operation of evaporators or evaporation train. In addition, removal of the oil component of the feedstock is advantageous to product alcohol production because oil present in the fermentor can break down into fatty acids and glycerin. The glycerin can accumulate in the water and reduce the amount of water that is available for recycling throughout the system. Thus, removal of the oil component of the feedstock increases the efficiency of the product alcohol production by increasing the amount of water that can be recycled through the system. Also, stable emulsions are less likely to occur by removal of oil. In some embodiments of the present invention, in the event that an emulsion forms, emulsions may be readily broken by mechanical processing, addition of protic solvents, or by other conventional means.

Figure 7D:
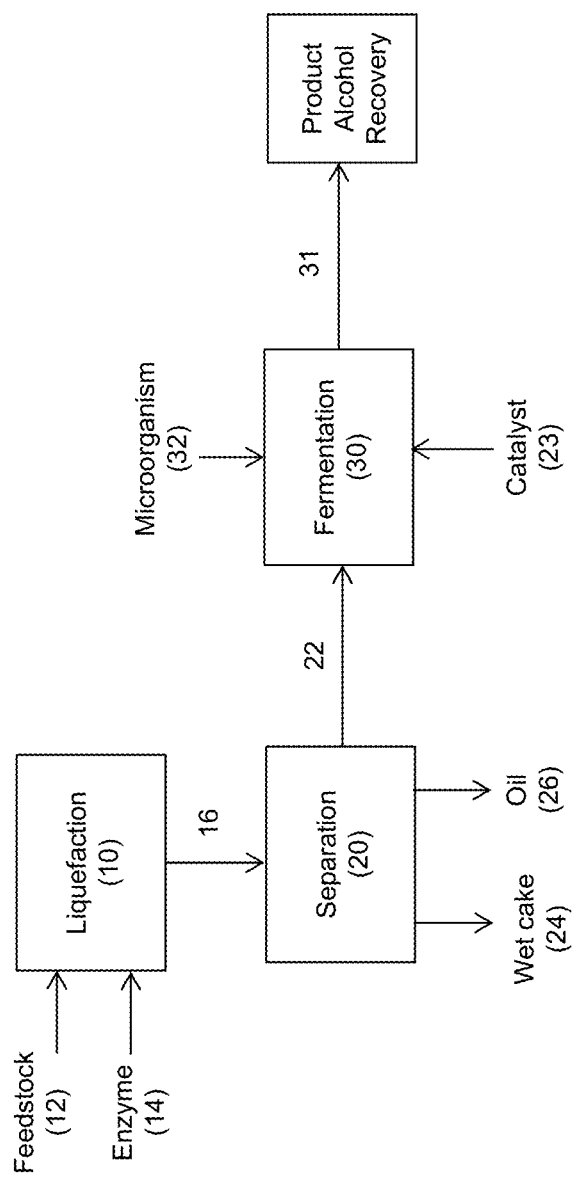

In another embodiment, referring to FIG. 7D, aqueous solution 22 may be conducted to fermentation 30 and catalyst 23 (e.g., lipase) may be added to fermentation 30, converting oil present in aqueous solution 22 to fatty acids and/or fatty esters. In some embodiments, fatty esters may be derived from the combination of fatty acids with an alcohol. In some embodiments, the alcohol may be any alcohol in fermentation 30 including a product alcohol. In some embodiments, the amount of oil in aqueous solution 22 converted to fatty acids and/or fatty esters may be at least about 50%, at least about 60%, at least about 70%, at least about 80%, at least about 90%, or at least about 95%. In some embodiments, the ratio of fatty esters and fatty acids generated by the conversion of oil may be about 75:25. In some embodiments, the ratio of fatty esters and fatty acids may be about 80:20. In some embodiments, catalyst 23 may be added to fermentation 30 in an amount to maintain a certain oil conversion rate.

Following fermentation 30, stream 31 comprising product alcohol, fatty acids, and fatty esters may be further processed for recovery of product alcohol. For example, stream 31 may be conducted to an external unit, for example, an external extractor or external extraction loop for the recovery of product alcohol. In some embodiments, the fatty acids and fatty esters in stream 31 may be used as an extractant. In some embodiments, the external unit may comprise extractant. In some embodiments, the extractant may comprise fatty acids and/or esters of fatty acids.

The present invention also provides processes and systems for recovering a product alcohol produced by a fermentative process. One such process for product alcohol recovery is liquid-liquid extraction. Using liquid-liquid extraction as an ISPR technique is best served by a liquid-liquid extraction process that maximizes the net present value of the capital investment required to practice the technology. An aspect of maximizing the net present value of a liquid-liquid extraction process is to avoid large capital and operating cost expenditures associated with separating extractant from fermentation broth.

In one embodiment of a liquid-liquid extraction process, extractant may be added directly to the fermentor, and fermentation broth and extractant may be mixed together in a way that effects mass transfer (e.g., transfer of product alcohol from fermentation broth to extractant) and allows the fermentation to proceed to high effective product alcohol titer. In such a process, if mixing is too intense or vigorous, the fermentation broth and extractant may have to be separated using a separation device such as a centrifuge. If mixing is not too intense, phase separation may be achieved through gravity settling brought on by the density difference between the extractant and the fermentation broth. In either case, additional fermentors may be required to overcome the loss of fermentor volume taken up by extractant added to the fermentor. Adding extractant directly to the fermentor may be carried out in batch, semi-batch, or continuous modes irrespective of phase separation within the fermentor. If continuous mode is employed and gravity separation of fermentation broth and extractant is not possible, then a separation device such as a centrifuge may be required for the separation of product alcohol from extractant. If the separation process employed to remove product alcohol from extractant is such that the microorganism present in the fermentation broth is viable the separation process, then separation of fermentation broth from product alcohol/extractant may not be required.

Another embodiment of a liquid-liquid extraction process may include an external extractor or extraction column. For example, fermentation broth from the fermentor may be conducted to an external extractor where the fermentation broth is mixed with extractant. The mixture of fermentation broth and extractant may then be separated, generating a fermentation broth stream leaner in product alcohol and an extractant stream richer in product alcohol. The leaner fermentation broth stream may be returned to the fermentor. The richer extractant stream may be processed further to separate at least a portion of product alcohol from the extractant for product alcohol recovery. In some embodiments, the rate of product alcohol recovery from the extractant stream may be set at a rate to maintain plant production. In some embodiments, the liquid-liquid extraction process may comprise one or more external liquid-liquid extractors.

In some embodiments, fermentation may occur in the fermentor and the external extractor. The additional volume of fermentation broth present in the external extractor may serve to increase the overall fermentor volume and therefore, may increase the overall production of product alcohol.

The performance of the external extractor with regard to removing product alcohol may depend on the surface area available for interfacial contact, the physical nature of the fermentation broth and extractant, the relative amounts of the two phases (e.g., fermentation broth phase and extractant phase) present in the external extractor, and the concentration driving force difference between the fermentation broth and extractant phases. Maximizing the efficiency of the external extractor for a given product alcohol concentration driving force may be accomplished by reducing the droplet size of the dispersed phase in the external extractor, for example, via nozzle design, internals design, and/or agitation. In some embodiments, the design and operation of the external extractor may provide enough mixing to effect adequate product alcohol transfer between the fermentation broth and extractant phases to maintain product alcohol productivity requirements.

In some instances, $CO_2$ from fermentation may be generated in the external extractor, leading to the formation of droplets which may interfere with phase separation. For example, droplets of fermentation broth may attach to $CO_2$ rising through the extractant phase. In some embodiments, the extractant phase may be maintained as the continuous phase to improve the coalescence of droplets. In some embodiments, the external extractor may include internals or exit ports for $CO_2$. For example, a coalescing pad may be added to the external extractor and/or the exit ports may be located to improve coalescence and recovery of the fermentation broth phase.

Conditions to separate product alcohol from fermentation broth may be deleterious to the microorganism present in the fermentation broth. In some embodiments, the microorganism may be separated from fermentation broth prior to contacting the fermentation broth with the extractant. In some embodiments, the microorganism may be separated from a mixture of fermentation broth and extractant prior to the separation (or processing) of this mixture. Any separation method capable of separating the microorganism from fermentation broth or mixture of fermentation broth and extractant may be used including, for example, centrifugation. By separating the microorganism prior to contacting the fermentation broth with extractant, it may be possible to use more rigorous extraction conditions such as higher temperatures and/or non-biocompatible extractants. If a separation method was used that was not deleterious to the microorganism, then separating the fermentation broth and extractant prior to product alcohol removal may not be required.

If extractant and fermentation broth are not separated, then the extractant may be included in the evaporator train feed and therefore, become a component of the syrup formed during evaporation, and possibly incorporated in animal feed. In some embodiments, extractant may be separated from the syrup using any separation means including, for example, centrifugation. A low boiling point (e.g., comparable to water) biocompatible extractant may not require such separation because the extractant and water may be recycled for use in the production process.

In a typical corn-to-product alcohol production plant, the water balance of the overall production process may be maintained by recycling water of the production plant with recycled water distilled in an evaporator train to remove salts and other dissolved solids of the beer. The resulting syrup from the evaporator train may be mixed with undissolved solids, and the mixture may be dried and sold as animal feed. Processes and systems for processing undissolved solids for animal feed are described, for example, in U.S. Patent Application Publication No. 2012/0164302; U.S. Patent Application Publication No. 2011/0315541; U.S. Patent Application Publication No. 2013/0164795; and PCT International Patent Application No. PCT/US2013/51571, the entire contents of each are herein incorporated by reference.

As described herein, undissolved solids may be removed from feedstock (or feedstock slurry) prior to the addition of the feedstock to fermentation. If undissolved solids are not removed upstream of fermentation, then centrifugation of the beer to remove undissolved solids may be necessary to avoid fouling of the evaporators. For example, in a commercial corn-to-product alcohol dry-grind production plant, undissolved solids content in an evaporator train feed may operate at about 3% total suspended solids, and may be as high as 3.5-4% total suspended solids. An upstream process that removes enough solids to maintain the percentage of total suspended solids at or below these percentage values may eliminate the need for centrifugation, for example, prior to conducting the beer to the evaporators (or evaporation train). The elimination of this centrifugation would result in a savings on the capital required to retrofit a dry-grind corn-to-product alcohol production plant.

By removing at least a portion of the undissolved solids present in the feedstock slurry prior to fermentation, the interfacial surface area between the fermentation broth and extractant phases in an external extractor may be increased by reducing the amount of undissolved solids at the interface, enhancing product alcohol transfer between the fermentation broth and the extractant and providing for a clean phase separation between the fermentation broth and extractant. A clean phase separation may also eliminate the need for additional separation steps (e.g., centrifugation) and therefore, a savings on capital expenses.

The separation of fermentation broth and extractant leaving the external extractor may be influenced by the solids content and particle size distribution of the solids content in the fermentation broth, the gas content and gas bubble size distribution in the fermentation broth, the physical properties of the fermentation broth and extractant including, but not limited to, viscosity, density, and surface tension as well as the design and operation of the external extractor and the design and operation of the fermentor. These properties may determine the need for separation devices (e.g., centrifuges) to separate the fermentation broth and extractant leaving the external extractor or the fermentor. Operating under conditions that eliminate the need for separation devices may minimize the capital expenditure to practice liquid-liquid extraction ISPR. In addition, minimizing the size of the extractors by maximizing the interfacial area between fermentation broth and extractant phases for a given set of fermentation broth and extractant physical properties can maintain the ability to inexpensively phase separate fermentation broth and extractant. By eliminating the capital and operating cost of separation devices such as centrifuges, the net present value of a dry grind corn-to-product alcohol production plant employing a liquid-liquid extraction ISPR process may be improved.

In another embodiment of the processes and systems described herein, the extractor design including phase separation capacity may be tailored to accommodate the physical properties of the fermentation broth and extractant. If undissolved solids are not removed from feedstock slurry or if the concentration of product alcohol in the fermentation broth is too low, it may not be possible to remove enough product alcohol to maintain plant productivity employing an extractor that does not include phase separation equipment. Therefore, the present invention provides for processes and systems that include solids removal as well as recovery of product alcohol utilizing an external extractor wherein the extractor has been designed to improve phase separation capacity for maximum product alcohol recovery.

Figure 8:
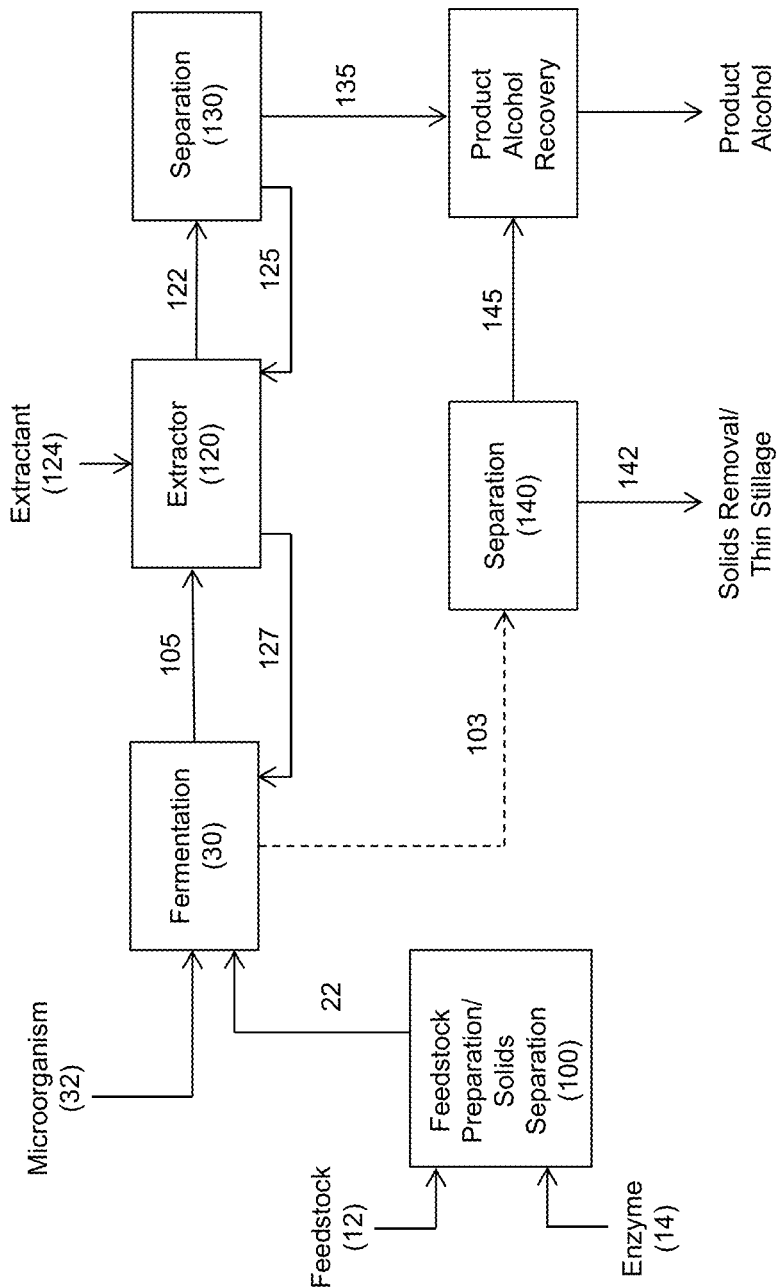
FIG. 8 schematically illustrates an exemplary fermentation process of the present invention including downstream processing.

An exemplary process of the present invention is described in FIG. 8. Some processes and streams in FIG. 8 have been identified using the same name and numbering as used in FIGS. 1-7 and represent the same or similar processes and streams as described in FIGS. 1-7.

Feedstock 12 may be processed and solids separated (100) as described herein with reference to FIGS. 1-7. Briefly, feedstock 12 may be liquefied to generate feedstock slurry comprising undissolved solids, fermentable sugars (or fermentable carbon source), and depending on the feedstock, oil. The feedstock slurry may then be subjected to separation methods to remove suspended solids, generating a wet cake, an aqueous solution 22 (or centrate) comprising dissolved fermentable sugars, and optionally an oil stream. Solids separation may be accomplished by a number of means including, but not limited to, decanter bowl centrifugation, three-phase centrifugation, disk stack centrifugation, filtering centrifugation, decanter centrifugation, filtration, vacuum filtration, belt filter, pressure filtration, membrane filtration, microfiltration, filtration using a screen, screen separation, grating, porous grating, flotation, hydrocyclone, filter press, screwpress, gravity settler, vortex separator, or combination thereof.

Aqueous solution 22 and microorganism 32 may be added to fermentation 30 where the fermentable sugars are fermented by microorganism 32 to produce stream 105 comprising product alcohol. In some embodiments, during fermentation, a portion of stream 105 may be transferred to extractor 120 (or extraction 120) where stream 105 is contacted with extractant 124. In some embodiments, extractant may be stored in an extractant storage tank or unit. In some embodiments, stream 105 may be removed from fermentation 30 when the concentration of product alcohol and/or other metabolic products reach a predetermined concentration. In some embodiments, the predetermined concentration may be a concentration of product alcohol and/or other metabolic products which negatively impact the metabolism of the microorganism. In some embodiments, stream 105 may be removed from fermentation 30 when fermentation is initiated. In some embodiments, stream 105 may be removed from fermentation 30 to minimize the effects of product alcohol on microorganism 32. In some embodiments, fermentation 30 may comprise one, two, three, four, five, six, seven, eight, or more fermentors.

In some embodiments, extractant may be added to fermentation 30. In some embodiments, a portion of fermentation broth comprising extractant may be transferred to extractor 120, and in some embodiments, extractant may be recovered from the fermentation broth comprising extractant. By adding extractant to fermentation 30, ISPR may be initiated in fermentation 30.

Product alcohol, or a portion thereof, transfers from stream 105 to extractant 124, and stream 122 comprising extractant richer in product alcohol may be conducted to separation 130. Stream 127 comprising fermentation broth leaner in product alcohol may be returned to fermentation 30. Separation 130 removes a portion of product alcohol from stream 122, and stream 125 comprising leaner extractant may be returned to extractor 120. In some embodiments, extractor 120 may be external to fermentation 30. In some embodiments, fermentation 30 may comprise an extractor. In some embodiments, extractant, fermentation broth, or both may be at least partially immiscible. Stream 135 may be conducted downstream for further processing (e.g., distillation) including recovery of product alcohol.

Over the course of extraction, there may be a loss of extractant or a portion of extractant. In some embodiments, extractant 124 may be replenished by the addition of extractant to extractor 120 or an extractant storage unit. In some embodiments, for example, where extractant may be derived from feedstock or feedstock slurry, extractant 124 may be replenished by converting oil in the feedstock or feedstock slurry to extractant. For example, a catalyst may be added to fermentation 30, converting oil in aqueous solution 22 to fatty acids and/or fatty esters (see, e.g., FIG. 7D), and a portion of stream 105 comprising product alcohol, fatty acids, and/or fatty esters may be transferred to extractor 120 where stream 105 may be contacted with extractant 124. Stream 122 comprising product alcohol-rich extractant, fatty acids, and/or fatty esters may be conducted to separation 130 generating stream 125 comprising leaner extractant, fatty acids, and/or fatty esters. In some embodiments, stream 125 may be further processed prior to its return to extractor 120. For example, fatty esters present in stream 125 may be subjected to hydrolysis generating a stream comprising product alcohol and fatty acids. This stream comprising product alcohol and fatty acids may be conducted to extractor 120, or this stream may be combined with stream 122 and the combined stream may be conducted to separation 130. In another embodiment, this stream comprising product alcohol and fatty acids may be conducted to separation 130 or this stream may be conducted to another separation unit generating a product alcohol stream and a fatty acid stream. The fatty acid stream may be conducted to extractor 120, and the product alcohol stream may be combined with stream 135 and further processed for product alcohol recovery.

In some embodiments, phase separation of fermentation broth and extractant after passing through an extractor may be insufficient such that an unacceptable level of dispersed extractant remains in the fermentation broth returning to the fermentor and/or an unacceptable level of fermentation broth droplets remain in the extractant advancing to distillation. In some embodiments, the phase separation of fermentation broth and extractant may be enhanced by processing a heterogeneous mixture exiting the top or bottom of an extractor through one or more hydrocyclones or similar vortex device. In some embodiments, a static mixer may be used in place of an extractor to bring fermentation broth and extractant into contact with each other and the heterogeneous mixture that is formed may be pumped through one or more hydrocyclones or similar vortex device to effect a separation of the aqueous (e.g., fermentation broth) and organic (e.g., extractant) phases. In some embodiments, one or more hydrocyclones or similar vortex device may be used to remove liquid or liquid droplets from a gas stream. In some embodiments, the gas stream may be from the fermentor. In some embodiments, the gas stream may be from a degassing device.

In a batch or semi-batch fermentation process, when a portion of the fermentable sugars has been metabolized by microorganism 32, stream 103 comprising beer may be conducted downstream to separation 140 to separate product alcohol from the beer. Stream 145 comprising product alcohol may be conducted downstream for further processing (e.g., distillation) including recovery of product alcohol. In a continuous fermentation process, stream 103 comprising beer may be conducted downstream to separation 140 to separate product alcohol from the beer. Stream 142 comprising whole stillage may be conducted downstream for further processing including solids removal and generation of thin stillage.

In some embodiments, fermentation 30 may comprise two or more fermentors, and stream 105 may comprise combined multiple streams from the two or more fermentors. In some embodiments, the combined multiple streams may be conducted to extractor 120. In some embodiments, stream 127 may be split and portions of stream 127 may be returned to the multiple fermentors. In some embodiments, extractor 120 may be a series of units connected together in parallel or in series.

In some embodiments, extraction may be conducted for a certain period of time. Extraction may be conducted, for example, until the concentration of product alcohol in fermentation 30 is low enough that separation 140 is not required. In some embodiments, extraction may be conducted for an extended period of time.

In some embodiments of the processes and systems described herein, a decanter may be used for phase separation. In some embodiments, a decanter may be used in combination with an extractor. In some embodiments, the surfaces of the decanter may be modified to improve phase separation. For example, surfaces of the decanter may be modified by the addition of hydrophilic and/or hydrophobic surfaces.

In some embodiments, oxygen, air, and/or nutrients may be added to stream 125 and/or stream 127. In some embodiments, the nutrients may be soluble in extractant. In some embodiments, the concentration of oxygen may be measured in the various streams, and may be used as part of a control loop to vary the flow of oxygen into the process. In some embodiments, mash may be added to extractor 120 to allow for higher effective titers. In some embodiments, separation 130 and 140 may be extractors. In some embodiments, these extractors may use water to extract product alcohol from extractant, and product alcohol may be subsequently separated from an aqueous phase. In some embodiments, extractant may be infused with solutes that enhance its capacity to extract product alcohol from fermentation broth. In some embodiments, a surge tank may be located between extractor 120 and separation 130 as a means to equilibrate the concentration of product alcohol in the extractant prior to separation (e.g., distillation).

In some embodiments, extractor 120 may be designed to utilize $CO_2$ generated during fermentation for the purpose of mixing fermentation broth and extractant. In some embodiments, extractor 120 may be designed to allow for ready disengagement of $CO_2$ in the fermentation broth. This design would facilitate the control of the level of mixing by $CO_2$ bubbles rising through extractor 120. In some embodiments, fermentation broth may be removed from fermentation 30 to minimize the concentration of $CO_2$ in stream 105. In some embodiments, the design of extractor disengagement zones may include surfaces to promote phase separation between fermentation broth and extractant. In some embodiments, hydrophilic and/or hydrophobic surfaces may be installed in the disengagement zones to improve phase separation. In some embodiments, the external extractor may include internals or exit ports for $CO_2$. For example, a coalescing pad may be added to the external extractor.

In some embodiments to minimize $CO_2$ mixing, the extractor may be designed with a small diameter at the bottom of the extractor, graduating to a large diameter at the top of the extractor (e.g., conical shape). In some embodiments, the extractor may be designed with a stepwise increase in diameter. For example, the extractor may comprise a first region of constant diameter flowed by a stepwise increase of diameter to a second region of constant diameter. In some embodiments, the extractor may further comprise a second stepwise increase of diameter to a third region of constant diameter. In some embodiments, the extractor may comprise one or more stepwise increases of diameter. In some embodiments, the extractor may comprise one or more regions of constant diameter.

Over the course of fermentation, the gas content (e.g., $CO_2$) of the fermentation broth changes, and these gases may be removed from the fermentation broth by utilizing a gas stripper. The amount of gas stripped from the fermentation broth may be adjusted by varying the flow through the gas stripper and/or the pressure of the gas stripper. In some embodiments, the amount of $CO_2$ in the fermentation broth may be reduced prior to transferring the fermentation broth to an extractor. For example, $CO_2$ may be stripped from the fermentation broth using a gas stripper or any means known to those skilled in the art. In some embodiments, removal of $CO_2$ may be performed at or below ambient pressure. In some embodiments, fermentation may continue in the extractor, and $CO_2$ may be produced by the microorganism. In some embodiments to minimize $CO_2$ mixing in the extractor, the residence time of the fermentation broth in the extractor may be reduced. In some embodiments, residence time may be reduced by modifying the height of the extractor. In some embodiments, the height of the extractor may be reduced. Reducing the height of the extractor may reduce the number of theoretical extraction stages. In some embodiments, to maintain the number of theoretical extraction stages, the extractor may be replaced with two or more extractors of reduced height. In some embodiments, the two or more extractors may be in series. In some embodiments, the two or more extractors may be connected. In some embodiments, the two or more extractors may be connected in such a way to maintain countercurrent flow. In some embodiments, a degassing stage may be added to one or more extraction stages.

Referring to FIG. 8, in some embodiments, the size of dispersed phase droplets in extractor 120 may be measured and adjusted through various means to enhance the rate of mass transfer. For example, droplet size may be measured using particle size analysis such as focused beam reflectance measurement (FBRM®) or particle vision and measurement (PVM®) technologies (Mettler-Toledo, LLC, Columbus Ohio). In some embodiments, the fermentation broth may be the dispersed phase and extractant may be the continuous phase, and under these conditions, solids present in the fermentation broth may interact to a lesser degree with the extractant. In some embodiments, conditions of separation 130 may be controlled to minimize oxidative and thermal instabilities effects on the extractant.

In some embodiments, the quality of the extractant may be monitored and extractant replenished at a frequency necessary for successful production of product alcohol. In some embodiments, extractant may be taken up by whole stillage solids. The whole stillage may be separated into liquid (e.g., thin stillage) and solid streams, and the solids may be washed to recover the extractant. In some embodiments, the temperature of extractor 120 may be adjusted to improve the efficiency of the overall process. In some embodiments, the flows of fermentation broth and extractant to extractor 120 may be co-current or countercurrent. In some embodiments, membranes may be used to minimize the mixing of fermentation broth and extractant. In some embodiments, extractant may be polymer beads or inorganic beads that absorb product alcohol. In some embodiments, the polymer beads or inorganic beads may be preferentially absorb product alcohol.

In some embodiments, measurements such as in-line, on-line, at-line, or real-time measurements may be used to measure the concentration of product alcohol and/or metabolic by-products in the various streams. These measurements may be used as part of a control loop to vary the flow between the various units or vessels (e.g., fermentation 30, extractor 120, separations 130 and 140, etc.) and to improve the overall process.

Figure 9:
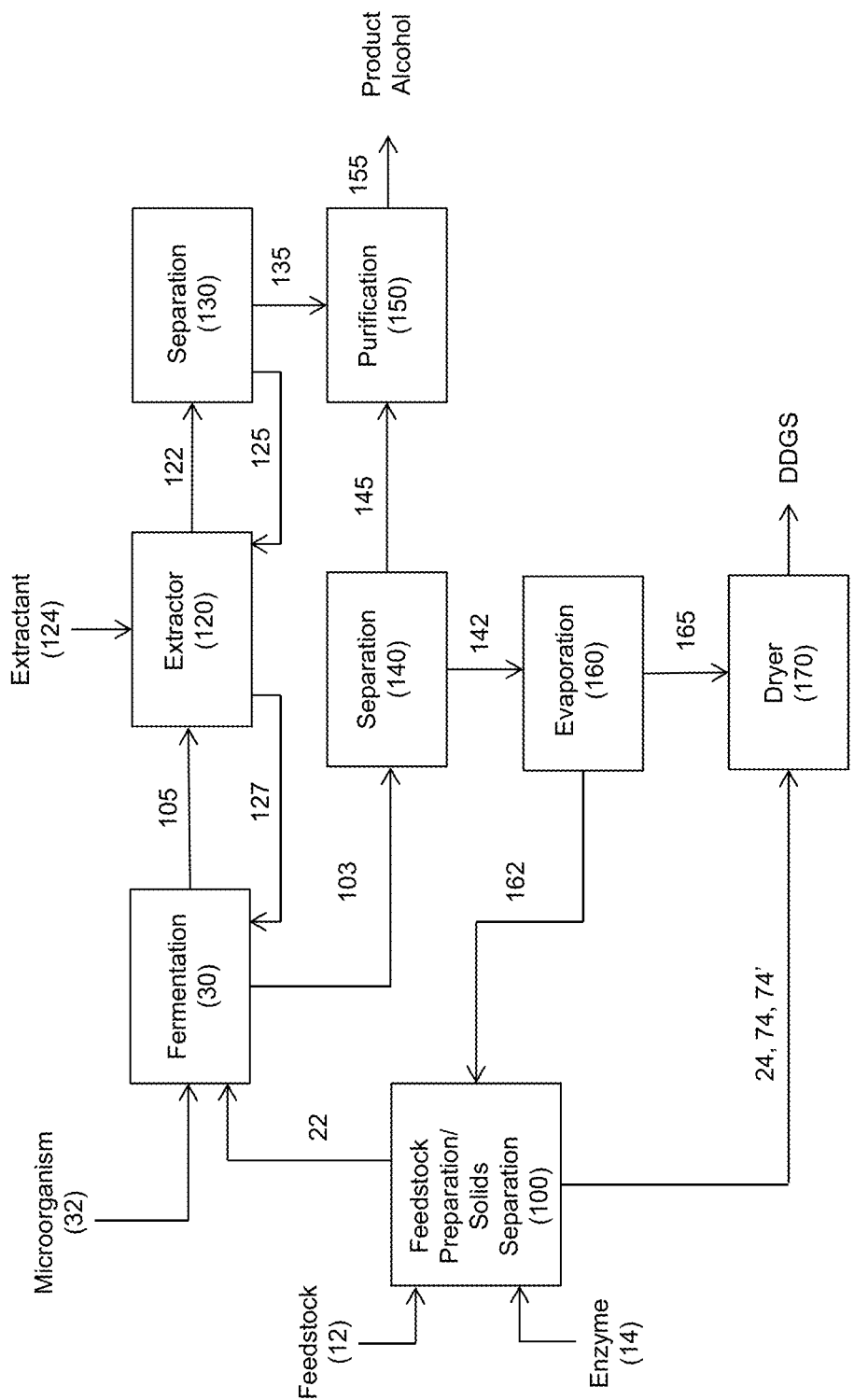
FIG. 9 schematically illustrates an exemplary fermentation process of the present invention including downstream processing.

Another exemplary process of the present invention is described in FIG. 9. Some processes and streams in FIG. 9 have been identified using the same name and numbering as used in FIGS. 1-8 and represent the same or similar processes and streams as described in FIGS. 1-8.

Feedstock 12 may be processed and solids separated (100) as described herein with reference to FIGS. 1-7. In some embodiments, feedstock 12 may be mixed with recycled water (e.g., stream 162) generated by evaporation 160. As described herein, feedstock slurry may be subjected to separation methods to remove suspended solids, generating a wet cake 24, an aqueous solution 22 (or centrate) comprising dissolved fermentable sugars, and depending on the feedstock, oil. Wet cake 24 may be dried in dryer 170 and used to produce DDGS. In some embodiments, wet cake 24 may be re-slurried with water (e.g., recycled water/stream 162) and subjected to separation to remove additional fermentable sugars, generating washed wet cake (e.g., 74, 74' as described in FIGS. 4 and 5). In some embodiments, wet cake streams 24, 74, and 74' may be combined and the combined wet cake streams may be dried in a dryer 170 and used to produce DDGS.

Aqueous solution 22 and microorganism 32 may be added to fermentation 30 where the fermentable sugars are metabolized by microorganism 32 to produce stream 105 comprising product alcohol. In some embodiments, enzyme may be added to fermentation 30. Stream 105 may be conducted to extractor 120, and may be contacted with extractant 124. Stream 127 comprising fermentation broth leaner in product alcohol may be returned to the fermentation 30 and stream 122 comprising extractant richer in product alcohol may be conducted to separation 130. In some embodiments, extractor 120 may be operated in such a way that stream 122 contains minimal cell mass and minimal substrate. Separation 130 may damage microorganism 32 or substrate resulting in a decrease in the fermentation rate. Operating extractor 120 with minimal cell mass and substrate may minimize any potential damage by separation 130. Stream 125 comprising leaner extractant may be returned to extractor 120. Stream 135 from separation 130 may be conducted to purification 150 for further processing including recovery of product alcohol. In some embodiments, extractant may be added to fermentation 30. In some embodiments, a portion of fermentation broth comprising extractant may be transferred to extractor 120, and in some embodiments, extractant may be recovered from the fermentation broth comprising extractant. In some embodiments, the flow rates of fermentation broth and extractant to extractor may be modified to improve phase separation. For example, lower overall flow rates entering the extractor in the early or later stages of fermentation can improve the phase separation of fermentation broth and extractant.

As described herein, after a batch fermentation process or as a steady effluent stream in a continuous fermentation process, stream 103 comprising beer may be conducted downstream to separation 140 to separate product alcohol from the whole stillage 142. Utilizing an upstream solids removal process may lower the undissolved solids content in the thin mash and therefore, it may not be necessary to centrifuge whole stillage 142 to remove solids. Thus, whole stillage 142 may be conducted directly to evaporation 160. Syrup 165 generated by evaporation 160 may be mixed with wet cake 24, 74, 74' in dryer 170 to form DDGS.

In some embodiments, backset comprising total suspended solids (TSS) from whole stillage may be used (or recycled) for feedstock slurry preparation. In some embodiments, whole stillage or a portion of whole stillage may be processed through a solids separation system including, but not limited to, turbo filtration or ultracentrifugation prior to evaporation, or whole stillage or a portion of whole stillage may be processed for self-cleaning water purification.

In some embodiments where coarse grain solids are removed from liquefied mash, the whole stillage that is produced may contain fine solids and insoluble microorganism fragments, and these dispersed solids may be removed using turbo filtration. Turbo filtration may include subjecting a feed suspension to centrifugal motion through a strainer that can retain fine solids. These fine solids when formed into a wet cake may contain some extractant that is absorbed both on the surface of and inside the pores of fine grain particles. In some instances, washing the wet cake with water is insufficient for recovering extractant from the wet cake. In some embodiments, a concentrated product alcohol stream such as the organic phase may be used to recover extractant from whole stillage wet cake. In some embodiments, this organic phase may be formed in a decanter. In some embodiments, the wet cake that has been washed with product alcohol may be subsequently washed with water to recover the product alcohol from the wet cake.

In some embodiments, the processes and systems described herein may include an extractant reservoir (or tank or vessel). Extractant may be added to the extractant reservoir and this extractant may be circulated to an extractor. In some embodiments, extractant may be conducted to an extractor and a stream from the extractor may be returned to the extractant reservoir. In some embodiments, extractant from an extractant reservoir may be circulated to an extractor and/or fermentor. In some embodiments, an extractant stream may be circulated between an extractant reservoir, an extractor, and a fermentor. In some embodiments, at the completion of fermentation, the contents of the extractant reservoir, extractor, and/or the fermentor may be further processed to recover product alcohol.

Figures 10A, 10B:
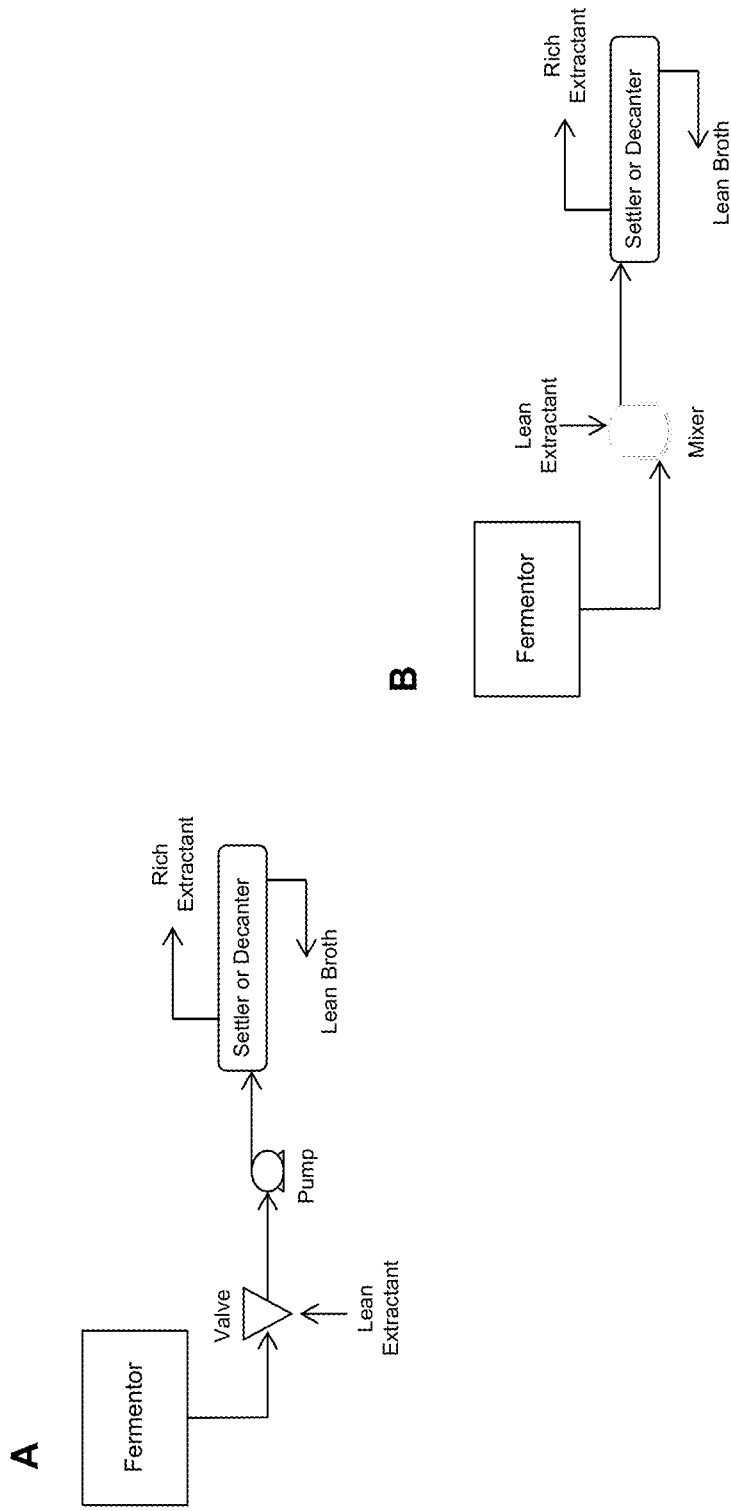
FIGS. 10A-10M illustrated various systems that may be used in the processes described herein.
Figures 10C, 10D:
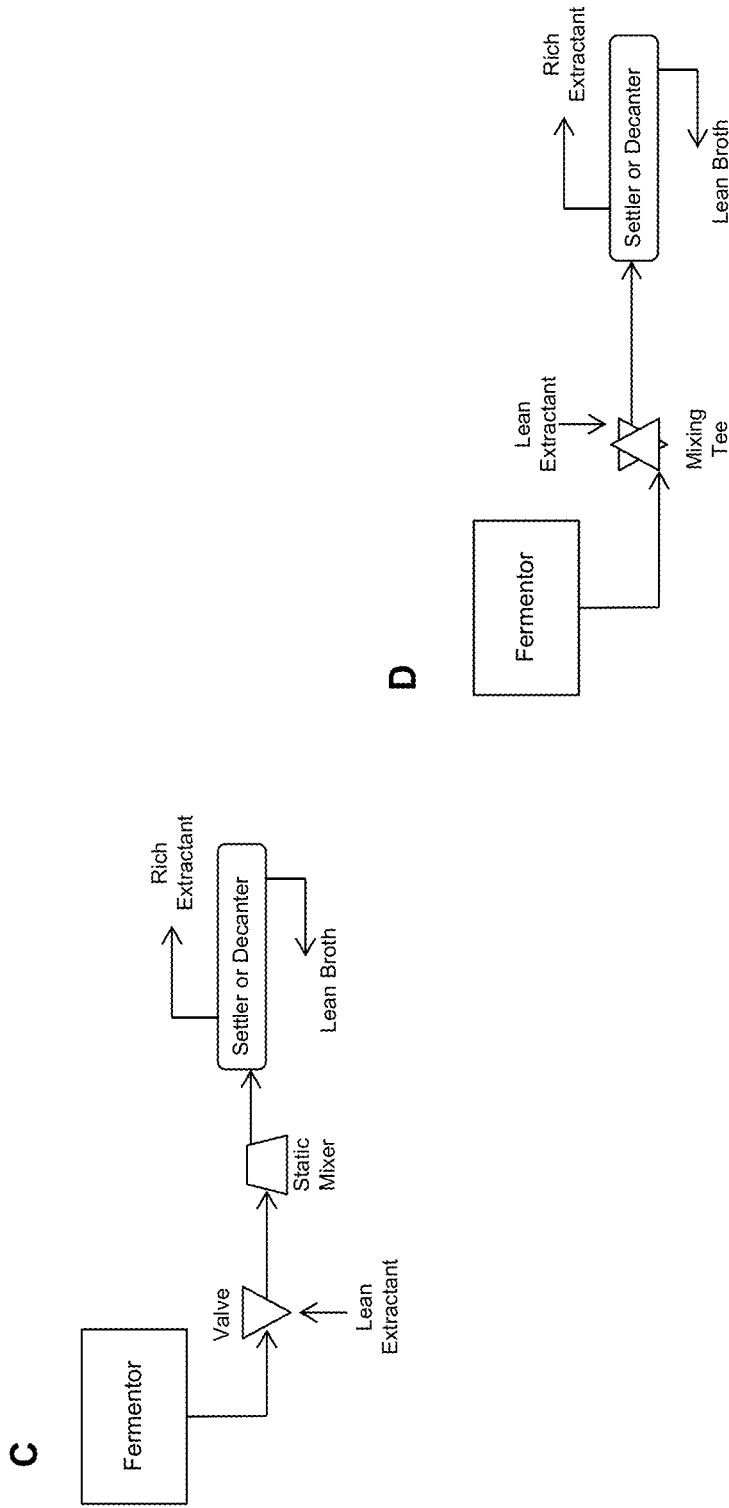
Figures 10E, 10F:
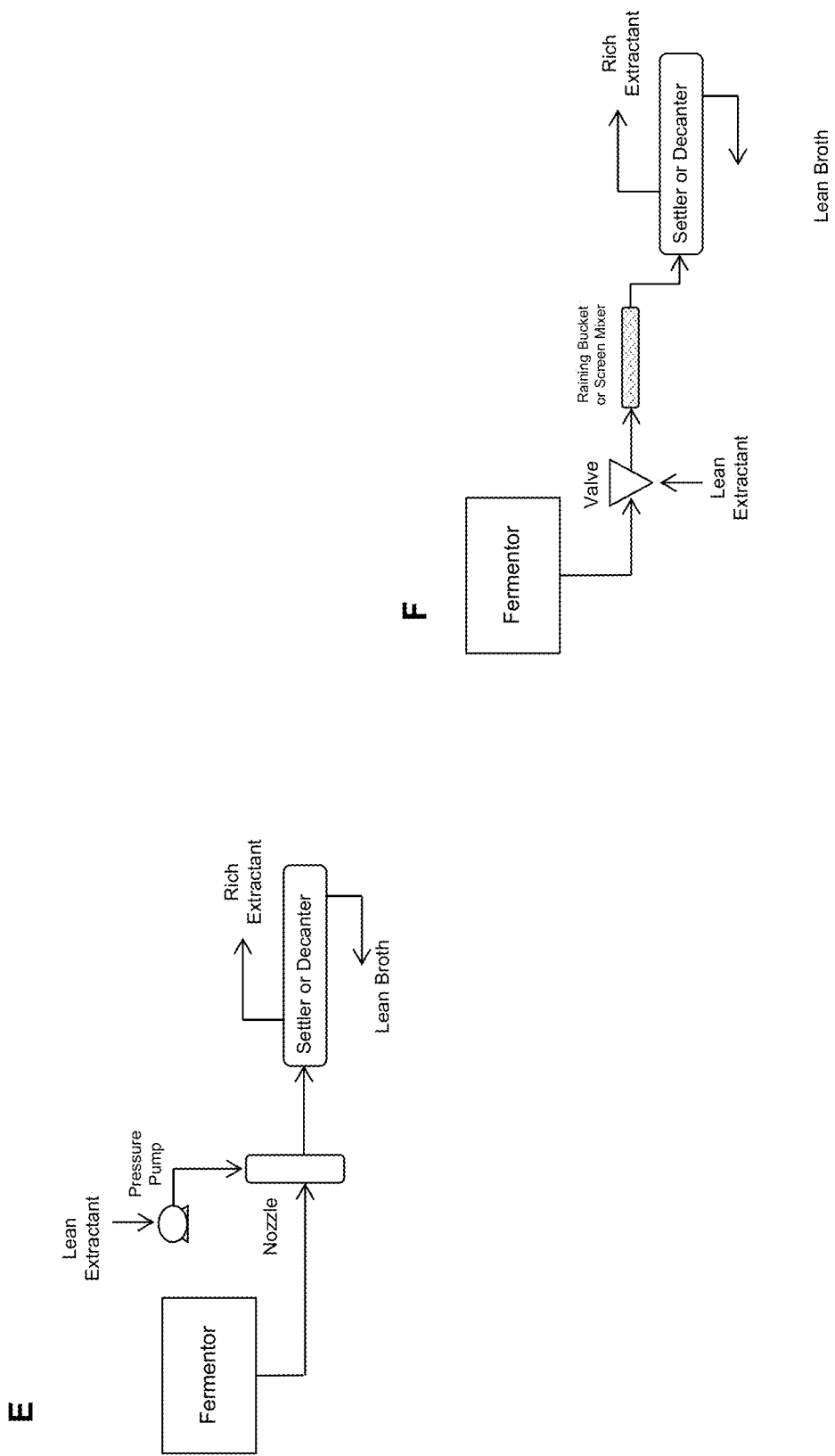
Figure 10G:
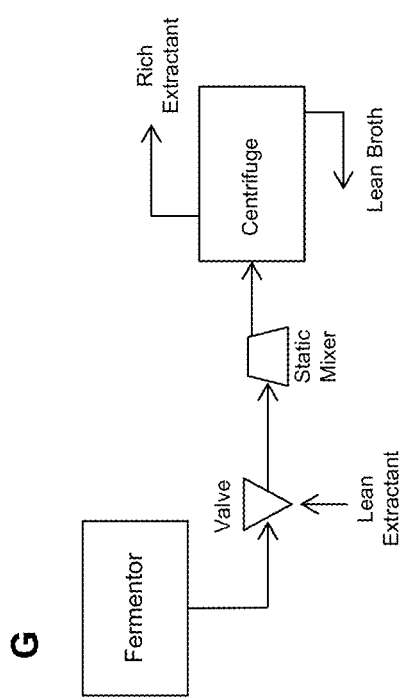
Figure 10H:
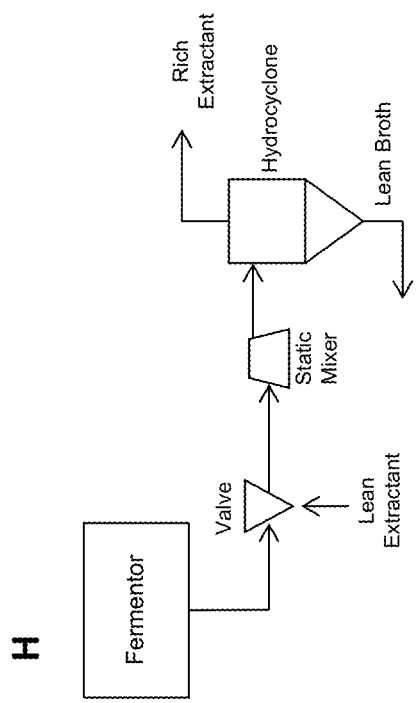

Separation or extraction of product alcohol from extractant may be accomplished using methods known in the art, including but not limited to, siphoning, decantation, centrifugation, gravity settler, membrane-assisted phase splitting, and the like. In some embodiments, extraction may be performed using, for example, mixer-settlers. Mixer-settlers are stagewise extractors and are available with various elements for mixing such as, pumps, agitators, static mixers, mixing tees, impingement devices, circulating screens, or raining buckets. Examples of mixer-settlers are shown in FIGS. 10A-10H. For example, FIG. 10A illustrates a mixer-settler using a pump as the source of mixing. FIG. 10B illustrates a mixer-settler using a mixer as the source of mixing. FIG. 10C illustrates a mixer-settler using a static mixer as the source of mixing. FIG. 10D illustrates a mixer-settler using a mixing tee as the source of mixing. FIG. 10E illustrates a mixer-settler using an impingement mixer as the source of mixing. FIG. 10F illustrates a mixer-settler using a raining bucket or meshed screen as the source of mixing. FIG. 10G illustrates a mixer-settler using a centrifuge as a settler. FIG. 10H illustrates a mixer-settler using a hydrocyclone or vortex separator as a settler. In some embodiments, one or more mixing devices may be used in the processes and systems as described herein.

In some embodiments, mixers may comprise agitators such as, for example, flat blades, pitched blade turbines, or curved propellers. Droplet size produced by agitated mixers may be controlled by agitator design, tank design, agitator speed, and mode of operation. For static mixers, droplet size may be controlled by the diameter of the mixer and flow rate. For example, droplet size may be controlled by varying the flow through the mixer over the course of the fermentation. In some embodiments, gases and mixers may be used for mixing purposes.

Figure 10I:
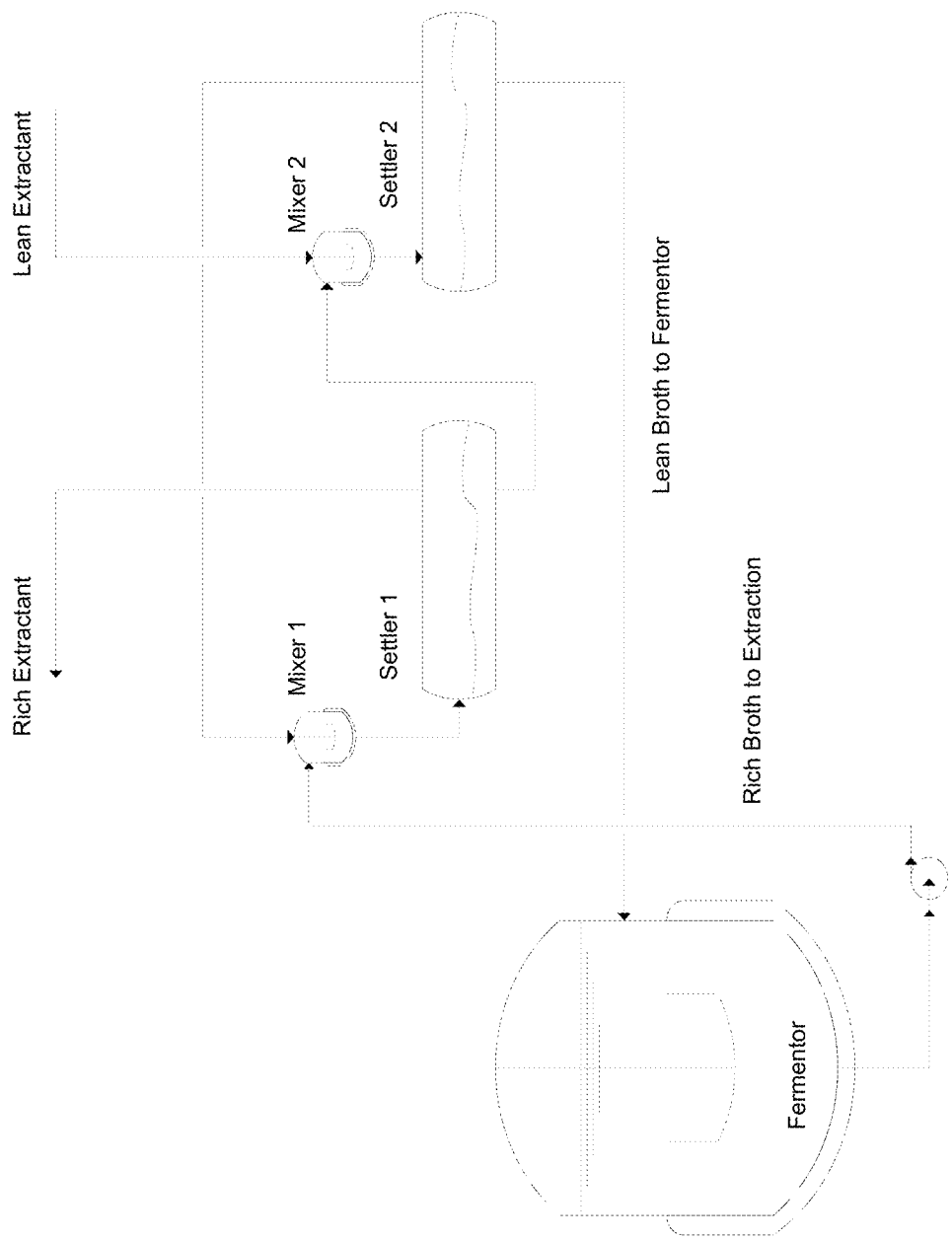
Figure 10J:
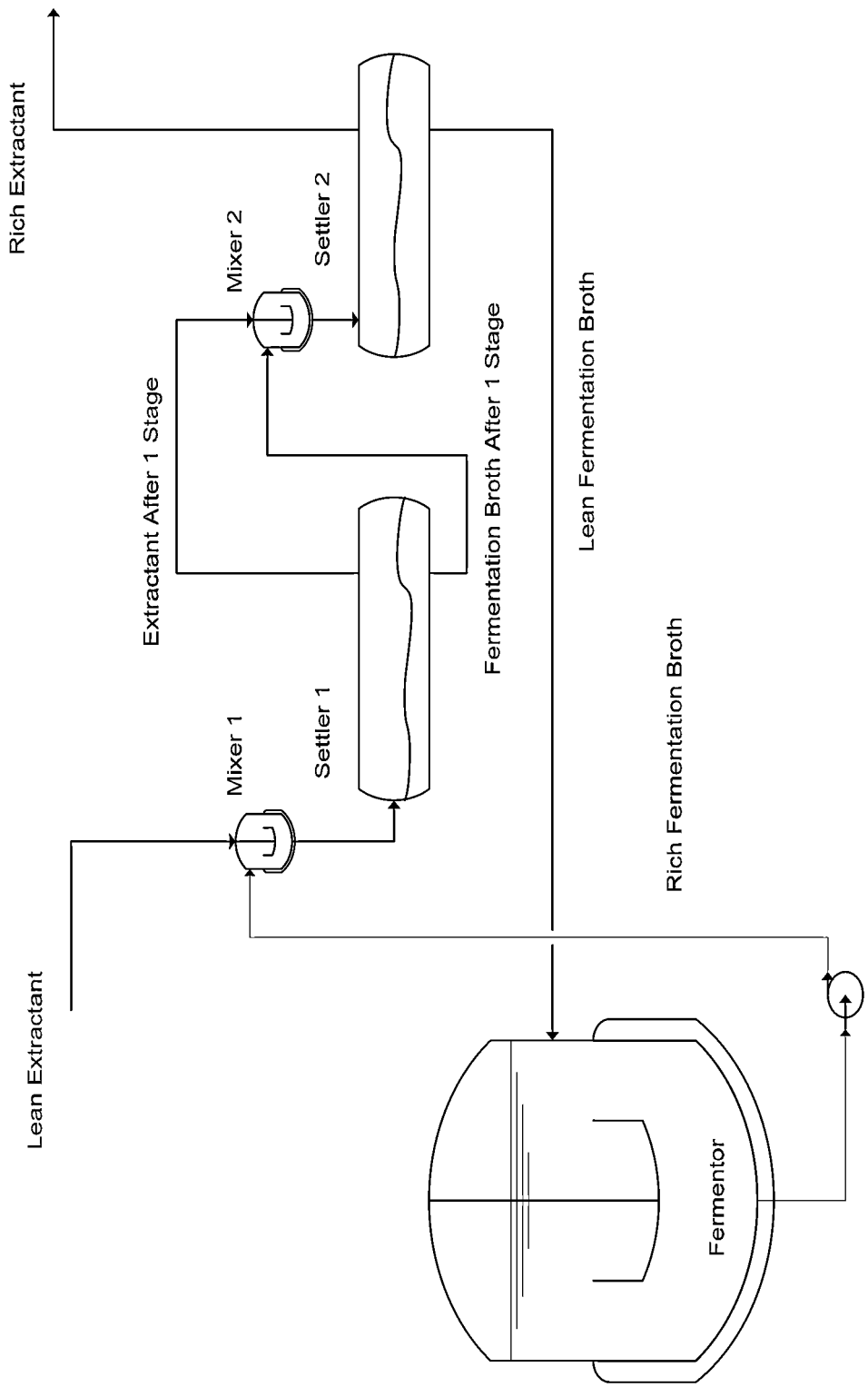

In some embodiments, one or more mixer-settlers may be used in the processes and systems as described herein. In some embodiments, the one or more mixer-settlers may be arranged in series or in countercurrent mode as illustrated in FIGS. 10I and 10J. In some embodiments, mixer-settlers may be stacked in a column arrangement, providing multiple mixing and settling zones. In some embodiments, the settler may comprise hydrophilic or hydrophobic surfaces to promote phase separation.

In another embodiment, column extractors or centrifugal extractors may be used in the processes and systems as described herein. Column extractors are differential extractors providing conditions for mass transfer over their length with a steadily changing concentration profile. The different types of differential extractors may be divided into non-mechanical, pulse-agitated, and rotary-agitated. Centrifugal extractors are a separate class of differential extractors with the Podbielniak® centrifugal contactor being one such type.

Figure 10K:
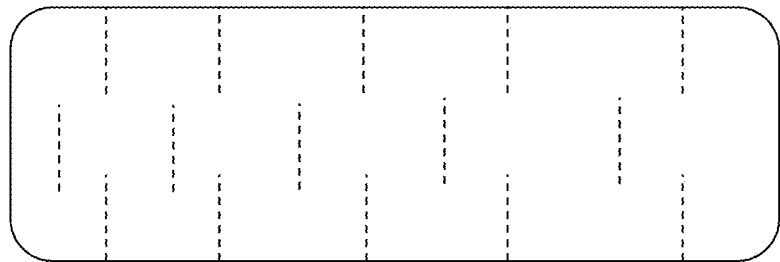
Figure 10K:
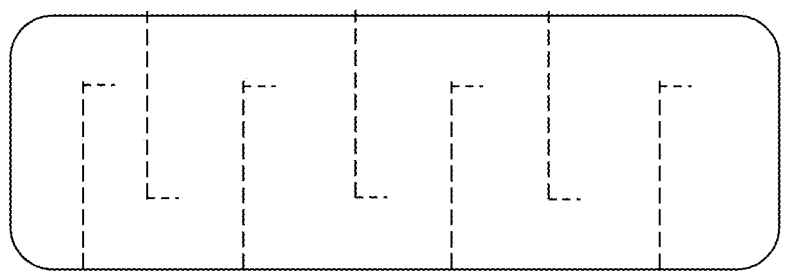
Figure 10K:
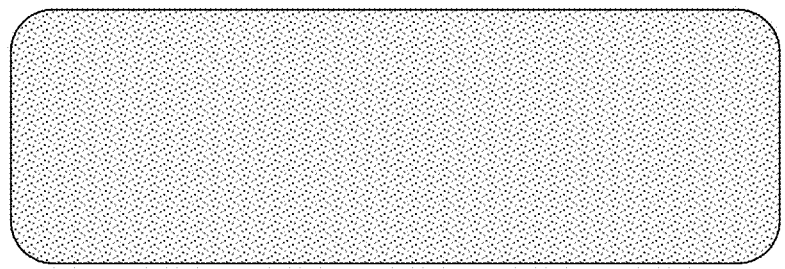

In some embodiments, non-mechanical spray towers may be used in the processes and systems as described herein. One example of a non-mechanical spray tower includes a non-mechanical spray tower without column internals. The number of nozzles and nozzle diameter may be used to determine droplet size. In some embodiments, the spray tower may have internals. In some embodiments, a spray tower may comprise helical piping. Helical piping may allow for droplet rise and additional mixing of fermentation broth and extractant. In some embodiments, non-mechanical extractors such as packed towers, sieve trays, and baffle trays may be used in the processes and systems as described herein. Examples of these extractors are shown in FIG. 10K. In some embodiments, the packing of such extractors may be random or structured.

Figure 10L:
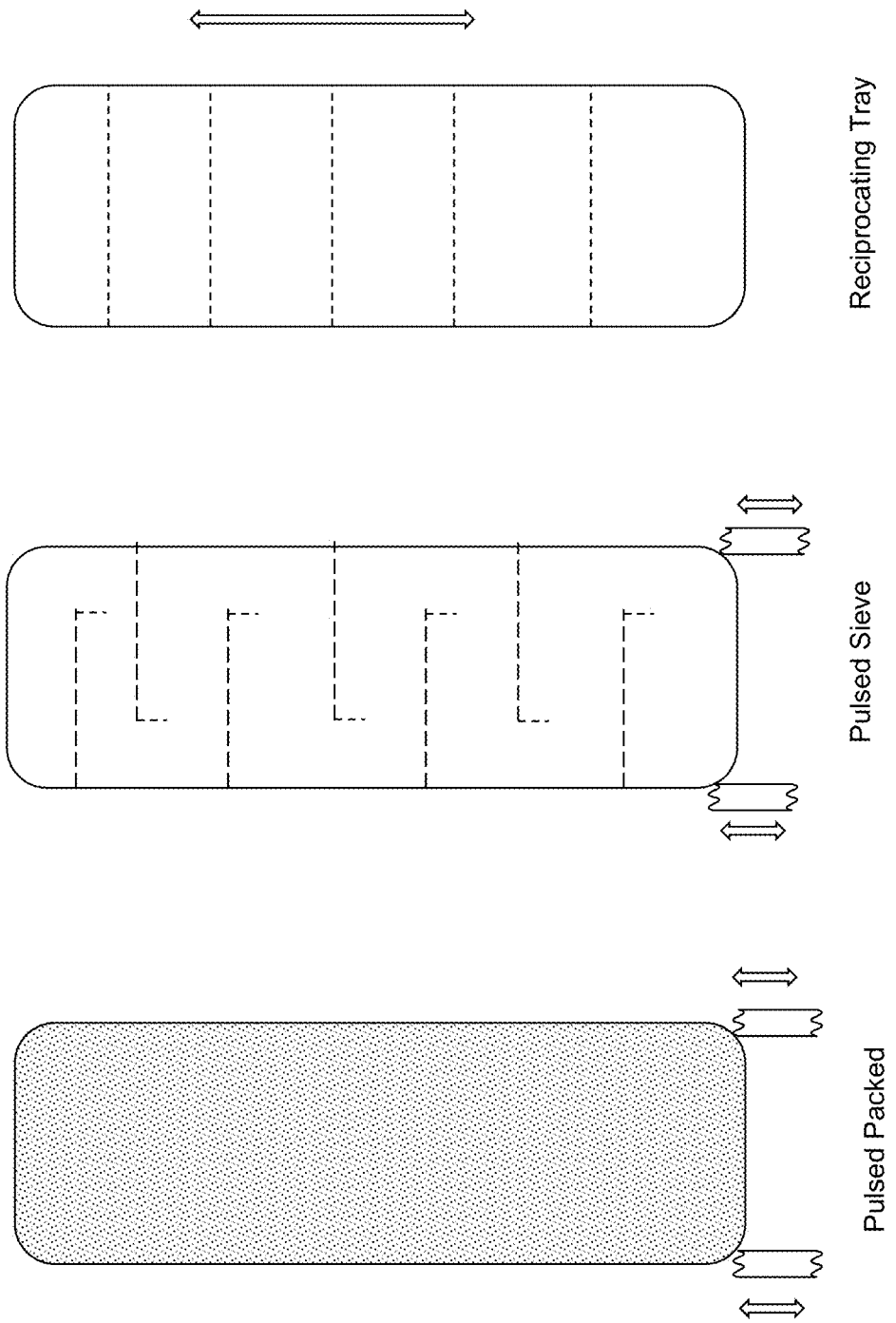
Figure 10M:
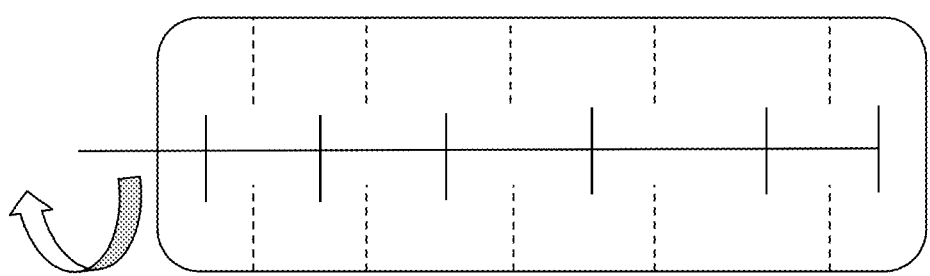

In some embodiments, pulsed-agitated extractors may be used in the processes and systems as described herein. Pulsed-agitated extractors have different designs as well including reciprocating trays or vibrating plates where the trays move in vertical fashion. The entire packed and/or sieve tray column can also vibrate in a vertical fashion to promote smaller dispersed phase droplets and more mass transfer. Examples of these extractors are shown in FIG. 10L. In some embodiments, rotary-agitated or rotating disc contactors may be used in the processes and systems as described herein. Examples of these extractors are shown in FIG. 10M.

In some embodiments, agitated extractors may be used in the processes and systems as described herein. For example, agitated extractors with centrifuges may provide high mass transfer rates and clean phase separation. In some embodiments, agitated columns may be used in the processes and systems as described herein. For example, agitated columns with internals may provide high mass transfer rates.

One aspect of a liquid-liquid extraction process is determining successful operating conditions for the extractor over the course of the constantly changing fermentation. For example, a typical corn-to-product alcohol batch fermentation employs an initial inoculum of microorganism (or cell mass) added to a certain volume of fermentation broth in the fermentor, followed by further filling of the fermentor to a specified volume. The fermentation is permitted to proceed until a pre-determined amount of the fermentable carbon source (e.g., sugar) is consumed. Over the course of batch fermentation, the concentrations of cell mass, reaction intermediates, reaction by-products, and substrate components change with time as do the physical properties of the fermentation broth including viscosity, density, and surface tension. To improve performance parameters of the fermentation, for example, rate, titer, and yield parameters of production and plant economics such as sales volume, return on investment, and profit, the extractor may be operated in a variable way to compensate for the changing fermentation broth. In addition, properties of a dynamic fermentation may impact the size limits of the extractor. Proper integration of the operation of the extractor and the fermentor may be benefit by use of mathematical models of the process (see, e.g., Daugulis and Kollerup, Biotechnology and Bioengineering 27:1345-1356, 1985). Augmenting the mathematical model, for example, setting the key model parameters with experimental data is also valuable. Design parameters for differential extractors to consider for improved rate, titer, and yield of the fermentation process include the maximum total flow to the extractor per cross-sectional area of the extractor column as well as the height of the extractor required to remove enough product alcohol at a given fermentation broth to extractant ratio. It may be necessary to change the maximum flow per unit area and extractor height during a batch fermentation. Another consideration for differential extractors is droplet size of the dispersed phase. Appropriate droplet size may be a balance between small enough to provide adequate mass transfer but large enough to allow for clean phase separation exiting the extractor. In stage-wise extractors, the mixing intensity required for efficient mass transfer, the corresponding time needed to settle, and/or energy needed to separate the phases are additional elements to consider. In either type of extractor, stage-wise or differential, the ratio of fermentation broth to extractant fed to the extractor plays a role in determining the size of the extractor.

In some embodiments, if an extractor of a fixed size were utilized and the maximum allowable flow that avoids flooding to the extractor varied from a low value to a high value (e.g., from ⅓ to ⅔ the maximum for a given extractor design) over the course of the fermentation owing to changes in the physical properties and concentrations of the fermentation broth, then the flows to the extractor may be varied, not exceeding the maximum flow, while still completing the fermentation in a reasonable time. In some embodiments, if an extractor is agitated, the speed of the agitation may be varied over the course of the fermentation to offset changes in the fermentation broth. Droplet size may be measured within the extractor, and the speed to maintain a fixed droplet size may be controlled throughout the fermentation to offset changes in the fermentation broth. The amount of mass transfer occurring at any time point may be assessed by measuring the concentrations of product alcohol in the inlet and outlet streams and adjusting conditions (e.g., flow, flow ratio, agitation) to control the mass transfer over the course of the fermentation.

In some embodiments, multiple extractors of different sizes may be utilized and conditions (e.g., flow, flow ratio, agitation) in each extractor may be adjusted to provide improved control of the fermentation process. In some embodiments, the ratio of fermentation broth to extractant may be modified to improve extraction efficiency, increase the concentration of product alcohol in the extractant (equivalent to increased efficiency), and reduce the required flows through the extractor.

In additional embodiments of the processes and systems described herein, there may be two or more fermentation broth or aqueous streams. An extractant phase that has absorbed product alcohol from a first aqueous stream may be brought into contact with a second aqueous stream that contains less product alcohol than the first aqueous stream or fermentation broth, enabling the transfer of product alcohol from the rich extractant phase to the second aqueous phase. In some embodiments, contacting the rich extractant with a dilute aqueous stream may take place in a multi-stage contacting device or in a static mixer followed by a settler. In some embodiments, contacting the rich extractant with a dilute aqueous stream may take place in the same device where lean extractant is contacted with fermentation broth. An extractor with perforated baffles would allow downflow of both fermentation broth and a dilute aqueous stream in separate compartments while an extractant that is lean in product alcohol may form a continuous phase throughout all compartments. An advantage of this configuration is a reduced amount of extractant would be needed in the production plant if the extractant remains confined to the closed volume of an extractor. Another advantage of this configuration is that the extractant is not subjected to potential degradation during distillation and therefore, may exhibit a longer service life. By transferring product alcohol to a homogeneous aqueous stream, the product alcohol may be conducted to more than one stripping column via partitioning of the dilute aqueous stream, taking into consideration column capacities and heat integration. The need to clean equipment that is exposed to an extractant may be reduced when product alcohol is extracted into an aqueous medium during or immediately after the product alcohol is extracted from fermentation broth.

In some embodiments, product alcohol may be transferred from fermentation broth to a second aqueous stream or an extractant across a barrier that is selective for product alcohol transport. In some embodiments, this barrier may be provided by a membrane material. The membrane material may be either organic or inorganic. Examples of membrane material include polymers and ceramics. In some embodiments, product alcohol may be separated from fermentation broth utilizing a hydrogel. In some embodiments, the hydrogel may comprise functional elements that promote interaction with a product alcohol such as, but not limited to, hydroxyl functionality, hydrocarbon character, network size, and the like. In some embodiments, a hydrogel may comprise a polymeric network structure or polymer formulations. Examples of polymer formulations include, but are not limited to, one or more of the following: acrylic acid, sodium acrylate, hydroxyethyl acrylate, methacrylate, hydroxybutyl acrylate, butylacrylate, vinylated polyethylene oxide, vinylated polypropylene oxide, vinylated polytetratmethylene oxide, acrylates and diacrylates of polyglycols, polyvinyl alcohol and hydrocarbon derivatized polyvinyl alcohol, and styrene and styrene derivatives. In some embodiments, the hydrogel may comprise hydroxyethyl acrylate and methacrylate, hydroxybutyl acrylate and methacrylate, or butylacrylate and methacrylate.

In other embodiments of the processes and systems described herein, fermentation broth may be removed from the bottom of the fermentor at above atmospheric pressure and passed through a first flash tank operating at atmospheric pressure to release dissolved gases such as $CO_2$. This first flash tank may be a degassing cyclone and the vapors from this first flash tank may be combined with vapors from the fermentor and directed to a scrubber. In some embodiments, the fermentation broth from the first flash tank may be passed through a second flash tank operating below atmospheric pressure to release more dissolved gases such as $CO_2$. This second flash tank may be a degassing cyclone and the vapors from this second flash tank may be re-compressed to atmospheric pressure, cooled, and partially condensed prior to being combined with vapors from the fermentor and being directed to a scrubber. The fermentation broth exiting this second flash tank may be pumped to an extraction column operating at above atmospheric pressure so that any remaining or newly formed dissolved gases will not lead to formation of a vapor phase in the extraction column.

In another embodiment of the processes and systems described herein, fermentation broth may be conducted to an extractor and contacted with extractant generating an aqueous stream and organic stream comprising extractant and product alcohol. This organic stream may be conducted to a flash tank (e.g., vacuum flash) for separation of product alcohol from extractant. In some embodiments, the extractant stream from the flash tank may be recycled to the extractor and/or the fermentor. In some embodiments, the organic stream may be conducted to a second extractor prior to the flash tank. This second extractor may be used to remove, for example, any residual water in the organic stream. The extractors may be siphons, decanters, centrifuges, gravity settlers, mixer-settlers, or combinations thereof. In some embodiments, the extractant may be an oil such as, but are not limited to, tallow, corn, canola, capric/caprylic triglycerides, castor, coconut, cottonseed, fish, jojoba, lard, linseed, neetsfoot, oiticica, palm, peanut, rapeseed, rice, safflower, soya, sunflower, tung, jatropha, and vegetable oil blends, or fatty acids derived therefrom.

In some embodiments of the processes and systems described herein, automatic self-cleaning filtration may be used in these processes and systems. Fermentation broth may be removed from a fermentor and may be cooled using a cooler (e.g., an existing cooler in a fermentation production facility) before entering an automatic self-cleaning filter. Some particulates may be retained on the screen medium of the filter as clarified mash passes through the filter. Additional filters may be simultaneously undergoing backflush where a portion of the clarified mash flows back through the screen carrying the particulates with it, discharging a concentrated solids stream. In some embodiments, a portion of the clarified mash may enter the top of an extractor while an extractant is fed in the bottom of the extractor. The clarified mash and extractant may be brought into contact either passively by density differences or with the aid of mechanical motion (e.g., a Karr® column) by means commonly used in the art. In some embodiments, an organic liquid stream of extractant containing product alcohol emerges from the top of the extractor and an aqueous liquid stream of fermentation broth that has been at least partially depleted of product alcohol relative to clarified mash emerges from the bottom of the extractor. The aqueous liquid stream and concentrated solids stream may be combined and returned to the fermentor. The extractant stream rich in product alcohol may be heated in a heat exchanger that transfers heat from an extractant stream that is lean in product alcohol and that originates from the bottom of the extractor. After releasing some heat, the lean extractant may be further cooled with water in a heat exchanger to reach a temperature that is suitable for fermentation. Circulation of fermentation broth may include a pathway through a heat transfer device and mass transfer device enabling the removal of heat and product alcohol per pass through an external cooling loop. Moreover, in some embodiments, the rate of heat and product alcohol removal may be balanced with the rate of heat and product alcohol production during fermentation by adjusting the circulation flow through the external cooling loop, adjusting the flow of cooling fluid in a heat exchanger, and/or adjusting the flow of extractant.

In some embodiments of the processes and systems described herein, phase separation of extractant from fermentation broth may be enhanced by modifying the temperature and/or pH of the process. For example, the process may be operated at temperatures and/or pH that are different than the temperature and/or pH of the fermentor. In some embodiments, the process may be operated at a reduced pH as compared to the fermentor. In some embodiments, the process may be operated at a higher temperature as compared to the fermentor. In some embodiments, the process may be operated at a reduced pH and a higher temperature as compared to the fermentor. A higher temperature can increase the kinetics of mass transfer of product alcohol between the aqueous and organic phases and may increase the kinetics of coalescence for extractant droplets dispersed in the aqueous phase and for aqueous droplets dispersed in the organic phase. In some embodiments, the temperature inside an extractor containing fermentation broth and extractant may be increased by heating the fermentation broth and/or extractant entering the extractor. The fermentation broth may be heated either directly with injection of water vapor or steam or indirectly via a heat exchanger. In some embodiments, the extractant feeding the extractor may originate from distillation where its temperature may already be elevated. In some embodiments, the extractant may be cooled to a temperature higher than the fermentation temperature.

In some embodiments, a reduced pH can minimize the solubility and dispersibility of extractant in the aqueous broth phase. In some embodiments, the extractant may be a fatty acid with a known associated pKa value. In some embodiments, the pH of the fermentation broth may be reduced to below the pKa of the extractant such that the carboxylic acid groups of the fatty acid are substantially protonated. In some embodiments, the pH may be reduced by introducing $CO_2$ gas into the fermentation broth or by injecting a small amount of liquid acids such as sulfuric acid or any other organic or inorganic acid into the fermentation broth. In some embodiments, the pH of the fermentation broth after separating from the extractant may be adjusted to the pH of fermentation.

In some embodiments where the extractant phase is the continuous phase, the aqueous phase may be distributed or dispersed in the extractant phase. For example, fermentation broth comprising product alcohol may be conducted to an extractor (e.g., external extractor) via a distributor or dispersal device. In some embodiments, the distributor or dispersal device may be a nozzle such as a spray nozzle. In some embodiments, the distributor or dispersal device may be a spray tower. As an example, droplets of fermentation broth may be passed through extractant, and product alcohol is transferred to the extractant. Droplets of fermentation broth coalesce at the bottom of the extractor and may be returned to the fermentor. Extractant comprising product alcohol may be further processed for recovery of product alcohol as described herein. In addition, at the completion of fermentation, residual product alcohol in the fermentor may also be further processed for recovery of product alcohol. In some embodiments, the extractant phase may be countercurrent.

In some embodiments where the extractant phase is the continuous phase and the aqueous phase is the dispersed phase, mass transfer rates may be improved by using electrostatic spraying to disperse the aqueous phase in the extractant phase. In some embodiments, one or more spray nozzles may be utilized for electrostatic spraying. In some embodiments, the one or more spray nozzles may be an anode. In some embodiments, the one or more spray nozzles may be a cathode.

In some embodiments, extractor effluent may be used to enhance phase separation. For example, a portion of rich extractant (i.e., extractant rich in product alcohol) from the top of the extractor may be returned to the top of the extractor as reflux, and the remaining rich extractant may be further processed for recovery of product alcohol. Also, a portion of lean fermentation broth from the bottom of the extractor may be returned to the bottom of the extractor as reflux and the remaining lean fermentation broth may be returned to the fermentor. In another embodiment, rich extractant may exit the top of the extractor into a decanter and separated into a heavy phase and light phase. The heavy phase from the decanter may be conducted to the top of the extractor to enhance phase separation. The light phase from the decanter may be may be further processed for recovery of product alcohol.

Figure 11A:
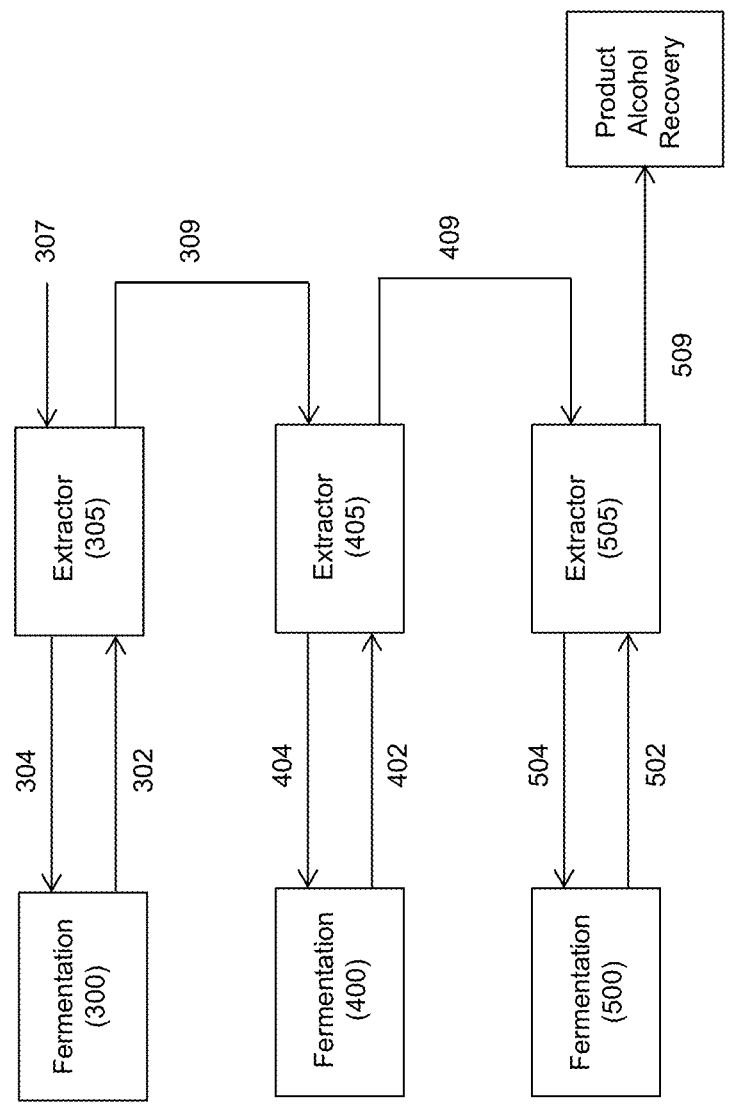
FIGS. 11A and 11B schematically illustrate multiple pass extractant flow systems.

In some embodiments of the processes and systems described herein, multiple pass extractant flow may be utilized for product alcohol recovery. For example, multiple fermentors and extractors may be used, where the fermentation cycle of each fermentor is at a different timepoint. Referring to FIG. 11A as an example, fermentor 300 is at an earlier timepoint as compared to fermentor 400 which is at an earlier timepoint as compared to fermentor 500. Fermentation broth comprising product alcohol 302 from fermentor 300 may be contacted with extractant 307 in extractor 305, and product alcohol may be transferred to extractant generating product alcohol-rich extractant 309. Product alcohol-rich extractant 309 from extractor 305 may be conducted to extractor 405. Fermentation broth comprising product alcohol 402 from fermentor 400 may be conducted to extractor 405, producing product alcohol-rich extractant 409. Product alcohol-rich extractant 409 may be conducted to extractor 505. Fermentation broth comprising product alcohol 502 from fermentor 500 may be conducted to extractor 505. Product alcohol-rich extractant 509 from extractor 505 may be processed for recovery of product alcohol. Product alcohol-lean fermentation broth (304, 404, 504) may be returned to fermentors 300, 400, and 500, respectively. The number of fermentors and extractors may vary depending on the operational facility. A benefit of this process is, for example, the reduction in total extractant processing and the size of the extractor.

Figure 11B:
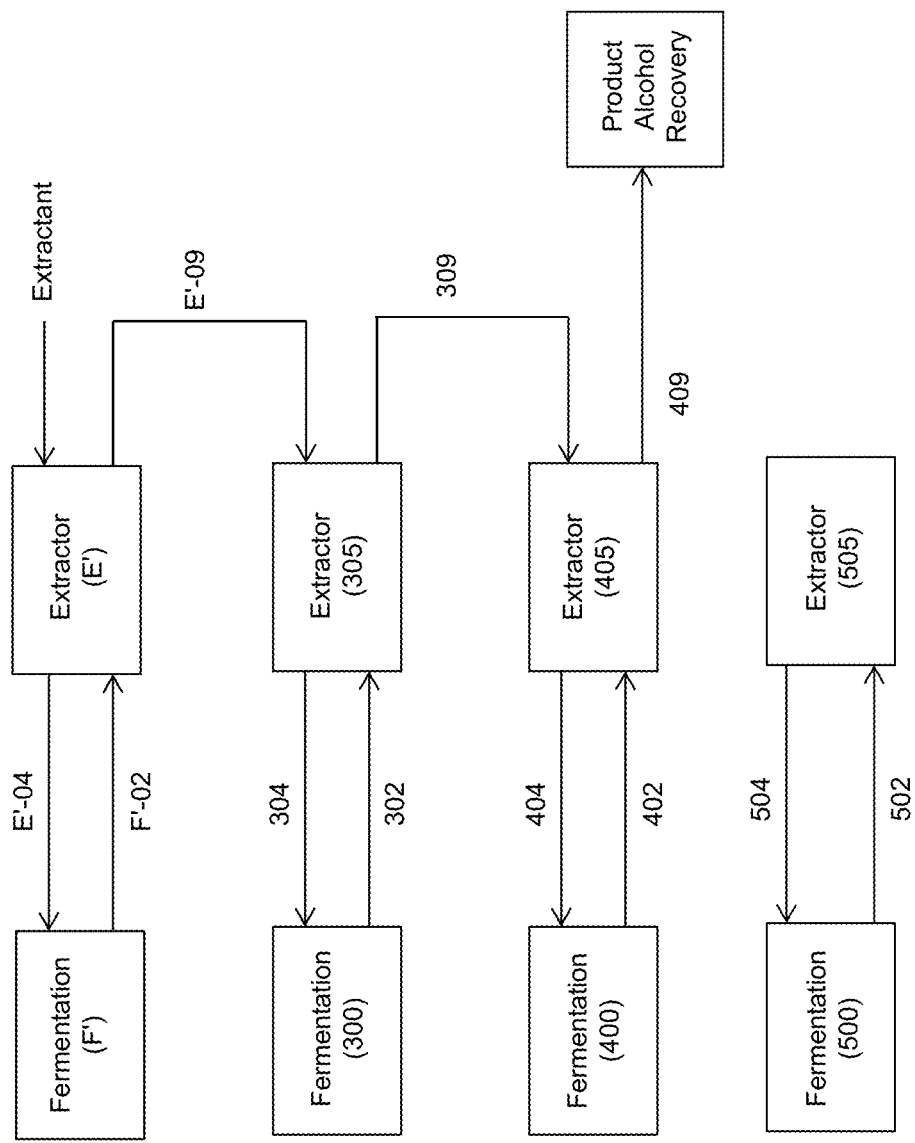

In another embodiment of this example, there may be an additional fermentor F' and an additional extractor E' (FIG. 11B). In this embodiment, when fermentor 500 (which is at a later timepoint compared to fermentors 300 and 400) has completed fermentation, fermentor 500 may be taken off-line, and in some embodiments, fermentor 500 may undergo sanitation and/or sterilization procedures such as clean-in-place (CIP) and sterilization-in-place (SIP) procedures. When fermentor 500 is taken off-line, fermentor F' may be brought on-line. In this embodiment, fermentor F' is at an earlier timepoint as compared to fermentor 300 which is at an earlier timepoint as compared to fermentor 400. Similar to the description for FIG. 11A, fermentation broth comprising product alcohol F'-02 from fermentor F' may be contacted with extractant in extractor E', and product alcohol may be transferred to extractant generating product alcohol-rich extractant E'-09. Product alcohol-rich extractant E'-09 from extractor E' may be conducted to extractor 305. Fermentation broth comprising product alcohol 302 from fermentor 300 may be conducted to extractor 305, producing product alcohol-rich extractant 309. Product alcohol-rich extractant 309 may be conducted to extractor 405. Fermentation broth comprising product alcohol 402 from fermentor 400 may be conducted to extractor 405. Product alcohol-rich extractant 409 from extractor 405 may be processed for recovery of product alcohol. Product alcohol-lean fermentation broth (F'-04, 304, 404) may be returned to fermentors F', 300, and 400, respectively. In some embodiments, this process may be repeated for multiple cycles, for example, at least one, at least two, at least three, at least four, at least five, at least ten, at least fifteen, at least twenty, or more cycles. In some embodiments, the process of taking fermentors off-line and putting additional fermentors on-line may be manual or automated. A benefit of this process is reduced extractor flow to product recovery (e.g., distillation).

In some embodiments, an extractant may reduce the flashpoint (i.e., flammability) of the product alcohol. Flashpoint refers to the lowest temperature at which flame propagation occurs across the surface of a liquid. Flashpoint may be measured, for example, using the ASTM D93-02 method ("Standard Test Methods for Flash Point by Pensky-Martens Closed Tester"). Reduction of the flashpoint of the product alcohol can improve the safety conditions of an alcohol production plant, for example, by minimizing the fire hazard of the potentially flammable product alcohol. By improving safety conditions, the risk of injury is minimized as well as the risk of property damage and revenue loss. In some embodiments where inactivation of the microorganism is required, an extractant may improve the inactivation of the microorganism.

In some embodiments, the processes described herein may be integrated extraction fermentation processes using on-line, in-line, at-line, and/or real-time measurements, for example, of concentrations and other physical properties of the fermentation broth and extractant. These measurements may be used, for example, in feed-back loops to adjust and control the conditions of the fermentation and/or the conditions of the extractor. In some embodiments, the concentration of product alcohol and/or other metabolites and substrates in the fermentation broth may be measured using any suitable measurement device for on-line, in-line, at-line, and/or real-time measurements. In some embodiments, the measurement device may be one or more of the following: Fourier transform infrared spectroscope (FTIR), near-infrared spectroscope (NIR), Raman spectroscope, high pressure liquid chromatography (HPLC), viscometer, densitometer, tensiometer, droplet size analyzer, pH meter, dissolved oxygen (DO) probe, and the like. In some embodiments, off-gas venting from the fermentor may be analyzed, for example, by an in-line mass spectrometer. Measuring off-gas venting from the fermentor may be used as a means to identify species present in the fermentation reaction. The concentration of product alcohol and other metabolites and substrates dissolved in the extractant may also be measured using the techniques and devices described herein.

In some embodiments, measured inputs may be sent to a controller and/or control system, and conditions within the fermentor (temperature, pH, nutrients, enzyme and/or substrate concentration) may be varied to maintain a concentration, concentration profile, and/or conditions within the extractor (fermentation broth flow, fermentation broth to extractant flow, agitation rate, droplet size, temperature, pH, DO content). Similarly, conditions within the extractor may be varied to maintain a concentration and/or concentration profile within the fermentor. By utilizing such a control system, process parameters may be maintained in such a way to improve overall plant productivity and economic goals. In some embodiments, real-time control of fermentation may be achieved by variation of concentrations of components (e.g., sugars, enzymes, nutrients, and the like) in the fermentor, variation of conditions within the extractor, or both.

As an example of an isobutanol fermentation process, the efficiency of isobutanol extraction in a Karr® column is continuously changing as the concentrations of starch, sugars and isobutanol change in the fermentation broth. In order to maximize the efficiency of the extractor, it may be advantageous to alter the rate at which isobutanol is removed from the fermentation broth to match the production profile of the isobutanol fermentation. Isobutanol concentrations in the extractant may be maximized resulting in more energy efficient distillation operations.

As part of a process control strategy, real-time measurements of isobutanol in the fermentation broth (e.g., column feed) may be coupled with real-time measurements of isobutanol in the extractant and in the lean fermentation broth. These measurements may be used to adjust the fermentation broth to extractant ratio (flows) to the extractor. The flexibility to match the rate of isobutanol extraction with the rate of isobutanol generation may allow the extractor to be operated efficiently throughout the extraction. In addition, by maintaining a high concentration of isobutanol in the extractant, the volumetric flow rate to the distillation columns can be minimized, resulting in an energy savings for distillation operations. Phase separation may also be monitored using real-time measurements, for example, by monitoring the rate of phase separation, extractant droplet size, and/or composition of fermentation broth. In some embodiments, phase separation may be monitored by conductivity measurements, dielectric measurements, viscoelastic measurements, or ultrasonic measurements. In some embodiments, an automated phase separation detection system may be used to monitor phase separation. This automated system may be used to adjust the flow rates of fermentation broth and extractant to and from the extractor and/or adjust the droplet size of extractant, for example, after mixing of fermentation broth and extractant. By using these real-time monitoring systems, clean phase separation of aqueous and organic phases may be accomplished.

As another example of process control strategy, droplet size may be measured using particle size analysis such as a process particle analyzer (J M Canty, Inc., Buffalo, N.Y.), focused beam reflectance measurement (FBRM®), or particle vision and measurement (PVM®) technologies (Mettler-Toledo, LLC, Columbus Ohio). In some embodiments, these measurements may be real-time in situ particle system characterizations. By monitoring droplet size in real time, changes in droplet shape and dimensions may be detected and process steps may be adjusted to modify droplet size and enhance the rate of mass transfer. For example, droplet size may be used to monitor the amount of extractant in fermentation broth. Following phase separation, some extractant may be present in the fermentation broth, and in some embodiments where the fermentation broth is recycled to the fermentor, monitoring droplet size would provide a means to minimize the amount of extractant in the fermentation broth returning to the fermentor. If the amount of extractant in the fermentation broth is too high, then phase separation may be improved, for example, by adjusting the droplet size of extractant in the extractor and/or adjusting the flow rates of fermentation broth and extractant to the extractor. These adjustments in the process steps can minimize the amount of extractant in the fermentation broth, as well as minimize the amount of extractant in thin stillage and DDGS.

In one embodiment of this control strategy, isobutanol in the fermentation broth would not exceed a concentration or setpoint at which the concentration of isobutanol becomes deleterious to the microorganism. The isobutanol fermentation broth setpoint may be adjusted higher or lower as the fermentation progresses based upon the trajectory of the fermentation. For example, continuous comparison of the concentration of isobutanol in the fermentation broth to a setpoint concentration of isobutanol can be utilized to modify fermentation broth to extractant ratios or flow rates of fermentation broth and extractant to an extractor. To monitor isobutanol concentrations in the fermentation broth, in situ measurements of the fermentation broth may be performed using Fourier transform infrared spectroscopy (FTIR), near infrared spectroscopy (NIR), and/or Raman spectroscopy. In addition, measurements of the fermentor headspace may be performed using FTIR, Raman spectroscopy, and/or mass spectrometry.

In some embodiments, efficient extractor operation may occur close to the point of extractor flooding. The use of real-time process control that utilizes concentration data from inlet and outlet streams may allow the extractor to be operated reliably near the point of flooding. In some embodiments, real-time extractant monitoring may be used to detect the partitioning of by-products from the fermentation broth or contaminants into the extractant. By-products such as alcohols, lipids, oils, and other fermentation components may reduce the extraction efficiency of the extractant. Numerous process monitoring techniques may be applied to this measurement including, but are not limited to, Fourier transform infrared spectroscopy (FTIR), near infrared spectroscopy (NIR), high performance liquid chromatography (HPLC), and nuclear magnetic resonance (NMR). The analytical technique selected to monitor the extractant for the presence of by-products or contamination may be a different technique than employed for real-time alcohol determination. Real-time data may be used to trigger the remediation of contaminated extractant or the purge of contaminated extractant from the process. These techniques as well as gas chromatography (GC) and supercritical fluid chromatography (SFC) may also be utilized to monitor thermal breakdown of extractant.

Figure 12:
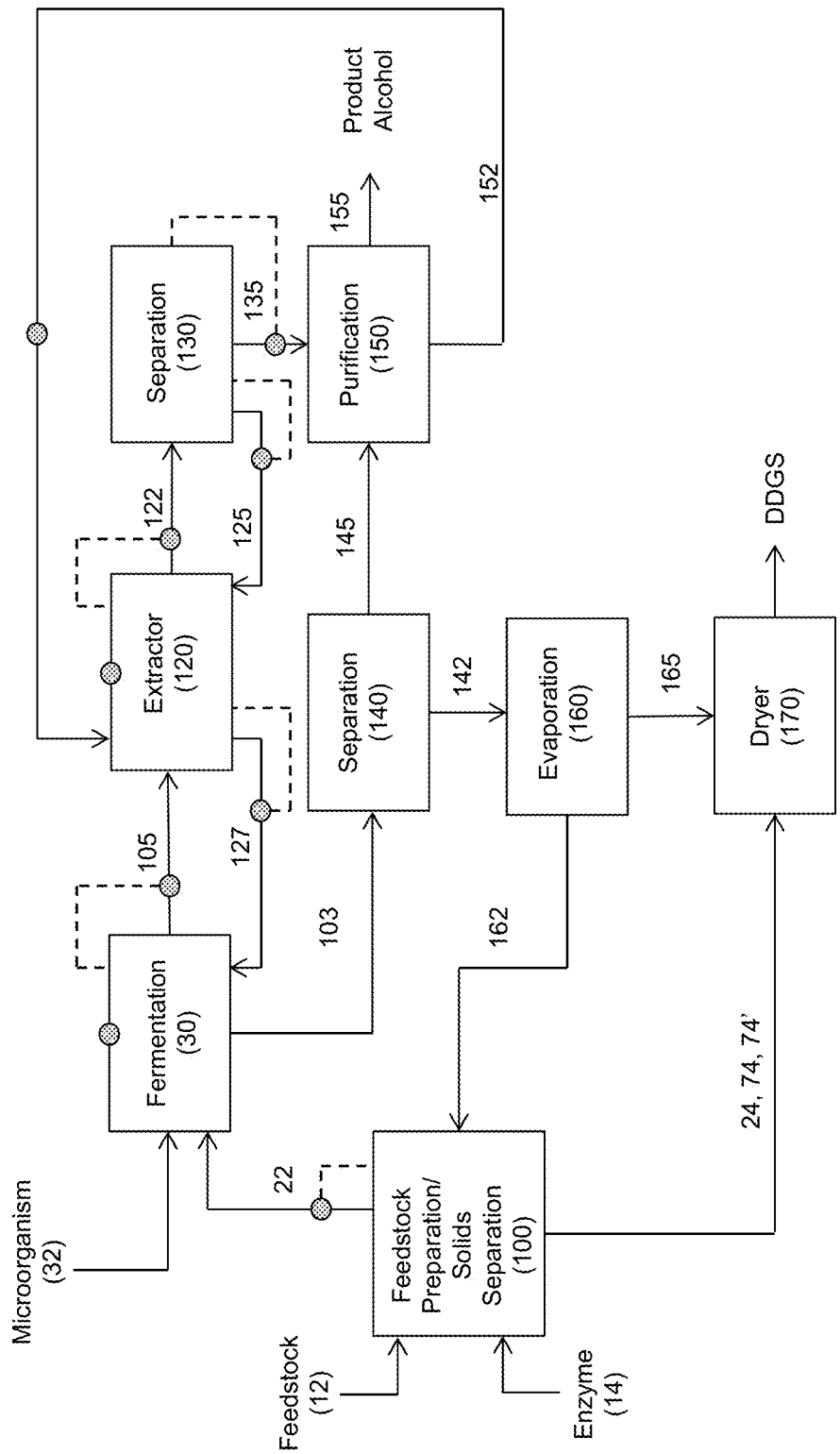
FIG. 12 schematically illustrates an exemplary fermentation process of the present invention utilizing on-line, in-line, at-line, and/or real-time measurements for monitoring fermentation processes.

Referring to FIG. 12, the systems and processes of the present invention may include means for on-line, in-line, at-line, and/or real-time measurements (circles represent measurement devices and dotted lines represent feedback loops). FIG. 12 is similar to FIG. 9, except for the addition of measurement devices for on-line, in-line, at-line, and/or real-time measurements, and therefore will not be described in detail again.

As an example, on-line measurements of aqueous stream 22 may be utilized to monitor the concentration of fermentable carbon sources (e.g., polysaccharides), oil, and/or dissolved oxygen. For example, FTIR may be used to monitor the dispersion of oil in aqueous stream 22, and process imaging may be used to monitor the concentration and size of oil droplets in the aqueous stream 22. In some embodiments, on-line measurements of fermentation 30 may be utilized to monitor removal rates of product alcohol. Measurements of fermentable carbon sources, dissolved oxygen, product alcohol, and by-products may be used to adjust the removal rate of product alcohol in order to maintain a concentration of product alcohol in fermentation 30 that is tolerable to microorganisms. By maintaining a setpoint product alcohol concentration, product inhibition and toxicity may be minimized.

On-line measurements of stream 105 and stream 122 may be used to operate process control feedback loops. For example, the concentration of product alcohol in stream 105 may be used to control the flow rate of this stream to extractor 120; and the concentration of product alcohol in stream 122 may be used to control the flow rate of this stream to separation 130 and to set the ratio of fermentation broth to extractant. In addition, on-line measurements of stream 105 and stream 122 may also be utilized to establish real-time product alcohol mass balance. Process control feedback loops for extractor 120 and separation 130 may be used to monitor the quality of phase separation of extractant and fermentation broth. For example, on-line measurement devices may be used to detect the balance of the separation of extractant and fermentation broth, and feed rates of extractant and fermentation broth may be adjusted accordingly to improve phase separation. On-line devices such as optical devices may be used to detect the presence of a rag layer (e.g., mixture of oil, aqueous solution, and solids) in, for example, extractor 120, and the ratio of fermentation broth to extractant may be adjusted to minimize the formation of a rag layer. On-line measurements of stream 135 from separation 130 may be used to monitor the presence of fermentation broth in this stream, and the presence of fermentation broth in stream 135 may indicate poor phase separation. If the concentration of fermentation broth in stream 135 exceeds a certain setpoint, process changes such as flow rate adjustments or adjustments to the ratio of fermentation broth to extractant may be implemented to improve phase separation. In addition, the concentration of product alcohol in stream 135 may be used as a process control feedback loop to ensure efficient operation of separation 130.

As another example, on-line measurements of the concentration of product alcohol in stream 127 may be used to monitor extraction efficiency and to maintain a concentration of product alcohol in fermentation 30 that is tolerable to microorganisms. In addition, stream 127 may be monitored for the presence of extractant as a means to minimize the amount of extractant returning to fermentation 30. For example, spectroscopic and process imaging techniques may be used to monitor the presence of extractant in stream 127. Furthermore, a certain concentration of extractant in stream 127 may be maintained to improve extraction efficiency and phase separation.

In another embodiment, stream 135 from separation 130 may be conducted to purification 150 for further processing including recovery of product alcohol and extractant 152. Extractant 152 may be conducted to extractor 120. On-line measurements may be used to monitor stream 152 for contaminants and degradation products. By monitoring stream 152, the potential for contamination of extractor 120 and fermentation 30 is minimized. If there is an increase in contaminants in stream 152, this stream may be further processed to remove these contaminants, for example, by absorption or chemical reaction.

Figure 13:
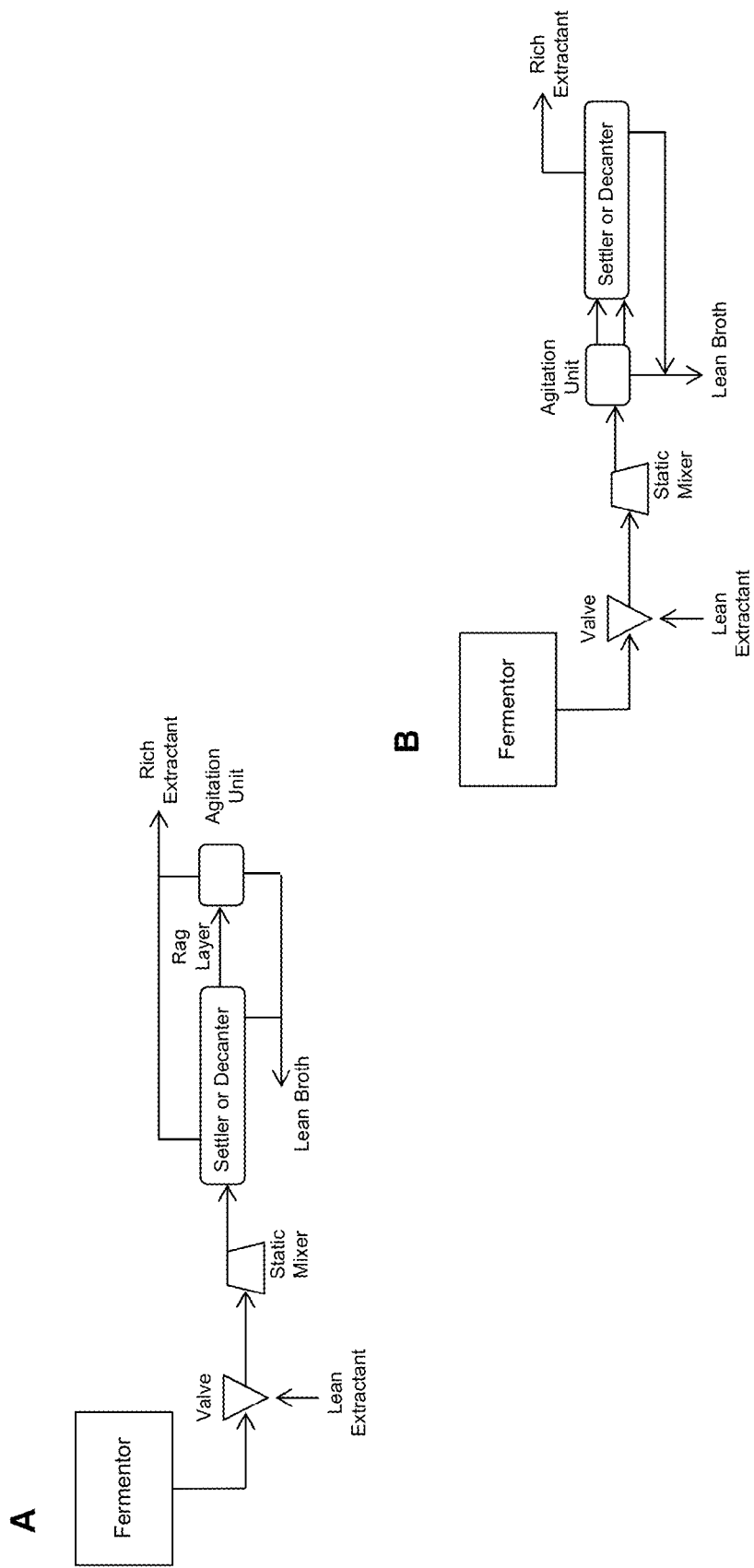
FIGS. 13A and 13B schematically illustrates exemplary processes of the present invention for mitigating formation of a rag layer.

During the extraction process, a rag layer may form at the interface of the aqueous and organic phases, and the rag layer, composed of solids and extractant (e.g., droplets of extractant), can accumulate and possibly interfere with phase separation. To mitigate the formation of rag layer, agitation of the aqueous and organic phases may be employed. For example, an impeller may be used to disperse the rag layer at the aqueous-organic interface. Also, fluid flow such as a recirculating loop or vibrations/oscillations may be used to disrupt rag formation. FIGS. 13A and 13B illustrate exemplary processes for mitigating formation of a rag layer. FIG. 13A exemplifies the use of a static mixer in combination with an agitation unit downstream of the settler or decanter for the treatment of a rag layer, and FIG. 13B exemplifies the use of a static mixer in combination with an agitation unit upstream of the settler or decanter for the treatment of a rag layer. In some embodiments, other devices such as coalescers or sonic agitation may be used to disperse the rag layer. In some embodiments, these devices may be integrated into the settler or decanter.

The processes and systems described herein may be conducted using batch, fed-batch, or continuous fermentation. Batch fermentation is a closed system in which the composition of the fermentation broth is established at the beginning of the fermentation and is not subjected to artificial alterations during the fermentation process. In some embodiments of batch fermentation, extractant may be added to the fermentor. In some embodiments, the volume of extractant may be about 20% to about 60% of the fermentor working volume.

Fed-batch fermentation is a variation of batch fermentation, in which substrates (e.g., fermentable sugars) are added in increments during the fermentation process. Fed-batch systems are useful when catabolite repression may inhibit the metabolism of the microorganism and where it is desirable to have limited amounts of substrate in the media. In some embodiments, concentrations of substrate and/or nutrients may be monitored during fermentation. In some embodiments, parameters such as pH, dissolved oxygen, and gases (e.g., $CO_2$) may be monitored during fermentation. From these measurements, the rate or amount of substrate and/or nutrients addition may be determined. In some embodiments, as the level or amount of fermentation broth decreases during fermentation, additional mash may be added to the fermentor to maintain the level or amount of fermentation broth, for example, maintain the level or amount of fermentation broth at the initiation of the fermentation process. In some embodiments of fed-batch fermentation, extractant may be added to the fermentor.

Continuous fermentation is an open system where fermentation broth is added continuously to a fermentor and an amount of fermentation broth is removed for further processing (e.g., recovery of product alcohol). In some embodiments, addition and removal of fermentation broth may be simultaneous. In some embodiments, equal amounts of fermentation broth may be added and removed from the fermentor. In some embodiments of continuous fermentation, extractant may be added to the fermentor. In some embodiments, the volume of extractant may be about 3% to about 50% of the fermentor working volume. In some embodiments, the volume of extractant may be about 3% to about 20% of the fermentor working volume. In some embodiments, the volume of extractant may be about 3% to about 10% of the fermentor working volume.

In some embodiments of the processes and systems described herein, gas stripping may be used to remove product alcohol from the fermentation broth. Gas stripping may be performed by providing one or more gases such as air, nitrogen, or carbon dioxide to the fermentation broth, thereby forming a product alcohol-containing gas phase. For example, gas stripping may be performed by sparging one or more gases through the fermentation broth. In some embodiments, the gas may be provided by the fermentation reaction. As an example, carbon dioxide may be provided as a by-product of the metabolism of a fermentable carbon source by the microorganism. In some embodiments, gas stripping may be used concurrently with extractant to remove product alcohol from the fermentation broth. Product alcohol may be recovered from the product alcohol-containing gas phase using methods known in the art, such as using a chilled water trap to condense the product alcohol, or scrubbing the gas phase with a solvent.

Recombinant Microorganisms and Biosynthetic Pathways

While not wishing to be bound by theory, it is believed that the processes described herein are useful in conjunction with any microorganism capable of producing fermentation products including alcohol-producing microorganism, particularly recombinant microorganisms which produce alcohol at titers above their tolerance levels.

Alcohol-producing microorganisms are known in the art. For example, fermentative oxidation of methane by methanotrophic bacteria (e.g., *Methylosinus trichosporium*) produces methanol, and the yeast strain CEN.PK113-7D (CBS 8340, the Centraal Buro voor Schimmelculture; van Dijken, et al., Enzyme Microb. Techno. 26:706-714, 2000) produces ethanol. Recombinant microorganisms which produce alcohol are also known in the art (e.g., Ohta, et al., Appl. Environ. Microbiol. 57:893-900, 1991; Underwood, et al., Appl. Environ. Microbiol. 68:1071-1081, 2002; Shen and Liao, Metab. Eng. 10:312-320, 2008; Hahnai, et al., Appl. Environ. Microbiol. 73:7814-7818, 2007; U.S. Pat. No. 5,514,583; U.S. Pat. No. 5,712,133; PCT Application Publication No. WO 1995/028476; Feldmann, et al., Appl. Microbiol. Biotechnol. 38: 354-361, 1992; Zhang, et al., Science 267:240-243, 1995; U.S. Patent Application Publication No. 2007/0031918 A1; U.S. Pat. No. 7,223,575; U.S. Pat. No. 7,741,119; U.S. Pat. No. 7,851,188; U.S. Patent Application Publication No. 2009/0203099 A1; U.S. Patent Application Publication No. 2009/0246846 A1; and PCT Application Publication No. WO 2010/075241, which are all herein incorporated by reference).

In addition, microorganisms may be modified using recombinant technologies to generate recombinant microorganisms capable of producing product alcohols such as ethanol and butanol. Microorganisms that may be recombinantly modified to produce a product alcohol via a biosynthetic pathway include members of the genera *Clostridium, Zymomonas, Escherichia, Salmonella, Serratia, Erwinia, Klebsiella, Shigella, Rhodococcus, Pseudomonas, Bacillus, Lactobacillus, Enterococcus, Alcaligenes, Klebsiella, Paenibacillus, Arthrobacter, Corynebacterium, Brevibacterium, Schizosaccharomyces, Kluyveromyces, Yarrowia, Pichia, Candida, Hansenula, Issatchenkia,* or *Saccharomyces*. In some embodiments, recombinant microorganisms may be selected from the group consisting of *Escherichia coli, Lactobacillus plantarum, Kluyveromyces lactis, Kluyveromyces marxianus* and *Saccharomyces cerevisiae*. In some embodiments, the recombinant microorganism is yeast. In some embodiments, the recombinant microorganism is crabtree-positive yeast selected from *Saccharomyces, Zygosaccharomyces, Schizosaccharomyces, Dekkera, Torulopsis, Brettanomyces,* and some species of *Candida*. Species of crabtree-positive yeast include, but are not limited to, *Saccharomyces cerevisiae, Saccharomyces kluyveri, Schizosaccharomyces pombe, Saccharomyces bayanus, Saccharomyces mikitae, Saccharomyces paradoxus, Zygosaccharomyces rouxii,* and *Candida glabrata*.

*Saccharomyces cerevisiae* are known in the art and are available from a variety of sources including, but not limited to, American Type Culture Collection (Rockville, Md.), Centraalbureau voor Schimmelcultures (CBS) Fungal Biodiversity Centre, LeSaffre, Gert Strand AB, Ferm Solutions, North American Bioproducts, Martrex, and Lallemand. *Saccharomyces cerevisiae* include, but are not limited to, BY4741, CEN.PK 113-7D, Ethanol Red® yeast, Ferm Pro™ yeast, Bio-Ferm® XR yeast, Gert Strand Prestige Batch Turbo alcohol yeast, Gert Strand Pot Distillers yeast, Gert Strand Distillers Turbo yeast, FerMax™ Green yeast, FerMax™ Gold yeast, Thermosacc® yeast, BG-1, PE-2, CAT-1, CBS7959, CBS7960, and CBS7961.

In some embodiments, the microorganism may be immobilized or encapsulated. For example, the microorganism may be immobilized or encapsulated using alginate, calcium alginate, or polyacrylamide gels, or through the induction of biofilm formation onto a variety of high surface area support matrices such as diatomite, celite, diatomaceous earth, silica gels, plastics, or resins. In some embodiments, ISPR may be used in combination with immobilized or encapsulated microorganisms. This combination may improve productivity such as specific volumetric productivity, metabolic rate, product alcohol yields, and tolerance to product alcohol. In addition, immobilization and encapsulation may minimize the effects of the process conditions such as shearing on the microorganisms.

The production of butanol utilizing fermentation, as well as microorganisms which produce butanol, is disclosed, for example, in U.S. Pat. No. 7,851,188, and U.S. Patent Application Publication Nos. 2007/0092957; 2007/0259410; 2007/0292927; 2008/0182308; 2008/0274525; 2009/0155870; 2009/0305363; and 2009/0305370, the entire contents of each are herein incorporated by reference. In some embodiments, the microorganism is engineered to contain a biosynthetic pathway. In some embodiments, the biosynthetic pathway is an engineered butanol biosynthetic pathway. In some embodiments, the biosynthetic pathway converts pyruvate to a fermentation product. In some embodiments, the biosynthetic pathway converts pyruvate as well as amino acids to a fermentation product. In some embodiments, at least one, at least two, at least three, or at least four polypeptides catalyzing substrate to product conversions of a pathway are encoded by heterologous polynucleotides in the microorganism. In some embodiments, all polypeptides catalyzing substrate to product conversions of a pathway are encoded by heterologous polynucleotides in the microorganism. In some embodiments, the polypeptide catalyzing the substrate to product conversions of acetolactate to 2,3-dihydroxyisovalerate and/or the polypeptide catalyzing the substrate to product conversion of isobutyraldehyde to isobutanol are capable of utilizing reduced nicotinamide adenine dinucleotide (NADH) as a cofactor.

Biosynthetic Pathways

Biosynthetic pathways for the production of isobutanol that may be used include those described in U.S. Pat. No. 7,851,188, which is incorporated herein by reference. In one embodiment, the isobutanol biosynthetic pathway comprises the following substrate to product conversions:
　a) pyruvate to acetolactate, which may be catalyzed, for example, by acetolactate synthase;
　b) acetolactate to 2,3-dihydroxyisovalerate, which may be catalyzed, for example, by acetohydroxy acid reductoisomerase;
　c) 2,3-dihydroxyisovalerate to α-ketoisovalerate, which may be catalyzed, for example, by acetohydroxy acid dehydratase;
　d) α-ketoisovalerate to isobutyraldehyde, which may be catalyzed, for example, by a branched-chain α-keto acid decarboxylase; and
　e) isobutyraldehyde to isobutanol, which may be catalyzed, for example, by a branched-chain alcohol dehydrogenase.

In another embodiment, the isobutanol biosynthetic pathway comprises the following substrate to product conversions:
　a) pyruvate to acetolactate, which may be catalyzed, for example, by acetolactate synthase;
　b) acetolactate to 2,3-dihydroxyisovalerate, which may be catalyzed, for example, by ketol-acid reductoisomerase;
　c) 2,3-dihydroxyisovalerate to a-ketoisovalerate, which may be catalyzed, for example, by dihydroxyacid dehydratase;
　d) α-ketoisovalerate to valine, which may be catalyzed, for example, by transaminase or valine dehydrogenase;
　e) valine to isobutylamine, which may be catalyzed, for example, by valine decarboxylase;
　f) isobutylamine to isobutyraldehyde, which may be catalyzed by, for example, omega transaminase; and
　g) isobutyraldehyde to isobutanol, which may be catalyzed, for example, by a branched-chain alcohol dehydrogenase.

In another embodiment, the isobutanol biosynthetic pathway comprises the following substrate to product conversions:
　a) pyruvate to acetolactate, which may be catalyzed, for example, by acetolactate synthase;
　b) acetolactate to 2,3-dihydroxyisovalerate, which may be catalyzed, for example, by acetohydroxy acid reductoisomerase;
　c) 2,3-dihydroxyisovalerate to α-ketoisovalerate, which may be catalyzed, for example, by acetohydroxy acid dehydratase;
　d) α-ketoisovalerate to isobutyryl-CoA, which may be catalyzed, for example, by branched-chain keto acid dehydrogenase;
　e) isobutyryl-CoA to isobutyraldehyde, which may be catalyzed, for example, by acylating aldehyde dehydrogenase; and
　f) isobutyraldehyde to isobutanol, which may be catalyzed, for example, by a branched-chain alcohol dehydrogenase.

Biosynthetic pathways for the production of 1-butanol that may be used include those described in U.S. Patent Application Publication No. 2008/0182308, which is incorporated herein by reference. In one embodiment, the 1-butanol biosynthetic pathway comprises the following substrate to product conversions:
　a) acetyl-CoA to acetoacetyl-CoA, which may be catalyzed, for example, by acetyl-CoA acetyltransferase;
　b) acetoacetyl-CoA to 3-hydroxybutyryl-CoA, which may be catalyzed, for example, by 3-hydroxybutyryl-CoA dehydrogenase;
　c) 3-hydroxybutyryl-CoA to crotonyl-CoA, which may be catalyzed, for example, by crotonase;
　d) crotonyl-CoA to butyryl-CoA, which may be catalyzed, for example, by butyryl-CoA dehydrogenase;
　e) butyryl-CoA to butyraldehyde, which may be catalyzed, for example, by butyraldehyde dehydrogenase; and
　f) butyraldehyde to 1-butanol, which may be catalyzed, for example, by butanol dehydrogenase.

Biosynthetic pathways for the production of 2-butanol that may be used include those described in U.S. Patent Application Publication No. 2007/0259410 and U.S. Patent Application Publication No. 2009/0155870, which are incorporated herein by reference. In one embodiment, the 2-butanol biosynthetic pathway comprises the following substrate to product conversions:
　a) pyruvate to alpha-acetolactate, which may be catalyzed, for example, by acetolactate synthase;
　b) alpha-acetolactate to acetoin, which may be catalyzed, for example, by acetolactate decarboxylase;
　c) acetoin to 3-amino-2-butanol, which may be catalyzed, for example, acetonin aminase;
　d) 3-amino-2-butanol to 3-amino-2-butanol phosphate, which may be catalyzed, for example, by aminobutanol kinase;
　e) 3-amino-2-butanol phosphate to 2-butanone, which may be catalyzed, for example, by aminobutanol phosphate phosphorylase; and
　f) 2-butanone to 2-butanol, which may be catalyzed, for example, by butanol dehydrogenase.

In another embodiment, the 2-butanol biosynthetic pathway comprises the following substrate to product conversions:
　a) pyruvate to alpha-acetolactate, which may be catalyzed, for example, by acetolactate synthase;
　b) alpha-acetolactate to acetoin, which may be catalyzed, for example, by acetolactate decarboxylase;
　c) acetoin to 2,3-butanediol, which may be catalyzed, for example, by butanediol dehydrogenase;
　d) 2,3-butanediol to 2-butanone, which may be catalyzed, for example, by dial dehydratase; and
　e) 2-butanone to 2-butanol, which may be catalyzed, for example, by butanol dehydrogenase.

Biosynthetic pathways for the production of 2-butanone that may be used include those described in U.S. Patent Application Publication No. 2007/0259410 and U.S. Patent Application Publication No. 2009/0155870, which are incorporated herein by reference. In one embodiment, the 2-butanone biosynthetic pathway comprises the following substrate to product conversions:
  a) pyruvate to alpha-acetolactate, which may be catalyzed, for example, by acetolactate synthase;
  b) alpha-acetolactate to acetoin, which may be catalyzed, for example, by acetolactate decarboxylase;
  c) acetoin to 3-amino-2-butanol, which may be catalyzed, for example, acetonin aminase;
  d) 3-amino-2-butanol to 3-amino-2-butanol phosphate, which may be catalyzed, for example, by aminobutanol kinase; and
  e) 3-amino-2-butanol phosphate to 2-butanone, which may be catalyzed, for example, by aminobutanol phosphate phosphorylase.

In another embodiment, the 2-butanone biosynthetic pathway comprises the following substrate to product conversions:
  a) pyruvate to alpha-acetolactate, which may be catalyzed, for example, by acetolactate synthase;
  b) alpha-acetolactate to acetoin which may be catalyzed, for example, by acetolactate decarboxylase;
  c) acetoin to 2,3-butanediol, which may be catalyzed, for example, by butanediol dehydrogenase; and
  d) 2,3-butanediol to 2-butanone, which may be catalyzed, for example, by diol dehydratase.

The terms "acetohydroxyacid synthase," "acetolactate synthase," and "acetolactate synthetase" (abbreviated "ALS") may be used interchangeably herein to refer to a polypeptide (or polypeptides) having enzyme activity that catalyzes the conversion of pyruvate to acetolactate and $CO_2$. Example acetolactate synthases are known by the EC number 2.2.1.6 (Enzyme Nomenclature 1992, Academic Press, San Diego). These unmodified enzymes are available from a number of sources, including, but not limited to, *Bacillus subtilis* (GenBank Nos: CAB15618 (SEQ ID NO: 1), Z99122 (SEQ ID NO: 2), NCBI (National Center for Biotechnology Information) amino acid sequence, NCBI nucleotide sequence, respectively), *Klebsiella pneumoniae* (GenBank Nos: AAA25079 (SEQ ID NO: 3), M73842 (SEQ ID NO: 4)), and *Lactococcus* lactis (GenBank Nos: AAA25161 (SEQ ID NO: 5), L16975 (SEQ ID NO: 6)).

The term "ketol-acid reductoisomerase" ("KARI"), "acetohydroxy acid isomeroreductase," and "acetohydroxy acid reductoisomerase" may be used interchangeably and refer to a polypeptide (or polypeptides) having enzyme activity that catalyzes the reaction of (S)-acetolactate to 2,3-dihydroxyisovalerate. Example KARI enzymes may be classified as EC number EC 1.1.1.86 (Enzyme Nomenclature 1992, Academic Press, San Diego), and are available from a vast array of microorganisms, including, but not limited to, *Escherichia coli* (GenBank Nos: NP_418222 (SEQ ID NO: 7), NC_000913 (SEQ ID NO: 8)), *Saccharomyces cerevisiae* (GenBank Nos: NP_013459 (SEQ ID NO: 9), NC_001144 (SEQ ID NO: 10)), *Methanococcus maripaludis* (GenBank Nos: CAF30210 (SEQ ID NO: 11), BX957220 (SEQ ID NO: 12)), and *Bacillus subtilis* (GenBank Nos: CAB14789 (SEQ ID NO: 13), Z99118 (SEQ ID NO: 14)). KARIs include Anaerostipes caccae KARI variants "K9G9" and "K9D3" (SEQ ID NOs: 15 and 16, respectively). Ketol-acid reductoisomerase (KARI) enzymes are described in U.S. Patent Application Publication Nos. 2008/0261230, 2009/0163376, and 2010/0197519, and PCT Application Publication No. WO/2011/041415, which are incorporated herein by reference. Examples of KARIs disclosed therein are those from *Lactococcus lactis*, *Vibrio cholera*, *Pseudomonas aeruginosa* PAO1, and *Pseudomonas fluorescens* PF5 mutants In some embodiments, the KARI utilizes NADH. In some embodiments, the KARI utilizes reduced nicotinamide adenine dinucleotide phosphate (NADPH).

The term "acetohydroxy acid dehydratase" and "dihydroxyacid dehydratase" ("DHAD") refers to a polypeptide (or polypeptides) having enzyme activity that catalyzes the conversion the conversion of 2,3-dihydroxyisovalerate to α-ketoisovalerate. Example acetohydroxy acid dehydratases are known by the EC number 4.2.1.9. Such enzymes are available from a vast array of microorganisms, including, but not limited to, *Escherichia coli* (GenBank Nos: YP_026248 (SEQ ID NO: 17), NC000913 (SEQ ID NO: 18)), *Saccharomyces cerevisiae* (GenBank Nos: NP_012550 (SEQ ID NO: 19), NC 001142 (SEQ ID NO: 20), *M. maripaludis* (GenBank Nos: CAF29874 (SEQ ID NO: 21), BX957219 (SEQ ID NO: 22)), *B. subtilis* (GenBank™ Nos: CAB14105 (SEQ ID NO: 23), Z99115 (SEQ ID NO: 24)), *L. lactis*, and *N. crassa*. U.S. Patent Application Publication No. 2010/0081154, and U.S. Pat. No. 7,851,188, which are incorporated herein by reference, describe dihydroxyacid dehydratases (DHADs), including a DHAD from *Streptococcus mutans*.

The term "branched-chain α-keto acid decarboxylase," "α-ketoacid decarboxylase," "α-ketoisovalerate decarboxylase," or "2-ketoisovalerate decarboxylase" ("KIVD") refers to a polypeptide (or polypeptides) having enzyme activity that catalyzes the conversion of α-ketoisovalerate to isobutyraldehyde and $CO_2$. Example branched-chain α-keto acid decarboxylases are known by the EC number 4.1.1.72 and are available from a number of sources, including, but not limited to, *Lactococcus lactis* (GenBank Nos: AAS49166 (SEQ ID NO: 25), AY548760 (SEQ ID NO: 26); CAG34226 (SEQ ID NO: 27), AJ746364 (SEQ ID NO: 28), *Salmonella typhimurium* (GenBank Nos: NP_461346 (SEQ ID NO: 29), NC_003197 (SEQ ID NO: 30)), *Clostridium acetobutylicum* (GenBank Nos: NP_149189 (SEQ ID NO: 31), NC_001988 (SEQ ID NO: 32)), *M. caseolyticus* (SEQ ID NO: 33), and *L. grayi* (SEQ ID NO: 34).

The term "branched-chain alcohol dehydrogenase" ("ADH") refers to a polypeptide (or polypeptides) having enzyme activity that catalyzes the conversion of isobutyraldehyde to isobutanol. Example branched-chain alcohol dehydrogenases are known by the EC number 1.1.1.265, but may also be classified under other alcohol dehydrogenases (specifically, EC 1.1.1.1 or 1.1.1.2). Alcohol dehydrogenases may be NADPH-dependent or NADH-dependent. Such enzymes are available from a number of sources, including, but not limited to, *Saccharomyces cerevisiae* (GenBank Nos: NP_010656 (SEQ ID NO: 35), NC_001136 (SEQ ID NO: 36), NP_014051 (SEQ ID NO: 37), NC_001145 (SEQ ID NO: 38)), *Escherichia coli* (GenBank Nos: NP_417484 (SEQ ID NO: 39), NC_000913 (SEQ ID NO: 40)), *C. acetobutylicum* (GenBank Nos: NP_349892 (SEQ ID NO: 41), NC_003030 (SEQ ID NO: 42); NP_349891 (SEQ ID NO: 43), NC_003030 (SEQ ID NO: 44)). U.S. Patent Application Publication No. 2009/0269823 describes SadB, an alcohol dehydrogenase (ADH) from *Achromobacter xylosoxidans*. Alcohol dehydrogenases also include horse liver ADH and *Beijerinkia indica* ADH (as described by U.S. Patent Application Publication No. 2011/0269199, which is incorporated herein by reference).

The term "butanol dehydrogenase" refers to a polypeptide (or polypeptides) having enzyme activity that catalyzes the conversion of isobutyraldehyde to isobutanol or the conversion of 2-butanone and 2-butanol. Butanol dehydrogenases are a subset of a broad family of alcohol dehydrogenases. Butanol dehydrogenase may be NAD- or NADP-dependent. The NAD-dependent enzymes are known as EC 1.1.1.1 and are available, for example, from *Rhodococcus ruber* (GenBank Nos: CAD36475, AJ491307). The NADP dependent enzymes are known as EC 1.1.1.2 and are available, for example, from *Pyrococcus furiosus* (GenBank Nos: AAC25556, AF013169). Additionally, a butanol dehydrogenase is available from *Escherichia coli* (GenBank Nos: NP 417484, NC_000913) and a cyclohexanol dehydrogenase is available from *Acinetobacter* sp. (GenBank Nos: AAG10026, AF282240). The term "butanol dehydrogenase" also refers to an enzyme that catalyzes the conversion of butyraldehyde to 1-butanol, using either NADH or NADPH as cofactor. Butanol dehydrogenases are available from, for example, *C. acetobutylicum* (GenBank Nos: NP_149325, NC_001988; this enzyme possesses both aldehyde and alcohol dehydrogenase activity); NP_349891, NC_003030; and NP_349892, NC_003030) and *Escherichia coli* (GenBank Nos: NP_417-484, NC_000913).

The term "branched-chain keto acid dehydrogenase" refers to a polypeptide (or polypeptides) having enzyme activity that catalyzes the conversion of α-ketoisovalerate to isobutyryl-CoA (isobutyryl-coenzyme A), typically using $NAD^+$ (nicotinamide adenine dinucleotide) as an electron acceptor. Example branched-chain keto acid dehydrogenases are known by the EC number 1.2.4.4. Such branched-chain keto acid dehydrogenases are comprised of four subunits and sequences from all subunits are available from a vast array of microorganisms, including, but not limited to, *Bacillus subtilis* (GenBank Nos: CAB14336 (SEQ ID NO: 45), Z99116 (SEQ ID NO: 46); CAB14335 (SEQ ID NO: 47), Z99116 (SEQ ID NO: 48); CAB14334 (SEQ ID NO: 49), Z99116 (SEQ ID NO: 50); and CAB14337 (SEQ ID NO: 51), Z99116 (SEQ ID NO: 52)) and *Pseudomonas putida* (GenBank Nos: AAA65614 (SEQ ID NO: 53), M57613 (SEQ ID NO: 54); AAA65615 (SEQ ID NO: 55), M57613 (SEQ ID NO: 56); AAA65617 (SEQ ID NO: 57), M57613 (SEQ ID NO: 58); and AAA65618 (SEQ ID NO: 59), M57613 (SEQ ID NO: 60)).

The term "acylating aldehyde dehydrogenase" refers to a polypeptide (or polypeptides) having enzyme activity that catalyzes the conversion of isobutyryl-CoA to isobutyraldehyde, typically using either NADH or NADPH as an electron donor. Example acylating aldehyde dehydrogenases are known by the EC numbers 1.2.1.10 and 1.2.1.57. Such enzymes are available from multiple sources, including, but not limited to, *Clostridium beijerinckii* (GenBank Nos: AAD31841 (SEQ ID NO: 61), AF157306 (SEQ ID NO: 62)), *Clostridium acetobutylicum* (GenBank Nos: NP_149325 (SEQ ID NO: 63), NC_001988 (SEQ ID NO: 64); NP_149199 (SEQ ID NO: 65), NC_001988 (SEQ ID NO: 66)), *Pseudomonas putida* (GenBank Nos: AAA89106 (SEQ ID NO: 67), U13232 (SEQ ID NO: 68)), and *Thermus thermophilus* (GenBank Nos: YP_145486 (SEQ ID NO: 69), NC_006461 (SEQ ID NO: 70)).

The term "transaminase" refers to a polypeptide (or polypeptides) having enzyme activity that catalyzes the conversion of α-ketoisovalerate to L-valine, using either alanine or glutamate as an amine donor. Example transaminases are known by the EC numbers 2.6.1.42 and 2.6.1.66. Such enzymes are available from a number of sources. Examples of sources for alanine-dependent enzymes include, but are not limited to, *Escherichia coli* (GenBank Nos: YP_026231 (SEQ ID NO: 71), NC_000913 (SEQ ID NO: 72)) and *Bacillus licheniformis* (GenBank Nos: YP_093743 (SEQ ID NO: 73), NC_006322 (SEQ ID NO: 74)). Examples of sources for glutamate-dependent enzymes include, but are not limited to, *Escherichia coli* (GenBank Nos: YP_026247 (SEQ ID NO: 75), NC_000913 (SEQ ID NO: 76)), *Saccharomyces cerevisiae* (GenBank Nos: NP_012682 (SEQ ID NO: 77), NC_001142 (SEQ ID NO: 78)) and *Methanobacterium thermoautotrophicum* (GenBank Nos: NP_276546 (SEQ ID NO: 79), NC_000916 (SEQ ID NO: 80)).

The term "valine dehydrogenase" refers to a polypeptide (or polypeptides) having enzyme activity that catalyzes the conversion of α-ketoisovalerate to L-valine, typically using NAD(P)H as an electron donor and ammonia as an amine donor. Example valine dehydrogenases are known by the EC numbers 1.4.1.8 and 1.4.1.9 and such enzymes are available from a number of sources, including, but not limited to, *Streptomyces coelicolor* (GenBank Nos: NP_628270 (SEQ ID NO: 81), NC003888 (SEQ ID NO: 82)) and *Bacillus subtilis* (GenBank Nos: CAB14339 (SEQ ID NO: 83), Z99116 (SEQ ID NO: 84)).

The term "valine decarboxylase" refers to a polypeptide (or polypeptides) having enzyme activity that catalyzes the conversion of L-valine to isobutylamine and $CO_2$. Example valine decarboxylases are known by the EC number 4.1.1.14. Such enzymes are found in *Streptomyces*, such as for example, *Streptomyces viridifaciens* (GenBank Nos: AAN10242 (SEQ ID NO: 85), AY116644 (SEQ ID NO: 86)).

The term "omega transaminase" refers to a polypeptide (or polypeptides) having enzyme activity that catalyzes the conversion of isobutylamine to isobutyraldehyde using a suitable amino acid as an amine donor. Example omega transaminases are known by the EC number 2.6.1.18 and are available from a number of sources, including, but not limited to, *Alcaligenes denitrificans* (AAP92672 (SEQ ID NO: 87), AY330220 (SEQ ID NO: 88)), *Ralstonia eutropha* (GenBank Nos: YP_294474 (SEQ ID NO: 89), NC007347 (SEQ ID NO: 90)), *Shewanella oneidensis* (GenBank Nos: NP_719046 (SEQ ID NO: 91), NC_004347 (SEQ ID NO: 92)), and *Pseudomonas putida* (GenBank Nos: AAN66223 (SEQ ID NO: 93), AE016776 (SEQ ID NO: 94)).

The term "acetyl-CoA acetyltransferase" refers to a polypeptide (or polypeptides) having enzyme activity that catalyzes the conversion of two molecules of acetyl-CoA to acetoacetyl-CoA and coenzyme A (CoA). Example acetyl-CoA acetyltransferases are acetyl-CoA acetyltransferases with substrate preferences (reaction in the forward direction) for a short chain acyl-CoA and acetyl-CoA and are classified as E.C. 2.3.1.9 [Enzyme Nomenclature 1992, Academic Press, San Diego]; although, enzymes with a broader substrate range (E.C. 2.3.1.16) will be functional as well. Acetyl-CoA acetyltransferases are available from a number of sources, for example, *Escherichia coli* (GenBank Nos: NP_416728, NC_000913; NCBI amino acid sequence, NCBI nucleotide sequence), *Clostridium acetobutylicum* (GenBank Nos: NP_349476.1, NC_003030; NP_149242, NC_001988, *Bacillus subtilis* (GenBank Nos: NP_390297, NC_000964), and *Saccharomyces cerevisiae* (GenBank Nos: NP_015297, NC_001148).

The term "3-hydroxybutyryl-CoA dehydrogenase" refers to a polypeptide (or polypeptides) having enzyme activity that catalyzes the conversion of acetoacetyl-CoA to 3-hydroxybutyryl-CoA. Example 3-hydroxybutyryl-CoA dehydrogenases may be NADH-dependent, with a substrate preference for (S)-3-hydroxybutyryl-CoA or (R)-3-hydroxybutyryl-CoA. Examples may be classified as E.C. 1.1.1.35 and E.C. 1.1.1.30, respectively. Additionally, 3-hydroxybutyryl-CoA dehydrogenases may be NADPH-dependent, with a substrate preference for (S)-3-hydroxybutyryl-CoA or (R)-3-hydroxybutyryl-CoA and are classified as E.C. 1.1.1.157 and E.C. 1.1.1.36, respectively. 3-Hydroxybutyryl-CoA dehydrogenases are available from a number of sources, for example, *Clostridium acetobutylicum* (GenBank Nos:

NP_349314, NC_003030), *Bacillus subtilis* (GenBank Nos: AAB09614, U29084), *Ralstonia eutropha* (GenBank Nos: YP_294481, NC_007347), and *Alcaligenes eutrophus* (GenBank Nos: AAA21973, J04987).

The term "crotonase" refers to a polypeptide (or polypeptides) having enzyme activity that catalyzes the conversion of 3-hydroxybutyryl-CoA to crotonyl-CoA and H$_2$O. Example crotonases may have a substrate preference for (S)-3-hydroxybutyryl-CoA or (R)-3-hydroxybutyryl-CoA and may be classified as E.C. 4.2.1.17 and E.C. 4.2.1.55, respectively. Crotonases are available from a number of sources, for example, *Escherichia coli* (GenBank Nos: NP_415911, NC_000913), *Clostridium acetobutylicum* (GenBank Nos: NP_349318, NC_003030), *Bacillus subtilis* (GenBank Nos: CAB13705, Z99113), and *Aeromonas caviae* (GenBank Nos: BAA21816, D88825).

The term "butyryl-CoA dehydrogenase" refers to a polypeptide (or polypeptides) having enzyme activity that catalyzes the conversion of crotonyl-CoA to butyryl-CoA. Example butyryl-CoA dehydrogenases may be NADH-dependent, NADPH-dependent, or flavin-dependent and may be classified as E.C. 1.3.1.44, E.C. 1.3.1.38, and E.C. 1.3.99.2, respectively. Butyryl-CoA dehydrogenases are available from a number of sources, for example, *Clostridium acetobutylicum* (GenBank Nos: NP_347102, NC_003030), *Euglena gracilis* (GenBank Nos: Q5EU90, AY741582), *Streptomyces collinus* (GenBank Nos: AAA92890, U37135), and *Streptomyces coelicolor* (GenBank Nos: CAA22721, AL939127).

The term "butyraldehyde dehydrogenase" refers to a polypeptide (or polypeptides) having enzyme activity that catalyzes the conversion of butyryl-CoA to butyraldehyde, using NADH or NADPH as cofactor. Butyraldehyde dehydrogenases with a preference for NADH are known as E.C. 1.2.1.57 and are available from, for example, *Clostridium beijerinckii* (GenBank Nos: AAD31841, AF157306) and *Clostridium acetobutylicum* (GenBank Nos: NP.sub.-149325, NC.sub.-001988).

The term "isobutyryl-CoA mutase" refers to a polypeptide (or polypeptides) having enzyme activity that catalyzes the conversion of butyryl-CoA to isobutyryl-CoA. This enzyme uses coenzyme B$_{12}$ as cofactor. Example isobutyryl-CoA mutases are known by the EC number 5.4.99.13. These enzymes are found in a number of *Streptomyces*, including, but not limited to, *Streptomyces cinnamonensis* (GenBank Nos: AAC08713 (SEQ ID NO: 95), U67612 (SEQ ID NO: 96); CAB59633 (SEQ ID NO: 97), AJ246005 (SEQ ID NO: 98)), *Streptomyces coelicolor* (GenBank Nos: CAB70645 (SEQ ID NO: 99), AL939123 (SEQ ID NO: 100); CAB92663 (SEQ ID NO: 101), AL939121 (SEQ ID NO: 102)), and *Streptomyces avermitilis* (GenBank Nos: NP_824008 (SEQ ID NO: 103), NC_003155 (SEQ ID NO: 104); NP_824637 (SEQ ID NO: 105), NC_003155 (SEQ ID NO: 106)).

The term "acetolactate decarboxylase" refers to a polypeptide (or polypeptides) having enzyme activity that catalyzes the conversion of alpha-acetolactate to acetoin. Example acetolactate decarboxylases are known as EC 4.1.1.5 and are available, for example, from *Bacillus subtilis* (GenBank Nos: AAA22223, L04470), *Klebsiella terrigena* (GenBank Nos: AAA25054, L04507) and *Klebsiella pneumoniae* (GenBank Nos: AAU43774, AY722056).

The term "acetoin aminase" or "acetoin transaminase" refers to a polypeptide (or polypeptides) having enzyme activity that catalyzes the conversion of acetoin to 3-amino-2-butanol. Acetoin aminase may utilize the cofactor pyridoxal 5'-phosphate or NADH or NADPH. The resulting product may have (R) or (S) stereochemistry at the 3-position. The pyridoxal phosphate-dependent enzyme may use an amino acid such as alanine or glutamate as the amino donor. The NADH- and NADPH-dependent enzymes may use ammonia as a second substrate. A suitable example of an NADH-dependent acetoin aminase, also known as amino alcohol dehydrogenase, is described by Ito, et al. (U.S. Pat. No. 6,432,688). An example of a pyridoxal-dependent acetoin aminase is the amine:pyruvate aminotransferase (also called amine:pyruvate transaminase) described by Shin and Kim (J. Org. Chem. 67:2848-2853, 2002).

The term "acetoin kinase" refers to a polypeptide (or polypeptides) having enzyme activity that catalyzes the conversion of acetoin to phosphoacetoin. Acetoin kinase may utilize ATP (adenosine triphosphate) or phosphoenolpyruvate as the phosphate donor in the reaction. Enzymes that catalyze the analogous reaction on the similar substrate dihydroxyacetone, for example, include enzymes known as EC 2.7.1.29 (Garcia-Alles, et al., Biochemistry 43:13037-13046, 2004).

The term "acetoin phosphate aminase" refers to a polypeptide (or polypeptides) having enzyme activity that catalyzes the conversion of phosphoacetoin to 3-amino-2-butanol O-phosphate. Acetoin phosphate aminase may use the cofactor pyridoxal 5'-phosphate, NADH, or NADPH. The resulting product may have (R) or (S) stereochemistry at the 3-position. The pyridoxal phosphate-dependent enzyme may use an amino acid such as alanine or glutamate. The NADH-dependent and NADPH-dependent enzymes may use ammonia as a second substrate. Although there are no reports of enzymes catalyzing this reaction on phosphoacetoin, there is a pyridoxal phosphate-dependent enzyme that is proposed to carry out the analogous reaction on the similar substrate serinol phosphate (Yasuta, et al., Appl. Environ. Microbial. 67:4999-5009, 2001).

The term "aminobutanol phosphate phospholyase," also called "amino alcohol O-phosphate lyase," refers to a polypeptide (or polypeptides) having enzyme activity that catalyzes the conversion of 3-amino-2-butanol O-phosphate to 2-butanone. Amino butanol phosphate phospho-lyase may utilize the cofactor pyridoxal 5'-phosphate. There are reports of enzymes that catalyze the analogous reaction on the similar substrate 1-amino-2-propanol phosphate (Jones, et al., Biochem J. 134:167-182, 1973). U.S. Patent Application Publication No. 2007/0259410 describes an aminobutanol phosphate phospho-lyase from the organism *Erwinia carotovora*.

The term "aminobutanol kinase" refers to a polypeptide (or polypeptides) having enzyme activity that catalyzes the conversion of 3-amino-2-butanol to 3-amino-2-butanol O-phosphate. Amino butanol kinase may utilize ATP as the phosphate donor. Although there are no reports of enzymes catalyzing this reaction on 3-amino-2-butanol, there are reports of enzymes that catalyze the analogous reaction on the similar substrates ethanolamine and 1-amino-2-propanol (Jones, et al., supra). U.S. Patent Application Publication No. 2009/0155870 describes, in Example 14, an amino alcohol kinase of *Erwinia carotovora* subsp. *Atroseptica*.

The term "butanediol dehydrogenase" also known as "acetoin reductase" refers to a polypeptide (or polypeptides) having enzyme activity that catalyzes the conversion of acetoin to 2,3-butanediol. Butanedial dehydrogenases are a subset of the broad family of alcohol dehydrogenases. Butanediol dehydrogenase enzymes may have specificity for production of (R)— or (S)-stereochemistry in the alcohol product. (S)-specific butanediol dehydrogenases are known as EC 1.1.1.76 and are available, for example, from *Klebsiella pneumoniae* (GenBank Nos: BBA13085, D86412). (R)-specific butanediol dehydrogenases are known as EC 1.1.1.4 and are available, for example, from *Bacillus cereus* (GenBank Nos. NP 830481, NC_004722; AAP07682, AE017000), and *Lactococcus* lactis (GenBank Nos. AAK04995, AE006323).

The term "butanediol dehydratase," also known as "dial dehydratase" or "propanediol dehydratase" refers to a polypeptide (or polypeptides) having enzyme activity that catalyzes the conversion of 2,3-butanediol to 2-butanone. Butanediol dehydratase may utilize the cofactor adenosyl cobalamin (also known as coenzyme Bw or vitamin B12; although vitamin B12 may refer also to other forms of cobalamin that are not coenzyme B12). Adenosyl cobalamin-dependent enzymes are known as EC 4.2.1.28 and are available, for example, from *Klebsiella oxytoca* (GenBank Nos: AA08099 (alpha subunit), D45071; BAA08100 (beta subunit), D45071; and BBA08101 (gamma subunit), D45071 (all three subunits are required for activity), and *Klebsiella pneumonia* (GenBank Nos: AAC98384 (alpha subunit), AF102064; GenBank Nos: AAC98385 (beta subunit), AF102064, GenBank Nos: AAC98386 (gamma subunit), AF102064). Other suitable dial dehydratases include, but are not limited to, B12-dependent dial dehydratases available from *Salmonella typhimurium* (GenBank Nos: AAB84102 (large subunit), AF026270; GenBank Nos: AAB84103 (medium subunit), AF026270; GenBank Nos: AAB84104 (small subunit), AF026270); and Lactobacillus collinoides (GenBank Nos: CAC82541 (large subunit), AJ297723; GenBank Nos: CAC82542 (medium subunit); AJ297723; GenBank Nos: CAD01091 (small subunit), AJ297723); and enzymes from *Lactobacillus brevis* (particularly strains CNRZ 734 and CNRZ 735, Speranza, et al., J. Agric. Food Chem. 45:3476-3480, 1997), and nucleotide sequences that encode the corresponding enzymes. Methods of dial dehydratase gene isolation are well known in the art (e.g., U.S. Pat. No. 5,686,276).

The term "pyruvate decarboxylase" refers to a polypeptide (or polypeptides) having enzyme activity that catalyzes the decarboxylation of pyruvic acid to acetaldehyde and carbon dioxide. Pyruvate dehydrogenases are known by the EC number 4.1.1.1. These enzymes are found in a number of yeast, including *Saccharomyces cerevisiae* (GenBank Nos: CAA97575 (SEQ ID NO: 107), CAA97705 (SEQ ID NO: 109), CAA97091 (SEQ ID NO: 111)).

It will be appreciated that microorganisms comprising an isobutanol biosynthetic pathway as provided herein may further comprise one or more additional modifications. U.S. Patent Application Publication No. 2009/0305363 (incorporated by reference) discloses increased conversion of pyruvate to acetolactate by engineering yeast for expression of a cytosol-localized acetolactate synthase and substantial elimination of pyruvate decarboxylase activity. In some embodiments, the microorganisms may comprise modifications to reduce glycerol-3-phosphate dehydrogenase activity and/or disruption in at least one gene encoding a polypeptide having pyruvate decarboxylase activity or a disruption in at least one gene encoding a regulatory element controlling pyruvate decarboxylase gene expression as described in U.S. Patent Application Publication No. 2009/0305363 (incorporated herein by reference), and/or modifications that provide for increased carbon flux through an Entner-Doudoroff Pathway or reducing equivalents balance as described in U.S. Patent Application Publication No. 2010/0120105 (incorporated herein by reference). Other modifications include integration of at least one polynucleotide encoding a polypeptide that catalyzes a step in a pyruvate-utilizing biosynthetic pathway. Other modifications include at least one deletion, mutation, and/or substitution in an endogenous polynucleotide encoding a polypeptide having acetolactate reductase activity. In some embodiments, the polypeptide having acetolactate reductase activity is YMR226c (SEQ ID NOs: 127, 128) of *Saccharomyces cerevisiae* or a homolog thereof. Additional modifications include a deletion, mutation, and/or substitution in an endogenous polynucleotide encoding a polypeptide having aldehyde dehydrogenase and/or aldehyde oxidase activity. In some embodiments, the polypeptide having aldehyde dehydrogenase activity is ALD6 from *Saccharomyces cerevisiae* or a homolog thereof. A genetic modification which has the effect of reducing glucose repression wherein the yeast production host cell is pdc- is described in U.S. Patent Application Publication No. 2011/0124060, incorporated herein by reference. In some embodiments, the pyruvate decarboxylase that is deleted or down-regulated is selected from the group consisting of: PDC1, PDC5, PDC6, and combinations thereof. In some embodiments, the pyruvate decarboxylase is selected from those enzymes in Table 1. In some embodiments, microorganisms may contain a deletion or down-regulation of a polynucleotide encoding a polypeptide that catalyzes the conversion of glyceraldehyde-3-phosphate to glycerate 1,3, bisphosphate. In some embodiments, the enzyme that catalyzes this reaction is glyceraldehyde-3-phosphate dehydrogenase.

TABLE 1

| SEQ ID Numbers of PDC Target Gene coding regions and Proteins | | |
|---|---|---|
| Description | SEQ ID NO: (Amino Acid) | SEQ ID NO: (Nucleic Acid) |
| PDC1 pyruvate decarboxylase from *Saccharomyces cerevisiae* | 107 | 108 |
| PDC5 pyruvate decarboxylase from *Saccharomyces cerevisiae* | 109 | 110 |
| PDC6 pyruvate decarboxylase *Saccharomyces cerevisiae* | 111 | 112 |
| pyruvate decarboxylase from *Candida glabrata* | 113 | 114 |
| PDC1 pyruvate decarboxylase from *Pichia stipitis* | 115 | 116 |
| PDC2 pyruvate decarboxylase from *Pichia stipitis* | 117 | 118 |
| pyruvate decarboxylase from *Kluyveromyces lactis* | 119 | 120 |
| pyruvate decarboxylase from *Yarrowia lipolytica* | 121 | 122 |
| pyruvate decarboxylase from *Schizosaccharomyces pombe* | 123 | 124 |
| pyruvate decarboxylase from *Zygosaccharomyces rouxii* | 125 | 126 |

In some embodiments, any particular nucleic acid molecule or polypeptide may be at least 80%, 85%, 90%, 95%, 96%, 97%, 98%, or 99% identical to a nucleotide sequence or polypeptide sequence described herein. The term "percent identity" as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. Identity and similarity can be readily calculated by known methods, including but not limited to those disclosed in: *Computational Molecular Biology* (Lesk, A. M., Ed.) Oxford University: NY (1988); *Biocomputing: Informatics and Genome Projects* (Smith, D. W., Ed.) Academic: NY (1993); *Computer Analysis of Sequence Data, Part I* (Griffin, A. M., and Griffin, H. G., Eds.) Humania: NJ (1994); *Sequence Analysis in Molecular Biology* (von Heinje, G., Ed.) Academic (1987); and *Sequence Analysis Primer* (Gribskov, M. and Devereux, J., Eds.) Stockton: NY (1991).

Methods to determine identity are designed to give the best match between the sequences tested. Methods to determine identity and similarity are codified in publicly available computer programs. Sequence alignments and percent identity calculations may be performed using the MegAlign™ program of the LASERGENE bioinformatics computing suite (DNASTAR Inc., Madison, Wis.). Multiple alignment of the sequences may be performed using the Clustal method of alignment which encompasses several varieties of the algorithm including the Clustal V method of alignment corresponding to the alignment method labeled Clustal V (disclosed by Higgins and Sharp, CABIOS. 5:151-153, 1989; Higgins, et al., Comput. Appl. Biosci. 8:189-191, 1992) and found in the MegAlign™ program of the LASERGENE bioinformatics computing suite (DNASTAR Inc.). For multiple alignments, the default values correspond to GAP PENALTY=10 and GAP LENGTH PENALTY=10. Default parameters for pairwise alignments and calculation of percent identity of protein sequences using the Clustal method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4. After alignment of the sequences using the Clustal V program, it is possible to obtain a percent identity by viewing the sequence distances table in the same program. Additionally the Clustal W method of alignment is available and corresponds to the alignment method labeled Clustal W (Higgins and Sharp, CABIOS. 5:151-153, 1989; Higgins, et al., Comput. Appl. Biosci. 8:189-191, 1992) and found in the MegAlign™ v6.1 program of the LASERGENE bioinformatics computing suite (DNASTAR Inc.). Default parameters for multiple alignment (GAP PENALTY=10, GAP LENGTH PENALTY=0.2, Delay Divergen Seqs(%)=30, DNA Transition Weight=0.5, Protein Weight Matrix=Gonnet Series, DNA Weight Matrix=IUB). After alignment of the sequences using the Clustal W program, it is possible to obtain a percent identity by viewing the sequence distances table in the same program.

Standard recombinant DNA and molecular cloning techniques are well known in the art and are described by Sambrook, et al. (Sambrook, J., Fritsch, E. F. and Maniatis, T. (Molecular Cloning: A Laboratory Manual; Cold Spring Harbor Laboratory Press, Cold Spring Harbor, 1989, here in referred to as Maniatis) and by Ausubel, et al. (Ausubel, et al., Current Protocols in Molecular Biology, pub. by Greene Publishing Assoc. and Wiley-Interscience, 1987). Examples of methods to construct microorganisms that comprise a butanol biosynthetic pathway are disclosed, for example, in U.S. Pat. No. 7,851,188, and U.S. Patent Application Publication Nos. 2007/0092957; 2007/0259410; 2007/0292927; 2008/0182308; 2008/0274525; 2009/0155870; 2009/0305363; and 2009/0305370, the entire contents of each are herein incorporated by reference.

Further, while various embodiments of the present invention have been described herein, it should be understood that they have been presented by way of example only, and not limitation. It will be apparent to persons skilled in the relevant art that various changes in form and detail can be made therein without departing from the spirit and scope of the invention. Thus, the breadth and scope of the present invention should not be limited by any of the described exemplary embodiments, but should be defined only in accordance with the claims and their equivalents.

All publications, patents, and patent applications mentioned in this specification are indicative of the level of skill of those skilled in the art to which this invention pertains, and are herein incorporated by reference to the same extent as if each individual publication, patent, or patent application was specifically and individually indicated to be incorporated by reference.

EXAMPLES

The following nonlimiting examples will further illustrate the invention. It should be understood that, while the following examples involve corn as feedstock, other biomass sources such as cane may be used for feedstock without departing from the present invention. Moreover, while the following examples involve ethanol and butanol, other alcohols or fermentation products may be produced without departing from the present invention.

The meaning of abbreviations is as follows: "atm" means atmosphere, "ccm" means cubic centimeter(s) per minute, "g/L" means gram(s) per liter, "g" means gram(s), "gpl" means gram(s) per liter, "gpm" means gallon(s) per minute, "h" or "hr" means hour(s), "HPLC" means high performance liquid chromatography, "kg" means kilogram(s), "L" means liter(s), "min" means minute(s), "mL" means milliliter(s), "ppm" means parts per million, "psig" means pound(s) per square inch, gauge, and "wt %" means weight percent.

Example 1

Process for Production and Recovery of Butanol Produced by Fermentation

The processes described herein may be demonstrated using computational modeling such as Aspen modeling (see, e.g., U.S. Pat. No. 7,666,282). For example, the commercial modeling software Aspen Plus® (Aspen Technology, Inc., Burlington, Mass.) may be used in conjunction with physical property databases such as DIPPR, available from American Institute of Chemical Engineers, Inc. (New York, N.Y.) to develop an Aspen model for an integrated butanol fermentation, purification, and water management process. This process modeling can perform many fundamental engineering calculations, for example, mass and energy balances, vapor/liquid equilibrium, and reaction rate computations. In order to generate an Aspen model, information input may include, for example, experimental data, water content and composition of feedstock, temperature for mash cooking and flashing, saccharification conditions (e.g., enzyme feed, starch conversion, temperature, pressure), fermentation conditions (e.g., microorganism feed, glucose conversion, temperature, pressure), degassing conditions, solvent columns, pre-flash columns, condensers, evaporators, centrifuges, etc.

Figure 14:
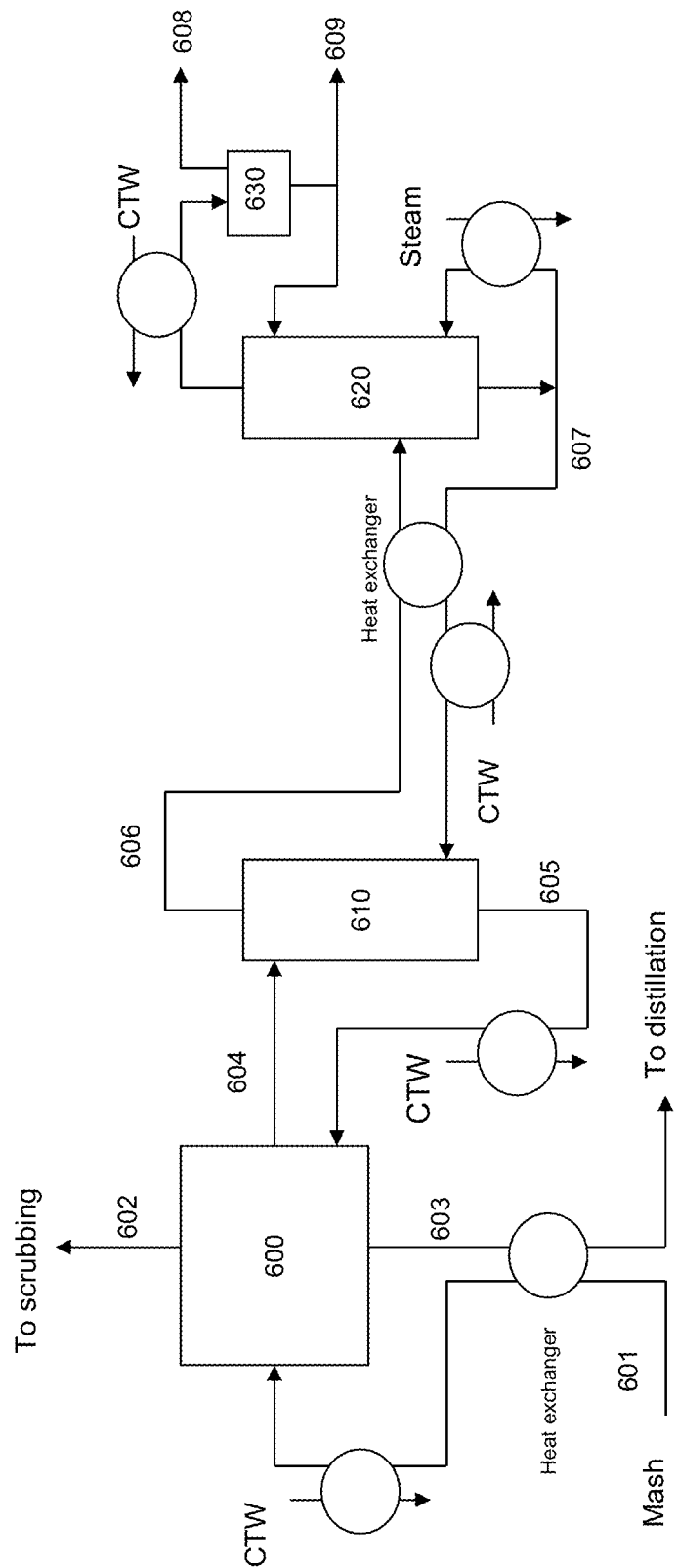
FIG. 14 schematically illustrates an exemplary process of the present invention including fermentation, extraction, and distillation processes.

An Aspen model was developed with rigorous material and energy balance in which 53400 kg/h of corn was mashed and fermented to produce isobutanol and in which most of the isobutanol was extracted during fermentation and distilled. This model included an approximation of sequenced batch fermentations as continuous processes. An example of this fermentation, extraction, and distillation process is illustrated in FIG. 14.

Liquefied corn mash 601 that was clarified to comprise 1.5 wt % suspended solids was pumped at 170.7 tonnes/h and 85° C. through a heat exchanger and a water cooler and fed to fermentation 600 at 32° C. Vapor stream 602 was vented at 17.2 tonnes/h at atmospheric pressure from fermentation 600 to a scrubber with an average continuous molar composition of 95.8% carbon dioxide, 3.4% water, and 0.8% isobutanol. An average beer stream 603 comprising 12.6 gpl isobutanol was discharged continuously from fermentation 600 and preheated through a heat exchanger by the mash 601 prior to being distilled for isobutanol recovery.

Stream 604 with 3875 tonnes/h combined average flow is removed from fermentation 600 at an average isobutanol concentration of 11.1 gpl and an average temperature of 32° C. and circulated through an extractor 610 for partial removal of isobutanol. The exiting aqueous broth 605 containing 7.9 gpl isobutanol is cooled by heat exchange with cooler tower water (CTW) to 30° C. prior to re-entering fermentation 600. A solvent comprising diisopropylbenzene enters the extractor 610 and exits as stream 606 comprising 30.1 gpl isobutanol. The extractor 610 provides effectively five theoretical liquid-liquid equilibrium stages for contacting fermentation broth with solvent. Stream 606 passes at 340 tonnes/h through a heat exchanger and enters the middle of twelve theoretical stages of distillation column 620. A reboiler is operating at 0.6 atm and 183° C. using 150 psig steam to produce solvent stream 607 comprising diisopropylbenzene and essentially no isobutanol that exchanges heat with solvent stream 606 through a heat exchanger and is further cooled by cooling water CTW prior to re-entering extractor 610. The overhead vapor of distillation column 620 is cooled CTW and condensed 630 to form 23.1 tonnes/h of reflux, 0.2 tonnes/h of a residual vapor off-gas 608, and 13.2 tonnes/h of product distillate 609 that comprises 99.2% isobutanol, 0.6% water, and 0.2% diisopropylbenzene.

Example 2

Process for Recovery of Ethanol Using an Extractant Column

A 1" diameter Karr® extraction column (Koch Modular Process Systems, Paramus, N.J.) was used to process fermentation broth that was produced during ethanol fermentation. The column contains a series of plates that run down the length of the column and which are attached to a central shaft. The shaft is attached to a drive which can move the perforated plates (¼" diameter perforations) up and down in a reciprocating motion. The frequency of the motion was a variable during testing, but both the stroke length of the oscillation (0.75") and the spacing of the trays (2") were fixed. The column used had a plate stack height of 3000 mm.

The top of the column was provided with an aqueous feed consisting of fermentation broth, while the bottom of the column was provided with a feed of corn oil fatty acids (COFA) as the extractant. The two feeds flowed countercurrent to one another through the column, and were collected as product at opposite ends of the column.

The fermentation broth was obtained using a fermentation protocol for production of ethanol from liquefied and saccharified corn mash from which, in some cases, some of the solids had been removed via centrifugation. In some cases, the extraction testing was done over the course of several days, such that a portion of the testing was done while $CO_2$ off-gassing was at or near its maximum, while another portion was done when off-gassing had effectively stopped. The COFA used in this work was distilled grade from Emery Oleochemicals (Cincinnati, Ohio).

Some experiments were run with COFA as the continuous phase in the column, while others were run with continuous aqueous phase. Experiments were also conducted with or without internals in place. Two types of internals were tested: stainless steel and polytetrafluoroethylene (PTFE). A range of flow rates were examined, in order to determine the flow regimes under which the column could be operated without flooding.

Impact of Dynamic Feed from Fermentation

During the course of the testing, it was determined that in some cases the column performance varied as the fermentation progressed. Early in the fermentation, the fermentation broth comprising the feed is high in sugar, at intermediate times a considerable amount of $CO_2$ (which can impact fluid flows) evolves from the fermentation broth, while at later times the concentration of ethanol in the fermentation broth is high. This temporal variation in the feed was reflected in variations in the capacity of the extraction column.

With conditions using PTFE plates and continuous COFA phase (no agitation), a difference was noted in performance when using fermentation broth collected when the fermentation was near the period of peak gas evolution ("intermediate broth") and toward the end of fermentation ("end broth"). Using end broth, a liquid throughput rate of 14 gpm/ft$^2$ (Sample 3E) was achieved without flooding the column. The maximum throughput for intermediate broth that could be achieved prior to flooding was less than to 9 gpm/ft$^2$ (Sample 4D), with noticeable differences in the size and appearance of the aqueous droplets. The droplet size of the aqueous phase was larger (with the formation of globules) in end broth as compared to intermediate broth.

Continuous Phase

The maximum column throughput was also impacted by the nature of the continuous phase. For end of fermentation conditions, running with continuous aqueous phase and stainless steel (S. Steel) internals, a total liquid capacity of almost 14 gpm/ft$^2$ was achieved (Sample 2B). For continuous organic phase and PTFE internals, the rate was less than 9 gpm/ft$^2$ (Sample 4D). Results are shown in Table 2. The abbreviation AQ refers to the aqueous phase and the abbreviation ORG refers to the organic phase. Referring to Table 2, the Phase was continuous, Sample refers to run conditions, Internals refer to the material of the internals, Nom. AQ refers to the nominal aqueous flow rate, Nom. ORG refers to nominal organic flow rate, Total Flow (ccm) refers to the total flow of the aqueous and organic feeds, and Total Flow (gpm/ft$^2$) refers to total flow per unit cross-sectional area.

TABLE 2

| Phase | Sample | Internals | Nom. AQ (ccm) | Nom. ORG (ccm) | Total Flow (ccm) | Total Flow (gpm/ft$^2$) |
|---|---|---|---|---|---|---|
| AQ | 1A | S. Steel | 160 | 60 | 220 | 10.7 |
| AQ | 1B | S. Steel | 100 | 30 | 130 | 6.3 |
| AQ | 1C | S. Steel | 89 | 20 | 109 | 5.3 |
| AQ | 1D | S. Steel | 120 | 65-101 | — | — |
| AQ | 1E | S. Steel | 135 | 60 | 195 | 9.4 |
| AQ | 1F | S. Steel | 132 | 50 | 182 | 8.8 |

TABLE 2-continued

| Phase | Sample | Internals | Nom. AQ (ccm) | Nom. ORG (ccm) | Total Flow (ccm) | Total Flow (gpm/ft²) |
|---|---|---|---|---|---|---|
| AQ | 1G | S. Steel | 150 | 50 | 200 | 9.7 |
| AQ | 1G' | S. Steel | 120 | 50 | 170 | 8.2 |
| AQ | 1H | S. Steel | 210 | 75 | 285 | 13.8 |
| AQ | 1I | S. Steel | 210 | 75 | 285 | 13.8 |
| AQ | 2A | S. Steel | 210 | 75 | 285 | 13.8 |
| AQ | 2B | S. Steel | 210 | 75 | 285 | 13.8 |
| AQ | 2C | S. Steel | 87 | 85 | 172 | 4.1 |
| ORG | 3A | PTFE | 100 | 50 | 150 | 7.3 |
| ORG | 3B | PTFE | 100 | 100 | 200 | 9.7 |
| ORG | 3C | PTFE | 200 | 100 | 300 | 14.5 |
| ORG | 3D | PTFE | 180 | 75 | 255 | 12.4 |
| ORG | 3E | PTFE | 180 | 120 | 300 | 14.5 |
| ORG | 3F | PTFE | 180 | 170 | 350 | 17.0 |
| ORG | 3G | PTFE | 180 | 60 | 240 | 11.6 |
| ORG | 3G | PTFE | 180 | 60 | 240 | 11.6 |
| ORG | 4A | PTFE | 110 | 70 | 180 | 8.7 |
| ORG | 4B | PTFE | 100 | 30 | 130 | 6.3 |
| ORG | 4C | PTFE | 100 | 60 | 160 | 7.7 |
| ORG | 4D | PTFE | 100 | 80 | 180 | 8.7 |
| ORG | 4E | PTFE | 85 | 60 | 145 | 7.0 |
| ORG | 4F | PTFE | 90 | 40 | 130 | 6.3 |
| ORG | 4G | PTFE | 70 | 40 | 110 | 5.3 |
| ORG | 4M | PTFE | 60 | 60 | 120 | 5.8 |
| ORG | 4N | PTFE | 80 | 80 | 160 | 7.7 |

When the column was operated without internals using feed comprised of fermentation broth near the end of fermentation, the choice of the continuous phase affected the column capacity. For continuous aqueous phase, it was possible to operate at approximately 25 gpm/ft² (Samples 2G and 2H). With continuous COFA phase, however, problems with flooding occurred at 18 m/ft² (Sample 2I). Results are shown in Table 3.

TABLE 3

| Phase | Nom. Aq (ccm) | Nom. Org. (ccm) | Total Flow (ccm) | Total Flow (gpm/ft²) |
|---|---|---|---|---|
| AQ | 200 | 75 | 275 | 13.3 |
| AQ | 200 | 75 | 275 | 13.3 |
| AQ | 200 | 75 | 275 | 13.3 |
| AQ | 200 | 120 | 320 | 15.5 |
| AQ | 240 | 160 | 400 | 19.4 |
| AQ | 240 | 160 | 400 | 19.4 |
| AQ | 320 | 170 | 490 | 23.7 |
| AQ | 390 | 170 | 560 | 27.1 |
| ORG | 210 | 170 | 380 | 18.4 |
| ORG | 210 | 170 | 380 | 18.4 |
| ORG | 60 | 60 | 120 | 5.8 |
| ORG | 80 | 60 | 140 | 6.8 |
| ORG | 80 | 80 | 160 | 7.7 |
| ORG | 90 | 90 | 180 | 8.7 |
| ORG | 100 | 100 | 200 | 9.7 |
| ORG | 150 | 50 | 200 | 9.7 |
| ORG | 170 | 60 | 230 | 11.1 |

Example 3

Effect of Fermentation Conditions on Extraction Column Capacity

The nature of fermentation broth is not static, but changes as the fermentation process progresses. In fermentation, the concentration of carbohydrates decreases as the carbohydrates are metabolized by microorganisms. This compositional change in the fermentation broth will alter physical parameters such as viscosity and surface tension of the fermentation broth, which have an effect on the extraction process. In addition to the changes in concentration, at intermediate times a considerable amount of $CO_2$ is evolved; and this $CO_2$ will impact the flow of the aqueous and organic liquids through the column.

A 1" diameter glass Karr® extraction column (Koch Modular Process Systems, Paramus, N.J.), outfitted with PTFE internals, was used to process fermentation broth from an ethanol fermentation. The processing was done at several timepoints during the course of the fermentation. Organic extractant (COFA) was the continuous phase in the column, with the fermentation broth passing through the column as droplets. Prior to the introduction of the fermentation broth to the column, the fermentation broth was passed through a tee in the line where $CO_2$ bubbles present in the feed were removed through a vent.

With static internals (no agitation), a difference was noted in performance when using fermentation broth taken during the period of peak gas evolution ("intermediate broth") compared to broth taken toward the end of fermentation ("end broth"). Using intermediate broth, a liquid throughput rate of 14 gpm/ft² was achieved. The maximum throughput (before column flooding) for the end broth was less than to 9 gpm/ft². There were noticeable differences in the size and appearance of the aqueous droplets. The droplet size of the aqueous phase was visibly larger for end broth as compared to intermediate broth.

Example 4

Effect of Isobutanol Concentration on Extraction Column Efficiency

During a typical fermentation process, the levels of product change with time. This dynamic concentration change can affect the mass transfer in an extraction process.

To demonstrate the effect of isobutanol concentration, a 1" diameter glass Karr® extraction column (Koch Modular Process Systems, Paramus, N.J.), outfitted with stainless steel internals, was used to process fermentation broth from a fermentation that contained approximately 3 g/L of isobutanol. The fermentation broth formed the continuous phase in the extractor, while the organic extractant (COFA) passed through the column as droplets. Although $CO_2$ production had essentially ceased, the fermentation broth was passed through a tee in the line where any $CO_2$ bubbles present in the feed were removed prior to the feed entering the extraction column.

Samples of the feed and exiting streams were analyzed for isobutanol by liquid chromatography (LC) or gas chromatography (GC). Results are shown in Table 4. Mass balances were done, and the height of an equilibrium transfer stage (HETS) calculated using Kremser equations. For the two data points on as-is fermentation broth, the HETS values were 10 and 13 feet.

Figure 15:
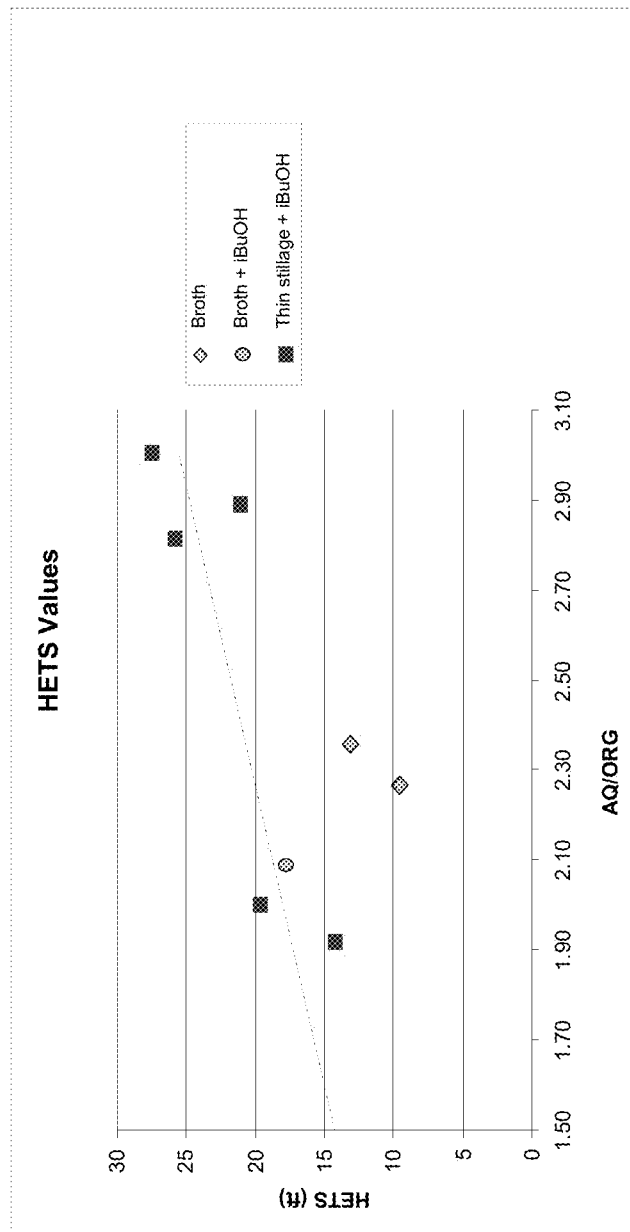
FIG. 15 shows the effects of the fermentation broth to extractant ratios (aq/org) on extraction column efficiency.

Isobutanol was then added to the fermentation broth to bring the concentration to 20 g/L. An extraction test was conducted and from the data, the HETS was found to be 18 feet. This value was some 50% higher than the values obtained on plain broth, and is in line with data obtained using thin stillage spiked with approximately 20 g/L isobutanol (see FIG. 15).

TABLE 4

| Aqueous phase | Flow of aqueous phase mL/min | Flow of organic phase mL/min | Isobutanol in the rich aqueous phase (LC) g/L | Isobutanol in the lean aqueous phase (LC) g/L | Isobutanol in the rich organic phase (GC) g/L | Isobutanol in the lean organic phase g/L | HETS ft |
|---|---|---|---|---|---|---|---|
| Broth | 192.5 | 85 | 2.80 | 1.21 | 3.3 | 0 | 10 |
| Broth | 247.5 | 105 | 3.14 | 1.65 | 3.6 | 0 | 13 |
| Broth with added iBuOH | 187.5 | 89.7 | 20.6 | 11.5 | 20.6 | 0 | 18 |

Example 5

ISPR Using an External Extraction Column

Fermentation broth from an isobutanol fermentation (10-liter scale) was circulated to a ⅝" diameter bench top Karr® column. The extraction solvent (COFA) was recycled from an extractant reservoir to the Karr® column. A control fermentation was run in which a volume of COFA was added to the fermentor to continuously extract isobutanol from the fermentation broth.

The Karr® column was run twice during the fermentation. The first run was at timepoint 4 to 7 hours of the fermentation and the second run was at timepoint 22 to 33 hours of the fermentation. Parameters such as $pO_2$ and pH were monitored for both fermentations. The measured $pO_2$ was lower for the run in which the Karr® column was used, as compared to the control run that did not use the Karr® column. Absolute pH values were similar for the Karr® column and the control, but the pH profiles were different for the two runs. The pH in the Karr® column run peaked early, flattened, then peaked again, versus a single gradual peak for the control.

Figure 16:
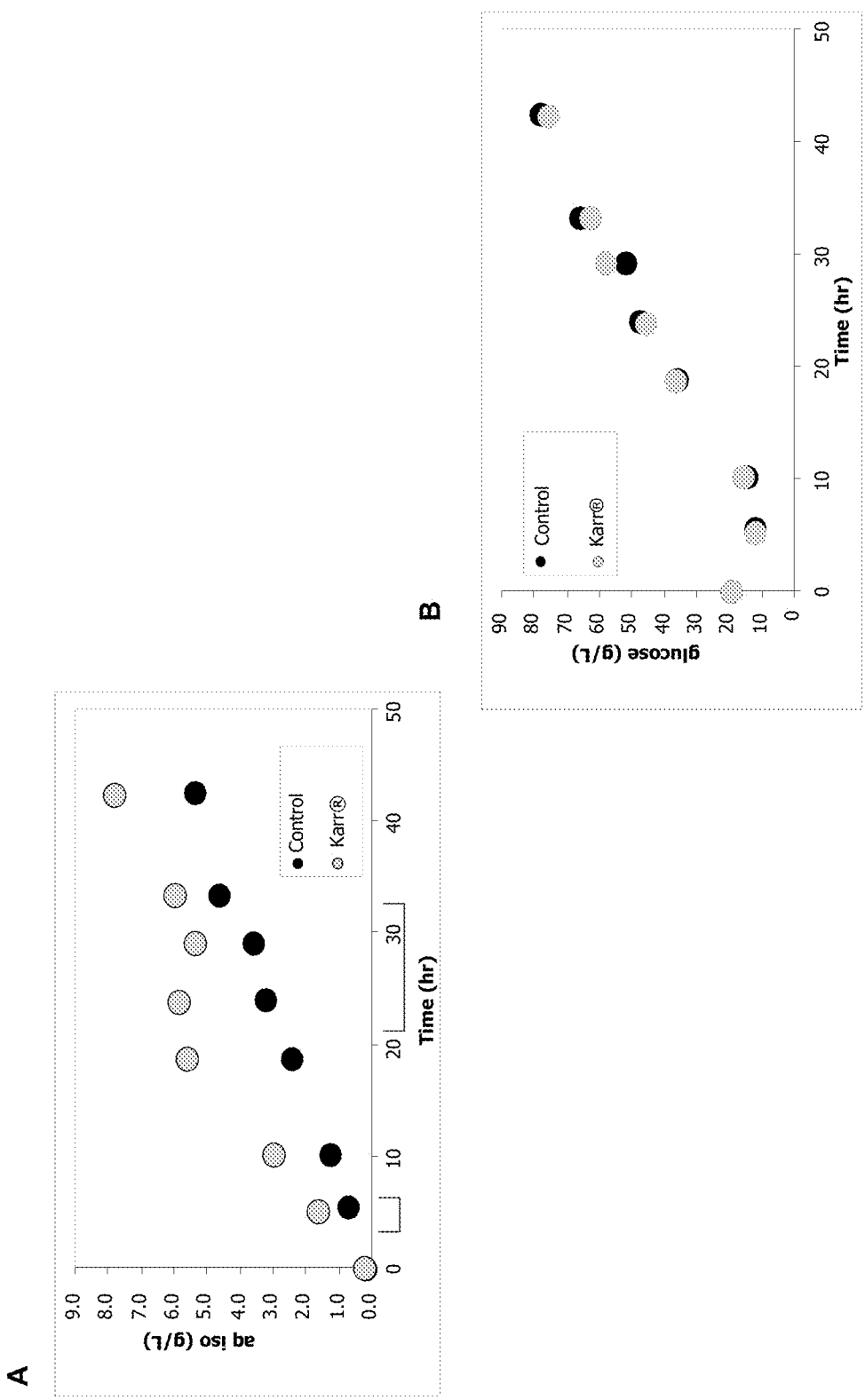
FIGS. 16A and 16B show the effects of ISPR using an external extraction column on isobutanol concentrations and glucose profiles.

Two aliquots of extraction solvent (1.8 liters each) were analyzed from the Karr® column. Samples were taken from each aliquot and analyzed for isobutanol content. The amount of isobutanol produced in the fermentation with the Karr® column was comparable to that produced in the control fermentation. The fermentation using the Karr® column produced a total of 82.4 grams isobutanol: approximately 34 grams were in 3.6 liters of organic phase and 48 grams in the aqueous phase. The control (30% by volume organic phase added to the fermentor) produced 90 g/L, 60 grams in 3 liters of organic phase and 30 grams in the aqueous phase. Isobutanol concentration in the aqueous phase was lower in the control due to the presence of COFA in the control fermentor from time zero, versus a non-zero start of extraction in the Karr® column run. For the Karr® column at 22 hours, isobutanol was extracted from the fermentor more quickly than it was being produced. Glucose profiles were generated for the control and Karr® column. The profiles were similar, indicating cell growth and metabolism were comparable. Results are shown in FIGS. 16A and 16B. Brackets indicate the time points (4 to 7 hours and 22 to 33 hours) when the Karr® column was in operation.

Example 6

ISPR Using Mixer-Settler

An external mixer settler system was used to continuously remove isobutanol from an active fermentation broth containing a microorganism that produced isobutanol (i.e., isobutanologen). The study used approximately 100 liters of fermentation broth inoculated with an isobutanol-producing microorganism (i.e., isobutanologen). The contents of the fermentor were re-circulated from the fermentor through the mixer-settler extraction system. The extractant, comprising distilled COFA which contained no isobutanol, was used on a once-through basis.

Figure 17:
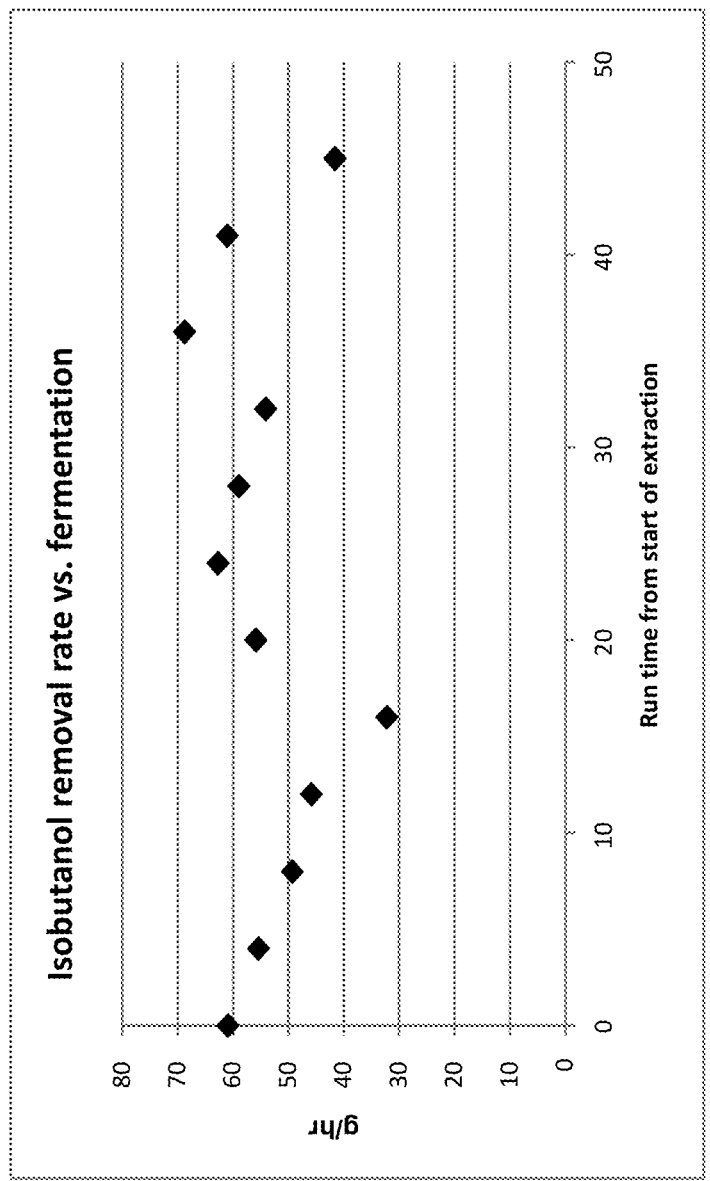
FIG. 17 show the effects of ISPR using a mixer-settler on isobutanol removal rates.

Two static mixers were tested. The majority of the test used a Kenics® stainless steel static mixer (½" in diameter with 36 mixing elements). Between hours 12 and 24 of the run, a plastic mixer was used (StaMixCo HT-11-12.6-24, StaMixCo LLC, Brooklyn, N.Y.). Fermentation broth and COFA were fed to opposite sides of a tee, from which the mixture flowed through the static mixer. The material exiting the static mixer was fed to the settler. The settler was made from a five-liter glass tank. A dip tube passed through the top of the settler, near the perimeter, and extended approximately halfway down the settler. The organic phase was withdrawn through a port at the top of the settler, while fermentation broth was removed from the bottom of the settler. The settler was fitted with an agitator that provided gentle mixing to the aqueous-organic interface in order to aid disengagement of the two liquid phases and thereby minimize accumulation of solids at the interface. Data collected during the run is presented in Table 5, and FIG. 17 shows the isobutanol removal rates that were achieved during the course of the fermentation. As can be seen from the data, isobutanol levels in the aqueous broth remained relatively constant, indicating that isobutanol was removed from the fermentation broth at about the same rate as it is being produced. Referring to Table 5, Elapsed Time is time from start of fermentation, AQ Flow is aqueous feed flow, ORG flow is organic feed flow, iB in AQ feed is isobutanol in the aqueous feed, and iB in ORG product is isobutanol in the rich organic product.

TABLE 5

| Elapsed Time (hr) | Type of Mixer* | AQ Flow (ccm) | ORG flow (ccm) | iB in AQ feed (g/L) | iB in ORG product (g/L) |
|---|---|---|---|---|---|
| 0.0 | A | 648 | 100 | 5.97 | 10.14 |
| 4.0 | A | 648 | 100 | 5.30 | 9.22 |
| 8.0 | A | 648 | 100 | 4.56 | 8.20 |
| 12.0 | A | 648 | 100 | 4.03 | 7.63 |
| 16.0 | B | 648 | 100 | 4.23 | 5.36 |
| 20.0 | B | 842.2 | 130 | 4.00 | 7.15 |
| 24.0 | B | 572.4 | 170 | 4.53 | 6.15 |
| 28.0 | A | 648 | 100 | 4.65 | 9.82 |
| 32.0 | A | 648 | 100 | 4.92 | 9.00 |
| 36.0 | A | 648 | 100 | 5.27 | 11.45 |
| 41.0 | A | 648 | 100 | 5.65 | 10.16 |
| 45.0 | A | 648 | 100 | 5.40 | 6.92 |

*A: ½" stainless Kenics ® mixer, 32 elements
B: StaMixCo HT-11-12.6-24, plastic mixer

Example 7

On-Line, At-Line, and Real-Time Measurements

A mash stream prepared from corn feedstock was conducted to a three-phase centrifuge generating three streams: mash, corn oil, and wet cake. On-line or at-line process measurements are employed, for example, to improve the recovery of starch/sugars and the quality of corn oil, and to maximize the amount of starch/sugars extracted from wet cake. Real-time measurements are used, for example, to control the addition of backset, cookwater, or water to slurry tanks to maintain a starch/sugar concentration set-point. The amount of starch/sugar extracted from the wet cake is maximized using the minimum amount of added water, and reducing the hydraulic load on the three-phase centrifuge.

Figure 18:
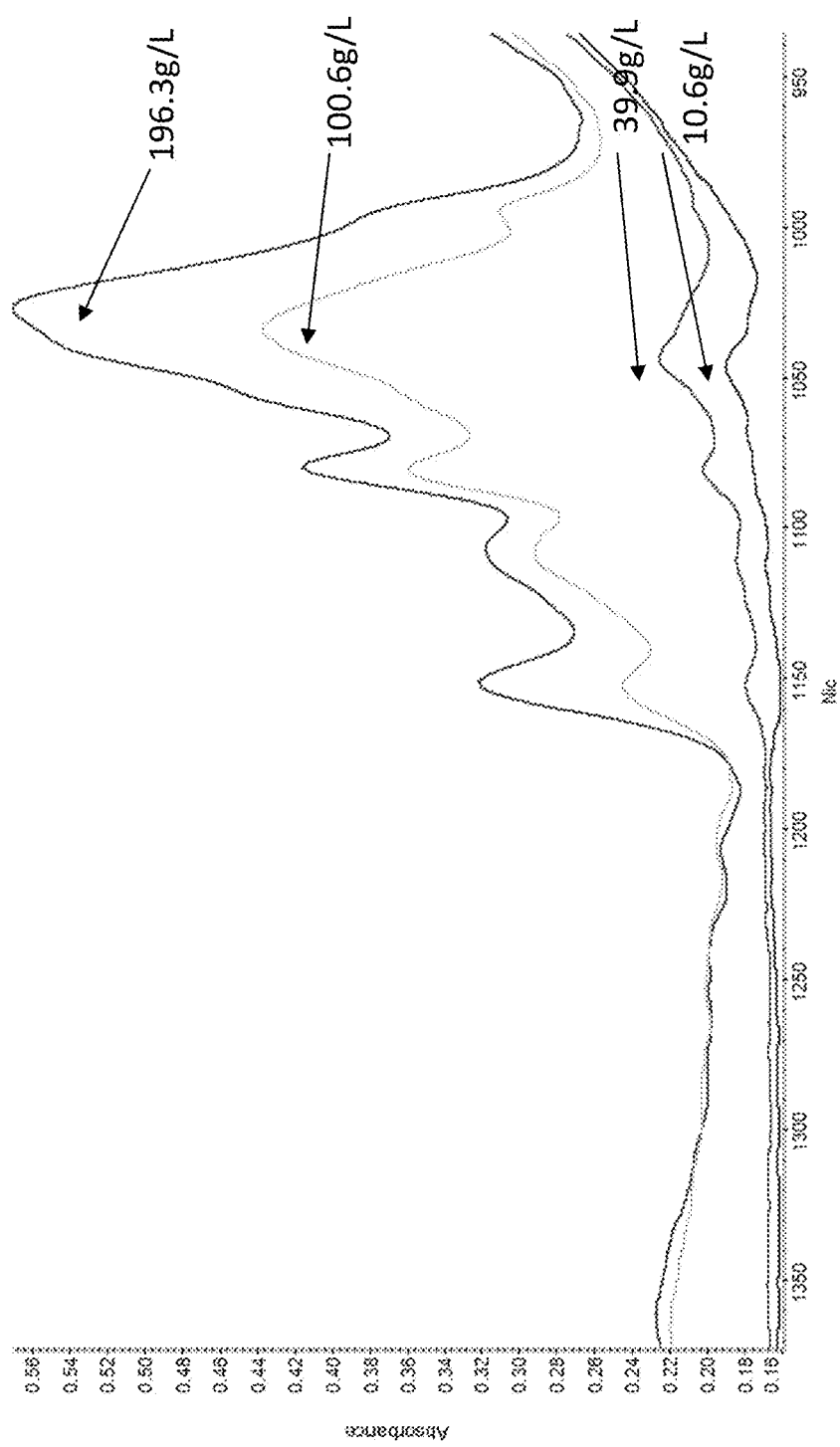
FIG. 18 shows FTIR spectra of the range of starch concentrations using in-line measurements.

Corn mash samples were analyzed using Fourier transform infrared spectroscopy (FTIR) with a diamond attenuated total reflectance (ATR) probe that allows for measurements in the presence of solids. The FTIR was calibrated by collecting spectra of standard samples in which total starch/sugar determinations using HPLC had been completed. The HPLC data was used to create a multivariate partial least squares (PLS) model for the FTIR. FTIR spectra were collected and a total starch concentration generated. FIG. 18 illustrates the range of starch concentrations used to calibrate the FTIR.

Figure 19:
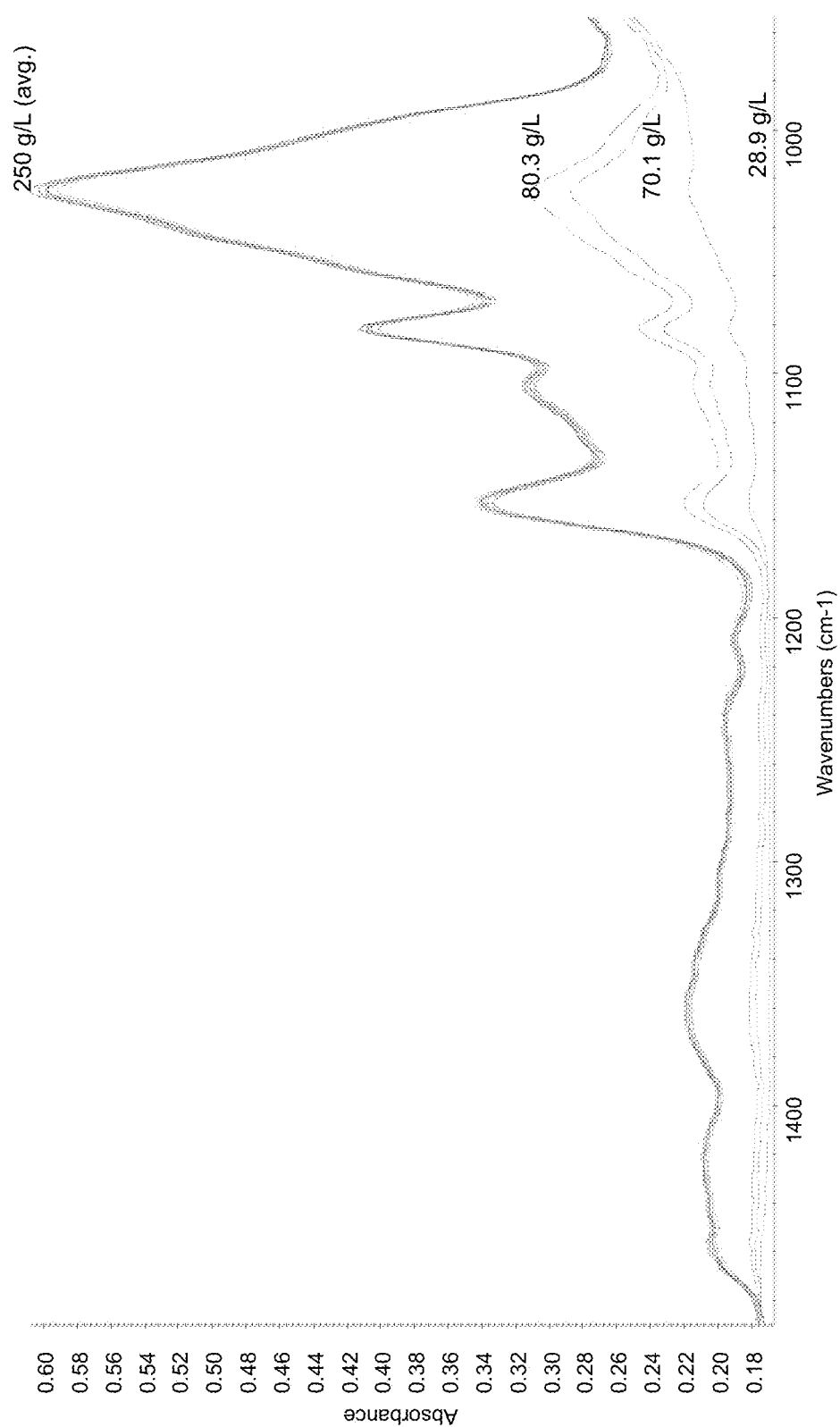
FIG. 19 shows FTIR spectra of the starch concentration of wet cake during processing of corn mash.

Corn mash with an average starting concentration of 250 g/L was fed to a three-phase centrifuge. The subsequent wet cake was re-slurried and the concentration of starch was measured on two samples: 80 g/L and 70 g/L. This slurry was then separated using a three-phase centrifuge and the wet cake re-slurried. The starch concentration of this slurry was determined to be 28.9 g/L. Results are shown in FIG. 19. These measurements were used to determine the correct amount of water to re-slurry the wet cake at each stage. Optimizing the water addition maximized the starch concentration and minimized the hydraulic load on the separation step. Moisture content of the wet cake was measured using near-infrared spectroscopy (NIR).

Corn oil quality is monitored in real-time and the data is used to control the three-phase centrifuge variables (e.g., feed rate, g forces, inlet flow rate, scroll speed). The quality of corn oil generated by the three-phase centrifuge was measured by monitoring the concentration of water carried into the corn oil during the separation. FTIR with a diamond ATR probe was used to collect corn oil spectra as it exited the three-phase centrifuge. The detection limit for water using the diamond ATR probe approach was approximately 500 ppm. Lower detection limits are achieved with the use of a flow cell with a longer effective path length.

Figure 20:
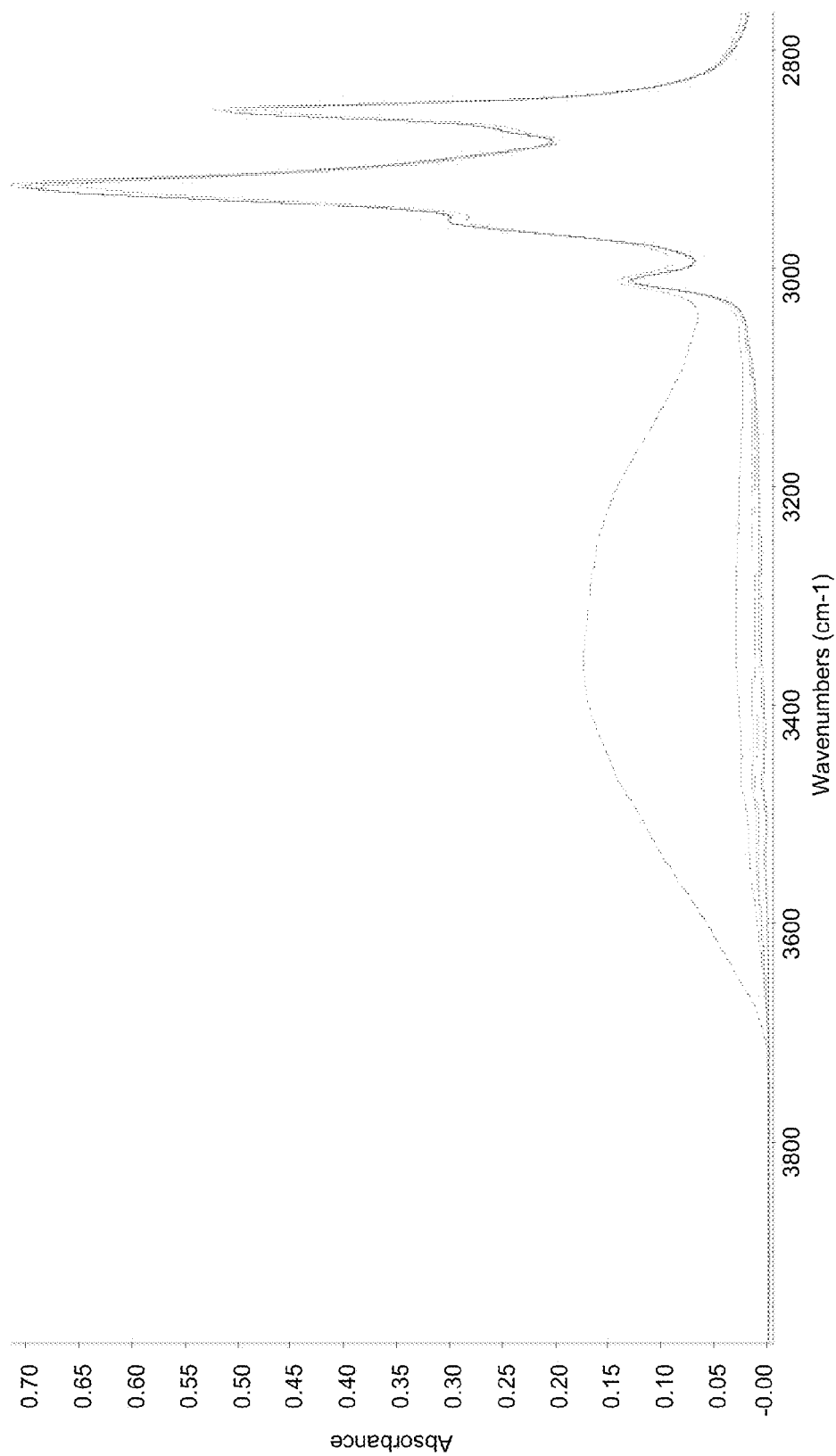
FIG. 20 shows FTIR spectra of corn oil during processing of corn mash.

FIG. 20 contains a series of infrared spectra of corn oils that contain a range of water concentrations in excess of percent level concentrations down to 100's of ppm. Water concentration was determined using the —OH stretching region between 3700 cm-1 and 3050 cm-1. The data indicated that a process FTIR may be used to generate real-time water concentration in oil data. Real-time water concentration data may be used to control the process variables of the three-phase centrifuge (e.g., feed rate, g forces, inlet flow rate, scroll speed). The operation of the three-phase centrifuge may be controlled to yield the highest quality corn oil or to maximize throughput while not exceeding a water set point.

Real-time extractant monitoring was used to detect and monitor thermal breakdown of the extractant. Detection of these thermal breakdown products in real-time is used to trigger remediation of the extractant or purging of the contaminated extractant from the process.

Figure 21:
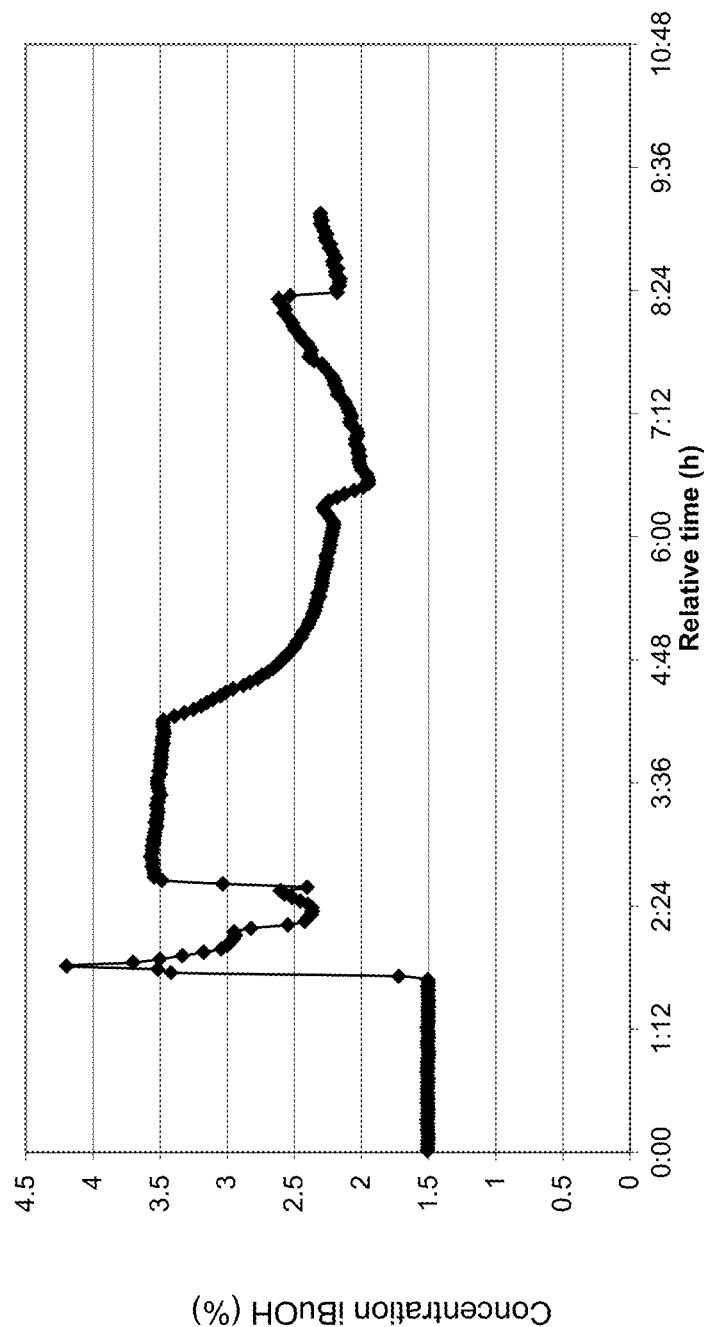
FIG. 21 demonstrates a real-time measurement of isobutanol in COFA.

FIG. 21 is an example of the real-time measurement of isobutanol-rich COFA. The data was collected using a Metter-Toledo ReactIR™ 247 using a diamond ATR sampling probe in a flow cell. The COFA stream was collected from the outlet of a 1-inch diameter Karr® column and pumped to the FTIR using a peristaltic pump. The FTIR was calibrated by creating COFA standards spiked with isobutanol and generating a multivariate PLS model.

Example 8

Droplet Size Analysis

This example describes the analysis of liquid extractant droplets after conducting a process stream containing fermentation broth and extractant (COFA) to a static mixer. A PVM® probe (Mettler-Toledo, LLC, Columbus Ohio) was inserted into the process stream approximately 24 hr after the process stream exited the static mixer. The PVM® probe was used to collect images every two minutes during a fermentation run. The images showed the presence of both COFA droplets ranging in size from 50 to 80 µm in diameter and $CO_2$ bubbles ranging in size from 200 and 400 µm in diameter. Monitoring droplet size in the process stream containing fermentation broth and COFA after the static mixer is used to ensure that the droplets remain below a particular average diameter to ensure good mass transfer of isobutanol into the COFA droplets The PVM® probe was also used to image the COFA droplets in the lean broth stream prior to return of the stream to the fermentor. The detection of COFA droplets in this stream is an indication of the amount of COFA returning to the fermentor. The PVM® probe was used to collect an image of the stream every two minutes during a fermentation. Unlike the stream exiting the static mixer, the lean broth stream had fewer and smaller droplets (10-40 µm). These measurements demonstrate the feasibility of using process imaging to monitor the amount of COFA returning to the fermentor.

Real-time average droplet size data from both sample points are used to monitor the phase separation of fermentation broth and COFA. An increase in the concentration or number of small COFA droplets detected in the lean fermentation broth recycle stream (after isobutanol extraction) can be an indicator that the phase separation of fermentation broth and COFA has degraded and too much COFA is exiting the extractor. To improve the quality of the phase separation and reduce the number or concentration of the COFA droplets returning to the fermentor in the lean broth stream, the average COFA droplet size is increased post static mixer.

Additional process variables that can impact average COFA droplet size include the concentration of polysaccharides in the fermentation broth, the ratio of fermentation broth to COFA, and total flow rate through the static mixer. As the fermentation progresses, flow rate and/or fermentation broth to COFA ratios may be changed to maintain a constant average COFA droplet size.

Example 9

Extractor Design

This example describes a method to design a large-scale extractor unit. Data from a pilot-scale extraction is used to estimate the size of the large-scale extractor unit. The effects of flow rate, agitation rate, and the presence or absence of internals on phase separation of the streams of the extractor unit from a pilot-scale extraction are determined The total flow and ratio of fermentation broth flow to extractant flow is varied at fixed temperature over the course of the fermentation, and the conditions under which phase separation discontinues are observed. The maximum achievable flow to the extractor unit per square foot of extractor unit flow surface area is recorded. The following equation is used to determine flow per unit area:

$$U = \frac{F}{A} \quad \text{(Equation 1)}$$

U=flow per unit area (gallons/minute/square foot)
F=total flow of fermentation broth and extractant to the extractor unit (gallons/minute)
A=cross-sectional area in direction of flow (square feet) for an extraction column this is given by $$\frac{\pi D^2}{4}$$

D=column diameter (feet).

The diameter of a large-scale extractor unit is estimated by the expected flow of fermentation broth and extractant to the extractor unit using the following equation:

$$D = \sqrt{\frac{4 F_{large\text{-}scale}}{\pi U}} \quad \text{(Equation 2)}$$

$F_{large\text{-}scale}$=Total flow of fermentation broth and extractant to the large-scale extractor (gallons/minute).

The height of the pilot-scale extractor unit is measured under different flow regimes including different flow rates, with and without internals present, different agitation rates, and at different concentrations of the product alcohol. Using this data, the number of theoretical stages achieved by the height of the extractor unit is estimated using the Kremser Equation (Seader and Henley, *Separation Process Principles*, 2nd edition, John Wiley & Sons, 2006, pp. 358-359):

$$n = \frac{\ln\left[\left(\frac{x_f - \frac{y_s}{m}}{x_n - \frac{y_s}{m}}\right)\left(1 - \frac{1}{E}\right) + \frac{1}{E}\right]}{\ln(E)} \quad \text{(Equation 3)}$$

$$E = \text{extraction factor} = m \frac{F_{broth}}{F_{extractant}}$$

$F_{broth}$=flow of broth to the extractor unit (gallons/minute)
$F_{extractant}$=flow of extractant to the extractor unit (gallons/minute)
m=partition coefficient for product alcohol in fermentation broth and extractant phases (g/L per g/L)
Xf=concentration of product alcohol in fermentation broth feed (g/L)
Xn=concentration of product alcohol in fermentation broth leaving the extractor unit (g/L)
Ys=concentration of product alcohol in extractant entering the extractor unit (g/L)
n=number of theoretical stages achieved by the height of the extractor unit Equation 3 is only valid when E 1.

The height of a theoretical stage for the extractor unit is given by the height of the extraction column used in the pilot-scale extraction divided by the number of theoretical stages realized in a given experiment. The number of theoretical stages required to achieve the separation at large-scale is estimated using the operating conditions expected at large-scale in Equation 4:

$$n = \frac{\ln\left[\left(\frac{x'_f - \frac{y'_s}{m}}{x'_n - \frac{y'_s}{m}}\right)\left(1 - \frac{1}{E'}\right) + \frac{1}{E'}\right]}{\ln(E')} \quad \text{(Equation 4)}$$

where ' indicates the condition of the large-scale extractor unit.

The product of the number of theoretical stages and height of a theoretical stage measured for similar flow conditions provides an estimate of the total height of the large-scale extractor unit. The flows and concentrations expected at a large-scale extractor unit are estimated using a dynamic fermentation model (e.g., Daugulis, et al., Biotech. Bioeng. 27:1345-1356, 1985).

While various embodiments of the present invention have been described herein, it should be understood that they have been presented by way of example only, and not limitation. It will be apparent to persons skilled in the relevant art that various changes in form and detail can be made therein without departing from the spirit and scope of the invention. Thus, the breadth and scope of the present invention should not be limited by any of the described exemplary embodiments, but should be defined only in accordance with the following claims and their equivalents.

All publications, patents and patent applications mentioned in this specification are indicative of the level of skill of those skilled in the art to which this invention pertains, and are herein incorporated by reference to the same extent as if each individual publication, patent or patent application was specifically and individually indicated to be incorporated by reference.

What is claimed:

1. A method for producing and recovering a product alcohol from a fermentation broth comprising:
    (a) providing a feedstock slurry comprising fermentable carbon source, undissolved solids, oil, and water;
    (b) separating the feedstock slurry by three-phase centrifugation to generate (i) an aqueous solution comprising fermentable carbon source, (ii) a wet cake comprising solids, and (iii) an oil stream;
    (c) adding the aqueous solution to a fermentation broth in a fermentor; wherein the fermentation broth comprises a microorganism that produces a product alcohol and whereby a product alcohol is produced;
    (d) conducting the fermentation broth of (c) to one or more external extractors, wherein the fermentation broth is mixed with an extractant forming an aqueous phase and an extractant phase and wherein the extractant phase is maintained as a continuous phase; and
    (e) recovering the product alcohol.

2. The method of claim 1, wherein the one or more external extractors is one or more siphons, decanters, centrifuges, gravity settlers, phase splitters, mixer-settlers, column extractors, centrifugal extractors, agitated extractors, hydrocyclones, spray towers, or combinations thereof.

3. The method of claim 1, wherein the product alcohol is transferred to the extractant phase.

4. The method of claim 3, wherein the product alcohol is recovered from the extractant phase by distillation.

5. The method of claim 1, wherein a portion of the extractant phase is returned to the extractor as reflux.

6. The method of claim 1, wherein the fermentation broth is conducted to the one or more external extractors via a distributor or dispersal device.

7. The method of claim 1, wherein the one or more external extractors comprise internals, exit ports for carbon dioxide, coalescing pads, or combinations thereof.

8. The method of claim 1, wherein the one or more external extractors comprise a conical shape.

9. The method of claim 1, wherein the one or more external extractors comprise a first region of constant diameter and a stepwise increase of diameter to a second region of constant diameter.

10. The method of claim 9, wherein the one or more external extractors further comprise a second stepwise increase of diameter to a third region of constant diameter.

11. The method of claim 1, wherein a heterogeneous mixture comprising the fermentation broth and the extractant is further processed through one or more hydrocyclones.

12. The method of claim 1, wherein the oil stream is hydrolyzed by one or more enzymes to form fatty acids.

13. The method of claim 12, wherein the fatty acids are added to the fermentation broth as the extractant.

14. The method of claim 12, wherein the one or more enzymes is one or more lipases or phospholipases.

15. The method of claim 1, wherein the product alcohol is ethanol, propanol, butanol, pentanol, hexanol, fusel alcohols, or mixtures thereof.

16. The method of claim 1, wherein the microorganism comprises a butanol biosynthetic pathway.

17. The method of claim 16, wherein the butanol biosynthetic pathway is a 1-butanol biosynthetic pathway, a 2-butanol biosynthetic pathway, or an isobutanol biosynthetic pathway.

* * * * *

SEQUENCE LISTING

<160> NUMBER OF SEQ ID NOS: 128

<210> SEQ ID NO 1
<211> LENGTH: 570
<212> TYPE: PRT
<213> ORGANISM: Bacillus subtilis

<400> SEQUENCE: 1

```
Met Thr Lys Ala Thr Lys Glu Gln Lys Ser Leu Val Lys Asn Arg Gly
1               5                   10                  15

Ala Glu Leu Val Val Asp Cys Leu Val Glu Gln Gly Thr His Val
            20                  25                  30

Phe Gly Ile Pro Gly Ala Lys Ile Asp Ala Val Phe Asp Ala Leu Gln
            35                  40                  45

Asp Lys Gly Pro Glu Ile Ile Val Ala Arg His Glu Gln Asn Ala Ala
        50                  55                  60

Phe Met Ala Gln Ala Val Gly Arg Leu Thr Gly Lys Pro Gly Val Val
65                  70                  75                  80

Leu Val Thr Ser Gly Pro Gly Ala Ser Asn Leu Ala Thr Gly Leu Leu
                85                  90                  95

Thr Ala Asn Thr Glu Gly Asp Pro Val Val Ala Leu Ala Gly Asn Val
            100                 105                 110

Ile Arg Ala Asp Arg Leu Lys Arg Thr His Gln Ser Leu Asp Asn Ala
            115                 120                 125

Ala Leu Phe Gln Pro Ile Thr Lys Tyr Ser Val Glu Val Gln Asp Val
        130                 135                 140

Lys Asn Ile Pro Glu Ala Val Thr Asn Ala Phe Arg Ile Ala Ser Ala
145                 150                 155                 160

Gly Gln Ala Gly Ala Ala Phe Val Ser Phe Pro Gln Asp Val Val Asn
                165                 170                 175

Glu Val Thr Asn Thr Lys Asn Val Arg Ala Val Ala Ala Pro Lys Leu
            180                 185                 190

Gly Pro Ala Ala Asp Asp Ala Ile Ser Ala Ala Ile Ala Lys Ile Gln
        195                 200                 205

Thr Ala Lys Leu Pro Val Val Leu Val Gly Met Lys Gly Gly Arg Pro
210                 215                 220

Glu Ala Ile Lys Ala Val Arg Lys Leu Leu Lys Lys Val Gln Leu Pro
225                 230                 235                 240

Phe Val Glu Thr Tyr Gln Ala Ala Gly Thr Leu Ser Arg Asp Leu Glu
                245                 250                 255

Asp Gln Tyr Phe Gly Arg Ile Gly Leu Phe Arg Asn Gln Pro Gly Asp
            260                 265                 270

Leu Leu Leu Glu Gln Ala Asp Val Val Leu Thr Ile Gly Tyr Asp Pro
        275                 280                 285

Ile Glu Tyr Asp Pro Lys Phe Trp Asn Ile Asn Gly Asp Arg Thr Ile
            290                 295                 300

Ile His Leu Asp Glu Ile Ile Ala Asp Ile Asp His Ala Tyr Gln Pro
305                 310                 315                 320

Asp Leu Glu Leu Ile Gly Asp Ile Pro Ser Thr Ile Asn His Ile Glu
                325                 330                 335

His Asp Ala Val Lys Val Glu Phe Ala Glu Arg Glu Gln Lys Ile Leu
            340                 345                 350

Ser Asp Leu Lys Gln Tyr Met His Glu Gly Glu Gln Val Pro Ala Asp
        355                 360                 365

Trp Lys Ser Asp Arg Ala His Pro Leu Glu Ile Val Lys Glu Leu Arg
370                 375                 380

Asn Ala Val Asp Asp His Val Thr Val Thr Cys Asp Ile Gly Ser His
385                 390                 395                 400

Ala Ile Trp Met Ser Arg Tyr Phe Arg Ser Tyr Glu Pro Leu Thr Leu
                405                 410                 415

Met Ile Ser Asn Gly Met Gln Thr Leu Gly Val Ala Leu Pro Trp Ala
```

```
                420           425           430
Ile Gly Ala Ser Leu Val Lys Pro Gly Glu Lys Val Val Ser Val Ser
                435           440           445

Gly Asp Gly Gly Phe Leu Phe Ser Ala Met Glu Leu Glu Thr Ala Val
            450           455           460

Arg Leu Lys Ala Pro Ile Val His Ile Val Trp Asn Asp Ser Thr Tyr
465             470           475               480

Asp Met Val Ala Phe Gln Gln Leu Lys Lys Tyr Asn Arg Thr Ser Ala
                485           490           495

Val Asp Phe Gly Asn Ile Asp Ile Val Lys Tyr Ala Glu Ser Phe Gly
            500           505           510

Ala Thr Gly Leu Arg Val Glu Ser Pro Asp Gln Leu Ala Asp Val Leu
            515           520           525

Arg Gln Gly Met Asn Ala Glu Gly Pro Val Ile Ile Asp Val Pro Val
            530           535           540

Asp Tyr Ser Asp Asn Ile Asn Leu Ala Ser Asp Lys Leu Pro Lys Glu
545             550           555               560

Phe Gly Glu Leu Met Lys Thr Lys Ala Leu
                565           570

<210> SEQ ID NO 2
<211> LENGTH: 1716
<212> TYPE: DNA
<213> ORGANISM: Bacillus subtilis

<400> SEQUENCE: 2
atgttgacaa agcaacaaa agaacaaaaa tcccttgtga aaacagagg ggcggagctt    60 gttgttgatt gcttagtgga gcaaggtgtc acacatgtat ttggcattcc aggtgcaaaa   120
attgatgcgg tatttgacgc tttacaagat aaaggacctg aaattatcgt tgcccggcac   180
gaacaaaacg cagcattcat ggcccaagca gtcggccgtt taactggaaa accgggagtc   240
gtgttagtca catcaggacc gggtgcctct aacttggcaa caggcctgct gacagcgaac   300
actgaaggag accctgtcgt tgcgcttgct ggaaacgtga ccgtgcaga tcgtttaaaa   360 cggacacatc aatctttgga taatgcggcg ctattccagc cgattacaaa atacagtgta   420
gaagttcaag atgtaaaaaa tataccggaa gctgttacaa atgcatttag gatagcgtca   480
gcagggcagg ctggggccgc ttttgtgagc tttccgcaag atgttgtgaa tgaagtcaca   540
aatacgaaaa acgtgcgtgc tgttgcagcg ccaaaactcg gtcctgcagc agatgatgca   600
atcagtgcgg ccatagcaaa aatccaaaca gcaaaacttc ctgtcgtttt ggtcggcatg   660
aaaggcggaa gaccggaagc aattaaagcg gttcgcaagc ttttgaaaaa ggttcagctt   720
ccatttgttg aaacatatca agctgccggt acccttccta gagatttaga ggatcaatat   780
tttggccgta tcggttttgt tcgcaaccag cctggcgatt tactgctaga gcaggcagat   840
gttgttctga cgatcggcta tgacccgatt gaatatgatc cgaaattctg gaatatcaat   900
ggagaccgga caattatcca tttagacgag attatcgctg acattgatca tgcttaccag   960
cctgatcttg aattgatcgg tgacattccg tccacgatca atcatatcga acacgatgct  1020
gtgaaagtgg aatttgcaga gcgtgagcag aaaatccttt ctgatttaaa acaatatatg  1080
catgaaggtg agcaggtgcc tgcagattgg aaatcagaca gagcgcaccc tcttgaaatc  1140
gttaaagagt gcgtaatgc agtcgatgat catgttacag taacttgcga tatcggttcg  1200
cacgccattt ggatgtcacg ttatttccgc agctacgagc cgttaacatt aatgatcagt  1260
```

```
aacggtatgc aaacactcgg cgttgcgctt ccttgggcaa tcggcgcttc attggtgaaa    1320
ccgggagaaa aagtggtttc tgtctctggt gacggcggtt tcttattctc agcaatggaa    1380
ttagagacag cagttcgact aaaagcacca attgtacaca ttgtatggaa cgacagcaca    1440
tatgacatgg ttgcattcca gcaattgaaa aaatataacc gtacatctgc ggtcgatttc    1500
ggaaatatcg atatcgtgaa atatgcggaa agcttcggag caactggctt gcgcgtagaa    1560
tcaccagacc agctggcaga tgttctgcgt caaggcatga acgctgaagg tcctgtcatc    1620
atcgatgtcc cggttgacta cagtgataac attaatttag caagtgacaa gcttccgaaa    1680
gaattcgggg aactcatgaa aacgaaagct ctctag                               1716
```

<210> SEQ ID NO 3
<211> LENGTH: 559
<212> TYPE: PRT
<213> ORGANISM: Klebsiella pneumoniae

<400> SEQUENCE: 3

```
Met Asp Lys Gln Tyr Pro Val Arg Gln Trp Ala His Gly Ala Asp Leu
1               5                   10                  15

Val Val Ser Gln Leu Glu Ala Gln Gly Val Arg Gln Val Phe Gly Ile
                20                  25                  30

Pro Gly Ala Lys Ile Asp Lys Val Phe Asp Ser Leu Leu Asp Ser Ser
            35                  40                  45

Ile Arg Ile Ile Pro Val Arg His Glu Ala Asn Ala Ala Phe Met Ala
        50                  55                  60

Ala Ala Val Gly Arg Ile Thr Gly Lys Ala Gly Val Ala Leu Val Thr
65                  70                  75                  80

Ser Gly Pro Gly Cys Ser Asn Leu Ile Thr Gly Met Ala Thr Ala Asn
                85                  90                  95

Ser Glu Gly Asp Pro Val Val Ala Leu Gly Gly Ala Val Lys Arg Ala
            100                 105                 110

Asp Lys Ala Lys Gln Val His Gln Ser Met Asp Thr Val Ala Met Phe
        115                 120                 125

Ser Pro Val Thr Lys Tyr Ala Ile Glu Val Thr Ala Pro Asp Ala Leu
    130                 135                 140

Ala Glu Val Val Ser Asn Ala Phe Arg Ala Ala Glu Gln Gly Arg Pro
145                 150                 155                 160

Gly Ser Ala Phe Val Ser Leu Pro Gln Asp Val Val Asp Gly Pro Val
                165                 170                 175

Ser Gly Lys Val Leu Pro Ala Ser Gly Ala Pro Gln Met Gly Ala Ala
            180                 185                 190

Pro Asp Asp Ala Ile Asp Gln Val Ala Lys Leu Ile Ala Gln Ala Lys
        195                 200                 205

Asn Pro Ile Phe Leu Leu Gly Leu Met Ala Ser Gln Pro Glu Asn Ser
    210                 215                 220

Lys Ala Leu Arg Arg Leu Leu Glu Thr Ser His Ile Pro Val Thr Ser
225                 230                 235                 240

Thr Tyr Gln Ala Ala Gly Ala Val Asn Gln Asp Asn Phe Ser Arg Phe
                245                 250                 255

Ala Gly Arg Val Gly Leu Phe Asn Asn Gln Ala Gly Asp Arg Leu Leu
            260                 265                 270

Gln Leu Ala Asp Leu Val Ile Cys Ile Gly Tyr Ser Pro Val Glu Tyr
        275                 280                 285

Glu Pro Ala Met Trp Asn Ser Gly Asn Ala Thr Leu Val His Ile Asp
```

```
                    290                 295                 300

Val Leu Pro Ala Tyr Glu Glu Arg Asn Tyr Thr Pro Asp Val Glu Leu
305                 310                 315                 320

Val Gly Asp Ile Ala Gly Thr Leu Asn Lys Leu Ala Gln Asn Ile Asp
            325                 330                 335

His Arg Leu Val Leu Ser Pro Gln Ala Ala Glu Ile Leu Arg Asp Arg
                340                 345                 350

Gln His Gln Arg Glu Leu Leu Asp Arg Arg Gly Ala Gln Leu Asn Gln
            355                 360                 365

Phe Ala Leu His Pro Leu Arg Ile Val Arg Ala Met Gln Asp Ile Val
370                 375                 380

Asn Ser Asp Val Thr Leu Thr Val Asp Met Gly Ser Phe His Ile Trp
385                 390                 395                 400

Ile Ala Arg Tyr Leu Tyr Thr Phe Arg Ala Arg Gln Val Met Ile Ser
                405                 410                 415

Asn Gly Gln Gln Thr Met Gly Val Ala Leu Pro Trp Ala Ile Gly Ala
            420                 425                 430

Trp Leu Val Asn Pro Glu Arg Lys Val Val Ser Val Ser Gly Asp Gly
                435                 440                 445

Gly Phe Leu Gln Ser Ser Met Glu Leu Glu Thr Ala Val Arg Leu Lys
            450                 455                 460

Ala Asn Val Leu His Leu Ile Trp Val Asp Asn Gly Tyr Asn Met Val
465                 470                 475                 480

Ala Ile Gln Glu Glu Lys Lys Tyr Gln Arg Leu Ser Gly Val Glu Phe
                485                 490                 495

Gly Pro Met Asp Phe Lys Ala Tyr Ala Glu Ser Phe Gly Ala Lys Gly
            500                 505                 510

Phe Ala Val Glu Ser Ala Glu Ala Leu Glu Pro Thr Leu Arg Ala Ala
                515                 520                 525

Met Asp Val Asp Gly Pro Ala Val Val Ala Ile Pro Val Asp Tyr Arg
            530                 535                 540

Asp Asn Pro Leu Leu Met Gly Gln Leu His Leu Ser Gln Ile Leu
545                 550                 555

<210> SEQ ID NO 4
<211> LENGTH: 2055
<212> TYPE: DNA
<213> ORGANISM: Klebsiella pneumoniae

<400> SEQUENCE: 4
tcgaccacgg ggtgctgacc ttcggcgaaa ttcacaagct gatgatcgac ctgcccgccg      60
acagcgcgtt cctgcaggct aatctgcatc ccgataatct cgatgccgcc atccgttccg     120
tagaaagtta agggggtcac atggacaaac agtatccggt acgccagtgg gcgcacggcg     180
ccgatctcgt cgtcagtcag ctggaagctc agggagtacg ccaggtgttc ggcatccccg     240
gcgccaaaat cgacaaggtc tttgattcac tgctggattc ctccattcgc attattccgg     300
tacgccacga agccaacgcc gcatttatgg ccgccgccgt cggacgcatt accggcaaag     360
cgggcgtggc gctggtcacc tccgtccggg ctgttccaa cctgatcacc ggcatggcca     420
ccgcgaacag cgaaggcgac ccggtggtgg ccctgggcgg cgcggtaaaa cgcgccgata     480
aagcgaagca ggtccaccag agtatggata cggtggcgat gttcagcccg gtcaccaaat     540
acgccatcga ggtgacggcg ccggatgcgc tggcggaagt ggtctccaac gccttccgcg     600
ccgccgagca gggccggccg ggcagcgcgt tcgttagcct gccgcaggat gtggtcgatg     660
```

```
gcccggtcag cggcaaagtg ctgccggcca gcggggcccc gcagatgggc gccgcgccgg    720
atgatgccat cgaccaggtg gcgaagctta tcgcccaggc gaagaacccg atcttcctgc    780
tcggcctgat ggccagccag ccggaaaaca gcaaggcgct gcgccgtttg ctggagacca    840
gccatattcc agtcaccagc acctatcagg ccgccggagc ggtgaatcag gataacttct    900
ctcgcttcgc cggccgggtt gggctgttta caaccaggc cggggaccgt ctgctgcagc    960
tcgccgacct ggtgatctgc atcggctaca gcccggtgga atacgaaccg gcgatgtgga   1020
acagcggcaa cgcgacgctg gtgcacatcg acgtgctgcc cgcctatgaa gagcgcaact   1080
acaccccgga tgtcgagctg gtgggcgata tcgccggcac tctcaacaag ctggcgcaaa   1140
atatcgatca tcggctggtg ctctccccgc aggcggcgga gatcctccgc gaccgccagc   1200
accagcgcga gctgctggac cgccgcggcg cgcagctcaa ccagtttgcc ctgcatcccc   1260
tgcgcatcgt tcgcgccatg caggatatcg tcaacagcga cgtcacgttg accgtggaca   1320
tgggcagctt ccatatctgg attgcccgct acctgtacac gttccgcgcc cgtcaggtga   1380
tgatctccaa cggccagcag accatgggcg tcgccctgcc ctgggctatc ggcgcctggc   1440
tggtcaatcc tgagcgcaaa gtggtctccg tctccggcga cggcggcttc ctgcagtcga   1500
gcatggagct ggagaccgcc gtccgcctga agccaacgt gctgcatctt atctgggtcg   1560
ataacggcta acatggtc gctatccagg aagagaaaaa atatcagcgc ctgtccggcg   1620
tcgagtttgg gccgatggat tttaaagcct atgccgaatc cttcggcgcg aaagggtttg   1680
ccgtggaaag cgccgaggcg ctggagccga ccctgcgcgc ggcgatggac gtcgacggcc   1740
cggcggtagt ggccatcccg gtggattatc gcgataaccc gctgctgatg ggccagctgc   1800
atctgagtca gattctgtaa gtcatcacaa taaggaaaga aaatgaaaa aagtcgcact   1860
tgttaccggc gccggccagg ggattggtaa agctatcgcc cttcgtctgg tgaaggatgg   1920
atttgccgtg gccattgccg attataacga cgccaccgcc aaagcggtcg cctccgaaat   1980
caaccaggcc ggcggccgcg ccatggcggt gaaagtggat gtttctgacc gcgaccaggt   2040
atttgccgcc gtcga                                                    2055
```

<210> SEQ ID NO 5
<211> LENGTH: 554
<212> TYPE: PRT
<213> ORGANISM: Lactococcus lactis

<400> SEQUENCE: 5

Met Ser Glu Lys Gln Phe Gly Ala Asn Leu Val Val Asp Ser Leu Ile
1               5                   10                  15

Asn His Lys Val Lys Tyr Val Phe Gly Ile Pro Gly Ala Lys Ile Asp
                20                  25                  30

Arg Val Phe Asp Leu Leu Glu Asn Glu Glu Gly Pro Gln Met Val Val
            35                  40                  45

Thr Arg His Glu Gln Gly Ala Ala Phe Met Ala Gln Ala Val Gly Arg
        50                  55                  60

Leu Thr Gly Glu Pro Gly Val Val Val Thr Ser Gly Pro Gly Val
65                  70                  75                  80

Ser Asn Leu Ala Thr Pro Leu Leu Thr Ala Thr Ser Glu Gly Asp Ala
                85                  90                  95

Ile Leu Ala Ile Gly Gly Gln Val Lys Arg Ser Asp Arg Leu Lys Arg
            100                 105                 110

Ala His Gln Ser Met Asp Asn Ala Gly Met Met Gln Ser Ala Thr Lys

-continued

```
            115                 120                 125
Tyr Ser Ala Glu Val Leu Asp Pro Asn Thr Leu Ser Glu Ser Ile Ala
            130                 135                 140
Asn Ala Tyr Arg Ile Ala Lys Ser Gly His Pro Gly Ala Thr Phe Leu
145                 150                 155                 160
Ser Ile Pro Gln Asp Val Thr Asp Ala Glu Val Ser Ile Lys Ala Ile
            165                 170                 175
Gln Pro Leu Ser Asp Pro Lys Met Gly Asn Ala Ser Ile Asp Asp Ile
            180                 185                 190
Asn Tyr Leu Ala Gln Ala Ile Lys Asn Ala Val Leu Pro Val Ile Leu
            195                 200                 205
Val Gly Ala Gly Ala Ser Asp Ala Lys Val Ala Ser Ser Leu Arg Asn
            210                 215                 220
Leu Leu Thr His Val Asn Ile Pro Val Val Glu Thr Phe Gln Gly Ala
225                 230                 235                 240
Gly Val Ile Ser His Asp Leu Glu His Thr Phe Tyr Gly Arg Ile Gly
            245                 250                 255
Leu Phe Arg Asn Gln Pro Gly Asp Met Leu Leu Lys Arg Ser Asp Leu
            260                 265                 270
Val Ile Ala Val Gly Tyr Asp Pro Ile Glu Tyr Glu Ala Arg Asn Trp
            275                 280                 285
Asn Ala Glu Ile Asp Ser Arg Ile Ile Val Ile Asp Asn Ala Ile Ala
            290                 295                 300
Glu Ile Asp Thr Tyr Tyr Gln Pro Glu Arg Glu Leu Ile Gly Asp Ile
305                 310                 315                 320
Ala Ala Thr Leu Asp Asn Leu Leu Pro Ala Val Arg Gly Tyr Lys Ile
            325                 330                 335
Pro Lys Gly Thr Lys Asp Tyr Leu Asp Gly Leu His Glu Val Ala Glu
            340                 345                 350
Gln His Glu Phe Asp Thr Glu Asn Thr Glu Glu Gly Arg Met His Pro
            355                 360                 365
Leu Asp Leu Val Ser Thr Phe Gln Glu Ile Val Lys Asp Asp Glu Thr
            370                 375                 380
Val Thr Val Asp Val Gly Ser Leu Tyr Ile Trp Met Ala Arg His Phe
385                 390                 395                 400
Lys Ser Tyr Glu Pro Arg His Leu Leu Phe Ser Asn Gly Met Gln Thr
            405                 410                 415
Leu Gly Val Ala Leu Pro Trp Ala Ile Thr Ala Ala Leu Leu Arg Pro
            420                 425                 430
Gly Lys Lys Val Tyr Ser His Ser Gly Asp Gly Gly Phe Leu Phe Thr
            435                 440                 445
Gly Gln Glu Leu Glu Thr Ala Val Arg Leu Asn Leu Pro Ile Val Gln
            450                 455                 460
Ile Ile Trp Asn Asp Gly His Tyr Asp Met Val Lys Phe Gln Glu Glu
465                 470                 475                 480
Met Lys Tyr Gly Arg Ser Ala Ala Val Asp Phe Gly Tyr Val Asp Tyr
            485                 490                 495
Val Lys Tyr Ala Glu Ala Met Arg Ala Lys Gly Tyr Arg Ala His Ser
            500                 505                 510
Lys Glu Glu Leu Ala Glu Ile Leu Lys Ser Ile Pro Asp Thr Thr Gly
            515                 520                 525
Pro Val Val Ile Asp Val Pro Leu Asp Tyr Ser Asp Asn Ile Lys Leu
            530                 535                 540
```

Ala Glu Lys Leu Leu Pro Glu Glu Phe Tyr
545                 550

<210> SEQ ID NO 6
<211> LENGTH: 3220
<212> TYPE: DNA
<213> ORGANISM: Lactococcus lactis

<400> SEQUENCE: 6

```
tagatccgga aacaactgat tacctgagtt aacttagcag aaattgcaga agataacggt      60
aatttggatg aagcattaaa ttacctttat caaattccgg tgaatgatga aaattatatt     120
gctgctttaa tcaaaattgc tgacttatat caatttgaag ttgattttga aacagcaatt     180
tctaagttag aagaagcaag agaattatcg gattctcctc tgattacttt tgctttggct     240
gagtcctact ttgaacaagg tgattattca gctgccatta ccgaatatgc aaaactttca     300
gaacgaaaaa ttttacatga aacaaaaatt tctatttatc aaagaattgg tgactcttat     360
gcccaattag gtaattttga gaatgccata tcatttcttg aaaaatcact tgaatttgat     420
gaaaaaccgg aaaccttgta taaaattgct cttctttatg agaaactca taatgaaaca      480
agagccattg ctaatttcaa acggttagaa aaaatggatg ttgaattttt gaactatgaa     540
ttagcctatg cccaaaccct agaagctaat caagaattta agctgcact agaaatggca      600
aagaaaggga tgaaaaaaaa tcctaatgcc gttcctctct acacttcgc ttcaaaaatt      660
tgtttcaaac ttaaggacaa agctgcagca gaacgttatc tcgtggatgc tttaaattta     720
ccagaattac atgacgaaac agtcttttg cttgctaatt tatacttcaa cgaagaagat      780
tttgaagctg tcattaatct tgaagagctt ttagaagatg aacatttatt agctaaatgg     840
cttttttgcag gagcacataa agctttggaa aatgattctg aagcggctgc tttgtatgaa     900
gaactcattc aaaccaatct gtcagagaat ccagagtttt tagaagacta tattgatttt     960
cttaaagaaa ttggtcaaat ttctaaaaca gaaccaatta ttgaacaata tttgaacttt    1020
gttccagatg atgaaaatat gagaaattta ctgacagact taaaaaataa ttactgacaa    1080
agctgtcagt aattatttt attgtaagct agaaaattca aaaacttgcg tcaaaataat    1140
tgtaaaaggt tctattatct gataaaatga ttgtgaagta atccaagaga ttatgaaata    1200
tgaattagaa caaatagagg taaaataaaa aatgtctgag aaacaatttg gggcgaactt    1260
ggttgtcgat agtttgatta accataaagt gaagtatgta tttgggattc caggagcaaa    1320
aattgaccgg ttttttgatt tattagaaaa tgaagaaggc cctcaaatgg tcgtgactcg    1380
tcatgagcaa ggagctgctt tcatggctca agctgtcggt cgtttaactg gcgaacctgg    1440
tgtagtagtt gttacgagtg ggcctggtgt atcaaacctt gcgactccgc ttttgaccgc    1500
gacatcagaa ggtgatgcta tttttggcta tcggtggaca agttaaacga agtgaccgtct    1560
taaacgtgcg caccaatcaa tggataatgc tggaatgatg caatcagcaa caaaatattc    1620
agcagaagtt cttgaccccta atacactttc tgaatcaatt gccaacgctt atcgtattgc    1680
aaaatcagga catccaggtg caactttctt atcaatcccc caagatgtaa cggatgccga    1740
agtatcaatc aaagccattc aaccactttc agacctaaa atggggaatg cctctattga     1800
tgacattaat tatttagcac aagcaattaa aaatgctgta ttgccagtaa ttttggttgg    1860
agctggtgct tcagatgcta agtcgcttat atccttgcgt aatctattga ctcatgttaa    1920
tattcctgtc gttgaaacat tccaaggtgc agggggtatt tcacatgatt tagaacatac    1980
ttttttatgga cgtatcggtc ttttccgcaa tcaaccaggc gatatgcttc tgaaacgttc    2040
```

```
tgaccttgtt attgctgttg gttatgaccc aattgaatat gaagctcgta actggaatgc   2100
agaaattgat agtcgaatta tcgttattga taatgccatt gctgaaattg atacttacta   2160
ccaaccagag cgtgaattaa ttggtgatat cgcagcaaca ttggataatc ttttaccagc   2220
tgttcgtggc tacaaaattc aaaaggaac aaaagattat ctcgatggcc ttcatgaagt    2280
tgctgagcaa cacgaatttg atactgaaaa tactgaagaa ggtagaatgc accctcttga   2340
tttggtcagc actttccaag aaatcgtcaa ggatgatgaa acagtaaccg ttgacgtagg   2400
ttcactctac atttggatgg cacgtcattt caaatcatac gaaccacgtc atctcctctt   2460
ctcaaacgga atgcaaacac tcggagttgc acttccttgg gcaattacag ccgcattgtt   2520
gcgcccaggt aaaaagttt attcacactc tggtgatgga ggcttccttt tcacagggca    2580
agaattggaa acagctgtac gtttgaatct tccaatcgtt caaattatct ggaatgacgg   2640
ccattatgat atggttaaat tccaagaaga aatgaaatat ggtcgttcag cagccgttga   2700
ttttggctat gttgattacg taaaatgc tgaagcaatg agagcaaaag gttaccgtgc     2760
acacagcaaa gaagaacttg ctgaaattct caaatcaatc ccagatacta ctggaccggt   2820
ggtaattgac gttccttggg actattctga taacattaaa ttagcagaaa aattattgcc   2880
tgaagagttt tattgattac aatcaagcaa tttgtggcat aacaaaataa agaagaagg    2940 ccttgaacac ctaagcgttc agggcctttt tttgtgaaat aaattagatg aaattacaa    3000 tgagttttgt gaaactagct tctagttgt gaaaaattgc ctataattgc cgaataaaaa    3060
tacccattta ccactccaag aggatgcttc aaattagcta ataccgtt ttagaggatg     3120 cgtaaaaaca acaaagagg atgagtatag aacgataaaa cttttttatg ataggttgag   3180
agaattgaat ataaaatata ataagtagaa ggcagcaatt                         3220
```

<210> SEQ ID NO 7
<211> LENGTH: 491
<212> TYPE: PRT
<213> ORGANISM: Escherichia coli

<400> SEQUENCE: 7

```
Met Ala Asn Tyr Phe Asn Thr Leu Asn Leu Arg Gln Gln Leu Ala Gln
1               5                   10                  15

Leu Gly Lys Cys Arg Phe Met Gly Arg Asp Glu Phe Ala Asp Gly Ala
            20                  25                  30

Ser Tyr Leu Gln Gly Lys Lys Val Ile Val Gly Cys Gly Ala Gln
        35                  40                  45

Gly Leu Asn Gln Gly Leu Asn Met Arg Asp Ser Gly Leu Asp Ile Ser
    50                  55                  60

Tyr Ala Leu Arg Lys Glu Ala Ile Ala Glu Lys Arg Ala Ser Trp Arg
65                  70                  75                  80

Lys Ala Thr Glu Asn Gly Phe Lys Val Gly Thr Tyr Glu Glu Leu Ile
                85                  90                  95

Pro Gln Ala Asp Leu Val Ile Asn Leu Thr Pro Asp Lys Gln His Ser
            100                 105                 110

Asp Val Val Arg Thr Val Gln Pro Leu Met Lys Asp Gly Ala Ala Leu
        115                 120                 125

Gly Tyr Ser His Gly Phe Asn Ile Val Glu Val Gly Glu Gln Ile Arg
    130                 135                 140

Lys Asp Ile Thr Val Val Met Val Ala Pro Lys Cys Pro Gly Thr Glu
145                 150                 155                 160
```

```
Val Arg Glu Glu Tyr Lys Arg Gly Phe Gly Val Pro Thr Leu Ile Ala
                165                 170                 175

Val His Pro Glu Asn Asp Pro Lys Gly Glu Gly Met Ala Ile Ala Lys
            180                 185                 190

Ala Trp Ala Ala Thr Gly Gly His Arg Ala Gly Val Leu Glu Ser
        195                 200                 205

Ser Phe Val Ala Glu Val Lys Ser Asp Leu Met Gly Glu Gln Thr Ile
    210                 215                 220

Leu Cys Gly Met Leu Gln Ala Gly Ser Leu Leu Cys Phe Asp Lys Leu
225                 230                 235                 240

Val Glu Glu Gly Thr Asp Pro Ala Tyr Ala Glu Lys Leu Ile Gln Phe
                245                 250                 255

Gly Trp Glu Thr Ile Thr Glu Ala Leu Lys Gln Gly Gly Ile Thr Leu
            260                 265                 270

Met Met Asp Arg Leu Ser Asn Pro Ala Lys Leu Arg Ala Tyr Ala Leu
        275                 280                 285

Ser Glu Gln Leu Lys Glu Ile Met Ala Pro Leu Phe Gln Lys His Met
    290                 295                 300

Asp Asp Ile Ile Ser Gly Glu Phe Ser Ser Gly Met Met Ala Asp Trp
305                 310                 315                 320

Ala Asn Asp Asp Lys Lys Leu Leu Thr Trp Arg Glu Glu Thr Gly Lys
                325                 330                 335

Thr Ala Phe Glu Thr Ala Pro Gln Tyr Glu Gly Lys Ile Gly Glu Gln
            340                 345                 350

Glu Tyr Phe Asp Lys Gly Val Leu Met Ile Ala Met Val Lys Ala Gly
        355                 360                 365

Val Glu Leu Ala Phe Glu Thr Met Val Asp Ser Gly Ile Ile Glu Glu
    370                 375                 380

Ser Ala Tyr Tyr Glu Ser Leu His Glu Leu Pro Leu Ile Ala Asn Thr
385                 390                 395                 400

Ile Ala Arg Lys Arg Leu Tyr Glu Met Asn Val Val Ile Ser Asp Thr
                405                 410                 415

Ala Glu Tyr Gly Asn Tyr Leu Phe Ser Tyr Ala Cys Val Pro Leu Leu
            420                 425                 430

Lys Pro Phe Met Ala Glu Leu Gln Pro Gly Asp Leu Gly Lys Ala Ile
        435                 440                 445

Pro Glu Gly Ala Val Asp Asn Gly Gln Leu Arg Asp Val Asn Glu Ala
    450                 455                 460

Ile Arg Ser His Ala Ile Glu Gln Val Gly Lys Lys Leu Arg Gly Tyr
465                 470                 475                 480

Met Thr Asp Met Lys Arg Ile Ala Val Ala Gly
                485                 490

<210> SEQ ID NO 8
<211> LENGTH: 1476
<212> TYPE: DNA
<213> ORGANISM: Escherichia coli

<400> SEQUENCE: 8
atggctaact acttcaatac actgaatctg cgccagcagc tggcacagct gggcaaatgt      60
cgctttatgg ccgcgatga attcgccgat ggcgcgagct accttcaggg taaaaaagta     120
gtcatcgtcg gctgtggcgc acagggtctg aaccagggcc tgaacatgcg tgattctggt     180
ctcgatatct cctacgctct gcgtaaagaa gcgattgccg agaagcgcgc gtcctggcgt     240
```

```
aaagcgaccg aaaatggttt taaagtgggt acttacgaag aactgatccc acaggcggat    300
ctggtgatta acctgacgcc ggacaagcag cactctgatg tagtgcgcac cgtacagcca    360
ctgatgaaag acggcgcggc gctgggctac tcgcacggtt tcaacatcgt cgaagtgggc    420
gagcagatcc gtaaagatat caccgtagtg atggttgcgc cgaaatgccc aggcaccgaa    480
gtgcgtgaag agtacaaacg tgggttcggc gtaccgacgc tgattgccgt tcacccggaa    540
aacgatccga aaggcgaagg catggcgatt gccaaagcct gggcggctgc aaccggtggt    600
caccgtgcgg gtgtgctgga atcgtccttc gttgcggaag tgaaatctga cctgatgggc    660
gagcaaacca tcctgtgcgg tatgttgcag gctggctctc tgctgtgctt cgacaagctg    720
gtggaagaag gtaccgatcc agcatacgca gaaaaactga ttcagttcgg ttgggaaacc    780
atcaccgaag cactgaaaca gggcggcatc accctgatga tggaccgtct ctctaacccg    840
gcgaaactgc gtgcttatgc gctttctgaa cagctgaaag agatcatggc accctgttc    900
cagaaacata tggacgacat catctccggc gaattctctt ccggtatgat ggcggactgg    960
gccaacgatg ataagaaact gctgacctgg cgtgaagaga ccggcaaaac cgcgtttgaa   1020
accgcgccgc agtatgaagg caaaatcggc gagcaggagt acttcgataa aggcgtactg   1080
atgattgcga tggtgaaagc gggcgttgaa ctggcgttcg aaaccatggt cgattccggc   1140
atcattgaag agtctgcata ttatgaatca ctgcacgagc tgccgctgat tgccaacacc   1200
atcgcccgta agcgtctgta cgaaatgaac gtggttatct ctgataccgc tgagtacggt   1260
aactatctgt tctcttacgc ttgtgtgccg ttgctgaaac cgtttatggc agagctgcaa   1320
ccgggcgacc tgggtaaagc tattccggaa ggcgcggtag ataacgggca actgcgtgat   1380
gtgaacgaag cgattcgcag ccatgcgatt gagcaggtag gtaagaaact gcgcggctat   1440
atgacagata tgaaacgtat tgctgttgcg ggttaa                             1476

<210> SEQ ID NO 9
<211> LENGTH: 395
<212> TYPE: PRT
<213> ORGANISM: Saccharomyces cerevisiae

<400> SEQUENCE: 9

Met Leu Arg Thr Gln Ala Ala Arg Leu Ile Cys Asn Ser Arg Val Ile
1               5                   10                  15

Thr Ala Lys Arg Thr Phe Ala Leu Ala Thr Arg Ala Ala Ala Tyr Ser
            20                  25                  30

Arg Pro Ala Ala Arg Phe Val Lys Pro Met Ile Thr Thr Arg Gly Leu
        35                  40                  45

Lys Gln Ile Asn Phe Gly Gly Thr Val Glu Thr Val Tyr Glu Arg Ala
    50                  55                  60

Asp Trp Pro Arg Glu Lys Leu Leu Asp Tyr Phe Lys Asn Asp Thr Phe
65                  70                  75                  80

Ala Leu Ile Gly Tyr Gly Ser Gln Gly Tyr Gly Gln Gly Leu Asn Leu
                85                  90                  95

Arg Asp Asn Gly Leu Asn Val Ile Ile Gly Val Arg Lys Asp Gly Ala
            100                 105                 110

Ser Trp Lys Ala Ala Ile Glu Asp Gly Trp Val Pro Gly Lys Asn Leu
        115                 120                 125

Phe Thr Val Glu Asp Ala Ile Lys Arg Gly Ser Tyr Val Met Asn Leu
    130                 135                 140

Leu Ser Asp Ala Ala Gln Ser Glu Thr Trp Pro Ala Ile Lys Pro Leu
145                 150                 155                 160
```

Leu Thr Lys Gly Lys Thr Leu Tyr Phe Ser His Gly Phe Ser Pro Val
            165                 170                 175

Phe Lys Asp Leu Thr His Val Glu Pro Pro Lys Asp Leu Asp Val Ile
            180                 185                 190

Leu Val Ala Pro Lys Gly Ser Gly Arg Thr Val Arg Ser Leu Phe Lys
            195                 200                 205

Glu Gly Arg Gly Ile Asn Ser Ser Tyr Ala Val Trp Asn Asp Val Thr
        210                 215                 220

Gly Lys Ala His Glu Lys Ala Gln Ala Leu Ala Val Ala Ile Gly Ser
225                 230                 235                 240

Gly Tyr Val Tyr Gln Thr Thr Phe Glu Arg Glu Val Asn Ser Asp Leu
            245                 250                 255

Tyr Gly Glu Arg Gly Cys Leu Met Gly Gly Ile His Gly Met Phe Leu
            260                 265                 270

Ala Gln Tyr Asp Val Leu Arg Glu Asn Gly His Ser Pro Ser Glu Ala
            275                 280                 285

Phe Asn Glu Thr Val Glu Glu Ala Thr Gln Ser Leu Tyr Pro Leu Ile
            290                 295                 300

Gly Lys Tyr Gly Met Asp Tyr Met Tyr Asp Ala Cys Ser Thr Thr Ala
305                 310                 315                 320

Arg Arg Gly Ala Leu Asp Trp Tyr Pro Ile Phe Lys Asn Ala Leu Lys
            325                 330                 335

Pro Val Phe Gln Asp Leu Tyr Glu Ser Thr Lys Asn Gly Thr Glu Thr
            340                 345                 350

Lys Arg Ser Leu Glu Phe Asn Ser Gln Pro Asp Tyr Arg Glu Lys Leu
            355                 360                 365

Glu Lys Glu Leu Asp Thr Ile Arg Asn Met Glu Ile Trp Lys Val Gly
            370                 375                 380

Lys Glu Val Arg Lys Leu Arg Pro Glu Asn Gln
385                 390                 395

<210> SEQ ID NO 10
<211> LENGTH: 1188
<212> TYPE: DNA
<213> ORGANISM: Saccharomyces cerevisiae

<400> SEQUENCE: 10
atgttgagaa ctcaagccgc cagattgatc tgcaactccc gtgtcatcac tgctaagaga      60
acctttgctt tggccacccg tgctgctgct tacagcagac cagctgcccg tttcgttaag     120
ccaatgatca ctacccgtgg tttgaagcaa atcaacttcg gtggtactgt tgaaaccgtc     180
tacgaaagag ctgactggcc aagagaaaag ttgttggact acttcaagaa cgacactttt     240
gctttgatcg gttacggttc ccaaggttac ggtcaaggtt tgaacttgag agacaacggt     300
ttgaacgtta tcattggtgt ccgtaaagat ggtgcttctt ggaaggctgc catcgaagac     360
ggttgggttc aggcaagaa cttgttcact gttgaagatg ctatcaagag aggtagttac     420
gttatgaact tgttgtccga tgccgctcaa tcagaaacct ggcctgctat caagccattg     480
ttgaccaagg gtaagacttt gtacttctcc cacggtttct ccccagtctt caaggacttg     540
actcacgttg aaccaccaaa ggacttagat gttatcttgg ttgctccaaa gggttccggt     600
agaactgtca gatctttgtt caaggaaggt cgtggtatta actcttctta cgccgtctgg     660
aacgatgtca ccgtaaggc tcacgaaaag gcccaagctt tggccgttgc cattggttcc     720
ggttacgttt accaaaccac tttcgaaaga gaagtcaact ctgacttgta cggtgaaaga     780

-continued

```
ggttgtttaa tgggtggtat ccacggtatg ttcttggctc aatacgacgt cttgagagaa    840
aacggtcact ccccatctga agctttcaac gaaaccgtcg aagaagctac ccaatctcta    900
tacccattga tcggtaagta cggtatggat tacatgtacg atgcttgttc caccaccgcc    960
agaagaggtg ctttggactg gtacccaatc ttcaagaatg ctttgaagcc tgttttccaa   1020
gacttgtacg aatctaccaa gaacggtacc gaaaccaaga gatctttgga attcaactct   1080
caacctgact acagagaaaa gctagaaaag gaattagaca ccatcagaaa catggaaatc   1140
tggaaggttg gtaaggaagt cagaaagttg agaccagaaa accaataa                1188
```

<210> SEQ ID NO 11
<211> LENGTH: 330
<212> TYPE: PRT
<213> ORGANISM: Methanococcus maripaludis
<400> SEQUENCE: 11

```
Met Lys Val Phe Tyr Asp Ser Asp Phe Lys Leu Asp Ala Leu Lys Glu
1               5                   10                  15

Lys Thr Ile Ala Val Ile Gly Tyr Gly Ser Gln Gly Arg Ala Gln Ser
            20                  25                  30

Leu Asn Met Lys Asp Ser Gly Leu Asn Val Val Gly Leu Arg Lys
        35                  40                  45

Asn Gly Ala Ser Trp Asn Asn Ala Lys Ala Asp Gly His Asn Val Met
    50                  55                  60

Thr Ile Glu Glu Ala Ala Glu Lys Ala Asp Ile Ile His Ile Leu Ile
65                  70                  75                  80

Pro Asp Glu Leu Gln Ala Glu Val Tyr Glu Ser Gln Ile Lys Pro Tyr
                85                  90                  95

Leu Lys Glu Gly Lys Thr Leu Ser Phe Ser His Gly Phe Asn Ile His
            100                 105                 110

Tyr Gly Phe Ile Val Pro Pro Lys Gly Val Asn Val Leu Val Ala
        115                 120                 125

Pro Lys Ser Pro Gly Lys Met Val Arg Arg Thr Tyr Glu Glu Gly Phe
    130                 135                 140

Gly Val Pro Gly Leu Ile Cys Ile Glu Ile Asp Ala Thr Asn Asn Ala
145                 150                 155                 160

Phe Asp Ile Val Ser Ala Met Ala Lys Gly Ile Gly Leu Ser Arg Ala
                165                 170                 175

Gly Val Ile Gln Thr Thr Phe Lys Glu Glu Thr Glu Thr Asp Leu Phe
            180                 185                 190

Gly Glu Gln Ala Val Leu Cys Gly Gly Val Thr Glu Leu Ile Lys Ala
        195                 200                 205

Gly Phe Glu Thr Leu Val Glu Ala Gly Tyr Ala Pro Glu Met Ala Tyr
    210                 215                 220

Phe Glu Thr Cys His Glu Leu Lys Leu Ile Val Asp Leu Ile Tyr Gln
225                 230                 235                 240

Lys Gly Phe Lys Asn Met Trp Asn Asp Val Ser Asn Thr Ala Glu Tyr
                245                 250                 255

Gly Gly Leu Thr Arg Arg Ser Arg Ile Val Thr Ala Asp Ser Lys Ala
            260                 265                 270

Ala Met Lys Glu Ile Leu Arg Glu Ile Gln Asp Gly Arg Phe Thr Lys
        275                 280                 285

Glu Phe Leu Leu Glu Lys Gln Val Ser Tyr Ala His Leu Lys Ser Met
    290                 295                 300
```

```
Arg Arg Leu Glu Gly Asp Leu Gln Ile Glu Glu Val Gly Ala Lys Leu
305                 310                 315                 320

Arg Lys Met Cys Gly Leu Glu Lys Glu Glu
                325                 330
```

<210> SEQ ID NO 12
<211> LENGTH: 993
<212> TYPE: DNA
<213> ORGANISM: Methanococcus maripaludis

<400> SEQUENCE: 12

```
atgaaggtat tctatgactc agattttaaa ttagatgctt taaaagaaaa aacaattgca      60
gtaatcggtt atggaagtca aggtagggca cagtccttaa acatgaaaga cagcggatta     120
aacgttgttg ttggtttaag aaaaaacggt gcttcatgga caacgctaaa gcagacggt     180
cacaatgtaa tgaccattga agaagctgct gaaaaagcgg acatcatcca tcttaata      240
cctgatgaat acaggcaga agtttatgaa agccagataa aaccataacct aaagaagga     300
aaaacactaa gcttttcaca tggttttaac atccactatg gattcattgt tccaccaaaa     360
ggagttaacg tggttttagt tgctccaaaa tcacctggaa aatggttag aagaacatac     420
gaagaaggtt tcggtgttcc aggtttaatc tgtattgaaa ttgatgcaac aaacaacgca     480
tttgatattg tttcagcaat ggcaaaagga atcggtttat caagagctgg agttatccag     540
acaactttca agaagaaac agaaactgac cttttcggtg aacaagctgt tttatgcggt     600
ggagttaccg aattaatcaa ggcaggattt gaaacactcg ttgaagcagg atacgcacca     660
gaaatggcat actttgaaac ctgccacgaa ttgaaattaa tcgttgactt aatctaccaa     720
aaaggattca aaaacatgtg gaacgatgta agtaacactg cagaatacgg cggacttaca     780
agaagaagca gaatcgttac agctgattca aaagctgcaa tgaaagaaat cttaagagaa     840
atccaagatg gaagattcac aaaagaattc cttctcgaaa acaggtaag ctatgctcat      900
ttaaaatcaa tgagaagact cgaaggagac ttacaaatcg aagaagtcgg cgcaaaatta     960
agaaaaatgt gcggtcttga aaagaagaa taa                                   993
```

<210> SEQ ID NO 13
<211> LENGTH: 342
<212> TYPE: PRT
<213> ORGANISM: Bacillus subtilis

<400> SEQUENCE: 13

```
Met Val Lys Val Tyr Tyr Asn Gly Asp Ile Lys Glu Asn Val Leu Ala
1               5                   10                  15

Gly Lys Thr Val Ala Val Ile Gly Tyr Gly Ser Gln Gly His Ala His
                20                  25                  30

Ala Leu Asn Leu Lys Glu Ser Gly Val Asp Val Ile Gly Val Arg
            35                  40                  45

Gln Gly Lys Ser Phe Thr Gln Ala Gln Glu Asp Gly His Lys Val Phe
        50                  55                  60

Ser Val Lys Glu Ala Ala Ala Gln Ala Glu Ile Ile Met Val Leu Leu
65                  70                  75                  80

Pro Asp Glu Gln Gln Lys Val Tyr Glu Ala Glu Ile Lys Asp Glu
                85                  90                  95

Leu Thr Ala Gly Lys Ser Leu Val Phe Ala His Gly Phe Asn Val His
            100                 105                 110

Phe His Gln Ile Val Pro Pro Ala Asp Val Asp Val Phe Leu Val Ala
```

```
            115                 120                 125
Pro Lys Gly Pro Gly His Leu Val Arg Arg Thr Tyr Glu Gln Gly Ala
        130                 135                 140
Gly Val Pro Ala Leu Phe Ala Ile Tyr Gln Asp Val Thr Gly Glu Ala
145                 150                 155                 160
Arg Asp Lys Ala Leu Ala Tyr Ala Lys Gly Ile Gly Gly Ala Arg Ala
                165                 170                 175
Gly Val Leu Glu Thr Thr Phe Lys Glu Thr Glu Thr Asp Leu Phe
            180                 185                 190
Gly Glu Gln Ala Val Leu Cys Gly Gly Leu Ser Ala Leu Val Lys Ala
                195                 200                 205
Gly Phe Glu Thr Leu Thr Glu Ala Gly Tyr Gln Pro Glu Leu Ala Tyr
        210                 215                 220
Phe Glu Cys Leu His Glu Leu Lys Leu Ile Val Asp Leu Met Tyr Glu
225                 230                 235                 240
Glu Gly Leu Ala Gly Met Arg Tyr Ser Ile Ser Asp Thr Ala Gln Trp
                245                 250                 255
Gly Asp Phe Val Ser Gly Pro Arg Val Val Asp Ala Lys Val Lys Glu
        260                 265                 270
Ser Met Lys Glu Val Leu Lys Asp Ile Gln Asn Gly Thr Phe Ala Lys
            275                 280                 285
Glu Trp Ile Val Glu Asn Gln Val Asn Arg Pro Arg Phe Asn Ala Ile
        290                 295                 300
Asn Ala Ser Glu Asn Glu His Gln Ile Glu Val Val Gly Arg Lys Leu
305                 310                 315                 320
Arg Glu Met Met Pro Phe Val Lys Gln Gly Lys Lys Glu Ala Val
                325                 330                 335
Val Ser Val Ala Gln Asn
            340

<210> SEQ ID NO 14
<211> LENGTH: 1476
<212> TYPE: DNA
<213> ORGANISM: Bacillus subtilis

<400> SEQUENCE: 14
atggctaact acttcaatac actgaatctg cgccagcagc tggcacagct gggcaaatgt      60
cgctttatgg ccgcgatga attcgccgat ggcgcgagct accttcaggg taaaaaagta     120
gtcatcgtcg gctgtggcgc acagggtctg aaccagggcc tgaacatgcg tgattctggt     180
ctcgatatct cctacgctct gcgtaaagaa gcgattgccg agaagcgcgc gtcctggcgt     240
aaagcgaccg aaaatggttt taaagtgggt acttacgaag aactgatccc acaggcggat     300
ctggtgatta acctgacgcc ggacaagcag cactctgatg tagtgcgcac cgtacagcca     360
ctgatgaaag acggcgcggc gctgggctac tcgcacggtt tcaacatcgt cgaagtgggc     420
gagcagatcc gtaaagatat caccgtagtg atggttgcgc gaaatgccc aggcaccgaa     480
gtgcgtgaag agtacaaacg tgggttcggc gtaccgacgc tgattgccgt tcacccggaa     540
aacgatccga aggcgaagg catggcgatt gccaaagcct gggcggctgc aaccggtggt     600
caccgtgcgg gtgtgctgga atcgtccttc gttgcggaag tgaaatctga cctgatgggc     660
gagcaaacca tcctgtgcgg tatgttgcag gctggctctc tgctgtgctt cgacaagctg     720
gtggaagaag gtaccgatcc agcatacgca gaaaaactga ttcagttcgg ttgggaaacc     780
atcaccgaag cactgaaaca gggcggcatc accctgatga tggaccgtct ctctaacccg     840
```

```
gcgaaactgc gtgcttatgc gctttctgaa cagctgaaag agatcatggc acccctgttc    900
cagaaacata tggacgacat catctccggc gaattctctt ccggtatgat ggcggactgg    960
gccaacgatg ataagaaact gctgacctgg cgtgaagaga ccggcaaaac cgcgtttgaa   1020
accgcgccgc agtatgaagg caaaatcggc gagcaggagt acttcgataa aggcgtactg   1080
atgattgcga tggtgaaagc gggcgttgaa ctggcgttcg aaaccatggt cgattccggc   1140
atcattgaag agtctgcata ttatgaatca ctgcacgagc tgccgctgat tgccaacacc   1200
atcgcccgta agcgtctgta cgaaatgaac gtggttatct ctgataccgc tgagtacggt   1260
aactatctgt tctcttacgc ttgtgtgccg ttgctgaaac cgtttatggc agagctgcaa   1320
ccgggcgacc tgggtaaagc tattccggaa ggcgcggtag ataacgggca actgcgtgat   1380
gtgaacgaag cgattcgcag ccatgcgatt gagcaggtag gtaagaaact gcgcggctat   1440
atgacagata tgaaacgtat tgctgttgcg ggttaa                            1476
```

<210> SEQ ID NO 15
<211> LENGTH: 343
<212> TYPE: PRT
<213> ORGANISM: Anaerostipes caccae

<400> SEQUENCE: 15

```
Met Glu Glu Cys Lys Met Ala Lys Ile Tyr Tyr Gln Glu Asp Cys Asn
1               5                   10                  15

Leu Ser Leu Leu Asp Gly Lys Thr Ile Ala Val Ile Gly Tyr Gly Ser
            20                  25                  30

Gln Gly His Ala His Ala Leu Asn Ala Lys Glu Ser Gly Cys Asn Val
        35                  40                  45

Ile Ile Gly Leu Tyr Glu Gly Ala Lys Glu Trp Lys Arg Ala Glu Glu
    50                  55                  60

Gln Gly Phe Glu Val Tyr Thr Ala Ala Glu Ala Lys Lys Ala Asp
65                  70                  75                  80

Ile Ile Met Ile Leu Ile Asn Asp Glu Lys Gln Ala Thr Met Tyr Lys
                85                  90                  95

Asn Asp Ile Glu Pro Asn Leu Glu Ala Gly Asn Met Leu Met Phe Ala
            100                 105                 110

His Gly Phe Asn Ile His Phe Gly Cys Ile Val Pro Pro Lys Asp Val
        115                 120                 125

Asp Val Thr Met Ile Ala Pro Lys Gly Pro Gly His Thr Val Arg Ser
    130                 135                 140

Glu Tyr Glu Glu Gly Lys Gly Val Pro Cys Leu Val Ala Val Glu Gln
145                 150                 155                 160

Asp Ala Thr Gly Lys Ala Leu Asp Met Ala Leu Ala Tyr Ala Leu Ala
                165                 170                 175

Ile Gly Gly Ala Arg Ala Gly Val Leu Glu Thr Thr Phe Arg Thr Glu
            180                 185                 190

Thr Glu Thr Asp Leu Phe Gly Glu Gln Ala Val Leu Cys Gly Val
        195                 200                 205

Cys Ala Leu Met Gln Ala Gly Phe Glu Thr Leu Val Glu Ala Gly Tyr
    210                 215                 220

Asp Pro Arg Asn Ala Tyr Phe Glu Cys Ile His Glu Met Lys Leu Ile
225                 230                 235                 240

Val Asp Leu Ile Tyr Gln Ser Gly Phe Ser Gly Met Arg Tyr Ser Ile
                245                 250                 255
```

Ser Asn Thr Ala Glu Tyr Gly Asp Tyr Ile Thr Gly Pro Lys Ile Ile
            260                 265                 270

Thr Glu Asp Thr Lys Lys Ala Met Lys Lys Ile Leu Ser Asp Ile Gln
        275                 280                 285

Asp Gly Thr Phe Ala Lys Asp Phe Leu Val Asp Met Ser Asp Ala Gly
    290                 295                 300

Ser Gln Val His Phe Lys Ala Met Arg Lys Leu Ala Ser Glu His Pro
305                 310                 315                 320

Ala Glu Val Val Gly Glu Glu Ile Arg Ser Leu Tyr Ser Trp Ser Asp
                325                 330                 335

Glu Asp Lys Leu Ile Asn Asn
            340

<210> SEQ ID NO 16
<211> LENGTH: 343
<212> TYPE: PRT
<213> ORGANISM: Anaerostipes caccae

<400> SEQUENCE: 16

Met Glu Glu Cys Lys Met Ala Lys Ile Tyr Tyr Gln Glu Asp Cys Asn
1               5                   10                  15

Leu Ser Leu Leu Asp Gly Lys Thr Ile Ala Val Ile Gly Tyr Gly Ser
            20                  25                  30

Gln Gly His Ala His Ala Leu Asn Ala Lys Glu Ser Gly Cys Asn Val
        35                  40                  45

Ile Ile Gly Leu Tyr Glu Gly Ala Lys Asp Trp Lys Arg Ala Glu Glu
    50                  55                  60

Gln Gly Phe Glu Val Tyr Thr Ala Ala Glu Ala Lys Lys Ala Asp
65                  70                  75                  80

Ile Ile Met Ile Leu Ile Asn Asp Glu Lys Gln Ala Thr Met Tyr Lys
                85                  90                  95

Asn Asp Ile Glu Pro Asn Leu Glu Ala Gly Asn Met Leu Met Phe Ala
            100                 105                 110

His Gly Phe Asn Ile His Phe Gly Cys Ile Val Pro Pro Lys Asp Val
        115                 120                 125

Asp Val Thr Met Ile Ala Pro Lys Gly Pro Gly His Thr Val Arg Ser
    130                 135                 140

Glu Tyr Glu Glu Gly Lys Gly Val Pro Cys Leu Val Ala Val Glu Gln
145                 150                 155                 160

Asp Ala Thr Gly Lys Ala Leu Asp Met Ala Leu Ala Tyr Ala Leu Ala
                165                 170                 175

Ile Gly Gly Ala Arg Ala Gly Val Leu Glu Thr Thr Phe Arg Thr Glu
            180                 185                 190

Thr Glu Thr Asp Leu Phe Gly Glu Gln Ala Val Leu Cys Gly Gly Val
        195                 200                 205

Cys Ala Leu Met Gln Ala Gly Phe Glu Thr Leu Val Glu Ala Gly Tyr
    210                 215                 220

Asp Pro Arg Asn Ala Tyr Phe Glu Cys Ile His Glu Met Lys Leu Ile
225                 230                 235                 240

Val Asp Leu Ile Tyr Gln Ser Gly Phe Ser Gly Met Arg Tyr Ser Ile
                245                 250                 255

Ser Asn Thr Ala Glu Tyr Gly Asp Tyr Ile Thr Gly Pro Lys Ile Ile
            260                 265                 270

Thr Glu Asp Thr Lys Lys Ala Met Lys Lys Ile Leu Ser Asp Ile Gln
        275                 280                 285

```
Asp Gly Thr Phe Ala Lys Asp Phe Leu Val Asp Met Ser Asp Ala Gly
            290                 295                 300

Ser Gln Val His Phe Lys Ala Met Arg Lys Leu Ala Ser Glu His Pro
305                 310                 315                 320

Ala Glu Val Val Gly Glu Ile Arg Ser Leu Tyr Ser Trp Ser Asp
                325                 330                 335

Glu Asp Lys Leu Ile Asn Asn
            340

<210> SEQ ID NO 17
<211> LENGTH: 616
<212> TYPE: PRT
<213> ORGANISM: Escherichia coli

<400> SEQUENCE: 17

Met Pro Lys Tyr Arg Ser Ala Thr Thr Thr His Gly Arg Asn Met Ala
1               5                   10                  15

Gly Ala Arg Ala Leu Trp Arg Ala Thr Gly Met Thr Asp Ala Asp Phe
            20                  25                  30

Gly Lys Pro Ile Ile Ala Val Val Asn Ser Phe Thr Gln Phe Val Pro
        35                  40                  45

Gly His Val His Leu Arg Asp Leu Gly Lys Leu Val Ala Glu Gln Ile
    50                  55                  60

Glu Ala Ala Gly Gly Val Ala Lys Glu Phe Asn Thr Ile Ala Val Asp
65                  70                  75                  80

Asp Gly Ile Ala Met Gly His Gly Gly Met Leu Tyr Ser Leu Pro Ser
                85                  90                  95

Arg Glu Leu Ile Ala Asp Ser Val Glu Tyr Met Val Asn Ala His Cys
            100                 105                 110

Ala Asp Ala Met Val Cys Ile Ser Asn Cys Asp Lys Ile Thr Pro Gly
        115                 120                 125

Met Leu Met Ala Ser Leu Arg Leu Asn Ile Pro Val Ile Phe Val Ser
    130                 135                 140

Gly Gly Pro Met Glu Ala Gly Lys Thr Lys Leu Ser Asp Gln Ile Ile
145                 150                 155                 160

Lys Leu Asp Leu Val Asp Ala Met Ile Gln Gly Ala Asp Pro Lys Val
                165                 170                 175

Ser Asp Ser Gln Ser Asp Gln Val Glu Arg Ser Ala Cys Pro Thr Cys
            180                 185                 190

Gly Ser Cys Ser Gly Met Phe Thr Ala Asn Ser Met Asn Cys Leu Thr
        195                 200                 205

Glu Ala Leu Gly Leu Ser Gln Pro Gly Asn Gly Ser Leu Leu Ala Thr
    210                 215                 220

His Ala Asp Arg Lys Gln Leu Phe Leu Asn Ala Gly Lys Arg Ile Val
225                 230                 235                 240

Glu Leu Thr Lys Arg Tyr Tyr Glu Gln Asn Asp Glu Ser Ala Leu Pro
                245                 250                 255

Arg Asn Ile Ala Ser Lys Ala Ala Phe Glu Asn Ala Met Thr Leu Asp
            260                 265                 270

Ile Ala Met Gly Gly Ser Thr Asn Thr Val Leu His Leu Leu Ala Ala
        275                 280                 285

Ala Gln Glu Ala Glu Ile Asp Phe Thr Met Ser Asp Ile Asp Lys Leu
    290                 295                 300

Ser Arg Lys Val Pro Gln Leu Cys Lys Val Ala Pro Ser Thr Gln Lys
```

```
                305                 310                 315                 320
        Tyr His Met Glu Asp Val His Arg Ala Gly Val Ile Gly Ile Leu
                        325                 330                 335
        Gly Glu Leu Asp Arg Ala Gly Leu Leu Asn Arg Asp Val Lys Asn Val
                        340                 345                 350
        Leu Gly Leu Thr Leu Pro Gln Thr Leu Glu Gln Tyr Asp Val Met Leu
                        355                 360                 365
        Thr Gln Asp Asp Ala Val Lys Asn Met Phe Arg Ala Gly Pro Ala Gly
                        370                 375                 380
        Ile Arg Thr Thr Gln Ala Phe Ser Gln Asp Cys Arg Trp Asp Thr Leu
        385                 390                 395                 400
        Asp Asp Asp Arg Ala Asn Gly Cys Ile Arg Ser Leu Glu His Ala Tyr
                        405                 410                 415
        Ser Lys Asp Gly Gly Leu Ala Val Leu Tyr Gly Asn Phe Ala Glu Asn
                        420                 425                 430
        Gly Cys Ile Val Lys Thr Ala Gly Val Asp Asp Ser Ile Leu Lys Phe
                        435                 440                 445
        Thr Gly Pro Ala Lys Val Tyr Glu Ser Gln Asp Asp Ala Val Glu Ala
                        450                 455                 460
        Ile Leu Gly Gly Lys Val Val Ala Gly Asp Val Val Ile Arg Tyr
        465                 470                 475                 480
        Glu Gly Pro Lys Gly Gly Pro Gly Met Gln Glu Met Leu Tyr Pro Thr
                        485                 490                 495
        Ser Phe Leu Lys Ser Met Gly Leu Gly Lys Ala Cys Ala Leu Ile Thr
                        500                 505                 510
        Asp Gly Arg Phe Ser Gly Gly Thr Ser Gly Leu Ser Ile Gly His Val
                        515                 520                 525
        Ser Pro Glu Ala Ala Ser Gly Gly Ser Ile Gly Leu Ile Glu Asp Gly
                        530                 535                 540
        Asp Leu Ile Ala Ile Asp Ile Pro Asn Arg Gly Ile Gln Leu Gln Val
        545                 550                 555                 560
        Ser Asp Ala Glu Leu Ala Ala Arg Arg Glu Ala Gln Asp Ala Arg Gly
                        565                 570                 575
        Asp Lys Ala Trp Thr Pro Lys Asn Arg Glu Arg Gln Val Ser Phe Ala
                        580                 585                 590
        Leu Arg Ala Tyr Ala Ser Leu Ala Thr Ser Ala Asp Lys Gly Ala Val
                        595                 600                 605
        Arg Asp Lys Ser Lys Leu Gly Gly
                610                 615

<210> SEQ ID NO 18
<211> LENGTH: 1851
<212> TYPE: DNA
<213> ORGANISM: Escherichia coli

<400> SEQUENCE: 18
atgcctaagt accgttccgc caccaccact catggtcgta atatggcggg tgctcgtgcg    60
ctgtggcgcg ccaccggaat gaccgacgcc gatttcggta agccgattat cgcggttgtg   120
aactcgttca cccaatttgt accgggtcac gtccatctgc gcgatctcgg taaactggtc   180
gccgaacaaa ttgaagcggc tggcggcgtt gccaaagagt tcaacaccat tgcggtggat   240
gatgggattg ccatgggcca cggggggatg ctttattcac tgccatctcg cgaactgatc   300
gctgattccg ttgagtatat ggtcaacgcc cactgcgccg acgccatggt ctgcatctct   360
```

```
aactgcgaca aaatcacccc ggggatgctg atggcttccc tgcgcctgaa tattccggtg   420
atctttgttt ccggcggccc gatggaggcc gggaaaacca aactttccga tcagatcatc   480
aagctcgatc tggttgatgc gatgatccag ggcgcagacc cgaaagtatc tgactcccag   540
agcgatcagg ttgaacgttc cgcgtgtccg acctgcggtt cctgctccgg atgtttacc    600
gctaactcaa tgaactgcct gaccgaagcg ctgggcctgt cgcagccggg caacggctcg   660
ctgctggcaa cccacgccga ccgtaagcag ctgttcctta tgctggtaa acgcattgtt    720
gaattgacca aacgttatta cgagcaaaac gacgaaagtg cactgccgcg taatatcgcc   780
agtaaggcgg cgtttgaaaa cgccatgacg ctggatatcg cgatgggtgg atcgactaac   840
accgtacttc acctgctggc ggcggcgcag gaagcggaaa tcgacttcac catgagtgat   900
atcgataagc tttcccgcaa ggttccacag ctgtgtaaag ttgcgccgag cacccagaaa   960
taccatatgg aagatgttca ccgtgctggt ggtgttatcg gtattctcgg cgaactggat   1020
cgcgcggggt tactgaaccg tgatgtgaaa aacgtacttg ccctgacgtt gccgcaaacg   1080
ctggaacaat acgacgttat gctgacccag gatgacgcgg taaaaaatat gttccgcgca   1140
ggtcctgcag gcattcgtac cacacaggca ttctcgcaag attgccgttg ggatacgctg   1200
gacgacgatc gcgccaatgg ctgtatccgc tcgctggaac acgcctacag caaagacggc   1260
ggcctggcgg tgctctacgg taactttgcg gaaaacggct gcatcgtgaa acggcaggc    1320
gtcgatgaca gcatcctcaa attcaccggc ccggcgaaag tgtacgaaag ccaggacgat   1380
gcggtagaag cgattctcgg cggtaaagtt gtcgccggag atgtggtagt aattcgctat   1440
gaaggcccga aaggcggtcc ggggatgcag gaaatgctct acccaaccag cttcctgaaa   1500
tcaatgggtc tcggcaaagc ctgtgcgctg atcaccgacg gtcgtttctc tggtggcacc   1560
tctggtctttt ccatcggcca cgtctcaccg gaagcggcaa cgcggcggcag cattggcctg   1620
attgaagatg gtgacctgat cgctatcgac atcccgaacc gtggcattca gttacaggta   1680
agcgatgccg aactggcggc cgtcgtgaa gcgcaggacg ctcgaggtga caaagcctgg   1740
acgccgaaaa atcgtgaacg tcaggtctcc tttgccctgc gtgcttatgc cagcctggca   1800
accagcgccg acaaaggcgc ggtgcgcgat aaatcgaaac tgggggggtta a           1851
```

<210> SEQ ID NO 19
<211> LENGTH: 585
<212> TYPE: PRT
<213> ORGANISM: Saccharomyces cerevisiae

<400> SEQUENCE: 19

```
Met Gly Leu Leu Thr Lys Val Ala Thr Ser Arg Gln Phe Ser Thr Thr
1               5                   10                  15

Arg Cys Val Ala Lys Lys Leu Asn Lys Tyr Ser Tyr Ile Ile Thr Glu
            20                  25                  30

Pro Lys Gly Gln Gly Ala Ser Gln Ala Met Leu Tyr Ala Thr Gly Phe
        35                  40                  45

Lys Lys Glu Asp Phe Lys Lys Pro Gln Val Gly Val Gly Ser Cys Trp
    50                  55                  60

Trp Ser Gly Asn Pro Cys Asn Met His Leu Leu Asp Leu Asn Asn Arg
65                  70                  75                  80

Cys Ser Gln Ser Ile Glu Lys Ala Gly Leu Lys Ala Met Gln Phe Asn
                85                  90                  95

Thr Ile Gly Val Ser Asp Gly Ile Ser Met Gly Thr Lys Gly Met Arg
            100                 105                 110
```

```
Tyr Ser Leu Gln Ser Arg Glu Ile Ile Ala Asp Ser Phe Glu Thr Ile
        115                 120                 125

Met Met Ala Gln His Tyr Asp Ala Asn Ile Ala Ile Pro Ser Cys Asp
130                 135                 140

Lys Asn Met Pro Gly Val Met Ala Met Gly Arg His Asn Arg Pro
145                 150                 155                 160

Ser Ile Met Val Tyr Gly Gly Thr Ile Leu Pro Gly His Pro Thr Cys
                165                 170                 175

Gly Ser Ser Lys Ile Ser Lys Asn Ile Asp Ile Val Ser Ala Phe Gln
            180                 185                 190

Ser Tyr Gly Glu Tyr Ile Ser Lys Gln Phe Thr Glu Glu Arg Glu
        195                 200                 205

Asp Val Val Glu His Ala Cys Pro Gly Pro Gly Ser Cys Gly Gly Met
        210                 215                 220

Tyr Thr Ala Asn Thr Met Ala Ser Ala Ala Glu Val Leu Gly Leu Thr
225                 230                 235                 240

Ile Pro Asn Ser Ser Phe Pro Ala Val Ser Lys Glu Lys Leu Ala
                245                 250                 255

Glu Cys Asp Asn Ile Gly Glu Tyr Ile Lys Lys Thr Met Glu Leu Gly
            260                 265                 270

Ile Leu Pro Arg Asp Ile Leu Thr Lys Glu Ala Phe Glu Asn Ala Ile
        275                 280                 285

Thr Tyr Val Val Ala Thr Gly Gly Ser Thr Asn Ala Val Leu His Leu
        290                 295                 300

Val Ala Val Ala His Ser Ala Gly Val Lys Leu Ser Pro Asp Asp Phe
305                 310                 315                 320

Gln Arg Ile Ser Asp Thr Thr Pro Leu Ile Gly Asp Phe Lys Pro Ser
                325                 330                 335

Gly Lys Tyr Val Met Ala Asp Leu Ile Asn Val Gly Gly Thr Gln Ser
            340                 345                 350

Val Ile Lys Tyr Leu Tyr Glu Asn Asn Met Leu His Gly Asn Thr Met
        355                 360                 365

Thr Val Thr Gly Asp Thr Leu Ala Glu Arg Ala Lys Lys Ala Pro Ser
370                 375                 380

Leu Pro Glu Gly Gln Glu Ile Ile Lys Pro Leu Ser His Pro Ile Lys
385                 390                 395                 400

Ala Asn Gly His Leu Gln Ile Leu Tyr Gly Ser Leu Ala Pro Gly Gly
                405                 410                 415

Ala Val Gly Lys Ile Thr Gly Lys Glu Gly Thr Tyr Phe Lys Gly Arg
            420                 425                 430

Ala Arg Val Phe Glu Glu Gly Ala Phe Ile Glu Ala Leu Glu Arg
        435                 440                 445

Gly Glu Ile Lys Lys Gly Glu Lys Thr Val Val Ile Arg Tyr Glu
        450                 455                 460

Gly Pro Arg Gly Ala Pro Gly Met Pro Glu Met Leu Lys Pro Ser Ser
465                 470                 475                 480

Ala Leu Met Gly Tyr Gly Leu Gly Lys Asp Val Ala Leu Leu Thr Asp
                485                 490                 495

Gly Arg Phe Ser Gly Gly Ser His Gly Phe Leu Ile Gly His Ile Val
            500                 505                 510

Pro Glu Ala Ala Glu Gly Gly Pro Ile Gly Leu Val Arg Asp Gly Asp
        515                 520                 525

Glu Ile Ile Ile Asp Ala Asp Asn Asn Lys Ile Asp Leu Leu Val Ser
```

Asp Lys Glu Met Ala Gln Arg Lys Gln Ser Trp Val Ala Pro Pro
545                 550                 555                 560

Arg Tyr Thr Arg Gly Thr Leu Ser Lys Tyr Ala Lys Leu Val Ser Asn
                565                 570                 575

Ala Ser Asn Gly Cys Val Leu Asp Ala
            580                 585

<210> SEQ ID NO 20
<211> LENGTH: 1131
<212> TYPE: DNA
<213> ORGANISM: Saccharomyces cerevisiae

<400> SEQUENCE: 20

```
atgaccttgg caccsctaga cgcctccaaa gttaagataa ctaccacaca acatgcatct      60
aagccaaaac cgaacagtga gttagtgttt ggcaagagct tcacggacca catgttaact     120
gcggaatgga cagctgaaaa agggtggggt accccagaga ttaaaccttaa tcaaaatctg    180
tctttagacc cttccgcggt ggttttccat tatgcttttg agctattcga agggatgaag    240
gcttacagaa cggtggacaa caaaattaca atgtttcgtc cagatatgaa tatgaagcgc    300
atgaataagt ctgctcagag aatctgtttg ccaacgttcg acccagaaga gttgattacc    360
ctaattggga aactgatcca gcaagataag tgcttagttc ctgaaggaaa aggttactct    420
ttatatatca ggcctacatt aatcggcact acggccggtt taggggtttc cacgcctgat    480
agagccttgc tatatgtcat ttgctgccct gtgggtcctt attacaaaac tggatttaag    540
gcggtcagac tggaagccac tgattatgcc acaagagctt ggccaggagg ctgtggtgac    600
aagaaactag gtgcaaacta cgcccccctgc gtcctgccac aattgcaagc tgcttcaagg    660
ggttaccaac aaaatttatg gctatttggt ccaaataaca acattactga agtcggcacc    720
atgaatgctt ttttcgtgtt taaagatagt aaaacgggca agaaggaact agttactgct    780
ccactagacg gtaccatttt ggaaggtgtt actagggatt ccattttaaa tcttgctaaa    840
gaaagactcg aaccaagtga atggaccatt agtgaacgct acttcactat aggcgaagtt    900
actgagagat ccaagaacgg tgaactactt gaagcctttg gttctggtac tgctgcgatt    960
gtttctccca ttaaggaaat cggctggaaa ggcgaacaaa ttaatattcc gttgttgccc   1020
ggcgaacaaa ccggtccatt ggccaaagaa gttgcacaat ggattaatgg aatccaatat   1080
ggcgagactg agcatggcaa ttggtcaagg gttgttactg atttgaactg a             1131
```

<210> SEQ ID NO 21
<211> LENGTH: 550
<212> TYPE: PRT
<213> ORGANISM: Methanococcus maripaludis

<400> SEQUENCE: 21

Met Ile Ser Asp Asn Val Lys Lys Gly Val Ile Arg Thr Pro Asn Arg
1               5                   10                  15

Ala Leu Leu Lys Ala Cys Gly Tyr Thr Asp Glu Asp Met Glu Lys Pro
                20                  25                  30

Phe Ile Gly Ile Val Asn Ser Phe Thr Glu Val Pro Gly His Ile
        35                  40                  45

His Leu Arg Thr Leu Ser Glu Ala Ala Lys His Gly Val Tyr Ala Asn
    50                  55                  60

Gly Gly Thr Pro Phe Glu Phe Asn Thr Ile Gly Ile Cys Asp Gly Ile
65                  70                  75                  80

```
Ala Met Gly His Glu Gly Met Lys Tyr Ser Leu Pro Ser Arg Glu Ile
            85                  90                  95

Ile Ala Asp Ala Val Glu Ser Met Ala Arg Ala His Gly Phe Asp Gly
            100                 105                 110

Leu Val Leu Ile Pro Thr Cys Asp Lys Ile Val Pro Gly Met Ile Met
            115                 120                 125

Gly Ala Leu Arg Leu Asn Ile Pro Phe Ile Val Thr Gly Gly Pro
            130                 135                 140

Met Leu Pro Gly Glu Phe Gln Gly Lys Lys Tyr Glu Leu Ile Ser Leu
145                 150                 155                 160

Phe Glu Gly Val Gly Glu Tyr Gln Val Gly Lys Ile Thr Glu Glu
                165                 170                 175

Leu Lys Cys Ile Glu Asp Cys Ala Cys Ser Gly Ala Gly Ser Cys Ala
                180                 185                 190

Gly Leu Tyr Thr Ala Asn Ser Met Ala Cys Leu Thr Glu Ala Leu Gly
            195                 200                 205

Leu Ser Leu Pro Met Cys Ala Thr Thr His Ala Val Asp Ala Gln Lys
    210                 215                 220

Val Arg Leu Ala Lys Lys Ser Gly Ser Lys Ile Val Asp Met Val Lys
225                 230                 235                 240

Glu Asp Leu Lys Pro Thr Asp Ile Leu Thr Lys Glu Ala Phe Glu Asn
                245                 250                 255

Ala Ile Leu Val Asp Leu Ala Leu Gly Gly Ser Thr Asn Thr Thr Leu
                260                 265                 270

His Ile Pro Ala Ile Ala Asn Glu Ile Glu Asn Lys Phe Ile Thr Leu
                275                 280                 285

Asp Asp Phe Asp Arg Leu Ser Asp Glu Val Pro His Ile Ala Ser Ile
    290                 295                 300

Lys Pro Gly Gly Glu His Tyr Met Ile Asp Leu His Asn Ala Gly Gly
305                 310                 315                 320

Ile Pro Ala Val Leu Asn Val Leu Lys Glu Lys Ile Arg Asp Thr Lys
                325                 330                 335

Thr Val Asp Gly Arg Ser Ile Leu Glu Ile Ala Glu Ser Val Lys Tyr
            340                 345                 350

Ile Asn Tyr Asp Val Ile Arg Lys Val Glu Ala Pro Val His Glu Thr
            355                 360                 365

Ala Gly Leu Arg Val Leu Lys Gly Asn Leu Ala Pro Asn Gly Cys Val
    370                 375                 380

Val Lys Ile Gly Ala Val His Pro Lys Met Tyr Lys His Asp Gly Pro
385                 390                 395                 400

Ala Lys Val Tyr Asn Ser Glu Asp Glu Ala Ile Ser Ala Ile Leu Gly
                405                 410                 415

Gly Lys Ile Val Glu Gly Asp Val Ile Val Ile Arg Tyr Glu Gly Pro
            420                 425                 430

Ser Gly Gly Pro Gly Met Arg Glu Met Leu Ser Pro Thr Ser Ala Ile
            435                 440                 445

Cys Gly Met Gly Leu Asp Asp Ser Val Ala Leu Ile Thr Asp Gly Arg
    450                 455                 460

Phe Ser Gly Gly Ser Arg Gly Pro Cys Ile Gly His Val Ser Pro Glu
465                 470                 475                 480

Ala Ala Ala Gly Gly Val Ile Ala Ile Glu Asn Gly Asp Ile Ile
                485                 490                 495
```

```
Lys Ile Asp Met Ile Glu Lys Glu Ile Asn Val Asp Leu Asp Ser
            500                 505                 510
Val Ile Lys Glu Arg Leu Ser Lys Leu Gly Gly Phe Glu Pro Lys Ile
        515                 520                 525
Lys Lys Gly Tyr Leu Ser Arg Tyr Ser Lys Leu Val Ser Ser Ala Asp
    530                 535                 540
Glu Gly Ala Val Leu Lys
545                 550

<210> SEQ ID NO 22
<211> LENGTH: 1653
<212> TYPE: DNA
<213> ORGANISM: Methanococcus maripaludis

<400> SEQUENCE: 22
atgataagtg ataacgtcaa aaagggagtt ataagaactc caaaccgagc tcttttaaag      60
gcttgcggat atacgacga agacatgaa aaaccattta ttggaattgt aaacagcttt      120
acagaagttg ttcccggcca cattcactta agaacattat cagaagcggc taaacatggt      180
gtttatgcaa acgtggaac accatttgaa tttaatacca ttggaatttg cgacggtatt      240
gcaatgggcc acgaaggtat gaaatactct ttaccttcaa gagaaattat tgcagacgct      300
gttgaatcaa tggcaagagc acatggattt gatggtcttg ttttaattcc tacgtgtgat      360
aaaatcgttc ctggaatgat aatgggtgct ttaagactaa cattccatt tattgtagtt      420
actggaggac caatgcttcc cggagaattc caaggtaaaa aatacgaact tatcagcctt      480
tttgaaggtg tcgagaata ccaagttgga aaaattactg aagaagagtt aaagtgcatt      540
gaagactgtg catgttcagg tgctggaagt tgtgcagggc tttacactgc aaacagtatg      600
gcctgcctta cagaagcttt gggactctct cttccaatgt gtgcaacaac gcatgcagtt      660
gatgcccaaa agttaggct tgctaaaaaa agtggctcaa aaattgttga tatggtaaaa      720
gaagacctaa aaccaacaga catattaaca aaagaagctt ttgaaaatgc tattttagtt      780
gaccttgcac ttggtggatc aacaaacaca acattacaca ttcctgcaat tgcaaatgaa      840
attgaaaata aattcataac tctcgatgac tttgacaggt taagcgatga agttccacac      900
attgcatcaa tcaaaccagg tggagaacac tacatgattg atttacacaa tgctggaggt      960
attcctgcgg tattgaacgt ttaaaagaa aaaattagag atacaaaaac agttgatgga     1020
agaagcattt tggaaatcgc agaatctgtt aaatacataa attcgacgt tataagaaaa     1080
gtggaagctc cggttcacga aactgctggt ttaagggttt taagggaaa tcttgctcca     1140
aacggttgcg ttgtaaaaat cggtgcagta catccgaaaa tgtacaaaca cgatggacct     1200
gcaaagtttt acaattccga agatgaagca atttctgcga tacttggcgg aaaaattgta     1260
gaaggggacg ttatagtaat cagatacgaa ggaccatcag gaggccctgg aatgagagaa     1320
atgctctccc caacttcagc aatctgtgga atgggtcttg atgacagcgt tgcattgatt     1380
actgatggaa gattcagtgg tggaagtagg ggcccatgta tcggacacgt ttctccagaa     1440
gctgcagctg gcggagtaat tgctgcaatt gaaaacgggg atatcatcaa aatcgacatg     1500
attgaaaaag aaataaatgt tgatttagat gaatcagtca ttaaagaaag actctcaaaa     1560
ctgggagaat ttgagcctaa aatcaaaaaa ggctatttat caagatactc aaaacttgtc     1620
tcatctgctg acgaaggggc agtttttaaaa taa                                  1653

<210> SEQ ID NO 23
<211> LENGTH: 558
```

<212> TYPE: PRT
<213> ORGANISM: Bacillus subtilis

<400> SEQUENCE: 23

```
Met Ala Glu Leu Arg Ser Asn Met Ile Thr Gln Gly Ile Asp Arg Ala
1               5                   10                  15

Pro His Arg Ser Leu Leu Arg Ala Ala Gly Val Lys Glu Glu Asp Phe
            20                  25                  30

Gly Lys Pro Phe Ile Ala Val Cys Asn Ser Tyr Ile Asp Ile Val Pro
        35                  40                  45

Gly His Val His Leu Gln Glu Phe Gly Lys Ile Val Lys Glu Ala Ile
    50                  55                  60

Arg Glu Ala Gly Gly Val Pro Phe Glu Phe Asn Thr Ile Gly Val Asp
65                  70                  75                  80

Asp Gly Ile Ala Met Gly His Ile Gly Met Arg Tyr Ser Leu Pro Ser
                85                  90                  95

Arg Glu Ile Ile Ala Asp Ser Val Glu Thr Val Val Ser Ala His Trp
            100                 105                 110

Phe Asp Gly Met Val Cys Ile Pro Asn Cys Asp Lys Ile Thr Pro Gly
        115                 120                 125

Met Leu Met Ala Ala Met Arg Ile Asn Ile Pro Thr Ile Phe Val Ser
    130                 135                 140

Gly Gly Pro Met Ala Ala Gly Arg Thr Ser Asp Gly Arg Lys Ile Ser
145                 150                 155                 160

Leu Ser Ser Val Phe Glu Gly Val Gly Ala Tyr Gln Ala Gly Lys Ile
                165                 170                 175

Asn Glu Asn Glu Leu Gln Glu Leu Glu Gln Phe Gly Cys Pro Thr Cys
            180                 185                 190

Gly Ser Cys Ser Gly Met Phe Thr Ala Asn Ser Met Asn Cys Leu Ser
        195                 200                 205

Glu Ala Leu Gly Leu Ala Leu Pro Gly Asn Gly Thr Ile Leu Ala Thr
    210                 215                 220

Ser Pro Glu Arg Lys Glu Phe Val Arg Lys Ser Ala Ala Gln Leu Met
225                 230                 235                 240

Glu Thr Ile Arg Lys Asp Ile Lys Pro Arg Asp Ile Val Thr Val Lys
                245                 250                 255

Ala Ile Asp Asn Ala Phe Ala Leu Asp Met Ala Leu Gly Gly Ser Thr
            260                 265                 270

Asn Thr Val Leu His Thr Leu Ala Leu Ala Asn Glu Ala Gly Val Glu
        275                 280                 285

Tyr Ser Leu Glu Arg Ile Asn Glu Val Ala Glu Arg Val Pro His Leu
    290                 295                 300

Ala Lys Leu Ala Pro Ala Ser Asp Val Phe Ile Glu Asp Leu His Glu
305                 310                 315                 320

Ala Gly Gly Val Ser Ala Leu Asn Glu Leu Ser Lys Lys Glu Gly
                325                 330                 335

Ala Leu His Leu Asp Ala Leu Thr Val Thr Gly Lys Thr Leu Gly Glu
            340                 345                 350

Thr Ile Ala Gly His Glu Val Lys Asp Tyr Asp Val Ile His Pro Leu
        355                 360                 365

Asp Gln Pro Phe Thr Glu Lys Gly Gly Leu Ala Val Leu Phe Gly Asn
    370                 375                 380

Leu Ala Pro Asp Gly Ala Ile Ile Lys Thr Gly Gly Val Gln Asn Gly
385                 390                 395                 400
```

```
Ile Thr Arg His Glu Gly Pro Ala Val Val Phe Asp Ser Gln Asp Glu
            405                 410                 415
Ala Leu Asp Gly Ile Ile Asn Arg Lys Val Lys Glu Gly Asp Val Val
        420                 425                 430
Ile Ile Arg Tyr Glu Gly Pro Lys Gly Gly Pro Gly Met Pro Glu Met
    435                 440                 445
Leu Ala Pro Thr Ser Gln Ile Val Gly Met Gly Leu Gly Pro Lys Val
450                 455                 460
Ala Leu Ile Thr Asp Gly Arg Phe Ser Gly Ala Ser Arg Gly Leu Ser
465                 470                 475                 480
Ile Gly His Val Ser Pro Glu Ala Ala Glu Gly Gly Pro Leu Ala Phe
                485                 490                 495
Val Glu Asn Gly Asp His Ile Ile Val Asp Ile Glu Lys Arg Ile Leu
            500                 505                 510
Asp Val Gln Val Pro Glu Glu Trp Glu Lys Arg Lys Ala Asn Trp
        515                 520                 525
Lys Gly Phe Glu Pro Lys Val Lys Thr Gly Tyr Leu Ala Arg Tyr Ser
    530                 535                 540
Lys Leu Val Thr Ser Ala Asn Thr Gly Gly Ile Met Lys Ile
545                 550                 555
```

```
<210> SEQ ID NO 24
<211> LENGTH: 1677
<212> TYPE: DNA
<213> ORGANISM: Bacillus subtilis

<400> SEQUENCE: 24
```

| | | | | |
|---|---|---|---|---|
| atggcagaat tacgcagtaa tatgatcaca caaggaatcg atagagctcc gcaccgcagt | 60 |
| ttgcttcgtg cagcaggggt aaaagaagag gatttcggca agccgtttat tgcggtgtgt | 120 |
| aattcataca ttgatatcgt tcccggtcat gttcacttgc aggagtttgg gaaaatcgta | 180 |
| aaagaagcaa tcagagaagc aggggggcgtt ccgtttgaat taataccat tggggtagat | 240 |
| gatggcatcg caatggggca tatcggtatg agatattcgc tgccaagccg tgaaattatc | 300 |
| gcagactctg tggaaacggt tgtatccgca cactggtttg acggaatggt ctgtattccg | 360 |
| aactgcgaca aaatcacacc gggaatgctt atggcggcaa tgcgcatcaa cattccgacg | 420 |
| attttttgtca gcggcggacc gatggcggca ggaagaacaa gttacgggcg aaaaatctcc | 480 |
| ctttcctcag tattcgaagg ggtaggcgcc taccaagcag ggaaaatcaa cgaaaacgag | 540 |
| cttcaagaac tagagcagtt cggatgccca acgtgcgggt cttgctcagg catgttttacg | 600 |
| gcgaactcaa tgaactgtct gtcagaagca cttggtcttg ctttgccggg taatggaacc | 660 |
| attctggcaa catctccgga acgcaaagag tttgtgagaa aatcggctgc gcaattaatg | 720 |
| gaaacgattc gcaaagatat caaaccgcgt gatattgtta cagtaaaagc gattgataac | 780 |
| gcgtttgcac tcgatatggc gctcggaggg tctacaaata ccgttcttca tacccttgcc | 840 |
| cttgcaaacg aagccggcgt tgaatactct ttagaacgca ttaacgaagt cgctgagcgc | 900 |
| gtgccgcact ggctaagct ggcgcctgca tcggatgtgt ttattgaaga tcttcacgaa | 960 |
| gcgggcggcg tttcagcggc tctgaatgag ctttcgaaga aagaaggagc gcttcattta | 1020 |
| gatgcgctga ctgttacagg aaaaactctt ggagaaacca ttgccggaca tgaagtaaag | 1080 |
| gattatgacg tcattcaccc gctggatcaa ccattcactg aaaagggagg ccttgctgtt | 1140 |
| ttattcggta atctagctcc ggacggcgct atcattaaaa caggcggcgt acagaatggg | 1200 |

-continued

```
attacaagac acgaagggcc ggctgtcgta ttcgattctc aggacgaggc gcttgacggc  1260
attatcaacc gaaaagtaaa agaaggcgac gttgtcatca tcagatacga agggccaaaa  1320
ggcggacctg gcatgccgga atgctggcg ccaacatccc aaatcgttgg aatgggactc  1380
gggccaaaag tggcattgat tacgacgga cgttttttccg gagcctcccg tggcctctca  1440
atcggccacg tatcacctga ggccgctgag ggcgggccgc ttgcctttgt tgaaaacgga  1500
gaccatatta tcgttgatat tgaaaaacgc atcttggatg tacaagtgcc agaagaagag  1560
tgggaaaaac gaaaagcgaa ctggaaaggt tttgaaccga aagtgaaaac cggctacctg  1620
gcacgttatt ctaaacttgt gacaagtgcc aacaccggcg gtattatgaa aatctag     1677
```

<210> SEQ ID NO 25
<211> LENGTH: 547
<212> TYPE: PRT
<213> ORGANISM: Lactococcus lactis

<400> SEQUENCE: 25

```
Met Tyr Thr Val Gly Asp Tyr Leu Leu Asp Arg Leu His Glu Leu Gly
  1               5                  10                  15

Ile Glu Glu Ile Phe Gly Val Pro Gly Asp Tyr Asn Leu Gln Phe Leu
             20                  25                  30

Asp Gln Ile Ile Ser Arg Glu Asp Met Lys Trp Ile Gly Asn Ala Asn
         35                  40                  45

Glu Leu Asn Ala Ser Tyr Met Ala Asp Gly Tyr Ala Arg Thr Lys Lys
     50                  55                  60

Ala Ala Ala Phe Leu Thr Thr Phe Gly Val Gly Glu Leu Ser Ala Ile
 65                  70                  75                  80

Asn Gly Leu Ala Gly Ser Tyr Ala Glu Asn Leu Pro Val Val Glu Ile
                 85                  90                  95

Val Gly Ser Pro Thr Ser Lys Val Gln Asn Asp Gly Lys Phe Val His
            100                 105                 110

His Thr Leu Ala Asp Gly Asp Phe Lys His Phe Met Lys Met His Glu
        115                 120                 125

Pro Val Thr Ala Ala Arg Thr Leu Leu Thr Ala Glu Asn Ala Thr Tyr
    130                 135                 140

Glu Ile Asp Arg Val Leu Ser Gln Leu Leu Lys Glu Arg Lys Pro Val
145                 150                 155                 160

Tyr Ile Asn Leu Pro Val Asp Val Ala Ala Ala Lys Ala Glu Lys Pro
                165                 170                 175

Ala Leu Ser Leu Glu Lys Glu Ser Ser Thr Thr Asn Thr Thr Glu Gln
            180                 185                 190

Val Ile Leu Ser Lys Ile Glu Glu Ser Leu Lys Asn Ala Gln Lys Pro
        195                 200                 205

Val Val Ile Ala Gly His Glu Val Ile Ser Phe Gly Leu Glu Lys Thr
    210                 215                 220

Val Thr Gln Phe Val Ser Glu Thr Lys Leu Pro Ile Thr Thr Leu Asn
225                 230                 235                 240

Phe Gly Lys Ser Ala Val Asp Glu Ser Leu Pro Ser Phe Leu Gly Ile
                245                 250                 255

Tyr Asn Gly Lys Leu Ser Glu Ile Ser Leu Lys Asn Phe Val Glu Ser
            260                 265                 270

Ala Asp Phe Ile Leu Met Leu Gly Val Lys Leu Thr Asp Ser Ser Thr
        275                 280                 285

Gly Ala Phe Thr His His Leu Asp Glu Asn Lys Met Ile Ser Leu Asn
```

```
        290                 295                 300
Ile Asp Glu Gly Ile Ile Phe Asn Lys Val Val Glu Asp Phe Asp Phe
305                 310                 315                 320

Arg Ala Val Val Ser Ser Leu Ser Glu Leu Lys Gly Ile Glu Tyr Glu
                325                 330                 335

Gly Gln Tyr Ile Asp Lys Gln Tyr Glu Phe Ile Pro Ser Ser Ala
            340                 345                 350

Pro Leu Ser Gln Asp Arg Leu Trp Gln Ala Val Glu Ser Leu Thr Gln
        355                 360                 365

Ser Asn Glu Thr Ile Val Ala Glu Gln Gly Thr Ser Phe Phe Gly Ala
    370                 375                 380

Ser Thr Ile Phe Leu Lys Ser Asn Ser Arg Phe Ile Gly Gln Pro Leu
385                 390                 395                 400

Trp Gly Ser Ile Gly Tyr Thr Phe Pro Ala Ala Leu Gly Ser Gln Ile
                405                 410                 415

Ala Asp Lys Glu Ser Arg His Leu Leu Phe Ile Gly Asp Gly Ser Leu
            420                 425                 430

Gln Leu Thr Val Gln Glu Leu Gly Leu Ser Ile Arg Glu Lys Leu Asn
        435                 440                 445

Pro Ile Cys Phe Ile Ile Asn Asn Asp Gly Tyr Thr Val Glu Arg Glu
    450                 455                 460

Ile His Gly Pro Thr Gln Ser Tyr Asn Asp Ile Pro Met Trp Asn Tyr
465                 470                 475                 480

Ser Lys Leu Pro Glu Thr Phe Gly Ala Thr Glu Asp Arg Val Val Ser
                485                 490                 495

Lys Ile Val Arg Thr Glu Asn Glu Phe Val Ser Val Met Lys Glu Ala
            500                 505                 510

Gln Ala Asp Val Asn Arg Met Tyr Trp Ile Glu Leu Val Leu Glu Lys
        515                 520                 525

Glu Asp Ala Pro Lys Leu Leu Lys Lys Met Gly Lys Leu Phe Ala Glu
    530                 535                 540

Gln Asn Lys
545

<210> SEQ ID NO 26
<211> LENGTH: 1828
<212> TYPE: DNA
<213> ORGANISM: Lactococcus lactis

<400> SEQUENCE: 26
tttaaataag tcaatatcgt tgacttattt agaagaaaga gttattcttt aaatgtcaag    60
ttagttgact aaattaaata taaaatatgg aggaatgtga tgtatacagt aggagattac   120
ctgttagacc gattacacga gttgggaatt gaagaaattt ttggagttcc tggtgactat   180
aacttacaat ttttagatca aattatttca cgcgaagata tgaaatggat tggaaatgct   240
aatgaattaa atgcttctta tatggctgat ggttatgctc gtactaaaaa agctgccgca   300
tttctcacca catttggagt cggcgaattg agtgcgatca atggactggc aggaagttat   360
gccgaaaatt taccagtagt agaaattgtt ggttcaccaa cttcaaaagt acaaatgac    420 ggaaaatttg tccatcatac actagcagat ggtgatttta acactttat gaagatgcat   480 gaacctgtta cagcagcgcg gactttactg acagcagaaa atgccacata tgaaattgac   540
cgagtacttt ctcaattact aaaagaaaga aaaccagtct atattaactt accagtcgat   600
gttgctgcag caaaagcaga gaagcctgca ttatctttag aaaaagaaag ctctacaaca   660
```

```
aatacaactg aacaagtgat tttgagtaag attgaagaaa gtttgaaaaa tgcccaaaaa      720
ccagtagtga ttgcaggaca cgaagtaatt agttttggtt tagaaaaaac ggtaactcag      780
tttgtttcag aaacaaaact accgattacg acactaaatt ttggtaaaag tgctgttgat      840
gaatctttgc cctcattttt aggaatatat aacgggaaac tttcagaaat cagtcttaaa      900
aattttgtgg agtccgcaga ctttatccta atgcttggag tgaagcttac ggactcctca      960
acaggtgcat tcacacatca tttagatgaa aataaaatga tttcactaaa catagatgaa     1020
ggataatttt tcaataaagt ggtagaagat tttgatttta gagcagtggt ttcttcttta     1080
tcagaattaa aaggaataga atatgaagga caatatattg ataagcaata tgaagaattt     1140
attccatcaa gtgctcccct atcacaagac cgtctatggc aggcagttga agtttgact       1200 caaagcaatg aaacaatcgt tgctgaacaa ggaacctcat tttttggagc ttcaacaatt     1260
ttcttaaaat caaatagtcg ttttattgga caacctttat ggggttctat tggatatact     1320
tttccagcgg ctttaggaag ccaaattgcg gataaagaga gcagacacct tttatttatt     1380
ggtgatggtt cacttcaact taccgtacaa gaattaggac tatcaatcag agaaaaactc     1440
aatccaattt gttttatcat aaataatgat ggttatacag ttgaaagaga atccacgga      1500 cctactcaaa gttataacga cattccaatg tggaattact cgaaattacc agaaacattt     1560
ggagcaacag aagatcgtgt agtatcaaaa attgttagaa cagagaatga atttgtgtct     1620
gtcatgaaag aagcccaagc agatgtcaat agaatgtatt ggatagaact agttttggaa     1680
aaagaagatg cgccaaaatt actgaaaaaa atgggtaaat tatttgctga gcaaaataaa     1740
tagatatcaa cggatgatga aaagtaaaat agacaaagtc caataatttt ataaaaagta     1800
aaaacattag gattttccta atgttttt                                        1828
```

<210> SEQ ID NO 27
<211> LENGTH: 548
<212> TYPE: PRT
<213> ORGANISM: Lactococcus lactis

<400> SEQUENCE: 27

```
Met Tyr Thr Val Gly Asp Tyr Leu Leu Asp Arg Leu His Glu Leu Gly
 1               5                  10                  15

Ile Glu Glu Ile Phe Gly Val Pro Gly Asp Tyr Asn Leu Gln Phe Leu
            20                  25                  30

Asp Gln Ile Ile Ser His Lys Asp Met Lys Trp Val Gly Asn Ala Asn
        35                  40                  45

Glu Leu Asn Ala Ser Tyr Met Ala Asp Gly Tyr Ala Arg Thr Lys Lys
    50                  55                  60

Ala Ala Ala Phe Leu Thr Thr Phe Gly Val Gly Glu Leu Ser Ala Val
65                  70                  75                  80

Asn Gly Leu Ala Gly Ser Tyr Ala Glu Asn Leu Pro Val Val Glu Ile
                85                  90                  95

Val Gly Ser Pro Thr Ser Lys Val Gln Asn Glu Gly Lys Phe Val His
            100                 105                 110

His Thr Leu Ala Asp Gly Asp Phe Lys His Phe Met Lys Met His Glu
        115                 120                 125

Pro Val Thr Ala Ala Arg Thr Leu Leu Thr Ala Glu Asn Ala Thr Val
    130                 135                 140

Glu Ile Asp Arg Val Leu Ser Ala Leu Leu Lys Glu Arg Lys Pro Val
145                 150                 155                 160
```

```
Tyr Ile Asn Leu Pro Val Asp Val Ala Ala Ala Lys Ala Glu Lys Pro
                165                 170                 175
Ser Leu Pro Leu Lys Lys Glu Asn Ser Thr Ser Asn Thr Ser Asp Gln
            180                 185                 190
Glu Ile Leu Asn Lys Ile Gln Glu Ser Leu Lys Asn Ala Lys Lys Pro
        195                 200                 205
Ile Val Ile Thr Gly His Glu Ile Ile Ser Phe Gly Leu Glu Lys Thr
    210                 215                 220
Val Thr Gln Phe Ile Ser Lys Thr Lys Leu Pro Ile Thr Thr Leu Asn
225                 230                 235                 240
Phe Gly Lys Ser Ser Val Asp Glu Ala Leu Pro Ser Phe Leu Gly Ile
                245                 250                 255
Tyr Asn Gly Thr Leu Ser Glu Pro Asn Leu Lys Glu Phe Val Glu Ser
            260                 265                 270
Ala Asp Phe Ile Leu Met Leu Gly Val Lys Leu Thr Asp Ser Ser Thr
        275                 280                 285
Gly Ala Phe Thr His His Leu Asn Glu Asn Lys Met Ile Ser Leu Asn
    290                 295                 300
Ile Asp Glu Gly Lys Ile Phe Asn Glu Arg Ile Gln Asn Phe Asp Phe
305                 310                 315                 320
Glu Ser Leu Ile Ser Ser Leu Leu Asp Leu Ser Glu Ile Glu Tyr Lys
                325                 330                 335
Gly Lys Tyr Ile Asp Lys Lys Gln Glu Asp Phe Val Pro Ser Asn Ala
            340                 345                 350
Leu Leu Ser Gln Asp Arg Leu Trp Gln Ala Val Glu Asn Leu Thr Gln
        355                 360                 365
Ser Asn Glu Thr Ile Val Ala Glu Gln Gly Thr Ser Phe Phe Gly Ala
    370                 375                 380
Ser Ser Ile Phe Leu Lys Ser Lys Ser His Phe Ile Gly Gln Pro Leu
385                 390                 395                 400
Trp Gly Ser Ile Gly Tyr Thr Phe Pro Ala Ala Leu Gly Ser Gln Ile
                405                 410                 415
Ala Asp Lys Glu Ser Arg His Leu Leu Phe Ile Gly Asp Gly Ser Leu
            420                 425                 430
Gln Leu Thr Val Gln Glu Leu Gly Leu Ala Ile Arg Glu Lys Ile Asn
        435                 440                 445
Pro Ile Cys Phe Ile Ile Asn Asn Asp Gly Tyr Thr Val Glu Arg Glu
    450                 455                 460
Ile His Gly Pro Asn Gln Ser Tyr Asn Asp Ile Pro Met Trp Asn Tyr
465                 470                 475                 480
Ser Lys Leu Pro Glu Ser Phe Gly Ala Thr Glu Asp Arg Val Val Ser
                485                 490                 495
Lys Ile Val Arg Thr Glu Asn Glu Phe Val Ser Val Met Lys Glu Ala
            500                 505                 510
Gln Ala Asp Pro Asn Arg Met Tyr Trp Ile Glu Leu Ile Leu Ala Lys
        515                 520                 525
Glu Gly Ala Pro Lys Val Leu Lys Lys Met Gly Lys Leu Phe Ala Glu
    530                 535                 540
Gln Asn Lys Ser
545

<210> SEQ ID NO 28
<211> LENGTH: 1954
<212> TYPE: DNA
```

<213> ORGANISM: Lactococcus lactis

<400> SEQUENCE: 28

```
ctagagtttt ctttagtcat aattcactcc ttttattagt ctattatact tgataattca        60
aataagtcaa tatcgttgac ttatttaaag aaaagcgtta ttctataaat gtcaagttga       120
ttgaccaata tataataaaa tatggaggaa tgcgatgtat acagtaggag attacctatt       180
agaccgatta cacgagttag gaattgaaga aattttttgga gtccctggag actataactt      240
acaattttta gatcaaatta tttcccacaa ggatatgaaa tgggtcggaa atgctaatga       300
attaaatgct tcatatatgg ctgatggcta tgctcgtact aaaaaagctg ccgcatttct       360
tacaaccttt ggagtaggtg aattgagtgc agttaatgga ttagcaggaa gttacgccga      420
aaatttacca gtagtagaaa tagtgggatc acctacatca aaagttcaaa atgaaggaaa      480
atttgttcat catacgctgg ctgacggtga ttttaaacac tttatgaaaa tgcacgaacc      540
tgttacagca gctcgaactt tactgacagc agaaaatgca accgttgaaa ttgaccgagt      600
actttctgca ctattaaaag aaagaaaacc tgtctatatc aacttaccag ttgatgttgc      660
tgctgcaaaa gcagagaaac cctcactccc tttgaaaaag gaaaactcaa cttcaaatac      720
aagtgaccaa gaaattttga acaaaattca agaaagcttg aaaaatgcca aaaaaccaat      780
cgtgattaca ggacatgaaa taattagttt tggcttagaa aaaacagtca ctcaatttat      840
ttcaaagaca aaactaccta ttacgacatt aaactttggt aaaagttcag ttgatgaagc      900
cctcccttca tttttaggaa tctataatgg tacactctca gagcctaatc ttaaagaatt      960
cgtggaatca gccgacttca tcttgatgct tggagttaaa ctcacagact cttcaacagg     1020
agccttcact catcatttaa atgaaaataa aatgatttca ctgaatatag atgaaggaaa     1080
aatatttaac gaaagaatcc aaaatttttga ttttgaatcc ctcatctcct ctctcttaga     1140
cctaagcgaa atagaataca aggaaaata tatcgataaa aagcaagaag actttgttcc      1200
atcaaatgcg cttttatcac aagaccgcct atggcaagca gttgaaaacc taactcaaag     1260
caatgaaaca atcgttgctg aacaagggac atcattcttt ggcgcttcat caattttctt     1320
aaaatcaaag agtcatttta ttggtcaacc cttatgggga tcaattggat atacattccc     1380
agcagcatta ggaagccaaa ttgcagataa agaaagcaga cacctttat ttattggtga      1440
tggttcactt caacttacag tgcaagaatt aggattagca atcagagaaa aaattaatcc     1500
aatttgcttt attatcaata atgatggtta tacagtcgaa agagaaattc atggaccaaa     1560
tcaaagctac aatgatattc caatgtggaa ttactcaaaa ttaccagaat cgtttggagc     1620
aacagaagat cgagtagtct caaaaatcgt tagaactgaa aatgaatttg tgtctgtcat     1680
gaaagaagct caagcagatc caaatagaat gtactggatt gagttaattt tggcaaaaga     1740
aggtgcacca aaagtactga aaaaatgggg caaactattt gctgaacaaa ataaatcata     1800
atttataaat agtaaaaaac attaggaaat acctaatgtt tttttgttga ctaaatcaat     1860
ccctcttttat atagaaaacc ttagtttctc aaagacaact taattaagcc tgccaaattg     1920
gaactcgcaa aatgtaatct atcctctgct ccta                                 1954
```

<210> SEQ ID NO 29
<211> LENGTH: 550
<212> TYPE: PRT
<213> ORGANISM: Salmonella typhimurium

<400> SEQUENCE: 29

Met Gln Asn Pro Tyr Thr Val Ala Asp Tyr Leu Leu Asp Arg Leu Ala

-continued

```
1               5                   10                  15
Gly Cys Gly Ile Gly His Leu Phe Gly Val Pro Gly Asp Tyr Asn Leu
            20                  25                  30

Gln Phe Leu Asp His Val Ile Asp His Pro Thr Leu Arg Trp Val Gly
            35                  40                  45

Cys Ala Asn Glu Leu Asn Ala Ala Tyr Ala Ala Asp Gly Tyr Ala Arg
50                      55                  60

Met Ser Gly Ala Gly Ala Leu Leu Thr Thr Phe Gly Val Gly Glu Leu
65                      70                  75                  80

Ser Ala Ile Asn Gly Ile Ala Gly Ser Tyr Ala Glu Tyr Val Pro Val
                    85                  90                  95

Leu His Ile Val Gly Ala Pro Cys Ser Ala Ala Gln Gln Arg Gly Glu
                    100                 105                 110

Leu Met His His Thr Leu Gly Asp Gly Asp Phe Arg His Phe Tyr Arg
                    115                 120                 125

Met Ser Gln Ala Ile Ser Ala Ala Ser Ala Ile Leu Asp Glu Gln Asn
            130                 135                 140

Ala Cys Phe Glu Ile Asp Arg Val Leu Gly Glu Met Leu Ala Ala Arg
145                     150                 155                 160

Arg Pro Gly Tyr Ile Met Leu Pro Ala Asp Val Ala Lys Lys Thr Ala
                    165                 170                 175

Ile Pro Pro Thr Gln Ala Leu Ala Leu Pro Val His Glu Ala Gln Ser
                    180                 185                 190

Gly Val Glu Thr Ala Phe Arg Tyr His Ala Arg Gln Cys Leu Met Asn
                    195                 200                 205

Ser Arg Arg Ile Ala Leu Leu Ala Asp Phe Leu Ala Gly Arg Phe Gly
            210                 215                 220

Leu Arg Pro Leu Leu Gln Arg Trp Met Ala Glu Thr Pro Ile Ala His
225                     230                 235                 240

Ala Thr Leu Leu Met Gly Lys Gly Leu Phe Asp Glu Gln His Pro Asn
                    245                 250                 255

Phe Val Gly Thr Tyr Ser Ala Gly Ala Ser Ser Lys Glu Val Arg Gln
                    260                 265                 270

Ala Ile Glu Asp Ala Asp Arg Val Ile Cys Val Gly Thr Arg Phe Val
            275                 280                 285

Asp Thr Leu Thr Ala Gly Phe Thr Gln Gln Leu Pro Ala Glu Arg Thr
            290                 295                 300

Leu Glu Ile Gln Pro Tyr Ala Ser Arg Ile Gly Glu Thr Trp Phe Asn
305                     310                 315                 320

Leu Pro Met Ala Gln Ala Val Ser Thr Leu Arg Glu Leu Cys Leu Glu
                    325                 330                 335

Cys Ala Phe Ala Pro Pro Thr Arg Ser Ala Gly Gln Pro Val Arg
                    340                 345                 350

Ile Asp Lys Gly Glu Leu Thr Gln Glu Ser Phe Trp Gln Thr Leu Gln
            355                 360                 365

Gln Tyr Leu Lys Pro Gly Asp Ile Ile Leu Val Asp Gln Gly Thr Ala
            370                 375                 380

Ala Phe Gly Ala Ala Leu Ser Leu Pro Asp Gly Ala Glu Val Val
385                     390                 395                 400

Leu Gln Pro Leu Trp Gly Ser Ile Gly Tyr Ser Leu Pro Ala Ala Phe
                    405                 410                 415

Gly Ala Gln Thr Ala Cys Pro Asp Arg Arg Val Ile Leu Ile Ile Gly
            420                 425                 430
```

Asp Gly Ala Ala Gln Leu Thr Ile Gln Glu Met Gly Ser Met Leu Arg
        435                 440                 445

Asp Gly Gln Ala Pro Val Ile Leu Leu Asn Asn Asp Gly Tyr Thr
    450                 455                 460

Val Glu Arg Ala Ile His Gly Ala Ala Gln Arg Tyr Asn Asp Ile Ala
465                 470                 475                 480

Ser Trp Asn Trp Thr Gln Ile Pro Pro Ala Leu Asn Ala Ala Gln Gln
                485                 490                 495

Ala Glu Cys Trp Arg Val Thr Gln Ala Ile Gln Leu Ala Glu Val Leu
            500                 505                 510

Glu Arg Leu Ala Arg Pro Gln Arg Leu Ser Phe Ile Glu Val Met Leu
        515                 520                 525

Pro Lys Ala Asp Leu Pro Glu Leu Leu Arg Thr Val Thr Arg Ala Leu
    530                 535                 540

Glu Ala Arg Asn Gly Gly
545                 550

<210> SEQ ID NO 30
<211> LENGTH: 1653
<212> TYPE: DNA
<213> ORGANISM: Salmonella typhimurium

<400> SEQUENCE: 30
ttatcccccg ttgcgggctt ccagcgcccg ggtcacggta cgcagtaatt ccggcagatc      60
ggcttttggc aacatcactt caataaatga cagacgttgt gggcgcgcca accgttcgag     120
gacctctgcc agttggatag cctgcgtcac ccgccagcac tccgcctgtt gcgccgcgtt     180
tagcgccggt ggtatctgcg tccagttcca gctcgcgatg tcgttatacc gctgggccgc     240
gccgtgaatg gcgcgctcta cggtatagcc gtcattgttg agcagcagga tgaccggcgc     300
ctgcccgtcg cgtaacatcg agcccatctc ctgaatcgtg agctgcgccg cgcatcgcc     360 gataatcaga atcacccgcc gatcgggaca ggcggtttgc gcgccaaacg cggcgggcaa     420
ggaatagccg atagaccccc acagcggctg taacacaact tccgcgccgt caggaagcga     480
cagcgcggca gcgccaaaag ctgctgtccc ctggtcgaca aggataatat ctccgggttt     540
gagatactgc tgtaaggttt gccagaagct ttcctgggtc agttctcctt tatcaatccg     600
cactggctgt ccggcggaac gcgtcggcgg cggcgcaaaa gcgcattcca ggcacagttc     660
gcgcagcgta gacaccgcct gcgccatcgg gaggttgaac caggtttcgc cgatgcgcga     720
cgcgtaaggc tgaatctcca gcgtgcgttc cgccggtaat tgttgggtaa atccggccgt     780
aagggtatcg acaaaacggg tgccgacgca gataaaccta tcggcgtcct ctatggcctg     840
acgcacttct ttgctgctgg cgccagcgct ataggtgcca acgaagttcg ggtgctgttc     900
atcaaaaagc cccttcccca tcagtagtgt cgcatgagcg atgggcgttt ccgccatcca     960
gcgctgcaac agtggtcgta aaccaaaacg cccggcaaga aagtcggcca atagcgcaat    1020
gcgccgactg ttcatcaggc actgacgggc gtgataacga aaggccgtct ccacgccgct    1080
ttgcgcttca tgcacgggca acgccagcgc ctgcgtaggt gggatggccg tttttttcgc    1140
cacatcggcg ggcaacatga tgtatcctgg cctgcgtgcg gcaagcattt cacccaacac    1200
gcggtcaatc tcgaaacagg cgttctgttc atctaatatt gcgctggcag cggatatcgc    1260
ctgactcatg cgataaaaat gacgaaaatc gccgtcaccg agggtatggt gcatcaattc    1320
gccacgctgc tgcgcagcgc tacagggcgc gccgacgata tgcaagaccg ggacatattc    1380

```
cgcgtaactg cccgcgatac cgttaatagc gctaagttct cccacgccaa aggtggtgag    1440
tagcgctcca gcgcccgaca tgcgcgcata gccgtccgcg gcataagcgg cgttcagctc    1500
attggcgcat cccacccaac gcagggtcgg gtggtcaatc acatggtcaa gaaactgcaa    1560
gttataatcg cccggtacgc caaaaagatg gccaatgccg catcctgcca gtctgtccag    1620
caaatagtcg gccacggtat aggggttttg cat                                 1653

<210> SEQ ID NO 31
<211> LENGTH: 554
<212> TYPE: PRT
<213> ORGANISM: Clostridium acetobutylicum

<400> SEQUENCE: 31
```

Met Lys Ser Glu Tyr Thr Ile Gly Arg Tyr Leu Leu Asp Arg Leu Ser
1               5                   10                  15

Glu Leu Gly Ile Arg His Ile Phe Gly Val Pro Gly Asp Tyr Asn Leu
            20                  25                  30

Ser Phe Leu Asp Tyr Ile Met Glu Tyr Lys Gly Ile Asp Trp Val Gly
        35                  40                  45

Asn Cys Asn Glu Leu Asn Ala Gly Tyr Ala Ala Asp Gly Tyr Ala Arg
    50                  55                  60

Ile Asn Gly Ile Gly Ala Ile Leu Thr Thr Phe Gly Val Gly Glu Leu
65                  70                  75                  80

Ser Ala Ile Asn Ala Ile Ala Gly Ala Tyr Ala Glu Gln Val Pro Val
                85                  90                  95

Val Lys Ile Thr Gly Ile Pro Thr Ala Lys Val Arg Asp Asn Gly Leu
            100                 105                 110

Tyr Val His His Thr Leu Gly Asp Gly Arg Phe Asp His Phe Phe Glu
        115                 120                 125

Met Phe Arg Glu Val Thr Val Ala Glu Ala Leu Leu Ser Glu Glu Asn
    130                 135                 140

Ala Ala Gln Glu Ile Asp Arg Val Leu Ile Ser Cys Trp Arg Gln Lys
145                 150                 155                 160

Arg Pro Val Leu Ile Asn Leu Pro Ile Asp Val Tyr Asp Lys Pro Ile
                165                 170                 175

Asn Lys Pro Leu Lys Pro Leu Leu Asp Tyr Thr Ile Ser Ser Asn Lys
            180                 185                 190

Glu Ala Ala Cys Glu Phe Val Thr Glu Ile Val Pro Ile Ile Asn Arg
        195                 200                 205

Ala Lys Lys Pro Val Ile Leu Ala Asp Tyr Gly Val Tyr Arg Tyr Gln
    210                 215                 220

Val Gln His Val Leu Lys Asn Leu Ala Glu Lys Thr Gly Phe Pro Val
225                 230                 235                 240

Ala Thr Leu Ser Met Gly Lys Gly Val Phe Asn Glu Ala His Pro Gln
                245                 250                 255

Phe Ile Gly Val Tyr Asn Gly Asp Val Ser Ser Pro Tyr Leu Arg Gln
            260                 265                 270

Arg Val Asp Glu Ala Asp Cys Ile Ile Ser Val Gly Val Lys Leu Thr
        275                 280                 285

Asp Ser Thr Thr Gly Gly Phe Ser His Gly Phe Ser Lys Arg Asn Val
    290                 295                 300

Ile His Ile Asp Pro Phe Ser Ile Lys Ala Lys Gly Lys Lys Tyr Ala
305                 310                 315                 320

Pro Ile Thr Met Lys Asp Ala Leu Thr Glu Leu Thr Ser Lys Ile Glu

```
                 325                 330                 335
His Arg Asn Phe Glu Asp Leu Asp Ile Lys Pro Tyr Lys Ser Asp Asn
            340                 345                 350

Gln Lys Tyr Phe Ala Lys Glu Lys Pro Ile Thr Gln Lys Arg Phe Phe
            355                 360                 365

Glu Arg Ile Ala His Phe Ile Lys Glu Lys Asp Val Leu Leu Ala Glu
            370                 375                 380

Gln Gly Thr Cys Phe Phe Gly Ala Ser Thr Ile Gln Leu Pro Lys Asp
385                 390                 395                 400

Ala Thr Phe Ile Gly Gln Pro Leu Trp Gly Ser Ile Gly Tyr Thr Leu
                405                 410                 415

Pro Ala Leu Leu Gly Ser Gln Leu Ala Asp Gln Lys Arg Arg Asn Ile
            420                 425                 430

Leu Leu Ile Gly Asp Gly Ala Phe Gln Met Thr Ala Gln Glu Ile Ser
            435                 440                 445

Thr Met Leu Arg Leu Gln Ile Lys Pro Ile Ile Phe Leu Ile Asn Asn
            450                 455                 460

Asp Gly Tyr Thr Ile Glu Arg Ala Ile His Gly Arg Glu Gln Val Tyr
465                 470                 475                 480

Asn Asn Ile Gln Met Trp Arg Tyr His Asn Val Pro Lys Val Leu Gly
                485                 490                 495

Pro Lys Glu Cys Ser Leu Thr Phe Lys Val Gln Ser Gly Thr Glu Leu
            500                 505                 510

Glu Lys Ala Leu Leu Val Ala Asp Lys Asp Cys Glu His Leu Ile Phe
            515                 520                 525

Ile Glu Val Val Met Asp Arg Tyr Asp Lys Pro Glu Pro Leu Glu Arg
            530                 535                 540

Leu Ser Lys Arg Phe Ala Asn Gln Asn Asn
545                 550

<210> SEQ ID NO 32
<211> LENGTH: 1665
<212> TYPE: DNA
<213> ORGANISM: Clostridium acetobutylicum

<400> SEQUENCE: 32
ttgaagagtg aatacacaat tggaagatat ttgttagacc gtttatcaga gttgggtatt      60
cggcatatct ttggtgtacc tggagattac aatctatcct ttttagacta tataatggag     120
tacaaaggga tagattgggt tggaaattgc aatgaattga atgctgggta tgctgctgat     180
ggatatgcaa gaataaatgg aattggagcc atacttacaa catttggtgt tggagaatta     240
agtgccatta cgcaattgc tggggcatac gctgagcaag ttccagttgt taaaattaca     300
ggtatcccca cagcaaaagt tagggacaat ggattatatg tacaccacac attaggtgac     360
ggaaggtttg atcactttt tgaaatgttt agagaagtaa cagttgctga ggcattacta     420
agcgaagaaa atgcagcaca agaaattgat cgtgttctta tttcatgctg agacaaaaa      480 cgtcctgttc ttataaattt accgattgat gtatatgata accaattaa caaaccatta      540 aagccattac tcgattatac tatttcaagt aacaaagagg ctgcatgtga atttgttaca     600
gaaatagtac ctataataaa tagggcaaaa aagcctgtta ttcttgcaga ttatggagta     660
tatcgttacc aagttcaaca tgtgcttaaa aacttggccg aaaaaaccgg atttcctgtg     720
gctacactaa gtatgggaaa aggtgttttc aatgaagcac accctcaatt tattggtgtt     780
tataatggtg atgtaagttc tccttattta aggcagcgag ttgatgaagc agactgcatt     840
```

```
attagcgttg gtgtaaaatt gacggattca accacagggg gattttctca tggattttct    900
aaaaggaatg taattcacat tgatcctttt tcaataaagg caaaaggtaa aaatatgca     960 cctattacga tgaaagatgc tttaacagaa ttaacaagta aaattgagca tagaaacttt   1020
gaggatttag atataaagcc ttacaaatca gataatcaaa agtattttgc aaaagagaag   1080
ccaattacac aaaaacgttt ttttgagcgt attgctcact ttataaaaga aaaagatgta   1140
ttattagcag aacagggtac atgctttttt ggtgcgtcaa ccatacaact acccaaagat   1200
gcaactttta ttggtcaacc tttatgggga tctattggat acacacttcc tgctttatta   1260
ggttcacaat tagctgatca aaaaaggcgt aatattcttt taattgggga tggtgcattt   1320
caaatgacag cacaagaaat ttcaacaatg cttcgtttac aaatcaaacc tattattttt   1380
ttaattaata cgatggtta tacaattgaa cgtgctattc atggtagaga acaagtatat     1440
aacaatattc aaatgtggcg atatcataat gttccaaagg ttttaggtcc taaagaatgc   1500
agcttaacct ttaaagtaca aagtgaaact gaacttgaaa aggctctttt agtggcagat   1560
aaggattgtg aacatttgat ttttatagaa gttgttatgg atcgttatga taaacccgag   1620
cctttagaac gtctttcgaa acgttttgca aatcaaaata attag                  1665

<210> SEQ ID NO 33
<211> LENGTH: 1641
<212> TYPE: DNA
<213> ORGANISM: Clostridium acetobutylicum

<400> SEQUENCE: 33
atgaaacaac gtatcgggca atacttgatc gatgccctac acgttaatgg tgtcgataag     60
atctttggag tcccaggtga tttcactta gccttttggg acgatatcat aagacatgac     120
aacgtggaat gggtgggaaa tactaatgag ttgaacgccg cttacgccgc tgatggttac    180
gctagagtta atggattagc cgctgtatct accacttttg gggttggcga gttatctgct    240
gtgaatggta ttgctggaag ttacgcagag cgtgttcctg taatcaaaat ctcaggcggt    300
ccttcatcag ttgctcaaca agagggtaga tatgtccacc attcattggg tgaaggaatc    360
tttgattcat attcaaagat gtacgctcac ataaccgcaa caactacaat cttatccgtt    420
gacaacgcag tcgacgaaat tgatagagtt attcattgtg ctttgaagga aaagaggcca    480
gtgcatattc atttgcctat tgacgtagcc ttaactgaga ttgaaatccc tcatgcacca    540
aaagtttaca cacgaatc ccagaacgtc gatgcttaca ttcaagctgt tgagaaaaag     600
ttaatgtctg caaaacaacc agtaatcata gcaggtcatg aaatcaattc attcaagttg    660
cacgaacaac tggaacagtt tgtcaatcag acaaacatcc ctgttgcaca actttccttg    720
ggtaagtctg ctttcaatga agagaatgaa cattaccttg gtatctacga tggcaaaatc    780
gcaaaggaaa atgtgagaga gtacgtcgac aatgctgatg tcatattgaa cataggtgcc    840
aaactgactg attctgctac agctggattt tcctacaagt tcgatacaaa caacataatc    900
tacattaacc ataatgactt caaagctgaa gatgtgattt ctgataatgt tcactgatt    960 gatcttgtga atggcctgaa ttctattgac tatagaaatg aaacacacta cccatcttat   1020
caaagatctg atatgaaata cgaattgaat gacgcaccac ttacacaatc taactatttc   1080
aaaatgatga acgcttttct agaaaaagat gacatcctac tagctgaaca aggtacatcc   1140
tttttcggcg catatgactt atcccctatac aagggaaatc agtttatcgg tcagccttta   1200
tgggggtcaa tagggtatac ttttccatct ttactaggaa gtcaactagc agacatgcat   1260
```

```
aggagaaaca ttttgcttat aggcgatggt agtttacaac ttactgttca agccctaagt    1320
acaatgatta gaaaggatat caaaccaatc attttcgtta tcaataacga cggttacacc    1380
gtcgaaagac ttatccacgg catggaagag ccatacaatg atatccaaat gtggaactac    1440
aagcaattgc cagaagtatt tggtggaaaa gatactgtaa aagttcatga tgctaaaacc    1500
tccaacgaac tgaaaactgt aatggattct gttaaagcag acaaagatca catgcatttc    1560
attgaagtgc atatggcagt agaggacgcc ccaaagaagt tgattgatat agctaaagcc    1620
tttagtgatg ctaacaagta a                                              1641

<210> SEQ ID NO 34
<211> LENGTH: 1647
<212> TYPE: DNA
<213> ORGANISM: Listeria grayi

<400> SEQUENCE: 34
atgtacaccg tcggccaata cttagtagac cgcttagaag agatcggcat cgataaggtt      60
tttggtgtcc cgggtgacta caacctgacc tttttggact acatccagaa ccacgaaggt     120
ctgagctggc aaggtaatac gaatgaactg aatgccgcgt acgcagctga tggctatgct     180
cgtgaacgcg gtgttagcgc tttggtcacg accttcggcg ttggtgagct gtccgcaatc     240
aatggcaccg caggtagctt cgcggagcaa gttccggtga ttcatatcgt gggcagcccg     300
accatgaatg ttcagagcaa caagaaactg gttcatcaca gcctgggtat gggcaacttt     360
cacaacttca gcgagatggc gaaagaagtc accgccgcaa ccacgatgct gacggaagag     420
aatgcggcgt cggagattga tcgtgttctg gaaaccgccc tgctggagaa cgcccagtg     480 tacatcaatc tgccgatcga cattgctcac aaggcgatcg tcaagccggc gaaagccctg     540
caaaccgaga gagctctgg cgagcgtgag gcacaactgg cggagatcat tctgagccat     600
ctggagaagg ctgcacagcc gattgtgatt gcgggtcacg agatcgcgcg cttccagatc     660
cgtgagcgtt tcgagaattg gattaatcaa acgaaactgc cggtgaccaa tctgcctac     720 ggcaagggta gcttcaacga agaaaacgag catttcattg gtacctatta tcctgcattt     780
agcgataaga acgtgctgga ctacgtggat aactccgact tgtcctgca cttggtggt     840 aaaatcattg ataacagcac ctccagcttc tccaaggct tcaaaccga gaacaccctg     900 actgcggcga cgatatcat tatgctgccg gactggagca cgtattctgg tattagctg     960 aatggcctgc tggccgagct ggaaaaactg aatttcacgt tgccgacac cgcagcaaag    1020 caggcggagt tggcggtgtt tgagccgcag gctgaaaccc cgttgaaaca ggaccgtttt    1080
caccaggcgg tgatgaattt tctgcaagct gacgatgtcc tggttacgga acagggcacc    1140 tcttctttg gcttgatgct ggcgcctctg aaaaagggta tgaacttgat ctcgcaaacg    1200 ctgtgggta gcattggtta cacgttgccg gcgatgattg gtagccaaat tgcggcaccg    1260
gagcgtcgtc atatcctgag cattggtgat ggtagctttc agctgactgc gcaggaaatg    1320
agcaccattt tccgtgagaa actgacccca gtcatcttca tcattaacaa tgatggctat    1380
accgttgagc gtgcgatcca tggcgaagat gaaagctata cgacattcc gacgtggaac    1440 ttgcaactgg tggcggaaac cttcggtggt gacgccgaaa ccgtcgacac tcacaatgtg    1500
ttcacggaga ctgatttcgc caacaccctg gcggcaattg acgcgacgcc gcagaaagca    1560
cacgttgtgg aagttcacat ggaacaaatg gatatgccgg agagcctgcg ccagatcggt    1620
ctggcactgt ccaagcagaa tagctaa                                        1647
```

<210> SEQ ID NO 35
<211> LENGTH: 312
<212> TYPE: PRT
<213> ORGANISM: Saccharomyces cerevisiae

<400> SEQUENCE: 35

Met Pro Ala Thr Leu Lys Asn Ser Ser Ala Thr Leu Lys Leu Asn Thr
1               5                   10                  15

Gly Ala Ser Ile Pro Val Leu Gly Phe Gly Thr Trp Arg Ser Val Asp
            20                  25                  30

Asn Asn Gly Tyr His Ser Val Ile Ala Ala Leu Lys Ala Gly Tyr Arg
        35                  40                  45

His Ile Asp Ala Ala Ile Tyr Leu Asn Glu Glu Val Gly Arg
    50                  55                  60

Ala Ile Lys Asp Ser Gly Val Pro Arg Glu Glu Ile Phe Ile Thr Thr
65                  70                  75                  80

Lys Leu Trp Gly Thr Glu Gln Arg Asp Pro Glu Ala Ala Leu Asn Lys
                85                  90                  95

Ser Leu Lys Arg Leu Gly Leu Asp Tyr Val Asp Leu Tyr Leu Met His
            100                 105                 110

Trp Pro Val Pro Leu Lys Thr Asp Arg Val Thr Asp Gly Asn Val Leu
        115                 120                 125

Cys Ile Pro Thr Leu Glu Asp Gly Thr Val Asp Ile Asp Thr Lys Glu
    130                 135                 140

Trp Asn Phe Ile Lys Thr Trp Glu Leu Met Gln Glu Leu Pro Lys Thr
145                 150                 155                 160

Gly Lys Thr Lys Ala Val Gly Val Ser Asn Phe Ser Ile Asn Asn Ile
                165                 170                 175

Lys Glu Leu Leu Glu Ser Pro Asn Asn Lys Val Val Pro Ala Thr Asn
            180                 185                 190

Gln Ile Glu Ile His Pro Leu Leu Pro Gln Asp Glu Leu Ile Ala Phe
        195                 200                 205

Cys Lys Glu Lys Gly Ile Val Val Glu Ala Tyr Ser Pro Phe Gly Ser
    210                 215                 220

Ala Asn Ala Pro Leu Leu Lys Glu Gln Ala Ile Ile Asp Met Ala Lys
225                 230                 235                 240

Lys His Gly Val Glu Pro Ala Gln Leu Ile Ile Ser Trp Ser Ile Gln
                245                 250                 255

Arg Gly Tyr Val Val Leu Ala Lys Ser Val Asn Pro Glu Arg Ile Val
            260                 265                 270

Ser Asn Phe Lys Ile Phe Thr Leu Pro Glu Asp Asp Phe Lys Thr Ile
        275                 280                 285

Ser Asn Leu Ser Lys Val His Gly Thr Lys Arg Val Val Asp Met Lys
    290                 295                 300

Trp Gly Ser Phe Pro Ile Phe Gln
305                 310

<210> SEQ ID NO 36
<211> LENGTH: 939
<212> TYPE: DNA
<213> ORGANISM: Saccharomyces cerevisiae

<400> SEQUENCE: 36
atgcctgcta cgttaaagaa ttcttctgct acattaaaac taaatactgg tgcctccatt      60
ccagtgttgg gtttcggcac ttggcgttcc gttgacaata acggttacca ttctgtaatt     120

-continued

```
gcagctttga aagctggata cagacacatt gatgctgcgg ctatctattt gaatgaagaa      180
gaagttggca gggctattaa agattccgga gtccctcgtg aggaaatttt tattactact      240
aagctttggg gtacggaaca acgtgatccg gaagctgctc taaacaagtc tttgaaaaga      300
ctaggcttgg attatgttga cctatatctg atgcattggc cagtgccttt gaaaaccgac      360
agagttactg atggtaacgt tctgtgcatt ccaacattag aagatggcac tgttgacatc      420
gatactaagg aatggaattt tatcaagacg tgggagttga tgcaagagtt gccaaagacg      480
ggcaaaacta aagccgttgg tgtctctaat ttttctatta acaacattaa agaattatta      540
gaatctccaa ataacaaggt ggtaccagct actaatcaaa ttgaaattca tccattgcta      600
ccacaagacg aattgattgc cttttgtaag gaaaagggta ttgttgttga agcctactca      660
ccatttggga gtgctaatgc tcctttacta aagagcaag caattattga tatggctaaa       720
aagcacggcg ttgagccagc acagcttatt atcagttgga gtattcaaag aggctacgtt      780
gttctggcca atcggttaa tcctgaaaga attgtatcca attttaagat tttcactctg       840
cctgaggatg atttcaagac tattagtaac ctatccaaag tgcatggtac aaagagagtc      900
gttgatatga agtggggatc cttcccaatt ttccaatga                              939
```

<210> SEQ ID NO 37
<211> LENGTH: 360
<212> TYPE: PRT
<213> ORGANISM: Saccharomyces cerevisiae

<400> SEQUENCE: 37

```
Met Ser Tyr Pro Glu Lys Phe Glu Gly Ile Ala Ile Gln Ser His Glu
 1               5                  10                  15

Asp Trp Lys Asn Pro Lys Lys Thr Lys Tyr Asp Pro Lys Pro Phe Tyr
            20                  25                  30

Asp His Asp Ile Asp Ile Lys Ile Glu Ala Cys Gly Val Cys Gly Ser
        35                  40                  45

Asp Ile His Cys Ala Ala Gly His Trp Gly Asn Met Lys Met Pro Leu
    50                  55                  60

Val Val Gly His Glu Ile Val Gly Lys Val Val Lys Leu Gly Pro Lys
65                  70                  75                  80

Ser Asn Ser Gly Leu Lys Val Gly Gln Arg Val Gly Val Gly Ala Gln
                85                  90                  95

Val Phe Ser Cys Leu Glu Cys Asp Arg Cys Lys Asn Asp Asn Glu Pro
            100                 105                 110

Tyr Cys Thr Lys Phe Val Thr Thr Tyr Ser Gln Pro Tyr Glu Asp Gly
        115                 120                 125

Tyr Val Ser Gln Gly Gly Tyr Ala Asn Tyr Val Arg Val His Glu His
    130                 135                 140

Phe Val Val Pro Ile Pro Glu Asn Ile Pro Ser His Leu Ala Ala Pro
145                 150                 155                 160

Leu Leu Cys Gly Gly Leu Thr Val Tyr Ser Pro Leu Val Arg Asn Gly
                165                 170                 175

Cys Gly Pro Gly Lys Lys Val Gly Ile Val Gly Leu Gly Gly Ile Gly
            180                 185                 190

Ser Met Gly Thr Leu Ile Ser Lys Ala Met Gly Ala Glu Thr Tyr Val
        195                 200                 205

Ile Ser Arg Ser Ser Arg Lys Arg Glu Asp Ala Met Lys Met Gly Ala
    210                 215                 220

Asp His Tyr Ile Ala Thr Leu Glu Glu Gly Asp Trp Gly Glu Lys Tyr
```

Phe Asp Thr Phe Asp Leu Ile Val Val Cys Ala Ser Ser Leu Thr Asp
225                 230                 235                 240
                245                             250                 255

Ile Asp Phe Asn Ile Met Pro Lys Ala Met Lys Val Gly Gly Arg Ile
                260                 265                 270

Val Ser Ile Ser Ile Pro Glu Gln His Glu Met Leu Ser Leu Lys Pro
        275                 280                 285

Tyr Gly Leu Lys Ala Val Ser Ile Ser Tyr Ser Ala Leu Gly Ser Ile
    290                 295                 300

Lys Glu Leu Asn Gln Leu Leu Lys Leu Val Ser Glu Lys Asp Ile Lys
305                 310                 315                 320

Ile Trp Val Glu Thr Leu Pro Val Gly Glu Ala Gly Val His Glu Ala
                325                 330                 335

Phe Glu Arg Met Glu Lys Gly Asp Val Arg Tyr Arg Phe Thr Leu Val
                340                 345                 350

Gly Tyr Asp Lys Glu Phe Ser Asp
        355                 360

<210> SEQ ID NO 38
<211> LENGTH: 1083
<212> TYPE: DNA
<213> ORGANISM: Saccharomyces cerevisiae

<400> SEQUENCE: 38
ctagtctgaa aattctttgt cgtagccgac taaggtaaat ctatatctaa cgtcacccett      60
ttccatcctt tcgaaggctt catggacgcc ggcttcacca acaggtaatg tttccaccca     120
aattttgata tcttttcag agactaattt caagagttgg ttcaattctt tgatggaacc      180
taaagcactg taagaaatgg agacagcctt taagccatat ggctttagcg ataacatttc     240
gtgttgttct ggtatagaga ttgagacaat tctaccacca accttcatag cctttggcat     300
aatgttgaag tcaatgtcgg taagggagga agcacagact acaatcaggt cgaaggtgtc     360
aaagtacttt tcaccccaat caccttcttc taatgtagca atgtagtgat cggcgcccat     420
cttcattgca tcttctcttt ttctcgaaga acgagaaata acatacgtct ctgccccat      480
ggctttggaa atcaatgtac ccatactgcc gataccacca agaccaacta taccaacttt     540
tttacctgga ccgcaaccgt tacgaaccaa tggagagtac acagtcaaac caccacataa     600
tagtggagca gccaaatgtg atggaatatt ctctgggata ggcaccacaa aatgttcatg     660
aactctgacg tagtttgcat agccaccctg cgacacatag ccgtcttcat aaggctgact     720
gtatgtggta acaaacttgg tgcagtatgg ttcattatca ttcttacaac ggtcacattc     780
caagcatgaa aagacttgag cacctacacc aacacgttga ccgactttca acccactgtt     840
tgacttgggc cctagcttga caacttttacc aacgatttca tgaccaacga ctagcggcat     900
cttcatattg ccccaatgac cagctgcaca atgaatatca ctaccgcaga caccacatgc     960
ttcgatctta atgtcaatgt catgatcgta aaatggtttt gggtcatact ttgtcttctt    1020
tgggttttc caatcttcgt gtgattgaat agcgatacct tcaaatttct caggataaga    1080
cat                                                                  1083

<210> SEQ ID NO 39
<211> LENGTH: 387
<212> TYPE: PRT
<213> ORGANISM: Escherichia coli

<400> SEQUENCE: 39

```
Met Asn Asn Phe Asn Leu His Thr Pro Thr Arg Ile Leu Phe Gly Lys
1               5                   10                  15

Gly Ala Ile Ala Gly Leu Arg Glu Gln Ile Pro His Asp Ala Arg Val
                20                  25                  30

Leu Ile Thr Tyr Gly Gly Ser Val Lys Lys Thr Gly Val Leu Asp
            35                  40                  45

Gln Val Leu Asp Ala Leu Lys Gly Met Asp Val Leu Glu Phe Gly Gly
50                  55                  60

Ile Glu Pro Asn Pro Ala Tyr Glu Thr Leu Met Asn Ala Val Lys Leu
65                  70                  75                  80

Val Arg Glu Gln Lys Val Thr Phe Leu Leu Ala Val Gly Gly Gly Ser
                85                  90                  95

Val Leu Asp Gly Thr Lys Phe Ile Ala Ala Ala Asn Tyr Pro Glu
                100                 105                 110

Asn Ile Asp Pro Trp His Ile Leu Gln Thr Gly Gly Lys Glu Ile Lys
            115                 120                 125

Ser Ala Ile Pro Met Gly Cys Val Leu Thr Leu Pro Ala Thr Gly Ser
130                 135                 140

Glu Ser Asn Ala Gly Ala Val Ile Ser Arg Lys Thr Thr Gly Asp Lys
145                 150                 155                 160

Gln Ala Phe His Ser Ala His Val Gln Pro Val Phe Ala Val Leu Asp
                165                 170                 175

Pro Val Tyr Thr Tyr Thr Leu Pro Pro Arg Gln Val Ala Asn Gly Val
                180                 185                 190

Val Asp Ala Phe Val His Thr Val Glu Gln Tyr Val Thr Lys Pro Val
                195                 200                 205

Asp Ala Lys Ile Gln Asp Arg Phe Ala Glu Gly Ile Leu Leu Thr Leu
210                 215                 220

Ile Glu Asp Gly Pro Lys Ala Leu Lys Glu Pro Glu Asn Tyr Asp Val
225                 230                 235                 240

Arg Ala Asn Val Met Trp Ala Ala Thr Gln Ala Leu Asn Gly Leu Ile
                245                 250                 255

Gly Ala Gly Val Pro Gln Asp Trp Ala Thr His Met Leu Gly His Glu
                260                 265                 270

Leu Thr Ala Met His Gly Leu Asp His Ala Gln Thr Leu Ala Ile Val
                275                 280                 285

Leu Pro Ala Leu Trp Asn Glu Lys Arg Asp Thr Lys Arg Ala Lys Leu
                290                 295                 300

Leu Gln Tyr Ala Glu Arg Val Trp Asn Ile Thr Glu Gly Ser Asp Asp
305                 310                 315                 320

Glu Arg Ile Asp Ala Ala Ile Ala Ala Thr Arg Asn Phe Phe Glu Gln
                325                 330                 335

Leu Gly Val Pro Thr His Leu Ser Asp Tyr Gly Leu Asp Gly Ser Ser
                340                 345                 350

Ile Pro Ala Leu Leu Lys Lys Leu Glu Glu His Gly Met Thr Gln Leu
                355                 360                 365

Gly Glu Asn His Asp Ile Thr Leu Asp Val Ser Arg Arg Ile Tyr Glu
                370                 375                 380

Ala Ala Arg
385

<210> SEQ ID NO 40
<211> LENGTH: 387
```

```
<212> TYPE: PRT
<213> ORGANISM: Escherichia coli

<400> SEQUENCE: 40

Met Asn Asn Phe Asn Leu His Thr Pro Thr Arg Ile Leu Phe Gly Lys
1               5                   10                  15

Gly Ala Ile Ala Gly Leu Arg Glu Gln Ile Pro His Asp Ala Arg Val
            20                  25                  30

Leu Ile Thr Tyr Gly Gly Ser Val Lys Lys Thr Gly Val Leu Asp
        35                  40                  45

Gln Val Leu Asp Ala Leu Lys Gly Met Asp Val Leu Glu Phe Gly Gly
    50                  55                  60

Ile Glu Pro Asn Pro Ala Tyr Glu Thr Leu Met Asn Ala Val Lys Leu
65                  70                  75                  80

Val Arg Glu Gln Lys Val Thr Phe Leu Leu Ala Val Gly Gly Gly Ser
                85                  90                  95

Val Leu Asp Gly Thr Lys Phe Ile Ala Ala Ala Asn Tyr Pro Glu
                100                 105                 110

Asn Ile Asp Pro Trp His Ile Leu Gln Thr Gly Gly Lys Glu Ile Lys
            115                 120                 125

Ser Ala Ile Pro Met Gly Cys Val Leu Thr Leu Pro Ala Thr Gly Ser
130                 135                 140

Glu Ser Asn Ala Gly Ala Val Ile Ser Arg Lys Thr Gly Asp Lys
145                 150                 155                 160

Gln Ala Phe His Ser Ala His Val Gln Pro Val Phe Ala Val Leu Asp
                165                 170                 175

Pro Val Tyr Thr Tyr Thr Leu Pro Pro Arg Gln Val Ala Asn Gly Val
            180                 185                 190

Val Asp Ala Phe Val His Thr Val Glu Gln Tyr Val Thr Lys Pro Val
            195                 200                 205

Asp Ala Lys Ile Gln Asp Arg Phe Ala Glu Gly Ile Leu Leu Thr Leu
210                 215                 220

Ile Glu Asp Gly Pro Lys Ala Leu Lys Glu Pro Glu Asn Tyr Asp Val
225                 230                 235                 240

Arg Ala Asn Val Met Trp Ala Ala Thr Gln Ala Leu Asn Gly Leu Ile
                245                 250                 255

Gly Ala Gly Val Pro Gln Asp Trp Ala Thr His Met Leu Gly His Glu
            260                 265                 270

Leu Thr Ala Met His Gly Leu Asp His Ala Gln Thr Leu Ala Ile Val
            275                 280                 285

Leu Pro Ala Leu Trp Asn Glu Lys Arg Asp Thr Lys Arg Ala Lys Leu
        290                 295                 300

Leu Gln Tyr Ala Glu Arg Val Trp Asn Ile Thr Glu Gly Ser Asp Asp
305                 310                 315                 320

Glu Arg Ile Asp Ala Ala Ile Ala Ala Thr Arg Asn Phe Phe Glu Gln
                325                 330                 335

Leu Gly Val Pro Thr His Leu Ser Asp Tyr Gly Leu Asp Gly Ser Ser
            340                 345                 350

Ile Pro Ala Leu Leu Lys Lys Leu Glu Glu His Gly Met Thr Gln Leu
        355                 360                 365

Gly Glu Asn His Asp Ile Thr Leu Asp Val Ser Arg Arg Ile Tyr Glu
370                 375                 380

Ala Ala Arg
385
```

<210> SEQ ID NO 41
<211> LENGTH: 389
<212> TYPE: PRT
<213> ORGANISM: Clostridium acetobutylicum

<400> SEQUENCE: 41

```
Met Leu Ser Phe Asp Tyr Ser Ile Pro Thr Lys Val Phe Phe Gly Lys
1               5                   10                  15

Gly Lys Ile Asp Val Ile Gly Glu Glu Ile Lys Lys Tyr Gly Ser Arg
            20                  25                  30

Val Leu Ile Val Tyr Gly Gly Ser Ile Lys Arg Asn Gly Ile Tyr
            35                  40                  45

Asp Arg Ala Thr Ala Ile Leu Lys Glu Asn Asn Ile Ala Phe Tyr Glu
        50                  55                  60

Leu Ser Gly Val Glu Pro Asn Pro Arg Ile Thr Thr Val Lys Lys Gly
65                  70                  75                  80

Ile Glu Ile Cys Arg Glu Asn Asn Val Asp Leu Val Leu Ala Ile Gly
                85                  90                  95

Gly Gly Ser Ala Ile Asp Cys Ser Lys Val Ile Ala Ala Gly Val Tyr
            100                 105                 110

Tyr Asp Gly Asp Thr Trp Asp Met Val Lys Asp Pro Ser Lys Ile Thr
        115                 120                 125

Lys Val Leu Pro Ile Ala Ser Ile Leu Thr Leu Ser Ala Thr Gly Ser
130                 135                 140

Glu Met Asp Gln Ile Ala Val Ile Ser Asn Met Glu Thr Asn Glu Lys
145                 150                 155                 160

Leu Gly Val Gly His Asp Asp Met Arg Pro Lys Phe Ser Val Leu Asp
                165                 170                 175

Pro Thr Tyr Thr Phe Thr Val Pro Lys Asn Gln Thr Ala Ala Gly Thr
            180                 185                 190

Ala Asp Ile Met Ser His Thr Phe Glu Ser Tyr Phe Ser Gly Val Glu
        195                 200                 205

Gly Ala Tyr Val Gln Asp Gly Ile Ala Glu Ala Ile Leu Arg Thr Cys
    210                 215                 220

Ile Lys Tyr Gly Lys Ile Ala Met Glu Lys Thr Asp Asp Tyr Glu Ala
225                 230                 235                 240

Arg Ala Asn Leu Met Trp Ala Ser Ser Leu Ala Ile Asn Gly Leu Leu
                245                 250                 255

Ser Leu Gly Lys Asp Arg Lys Trp Ser Cys His Pro Met Glu His Glu
            260                 265                 270

Leu Ser Ala Tyr Tyr Asp Ile Thr His Gly Val Gly Leu Ala Ile Leu
        275                 280                 285

Thr Pro Asn Trp Met Glu Tyr Ile Leu Asn Asp Asp Thr Leu His Lys
    290                 295                 300

Phe Val Ser Tyr Gly Ile Asn Val Trp Gly Ile Asp Lys Asn Lys Asp
305                 310                 315                 320

Asn Tyr Glu Ile Ala Arg Glu Ala Ile Lys Asn Thr Arg Glu Tyr Phe
                325                 330                 335

Asn Ser Leu Gly Ile Pro Ser Lys Leu Arg Glu Val Gly Ile Gly Lys
            340                 345                 350

Asp Lys Leu Glu Leu Met Ala Lys Gln Ala Val Arg Asn Ser Gly Gly
        355                 360                 365

Thr Ile Gly Ser Leu Arg Pro Ile Asn Ala Glu Asp Val Leu Glu Ile
```

Phe Lys Lys Ser Tyr
385

<210> SEQ ID NO 42
<211> LENGTH: 1170
<212> TYPE: DNA
<213> ORGANISM: Clostridium acetobutylicum

<400> SEQUENCE: 42

```
ttaataagat tttttaaata tctcaagaac atcctctgca tttattggtc ttaaacttcc      60
tattgttcct ccagaatttc taacagcttg ctttgccatt agttctagtt tatcttttcc     120
tattccaact tctctaagct ttgaaggaat acccaatgaa ttaaagtatt ctctcgtatt     180
tttaatagcc tctcgtgcta tttcatagtt atctttgttc ttgtctattc cccaaacatt     240
tattccataa gaaacaaatt tatgaagtgt atcgtcattt agaatatatt ccatccaatt     300
aggtgttaaa attgcaagtc ctacaccatg tgttatatca taatatgcac ttaactcgtg     360
ttccatagga tgacaactcc atttctatc cttaccaagt gataatagac catttatagc     420
taaacttgaa gcccacatca aattagctct agcctcgtaa tcatcagtct tctccattgc     480
tattttttcca tactttatac atgttcttaa gattgcttct gctataccgt cctgcacata     540
agcaccttca acaccactaa agtaagattc aaaggtgtga ctcataatgt cagctgttcc     600
cgctgctgtt tgattttttag gtactgtaaa agtatatgta ggatctaaca ctgaaaattt     660
aggtctcata tcatcatgtc ctactccaag cttttcatta gtctccatat ttgaaattac     720
tgcaatttga tccatttcag accctgttgc tgaaagagta agtatacttg caattggaag     780
aactttagtt attttagatg gatctttaac catgtcccat gtatcgccat cataataaac     840
tccagctgca attaccttag aacagtctat tgcacttcct cccctattg ctaatactaa     900
atccacatta ttttctctac atatttctat gcctttttt actgttgtta tcctaggatt     960
tggctctact cctgaaagtt catagaaagc tatattgttt tctttttaata tagctgttgc    1020
tctatcatat ataccgttcc tttttatact tcctccgcca taaactataa gcactcttga    1080
gccatatttc ttaatttctt ctccaattac gtctattttt ccttttccaa aaaaaacttt    1140
agttggtatt gaataatcaa aacttagcat                                     1170
```

<210> SEQ ID NO 43
<211> LENGTH: 390
<212> TYPE: PRT
<213> ORGANISM: Clostridium acetobutylicum

<400> SEQUENCE: 43

Met Val Asp Phe Glu Tyr Ser Ile Pro Thr Arg Ile Phe Phe Gly Lys
1               5                   10                  15

Asp Lys Ile Asn Val Leu Gly Arg Glu Leu Lys Lys Tyr Gly Ser Lys
                20                  25                  30

Val Leu Ile Val Tyr Gly Gly Gly Ser Ile Lys Arg Asn Gly Ile Tyr
            35                  40                  45

Asp Lys Ala Val Ser Ile Leu Glu Lys Asn Ser Ile Lys Phe Tyr Glu
        50                  55                  60

Leu Ala Gly Val Glu Pro Asn Pro Arg Val Thr Thr Val Glu Lys Gly
65                  70                  75                  80

Val Lys Ile Cys Arg Glu Asn Gly Val Glu Val Leu Ala Ile Gly
                85                  90                  95

```
Gly Gly Ser Ala Ile Asp Cys Ala Lys Val Ile Ala Ala Ala Cys Glu
            100                 105                 110

Tyr Asp Gly Asn Pro Trp Asp Ile Val Leu Asp Gly Ser Lys Ile Lys
        115                 120                 125

Arg Val Leu Pro Ile Ala Ser Ile Leu Thr Ile Ala Ala Thr Gly Ser
    130                 135                 140

Glu Met Asp Thr Trp Ala Val Ile Asn Asn Met Asp Thr Asn Glu Lys
145                 150                 155                 160

Leu Ile Ala Ala His Pro Asp Met Ala Pro Lys Phe Ser Ile Leu Asp
                165                 170                 175

Pro Thr Tyr Thr Tyr Thr Val Pro Thr Asn Gln Thr Ala Ala Gly Thr
            180                 185                 190

Ala Asp Ile Met Ser His Ile Phe Glu Val Tyr Phe Ser Asn Thr Lys
        195                 200                 205

Thr Ala Tyr Leu Gln Asp Arg Met Ala Glu Ala Leu Leu Arg Thr Cys
    210                 215                 220

Ile Lys Tyr Gly Gly Ile Ala Leu Glu Lys Pro Asp Asp Tyr Glu Ala
225                 230                 235                 240

Arg Ala Asn Leu Met Trp Ala Ser Ser Leu Ala Ile Asn Gly Leu Leu
                245                 250                 255

Thr Tyr Gly Lys Asp Thr Asn Trp Ser Val His Leu Met Glu His Glu
            260                 265                 270

Leu Ser Ala Tyr Tyr Asp Ile Thr His Gly Val Gly Leu Ala Ile Leu
        275                 280                 285

Thr Pro Asn Trp Met Glu Tyr Ile Leu Asn Asn Asp Thr Val Tyr Lys
    290                 295                 300

Phe Val Glu Tyr Gly Val Asn Val Trp Gly Ile Asp Lys Glu Lys Asn
305                 310                 315                 320

His Tyr Asp Ile Ala His Gln Ala Ile Gln Lys Thr Arg Asp Tyr Phe
                325                 330                 335

Val Asn Val Leu Gly Leu Pro Ser Arg Leu Arg Asp Val Gly Ile Glu
            340                 345                 350

Glu Glu Lys Leu Asp Ile Met Ala Lys Glu Ser Val Lys Leu Thr Gly
        355                 360                 365

Gly Thr Ile Gly Asn Leu Arg Pro Val Asn Ala Ser Glu Val Leu Gln
    370                 375                 380

Ile Phe Lys Lys Ser Val
385                 390

<210> SEQ ID NO 44
<211> LENGTH: 1173
<212> TYPE: DNA
<213> ORGANISM: Clostridium acetobutylicum

<400> SEQUENCE: 44
gtggttgatt tcgaatattc aataccaact agaattttt tcggtaaaga taagataaat    60
gtacttggaa gagagcttaa aaaatatggt tctaaagtgc ttatagttta tggtggagga   120
agtataaaga gaaatggaat atatgataaa gctgtaagta tacttgaaaa aacagtatt    180 aaattttatg aacttgcagg agtagagcca atccaagag taactacagt tgaaaaagga   240
gttaaaatat gtagagaaaa tggagttgaa gtagtactag ctataggtgg aggaagtgca   300
atagattgcg caaaggttat agcagcagca tgtgaatatg atggaaatcc atgggatatt   360
gtgttagatg gctcaaaaat aaaaagggtg cttcctatag ctagtatatt aaccattgct   420
```

-continued

```
gcaacaggat cagaaatgga tacgtgggca gtaataaata atatggatac aaacgaaaaa      480
ctaattgcgg cacatccaga tatggctcct aagttttcta tattagatcc aacgtatacg      540
tataccgtac ctaccaatca aacagcagca ggaacagctg atattatgag tcatatattt      600
gaggtgtatt ttagtaatac aaaaacagca tatttgcagg atagaatggc agaagcgtta      660
ttaagaactt gtattaaata tggaggaata gctcttgaga agccggatga ttatgaggca      720
agagccaatc taatgtgggc ttcaagtctt gcgataaatg gacttttaac atatggtaaa      780
gacactaatt ggagtgtaca cttaatggaa catgaattaa gtgcttatta cgacataaca      840
cacggcgtag ggcttgcaat tttaacacct aattggatgg agtatatttt aaataatgat      900
acagtgtaca agtttgttga atatggtgta aatgtttggg gaatagacaa agaaaaaaat      960
cactatgaca tagcacatca agcaatacaa aaacaagag attactttgt aaatgtacta     1020
ggtttaccat ctagactgag agatgttgga attgaagaag aaaaattgga cataatggca     1080
aaggaatcag taaagcttac aggaggaacc ataggaaacc taagaccagt aaacgcctcc     1140
gaagtcctac aaatattcaa aaatctgtg taa                                   1173
```

<210> SEQ ID NO 45
<211> LENGTH: 330
<212> TYPE: PRT
<213> ORGANISM: Bacillus subtilis

<400> SEQUENCE: 45

```
Met Ser Thr Asn Arg His Gln Ala Leu Gly Leu Thr Asp Gln Glu Ala
1               5                   10                  15

Val Asp Met Tyr Arg Thr Met Leu Leu Ala Arg Lys Ile Asp Glu Arg
            20                  25                  30

Met Trp Leu Leu Asn Arg Ser Gly Lys Ile Pro Phe Val Ile Ser Cys
        35                  40                  45

Gln Gly Gln Glu Ala Ala Gln Val Gly Ala Ala Phe Ala Leu Asp Arg
    50                  55                  60

Glu Met Asp Tyr Val Leu Pro Tyr Tyr Arg Asp Met Gly Val Val Leu
65                  70                  75                  80

Ala Phe Gly Met Thr Ala Lys Asp Leu Met Met Ser Gly Phe Ala Lys
                85                  90                  95

Ala Ala Asp Pro Asn Ser Gly Arg Gln Met Pro Gly His Phe Gly
            100                 105                 110

Gln Lys Lys Asn Arg Ile Val Thr Gly Ser Ser Pro Val Thr Thr Gln
        115                 120                 125

Val Pro His Ala Val Gly Ile Ala Leu Ala Gly Arg Met Glu Lys Lys
    130                 135                 140

Asp Ile Ala Ala Phe Val Thr Phe Gly Glu Gly Ser Ser Asn Gln Gly
145                 150                 155                 160

Asp Phe His Glu Gly Ala Asn Phe Ala Ala Val His Lys Leu Pro Val
                165                 170                 175

Ile Phe Met Cys Glu Asn Asn Lys Tyr Ala Ile Ser Val Pro Tyr Asp
            180                 185                 190

Lys Gln Val Ala Cys Glu Asn Ile Ser Asp Arg Ala Ile Gly Tyr Gly
        195                 200                 205

Met Pro Gly Val Thr Val Asn Gly Asn Asp Pro Leu Glu Val Tyr Gln
    210                 215                 220

Ala Val Lys Glu Ala Arg Glu Arg Ala Arg Gly Glu Gly Pro Thr
225                 230                 235                 240
```

```
Leu Ile Glu Thr Ile Ser Tyr Arg Leu Thr Pro His Ser Ser Asp Asp
                245                 250                 255

Asp Asp Ser Ser Tyr Arg Gly Arg Glu Glu Val Glu Glu Ala Lys Lys
            260                 265                 270

Ser Asp Pro Leu Leu Thr Tyr Gln Ala Tyr Leu Lys Glu Thr Gly Leu
        275                 280                 285

Leu Ser Asp Glu Ile Glu Gln Thr Met Leu Asp Glu Ile Met Ala Ile
    290                 295                 300

Val Asn Glu Ala Thr Asp Glu Ala Glu Asn Ala Pro Tyr Ala Ala Pro
305                 310                 315                 320

Glu Ser Ala Leu Asp Tyr Val Tyr Ala Lys
                325                 330

<210> SEQ ID NO 46
<211> LENGTH: 993
<212> TYPE: DNA
<213> ORGANISM: Bacillus subtilis

<400> SEQUENCE: 46
atgagtacaa accgacatca agcactaggg ctgactgatc aggaagccgt tgatatgtat    60
agaaccatgc tgttagcaag aaaaatcgat gaaagaatgt ggctgttaaa ccgttctggc   120
aaaattccat ttgtaatctc ttgtcaagga caggaagcag cacaggtagg agcggctttc   180
gcacttgacc gtgaaatgga ttatgtattg ccgtactaca gagacatggg tgtcgtgctc   240
gcgtttggca tgacagcaaa ggacttaatg atgtccgggt tgcaaaagc agcagatccg   300 aactcaggag gccgccagat gccgggacat ttcggacaaa agaaaaaccg cattgtgacg   360
ggatcatctc cggttacaac gcaagtgccg cacgcagtcg gtattgcgct tgcgggacgt   420
atggagaaaa aggatatcgc agcctttgtt acattcgggg aagggtcttc aaaccaaggc   480
gatttccatg aaggggcaaa ctttgccgct gtccataagc tgccggttat tttcatgtgt   540
gaaaacaaca aatacgcaat ctcagtgcct tacgataagc aagtcgcatg tgagaacatt   600
tccgaccgtg ccataggcta tgggatgcct ggcgtaactg tgaatggaaa tgatccgctg   660
gaagtttatc aagcggttaa agaagcacgc gaaagggcac gcagaggaga aggcccgaca   720
ttaattgaaa cgatttctta ccgccttaca ccacattcca gtgatgacga tgacagcagc   780
tacagaggcc gtgaagaagt agaggaagcg aaaaaaagtg atcccctgct tacttatcaa   840
gcttacttaa aggaaacagg cctgctgtcc gatgagatag aacaaaccat gctggatgaa   900
attatggcaa tcgtaaatga agcgacggat gaagcggaga acgccccata tgcagctcct   960
gagtcagcgc ttgattatgt ttatgcgaag tag                                993

<210> SEQ ID NO 47
<211> LENGTH: 327
<212> TYPE: PRT
<213> ORGANISM: Bacillus subtilis

<400> SEQUENCE: 47

Met Ser Val Met Ser Tyr Ile Asp Ala Ile Asn Leu Ala Met Lys Glu
1               5                   10                  15

Glu Met Glu Arg Asp Ser Arg Val Phe Val Leu Gly Glu Asp Val Gly
            20                  25                  30

Arg Lys Gly Gly Val Phe Lys Ala Thr Ala Gly Leu Tyr Glu Gln Phe
        35                  40                  45

Gly Glu Glu Arg Val Met Asp Thr Pro Leu Ala Glu Ser Ala Ile Ala
    50                  55                  60
```

```
Gly Val Gly Ile Gly Ala Ala Met Tyr Gly Met Arg Pro Ile Ala Glu
 65                  70                  75                  80

Met Gln Phe Ala Asp Phe Ile Met Pro Ala Val Asn Gln Ile Ile Ser
                 85                  90                  95

Glu Ala Ala Lys Ile Arg Tyr Arg Ser Asn Asn Asp Trp Ser Cys Pro
            100                 105                 110

Ile Val Val Arg Ala Pro Tyr Gly Gly Val His Gly Ala Leu Tyr
        115                 120                 125

His Ser Gln Ser Val Glu Ala Ile Phe Ala Asn Gln Pro Gly Leu Lys
130                 135                 140

Ile Val Met Pro Ser Thr Pro Tyr Asp Ala Lys Gly Leu Leu Lys Ala
145                 150                 155                 160

Ala Val Arg Asp Glu Asp Pro Val Leu Phe Phe Glu His Lys Arg Ala
                165                 170                 175

Tyr Arg Leu Ile Lys Gly Glu Val Pro Ala Asp Asp Tyr Val Leu Pro
            180                 185                 190

Ile Gly Lys Ala Asp Val Lys Arg Glu Gly Asp Asp Ile Thr Val Ile
        195                 200                 205

Thr Tyr Gly Leu Cys Val His Phe Ala Leu Gln Ala Ala Glu Arg Leu
210                 215                 220

Glu Lys Asp Gly Ile Ser Ala His Val Asp Leu Arg Thr Val Tyr
225                 230                 235                 240

Pro Leu Asp Lys Glu Ala Ile Ile Glu Ala Ala Ser Lys Thr Gly Lys
                245                 250                 255

Val Leu Leu Val Thr Glu Asp Thr Lys Glu Gly Ser Ile Met Ser Glu
            260                 265                 270

Val Ala Ala Ile Ile Ser Glu His Cys Leu Phe Asp Leu Asp Ala Pro
        275                 280                 285

Ile Lys Arg Leu Ala Gly Pro Asp Ile Pro Ala Met Pro Tyr Ala Pro
290                 295                 300

Thr Met Glu Lys Tyr Phe Met Val Asn Pro Asp Lys Val Glu Ala Ala
305                 310                 315                 320

Met Arg Glu Leu Ala Glu Phe
                325

<210> SEQ ID NO 48
<211> LENGTH: 984
<212> TYPE: DNA
<213> ORGANISM: Bacillus subtilis

<400> SEQUENCE: 48
atgtcagtaa tgtcatatat tgatgcaatc aatttggcga tgaaagaaga aatggaacga      60
gattctcgcg ttttcgtcct tggggaagat gtaggaagaa aaggcggtgt gtttaaagcg     120
acagcgggac tctatgaaca atttggggaa gagcgcgtta tggatacgcc gcttgctgaa     180
tctgcaatcg caggagtcgg tatcggagcg gcaatgtacg gaatgagacc gattgctgaa     240
atgcagtttg ctgatttcat tatgccggca gtcaaccaaa ttatttctga agcggctaaa     300
atccgctacc gcagcaacaa tgactggagc tgtccgattg tcgtcagagc gccatacggc     360
ggaggcgtgc acggagccct gtatcattct caatcagtcg aagcaatttt cgccaaccag     420
cccggactga aaattgtcat gccatcaaca ccatatgacg cgaaagggct cttaaaagcc     480
gcagttcgtg acgaagaccc cgtgctgttt tttgagcaca gcggcata ccgtctgata     540 aagggcgagg ttccggctga tgattatgtc ctgccaatcg gcaaggcgga cgtaaaaagg     600
```

```
gaaggcgacg acatcacagt gatcacatac ggcctgtgtg tccacttcgc cttacaagct     660
gcagaacgtc tcgaaaaaga tggcatttca gcgcatgtgg tggatttaag aacagtttac     720
ccgcttgata agaagccat catcgaagct gcgtccaaaa ctggaaaggt tcttttggtc      780
acagaagata caaaagaagg cagcatcatg agcgaagtag ccgcaattat atccgagcat     840
tgtctgttcg acttagacgc gccgatcaaa cggcttgcag gtcctgatat tccggctatg     900
ccttatgcgc cgacaatgga aaaatacttt atggtcaacc ctgataaagt ggaagcggcg     960
atgagagaat tagcggagtt ttaa                                             984
```

<210> SEQ ID NO 49
<211> LENGTH: 424
<212> TYPE: PRT
<213> ORGANISM: Bacillus subtilis

<400> SEQUENCE: 49

```
Met Ala Ile Glu Gln Met Thr Met Pro Gln Leu Gly Glu Ser Val Thr
1               5                   10                  15

Glu Gly Thr Ile Ser Lys Trp Leu Val Ala Pro Gly Asp Lys Val Asn
            20                  25                  30

Lys Tyr Asp Pro Ile Ala Glu Val Met Thr Asp Lys Val Asn Ala Glu
        35                  40                  45

Val Pro Ser Ser Phe Thr Gly Thr Ile Thr Glu Leu Val Gly Glu Glu
    50                  55                  60

Gly Gln Thr Leu Gln Val Gly Glu Met Ile Cys Lys Ile Glu Thr Glu
65                  70                  75                  80

Gly Ala Asn Pro Ala Glu Gln Lys Gln Glu Gln Pro Ala Ala Ser Glu
                85                  90                  95

Ala Ala Glu Asn Pro Val Ala Lys Ser Ala Gly Ala Ala Asp Gln Pro
            100                 105                 110

Asn Lys Lys Arg Tyr Ser Pro Ala Val Leu Arg Leu Ala Gly Glu His
        115                 120                 125

Gly Ile Asp Leu Asp Gln Val Thr Gly Thr Gly Ala Gly Gly Arg Ile
    130                 135                 140

Thr Arg Lys Asp Ile Gln Arg Leu Ile Glu Thr Gly Gly Val Gln Glu
145                 150                 155                 160

Gln Asn Pro Glu Glu Leu Lys Thr Ala Ala Pro Ala Pro Lys Ser Ala
                165                 170                 175

Ser Lys Pro Glu Pro Lys Glu Val Thr Ser Tyr Pro Ala Ser Ala Ala
            180                 185                 190

Gly Asp Lys Glu Ile Pro Val Thr Gly Val Arg Lys Ala Ile Ala Ser
        195                 200                 205

Asn Met Lys Arg Ser Lys Thr Glu Ile Pro His Ala Trp Thr Met Met
    210                 215                 220

Glu Val Asp Val Thr Asn Met Val Ala Tyr Arg Asn Ser Ile Lys Asp
225                 230                 235                 240

Ser Phe Lys Lys Thr Glu Gly Phe Asn Leu Thr Phe Phe Ala Phe Phe
                245                 250                 255

Val Lys Ala Val Ala Gln Ala Leu Lys Glu Phe Pro Gln Met Asn Ser
            260                 265                 270

Met Trp Ala Gly Asp Lys Ile Ile Gln Lys Lys Asp Ile Asn Ile Ser
        275                 280                 285

Ile Ala Val Ala Thr Glu Asp Ser Leu Phe Val Pro Val Ile Lys Asn
    290                 295                 300
```

Ala Asp Glu Lys Thr Ile Lys Gly Ile Ala Lys Asp Ile Thr Gly Leu
305                 310                 315                 320

Ala Lys Lys Val Arg Asp Gly Lys Leu Thr Ala Asp Asp Met Gln Gly
                325                 330                 335

Gly Thr Phe Thr Val Asn Asn Thr Gly Ser Phe Gly Ser Val Gln Ser
            340                 345                 350

Met Gly Ile Ile Asn Tyr Pro Gln Ala Ala Ile Leu Gln Val Glu Ser
        355                 360                 365

Ile Val Lys Arg Pro Val Val Met Asp Asn Gly Met Ile Ala Val Arg
    370                 375                 380

Asp Met Val Asn Leu Cys Leu Ser Leu Asp His Arg Val Leu Asp Gly
385                 390                 395                 400

Leu Val Cys Gly Arg Phe Leu Gly Arg Val Lys Gln Ile Leu Glu Ser
                405                 410                 415

Ile Asp Glu Lys Thr Ser Val Tyr
            420

<210> SEQ ID NO 50
<211> LENGTH: 1275
<212> TYPE: DNA
<213> ORGANISM: Bacillus subtilis

<400> SEQUENCE: 50

```
atggcaattg aacaaatgac gatgccgcag cttggagaaa gcgtaacaga ggggacgatc     60
agcaaatggc ttgtcgcccc cggtgataaa gtgaacaaat acgatccgat cgcggaagtc    120
atgacagata aggtaaatgc agaggttccg tcttcttttta ctggtacgat aacagagctt    180
gtgggagaag aaggccaaac cctgcaagtc ggagaaatga tttgcaaaat tgaaacagaa    240
ggcgcgaatc cggctgaaca aaaacaagaa cagccagcag catcagaagc cgctgagaac    300
cctgttgcaa aaagtgctgg agcagccgat cagcccaata aaaagcgcta ctcgccagct    360
gttctccgtt tggccggaga gcacggcatt gacctcgatc aagtgacagg aactggtgcc    420
ggcgggcgca tcacacgaaa agatattcag cgcttaattg aaacaggcgg cgtgcaagaa    480
cagaatcctg aggagctgaa aacagcagct cctgcaccga gtctgcatc aaaacctgag    540
ccaaaagaag agacgtcata tcctgcgtct gcagccggtg ataaagaaat ccctgtcaca    600
ggtgtaagaa aagcaattgc ttccaatatg aagcgaagca aacagaaat tccgcatgct    660
tggacgatga tggaagtcga cgtcacaaat atggttgcat atcgcaacag tataaaagat    720
tcttttaaga agacagaagg ctttaattta acgttcttcg ccttttttgt aaaagcggtc    780
gctcaggcgt taaagaatt cccgcaaatg aatagcatgt gggcggggga caaaattatt    840
cagaaaaagg atatcaatat ttcaattgca gttgccacag aggattcttt atttgttccg    900
gtgattaaaa acgctgatga aaaacaatt aaaggcattg cgaaagacat taccggccta    960
gctaaaaaag taagagacgg aaaactcact gcagatgaca tgcagggagg cacgtttacc   1020
gtcaacaaca caggttcgtt cgggtctgtt cagtcgatgg gcattatcaa ctaccctcag   1080
gctgcgattc ttcaagtaga atccatcgtc aaacgcccgg ttgtcatgga caatggcatg   1140
attgctgtca gagacatggt taatctgtgc ctgtcattag atcacagagt gcttgacggt   1200
ctcgtgtgcg gacgattcct cggacgagtg aaacaaattt tagaatcgat tgacgagaag   1260
acatctgttt actaa                                                    1275
```

<210> SEQ ID NO 51

-continued

```
<211> LENGTH: 474
<212> TYPE: PRT
<213> ORGANISM: Bacillus subtilis

<400> SEQUENCE: 51

Met Ala Thr Glu Tyr Asp Val Val Ile Leu Gly Gly Thr Gly Gly
1               5                   10                  15

Tyr Val Ala Ala Ile Arg Ala Ala Gln Leu Gly Leu Lys Thr Ala Val
            20                  25                  30

Val Glu Lys Glu Lys Leu Gly Gly Thr Cys Leu His Lys Gly Cys Ile
        35                  40                  45

Pro Ser Lys Ala Leu Leu Arg Ser Ala Glu Val Tyr Arg Thr Ala Arg
50                  55                  60

Glu Ala Asp Gln Phe Gly Val Glu Thr Ala Gly Val Ser Leu Asn Phe
65                  70                  75                  80

Glu Lys Val Gln Gln Arg Lys Gln Ala Val Val Asp Lys Leu Ala Ala
                85                  90                  95

Gly Val Asn His Leu Met Lys Lys Gly Lys Ile Asp Val Tyr Thr Gly
            100                 105                 110

Tyr Gly Arg Ile Leu Gly Pro Ser Ile Phe Ser Pro Leu Pro Gly Thr
        115                 120                 125

Ile Ser Val Glu Arg Gly Asn Gly Glu Glu Asn Asp Met Leu Ile Pro
    130                 135                 140

Lys Gln Val Ile Ile Ala Thr Gly Ser Arg Pro Arg Met Leu Pro Gly
145                 150                 155                 160

Leu Glu Val Asp Gly Lys Ser Val Leu Thr Ser Asp Glu Ala Leu Gln
                165                 170                 175

Met Glu Glu Leu Pro Gln Ser Ile Ile Ile Val Gly Gly Gly Val Ile
            180                 185                 190

Gly Ile Glu Trp Ala Ser Met Leu His Asp Phe Gly Val Lys Val Thr
        195                 200                 205

Val Ile Glu Tyr Ala Asp Arg Ile Leu Pro Thr Glu Asp Leu Glu Ile
    210                 215                 220

Ser Lys Glu Met Glu Ser Leu Leu Lys Lys Lys Gly Ile Gln Phe Ile
225                 230                 235                 240

Thr Gly Ala Lys Val Leu Pro Asp Thr Met Thr Lys Thr Ser Asp Asp
                245                 250                 255

Ile Ser Ile Gln Ala Glu Lys Asp Gly Glu Thr Val Thr Tyr Ser Ala
            260                 265                 270

Glu Lys Met Leu Val Ser Ile Gly Arg Gln Ala Asn Ile Glu Gly Ile
        275                 280                 285

Gly Leu Glu Asn Thr Asp Ile Val Thr Glu Asn Gly Met Ile Ser Val
    290                 295                 300

Asn Glu Ser Cys Gln Thr Lys Glu Ser His Ile Tyr Ala Ile Gly Asp
305                 310                 315                 320

Val Ile Gly Gly Leu Gln Leu Ala His Val Ala Ser His Glu Gly Ile
                325                 330                 335

Ile Ala Val Glu His Phe Ala Gly Leu Asn Pro His Pro Leu Asp Pro
            340                 345                 350

Thr Leu Val Pro Lys Cys Ile Tyr Ser Ser Pro Glu Ala Ala Ser Val
        355                 360                 365

Gly Leu Thr Glu Asp Glu Ala Lys Ala Asn Gly His Asn Val Lys Ile
    370                 375                 380

Gly Lys Phe Pro Phe Met Ala Ile Gly Lys Ala Leu Val Tyr Gly Glu
```

```
                385                 390                 395                 400
Ser Asp Gly Phe Val Lys Ile Val Ala Asp Arg Asp Thr Asp Ile
                    405                 410                 415

Leu Gly Val His Met Ile Gly Pro His Val Thr Asp Met Ile Ser Glu
                420                 425                 430

Ala Gly Leu Ala Lys Val Leu Asp Ala Thr Pro Trp Glu Val Gly Gln
            435                 440                 445

Thr Ile His Pro His Pro Thr Leu Ser Glu Ala Ile Gly Glu Ala Ala
        450                 455                 460

Leu Ala Ala Asp Gly Lys Ala Ile His Phe
465                 470

<210> SEQ ID NO 52
<211> LENGTH: 1425
<212> TYPE: DNA
<213> ORGANISM: Bacillus subtilis

<400> SEQUENCE: 52
```

| | | | | |
|---|---|---|---|---|
| atggcaactg agtatgacgt agtcattctg gcggcggta ccggcggtta tgttgcggcc | 60 |
| atcagagccg ctcagctcgg cttaaaaaca gccgttgtgg aaaaggaaaa actcggggga | 120 |
| acatgtctgc ataaaggctg tatcccgagt aaagcgctgc ttagaagcgc agaggtatac | 180 |
| cggacagctc gtgaagccga tcaattcgga gtggaaacgg ctggcgtgtc cctcaacttt | 240 |
| gaaaaagtgc agcagcgtaa gcaagccgtt gttgataagc ttgcagcggg tgtaaatcat | 300 |
| ttaatgaaaa aaggaaaaat tgacgtgtac accggtatatg gacgtatcct ggaccgtca | 360 |
| atcttctctc cgctgccggg aacaatttct gttgagcggg gaaatggcga agaaaatgac | 420 |
| atgctgatcc cgaaacaagt gatcattgca acaggatcaa gaccgagaat gcttccgggt | 480 |
| cttgaagtgg acggtaagtc tgtactgact tcagatgagg cgctccaaat ggaggagctg | 540 |
| ccacagtcaa tcatcattgt cggcggaggg gttatcggta tcgaatgggc gtctatgctt | 600 |
| catgattttg gcgttaaggt aacggttatt gaatacgcgg atcgcatatt gccgactgaa | 660 |
| gatctagaga tttcaaaaga aatggaaagt cttcttaaga aaaaaggcat ccagttcata | 720 |
| acaggggcaa aagtgctgcc tgacacaatg acaaaaacat cagacgatat cagcatacaa | 780 |
| gcggaaaaag acggagaaac cgttacctat tctgctgaga aaatgcttgt ttccatcggc | 840 |
| agacaggcaa atatcgaagg catcggccta gagaacaccg atattgttac tgaaaatggc | 900 |
| atgatttcag tcaatgaaag ctgccaaacg aaggaatctc atatttatgc aatcggagac | 960 |
| gtaatcggtg gcctgcagtt agctcacgtt gcttcacatg agggaattat tgctgttgag | 1020 |
| cattttgcag gtctcaatcc gcatccgctt gatccgacgc ttgtgccgaa gtgcatttac | 1080 |
| tcaagccctg aagctgccag tgtcggctta accgaagacg aagcaaaggc gaacgggcat | 1140 |
| aatgtcaaaa tcggcaagtt cccatttatg gcgattggaa aagcgcttgt atacggtgaa | 1200 |
| agcgacggtt ttgtcaaaat cgtggctgac cgagatacag atgatattct cggcgttcat | 1260 |
| atgattggcc cgcatgtcac cgacatgatt tctgaagcgg tcttgccaa agtgctggac | 1320 |
| gcaacaccgt gggaggtcgg gcaaacgatt cacccgcatc caacgctttc tgaagcaatt | 1380 |
| ggagaagctg cgcttgccgc agatggcaaa gccattcatt tttaa | 1425 |

```
<210> SEQ ID NO 53
<211> LENGTH: 410
<212> TYPE: PRT
<213> ORGANISM: Pseudomonas putida
```

```
<400> SEQUENCE: 53

Met Asn Glu Tyr Ala Pro Leu Arg Leu His Val Pro Glu Pro Thr Gly
1               5                   10                  15

Arg Pro Gly Cys Gln Thr Asp Phe Ser Tyr Leu Arg Leu Asn Asp Ala
            20                  25                  30

Gly Gln Ala Arg Lys Pro Pro Val Asp Val Asp Ala Ala Asp Thr Ala
        35                  40                  45

Asp Leu Ser Tyr Ser Leu Val Arg Val Leu Asp Glu Gln Gly Asp Ala
    50                  55                  60

Gln Gly Pro Trp Ala Glu Asp Ile Asp Pro Gln Ile Leu Arg Gln Gly
65                  70                  75                  80

Met Arg Ala Met Leu Lys Thr Arg Ile Phe Asp Ser Arg Met Val Val
                85                  90                  95

Ala Gln Arg Gln Lys Lys Met Ser Phe Tyr Met Gln Ser Leu Gly Glu
            100                 105                 110

Glu Ala Ile Gly Ser Gly Gln Ala Leu Ala Leu Asn Arg Thr Asp Met
        115                 120                 125

Cys Phe Pro Thr Tyr Arg Gln Gln Ser Ile Leu Met Ala Arg Asp Val
    130                 135                 140

Ser Leu Val Glu Met Ile Cys Gln Leu Leu Ser Asn Glu Arg Asp Pro
145                 150                 155                 160

Leu Lys Gly Arg Gln Leu Pro Ile Met Tyr Ser Val Arg Glu Ala Gly
                165                 170                 175

Phe Phe Thr Ile Ser Gly Asn Leu Ala Thr Gln Phe Val Gln Ala Val
            180                 185                 190

Gly Trp Ala Met Ala Ser Ala Ile Lys Gly Asp Thr Lys Ile Ala Ser
        195                 200                 205

Ala Trp Ile Gly Asp Gly Ala Thr Ala Glu Ser Asp Phe His Thr Ala
    210                 215                 220

Leu Thr Phe Ala His Val Tyr Arg Ala Pro Val Ile Leu Asn Val Val
225                 230                 235                 240

Asn Asn Gln Trp Ala Ile Ser Thr Phe Gln Ala Ile Ala Gly Gly Glu
                245                 250                 255

Ser Thr Thr Phe Ala Gly Arg Gly Val Gly Cys Gly Ile Ala Ser Leu
            260                 265                 270

Arg Val Asp Gly Asn Asp Phe Val Ala Val Tyr Ala Ala Ser Arg Trp
        275                 280                 285

Ala Ala Glu Arg Ala Arg Arg Gly Leu Gly Pro Ser Leu Ile Glu Trp
    290                 295                 300

Val Thr Tyr Arg Ala Gly Pro His Ser Thr Ser Asp Asp Pro Ser Lys
305                 310                 315                 320

Tyr Arg Pro Ala Asp Asp Trp Ser His Phe Pro Leu Gly Asp Pro Ile
                325                 330                 335

Ala Arg Leu Lys Gln His Leu Ile Lys Ile Gly His Trp Ser Glu Glu
            340                 345                 350

Glu His Gln Ala Thr Thr Ala Glu Phe Glu Ala Ala Val Ile Ala Ala
        355                 360                 365

Gln Lys Glu Ala Glu Gln Tyr Gly Thr Leu Ala Asn Gly His Ile Pro
    370                 375                 380

Ser Ala Ala Ser Met Phe Glu Asp Val Tyr Lys Glu Met Pro Asp His
385                 390                 395                 400

Leu Arg Arg Gln Arg Gln Glu Leu Gly Val
                405                 410
```

<210> SEQ ID NO 54
<211> LENGTH: 6643
<212> TYPE: DNA
<213> ORGANISM: Pseudomonas putida

<400> SEQUENCE: 54

| | | | | | | |
|---|---|---|---|---|---|---|
| gcatgcctgc | aggccgccga | tgaaatggtg | gaaggtatcg | gtaggctggc | cctgctcatc | 60 |
| gctgaacacg | ttacgcccgc | tgccggtatc | gaccaggctc | tggtgaatat | gcatggaact | 120 |
| gccaggcgtg | cgcgccagcg | gtttggccat | gcacaccacg | gtcagcccgt | gcttgagtgc | 180 |
| cacttccttg | agcaggtgtt | tgaacaggaa | ggtctggtcg | gccagcagca | gcgggtcgcc | 240 |
| atgtagcaag | ttgatctcga | actggctgac | gcccatttcg | tgcatgaagg | tgtcgcgcgg | 300 |
| caggccgagc | gcggccatgc | actggtacac | ctcattgaag | aacgggcgca | ggccgttgtt | 360 |
| ggaactgaca | ctgaacgccg | aatggcccag | ctcgcggcgg | ccgtcggtgc | ccagcggtgg | 420 |
| ctggaacggc | tgctgcgggt | cactgttggg | ggcaaacacg | aagaactcaa | gctcggtcgc | 480 |
| cactaccggt | gccagaccca | acgctgcgta | gcggcgatc | acggccttca | gctggccccg | 540 |
| ggtggacagt | gccgagggcc | ggccatccag | ttcattggca | tcgcagatgg | ccagggcgcg | 600 |
| accgtcatcg | ctccagggca | agcgatgaac | ctggctgggt | tccgctacca | acgccaggtc | 660 |
| gccgtcgtcg | cagccgtaga | atttcgccgg | cgggtagccg | cccatgatgc | attgcagcag | 720 |
| caccccacgg | gccatctgca | ggcggcggcc | ttcgagaaag | ccttcggcgg | tcatcacctt | 780 |
| gccgcgtggg | acgccgttga | ggtcgggggt | gacgcattcg | atttcatcga | tgccctggag | 840 |
| ctgagcgatg | ctcatgacgc | ttgtccttgt | tgttgtaggc | tgacaacaac | ataggctggg | 900 |
| ggtgtttaaa | atatcaagca | gcctctcgaa | cgcctgggc | ctcttctatt | cgcgcaaggt | 960 |
| catgccattg | gccggcaacg | gcaaggctgt | cttgtagcgc | acctgtttca | aggcaaaact | 1020 |
| cgagcggata | ttcgccacac | ccggcaaccg | ggtcaggtaa | tcgagaaacc | gctccagcgc | 1080 |
| ctggatactc | ggcagcagta | cccgcaacag | gtagtccggg | tcgcccgtca | tcaggtagca | 1140 |
| ctccatcacc | tcgggccgtt | cggcaatttc | ttcctcgaag | cggtgcagcg | actgctctac | 1200 |
| ctgttttttcc | aggctgacat | ggatgaacac | attcacatcc | agcccaacg | cctcgggcga | 1260 |
| caacaaggtc | acctgctggc | ggatcacccc | cagttcttcc | atggcccgca | cccggttgaa | 1320 |
| acagggcgtg | ggcgacaggt | tgaccgagcg | tgccagctcg | gcgttggtga | tgcgggcgtt | 1380 |
| ttcctgcagg | ctgttgagaa | tgccgatatc | ggtacgatcg | agtttgcgca | tgagacaaaa | 1440 |
| tcaccggttt | tttgtgttta | tgcggaatgt | ttatctgccc | cgctcggcaa | aggcaatcaa | 1500 |
| cttgagagaa | aaattctcct | gccggaccac | taagatgtag | gggacgctga | cttaccagtc | 1560 |
| acaagccggt | actcagcggc | ggccgcttca | gagctcacaa | aaacaaatac | ccgagcgagc | 1620 |
| gtaaaaagca | tgaacgagta | cgccccctg | cgtttgcatg | tgcccgagcc | caccggccgg | 1680 |
| ccaggctgcc | agaccgattt | ttcctacctg | cgcctgaacg | atgcaggtca | agcccgtaaa | 1740 |
| ccccctgtcg | atgtcgacgc | tgccgacacc | gccgacctgt | cctacagcct | ggtccgcgtg | 1800 |
| ctcgacgagc | aaggcgacgc | ccaaggcccg | tgggctgaag | acatcgaccc | gcagatcctg | 1860 |
| cgccaaggca | tgcgcgccat | gctcaagacg | cggatcttcg | acagccgcat | ggtggttgcc | 1920 |
| cagcgccaga | agaagatgtc | cttctacatg | cagagcctgg | gcgaagaagc | catcggcagc | 1980 |
| ggccaggcgc | tggcgcttaa | ccgcaccgac | atgtgcttcc | ccacctaccg | tcagcaaagc | 2040 |
| atcctgatgg | cccgcgacgt | gtcgctggtg | gagatgatct | gccagttgct | gtccaacgaa | 2100 |

-continued

```
cgcgaccccc tcaagggccg ccagctgccg atcatgtact cggtacgcga ggccggcttc    2160
ttcaccatca gcggcaacct ggcgacccag ttcgtgcagg cggtcggctg ggccatggcc    2220
tcggcgatca agggcgatac caagattgcc tcggcctgga tcggcgacgg cgccactgcc    2280
gaatcggact ccacaccgc cctcaccttt gcccacgttt accgcgcccc ggtgatcctc     2340
aacgtggtca caaccagtg ggccatctca accttccagg ccatcgccgg tggcgagtcg     2400
accaccttcg ccggccgtgg cgtgggctgc ggcatcgctt cgctgcgggt ggacggcaac    2460
gacttcgtcg ccgtttacgc cgcttcgcgc tgggctgccg aacgtgcccg ccgtggtttg    2520
ggcccgagcc tgatcgagtg ggtcacctac cgtgccggcc cgcactcgac ctcggacgac    2580
ccgtccaagt accgccctgc cgatgactgg agccacttcc cgctgggtga cccgatcgcc    2640
cgcctgaagc agcacctgat caagatcggc cactggtccg aagaagaaca ccaggccacc    2700
acggccgagt tcgaagcggc cgtgattgct gcgcaaaaag aagccgagca gtacggcacc    2760
ctggccaacg gtcacatccc gagcgccgcc tcgatgttcg aggacgtgta caaggagatg    2820
cccgaccacc tgcgccgcca acgccaggaa ctggggggttt gagatgaacg accacaacaa    2880
cagcatcaac ccggaaaccg ccatggccac cactaccatg accatgatcc aggccctgcg    2940
ctcggccatg gatgtcatgc ttgagcgcga cgacaatgtg gtggtgtacg ccaggacgt     3000
cggctacttc ggcggcgtgt tccgctgcac cgaaggcctg cagaccaagt acggcaagtc    3060
ccgcgtgttc gacgcgccca tctctgaaag cggcatcgtc ggcaccgccg tgggcatggg    3120
tgcctacggc ctgcgcccgg tggtggaaat ccagttcgct gactacttct acccggcctc    3180
cgaccagatc gtttctgaaa tggcccgcct gcgctaccgt tcggccggcg agttcatcgc    3240
cccgctgacc ctgcgtatgc cctgcggtgg cggtatctat ggcggccaga cacacagcca    3300
gagcccggaa gcgatgttca ctcaggtgtg cggcctgcgc accgtaatgc catccaaccc    3360
gtacgacgcc aaaggcctgc tgattgcctc gatcgaatgc gacgacccgg tgatcttcct    3420
ggagcccaag cgcctgtaca cggcccgtt cgacggccac catgaccgcc cggttacgcc     3480
gtggtcgaaa cacccgcaca gcgccgtgcc cgatggctac tacaccgtgc cactggacaa    3540
ggccgccatc acccgccccg gcaatgacgt gagcgtgctc acctatggca ccaccgtgta    3600
cgtggcccag gtggccgccg aagaaagtgg cgtggatgcc gaagtgatcg acctgcgcag    3660
cctgtgccg ctagacctgg acaccatcgt cgagtcggtg aaaaagaccg gccgttgcgt    3720
ggtagtacac gaggccaccc gtacttgtgg cttttggcgca gaactggtgt cgctggtgca    3780
ggagcactgc ttccaccacc tggaggcgcc gatcgagcgc gtcaccggtt gggacacccc    3840
ctaccctcac gcgcaggaat gggcttactt cccagggcct tcgcgggtag gtgcggcatt    3900
gaaaaaggtc atggaggtct gaatgggcac gcacgtcatc aagatgccgg acattggcga    3960
aggcatcgcg caggtcgaat tggtggaatg gttcgtcaag gtgggcgaca tcatcgccga    4020
ggaccaagtg gtagccgacg tcatgaccga caaggccacc gtggaaatcc cgtcgccggt    4080
cagcggcaag gtgctggccc tgggtggcca gccaggtgaa gtgatggcgg tcggcagtga    4140
gctgatccgc atcgaagtgg aaggcagcgg caaccatgtg gatgtgccgc aagccaagcc    4200
ggccgaagtg cctgcggcac cggtagccgc taaacctgaa ccacagaaag acgttaaacc    4260
ggcggcgtac caggcgtcag ccagccacga ggcagcgccc atcgtgccgc gccagccggg    4320
cgacaagccg ctggcctcgc cggcggtgcg caaacgcgcc ctcgatgccg gcatcgaatt    4380
gcgttatgtg cacggcagcg gcccggccgg gcgcatcctg cacgaagacc tcgacgcgtt    4440
catgagcaaa ccgcaaagcg ctgccgggca accccccaat ggctatgcca ggcgcaccga    4500
```

```
cagcgagcag gtgccggtga tcggcctgcg ccgcaagatc gcccagcgca tgcaggacgc    4560
caagcgccgg gtcgcgcact tcagctatgt ggaagaaatc gacgtcaccg ccctggaagc    4620
cctgcgccag cagctcaaca gcaagcacgg cgacagccgc ggcaagctga cactgctgcc    4680
gttcctggtg cgcgccctgg tcgtggcact gcgtgacttc ccgcagataa acgccaccta    4740
cgatgacgaa gcgcagatca tcacccgcca tggcgcggtg catgtgggca tcgccaccca    4800
aggtgacaac ggcctgatgg tacccgtgct gcgccacgcc gaagcgggca gcctgtgggc    4860
caatgccggt gagatttcac gcctggccaa cgctgcgcgc aacaacaagg ccagccgcga    4920
agagctgtcc ggttcgacca ttaccctgac cagcctcggc gccctgggcg catcgtcag    4980 cacgccggtg gtcaacaccc cggaagtggc gatcgtcggt gtcaaccgca tggttgagcg    5040
gcccgtggtg atcgacggcc agatcgtcgt gcgcaagatg atgaacctgt ccagctcgtt    5100
cgaccaccgc gtggtcgatg gcatggacgc cgccctgttc atccaggccg tgcgtggcct    5160
gctcgaacaa cccgcctgcc tgttcgtgga gtgagcatgc aacagactat ccagacaacc    5220
ctgttgatca tcggcggcgg ccctggcggc tatgtggcgg ccatccgcgc cgggcaactg    5280
ggcatcccta ccgtgctggt ggaaggccag gcgctgggcg gtacctgcct gaacatcggc    5340
tgcattccgt ccaaggcgct gatccatgtg gccgagcagt ccaccaggc ctcgcgcttt    5400 accgaaccct cgccgctggg catcagcgtg gcttcgccac gctggacat cggccagagc    5460 gtggcctgga agacggcat cgtcgatcgc ctgaccactg tgtcgccgc cctgctgaaa    5520 aagcacgggg tgaaggtggt gcacggctgg gccaaggtgc ttgatggcaa gcaggtcgag    5580
gtggatggcc agcgcatcca gtgcgagcac ctgttgctgg ccacgggctc cagcagtgtc    5640
gaactgccga tgctgccgtt gggtgggccg gtgatttcct cgaccgaggc cctggcaccg    5700
aaagccctgc cgcaacacct ggtggtggtg ggcggtggct acatcggcct ggagctgggt    5760
atcgcctacc gcaagctcgg cgcgcaggtc agcgtggtgg aagcgcgcga gcgcatcctg    5820
ccgacttacg acagcgaact gaccgcccg gtggccgagt cgctgaaaaa gctgggtatc    5880
gccctgcacc ttggccacag cgtcgaaggt tacgaaaatg gctgcctgct ggccaacgat    5940
ggcaagggcg gacaactgcg cctggaagcc gaccgggtgc tggtgccgt gggccgccgc    6000 ccacgcacca agggcttcaa cctggaatgc ctggacctga agatgaatgg tgccgcgatt    6060
gccatcgacg agcgctgcca gaccagcatg cacaacgtct gggccatcgg cgacgtggcc    6120
ggcgaaccga tgctggcgca ccgggccatg cccagggcg agatggtggc cgagatcatc    6180
gccggcaagg cacgccgctt cgaacccgct gcgatagccg ccgtgtgctt caccgacccg    6240
gaagtggtcg tggtcggcaa gacgccggaa caggccagtc agcaaggcct ggactgcatc    6300
gtcgcgcagt tcccgttcgc cgccaacggc cgggccatga gcctggagtc gaaaagcggt    6360
ttcgtgcgcg tggtcgcgcg gcgtgacaac cacctgatcc tgggctggca agcggttggc    6420
gtggcggttt ccgagctgtc cacggcgttt gcccagtcgc tggagatggg tgcctgcctg    6480
gaggatgtgg ccggtaccat ccatgcccac ccgaccctgg gtgaagcggt acaggaagcg    6540
gcactgcgtg ccctgggcca cgccctgcat atctgacact gaagcggccg aggccgattt    6600
ggcccgccgc gccgagaggc gctgcgggtc ttttttatac ctg                     6643
```

<210> SEQ ID NO 55
<211> LENGTH: 352
<212> TYPE: PRT
<213> ORGANISM: Pseudomonas putida

<400> SEQUENCE: 55

| | | | | | | | | | | | | | | |
|---|---|---|---|---|---|---|---|---|---|---|---|---|---|---|
| Met | Asn | Asp | His | Asn | Asn | Ser | Ile | Asn | Pro | Glu | Thr | Ala | Met | Ala | Thr |
| 1 | | | | 5 | | | | | 10 | | | | | 15 | |
| Thr | Thr | Met | Thr | Met | Ile | Gln | Ala | Leu | Arg | Ser | Ala | Met | Asp | Val | Met |
| | | | 20 | | | | | 25 | | | | | 30 | | |
| Leu | Glu | Arg | Asp | Asp | Asn | Val | Val | Tyr | Gly | Gln | Asp | Val | Gly | Tyr |
| | | 35 | | | | | 40 | | | | | 45 | | |
| Phe | Gly | Gly | Val | Phe | Arg | Cys | Thr | Glu | Gly | Leu | Gln | Thr | Lys | Tyr | Gly |
| | 50 | | | | | 55 | | | | | 60 | | | | |
| Lys | Ser | Arg | Val | Phe | Asp | Ala | Pro | Ile | Ser | Glu | Ser | Gly | Ile | Val | Gly |
| 65 | | | | | 70 | | | | | 75 | | | | | 80 |
| Thr | Ala | Val | Gly | Met | Gly | Ala | Tyr | Gly | Leu | Arg | Pro | Val | Val | Glu | Ile |
| | | | | 85 | | | | | 90 | | | | | 95 | |
| Gln | Phe | Ala | Asp | Tyr | Phe | Tyr | Pro | Ala | Ser | Asp | Gln | Ile | Val | Ser | Glu |
| | | | 100 | | | | | 105 | | | | | 110 | | |
| Met | Ala | Arg | Leu | Arg | Tyr | Arg | Ser | Ala | Gly | Glu | Phe | Ile | Ala | Pro | Leu |
| | | 115 | | | | | 120 | | | | | 125 | | | |
| Thr | Leu | Arg | Met | Pro | Cys | Gly | Gly | Ile | Tyr | Gly | Gly | Gln | Thr | His |
| 130 | | | | | 135 | | | | | 140 | | | | | |
| Ser | Gln | Ser | Pro | Glu | Ala | Met | Phe | Thr | Gln | Val | Cys | Gly | Leu | Arg | Thr |
| 145 | | | | | 150 | | | | | 155 | | | | | 160 |
| Val | Met | Pro | Ser | Asn | Pro | Tyr | Asp | Ala | Lys | Gly | Leu | Leu | Ile | Ala | Ser |
| | | | | 165 | | | | | 170 | | | | | 175 | |
| Ile | Glu | Cys | Asp | Asp | Pro | Val | Ile | Phe | Leu | Glu | Pro | Lys | Arg | Leu | Tyr |
| | | | 180 | | | | | 185 | | | | | 190 | | |
| Asn | Gly | Pro | Phe | Asp | Gly | His | His | Asp | Arg | Pro | Val | Thr | Pro | Trp | Ser |
| | | | 195 | | | | | 200 | | | | | 205 | | |
| Lys | His | Pro | His | Ser | Ala | Val | Pro | Asp | Gly | Tyr | Tyr | Thr | Val | Pro | Leu |
| | 210 | | | | | 215 | | | | | 220 | | | | |
| Asp | Lys | Ala | Ala | Ile | Thr | Arg | Pro | Gly | Asn | Asp | Val | Ser | Val | Leu | Thr |
| 225 | | | | | 230 | | | | | 235 | | | | | 240 |
| Tyr | Gly | Thr | Thr | Val | Tyr | Val | Ala | Gln | Val | Ala | Ala | Glu | Glu | Ser | Gly |
| | | | | 245 | | | | | 250 | | | | | 255 | |
| Val | Asp | Ala | Glu | Val | Ile | Asp | Leu | Arg | Ser | Leu | Trp | Pro | Leu | Asp | Leu |
| | | | 260 | | | | | 265 | | | | | 270 | | |
| Asp | Thr | Ile | Val | Glu | Ser | Val | Lys | Lys | Thr | Gly | Arg | Cys | Val | Val | Val |
| | | 275 | | | | | 280 | | | | | 285 | | | |
| His | Glu | Ala | Thr | Arg | Thr | Cys | Gly | Phe | Gly | Ala | Glu | Leu | Val | Ser | Leu |
| | 290 | | | | | 295 | | | | | 300 | | | | |
| Val | Gln | Glu | His | Cys | Phe | His | His | Leu | Glu | Ala | Pro | Ile | Glu | Arg | Val |
| 305 | | | | | 310 | | | | | 315 | | | | | 320 |
| Thr | Gly | Trp | Asp | Thr | Pro | Tyr | Pro | His | Ala | Gln | Glu | Trp | Ala | Tyr | Phe |
| | | | | 325 | | | | | 330 | | | | | 335 | |
| Pro | Gly | Pro | Ser | Arg | Val | Gly | Ala | Ala | Leu | Lys | Lys | Val | Met | Glu | Val |
| | | | 340 | | | | | 345 | | | | | 350 | | |

<210> SEQ ID NO 56
<211> LENGTH: 6643
<212> TYPE: DNA
<213> ORGANISM: Pseudomonas putida

<400> SEQUENCE: 56

```
gcatgcctgc aggccgccga tgaaatggtg gaaggtatcg gtaggctggc cctgctcatc    60
gctgaacacg ttacgcccgc tgccggtatc gaccaggctc tggtgaatat gcatggaact   120
```

```
gccaggcgtg cgcgccagcg gtttggccat gcacaccacg gtcagccgt gcttgagtgc    180 cacttccttg agcaggtgtt tgaacaggaa ggtctggtcg ccagcagca gcgggtcgcc    240 atgtagcaag ttgatctcga actggctgac gcccatttcg tgcatgaagg tgtcgcgcgg    300
caggccgagc gcggccatgc actggtacac ctcattgaag aacgggcgca ggccgttgtt    360
ggaactgaca ctgaacgccg aatggcccag ctcgcggcgg ccgtcggtgc ccagcggtgg    420
ctggaacggc tgctgcgggt cactgttggg ggcaaacacg aagaactcaa gctcggtcgc    480
cactaccggt gccagaccca acgctgcgta gcgggcgatc acggccttca gctggccccg    540
ggtggacagt gccgagggcc ggccatccag ttcattggca tcgcagatgg ccagggcgcg    600
accgtcatcg ctccagggca agcgatgaac ctggctgggt tccgctacca acgccaggtc    660
gccgtcgtcg cagccgtaga atttcgccgg cgggtagccg cccatgatgc attgcagcag    720
caccccacgg gccatctgca ggcggcggcc ttcgagaaag ccttcggcgg tcatcacctt    780
gccgcgtggg acgccgttga ggtcgggggt gacgcattcg atttcatcga tgccctggag    840
ctgagcgatg ctcatgacgc ttgtccttgt tgttgtaggc tgacaacaac ataggctggg    900
ggtgtttaaa atatcaagca gcctctcgaa cgcctgggc ctcttctatt cgcgcaaggt    960
catgccattg gccggcaacg gcaaggctgt cttgtagcgc acctgtttca aggcaaaact   1020
cgagcggata ttcgccacac ccggcaaccg ggtcaggtaa tcgagaaacc gctccagcgc   1080
ctggatactc ggcagcagta cccgcaacag gtagtccggg tcgcccgtca tcaggtagca   1140
ctccatcacc tcgggccgtt cggcaatttc ttcctcgaag cggtgcagcg actgctctac   1200 ctgttttcc aggctgacat ggatgaacac attcacatcc agccccaacg cctcgggcga   1260
caacaaggtc acctgctggc ggatcacccc cagttcttcc atggcccgca cccgttgaa   1320 acagggcgtg ggcgacaggt tgaccgagcg tgccagctcg gcgttggtga tcgggcgtt   1380 ttcctgcagg ctgttgagaa tgccgatatc ggtacgatcg agtttgcgca tgagacaaaa   1440
tcaccggttt tttgtgttta tgcggaatgt ttatctgccc cgctcggcaa aggcaatcaa   1500
cttgagagaa aaattctcct gccggaccac taagatgtag gggacgctga cttaccagtc   1560
acaagccggt actcagcggc ggccgcttca gagctcacaa aaacaaatac ccgagcgagc   1620
gtaaaaagca tgaacgagta cgccccctg cgtttgcatg tgcccgagcc caccggccgg   1680
ccaggctgcc agaccgattt ttcctacctg cgcctgaacg atgcaggtca agcccgtaaa   1740 cccccctgtcg atgtcgacgc tgccgacacc gccgacctgt cctacagcct ggtccgcgtg   1800
ctcgacgagc aaggcgacgc ccaaggcccg tgggctgaag acatcgaccc gcagatcctg   1860
cgccaaggca tgcgcgccat gctcaagacg cggatcttcg acagccgcat ggtggttgcc   1920
cagcgccaga agaagatgtc cttctacatg cagagcctgg gcgaagaagc catcggcagc   1980
ggccaggcgc tggcgcttaa ccgcaccgac atgtgcttcc ccacctaccg tcagcaaagc   2040
atcctgatgg cccgcgacgt gtcgctggtg gagatgatct gccagttgct gtccaacgaa   2100
cgcgaccccc tcaagggccg ccagctgccg atcatgtact cggtacgcga ggccggcttc   2160
ttcaccatca gcggcaacct ggcgacccag ttcgtgcagg cggtcggctg gccatggcc   2220 tcggcgatca agggcgatac caagattgcc tcggcctgga tcgcgacgg cgccactgcc   2280 gaatcggact ccacaccgc cctcaccttt gcccacgttt accgcgcccc ggtgatcctc   2340
aacgtggtca caaccagtg ggccatctca accttccagg ccatcgccgg tggcgagtcg   2400
accaccttcg ccggccgtgg cgtgggctgc ggcatcgctt cgctgcgggt ggacggcaac   2460
```

```
gacttcgtcg ccgtttacgc cgcttcgcgc tgggctgccg aacgtgcccg ccgtggtttg      2520
ggcccgagcc tgatcgagtg ggtcacctac cgtgccggcc cgcactcgac ctcggacgac      2580
ccgtccaagt accgccctgc cgatgactgg agccacttcc cgctgggtga cccgatcgcc      2640
cgcctgaagc agcacctgat caagatcggc cactggtccg aagaagaaca ccaggccacc      2700
acggccgagt tcgaagcggc cgtgattgct gcgcaaaaag aagccgagca gtacggcacc      2760
ctggccaacg gtcacatccc gagcgccgcc tcgatgttcg aggacgtgta caaggagatg      2820
cccgaccacc tgcgccgcca acgccaggaa ctggggggttt gagatgaacg accacaacaa      2880
cagcatcaac ccggaaaccg ccatggccac cactaccatg accatgatcc aggccctgcg      2940
ctcggccatg gatgtcatgc ttgagcgcga cgacaatgtg gtggtgtacg gccaggacgt      3000
cggctacttc ggcggcgtgt ccgctgcac cgaaggcctg cagaccaagt acggcaagtc      3060
ccgcgtgttc gacgcgccca tctctgaaag cggcatcgtc ggcaccgccg tgggcatggg      3120
tgcctacggc ctgcgcccgg tggtggaaat ccagttcgct gactacttct acccggcctc      3180
cgaccagatc gtttctgaaa tggcccgcct gcgctaccgt tcggccggcg agttcatcgc      3240
cccgctgacc ctgcgtatgc cctgcggtgg cggtatctat ggcggccaga cacacagcca      3300
gagcccggaa gcgatgttca ctcaggtgtg cggcctgcgc accgtaatgc catccaaccc      3360
gtacgacgcc aaaggcctgc tgattgcctc gatcgaatgc gacgacccgg tgatcttcct      3420
ggagcccaag cgcctgtaca acggcccgtt cgacggccac catgaccgcc cggttacgcc      3480
gtggtcgaaa cacccgcaca gcgccgtgcc cgatggctac tacaccgtgc cactggacaa      3540
ggccgccatc acccgccccg gcaatgacgt gagcgtgctc acctatggca ccaccgtgta      3600
cgtggcccag gtggccgccg aagaaagtgg cgtggatgcc gaagtgatcg acctgcgcag      3660
cctgtggccg ctagacctgg acaccatcgt cgagtcggtg aaaaagaccg gccgttgcgt      3720
ggtagtacac gaggccaccc gtacttgtgg cttttggcgca gaactggtgt cgctggtgca      3780
ggagcactgc ttccaccacc tggaggcgcc gatcgagcgc gtcaccggtt gggacacccc      3840
ctaccctcac gcgcaggaat gggcttactt cccagggcct tcgcgggtag gtgcggcatt      3900
gaaaaaggtc atggaggtct gaatgggcac gcacgtcatc aagatgccgg acattggcga      3960
aggcatcgcg caggtcgaat tggtggaatg gttcgtcaag gtgggcgaca tcatcgccga      4020
ggaccaagtg gtagccgacg tcatgaccga caaggccacc gtggaaatcc cgtcgccggt      4080
cagcggcaag gtgctggccc tgggtggcca gccaggtgaa gtgatggcgg tcggcagtga      4140
gctgatccgc atcgaagtgg aaggcagcgg caaccatgtg gatgtgccgc aagccaagcc      4200
ggccgaagtg cctgcggcac cggtagccgc taaacctgaa ccacagaaag acgttaaacc      4260
ggcggcgtac caggcgtcag ccagccacga ggcagcgccc atcgtgccgc gccagccggg      4320
cgacaagccg ctggcctcgc cggcggtgcg caaacgcgcc ctcgatgccg gcatcgaatt      4380
gcgttatgtg cacggcagcg gcccggccgg gcgcatcctg cacgaagacc tcgacgcgtt      4440
catgagcaaa ccgcaaagcg ctgccgggca acccccaat ggctatgcca ggcgcaccga      4500
cagcgagcag gtgccggtga tcggcctgcg ccgcaagatc gcccagcgca tgcaggacgc      4560
caagcgccgg gtcgcgcact tcagctatgt ggaagaaatc gacgtcaccg ccctggaagc      4620
cctgcgccag cagctcaaca gcaagcacgg cgacagccgc ggcaagctga cactgctgcc      4680
gttcctggtg cgcgccctgg tcgtggcact gcgtgacttc ccgcagataa acgccaccta      4740
cgatgacgaa gcgcagatca tcaccccgcca tggcgcggtg catgtgggca tcgccaccca      4800
aggtgacaac ggcctgatgg tacccgtgct gcgccacgcc gaagcgggca gcctgtgggc      4860
```

```
caatgccggt gagatttcac gcctggccaa cgctgcgcgc aacaacaagg ccagccgcga    4920
agagctgtcc ggttcgacca ttaccctgac cagcctcggc gccctgggcg gcatcgtcag    4980
cacgccggtg gtcaacaccc cggaagtggc gatcgtcggt gtcaaccgca tggttgagcg    5040
gcccgtggtg atcgacggcc agatcgtcgt gcgcaagatg atgaacctgt ccagctcgtt    5100
cgaccaccgc gtggtcgatg gcatggacgc cgccctgttc atccaggccg tgcgtggcct    5160
gctcgaacaa cccgcctgcc tgttcgtgga gtgagcatgc aacagactat ccagacaacc    5220
ctgttgatca tcggcggcgg ccctggcggc tatgtggcgg ccatccgcgc cgggcaactg    5280
ggcatcccta ccgtgctggt ggaaggccag gcgctgggcg gtacctgcct gaacatcggc    5340
tgcattccgt ccaaggcgct gatccatgtg gccgagcagt tccaccaggc ctcgcgcttt    5400
accgaaccct cgccgctggg catcagcgtg gcttcgccac gcctggacat cggccagagc    5460
gtggcctgga agacggcat cgtcgatcgc ctgaccactg tgtcgccgc cctgctgaaa     5520
aagcacgggg tgaaggtggt gcacggctgg gccaaggtgc ttgatggcaa gcaggtcgag    5580
gtggatggcc agcgcatcca gtgcgagcac ctgttgctgg ccacgggctc cagcagtgtc    5640
gaactgccga tgctgccgtt gggtgggccg gtgatttcct cgaccgaggc cctggcaccg    5700
aaagccctgc cgcaacacct ggtggtggtg ggcggtggct acatcggcct ggagctgggt    5760
atcgcctacc gcaagctcgg cgcgcaggtc agcgtggtgg aagcgcgcga gcgcatcctg    5820
ccgacttacg acagcgaact gaccgccccg gtggccgagt cgctgaaaaa gctgggtatc    5880
gccctgcacc ttggccacag cgtcgaaggt tacgaaaatg ctgcctgct ggccaacgat     5940
ggcaagggcg gacaactgcg cctggaagcc gacggggtgc tggtggccgt gggccgccgc    6000
ccacgcacca agggcttcaa cctggaatgc ctggacctga agatgaatgg tgccgcgatt    6060
gccatcgacg agcgctgcca gaccagcatg cacaacgtct gggccatcgg cgacgtggcc    6120
ggcgaaccga tgctggcgca ccgggccatg gcccagggcg agatggtggc cgagatcatc    6180
gccggcaagg cacgccgctt cgaacccgct gcgatagccg ccgtgtgctt caccgacccg    6240
gaagtggtcg tggtcggcaa gacgccggaa caggccagtc agcaaggcct ggactgcatc    6300
gtcgcgcagt tcccgttcgc cgccaacggc cgggccatga gcctggagtc gaaaagcggt    6360
ttcgtgcgcg tggtcgcgcg gcgtgacaac cacctgatcc tgggctggca gcggttggc     6420
gtggcggttt ccgagctgtc cacggcgttt gcccagtcgc tggagatggg tgcctgcctg    6480
gaggatgtgg ccggtaccat ccatgcccac ccgaccctgg gtgaagcggt acaggaagcg    6540
gcactgcgtg ccctgggcca cgccctgcat atctgacact gaagcggccg aggccgattt    6600
ggcccgccgc gccgagaggc gctgcgggtc ttttttatac ctg                     6643
```

<210> SEQ ID NO 57
<211> LENGTH: 423
<212> TYPE: PRT
<213> ORGANISM: Pseudomonas putida

<400> SEQUENCE: 57

```
Met Gly Thr His Val Ile Lys Met Pro Asp Ile Gly Glu Gly Ile Ala
1               5                   10                  15

Gln Val Glu Leu Val Glu Trp Phe Val Lys Val Gly Asp Ile Ile Ala
            20                  25                  30

Glu Asp Gln Val Val Ala Asp Val Met Thr Asp Lys Ala Thr Val Glu
        35                  40                  45

Ile Pro Ser Pro Val Ser Gly Lys Val Leu Ala Leu Gly Gly Gln Pro
```

```
            50                  55                  60
Gly Glu Val Met Ala Val Gly Ser Glu Leu Ile Arg Ile Glu Val Glu
 65                  70                  75                  80

Gly Ser Gly Asn His Val Asp Val Pro Gln Ala Lys Pro Ala Glu Val
                 85                  90                  95

Pro Ala Ala Pro Val Ala Ala Lys Pro Glu Pro Gln Lys Asp Val Lys
            100                 105                 110

Pro Ala Ala Tyr Gln Ala Ser Ala Ser His Glu Ala Ala Pro Ile Val
            115                 120                 125

Pro Arg Gln Pro Gly Asp Lys Pro Leu Ala Ser Pro Ala Val Arg Lys
            130                 135                 140

Arg Ala Leu Asp Ala Gly Ile Glu Leu Arg Tyr Val His Gly Ser Gly
145                 150                 155                 160

Pro Ala Gly Arg Ile Leu His Glu Asp Leu Asp Ala Phe Met Ser Lys
                165                 170                 175

Pro Gln Ser Ala Ala Gly Gln Thr Pro Asn Gly Tyr Ala Arg Arg Thr
            180                 185                 190

Asp Ser Glu Gln Val Pro Val Ile Gly Leu Arg Arg Lys Ile Ala Gln
            195                 200                 205

Arg Met Gln Asp Ala Lys Arg Arg Val Ala His Phe Ser Tyr Val Glu
            210                 215                 220

Glu Ile Asp Val Thr Ala Leu Glu Ala Leu Arg Gln Gln Leu Asn Ser
225                 230                 235                 240

Lys His Gly Asp Ser Arg Gly Lys Leu Thr Leu Leu Pro Phe Leu Val
                245                 250                 255

Arg Ala Leu Val Val Ala Leu Arg Asp Phe Pro Gln Ile Asn Ala Thr
            260                 265                 270

Tyr Asp Asp Glu Ala Gln Ile Ile Thr Arg His Gly Ala Val His Val
            275                 280                 285

Gly Ile Ala Thr Gln Gly Asp Asn Gly Leu Met Val Pro Val Leu Arg
            290                 295                 300

His Ala Glu Ala Gly Ser Leu Trp Ala Asn Ala Gly Glu Ile Ser Arg
305                 310                 315                 320

Leu Ala Asn Ala Ala Arg Asn Asn Lys Ala Ser Arg Glu Glu Leu Ser
                325                 330                 335

Gly Ser Thr Ile Thr Leu Thr Ser Leu Gly Ala Leu Gly Gly Ile Val
            340                 345                 350

Ser Thr Pro Val Val Asn Thr Pro Glu Val Ala Ile Val Gly Val Asn
            355                 360                 365

Arg Met Val Glu Arg Pro Val Val Ile Asp Gly Gln Ile Val Val Arg
370                 375                 380

Lys Met Met Asn Leu Ser Ser Ser Phe Asp His Arg Val Val Asp Gly
385                 390                 395                 400

Met Asp Ala Ala Leu Phe Ile Gln Ala Val Arg Gly Leu Leu Glu Gln
                405                 410                 415

Pro Ala Cys Leu Phe Val Glu
            420

<210> SEQ ID NO 58
<211> LENGTH: 6643
<212> TYPE: DNA
<213> ORGANISM: Pseudomonas putida

<400> SEQUENCE: 58
```

-continued

```
gcatgcctgc aggccgccga tgaaatggtg aaggtatcg gtaggctggc cctgctcatc      60
gctgaacacg ttacgcccgc tgccggtatc gaccaggctc tggtgaatat gcatggaact    120
gccaggcgtg cgcgccagcg gtttggccat gcacaccacg gtcagcccgt gcttgagtgc    180
cacttccttg agcaggtgtt tgaacaggaa ggtctggtcg ccagcagca gcgggtcgcc    240
atgtagcaag ttgatctcga actggctgac gcccatttcg tgcatgaagg tgtcgcgcgg    300
caggccgagc gcggccatgc actggtacac ctcattgaag aacgggcgca ggccgttgtt    360
ggaactgaca ctgaacgccg aatggcccag ctcgcggcgg ccgtcggtgc ccagcggtgg    420
ctggaacggc tgctgcgggt cactgttggg ggcaaacacg aagaactcaa gctcggtcgc    480
cactaccggt gccagaccca cgctgcgta gcgggcgatc acggccttca gctggccccg    540
ggtggacagt gccgagggcc ggccatccag ttcattggca tcgcagatgg ccagggcgcg    600
accgtcatcg ctccagggca agcgatgaac ctggctgggt tccgctacca acgccaggtc    660
gccgtcgtcg cagccgtaga atttcgccgg cgggtagccg cccatgatgc attgcagcag    720
cacccccacg gccatctgca ggcggcggcc ttcgagaaag ccttcggcgg tcatcacctt    780
gccgcgtggg acgccgttga ggtcgggggt gacgcattcg atttcatcga tgccctggag    840
ctgagcgatg ctcatgacgc ttgtccttgt tgttgtaggc tgacaacaac ataggctggg    900
ggtgtttaaa atatcaagca gcctctcgaa cgcctggggc ctcttctatt cgcgcaaggt    960
catgccattg gccggcaacg gcaaggctgt cttgtagcgc acctgtttca aggcaaaact   1020
cgagcggata ttcgccacac ccggcaaccg ggtcaggtaa tcgagaaacc gctccagcgc   1080
ctggatactc ggcagcagta cccgcaacag gtagtccggg tcgcccgtca tcaggtagca   1140
ctccatcacc tcgggccgtt cggcaatttc ttcctcgaag cggtgcagcg actgctctac   1200
ctgttttttcc aggctgacat ggatgaacac attcacatcc agcccaacg cctcgggcga   1260
caacaaggtc acctgctggc ggatcacccc cagttcttcc atggcccgca cccggttgaa   1320
acagggcgtg ggcgacaggt tgaccgagcg tgccagctcg gcgttggtga tgcgggcgtt   1380
ttcctgcagg ctgttgagaa tgccgatatc ggtacgatcg agtttgcgca tgagacaaaa   1440
tcaccggttt tttgtgttta tgcggaatgt ttatctgccc cgctcggcaa aggcaatcaa   1500
cttgagagaa aaattctcct gccggaccac taagatgtag gggacgctga cttaccagtc   1560
acaagccggt actcagcggc ggccgcttca gagctcacaa aaacaaatac ccgagcgagc   1620
gtaaaagcga tgaacgagta cgccccctg cgtttgcatg tgcccgagcc caccggccgg   1680
ccaggctgcc agaccgattt ttcctacctg cgcctgaacg atgcaggtca agcccgtaaa   1740
ccccctgtcg atgtcgacgc tgccgacacc gccgacctgt cctacagcct ggtccgcgtg   1800
ctcgacgagc aaggcgacgc caaggcccg tgggctgaag acatcgaccc gcagatcctg   1860
cgccaaggca tgcgcgccat gctcaagacg cggatcttcg acagccgcat ggtggtttgcc   1920
cagcgccaga agaagatgtc cttctacatg cagagcctgg gcgaagaagc catcggcagc   1980
ggccaggcgc tggcgcttaa ccgcaccgac atgtgcttcc ccacctaccg tcagcaaagc   2040
atcctgatgg cccgcgacgt gtcgctggtg gagatgatct gccagttgct gtccaacgaa   2100
cgcgaccccc tcaagggccg ccagctgccg atcatgtact cggtacgcga ggccggcttc   2160
ttcaccatca gcggcaacct ggcgacccag ttcgtgcagg cggtcggctg ggccatggcc   2220
tcggcgatca agggcgatac caagattgcc tcggcctgga tcggcgacgg cgccactgcc   2280
gaatcggact ccacaccgc cctcacccttt gcccacgttt accgcgcccc ggtgatcctc   2340
aacgtggtca caaccagtg ggccatctca accttccagg ccatcgccgg tggcgagtcg   2400
```

```
accaccttcg ccggccgtgg cgtgggctgc ggcatcgctt cgctgcgggt ggacggcaac    2460
gacttcgtcg ccgtttacgc cgcttcgcgc tgggctgccg aacgtgcccg ccgtggtttg    2520
ggcccgagcc tgatcgagtg ggtcacctac cgtgccggcc cgcactcgac ctcggacgac    2580
ccgtccaagt accgccctgc cgatgactgg agccacttcc cgctgggtga cccgatcgcc    2640
cgcctgaagc agcacctgat caagatcggc cactggtccg aagaagaaca ccaggccacc    2700
acggccgagt tcgaagcggc cgtgattgct gcgcaaaaag aagccgagca gtacggcacc    2760
ctggccaacg gtcacatccc gagcgccgcc tcgatgttcg aggacgtgta caaggagatg    2820
cccgaccacc tgcgccgcca acgccaggaa ctgggggttt gagatgaacg accacaacaa    2880
cagcatcaac ccggaaaccg ccatggccac cactaccatg accatgatcc aggccctgcg    2940
ctcggccatg gatgtcatgc ttgagcgcga cgacaatgtg gtggtgtacg ccaggacgt    3000 cggctacttc ggcggcgtgt tccgctgcac cgaaggcctg cagaccaagt acggcaagtc    3060
ccgcgtgttc gacgcgccca tctctgaaag cggcatcgtc ggcaccgccg tgggcatggg    3120
tgcctacggc ctgcgcccgg tggtggaaat ccagttcgct gactacttct acccggcctc    3180
cgaccagatc gtttctgaaa tggcccgcct gcgctaccgt tcggccggcg agttcatcgc    3240
cccgctgacc ctgcgtatgc cctgcggtgg cggtatctat ggcggccaga cacacagcca    3300
gagcccggaa gcgatgttca ctcaggtgtg cggcctgcgc accgtaatgc catccaaccc    3360
gtacgacgcc aaaggcctgc tgattgcctc gatcgaatgc gacgacccgg tgatcttcct    3420
ggagcccaag cgcctgtaca acggcccgtt cgacggccac catgaccgcc cggttacgcc    3480
gtggtcgaaa caccgcaca gcgccgtgcc cgatggctac tacaccgtgc cactggacaa    3540
ggccgccatc acccgccccg gcaatgacgt gagcgtgctc acctatggca ccaccgtgta    3600
cgtggcccag gtggccgccg aagaaagtgg cgtggatgcc gaagtgatcg acctgcgcag    3660
cctgtggccg ctagacctgg acaccatcgt cgagtcggtg aaaaagaccg gccgttgcgt    3720
ggtagtacac gaggccaccc gtacttgtgg cttttggcgca gaactggtgt cgctggtgca    3780
ggagcactgc ttccaccacc tggaggcgcc gatcgagcgc gtcaccggtt gggacacccc    3840
ctaccctcac gcgcaggaat gggcttactt cccagggcct tcgcgggtag gtgcggcatt    3900
gaaaaaggtc atggaggtct gaatgggcac gcacgtcatc aagatgccgg acattggcga    3960
aggcatcgcg caggtcgaat tggtggaatg gttcgtcaag gtgggcgaca tcatcgccga    4020
ggaccaagtg gtagccgacg tcatgaccga caaggccacc gtggaaatcc cgtcgccggt    4080
cagcggcaag gtgctggccc tgggtggcca gccaggtgaa gtgatggcgg tcggcagtga    4140
gctgatccgc atcgaagtgg aaggcagcgg caaccatgtg gatgtgccgc aagccaagcc    4200
ggccgaagtg cctgcggcac cggtagccgc taaacctgaa ccacagaaag acgttaaacc    4260
ggcggcgtac caggcgtcag ccagccacga ggcagcgccc atcgtgccgc gccagccggg    4320
cgacaagccg ctgcctcgc cggcggtgcg caaacgcgcc ctcgatgccg gcatcgaatt    4380
gcgttatgtg cacggcagcg gcccggccgg gcgcatcctg cacgaagacc tcgacgcgtt    4440
catgagcaaa ccgcaaagcg ctgccgggca aaccccccaat ggctatgcca ggcgcaccga    4500
cagcgagcag gtgccggtga tcggcctgcg ccgcaagatc gcccagcgca tgcaggacgc    4560
caagcgccgg gtcgcgcact tcagctatgt ggaagaaatc gacgtcaccg ccctggaagc    4620
cctgcgccag cagctcaaca gcaagcacgg cgacagccgc ggcaagctga cactgctgcc    4680
gttcctggtg cgcgccctgg tcgtggcact gcgtgacttc ccgcagataa acgccaccta    4740
```

-continued

| | |
|---|---|
| cgatgacgaa gcgcagatca tcacccgcca tggcgcggtg catgtgggca tcgccaccca | 4800 |
| aggtgacaac ggcctgatgg tacccgtgct gcgccacgcc gaagcgggca gcctgtgggc | 4860 |
| caatgccggt gagatttcac gcctggccaa cgctgcgcgc aacaacaagg ccagccgcga | 4920 |
| agagctgtcc ggttcgacca ttaccctgac cagcctcggc gccctgggcg catcgtcag | 4980 |
| cacgccggtg gtcaacaccc cggaagtggc gatcgtcggt gtcaaccgca tggttgagcg | 5040 |
| gcccgtggtg atcgacggcc agatcgtcgt gcgcaagatg atgaacctgt ccagctcgtt | 5100 |
| cgaccaccgc gtggtcgatg gcatggacgc cgccctgttc atccaggccg tgcgtggcct | 5160 |
| gctcgaacaa cccgcctgcc tgttcgtgga gtgagcatgc aacagactat ccagacaacc | 5220 |
| ctgttgatca tcggcggcgg ccctggcggc tatgtggcgg ccatccgcgc cgggcaactg | 5280 |
| ggcatcccta ccgtgctggt ggaaggccag gcgctgggcg gtacctgcct gaacatcggc | 5340 |
| tgcattccgt ccaaggcgct gatccatgtg gccgagcagt ccaccaggc ctcgcgcttt | 5400 |
| accgaaccct cgccgctggg catcagcgtg cttcgccac gcctggacat cggccagagc | 5460 |
| gtggcctgga aagacggcat cgtcgatcgc ctgaccactg tgtcgccgc cctgctgaaa | 5520 |
| aagcacgggg tgaaggtggt gcacggctgg gccaaggtgc ttgatggcaa gcaggtcgag | 5580 |
| gtggatggcc agcgcatcca gtgcgagcac ctgttgctgg ccacgggctc cagcagtgtc | 5640 |
| gaactgccga tgctgccgtt gggtgggccg tgatttcct cgaccgaggc cctggcaccg | 5700 |
| aaagccctgc cgcaacacct ggtggtggtg gcggtggct acatcggcct ggagctgggt | 5760 |
| atcgcctacc gcaagctcgg cgcgcaggtc agcgtggtgg aagcgcgcga gcgcatcctg | 5820 |
| ccgacttacg acagcgaact gaccgccccg gtggccgagt cgctgaaaaa gctgggtatc | 5880 |
| gccctgcacc ttggccacag cgtcgaaggt tacgaaaatg gctgcctgct ggccaacgat | 5940 |
| ggcaagggcg gacaactgcg cctggaagcc gaccgggtgc tggtggccgt gggccgccgc | 6000 |
| ccacgcacca agggcttcaa cctggaatgc ctggacctga agatgaatgg tgccgcgatt | 6060 |
| gccatcgacg agcgctgcca gaccagcatg cacaacgtct gggccatcgg cgacgtggcc | 6120 |
| ggcgaaccga tgctggcgca ccgggccatg gcccagggcg agatggtggc cgagatcatc | 6180 |
| gccggcaagg cacgccgctt cgaacccgct gcgatagccg ccgtgtgctt caccgacccg | 6240 |
| gaagtggtcg tggtcggcaa gacgccggaa caggccagtc agcaaggcct ggactgcatc | 6300 |
| gtcgcgcagt tcccgttcgc cgccaacggc cgggccatga gcctggagtc gaaaagcggt | 6360 |
| ttcgtgcgcg tggtcgcgcg gcgtgacaac cacctgatcc tgggctggca gcggttggc | 6420 |
| gtggcggttt ccgagctgtc cacggcgttt gcccagtcgc tggagatggg tgcctgcctg | 6480 |
| gaggatgtgg ccggtaccat ccatgcccac ccgaccctgg gtgaagcggt acaggaagcg | 6540 |
| gcactgcgtg ccctgggcca cgccctgcat atctgacact gaagcggccg aggccgattt | 6600 |
| ggcccgccgc gccgagaggc gctgcgggtc tttttttatac ctg | 6643 |

<210> SEQ ID NO 59
<211> LENGTH: 459
<212> TYPE: PRT
<213> ORGANISM: Pseudomonas putida

<400> SEQUENCE: 59

Met Gln Gln Thr Ile Gln Thr Thr Leu Leu Ile Ile Gly Gly Gly Pro
1               5                   10                  15

Gly Gly Tyr Val Ala Ala Ile Arg Ala Gly Gln Leu Gly Ile Pro Thr
            20                  25                  30

Val Leu Val Glu Gly Gln Ala Leu Gly Gly Thr Cys Leu Asn Ile Gly

```
            35                  40                  45
Cys Ile Pro Ser Lys Ala Leu Ile His Val Ala Glu Gln Phe His Gln
 50                  55                  60

Ala Ser Arg Phe Thr Glu Pro Ser Pro Leu Gly Ile Ser Val Ala Ser
 65                  70                  75                  80

Pro Arg Leu Asp Ile Gly Gln Ser Val Ala Trp Lys Asp Gly Ile Val
                 85                  90                  95

Asp Arg Leu Thr Thr Gly Val Ala Ala Leu Leu Lys Lys His Gly Val
                100                 105                 110

Lys Val Val His Gly Trp Ala Lys Val Leu Asp Gly Lys Gln Val Glu
                115                 120                 125

Val Asp Gly Gln Arg Ile Gln Cys Glu His Leu Leu Leu Ala Thr Gly
        130                 135                 140

Ser Ser Ser Val Glu Leu Pro Met Leu Pro Leu Gly Gly Pro Val Ile
145                 150                 155                 160

Ser Ser Thr Glu Ala Leu Ala Pro Lys Ala Leu Pro Gln His Leu Val
                165                 170                 175

Val Val Gly Gly Gly Tyr Ile Gly Leu Glu Leu Gly Ile Ala Tyr Arg
                180                 185                 190

Lys Leu Gly Ala Gln Val Ser Val Val Glu Ala Arg Glu Arg Ile Leu
        195                 200                 205

Pro Thr Tyr Asp Ser Glu Leu Thr Ala Pro Val Ala Glu Ser Leu Lys
210                 215                 220

Lys Leu Gly Ile Ala Leu His Leu Gly His Ser Val Glu Gly Tyr Glu
225                 230                 235                 240

Asn Gly Cys Leu Leu Ala Asn Asp Gly Lys Gly Gln Leu Arg Leu
                245                 250                 255

Glu Ala Asp Arg Val Leu Val Ala Val Gly Arg Arg Pro Arg Thr Lys
                260                 265                 270

Gly Phe Asn Leu Glu Cys Leu Asp Leu Lys Met Asn Gly Ala Ala Ile
        275                 280                 285

Ala Ile Asp Glu Arg Cys Gln Thr Ser Met His Asn Val Trp Ala Ile
290                 295                 300

Gly Asp Val Ala Gly Glu Pro Met Leu Ala His Arg Ala Met Ala Gln
305                 310                 315                 320

Gly Glu Met Val Ala Glu Ile Ile Ala Gly Lys Ala Arg Arg Phe Glu
                325                 330                 335

Pro Ala Ala Ile Ala Ala Val Cys Phe Thr Asp Pro Glu Val Val Val
                340                 345                 350

Val Gly Lys Thr Pro Glu Gln Ala Ser Gln Gln Gly Leu Asp Cys Ile
        355                 360                 365

Val Ala Gln Phe Pro Phe Ala Ala Asn Gly Arg Ala Met Ser Leu Glu
370                 375                 380

Ser Lys Ser Gly Phe Val Arg Val Val Ala Arg Arg Asp Asn His Leu
385                 390                 395                 400

Ile Leu Gly Trp Gln Ala Val Gly Val Ala Val Ser Glu Leu Ser Thr
                405                 410                 415

Ala Phe Ala Gln Ser Leu Glu Met Gly Ala Cys Leu Glu Asp Val Ala
                420                 425                 430

Gly Thr Ile His Ala His Pro Thr Leu Gly Glu Ala Val Gln Glu Ala
        435                 440                 445

Ala Leu Arg Ala Leu Gly His Ala Leu His Ile
450                 455
```

<210> SEQ ID NO 60
<211> LENGTH: 6643
<212> TYPE: DNA
<213> ORGANISM: Pseudomonas putida

<400> SEQUENCE: 60

| | |
|---|---|
| gcatgcctgc aggccgccga tgaaatggtg gaaggtatcg gtaggctggc cctgctcatc | 60 |
| gctgaacacg ttacgcccgc tgccggtatc gaccaggctc tggtgaatat gcatggaact | 120 |
| gccaggcgtg cgcgccagcg gtttggccat gcacaccacg gtcagcccgt gcttgagtgc | 180 |
| cacttccttg agcaggtgtt tgaacaggaa ggtctggtcg ccagcagca gcgggtcgcc | 240 |
| atgtagcaag ttgatctcga actggctgac gcccatttcg tgcatgaagg tgtcgcgcgg | 300 |
| caggccgagc gcggccatgc actggtacac ctcattgaag aacgggcgca ggccgttgtt | 360 |
| ggaactgaca ctgaacgccg aatggcccag ctcgcggcgg ccgtcggtgc ccagcggtgg | 420 |
| ctggaacggc tgctgcgggt cactgttggg ggcaaacacg aagaactcaa gctcggtcgc | 480 |
| cactaccggt gccagaccca cgctgcgta gcgggcgatc acggccttca gctggccccg | 540 |
| ggtggacagt gccgagggcc ggccatccag ttcattggca tcgcagatgg ccagggcgcg | 600 |
| accgtcatcg ctccagggca agcgatgaac ctggctgggt tccgctacca cgccaggtc | 660 |
| gccgtcgtcg cagccgtaga atttcgccgg cgggtagccg cccatgatgc attgcagcag | 720 |
| caccccacgg gccatctgca ggcggcggcc ttcgagaaag ccttcggcgg tcatcacctt | 780 |
| gccgcgtggg acgccgttga ggtcgggggt gacgcattcg atttcatcga tgccctggag | 840 |
| ctgagcgatg ctcatgacgc ttgtccttgt tgttgtaggc tgacaacaac ataggctggg | 900 |
| ggtgtttaaa atatcaagca gcctctcgaa cgcctgggc ctcttctatt cgcgcaaggt | 960 |
| catgccattg gccggcaacg gcaaggctgt cttgtagcgc acctgtttca aggcaaaact | 1020 |
| cgagcggata ttcgccacac ccggcaaccg ggtcaggtaa tcgagaaacc gctccagcgc | 1080 |
| ctggatactc ggcagcagta cccgcaacag gtagtccggg tcgcccgtca tcaggtagca | 1140 |
| ctccatcacc tcgggccgtt cggcaatttc ttcctgaag cggtgcagcg actgctctac | 1200 |
| ctgtttttcc aggctgacat ggatgaacac attcacatcc agcccaacg cctcgggcga | 1260 |
| caacaaggtc acctgctggc ggatcacccc cagttcttcc atgcccgca cccggttgaa | 1320 |
| acagggcgtg ggcgacaggt tgaccgagcg tgccagctcg gcgttggtga tgcgggcgtt | 1380 |
| ttcctgcagg ctgttgagaa tgccgatatc ggtacgatcg agtttgcgca tgagacaaaa | 1440 |
| tcaccggttt tttgtgttta tgcggaatgt ttatctgccc cgctcggcaa aggcaatcaa | 1500 |
| cttgagagaa aaattctcct gccggaccac taagatgtag gggacgctga cttaccagtc | 1560 |
| acaagccggt actcagcggc ggccgcttca gagctcacaa aaacaaatac cgagcgagc | 1620 |
| gtaaaaagca tgaacgagta cgcccccctg cgtttgcatg tgcccgagcc caccggccgg | 1680 |
| ccaggctgcc agaccgattt ttcctacctg cgcctgaacg atgcaggtca agcccgtaaa | 1740 |
| cccccctgtcg atgtcgacgc tgccgacacc gccgacctgt cctacagcct ggtccgcgtg | 1800 |
| ctcgacgagc aaggcgacgc ccaaggcccg tgggctgaag acatcgaccc gcagatcctg | 1860 |
| cgccaaggca tgcgcgccat gctcaagacg cggatcttcg acagccgcat ggtggttgcc | 1920 |
| cagcgccaga agaagatgtc cttctacatg cagagcctgg gcgaagaagc catcggcagc | 1980 |
| ggccaggcgc tggcgcttaa ccgcaccgac atgtgcttcc ccacctaccg tcagcaaagc | 2040 |
| atcctgatgg cccgcgacgt gtcgctggtg gagatgatct gccagttgct gtccaacgaa | 2100 |

```
cgcgaccccc tcaagggccg ccagctgccg atcatgtact cggtacgcga ggccggcttc    2160
ttcaccatca gcggcaacct ggcgacccag ttcgtgcagg cggtcggctg ggccatggcc    2220
tcggcgatca agggcgatac caagattgcc tcggcctgga tcgcgacgg cgccactgcc     2280 gaatcggact ccacaccgc cctcaccttt gcccacgttt accgcgcccc ggtgatcctc      2340
aacgtggtca caaccagtg ggccatctca accttccagg ccatcgccgg tggcgagtcg      2400
accaccttcg ccggccgtgg cgtgggctgc ggcatcgctt cgctgcgggt ggacggcaac    2460
gacttcgtcg ccgtttacgc cgcttcgcgc tgggctgccg aacgtgcccg ccgtggtttg    2520
ggcccgagcc tgatcgagtg ggtcacctac cgtgccggcc cgcactcgac ctcggacgac   2580
ccgtccaagt accgccctgc cgatgactgg agccacttcc cgctgggtga cccgatcgcc    2640
cgcctgaagc agcacctgat caagatcggc cactggtccg aagaagaaca ccaggccacc    2700
acggccgagt tcgaagcggc cgtgattgct gcgcaaaaag aagccgagca gtacggcacc    2760
ctggccaacg gtcacatccc gagcgccgcc tcgatgttcg aggacgtgta caaggagatg    2820
cccgaccacc tgcgccgcca acgccaggaa ctggggtttt gagatgaacg accacaacaa   2880
cagcatcaac ccggaaaccg ccatggccac cactaccatg accatgatcc aggccctgcg    2940
ctcggccatg gatgtcatgc ttgagcgcga cgacaatgtg gtggtgtacg ccaggacgt     3000 cggctacttc ggcggcgtgt tccgctgcac cgaaggcctg cagaccaagt acggcaagtc    3060
ccgcgtgttc gacgcgccca tctctgaaag cggcatcgtc ggcaccgccg tgggcatggg    3120
tgcctacggc ctgcgcccgg tggtggaaat ccagttcgct gactacttct acccggcctc    3180
cgaccagatc gtttctgaaa tggcccgcct gcgctaccgt tcggccggcg agttcatcgc    3240
cccgctgacc ctgcgtatgc cctgcggtgg cggtatctat ggcggccaga cacacagcca   3300
gagcccggaa gcgatgttca ctcaggtgtg cggcctgcgc accgtaatgc catccaaccc    3360
gtacgacgcc aaaggcctgc tgattgcctc gatcgaatgc gacgacccgg tgatcttcct    3420
ggagcccaag cgcctgtaca acggcccgtt cgacggccac catgaccgcc cggttacgcc    3480
gtggtcgaaa cacccgcaca gcgccgtgcc cgatggctac tacaccgtgc cactggacaa    3540
ggccgccatc acccgccccg gcaatgacgt gagcgtgctc acctatggca ccaccgtgta   3600
cgtggcccag gtggccgccg aagaaagtgg cgtggatgcc gaagtgatcg acctgcgcag    3660 cctgtgccg ctagacctgg acaccatcgt cgagtcggtg aaaaagaccg gccgttgcgt    3720
ggtagtacac gaggccaccc gtacttgtgg cttggcgca gaactggtgt cgctggtgca    3780
ggagcactgc ttccaccacc tggaggcgcc gatcgagcgc gtcaccggtt gggacacccc    3840
ctaccctcac gcgcaggaat gggcttactt cccagggcct tcgcgggtag gtgcggcatt   3900
gaaaaaggtc atggaggtct gaatgggcac gcacgtcatc aagatgccgg acattggcga   3960
aggcatcgcg caggtcgaat tggtggaatg gttcgtcaag gtgggcgaca tcatcgccga    4020
ggaccaagtg gtagccgacg tcatgaccga caaggccacc gtggaaatcc cgtcgccggt    4080
cagcggcaag gtgctggccc tgggtggcca gccaggtgaa gtgatggcgg tcggcagtga   4140
gctgatccgc atcgaagtgg aaggcagcgg caaccatgtg gatgtgccgc aagccaagcc   4200
ggccgaagtg cctgcggcac cggtagccgc taaacctgaa ccacagaaag acgttaaacc    4260
ggcggcgtac caggcgtcag ccagccacga ggcagcgccc atcgtgccgc gccagccggg   4320
cgacaagccg ctggcctcgc cggccggtgcg caaacgcgcc ctcgatgccg gcatcgaatt    4380
gcgttatgtg cacggcagcg gccggccgg gcgcatcctg cacgaagacc tcgacgcgtt    4440
catgagcaaa ccgcaaagcg ctgccgggca acccccaat ggctatgcca ggcgcaccga     4500
```

```
cagcgagcag gtgccggtga tcggcctgcg ccgcaagatc gcccagcgca tgcaggacgc    4560
caagcgccgg gtcgcgcact tcagctatgt ggaagaaatc gacgtcaccg ccctggaagc    4620
cctgcgccag cagctcaaca gcaagcacgg cgacagccgc ggcaagctga cactgctgcc    4680
gttcctggtg cgcgccctgg tcgtggcact gcgtgacttc ccgcagataa cgccaccta    4740 cgatgacgaa gcgcagatca tcacccgcca tggcgcggtg catgtgggca tcgccaccca    4800
aggtgacaac ggcctgatgg tacccgtgct gcgccacgcc gaagcgggca gcctgtgggc    4860
caatgccggt gagatttcac gcctggccaa cgctgcgcgc aacaacaagg ccagccgcga    4920
agagctgtcc ggttcgacca ttaccctgac cagcctcggc gccctgggcg catcgtcag    4980 cacgccggtg gtcaacaccc cggaagtggc gatcgtcggt gtcaaccgca tggttgagcg    5040
gcccgtggtg atcgacggcc agatcgtcgt gcgcaagatg atgaacctgt ccagctcgtt    5100
cgaccaccgc gtggtcgatg gcatggacgc cgccctgttc atccaggccg tgcgtggcct    5160
gctcgaacaa cccgcctgcc tgttcgtgga gtgagcatgc aacagactat ccagacaacc    5220
ctgttgatca tcggcggcgg ccctggcggc tatgtggcgg ccatccgcgc cgggcaactg    5280
ggcatcccta ccgtgctggt ggaaggccag gcgctgggcg gtacctgcct gaacatcggc    5340
tgcattccgt ccaaggcgct gatccatgtg gccgagcagt tccaccaggc ctcgcgcttt    5400
accgaaccct cgccgctggg catcagcgtg gcttcgccac gctggacat cggccagagc    5460 gtggcctgga aagacggcat cgtcgatcgc ctgaccactg gtgtcgccgc cctgctgaaa    5520
aagcacgggg tgaaggtggt gcacggctgg gccaaggtgc ttgatggcaa gcaggtcgag    5580
gtggatggcc agcgcatcca gtgcgagcac ctgttgctgg ccacgggctc cagcagtgtc    5640
gaactgccga tgctgccgtt gggtgggccg gtgatttcct cgaccgaggc cctggcaccg    5700
aaagccctgc cgcaacacct ggtggtggtg ggcggtggcc acatcggcct ggagctgggt    5760
atcgcctacc gcaagctcgg cgcgcaggtc agcgtggtgg aagcgcgcga gcgcatcctg    5820
ccgacttacg acagcgaact gaccgccccg gtggccgagt cgctgaaaaa gctgggtatc    5880
gccctgcacc ttggccacag cgtcgaaggt tacgaaaatg gctgcctgct ggccaacgat    5940
ggcaagggcg gacaactgcg cctggaagcc gaccgggtgc tggtgccgt gggccgccgc    6000 ccacgcacca agggcttcaa cctggaatgc ctggacctga agatgaatgg tgccgcgatt    6060
gccatcgacg agcgctgcca gaccagcatg cacaacgtct gggccatcgg cgacgtggcc    6120
ggcgaaccga tgctggcgca ccgggccatg gcccagggcg agatggtggc cgagatcatc    6180
gccggcaagg cacgccgctt cgaacccgct gcgatagccg ccgtgtgctt caccgacccg    6240
gaagtggtcg tggtcggcaa gacgccggaa caggccagtc agcaaggcct ggactgcatc    6300
gtcgcgcagt tccgttcgc cgccaacggc cgggccatga gcctggagtc gaaaagcggt    6360
ttcgtgcgcg tggtcgcgcg gcgtgacaac cacctgatcc tgggctggca gcggttggc    6420 gtggcggttt ccgagctgtc cacggcgttt gcccagtcgc tggagatggg tgcctgcctg    6480
gaggatgtgg ccggtaccat ccatgcccac ccgaccctgg gtgaagcggt acaggaagcg    6540
gcactgcgtg ccctgggcca cgccctgcat atctgacact gaagcggccg aggccgattt    6600
ggcccgccgc gccgagaggc gctgcgggtc tttttttatac ctg                     6643
```

<210> SEQ ID NO 61
<211> LENGTH: 468
<212> TYPE: PRT
<213> ORGANISM: Clostridium beijerinckii

```
<400> SEQUENCE: 61

Met Asn Lys Asp Thr Leu Ile Pro Thr Thr Lys Asp Leu Lys Leu Lys
1               5                   10                  15

Thr Asn Val Glu Asn Ile Asn Leu Lys Asn Tyr Lys Asp Asn Ser Ser
            20                  25                  30

Cys Phe Gly Val Phe Glu Asn Val Glu Asn Ala Ile Asn Ser Ala Val
        35                  40                  45

His Ala Gln Lys Ile Leu Ser Leu His Tyr Thr Lys Glu Gln Arg Glu
    50                  55                  60

Lys Ile Ile Thr Glu Ile Arg Lys Ala Ala Leu Glu Asn Lys Glu Val
65                  70                  75                  80

Leu Ala Thr Met Ile Leu Glu Glu Thr His Met Gly Arg Tyr Glu Asp
                85                  90                  95

Lys Ile Leu Lys His Glu Leu Val Ala Lys Tyr Thr Pro Gly Thr Glu
            100                 105                 110

Asp Leu Thr Thr Thr Ala Trp Ser Gly Asp Asn Gly Leu Thr Val Val
        115                 120                 125

Glu Met Ser Pro Tyr Gly Val Ile Gly Ala Ile Thr Pro Ser Thr Asn
130                 135                 140

Pro Thr Glu Thr Val Ile Cys Asn Ser Ile Gly Met Ile Ala Ala Gly
145                 150                 155                 160

Asn Ala Val Val Phe Asn Gly His Pro Gly Ala Lys Lys Cys Val Ala
                165                 170                 175

Phe Ala Ile Glu Met Ile Asn Lys Ala Ile Ser Cys Gly Gly Pro
            180                 185                 190

Glu Asn Leu Val Thr Thr Ile Lys Asn Pro Thr Met Glu Ser Leu Asp
            195                 200                 205

Ala Ile Ile Lys His Pro Leu Ile Lys Leu Leu Cys Gly Thr Gly Gly
210                 215                 220

Pro Gly Met Val Lys Thr Leu Asn Ser Gly Lys Lys Ala Ile Gly
225                 230                 235                 240

Ala Gly Ala Gly Asn Pro Pro Val Ile Val Asp Asp Thr Ala Asp Ile
                245                 250                 255

Glu Lys Ala Gly Lys Ser Ile Ile Glu Gly Cys Ser Phe Asp Asn Asn
            260                 265                 270

Leu Pro Cys Ile Ala Glu Lys Glu Val Phe Val Phe Glu Asn Val Ala
            275                 280                 285

Asp Asp Leu Ile Ser Asn Met Leu Lys Asn Asn Ala Val Ile Ile Asn
290                 295                 300

Glu Asp Gln Val Ser Lys Leu Ile Asp Leu Val Leu Gln Lys Asn Asn
305                 310                 315                 320

Glu Thr Gln Glu Tyr Phe Ile Asn Lys Lys Trp Val Gly Lys Asp Ala
                325                 330                 335

Lys Leu Phe Ser Asp Glu Ile Asp Val Glu Ser Pro Ser Asn Ile Lys
            340                 345                 350

Cys Ile Val Cys Glu Val Asn Ala Asn His Pro Phe Val Met Thr Glu
            355                 360                 365

Leu Met Met Pro Ile Leu Pro Ile Val Arg Val Lys Asp Ile Asp Glu
        370                 375                 380

Ala Val Lys Tyr Thr Lys Ile Ala Glu Gln Asn Arg Lys His Ser Ala
385                 390                 395                 400

Tyr Ile Tyr Ser Lys Asn Ile Asp Asn Leu Asn Arg Phe Glu Arg Glu
                405                 410                 415
```

```
Ile Asp Thr Thr Ile Phe Val Lys Asn Ala Lys Ser Phe Ala Gly Val
            420                 425                 430

Gly Tyr Glu Ala Glu Gly Phe Thr Thr Phe Thr Ile Ala Gly Ser Thr
        435                 440                 445

Gly Glu Gly Ile Thr Ser Ala Arg Asn Phe Thr Arg Gln Arg Arg Cys
450                 455                 460

Val Leu Ala Gly
465

<210> SEQ ID NO 62
<211> LENGTH: 6558
<212> TYPE: DNA
<213> ORGANISM: Clostridium beijerinckii

<400> SEQUENCE: 62
aagcttaaaa tatccatagg ctattgttaa taagactata gcgcttaata ctctaagcgc      60
accatctaaa aaattataca taggaattgg ataaactcca atcttctcca taatactttt     120
cataggtgaa attgatatta taattaaggc tgcataaagc aaactcatat ctccaataaa     180
tgtcactatc ataggtaatt tccttttcat gttcacatac tcccccgtat tctataataa     240
tttacaataa acttccatca caaataaatt ataacatata ttgtaaatat agttttatta     300
ttcgcatatt tatagataaa caatatataa cttagactta tgcaataacc taccgaaagt     360
aaaaacattg ttatttcaca ggactatgaa aatttcgctg aaagtactaa attgcaggtt     420
gcaccactaa tgcttgctcc caatttcatt gtgacaagca ttagttgaac aacctacaat     480
taagagcctt taacagctca tttccaatgc ctgctacata aaaatgtttc tactttctaa     540
tatggtattt acttcaaagt gtaaatcaaa ttcttaagtt gtttatctat atagggttcc     600
atattgataa caatacatat ctactgtttc aatttcatga ataccagcga tattgaaatt     660
ttgtaagttt gaatatcatt gtgaaaccct atatatcaaa tacaatctca aaattataca     720
aaaagatccc aacttcacaa tatgaatttg agatcttcta tcttaacttc ttcaatatt     780
ttaagattat ttatactgcg tgcaaatctt ctataagtat caattatcag ctatgtacat     840
tgatagtgga cttgtaatct gaacagctta tatatttaca cttttaagtt ctcttccact     900
aaccctgct tgaaacttc tcataaacaa atcgaaagta cctttaatta gctgtgcatt     960
ctcaaactca gaatttaact taagtacttc aattgccgct tcgatagtat agagctctcc    1020
ttctgaagca ccttttctta aagtatattc tgatttatta attggattta atgaaattct    1080
tggaagcttc tttaagtagt cgctctttct tagtatcttc tctgcttctt tccatgtgcc    1140
atctaagata taaatgctg gaattttttc tgaatcttta catttagact ttctttctag    1200
aggttcatca tcatccatag gaaataatac acgtatttca taatcatcgc tattaatata    1260
ttcaattaat ttttcaggag tctttactct ctcccaaaga attaactcag ttgattctgg    1320
attaccaat ttcaataatc tagcggtatt tgaaggccta ctaaattctc tttctgttga    1380
taatatcaat atctttgctt ttgtctctat tttaggcaca atatcgcaga tacaatttat    1440
tattggcaac ccacatttat tgcagctctc atataactta gtaatttgct taactttaaa    1500
ttcagactcc atttaccctc cattattagt tggttagtgt gtcatatctt cttgctatta    1560
ctaactgatt ataacatatg tattcaatat atcactccta gttttcaaag cactggcaat    1620
acgaattaca aattaatttc tggatttatg tcagtatttc attaataaaa ggtcggactt    1680
ttaagatact tgtttagct attgatcata tttattaaag actatgcatt taatgtataa    1740
```

```
ttataatgaa tattatcaat aatatttatt ttatattaca atcttacagt ctttattcta    1800
aatttcactc aaataccaaa cgagctttat tcataaacaa tatataacaa taattccaaa    1860
ataatacgat attttatctg taacagccat ataaaaaaaa tatcatatag tcttgtcatt    1920
tgataacgtt ttgtcttcct tatatttact ttttcggttt aataggttga ttctgtaaat    1980
tttagtgata acatatattt gatgacatta aaaatttaat atttcatata aattttttaat   2040
gtctattaat ttttaaatca caaggaggaa tagttcatga ataaagacac actaatacct    2100
acaactaaag atttaaaatt aaaaacaaat gttgaaaaca ttaatttaaa gaactacaag    2160
gataattctt catgtttcgg agtattcgaa aatgttgaaa atgctataaa cagcgctgta    2220
cacgcgcaaa agatattatc ccttcattat acaaaagaac aaagagaaaa aatcataact    2280
gagataagaa aggccgcatt agaaaataaa gaggttttag ctaccatgat tctggaagaa    2340
acacatatgg gaaggtatga agataaaata ttaaagcatg aattagtagc taaatatact    2400
cctggtacag aagatttaac tactactgct tggtcaggtg ataatggtct tacagttgta    2460
gaaatgtctc catatggcgt tataggtgca ataactcctt ctacgaatcc aactgaaact    2520
gtaatatgta atagcatcgg catgatagct gctggaaatg ctgtagtatt taacggacac    2580
ccaggcgcta aaaatgtgt tgcttttgct attgaaatga taaataaagc aattatttca    2640
tgtggcggtc ctgagaattt agtaacaact ataaaaaatc caactatgga atccctagat    2700
gcaattatta agcatccttt aataaaactt ctttgcggaa ctggaggtcc aggaatggta    2760
aaaaccctct taaattctgg caagaaagct ataggtgctg gtgctggaaa tccaccagtt    2820
attgtagatg ataccgctga tataaaaag gctggtaaga gtatcattga aggctgttct    2880
tttgataata atttaccttg tattgcagaa aagaagtat ttgtttttga gaatgttgca    2940
gatgatttaa tatctaacat gctaaaaaat aatgctgtaa ttataaatga agatcaagta    3000
tcaaaattaa tagatttagt attacaaaaa aataatgaaa ctcaagaata ctttataaac    3060
aaaaaatggg taggaaaaga tgcaaaatta ttctcagatg aaatagatgt tgagtctcct    3120
tcaaatatta aatgcatagt ctgcgaagta aatgcaaatc atccatttgt catgacagaa    3180
ctcatgatgc caatattacc aattgtaaga gttaaagata tagatgaagc tgttaaatat    3240
acaaagatag cagaacaaaa tagaaaacat agtgcctata tttattctaa aaatatagac    3300
aacctaaata gatttgaaag agaaattgat actactattt ttgtaaagaa tgctaaatct    3360
tttgctggtg ttggttatga agctgaagga tttacaactt tcactattgc tggatctact    3420
ggtgaaggca taacctctgc aagaaatttt caagacaaa gaagatgtgt acttgccggc    3480
taacttcttg ctaaatttat acatttattc acataacttt aatatgcaat gttcccacaa    3540
aatattaaaa actatttaga agggagatat taaatgaata aattagtaaa attaacagat    3600
ttaaagcgca ttttcaaaga tggtatgaca attatggttg ggggttttt agattgtgga    3660
actcctgaaa atattataga tatgctagtt gatttaaata taaaaaatct gactattata    3720
agcaatgata cagcttttcc taataaagga ataggaaaac ttattgtaaa tggtcaagtt    3780
tctaaagtaa ttgcttcaca tattggaact aatcctgaaa ctgggaaaaa aatgagctct    3840
ggtgaactta agttgagct ttctccacaa ggaacactga tcgaaagaat tcgtgcagct    3900
ggatctggac tcggaggtgt attaactcca accggacttg gactatcgt tgaagaaggt    3960
aagaaaaaag ttactatcgg tggcaaagaa tatctattag aacttccttt atccgctgat    4020
gtttcattaa taaaaggtag cattgtagat gaatttggaa ataccttcta tagagctgct    4080
actaaaaatt tcaatccata tatggcaatg gctgcaaaaa cagttatagt tgaagcagaa    4140
```

```
aatttagtta aatgtgaaga tttaaaaaga gatgccataa tgactcctgg cgtattagta   4200
gattatatcg ttaaggaggc ggcttaattg attgtagata aagttttagc aaaagagata   4260
attgccaaaa gagttgcaaa agaactaaaa aaaggccaac tcgtaaacct tggaatagga   4320
cttccaactt tagtagctaa ttatgtgcca aaagaaatga acattacttt cgaatcagaa   4380
aatggcatgg ttggcatggc acaaatggcc tcatcaggtg aaaatgaccc agatataata   4440
aatgctggtg gggaatatgt aacattatta cctcaaggtg catttttga tagttcaacg    4500 tcttttgcac taataagagg aggacatgtt gatgttgctg ttcttggtgc tctagaagtt   4560
gatgaagaag gtaatttagc taactggatt gttccaaata aaattgtccc aggtatggga   4620
ggcgccatgg atttggcaat aggcgcaaaa aaaataatag tggcaatgca acatacagga   4680
aaaggtaaac ctaaaatcgt aaaaaaatgt actctcccac ttactgctaa ggctcaggta   4740
gatttaattg ttacagaact ttgtgtaatt gatgtaacaa atgatggttt acttttcaga   4800
gaaattcata aagatacaac tattgatgaa ataaaatttt taacagatgc agatttaatt   4860
attcccgaca acttaaaaat tatggatatc taaatcattc tattttaaat ataaacttt    4920 aaaaatctta tgtattaaaa actaagaaaa gaggttgatt attttatgtt agaaagtgaa   4980
gtatctaaac aaattacaac tccacttgct gctccagcgt ttcctagagg accatataga   5040
tttcacaata gagaatatct aaacattatt tatcgaactg atttagatgc tcttcgaaaa   5100
atagtaccag agccacttga attagatgga gcatatgtta ggtttgagat gatggctatg   5160
cctgatacaa ccggactagg ctcatatact gagtgtggtc aagccattcc agtaaaaat   5220 aatgaggtta aaggtgacta cttgcatatg atgtacctag ataatgaacc tgctattgct   5280
gttggaagag aaagcagtgc ttatcccaaa aagttcggct atccaaagct atttgttgat   5340
tcagacgccc tagttggcgc ccttaagtat ggtgcattac cggtagttac tgcgacgatg   5400
ggatataagc atgagcccct agatcttaaa gaagcctata ctcaaattgc aagacccaat   5460
ttcatgctaa aaatcattca aggttatgat ggtaagccaa gaatttgtga actcatctgt   5520
gcagaaaata ctgatataac tatccacggt gcttggactg gaagtgcacg cctacaatta   5580
tttagccatg cactagctcc tcttgctgat ttacctgtat tagagatcgt atcagcatct   5640
catatcctaa cagatttaac tcttggaaca cctaaggttg tacatgatta tctttcagta   5700
aaataaaagc aatatagaat aaccactaca aaagtagtgg ttattctata ttttaaatca   5760
aactgtaaaa cttaagtttt atagtaccta ataatatttt actaccagca ttagattagt   5820
taaaatacaa agtttgtggt aaaagtattt tagattgcat aatagccttc tatacttta    5880 acaatataac caattgctca ccatctgctt agaatatgct tctttaagct ctaaaataca   5940 tataaaaag taggaatttc ttattaaaat tcctacttat attatatata aatttaatcg    6000
ttaggtttta ttcgcattgt tcctctttaa tttatctctt ataacatttt attataattg   6060
ttcatataat taattcaata tactattata tattttcaag cattaataat tattcagcat   6120
ctgtcattac atatgcttcc atactttgac ttcttattaa atcatagcta atccatccat   6180
agccattgat tccccagtct ttaccccatg aatttattat ttttacagct ttttactat    6240 catcataacc aactacgcaa actgcatgac cacctctatt ttctccatca atctggtcat   6300
aaattggatt atcagaattt aaattatcaa aatctggata tactgatatt ccaataacta   6360
ctggatttcc agctgctatt tgtgcccttta ttgcattata gtcaccatct ggaagttgac   6420
tccaactttt tgctttatat ttggctgcat tagccttttg ttcatctgta ggtgtaacct   6480
```

-continued cccaactata ttcactacca tcataaggca tatcagataa tgtagtacaa ccttgttctt    6540
ctaataattt aaatgcat    6558

<210> SEQ ID NO 63
<211> LENGTH: 862
<212> TYPE: PRT
<213> ORGANISM: Clostridium acetobutylicum

<400> SEQUENCE: 63

Met Lys Val Thr Thr Val Lys Glu Leu Asp Glu Lys Leu Lys Val Ile
1               5                   10                  15

Lys Glu Ala Gln Lys Lys Phe Ser Cys Tyr Ser Gln Glu Met Val Asp
            20                  25                  30

Glu Ile Phe Arg Asn Ala Ala Met Ala Ala Ile Asp Ala Arg Ile Glu
        35                  40                  45

Leu Ala Lys Ala Ala Val Leu Glu Thr Gly Met Gly Leu Val Glu Asp
    50                  55                  60

Lys Val Ile Lys Asn His Phe Ala Gly Glu Tyr Ile Tyr Asn Lys Tyr
65                  70                  75                  80

Lys Asp Glu Lys Thr Cys Gly Ile Ile Glu Arg Asn Glu Pro Tyr Gly
                85                  90                  95

Ile Thr Lys Ile Ala Glu Pro Ile Gly Val Val Ala Ala Ile Ile Pro
            100                 105                 110

Val Thr Asn Pro Thr Ser Thr Thr Ile Phe Lys Ser Leu Ile Ser Leu
        115                 120                 125

Lys Thr Arg Asn Gly Ile Phe Phe Ser Pro His Pro Arg Ala Lys Lys
    130                 135                 140

Ser Thr Ile Leu Ala Ala Lys Thr Ile Leu Asp Ala Ala Val Lys Ser
145                 150                 155                 160

Gly Ala Pro Glu Asn Ile Ile Gly Trp Ile Asp Glu Pro Ser Ile Glu
                165                 170                 175

Leu Thr Gln Tyr Leu Met Gln Lys Ala Asp Ile Thr Leu Ala Thr Gly
            180                 185                 190

Gly Pro Ser Leu Val Lys Ser Ala Tyr Ser Ser Gly Lys Pro Ala Ile
        195                 200                 205

Gly Val Gly Pro Gly Asn Thr Pro Val Ile Ile Asp Glu Ser Ala His
    210                 215                 220

Ile Lys Met Ala Val Ser Ser Ile Ile Leu Ser Lys Thr Tyr Asp Asn
225                 230                 235                 240

Gly Val Ile Cys Ala Ser Glu Gln Ser Val Ile Val Leu Lys Ser Ile
                245                 250                 255

Tyr Asn Lys Val Lys Asp Glu Phe Gln Glu Arg Gly Ala Tyr Ile Ile
            260                 265                 270

Lys Lys Asn Glu Leu Asp Lys Val Arg Glu Val Ile Phe Lys Asp Gly
        275                 280                 285

Ser Val Asn Pro Lys Ile Val Gly Gln Ser Ala Tyr Thr Ile Ala Ala
    290                 295                 300

Met Ala Gly Ile Lys Val Pro Lys Thr Thr Arg Ile Leu Ile Gly Glu
305                 310                 315                 320

Val Thr Ser Leu Gly Glu Glu Pro Phe Ala His Glu Lys Leu Ser
                325                 330                 335

Pro Val Leu Ala Met Tyr Glu Ala Asp Asn Phe Asp Asp Ala Leu Lys
            340                 345                 350

Lys Ala Val Thr Leu Ile Asn Leu Gly Gly Leu Gly His Thr Ser Gly

```
                355                 360                 365
Ile Tyr Ala Asp Glu Ile Lys Ala Arg Asp Lys Ile Asp Arg Phe Ser
370                 375                 380

Ser Ala Met Lys Thr Val Arg Thr Phe Val Asn Ile Pro Thr Ser Gln
385                 390                 395                 400

Gly Ala Ser Gly Asp Leu Tyr Asn Phe Arg Ile Pro Pro Ser Phe Thr
                405                 410                 415

Leu Gly Cys Gly Phe Trp Gly Gly Asn Ser Val Ser Glu Asn Val Gly
                420                 425                 430

Pro Lys His Leu Leu Asn Ile Lys Thr Val Ala Glu Arg Arg Glu Asn
                435                 440                 445

Met Leu Trp Phe Arg Val Pro His Lys Val Tyr Phe Lys Phe Gly Cys
                450                 455                 460

Leu Gln Phe Ala Leu Lys Asp Leu Lys Asp Leu Lys Lys Lys Arg Ala
465                 470                 475                 480

Phe Ile Val Thr Asp Ser Asp Pro Tyr Asn Leu Asn Tyr Val Asp Ser
                485                 490                 495

Ile Ile Lys Ile Leu Glu His Leu Asp Ile Asp Phe Lys Val Phe Asn
                500                 505                 510

Lys Val Gly Arg Glu Ala Asp Leu Lys Thr Ile Lys Lys Ala Thr Glu
                515                 520                 525

Glu Met Ser Ser Phe Met Pro Asp Thr Ile Ile Ala Leu Gly Gly Thr
                530                 535                 540

Pro Glu Met Ser Ser Ala Lys Leu Met Trp Val Leu Tyr Glu His Pro
545                 550                 555                 560

Glu Val Lys Phe Glu Asp Leu Ala Ile Lys Phe Met Asp Ile Arg Lys
                565                 570                 575

Arg Ile Tyr Thr Phe Pro Lys Leu Gly Lys Lys Ala Met Leu Val Ala
                580                 585                 590

Ile Thr Thr Ser Ala Gly Ser Gly Ser Glu Val Thr Pro Phe Ala Leu
                595                 600                 605

Val Thr Asp Asn Asn Thr Gly Asn Lys Tyr Met Leu Ala Asp Tyr Glu
                610                 615                 620

Met Thr Pro Asn Met Ala Ile Val Asp Ala Glu Leu Met Met Lys Met
625                 630                 635                 640

Pro Lys Gly Leu Thr Ala Tyr Ser Gly Ile Asp Ala Leu Val Asn Ser
                645                 650                 655

Ile Glu Ala Tyr Thr Ser Val Tyr Ala Ser Glu Tyr Thr Asn Gly Leu
                660                 665                 670

Ala Leu Glu Ala Ile Arg Leu Ile Phe Lys Tyr Leu Pro Glu Ala Tyr
                675                 680                 685

Lys Asn Gly Arg Thr Asn Glu Lys Ala Arg Glu Lys Met Ala His Ala
                690                 695                 700

Ser Thr Met Ala Gly Met Ala Ser Ala Asn Ala Phe Leu Gly Leu Cys
705                 710                 715                 720

His Ser Met Ala Ile Lys Leu Ser Ser Glu His Asn Ile Pro Ser Gly
                725                 730                 735

Ile Ala Asn Ala Leu Leu Ile Glu Glu Val Ile Lys Phe Asn Ala Val
                740                 745                 750

Asp Asn Pro Val Lys Gln Ala Pro Cys Pro Gln Tyr Lys Tyr Pro Asn
                755                 760                 765

Thr Ile Phe Arg Tyr Ala Arg Ile Ala Asp Tyr Ile Lys Leu Gly Gly
                770                 775                 780
```

```
Asn Thr Asp Glu Glu Lys Val Asp Leu Leu Ile Asn Lys Ile His Glu
785                 790                 795                 800

Leu Lys Lys Ala Leu Asn Ile Pro Thr Ser Ile Lys Asp Ala Gly Val
            805                 810                 815

Leu Glu Glu Asn Phe Tyr Ser Ser Leu Asp Arg Ile Ser Glu Leu Ala
        820                 825                 830

Leu Asp Asp Gln Cys Thr Gly Ala Asn Pro Arg Phe Pro Leu Thr Ser
    835                 840                 845

Glu Ile Lys Glu Met Tyr Ile Asn Cys Phe Lys Lys Gln Pro
850                 855                 860
```

<210> SEQ ID NO 64
<211> LENGTH: 1665
<212> TYPE: DNA
<213> ORGANISM: Clostridium acetobutylicum

<400> SEQUENCE: 64

| | |
|---|---:|
| ttgaagagtg aatacacaat tggaagatat tgttagacc gtttatcaga gttgggtatt | 60 |
| cggcatatct ttggtgtacc tggagattac aatctatcct ttttagacta tataatggag | 120 |
| tacaaaggga tagattgggt tggaaattgc aatgaattga atgctgggta tgctgctgat | 180 |
| ggatatgcaa gaataaatgg aattggagcc atacttacaa catttggtgt tggagaatta | 240 |
| agtgccatta acgcaattgc tggggcatac gctgagcaag ttccagttgt taaaattaca | 300 |
| ggtatcccca cagcaaaagt tagggacaat ggattatatg tacaccacac attaggtgac | 360 |
| ggaaggtttg atcactttt tgaaatgttt agagaagtaa cagttgctga ggcattacta | 420 |
| agcgaagaaa atgcagcaca agaaattgat cgtgttctta tttcatgctg gagacaaaaa | 480 |
| cgtcctgttc ttataaattt accgattgat gtatatgata aaccaattaa caaaccatta | 540 |
| aagccattac tcgattatac tatttcaagt aacaaagagg ctgcatgtga atttgttaca | 600 |
| gaaatagtac ctataataaa tagggcaaaa agcctgtta tcttgcaga ttatggagta | 660 |
| tatcgttacc aagttcaaca tgtgcttaaa acttggccg aaaaaaccgg atttcctgtg | 720 |
| gctacactaa gtatgggaaa aggtgtttc aatgaagcac accctcaatt tattggtgtt | 780 |
| tataatggtg atgtaagttc tccttattta aggcagcgag ttgatgaagc agactgcatt | 840 |
| attagcgttg gtgtaaaatt gacggattca accacagggg gattttctca tggattttct | 900 |
| aaaaggaatg taattcacat tgatcctttt tcaataaagg caaaaggtaa aaaatatgca | 960 |
| cctattacga tgaagatgc tttaacagaa ttaacaagta aaattgagca tagaaacttt | 1020 |
| gaggatttag atataaagcc ttacaaatca gataatcaaa agtattttgc aaaagagaag | 1080 |
| ccaattacac aaaacgttt ttttgagcgt attgctcact ttataaaaga aaagatgta | 1140 |
| ttattagcag aacagggtac atgctttttt ggtgcgtcaa ccatacaact acccaaagat | 1200 |
| gcaacttta ttggtcaacc tttatgggga tctattggat acacacttcc tgctttatta | 1260 |
| ggttcacaat tagctgatca aaaaaggcgt aatattcttt aattgggga tggtgcattt | 1320 |
| caaatgacag cacaagaaat ttcaacaatg cttcgtttac aaatcaaacc tattattttt | 1380 |
| ttaattaata cgatggtta tacaattgaa cgtgctattc atggtagaga acaagtatat | 1440 |
| aacaatattc aaatgtggcg atatcataat gttccaaagg ttttaggtcc taagaatgc | 1500 |
| agcttaacct ttaaagtaca aagtgaaact gaacttgaaa aggctctttt agtggcagat | 1560 |
| aaggattgtg aacattgat ttttatgaa gttgttatgg atcgttatga taacccgag | 1620 |
| cctttagaac gtctttcgaa acgttttgca aatcaaaata attag | 1665 |

<210> SEQ ID NO 65
<211> LENGTH: 858
<212> TYPE: PRT
<213> ORGANISM: Clostridium acetobutylicum

<400> SEQUENCE: 65

```
Met Lys Val Thr Asn Gln Lys Glu Leu Lys Gln Lys Leu Asn Glu Leu
1               5                   10                  15

Arg Glu Ala Gln Lys Lys Phe Ala Thr Tyr Thr Gln Glu Gln Val Asp
            20                  25                  30

Lys Ile Phe Lys Gln Cys Ala Ile Ala Ala Lys Glu Arg Ile Asn
        35                  40                  45

Leu Ala Lys Leu Ala Val Glu Glu Thr Gly Ile Gly Leu Val Glu Asp
    50                  55                  60

Lys Ile Ile Lys Asn His Phe Ala Ala Glu Tyr Ile Tyr Asn Lys Tyr
65                  70                  75                  80

Lys Asn Glu Lys Thr Cys Gly Ile Ile Asp His Asp Asp Ser Leu Gly
                85                  90                  95

Ile Thr Lys Val Ala Glu Pro Ile Gly Ile Val Ala Ala Ile Val Pro
            100                 105                 110

Thr Thr Asn Pro Thr Ser Thr Ala Ile Phe Lys Ser Leu Ile Ser Leu
        115                 120                 125

Lys Thr Arg Asn Ala Ile Phe Phe Ser Pro His Pro Arg Ala Lys Lys
    130                 135                 140

Ser Thr Ile Ala Ala Ala Lys Leu Ile Leu Asp Ala Ala Val Lys Ala
145                 150                 155                 160

Gly Ala Pro Lys Asn Ile Ile Gly Trp Ile Asp Glu Pro Ser Ile Glu
                165                 170                 175

Leu Ser Gln Asp Leu Met Ser Glu Ala Asp Ile Ile Leu Ala Thr Gly
            180                 185                 190

Gly Pro Ser Met Val Lys Ala Ala Tyr Ser Ser Gly Lys Pro Ala Ile
        195                 200                 205

Gly Val Gly Ala Gly Asn Thr Pro Ala Ile Ile Asp Glu Ser Ala Asp
    210                 215                 220

Ile Asp Met Ala Val Ser Ser Ile Ile Leu Ser Lys Thr Tyr Asp Asn
225                 230                 235                 240

Gly Val Ile Cys Ala Ser Glu Gln Ser Ile Leu Val Met Asn Ser Ile
                245                 250                 255

Tyr Glu Lys Val Lys Glu Glu Phe Val Lys Arg Gly Ser Tyr Ile Leu
            260                 265                 270

Asn Gln Asn Glu Ile Ala Lys Ile Lys Glu Thr Met Phe Lys Asn Gly
        275                 280                 285

Ala Ile Asn Ala Asp Ile Val Gly Lys Ser Ala Tyr Ile Ile Ala Lys
    290                 295                 300

Met Ala Gly Ile Glu Val Pro Gln Thr Thr Lys Ile Leu Ile Gly Glu
305                 310                 315                 320

Val Gln Ser Val Glu Lys Ser Glu Leu Phe Ser His Glu Lys Leu Ser
                325                 330                 335

Pro Val Leu Ala Met Tyr Lys Val Lys Asp Phe Asp Glu Ala Leu Lys
            340                 345                 350

Lys Ala Gln Arg Leu Ile Glu Leu Gly Gly Ser Gly His Thr Ser Ser
        355                 360                 365

Leu Tyr Ile Asp Ser Gln Asn Asn Lys Asp Lys Val Lys Glu Phe Gly
```

```
                 370                 375                 380
Leu Ala Met Lys Thr Ser Arg Thr Phe Ile Asn Met Pro Ser Ser Gln
385                 390                 395                 400

Gly Ala Ser Gly Asp Leu Tyr Asn Phe Ala Ile Ala Pro Ser Phe Thr
                405                 410                 415

Leu Gly Cys Gly Thr Trp Gly Gly Asn Ser Val Ser Gln Asn Val Glu
                420                 425                 430

Pro Lys His Leu Leu Asn Ile Lys Ser Val Ala Glu Arg Arg Glu Asn
                435                 440                 445

Met Leu Trp Phe Lys Val Pro Gln Lys Ile Tyr Phe Lys Tyr Gly Cys
            450                 455                 460

Leu Arg Phe Ala Leu Lys Glu Leu Lys Asp Met Asn Lys Lys Arg Ala
465                 470                 475                 480

Phe Ile Val Thr Asp Lys Asp Leu Phe Lys Leu Gly Tyr Val Asn Lys
                485                 490                 495

Ile Thr Lys Val Leu Asp Glu Ile Asp Ile Lys Tyr Ser Ile Phe Thr
                500                 505                 510

Asp Ile Lys Ser Asp Pro Thr Ile Asp Ser Val Lys Lys Gly Ala Lys
                515                 520                 525

Glu Met Leu Asn Phe Glu Pro Asp Thr Ile Ile Ser Ile Gly Gly Gly
            530                 535                 540

Ser Pro Met Asp Ala Ala Lys Val Met His Leu Leu Tyr Glu Tyr Pro
545                 550                 555                 560

Glu Ala Glu Ile Glu Asn Leu Ala Ile Asn Phe Met Asp Ile Arg Lys
                565                 570                 575

Arg Ile Cys Asn Phe Pro Lys Leu Gly Thr Lys Ala Ile Ser Val Ala
                580                 585                 590

Ile Pro Thr Thr Ala Gly Thr Gly Ser Glu Ala Thr Pro Phe Ala Val
            595                 600                 605

Ile Thr Asn Asp Glu Thr Gly Met Lys Tyr Pro Leu Thr Ser Tyr Glu
            610                 615                 620

Leu Thr Pro Asn Met Ala Ile Ile Asp Thr Glu Leu Met Leu Asn Met
625                 630                 635                 640

Pro Arg Lys Leu Thr Ala Ala Thr Gly Ile Asp Ala Leu Val His Ala
                645                 650                 655

Ile Glu Ala Tyr Val Ser Val Met Ala Thr Asp Tyr Thr Asp Glu Leu
                660                 665                 670

Ala Leu Arg Ala Ile Lys Met Ile Phe Lys Tyr Leu Pro Arg Ala Tyr
                675                 680                 685

Lys Asn Gly Thr Asn Asp Ile Glu Ala Arg Glu Lys Met Ala His Ala
            690                 695                 700

Ser Asn Ile Ala Gly Met Ala Phe Ala Asn Ala Phe Leu Gly Val Cys
705                 710                 715                 720

His Ser Met Ala His Lys Leu Gly Ala Met His His Val Pro His Gly
                725                 730                 735

Ile Ala Cys Ala Val Leu Ile Glu Glu Val Ile Lys Tyr Asn Ala Thr
                740                 745                 750

Asp Cys Pro Thr Lys Gln Thr Ala Phe Pro Gln Tyr Lys Ser Pro Asn
                755                 760                 765

Ala Lys Arg Lys Tyr Ala Glu Ile Ala Glu Tyr Leu Asn Leu Lys Gly
            770                 775                 780

Thr Ser Asp Thr Glu Lys Val Thr Ala Leu Ile Glu Ala Ile Ser Lys
785                 790                 795                 800
```

```
Leu Lys Ile Asp Leu Ser Ile Pro Gln Asn Ile Ser Ala Ala Gly Ile
            805                 810                 815

Asn Lys Lys Asp Phe Tyr Asn Thr Leu Asp Lys Met Ser Glu Leu Ala
        820                 825                 830

Phe Asp Asp Gln Cys Thr Thr Ala Asn Pro Arg Tyr Pro Leu Ile Ser
        835                 840                 845

Glu Leu Lys Asp Ile Tyr Ile Lys Ser Phe
        850                 855

<210> SEQ ID NO 66
<211> LENGTH: 2589
<212> TYPE: DNA
<213> ORGANISM: Clostridium acetobutylicum

<400> SEQUENCE: 66
```

| | | | | | |
|---|---|---|---|---|---|
| atgaaagtca | caacagtaaa | ggaattagat | gaaaaactca | aggtaattaa | agaagctcaa | 60 |
| aaaaaattct | cttgttactc | gcaagaaatg | gttgatgaaa | tctttagaaa | tgcagcaatg | 120 |
| gcagcaatcg | acgcaaggat | agagctagca | aaagcagctg | ttttggaaac | cggtatgggc | 180 |
| ttagttgaag | acaaggttat | aaaaaatcat | tttgcaggcg | aatacatcta | aacaaatat | 240 |
| aaggatgaaa | aaacctgcgg | tataattgaa | cgaaatgaac | cctacggaat | tacaaaaata | 300 |
| gcagaaccta | taggagttgt | agctgctata | atccctgtaa | caaacccccac | atcaacaaca | 360 |
| atatttaaat | ccttaatatc | ccttaaaact | agaaatggaa | ttttcttttc | gcctcaccca | 420 |
| agggcaaaaa | aatccacaat | actagcagct | aaaacaatac | ttgatgcagc | cgttaagagt | 480 |
| ggtgccccgg | aaaatataat | aggttggata | gatgaaccctt | caattgaact | aactcaatat | 540 |
| ttaatgcaaa | aagcagatat | aaccccttgca | actggtggtc | cctcactagt | taaatctgct | 600 |
| tattcttccg | gaaaaccagc | aataggtgtt | ggtccgggta | cacccccagt | aataattgat | 660 |
| gaatctgctc | atataaaaaat | ggcagtaagt | tcaattatat | tatccaaaac | ctatgataat | 720 |
| ggtgttatat | gtgcttctga | acaatctgta | atagtcttaa | aatccatata | taacaaggta | 780 |
| aaagatgagt | tccaagaaag | aggagcttat | ataataaaga | aaacgaatt | ggataaagtc | 840 |
| cgtgaagtga | tttttaaaga | tggatccgta | aaccctaaaa | tagtcggaca | gtcagcttat | 900 |
| actatagcag | ctatggctgg | cataaaagta | cctaaaacca | caagaatatt | aataggagaa | 960 |
| gttacctcct | taggtgaaga | agaaccttt | gcccacgaaa | aactatctcc | tgttttggct | 1020 |
| atgtatgagg | ctgacaattt | tgatgatgct | ttaaaaaag | cagtaactct | aataaactta | 1080 |
| ggaggcctcg | ccatacctc | aggaatatat | gcagatgaaa | taaaagcacg | agataaaata | 1140 |
| gatagattta | gtagtgccat | gaaaaccgta | agaacctttg | taaatatccc | aacctcacaa | 1200 |
| ggtgcaagtg | gagatctata | taattttaga | ataccacctt | ctttcacgct | tggctgcgga | 1260 |
| ttttggggag | gaaattctgt | tccgagaat | gttggtccaa | acatctttt | gaatattaaa | 1320 |
| accgtagctg | aaaggagaga | aaacatgctt | tggtttagag | ttccacataa | agtatatttt | 1380 |
| aagttcggtt | gtcttcaatt | tgctttaaaa | gatttaaaag | atctaaagaa | aaaaagagcc | 1440 |
| tttatagtta | ctgatagtga | cccctataat | ttaaactatg | ttgattcaat | aataaaaata | 1500 |
| cttgagcacc | tagatattga | ttttaaagta | tttaataagg | ttggaagaga | agctgatctt | 1560 |
| aaaaccataa | aaaagcaac | tgaagaaatg | tcctcctta | tgccagacac | tataatagct | 1620 |
| ttaggtggta | cccctgaaat | gagctctgca | aagctaatgt | gggtactata | tgaacatcca | 1680 |
| gaagtaaaat | ttgaagatct | tgcaataaaa | tttatggaca | taagaaagag | aatatatact | 1740 |

```
ttcccaaaac tcggtaaaaa ggctatgtta gttgcaatta caacttctgc tggttccggt    1800
tctgaggtta ctccttttgc tttagtaact gacaataaca ctggaaataa gtacatgtta    1860
gcagattatg aaatgacacc aaatatggca attgtagatg cagaacttat gatgaaaatg    1920
ccaaagggat taaccgctta ttcaggtata gatgcactag taaatagtat agaagcatac    1980
acatccgtat atgcttcaga atacacaaac ggactagcac tagaggcaat acgattaata    2040
tttaaatatt tgcctgaggc ttacaaaaac ggaagaacca atgaaaaagc aagagagaaa    2100
atggctcacg cttcaactat ggcaggtatg gcatccgcta atgcatttct aggtctatgt    2160
cattccatgg caataaaatt aagttcagaa cacaatattc ctagtggcat tgccaatgca    2220
ttactaatag aagaagtaat aaaatttaac gcagttgata atcctgtaaa acaagcccct    2280
tgcccacaat ataagtatcc aaacaccata tttagatatg ctcgaattgc agattatata    2340
aagcttggag gaaatactga tgaggaaaag gtagatctct taattaacaa atacatgaa     2400 ctaaaaaaag ctttaaatat accaacttca ataaggatg caggtgtttt ggaggaaaac     2460
ttctattcct cccttgatag aatatctgaa cttgcactag atgatcaatg cacaggcgct    2520
aatcctagat ttcctcttac aagtgagata aagaaatgt atataaattg ttttaaaaaa     2580
caaccttaa                                                            2589
```

<210> SEQ ID NO 67
<211> LENGTH: 307
<212> TYPE: PRT
<213> ORGANISM: Pseudomonas putida

<400> SEQUENCE: 67

```
Met Ser Lys Lys Leu Lys Ala Ala Ile Ile Gly Pro Gly Asn Ile Gly
1               5                   10                  15

Thr Asp Leu Val Met Lys Met Leu Arg Ser Glu Trp Ile Glu Pro Val
            20                  25                  30

Trp Met Val Gly Ile Asp Pro Asn Ser Asp Gly Leu Lys Arg Ala Arg
        35                  40                  45

Asp Phe Gly Met Lys Thr Thr Ala Glu Gly Val Asp Gly Leu Leu Pro
    50                  55                  60

His Val Leu Asp Asp Asp Ile Arg Ile Ala Phe Asp Ala Thr Ser Ala
65                  70                  75                  80

Tyr Val His Ala Glu Asn Ser Arg Lys Leu Asn Ala Leu Gly Val Leu
                85                  90                  95

Met Val Asp Leu Thr Pro Ala Ala Ile Gly Pro Tyr Cys Val Pro Pro
            100                 105                 110

Val Asn Leu Lys Gln His Val Gly Arg Leu Glu Met Asn Val Asn Met
        115                 120                 125

Val Thr Cys Gly Gly Gln Ala Thr Ile Pro Met Val Ala Ala Val Ser
    130                 135                 140

Arg Val Gln Pro Val Ala Tyr Ala Glu Ile Val Ala Thr Val Ser Ser
145                 150                 155                 160

Arg Ser Val Gly Pro Gly Thr Arg Lys Asn Ile Asp Glu Phe Thr Arg
                165                 170                 175

Thr Thr Ala Gly Ala Ile Glu Val Gly Gly Ala Arg Glu Gly Lys
            180                 185                 190

Ala Ile Ile Val Ile Asn Pro Ala Glu Pro Pro Leu Met Met Arg Asp
        195                 200                 205

Thr Ile His Cys Leu Thr Asp Ser Glu Pro Asp Gln Ala Ala Ile Thr
    210                 215                 220
```

```
Ala Ser Val His Ala Met Ile Ala Glu Val Gln Lys Tyr Val Pro Gly
225                 230                 235                 240

Tyr Arg Leu Lys Asn Gly Pro Val Phe Asp Gly Asn Arg Val Ser Ile
            245                 250                 255

Phe Met Glu Val Glu Gly Leu Gly Asp Tyr Leu Pro Lys Tyr Ala Gly
        260                 265                 270

Asn Leu Asp Ile Met Thr Ala Ala Leu Arg Thr Gly Glu Met Phe
        275                 280                 285

Ala Glu Glu Ile Ala Ala Gly Thr Ile Gln Leu Pro Arg Arg Asp Ile
    290                 295                 300

Ala Leu Ala
305

<210> SEQ ID NO 68
<211> LENGTH: 2180
<212> TYPE: DNA
<213> ORGANISM: Pseudomonas putida

<400> SEQUENCE: 68 ggtaccctg gagccggtca aggccggcga cttcatgcgc gtcgagatcg gcggcatcgg      60
cagcgcctcc gtgcgcttca cctgatcgaa cagaggacaa acccatgagc aagaaactca    120
aggcggccat cataggcccc ggcaatatcg gtaccgatct ggtgatgaag atgctccgtt    180
ccgagtggat tgagccggtg tggatggtcg gcatcgaccc caactccgac ggcctcaaac    240
gcgcccgcga tttcggcatg aagaccacag ccgaaggcgt cgacggcctg ctcccgcacg    300
tgctggacga cgacatccgc atcgccttcg acgccacctc ggcctatgtg catgccgaga    360
atagccgcaa gctcaacgcg cttggcgtgc tgatggtcga cctgaccccg gcggccatcg    420
gcccctactg cgtgccgccg gtcaacctca agcagcatgt cggccgcctg gaaatgaacg    480
tcaacatggt cacctgcggc ggccaggcca ccatccccat ggtcgccgcg gtgtcccgcg    540
tgcagccggt ggcctacgcc gagatcgtcg ccaccgtctc ctcgcgctcg gtcggcccgg    600
gcacgcgcaa gaacatcgac gagttcaccc gcaccaccgc cggcgccatc gagcaggtcg    660
gcggcgccag ggaaggcaag gcgatcatcg tcatcaaccc ggccgagccg ccgctgatga    720
tgcgcgacac catccactgc ctgaccgaca gcgagccgga ccaggctgcg atcaccgctt    780
cggttcacgc gatgatcgcc gaggtgcaga aatacgtgcc cggctaccgc ctgaagaacg    840
gcccggtgtt cgacggcaac cgcgtgtcga tcttcatgga agtcgaaggc ctgggcgact    900
acctgcccaa gtacgccggc aacctcgaca tcatgaccgc cgccgcgctg cgtaccggcg    960
agatgttcgc cgaggaaatc gccgccggca ccattcaact gccgcgtcgc gacatcgcgc   1020
tggcttgagg agtagcacca tgaatttgca cggcaagagc gtcatcctgc acgacatgag   1080
cctgcgcgac ggcatgcacg ccaagcgcca ccagatcagc ctggagcaga tggtcgcggt   1140
cgccaccggc tcgatcaagc cggtatgcc gctgatcgag atcacccacg cgacggcct    1200
cggcggtcgt tcgatcaact acggcttccc ggcccacagt gacgaggagt acctgcgcgc   1260
ggtgatcccg cagctcaagc aggccaaagt ctcggcgctg ctgctgcccg gcatcggcac   1320
cgtcgaccac ctgaagatgg ccctggactg cggcgtctcg actattcgcg tggccacccc a  1380
ctgtaccgag gcggatgtct ccgagcagca catcggcatg gcgcgcaagc tggggtcga    1440
caccgtcggc ttcctgatga tggcgcacat gatcagcgcc gagaaagtcc tggagcaggc   1500
caagctgatg gaaagctatg gtgccaactg catctactgc accgactcgg ccggctacat   1560
```

-continued

```
gctgcctgat gaagtcagcg agaaaatcgg cctcctgcgc gccgagctga acccggccac    1620
cgaagtcggc ttccacggcc accacaacat gggcatggct atcgccaact cgctggccgc    1680
catcgaagcc ggtgccgcgc gcatcgacgg ctcggtcgcc ggcctcggcg ccggtgccgg    1740
caacaccccg ctggaagtgt tcgtcgcagt gtgcaaacgc atgggcgtgg agaccggcat    1800
cgacctgtac aagatcatgg acgtggccga ggacctggtg gtgccgatga tggatcagcc    1860
gatccgcgtc gaccgcgacg ccctgaccct gggctacgcc ggggtgtaca gctcgttcct    1920
gctgttcgcc cagcgcgccg agaagaaata tggcgtgtcg gcccgcgaca tcctggtcga    1980
actgggccgg cgcggcaccg tcggtggcca ggaagacatg atcgaagacc tcgccctgga    2040
catggcccgg gcccgtcagc agcagaaggt gagcgcatga accgtaccct gacccgcgaa    2100
caggtgctgg ccctgccgga gcacatcgaa aacgccgagc tgaatgtcca cgacatcggc    2160
aaggtgacca acgattttcc                                                 2180
```

<210> SEQ ID NO 69
<211> LENGTH: 307
<212> TYPE: PRT
<213> ORGANISM: Thermus thermophilus

<400> SEQUENCE: 69

```
Met Ser Glu Arg Val Lys Val Ala Ile Leu Gly Ser Gly Asn Ile Gly
1               5                   10                  15

Thr Asp Leu Met Tyr Lys Leu Leu Lys Asn Pro Gly His Met Glu Leu
            20                  25                  30

Val Ala Val Gly Ile Asp Pro Lys Ser Glu Gly Leu Ala Arg Ala
        35                  40                  45

Arg Ala Leu Gly Leu Glu Ala Ser His Glu Gly Ile Ala Tyr Ile Leu
    50                  55                  60

Glu Arg Pro Glu Ile Lys Ile Val Phe Asp Ala Thr Ser Ala Lys Ala
65                  70                  75                  80

His Val Arg His Ala Lys Leu Leu Arg Glu Ala Gly Lys Ile Ala Ile
                85                  90                  95

Asp Leu Thr Pro Ala Ala Arg Gly Pro Tyr Val Val Pro Pro Val Asn
            100                 105                 110

Leu Lys Glu His Leu Asp Lys Asp Asn Val Asn Leu Ile Thr Cys Gly
        115                 120                 125

Gly Gln Ala Thr Ile Pro Leu Val Tyr Ala Val His Arg Val Ala Pro
    130                 135                 140

Val Leu Tyr Ala Glu Met Val Ser Thr Val Ala Ser Arg Ser Ala Gly
145                 150                 155                 160

Pro Gly Thr Arg Gln Asn Ile Asp Glu Phe Thr Phe Thr Thr Ala Arg
                165                 170                 175

Gly Leu Glu Ala Ile Gly Gly Ala Lys Lys Gly Lys Ala Ile Ile Ile
            180                 185                 190

Leu Asn Pro Ala Glu Pro Pro Ile Leu Met Thr Asn Thr Val Arg Cys
        195                 200                 205

Ile Pro Glu Asp Glu Gly Phe Asp Arg Glu Ala Val Val Ala Ser Val
    210                 215                 220

Arg Ala Met Glu Arg Glu Val Gln Ala Tyr Val Pro Gly Tyr Arg Leu
225                 230                 235                 240

Lys Ala Asp Pro Val Phe Glu Arg Leu Pro Thr Pro Trp Gly Glu Arg
                245                 250                 255

Thr Val Val Ser Met Leu Leu Glu Val Glu Gly Ala Gly Asp Tyr Leu
```

```
                  260                 265                 270
Pro Lys Tyr Ala Gly Asn Leu Asp Ile Met Thr Ala Ser Ala Arg Arg
            275                 280                 285

Val Gly Glu Val Phe Ala Gln His Leu Leu Gly Lys Pro Val Glu Glu
            290                 295                 300

Val Val Ala
305

<210> SEQ ID NO 70
<211> LENGTH: 924
<212> TYPE: DNA
<213> ORGANISM: Thermus thermophilus

<400> SEQUENCE: 70
atgtccgaaa gggttaaggt agccatcctg ggctccggca acatcgggac ggacctgatg      60
tacaagctcc tgaagaaccc gggccacatg agcttgtgg cggtggtggg gatagacccc     120
aagtccgagg gcctggcccg ggcgcgggcc ttagggttag aggcgagcca cgaagggatc     180
gcctacatcc tggagaggcc ggagatcaag atcgtctttg acgccaccag cgccaaggcc     240
cacgtgcgcc acgccaagct cctgagggag gcggggaaga tcgccataga cctcacgccg     300
gcggcccggg gcccttacgt ggtgcccccg gtgaacctga aggaacacct ggacaaggac     360
aacgtgaacc tcatcacctg cgggggggcag gccaccatcc ccctggtcta cgcggtgcac     420
cgggtggccc ccgtgctcta cgcggagatg gtctccacgg tggcctcccg ctccgcgggc     480
cccggcaccc ggcagaacat cgacgagttc accttcacca ccgcccgggg cctggaggcc     540
atcggggggg ccaagaaggg gaaggccatc atcatcctga accggcgga accccccatc     600 ctcatgacca acaccgtgcg ctgcatcccc gaggacgagg gctttgaccg ggaggccgtg     660
gtggcgagcg tccgggccat ggagcgggag gtccaggcct acgtgcccgg ctaccgcctg     720
aaggcggacc cggtgtttga gaggcttccc accccctggg gggagcgcac cgtggtctcc     780
atgctcctgg aggtggaggg ggcgggggac tatttgccca aatacgccgg caacctggac     840
atcatgacgg cttctgcccg gagggtgggg gaggtcttcg cccagcacct cctggggaag     900
cccgtggagg aggtggtggc gtga                                            924

<210> SEQ ID NO 71
<211> LENGTH: 417
<212> TYPE: PRT
<213> ORGANISM: Escherichia coli

<400> SEQUENCE: 71

Met Thr Phe Ser Leu Phe Gly Asp Lys Phe Thr Arg His Ser Gly Ile
1               5                   10                  15

Thr Leu Leu Met Glu Asp Leu Asn Asp Gly Leu Arg Thr Pro Gly Ala
            20                  25                  30

Ile Met Leu Gly Gly Gly Asn Pro Ala Gln Ile Pro Glu Met Gln Asp
        35                  40                  45

Tyr Phe Gln Thr Leu Leu Thr Asp Met Leu Glu Ser Gly Lys Ala Thr
    50                  55                  60

Asp Ala Leu Cys Asn Tyr Asp Gly Pro Gln Gly Lys Thr Glu Leu Leu
65                  70                  75                  80

Thr Leu Leu Ala Gly Met Leu Arg Glu Lys Leu Gly Trp Asp Ile Glu
                85                  90                  95

Pro Gln Asn Ile Ala Leu Thr Asn Gly Ser Gln Ser Ala Phe Phe Tyr
            100                 105                 110
```

```
Leu Phe Asn Leu Phe Ala Gly Arg Arg Ala Asp Gly Arg Val Lys Lys
            115                 120                 125

Val Leu Phe Pro Leu Ala Pro Glu Tyr Ile Gly Tyr Ala Asp Ala Gly
        130                 135                 140

Leu Glu Glu Asp Leu Phe Val Ser Ala Arg Pro Asn Ile Glu Leu Leu
145                 150                 155                 160

Pro Glu Gly Gln Phe Lys Tyr His Val Asp Phe Glu His Leu His Ile
                165                 170                 175

Gly Glu Glu Thr Gly Met Ile Cys Val Ser Arg Pro Thr Asn Pro Thr
            180                 185                 190

Gly Asn Val Ile Thr Asp Glu Glu Leu Leu Lys Leu Asp Ala Leu Ala
        195                 200                 205

Asn Gln His Gly Ile Pro Leu Val Ile Asp Asn Ala Tyr Gly Val Pro
    210                 215                 220

Phe Pro Gly Ile Ile Phe Ser Glu Ala Arg Pro Leu Trp Asn Pro Asn
225                 230                 235                 240

Ile Val Leu Cys Met Ser Leu Ser Lys Leu Gly Leu Pro Gly Ser Arg
                245                 250                 255

Cys Gly Ile Ile Ile Ala Asn Glu Lys Ile Ile Thr Ala Ile Thr Asn
            260                 265                 270

Met Asn Gly Ile Ile Ser Leu Ala Pro Gly Gly Ile Gly Pro Ala Met
        275                 280                 285

Met Cys Glu Met Ile Lys Arg Asn Asp Leu Leu Arg Leu Ser Glu Thr
    290                 295                 300

Val Ile Lys Pro Phe Tyr Tyr Gln Arg Val Gln Glu Thr Ile Ala Ile
305                 310                 315                 320

Ile Arg Arg Tyr Leu Pro Glu Asn Arg Cys Leu Ile His Lys Pro Glu
                325                 330                 335

Gly Ala Ile Phe Leu Trp Leu Trp Phe Lys Asp Leu Pro Ile Thr Thr
            340                 345                 350

Lys Gln Leu Tyr Gln Arg Leu Lys Ala Arg Gly Val Leu Met Val Pro
        355                 360                 365

Gly His Asn Phe Phe Pro Gly Leu Asp Lys Pro Trp Pro His Thr His
    370                 375                 380

Gln Cys Met Arg Met Asn Tyr Val Pro Glu Pro Glu Lys Ile Glu Ala
385                 390                 395                 400

Gly Val Lys Ile Leu Ala Glu Glu Ile Glu Arg Ala Trp Ala Glu Ser
                405                 410                 415

His

<210> SEQ ID NO 72
<211> LENGTH: 417
<212> TYPE: PRT
<213> ORGANISM: Escherichia coli

<400> SEQUENCE: 72

Met Thr Phe Ser Leu Phe Gly Asp Lys Phe Thr Arg His Ser Gly Ile
1               5                   10                  15

Thr Leu Leu Met Glu Asp Leu Asn Asp Gly Leu Arg Thr Pro Gly Ala
            20                  25                  30

Ile Met Leu Gly Gly Gly Asn Pro Ala Gln Ile Pro Glu Met Gln Asp
        35                  40                  45

Tyr Phe Gln Thr Leu Leu Thr Asp Met Leu Glu Ser Gly Lys Ala Thr
    50                  55                  60
```

Asp Ala Leu Cys Asn Tyr Asp Gly Pro Gln Gly Lys Thr Glu Leu Leu
65                  70                  75                  80

Thr Leu Leu Ala Gly Met Leu Arg Glu Lys Leu Gly Trp Asp Ile Glu
                85                  90                  95

Pro Gln Asn Ile Ala Leu Thr Asn Gly Ser Gln Ser Ala Phe Phe Tyr
            100                 105                 110

Leu Phe Asn Leu Phe Ala Gly Arg Arg Ala Asp Gly Arg Val Lys Lys
            115                 120                 125

Val Leu Phe Pro Leu Ala Pro Glu Tyr Ile Gly Tyr Ala Asp Ala Gly
130                 135                 140

Leu Glu Glu Asp Leu Phe Val Ser Ala Arg Pro Asn Ile Glu Leu Leu
145                 150                 155                 160

Pro Glu Gly Gln Phe Lys Tyr His Val Asp Phe Glu His Leu His Ile
                165                 170                 175

Gly Glu Glu Thr Gly Met Ile Cys Val Ser Arg Pro Thr Asn Pro Thr
            180                 185                 190

Gly Asn Val Ile Thr Asp Glu Glu Leu Leu Lys Leu Asp Ala Leu Ala
            195                 200                 205

Asn Gln His Gly Ile Pro Leu Val Ile Asp Asn Ala Tyr Gly Val Pro
210                 215                 220

Phe Pro Gly Ile Ile Phe Ser Glu Ala Arg Pro Leu Trp Asn Pro Asn
225                 230                 235                 240

Ile Val Leu Cys Met Ser Leu Ser Lys Leu Gly Leu Pro Gly Ser Arg
                245                 250                 255

Cys Gly Ile Ile Ile Ala Asn Glu Lys Ile Ile Thr Ala Ile Thr Asn
            260                 265                 270

Met Asn Gly Ile Ile Ser Leu Ala Pro Gly Gly Ile Gly Pro Ala Met
            275                 280                 285

Met Cys Glu Met Ile Lys Arg Asn Asp Leu Leu Arg Leu Ser Glu Thr
290                 295                 300

Val Ile Lys Pro Phe Tyr Tyr Gln Arg Val Gln Glu Thr Ile Ala Ile
305                 310                 315                 320

Ile Arg Arg Tyr Leu Pro Glu Asn Arg Cys Leu Ile His Lys Pro Glu
                325                 330                 335

Gly Ala Ile Phe Leu Trp Leu Trp Phe Lys Asp Leu Pro Ile Thr Thr
            340                 345                 350

Lys Gln Leu Tyr Gln Arg Leu Lys Ala Arg Gly Val Leu Met Val Pro
            355                 360                 365

Gly His Asn Phe Phe Pro Gly Leu Asp Lys Pro Trp Pro His Thr His
370                 375                 380

Gln Cys Met Arg Met Asn Tyr Val Pro Glu Pro Glu Lys Ile Glu Ala
385                 390                 395                 400

Gly Val Lys Ile Leu Ala Glu Glu Ile Glu Arg Ala Trp Ala Glu Ser
                405                 410                 415

His

<210> SEQ ID NO 73
<211> LENGTH: 425
<212> TYPE: PRT
<213> ORGANISM: Bacillus licheniformis

<400> SEQUENCE: 73

Met Lys Pro Pro Leu Ser Lys Ile Gly Glu Lys Met Ile Glu Lys Thr
1               5                   10                  15

```
Gly Val Arg Ala Val Met Ser Asp Ile Gln Glu Val Leu Ala Gly Gly
             20                  25                  30

Glu Arg Ser Tyr Ile Asn Leu Ser Ala Gly Asn Pro Met Ile Leu Pro
         35                  40                  45

Gly Val Ser Ala Met Trp Lys Ser Ala Leu Ala Asp Leu Leu Asp Asp
 50                  55                  60

Asp Arg Phe Ser Ser Val Ile Gly Gln Tyr Gly Ser Ser Tyr Gly Thr
65                   70                  75                  80

Asp Glu Leu Ile Ala Ser Val Val Arg Phe Phe Ser Glu Arg Tyr Ser
             85                  90                  95

Ala Gly Ile Arg Lys Glu Asn Val Leu Ile Thr Ala Gly Ser Gln Gln
         100                 105                 110

Leu Phe Phe Leu Ala Ile Asn Ser Phe Cys Gly Met Gly Ser Gly Ser
         115                 120                 125

Val Met Lys Lys Ala Leu Ile Pro Met Leu Pro Asp Tyr Ser Gly Tyr
 130                 135                 140

Ser Gly Ala Ala Leu Glu Arg Glu Met Ile Glu Gly Ile Pro Pro Leu
145                 150                 155                 160

Ile Ser Lys Leu Asp Asp His Thr Phe Arg Tyr Glu Leu Asp Arg Lys
             165                 170                 175

Gly Phe Leu Glu Arg Met Arg Ile Gly Ala Val Leu Leu Ser Arg Pro
         180                 185                 190

Asn Asn Pro Cys Gly Asn Ile Leu Pro Lys Glu Asp Val Ala Phe Ile
         195                 200                 205

Ser Asp Ala Cys Arg Glu Ala Asn Val Pro Leu Phe Ile Asp Ser Ala
 210                 215                 220

Tyr Ala Pro Pro Phe Pro Ala Ile His Phe Ile Asp Met Glu Pro Ile
225                 230                 235                 240

Phe Asn Glu Gln Ile Ile His Cys Met Ser Leu Ser Lys Ala Gly Leu
             245                 250                 255

Pro Gly Glu Arg Ile Gly Ile Ala Ile Gly Pro Ser Arg Tyr Ile Gln
         260                 265                 270

Ala Met Glu Ala Phe Gln Ser Asn Ala Ala Ile His Ser Ser Arg Leu
         275                 280                 285

Gly Gln Tyr Met Ala Ala Ser Val Leu Asn Asp Gly Arg Leu Ala Asp
 290                 295                 300

Val Ser Leu Asn Glu Val Arg Pro Tyr Tyr Arg Asn Lys Phe Met Leu
305                 310                 315                 320

Leu Lys Glu Thr Leu Leu Cys Lys Met Pro Glu Asp Ile Lys Trp Tyr
             325                 330                 335

Leu His Gln Gly Glu Gly Ser Leu Phe Gly Trp Leu Trp Phe Glu Asp
         340                 345                 350

Leu Pro Val Thr Asp Ala Ala Leu Tyr Glu Tyr Met Lys Ala Asp Gly
         355                 360                 365

Val Ile Ile Val Pro Gly Ser Ser Phe Phe His Arg Gln Ser Arg Arg
 370                 375                 380

Leu Ala His Ser His Gln Cys Ile Arg Ile Ser Leu Thr Ala Ala Asp
385                 390                 395                 400

Glu Asp Ile Ile Arg Gly Ile Asp Val Leu Ala Lys Ile Ala Lys Gly
             405                 410                 415

Val Tyr Glu Lys Gln Val Glu Tyr Leu
         420                 425
```

<210> SEQ ID NO 74
<211> LENGTH: 1278
<212> TYPE: DNA
<213> ORGANISM: Bacillus licheniformis

<400> SEQUENCE: 74

```
ttataagtat tcaacctgtt tctcatatac acccttcgca attttagcta aaacatcgat      60
tcccttata atatcttcat ccgccgcggt taggctgatt cgtatacact ggtgtgaatg     120
cgccaggcgc cgggattgac ggtgaaagaa agatgatccg ggaacgataa tgactccatc     180
cgctttcata tactcataca gcgctgcatc ggtcaccggc aggtcttcaa accacagcca     240
tccgaaaagc gatccttccc cttgatgcag ataccatttg atgtcttcag gcatcttgca     300
taaaagcgtt tccttgagca gcatgaattt attgcggtaa tatggcctga cttcattcag     360
cgacacgtcg gcgaggcgcc cgtcattcaa tactgatgca gccatatact gccccagcct     420
tgaagaatgg atcgccgcat tcgactgaaa agcttccatt gcctgaatat accgggacgg     480
cccgatggcg attccgatcc tttcgccagg caggccggct tttgaaaggc tcatacagtg     540
aatgatctgc tcgttgaaaa tcggttccat gtcgataaag tgaatcgccg gaaaaggcgg     600
agcatatgcg gaatcaatga acagcggaac attcgcttct cggcatgcgt ctgaaatgaa     660
tgctacatct tctttaggca agatgttttcc gcaaggattg ttcgggcgcg atagcaagac     720
agcaccgatg cgcatcctct ctaaaaaccc cttacggtcg agctcatatc gaaacgtatg     780
atcatccaat ttcgatatga gcggagggat cccctcaatc atctcccgct ccagtgccgc     840
cccgctgtat cccgaatagt caggcagcat cgggatcaag gcttttttca tcacagatcc     900
gcttcccatt ccgcaaaacg aattgatcgc cagaaaaaac agctgctggc ttccggctgt     960
aatcaacacg ttctctttc gaatgccggc gctataccgc tctgaaaaga gcggacaac    1020
acttgcaatc agttcatcgg ttccatagct cgatccgtat tggccgatca ccgaagaaaa    1080
cctgtcatcg tcaaggagat cggcaagagc cgacttccac atggctgaca cgccgggcaa    1140
aatcatcgga ttgcccgcac ttaaattaat gtatgaccgt tcaccgccgg ccaggacttc    1200
ctgaatatcg ctcatcacag ccctgacccc tgtttctca atcattttct ctccgatttt    1260
gcttaatggc ggcttcac                                                  1278
```

<210> SEQ ID NO 75
<211> LENGTH: 309
<212> TYPE: PRT
<213> ORGANISM: Escherichia coli

<400> SEQUENCE: 75

Met Thr Thr Lys Lys Ala Asp Tyr Ile Trp Phe Asn Gly Glu Met Val
1               5                   10                  15

Arg Trp Glu Asp Ala Lys Val His Val Met Ser His Ala Leu His Tyr
                20                  25                  30

Gly Thr Ser Val Phe Glu Gly Ile Arg Cys Tyr Asp Ser His Lys Gly
            35                  40                  45

Pro Val Val Phe Arg His Arg Glu His Met Gln Arg Leu His Asp Ser
        50                  55                  60

Ala Lys Ile Tyr Arg Phe Pro Val Ser Gln Ser Ile Asp Glu Leu Met
65                  70                  75                  80

Glu Ala Cys Arg Asp Val Ile Arg Lys Asn Asn Leu Thr Ser Ala Tyr
                85                  90                  95

Ile Arg Pro Leu Ile Phe Val Gly Asp Val Gly Met Gly Val Asn Pro

|  |  | 100 |  |  |  | 105 |  |  |  | 110 |  |
|---|---|---|---|---|---|---|---|---|---|---|---|

Pro Ala Gly Tyr Ser Thr Asp Val Ile Ile Ala Ala Phe Pro Trp Gly
            115                    120                    125

Ala Tyr Leu Gly Ala Glu Ala Leu Glu Gln Gly Ile Asp Ala Met Val
130                    135                    140

Ser Ser Trp Asn Arg Ala Ala Pro Asn Thr Ile Pro Thr Ala Ala Lys
145                    150                    155                    160

Ala Gly Gly Asn Tyr Leu Ser Ser Leu Leu Val Gly Ser Glu Ala Arg
            165                    170                    175

Arg His Gly Tyr Gln Glu Gly Ile Ala Leu Asp Val Asn Gly Tyr Ile
            180                    185                    190

Ser Glu Gly Ala Gly Glu Asn Leu Phe Glu Val Lys Asp Gly Val Leu
            195                    200                    205

Phe Thr Pro Pro Phe Thr Ser Ser Ala Leu Pro Gly Ile Thr Arg Asp
            210                    215                    220

Ala Ile Ile Lys Leu Ala Lys Glu Leu Gly Ile Glu Val Arg Glu Gln
225                    230                    235                    240

Val Leu Ser Arg Glu Ser Leu Tyr Leu Ala Asp Glu Val Phe Met Ser
            245                    250                    255

Gly Thr Ala Ala Glu Ile Thr Pro Val Arg Ser Val Asp Gly Ile Gln
            260                    265                    270

Val Gly Glu Gly Arg Cys Gly Pro Val Thr Lys Arg Ile Gln Gln Ala
            275                    280                    285

Phe Phe Gly Leu Phe Thr Gly Glu Thr Glu Asp Lys Trp Gly Trp Leu
            290                    295                    300

Asp Gln Val Asn Gln
305

<210> SEQ ID NO 76
<211> LENGTH: 1476
<212> TYPE: DNA
<213> ORGANISM: Escherichia coli

<400> SEQUENCE: 76

```
atggctaact acttcaatac actgaatctg cgccagcagc tggcacagct gggcaaatgt      60
cgctttatgg ccgcgatga attcgccgat ggcgcgagct accttcaggg taaaaaagta    120
gtcatcgtcg ctgtggcgc acagggtctg aaccagggcc tgaacatgcg tgattctggt    180
ctcgatatct cctacgctct gcgtaaagaa gcgattgccg agaagcgcgc gtcctggcgt    240
aaagcgaccg aaaatggttt taagtgggt acttacgaag aactgatccc acaggcggat    300
ctggtgatta acctgacgcc ggacaagcag cactctgatg tagtgcgcac cgtacagcca    360
ctgatgaaag acggcgcggc gctgggctac tcgcacggtt tcaacatcgt cgaagtgggc    420
gagcagatcc gtaaagatat caccgtagtg atggttgcgc gaaatgcccc aggcaccgaa    480
gtgcgtgaag agtacaaacg tgggttcggc gtaccgacgc tgattgccgt tcacccggaa    540
aacgatccga aggcgaagg catggcgatt gccaaagcct gggcggctgc aaccggtggt    600
caccgtgcgg gtgtgctgga atcgtccttc gttgcggaag tgaaatctga cctgatgggc    660
gagcaaacca tcctgtgcgg tatgttcag gctggctctc tgctgtgctt cgacaagctg    720
gtggaagaag gtaccgatcc agcatacgca gaaaaactga ttcagttcgg ttgggaaacc    780
atcaccgaag cactgaaaca gggcggcatc accctgatga tggaccgtct ctctaacccg    840
gcgaaactgc gtgcttatgc gctttctgaa cagctgaaag atcatggc accctgttc      900
```

-continued

```
cagaaacata tggacgacat catctccggc gaattctctt ccggtatgat ggcggactgg    960
gccaacgatg ataagaaact gctgacctgg cgtgaagaga ccggcaaaac cgcgtttgaa   1020
accgcgccgc agtatgaagg caaaatcggc gagcaggagt acttcgataa aggcgtactg   1080
atgattgcga tggtgaaagc gggcgttgaa ctggcgttcg aaaccatggt cgattccggc   1140
atcattgaag agtctgcata ttatgaatca ctgcacgagc tgccgctgat tgccaacacc   1200
atcgcccgta agcgtctgta cgaaatgaac gtggttatct ctgataccgc tgagtacggt   1260
aactatctgt tctcttacgc ttgtgtgccg ttgctgaaac cgtttatggc agagctgcaa   1320
ccgggcgacc tgggtaaagc tattccggaa ggcgcggtag ataacgggca actgcgtgat   1380
gtgaacgaag cgattcgcag ccatgcgatt gagcaggtag gtaagaaact gcgcggctat   1440
atgacagata tgaaacgtat tgctgttgcg ggttaa                            1476
```

<210> SEQ ID NO 77
<211> LENGTH: 376
<212> TYPE: PRT
<213> ORGANISM: Saccharomyces cerevisiae

<400> SEQUENCE: 77

```
Met Thr Leu Ala Pro Leu Asp Ala Ser Lys Val Lys Ile Thr Thr Thr
1               5                   10                  15

Gln His Ala Ser Lys Pro Lys Pro Asn Ser Glu Leu Val Phe Gly Lys
            20                  25                  30

Ser Phe Thr Asp His Met Leu Thr Ala Glu Trp Thr Ala Glu Lys Gly
        35                  40                  45

Trp Gly Thr Pro Glu Ile Lys Pro Tyr Gln Asn Leu Ser Leu Asp Pro
    50                  55                  60

Ser Ala Val Val Phe His Tyr Ala Phe Glu Leu Phe Glu Gly Met Lys
65                  70                  75                  80

Ala Tyr Arg Thr Val Asp Asn Lys Ile Thr Met Phe Arg Pro Asp Met
                85                  90                  95

Asn Met Lys Arg Met Asn Lys Ser Ala Gln Arg Ile Cys Leu Pro Thr
            100                 105                 110

Phe Asp Pro Glu Glu Leu Ile Thr Leu Ile Gly Lys Leu Ile Gln Gln
        115                 120                 125

Asp Lys Cys Leu Val Pro Glu Gly Lys Gly Tyr Ser Leu Tyr Ile Arg
    130                 135                 140

Pro Thr Leu Ile Gly Thr Thr Ala Gly Leu Gly Val Ser Thr Pro Asp
145                 150                 155                 160

Arg Ala Leu Leu Tyr Val Ile Cys Cys Pro Val Gly Pro Tyr Tyr Lys
                165                 170                 175

Thr Gly Phe Lys Ala Val Arg Leu Glu Ala Thr Asp Tyr Ala Thr Arg
            180                 185                 190

Ala Trp Pro Gly Gly Cys Gly Asp Lys Lys Leu Gly Ala Asn Tyr Ala
        195                 200                 205

Pro Cys Val Leu Pro Gln Leu Gln Ala Ala Ser Arg Gly Tyr Gln Gln
    210                 215                 220

Asn Leu Trp Leu Phe Gly Pro Asn Asn Asn Ile Thr Glu Val Gly Thr
225                 230                 235                 240

Met Asn Ala Phe Phe Val Phe Lys Asp Ser Lys Thr Gly Lys Lys Glu
                245                 250                 255

Leu Val Thr Ala Pro Leu Asp Gly Thr Ile Leu Glu Gly Val Thr Arg
            260                 265                 270
```

```
Asp Ser Ile Leu Asn Leu Ala Lys Glu Arg Leu Pro Ser Glu Trp
            275                 280                 285

Thr Ile Ser Glu Arg Tyr Phe Thr Ile Gly Glu Val Thr Glu Arg Ser
    290                 295                 300

Lys Asn Gly Glu Leu Leu Glu Ala Phe Gly Ser Gly Thr Ala Ala Ile
305                 310                 315                 320

Val Ser Pro Ile Lys Glu Ile Gly Trp Lys Gly Glu Gln Ile Asn Ile
                325                 330                 335

Pro Leu Leu Pro Gly Glu Gln Thr Gly Pro Leu Ala Lys Glu Val Ala
            340                 345                 350

Gln Trp Ile Asn Gly Ile Gln Tyr Gly Glu Thr Glu His Gly Asn Trp
        355                 360                 365

Ser Arg Val Val Thr Asp Leu Asn
    370                 375

<210> SEQ ID NO 78
<211> LENGTH: 376
<212> TYPE: PRT
<213> ORGANISM: Saccharomyces cerevisiae

<400> SEQUENCE: 78

Met Thr Leu Ala Pro Leu Asp Ala Ser Lys Val Lys Ile Thr Thr Thr
1               5                   10                  15

Gln His Ala Ser Lys Pro Lys Pro Asn Ser Glu Leu Val Phe Gly Lys
            20                  25                  30

Ser Phe Thr Asp His Met Leu Thr Ala Glu Trp Thr Ala Glu Lys Gly
        35                  40                  45

Trp Gly Thr Pro Glu Ile Lys Pro Tyr Gln Asn Leu Ser Leu Asp Pro
    50                  55                  60

Ser Ala Val Val Phe His Tyr Ala Phe Glu Leu Phe Glu Gly Met Lys
65                  70                  75                  80

Ala Tyr Arg Thr Val Asp Asn Lys Ile Thr Met Phe Arg Pro Asp Met
                85                  90                  95

Asn Met Lys Arg Met Asn Lys Ser Ala Gln Arg Ile Cys Leu Pro Thr
            100                 105                 110

Phe Asp Pro Glu Glu Leu Ile Thr Leu Ile Gly Lys Leu Ile Gln Gln
        115                 120                 125

Asp Lys Cys Leu Val Pro Glu Gly Lys Gly Tyr Ser Leu Tyr Ile Arg
    130                 135                 140

Pro Thr Leu Ile Gly Thr Thr Ala Gly Leu Gly Val Ser Thr Pro Asp
145                 150                 155                 160

Arg Ala Leu Leu Tyr Val Ile Cys Cys Pro Val Gly Pro Tyr Tyr Lys
                165                 170                 175

Thr Gly Phe Lys Ala Val Arg Leu Glu Ala Thr Asp Tyr Ala Thr Arg
            180                 185                 190

Ala Trp Pro Gly Gly Cys Gly Asp Lys Lys Leu Gly Ala Asn Tyr Ala
        195                 200                 205

Pro Cys Val Leu Pro Gln Leu Gln Ala Ala Ser Arg Gly Tyr Gln Gln
    210                 215                 220

Asn Leu Trp Leu Phe Gly Pro Asn Asn Ile Thr Glu Val Gly Thr
225                 230                 235                 240

Met Asn Ala Phe Phe Val Phe Lys Asp Ser Lys Thr Gly Lys Lys Glu
                245                 250                 255

Leu Val Thr Ala Pro Leu Asp Gly Thr Ile Leu Glu Gly Val Thr Arg
            260                 265                 270
```

```
Asp Ser Ile Leu Asn Leu Ala Lys Glu Arg Leu Glu Pro Ser Glu Trp
            275                 280                 285

Thr Ile Ser Glu Arg Tyr Phe Thr Ile Gly Glu Val Thr Glu Arg Ser
        290                 295                 300

Lys Asn Gly Glu Leu Leu Glu Ala Phe Gly Ser Gly Thr Ala Ala Ile
305                 310                 315                 320

Val Ser Pro Ile Lys Glu Ile Gly Trp Lys Gly Glu Gln Ile Asn Ile
                325                 330                 335

Pro Leu Leu Pro Gly Glu Gln Thr Gly Pro Leu Ala Lys Glu Val Ala
            340                 345                 350

Gln Trp Ile Asn Gly Ile Gln Tyr Gly Glu Thr Glu His Gly Asn Trp
        355                 360                 365

Ser Arg Val Val Thr Asp Leu Asn
            370                 375

<210> SEQ ID NO 79
<211> LENGTH: 330
<212> TYPE: PRT
<213> ORGANISM: Methanobacterium thermoautotrophicum

<400> SEQUENCE: 79

Met Arg Leu Trp Arg Ala Leu Tyr Arg Pro Pro Thr Ile Thr Tyr Pro
1               5                   10                  15

Ser Lys Ser Pro Glu Val Ile Ile Met Ser Cys Glu Ala Ser Gly Lys
                20                  25                  30

Ile Trp Leu Asn Gly Glu Met Val Glu Trp Glu Glu Ala Thr Val His
            35                  40                  45

Val Leu Ser His Val Val His Tyr Gly Ser Ser Val Phe Glu Gly Ile
        50                  55                  60

Arg Cys Tyr Arg Asn Ser Lys Gly Ser Ala Ile Phe Arg Leu Arg Glu
65                  70                  75                  80

His Val Lys Arg Leu Phe Asp Ser Ala Lys Ile Tyr Arg Met Asp Ile
                85                  90                  95

Pro Tyr Thr Gln Glu Gln Ile Cys Asp Ala Ile Val Glu Thr Val Arg
            100                 105                 110

Glu Asn Gly Leu Glu Glu Cys Tyr Ile Arg Pro Val Val Phe Arg Gly
        115                 120                 125

Tyr Gly Glu Met Gly Val His Pro Val Asn Cys Pro Val Asp Val Ala
    130                 135                 140

Val Ala Ala Trp Glu Trp Gly Ala Tyr Leu Gly Ala Glu Ala Leu Glu
145                 150                 155                 160

Val Gly Val Asp Ala Gly Val Ser Thr Trp Arg Arg Met Ala Pro Asn
                165                 170                 175

Thr Met Pro Asn Met Ala Lys Ala Gly Gly Asn Tyr Leu Asn Ser Gln
            180                 185                 190

Leu Ala Lys Met Glu Ala Val Arg His Gly Tyr Asp Glu Ala Ile Met
        195                 200                 205

Leu Asp Tyr His Gly Tyr Ile Ser Glu Gly Ser Gly Glu Asn Ile Phe
    210                 215                 220

Leu Val Ser Glu Gly Glu Ile Tyr Thr Pro Pro Val Ser Ser Ser Leu
225                 230                 235                 240

Leu Arg Gly Ile Thr Arg Asp Ser Val Ile Lys Ile Ala Arg Thr Glu
                245                 250                 255

Gly Val Thr Val His Glu Glu Pro Ile Thr Arg Glu Met Leu Tyr Ile
```

```
            260                 265                 270
Ala Asp Glu Ala Phe Phe Thr Gly Thr Ala Ala Glu Ile Thr Pro Ile
            275                 280                 285

Arg Ser Val Asp Gly Ile Glu Ile Gly Ala Gly Arg Arg Gly Pro Val
            290                 295                 300

Thr Lys Leu Leu Gln Asp Glu Phe Phe Arg Ile Ile Arg Ala Glu Thr
305                 310                 315                 320

Glu Asp Ser Phe Gly Trp Leu Thr Tyr Ile
                325                 330

<210> SEQ ID NO 80
<211> LENGTH: 993
<212> TYPE: DNA
<213> ORGANISM: Methanobacterium thermoautotrophicum

<400> SEQUENCE: 80
tcagatgtag gtgagccatc cgaagctgtc ctctgtctct gccctgatta tcctgaagaa    60
ctcatcctgc agcagctttg taacgggacc ccttcgcccg caccatatct ctataccatc   120
aactgatctg atgggtgtta tctctgcggc tgtacctgtg aagaaggcct catctgcgat   180
gtagagcatc tccctggtta tgggttcctc atgcacggta cacccctcgg tcctggctat   240
ctttattacg gagtcccttg ttatccccct cagaagggat gatgaaacag ggggggtgta   300
aatttcaccc tcactgacga ggaatatgtt ctccccgcta ccctcactta tgtagccatg   360
gtagtccagc attatggcct catcatagcc gtgtctcaca gcctccatct tggcaagctg   420
tgagttgagg tagttaccgc cggccttgc catgttgggc attgtgtttg gtgccatcct   480
ccgccaggtt gaaacaccag catcgacacc aacctcaagg gcctctgcac ccagataggc   540
cccccattcc caggcagcca cagcgacgtc cactgggcag ttcaccgggt gaacacccat   600
ctcaccgtat ccctgaata ccacgggtct tatatagcac tcctcaagtc cgttctccct   660
gacggtctca actatggcat cacatatctg ctcctgggtg tagggtatgt ccatccggta   720
tatctttgca gaatcaaaaa ggcgtttaac atgctcccgc aaacggaaga tggctgaccc   780
cttactgttc ctgtagcacc ttattccctc aaagacagat gatccataat gcacaacatg   840
tgagagtacg tggacggtgg cttcttccca ttcaaccatt tcaccgtttta accatatctt   900 tccactggct tcgcatgaca tgataataac ctcaggtgat ttactaggat aggttatggt   960
tggaggccta taatgctctc ccataaccgc aa                                 993

<210> SEQ ID NO 81
<211> LENGTH: 364
<212> TYPE: PRT
<213> ORGANISM: Streptomyces coelicolor

<400> SEQUENCE: 81

Met Thr Asp Val Asn Gly Ala Pro Ala Asp Val Leu His Thr Leu Phe
1               5                   10                  15

His Ser Asp Gln Gly Gly His Glu Gln Val Val Leu Cys Gln Asp Arg
                20                  25                  30

Ala Ser Gly Leu Lys Ala Val Ile Ala Leu His Ser Thr Ala Leu Gly
            35                  40                  45

Pro Ala Leu Gly Gly Thr Arg Phe Tyr Pro Tyr Ala Ser Glu Ala Glu
        50                  55                  60

Ala Val Ala Asp Ala Leu Asn Leu Ala Arg Gly Met Ser Tyr Lys Asn
65                  70                  75                  80
```

```
Ala Met Ala Gly Leu Asp His Gly Gly Lys Ala Val Ile Ile Gly
                85                  90                  95
Asp Pro Glu Gln Ile Lys Ser Glu Glu Leu Leu Ala Tyr Gly Arg
            100                 105                 110
Phe Val Ala Ser Leu Gly Gly Arg Tyr Val Thr Ala Cys Asp Val Gly
            115                 120                 125
Thr Tyr Val Ala Asp Met Asp Val Val Ala Arg Glu Cys Arg Trp Thr
        130                 135                 140
Thr Gly Arg Ser Pro Glu Asn Gly Gly Ala Gly Asp Ser Ser Val Leu
145                 150                 155                 160
Thr Ser Phe Gly Val Tyr Gln Gly Met Arg Ala Ala Gln His Leu
                165                 170                 175
Trp Gly Asp Pro Thr Leu Arg Asp Arg Thr Val Gly Ile Ala Gly Val
            180                 185                 190
Gly Lys Val Gly His His Leu Val Glu His Leu Leu Ala Glu Gly Ala
        195                 200                 205
His Val Val Val Thr Asp Val Arg Lys Asp Val Arg Gly Ile Thr
    210                 215                 220
Glu Arg His Pro Ser Val Val Ala Val Ala Asp Thr Asp Ala Leu Ile
225                 230                 235                 240
Arg Val Glu Asn Leu Asp Ile Tyr Ala Pro Cys Ala Leu Gly Ala
                245                 250                 255
Leu Asn Asp Asp Thr Val Pro Val Leu Thr Ala Lys Val Val Cys Gly
            260                 265                 270
Ala Ala Asn Asn Gln Leu Ala His Pro Gly Val Glu Lys Asp Leu Ala
        275                 280                 285
Asp Arg Gly Ile Leu Tyr Ala Pro Asp Tyr Val Val Asn Ala Gly Gly
    290                 295                 300
Val Ile Gln Val Ala Asp Glu Leu His Gly Phe Asp Phe Asp Arg Cys
305                 310                 315                 320
Lys Ala Lys Ala Ser Lys Ile Tyr Asp Thr Thr Leu Ala Ile Phe Ala
                325                 330                 335
Arg Ala Lys Glu Asp Gly Ile Pro Pro Ala Ala Ala Asp Arg Ile
            340                 345                 350
Ala Glu Gln Arg Met Ala Glu Ala Arg Pro Arg Pro
        355                 360

<210> SEQ ID NO 82
<211> LENGTH: 1095
<212> TYPE: DNA
<213> ORGANISM: Streptomyces coelicolor

<400> SEQUENCE: 82
tcacggccgg ggacgggcct ccgccatccg ctgctcggcg atccggtcgg ccgccgcggc      60
cggcggaata ccgtcctcct tcgcacgtgc aatatggcc agcgtggtgt cgtagatctt     120
cgaggccttc gccttgcacc ggtcgaagtc gaacccgtgc agctcgtcgg cgacctggat     180
gacaccgccg gcgttcacca catagtccgg cgcgtagagg atcccgcggt cggcgaggtc     240
cttctcgacg cccgggtggg cgagctggtt gttggccgcg ccgcacacca ccttggcggt     300
cagcaccggc acggtgtcgt cgttcagcgc gccgccgagc gcgcagggcg cgtagatgtc     360
caggttctcc acccggatca gcgcgtcggt gtcggcgacg gcgaccaccg acgggtgccg     420
ctccgtgatc ccgcgcacca cgtccttgcg cacgtccgtg acgacgacgt gggcgccctc     480
ggcgagcagg tgctcgacca ggtggtggcc gaccttgccg acgcccgcga tgccgacggt     540
```

-continued

```
gcggtcgcgc agcgtcgggt cgccccacag gtgctgggcg gcggcccgca tgccctggta    600
gacgccgaag gaggtgagca cggaggagtc gcccgcgccg ccgttctccg gggaacgccc    660
ggtcgtccag cggcactcgc gggccacgac gtccatgtcg gcgacgtagg tgccgacgtc    720
gcacgcggtg acgtagcggc cgcccagcga ggcgacgaac cggccgtagg cgaggagcag    780
ctcctcgctc ttgatctgct ccggatcgcc gatgatcacg gccttgccgc accgtggtc     840 cagaccggcc atggcgttct tgtacgacat cccgcgggcg aggttcagcg cgtcggcgac    900
ggcctccgcc tcgctcgcgt acgggtagaa gcgggtaccg ccgagcgccg ggcccagggc    960
ggtggagtgg agggcgatca cggccttgag gccgctggca cggtcctggc agagcacgac   1020
ttgctcatgt ccccccctgat ccgagtggaa cagggtgtgc agtacatcag caggtgcgcc   1080
gtttacgtcg gtcac                                                    1095
```

<210> SEQ ID NO 83
<211> LENGTH: 364
<212> TYPE: PRT
<213> ORGANISM: Bacillus subtilis

<400> SEQUENCE: 83

```
Met Glu Leu Phe Lys Tyr Met Glu Lys Tyr Asp Tyr Glu Gln Leu Val
1               5                   10                  15

Phe Cys Gln Asp Glu Gln Ser Gly Leu Lys Ala Ile Ile Ala Ile His
                20                  25                  30

Asp Thr Thr Leu Gly Pro Ala Leu Gly Gly Thr Arg Met Trp Thr Tyr
            35                  40                  45

Glu Asn Glu Glu Ala Ala Ile Glu Asp Ala Leu Arg Leu Ala Arg Gly
        50                  55                  60

Met Thr Tyr Lys Asn Ala Ala Gly Leu Asn Leu Gly Gly Gly Lys
65                  70                  75                  80

Thr Val Ile Ile Gly Asp Pro Arg Lys Asp Lys Asn Glu Glu Met Phe
                85                  90                  95

Arg Ala Phe Gly Arg Tyr Ile Gln Gly Leu Asn Gly Arg Tyr Ile Thr
                100                 105                 110

Ala Glu Asp Val Gly Thr Thr Val Glu Asp Met Asp Ile Ile His Asp
            115                 120                 125

Glu Thr Asp Tyr Val Thr Gly Ile Ser Pro Ala Phe Gly Ser Ser Gly
        130                 135                 140

Asn Pro Ser Pro Val Thr Ala Tyr Gly Val Tyr Arg Gly Met Lys Ala
145                 150                 155                 160

Ala Ala Lys Ala Ala Phe Gly Thr Asp Ser Leu Glu Gly Lys Thr Ile
                165                 170                 175

Ala Val Gln Gly Val Gly Asn Val Ala Tyr Asn Leu Cys Arg His Leu
            180                 185                 190

His Glu Glu Gly Ala Asn Leu Ile Val Thr Asp Ile Asn Lys Gln Ser
        195                 200                 205

Val Gln Arg Ala Val Glu Asp Phe Gly Ala Arg Ala Val Asp Pro Asp
    210                 215                 220

Asp Ile Tyr Ser Gln Asp Cys Asp Ile Tyr Ala Pro Cys Ala Leu Gly
225                 230                 235                 240

Ala Thr Ile Asn Asp Asp Thr Ile Lys Gln Leu Lys Ala Lys Val Ile
                245                 250                 255

Ala Gly Ala Ala Asn Asn Gln Leu Lys Glu Thr Arg His Gly Asp Gln
            260                 265                 270
```

```
Ile His Glu Met Gly Ile Val Tyr Ala Pro Asp Tyr Val Ile Asn Ala
            275                 280                 285

Gly Gly Val Ile Asn Val Ala Asp Glu Leu Tyr Gly Tyr Asn Ala Glu
        290                 295                 300

Arg Ala Leu Lys Lys Val Glu Gly Ile Tyr Gly Asn Ile Glu Arg Val
305                 310                 315                 320

Leu Glu Ile Ser Gln Arg Asp Gly Ile Pro Ala Tyr Leu Ala Ala Asp
                325                 330                 335

Arg Leu Ala Glu Glu Arg Ile Glu Arg Met Arg Arg Ser Arg Ser Gln
                340                 345                 350

Phe Leu Gln Asn Gly His Ser Val Leu Ser Arg Arg
                355                 360

<210> SEQ ID NO 84
<211> LENGTH: 364
<212> TYPE: PRT
<213> ORGANISM: Bacillus subtilis

<400> SEQUENCE: 84

Met Glu Leu Phe Lys Tyr Met Glu Lys Tyr Asp Tyr Glu Gln Leu Val
1               5                   10                  15

Phe Cys Gln Asp Glu Gln Ser Gly Leu Lys Ala Ile Ala Ile His
            20                  25                  30

Asp Thr Thr Leu Gly Pro Ala Leu Gly Gly Thr Arg Met Trp Thr Tyr
                35                  40                  45

Glu Asn Glu Glu Ala Ala Ile Glu Asp Ala Leu Arg Leu Ala Arg Gly
    50                  55                  60

Met Thr Tyr Lys Asn Ala Ala Ala Gly Leu Asn Leu Gly Gly Gly Lys
65                  70                  75                  80

Thr Val Ile Ile Gly Asp Pro Arg Lys Asp Lys Asn Glu Glu Met Phe
                85                  90                  95

Arg Ala Phe Gly Arg Tyr Ile Gln Gly Leu Asn Gly Arg Tyr Ile Thr
            100                 105                 110

Ala Glu Asp Val Gly Thr Thr Val Glu Asp Met Asp Ile Ile His Asp
        115                 120                 125

Glu Thr Asp Tyr Val Thr Gly Ile Ser Pro Ala Phe Gly Ser Ser Gly
    130                 135                 140

Asn Pro Ser Pro Val Thr Ala Tyr Gly Val Tyr Arg Gly Met Lys Ala
145                 150                 155                 160

Ala Ala Lys Ala Ala Phe Gly Thr Asp Ser Leu Glu Gly Lys Thr Ile
                165                 170                 175

Ala Val Gln Gly Val Gly Asn Val Ala Tyr Asn Leu Cys Arg His Leu
            180                 185                 190

His Glu Glu Gly Ala Asn Leu Ile Val Thr Asp Ile Asn Lys Gln Ser
        195                 200                 205

Val Gln Arg Ala Val Glu Asp Phe Gly Ala Arg Ala Val Asp Pro Asp
    210                 215                 220

Asp Ile Tyr Ser Gln Asp Cys Asp Ile Tyr Ala Pro Cys Ala Leu Gly
225                 230                 235                 240

Ala Thr Ile Asn Asp Asp Thr Ile Lys Gln Leu Lys Ala Lys Val Ile
                245                 250                 255

Ala Gly Ala Ala Asn Asn Gln Leu Lys Glu Thr Arg His Gly Asp Gln
            260                 265                 270

Ile His Glu Met Gly Ile Val Tyr Ala Pro Asp Tyr Val Ile Asn Ala
```

```
            275                 280                 285
Gly Gly Val Ile Asn Val Ala Asp Glu Leu Tyr Gly Tyr Asn Ala Glu
    290                 295                 300
Arg Ala Leu Lys Lys Val Glu Gly Ile Tyr Gly Asn Ile Glu Arg Val
305                 310                 315                 320
Leu Glu Ile Ser Gln Arg Asp Gly Ile Pro Ala Tyr Leu Ala Ala Asp
                325                 330                 335
Arg Leu Ala Glu Glu Arg Ile Glu Arg Met Arg Arg Ser Arg Ser Gln
                340                 345                 350
Phe Leu Gln Asn Gly His Ser Val Leu Ser Arg Arg
                355                 360

<210> SEQ ID NO 85
<211> LENGTH: 594
<212> TYPE: PRT
<213> ORGANISM: Streptomyces viridifaciens

<400> SEQUENCE: 85

Met Ser Thr Ser Ser Ala Ser Ser Gly Pro Asp Leu Pro Phe Gly Pro
1               5                   10                  15
Glu Asp Thr Pro Trp Gln Lys Ala Phe Ser Arg Leu Arg Ala Val Asp
                20                  25                  30
Gly Val Pro Arg Val Thr Ala Pro Ser Ser Asp Pro Arg Glu Val Tyr
            35                  40                  45
Met Asp Ile Pro Glu Ile Pro Phe Ser Lys Val Gln Ile Pro Pro Asp
        50                  55                  60
Gly Met Asp Glu Gln Gln Tyr Ala Glu Ala Glu Ser Leu Phe Arg Arg
65                  70                  75                  80
Tyr Val Asp Ala Gln Thr Arg Asn Phe Ala Gly Tyr Gln Val Thr Ser
                85                  90                  95
Asp Leu Asp Tyr Gln His Leu Ser His Tyr Leu Asn Arg His Leu Asn
                100                 105                 110
Asn Val Gly Asp Pro Tyr Glu Ser Ser Ser Tyr Thr Leu Asn Ser Lys
            115                 120                 125
Val Leu Glu Arg Ala Val Leu Asp Tyr Phe Ala Ser Leu Trp Asn Ala
        130                 135                 140
Lys Trp Pro His Asp Ala Ser Asp Pro Glu Thr Tyr Trp Gly Tyr Val
145                 150                 155                 160
Leu Thr Met Gly Ser Ser Glu Gly Asn Leu Tyr Gly Leu Trp Asn Ala
                165                 170                 175
Arg Asp Tyr Leu Ser Gly Lys Leu Leu Arg Arg Gln His Arg Glu Ala
                180                 185                 190
Gly Gly Asp Lys Ala Ser Val Val Tyr Thr Gln Ala Leu Arg His Glu
            195                 200                 205
Gly Gln Ser Pro His Ala Tyr Glu Pro Val Ala Phe Phe Ser Gln Asp
        210                 215                 220
Thr His Tyr Ser Leu Thr Lys Ala Val Arg Val Leu Gly Ile Asp Thr
225                 230                 235                 240
Phe His Ser Ile Gly Ser Ser Arg Tyr Pro Asp Glu Asn Pro Leu Gly
                245                 250                 255
Pro Gly Thr Pro Trp Pro Thr Glu Val Pro Ser Val Asp Gly Ala Ile
                260                 265                 270
Asp Val Asp Lys Leu Ala Ser Leu Val Arg Phe Phe Ala Ser Lys Gly
            275                 280                 285
```

```
Tyr Pro Ile Leu Val Ser Leu Asn Tyr Gly Ser Thr Phe Lys Gly Ala
        290                 295                 300

Tyr Asp Asp Val Pro Ala Val Ala Gln Ala Val Arg Asp Ile Cys Thr
305                 310                 315                 320

Glu Tyr Gly Leu Asp Arg Arg Val Tyr His Asp Arg Ser Lys Asp
                325                 330                 335

Ser Asp Phe Asp Glu Arg Ser Gly Phe Trp Ile His Ile Asp Ala Ala
            340                 345                 350

Leu Gly Ala Gly Tyr Ala Pro Tyr Leu Gln Met Ala Arg Asp Ala Gly
                355                 360                 365

Met Val Glu Glu Ala Pro Pro Val Phe Asp Phe Arg Leu Pro Glu Val
370                 375                 380

His Ser Leu Thr Met Ser Gly His Lys Trp Met Gly Thr Pro Trp Ala
385                 390                 395                 400

Cys Gly Val Tyr Met Thr Arg Thr Gly Leu Gln Met Thr Pro Pro Lys
                405                 410                 415

Ser Ser Glu Tyr Ile Gly Ala Ala Asp Thr Thr Phe Ala Gly Ser Arg
            420                 425                 430

Asn Gly Phe Ser Ser Leu Leu Leu Trp Asp Tyr Leu Ser Arg His Ser
            435                 440                 445

Tyr Asp Asp Leu Val Arg Leu Ala Ala Asp Cys Asp Arg Leu Ala Gly
450                 455                 460

Tyr Ala His Asp Arg Leu Leu Thr Leu Gln Asp Lys Leu Gly Met Asp
465                 470                 475                 480

Leu Trp Val Ala Arg Ser Pro Gln Ser Leu Thr Val Arg Phe Arg Gln
                485                 490                 495

Pro Cys Ala Asp Ile Val Arg Lys Tyr Ser Leu Ser Cys Glu Thr Val
            500                 505                 510

Tyr Glu Asp Asn Glu Gln Arg Thr Tyr Val His Leu Tyr Ala Val Pro
        515                 520                 525

His Leu Thr Arg Glu Leu Val Asp Glu Leu Val Arg Asp Leu Arg Gln
    530                 535                 540

Pro Gly Ala Phe Thr Asn Ala Gly Ala Leu Glu Gly Glu Ala Trp Ala
545                 550                 555                 560

Gly Val Ile Asp Ala Leu Gly Arg Pro Asp Pro Asp Gly Thr Tyr Ala
                565                 570                 575

Gly Ala Leu Ser Ala Pro Ala Ser Gly Pro Arg Ser Glu Asp Gly Gly
            580                 585                 590

Gly Ser

<210> SEQ ID NO 86
<211> LENGTH: 1785
<212> TYPE: DNA
<213> ORGANISM: Streptomyces viridifaciens

<400> SEQUENCE: 86
gtgtcaactt cctccgcttc ttccgggccg gacctcccct tcgggcccga ggacacgcca      60
tggcagaagg ccttcagcag gctgcgggcg gtggatggcg tgccgcgcgt caccgcgccg     120
tccagtgatc cgcgtgaggt ctacatggac atcccggaga tcccttctc caaggtccag     180 atcccccgg acggaatgga cgagcagcag tacgcagagg ccgagagcct cttccgccgc     240
tacgtagacg cccagacccg caacttcgcg ggataccagg tcaccagcga cctcgactac     300
cagcacctca gtcactatct caaccggcat ctgaacaacg tcggcgatcc ctatgagtcc     360
```

```
agctcctaca cgctgaactc caaggtcctt gagcgagccg ttctcgacta cttcgcctcc    420
ctgtggaacg ccaagtggcc ccatgacgca agcgatccgg aaacgtactg gggttacgtg    480
ctgaccatgg gctccagcga aggcaacctg tacgggttgt ggaacgcacg ggactatctg    540
tcgggcaagc tgctgcggcg ccagcaccgg gaggccggcg cgacaaggc ctcggtcgtc    600
tacacgcaag cgctgcgaca cgaagggcag agtccgcatg cctacgagcc ggtggcgttc    660
ttctcgcagg acacgcacta ctcgctcacg aaggccgtgc gggttctggg catcgacacc    720
ttccacagca tcggcagcag tcggtatccg gacgagaacc cgctgggccc cggcactccg    780
tggccgaccg aagtgccctc ggttgacggt gccatcgatg tcgacaaact cgcctcgttg    840
gtccgcttct tcgccagcaa gggctacccg atactggtca gcctcaacta cgggtcaacg    900
ttcaagggcg cctacgacga cgtcccggcc gtggcacagg ccgtgcggga catctgcacg    960
gaatacggtc tggatcggcg gcgggtatac cacgaccgca gtaaggacag tgacttcgac    1020
gagcgcagcg gcttctggat ccacatcgat gccgccctgg gggcgggcta cgctccctac    1080
ctgcagatgg cccgggatgc cggcatggtc gaggaggcgc cgcccgtttt cgacttccgg    1140
ctcccggagg tgcactcgct gaccatgagc ggccacaagt ggatgggaac accgtgggca    1200
tgcggtgtct acatgacacg gaccgggctg cagatgaccc cgccgaagtc gtccgagtac    1260
atcggggcgg ccgacaccac cttcgcgggc tcccgcaacg gcttctcgtc actgctgctg    1320
tgggactacc tgtcccggca ttcgtatgac gatctggtgc cctggccgc cgactgcgac    1380
cggctggccg gctacgccca cgaccggttg ctgaccttgc aggacaaact cggcatggat    1440
ctgtgggtcg cccgcagccc gcagtccctc acggtgcgct tccgtcagcc atgtgcagac    1500
atcgtccgca gtactcgct gtcgtgtgag acggtctacg aagacaacga gcaacggacc    1560
tacgtacatc tctacgccgt tccccacctc actcgggaac tcgtggatga gctcgtgcgc    1620
gatctgcgcc agcccggagc cttcaccaac gctggtgcac tggaggggga ggcctgggcc    1680
ggggtgatcg atgccctcgg ccgccccgac cccgacggaa cctatgccgg cgccttgagc    1740
gctccggctt ccggcccccg ctccgaggac ggcggcggga gctga                   1785

<210> SEQ ID NO 87
<211> LENGTH: 440
<212> TYPE: PRT
<213> ORGANISM: Alcaligenes denitrificans

<400> SEQUENCE: 87

Met Ser Ala Ala Lys Leu Pro Asp Leu Ser His Leu Trp Met Pro Phe
1               5                   10                  15

Thr Ala Asn Arg Gln Phe Lys Ala Asn Pro Arg Leu Leu Ala Ser Ala
            20                  25                  30

Lys Gly Met Tyr Tyr Thr Ser Phe Asp Gly Arg Gln Ile Leu Asp Gly
        35                  40                  45

Thr Ala Gly Leu Trp Cys Val Asn Ala Gly His Cys Arg Glu Glu Ile
    50                  55                  60

Val Ser Ala Ile Ala Ser Gln Ala Gly Val Met Asp Tyr Ala Pro Gly
65                  70                  75                  80

Phe Gln Leu Gly His Pro Leu Ala Phe Glu Ala Ala Thr Ala Val Ala
                85                  90                  95

Gly Leu Met Pro Gln Gly Leu Asp Arg Val Phe Phe Thr Asn Ser Gly
            100                 105                 110

Ser Glu Ser Val Asp Thr Ala Leu Lys Ile Ala Leu Ala Tyr His Arg
        115                 120                 125
```

```
Ala Arg Gly Glu Ala Gln Arg Thr Arg Leu Ile Gly Arg Glu Arg Gly
        130                 135                 140

Tyr His Gly Val Gly Phe Gly Gly Ile Ser Val Gly Gly Ile Ser Pro
145                 150                 155                 160

Asn Arg Lys Thr Phe Ser Gly Ala Leu Leu Pro Ala Val Asp His Leu
                165                 170                 175

Pro His Thr His Ser Leu Glu His Asn Ala Phe Thr Arg Gly Gln Pro
                180                 185                 190

Glu Trp Gly Ala His Leu Ala Asp Glu Leu Glu Arg Ile Ile Ala Leu
            195                 200                 205

His Asp Ala Ser Thr Ile Ala Ala Val Ile Val Glu Pro Met Ala Gly
        210                 215                 220

Ser Thr Gly Val Leu Val Pro Pro Lys Gly Tyr Leu Glu Lys Leu Arg
225                 230                 235                 240

Glu Ile Thr Ala Arg His Gly Ile Leu Leu Ile Phe Asp Glu Val Ile
                245                 250                 255

Thr Ala Tyr Gly Arg Leu Gly Glu Ala Thr Ala Ala Ala Tyr Phe Gly
                260                 265                 270

Val Thr Pro Asp Leu Ile Thr Met Ala Lys Gly Val Ser Asn Ala Ala
            275                 280                 285

Val Pro Ala Gly Ala Val Ala Val Arg Arg Glu Val His Asp Ala Ile
        290                 295                 300

Val Asn Gly Pro Gln Gly Gly Ile Glu Phe Phe His Gly Tyr Thr Tyr
305                 310                 315                 320

Ser Ala His Pro Leu Ala Ala Ala Val Leu Ala Thr Leu Asp Ile
                325                 330                 335

Tyr Arg Arg Glu Asp Leu Phe Ala Arg Ala Arg Lys Leu Ser Ala Ala
            340                 345                 350

Phe Glu Glu Ala Ala His Ser Leu Lys Gly Ala Pro His Val Ile Asp
        355                 360                 365

Val Arg Asn Ile Gly Leu Val Ala Gly Ile Glu Leu Ser Pro Arg Glu
370                 375                 380

Gly Ala Pro Gly Ala Arg Ala Glu Ala Phe Gln Lys Cys Phe Asp
385                 390                 395                 400

Thr Gly Leu Met Val Arg Tyr Thr Gly Asp Ile Leu Ala Val Ser Pro
                405                 410                 415

Pro Leu Ile Val Asp Glu Asn Gln Ile Gly Gln Ile Phe Glu Gly Ile
            420                 425                 430

Gly Lys Val Leu Lys Glu Val Ala
        435                 440

<210> SEQ ID NO 88
<211> LENGTH: 1947
<212> TYPE: DNA
<213> ORGANISM: Alcaligenes denitrificans

<400> SEQUENCE: 88
ttcgatggcg cgctgcacgg cggccaccag ctgctccacc aggggtgggc gcctgcccgc      60
gcgcgcggtc gggctggaaa tcgatcatgg atgaatctat acagttgtca tgattgcaac     120
tatacagtta gcccgttttg cggcaattgt atattttcat tcgctcgtgg acgtccgaga     180
atcggtttga tcgcgccgcc cgcccctttc gcgcagcgg cgtttctttt cctccggagt      240
ctccccatga gcgctgccaa actgcccgac ctgtcccacc tctggatgcc ctttaccgcc     300
```

```
aaccggcagt tcaaggcgaa cccccgcctg ctggcctcgg ccaagggcat gtactacacg    360
tctttcgacg gccgccagat cctggacggc acggccggcc tgtggtgcgt gaacgccggc    420
cactgccgcg aagaaatcgt ctccgccatc gccagccagg ccggcgtcat ggactacgcg    480
ccggggttcc agctcggcca cccgctggcc ttcgaggccg ccaccgccgt ggccggcctg    540
atgccgcagg gcctggaccg cgtgttcttc accaattcgg gctccgaatc ggtggacacc    600
gcgctgaaga tcgccctggc ctaccaccgc gcgcgcggcg aggcgcagcg cacccgcctc    660
atcgggcgcg agcgcggcta ccacggcgtg ggcttcggcg catttccgt gggcggcatc    720 tcgcccaacc gcaagacctt ctccggcgcg ctgctgccgg ccgtggacca cctgccgcac    780
acccacagcc tggaacacaa cgccttcacg cgcggccagc ccgagtgggg cgcgcacctg    840
gccgacgagt tggaacgcat catcgccctg cacgacgcct ccaccatcgc ggccgtgatc    900
gtcgagccca tggccggctc caccggcgtg ctcgtcccgc ccaagggcta tctcgaaaaa    960
ctgcgcgaaa tcaccgcccg ccacggcatt ctgctgatct tcgacgaagt catcaccgcg   1020 tacgccgcc tgggcgaggc caccgccgcg gcctatttcg gcgtaacgcc cgacctcatc   1080
accatggcca agggcgtgag caacgccgcc gttccggccg gcgccgtcgc ggtgcgccgc   1140
gaagtgcatg acgccatcgt caacggaccg caaggcggca tcgagttctt ccacggctac   1200
acctactcgg cccaccccgct ggccgccgcc gccgtgctcg ccacgctgga catctaccgc   1260
cgcgaagacc tgttcgcccg cgcccgcaag ctgtcggccg cgttcgagga agccgcccac   1320
agcctcaagg gcgcgccgca cgtcatcgac gtgcgcaaca tcggcctggt ggccggcatc   1380
gagctgtcgc cgcgcgaagg cgccccgggc gcgcgcgccg ccgaagcctt ccagaaatgc   1440
ttcgacaccg gcctcatggt gcgctacacg ggcgacatcc tcgcggtgtc gcctccgctc   1500
atcgtcgacg aaaaccagat cggccagatc ttcgagggca tcgcaaggt gctcaaggaa   1560 gtggcttagg gtgaacacgc cctgagccgg ccccggcagg aaacgcgccg ccgcgcggcg   1620
gcgcgtccat cgaactcccg catcgagctt ttgcattcat gaagaaaatc acgcatttca   1680
tcaacggcca gccccacgaa ggccgcagca accgctacac cgagggcttc aacccggcca   1740
cgggcgagtc gtctcctcga tctgcctggg cggggccgaa gaagtggacc tggccgtggc   1800
ggccgcccgc gcggccttc ccgcctggtc cgaaacgccg gcgctcaagc gcgcgcgcgt   1860
gctgttcaac ttcaaggcgc tgctggacaa gcaccaggac gagctggccg cgctcatcac   1920
gcgcgagcac ggcaaggtgt tttccga                                         1947

<210> SEQ ID NO 89
<211> LENGTH: 443
<212> TYPE: PRT
<213> ORGANISM: Ralstonia eutropha

<400> SEQUENCE: 89

Met Asp Ala Ala Lys Thr Val Ile Pro Asp Leu Asp Ala Leu Trp Met
1               5                   10                  15

Pro Phe Thr Ala Asn Arg Gln Tyr Lys Ala Ala Pro Arg Leu Leu Ala
                20                  25                  30

Ser Ala Ser Gly Met Tyr Tyr Thr Thr His Asp Gly Arg Gln Ile Leu
            35                  40                  45

Asp Gly Cys Ala Gly Leu Trp Cys Val Ala Ala Gly His Cys Arg Lys
        50                  55                  60

Glu Ile Ala Glu Ala Val Ala Arg Gln Ala Ala Thr Leu Asp Tyr Ala
65                  70                  75                  80
```

```
Pro Pro Phe Gln Met Gly His Pro Leu Ser Phe Glu Ala Ala Thr Lys
                85                  90                  95
Val Ala Ala Ile Met Pro Gln Gly Leu Asp Arg Ile Phe Phe Thr Asn
            100                 105                 110
Ser Gly Ser Glu Ser Val Asp Thr Ala Leu Lys Ile Ala Leu Ala Tyr
        115                 120                 125
His Arg Ala Arg Gly Glu Gly Gln Arg Thr Arg Phe Ile Gly Arg Glu
    130                 135                 140
Arg Gly Tyr His Gly Val Gly Phe Gly Gly Met Ala Val Gly Gly Ile
145                 150                 155                 160
Gly Pro Asn Arg Lys Ala Phe Ser Ala Asn Leu Met Pro Gly Thr Asp
                165                 170                 175
His Leu Pro Ala Thr Leu Asn Ile Ala Glu Ala Ala Phe Ser Lys Gly
            180                 185                 190
Gln Pro Thr Trp Gly Ala His Leu Ala Asp Glu Leu Glu Arg Ile Val
        195                 200                 205
Ala Leu His Asp Pro Ser Thr Ile Ala Ala Val Ile Val Glu Pro Leu
    210                 215                 220
Ala Gly Ser Ala Gly Val Leu Val Pro Pro Val Gly Tyr Leu Asp Lys
225                 230                 235                 240
Leu Arg Glu Ile Thr Thr Lys His Gly Ile Leu Leu Ile Phe Asp Glu
                245                 250                 255
Val Ile Thr Ala Phe Gly Arg Leu Gly Thr Ala Thr Ala Ala Glu Arg
            260                 265                 270
Phe Lys Val Thr Pro Asp Leu Ile Thr Met Ala Lys Ala Ile Asn Asn
        275                 280                 285
Ala Ala Val Pro Met Gly Ala Val Ala Val Arg Arg Glu Val His Asp
    290                 295                 300
Thr Val Val Asn Ser Ala Ala Pro Gly Ala Ile Glu Leu Ala His Gly
305                 310                 315                 320
Tyr Thr Tyr Ser Gly His Pro Leu Ala Ala Ala Ala Ile Ala Thr
                325                 330                 335
Leu Asp Leu Tyr Gln Arg Glu Asn Leu Phe Gly Arg Ala Ala Glu Leu
            340                 345                 350
Ser Pro Val Phe Glu Ala Ala Val His Ser Val Arg Ser Ala Pro His
        355                 360                 365
Val Lys Asp Ile Arg Asn Leu Gly Met Val Ala Gly Ile Glu Leu Glu
    370                 375                 380
Pro Arg Pro Gly Gln Pro Gly Ala Arg Ala Tyr Glu Ala Phe Leu Lys
385                 390                 395                 400
Cys Leu Glu Arg Gly Val Leu Val Arg Tyr Thr Gly Asp Ile Leu Ala
                405                 410                 415
Phe Ser Pro Pro Leu Ile Ile Ser Glu Ala Gln Ile Ala Glu Leu Phe
            420                 425                 430
Asp Thr Val Lys Gln Ala Leu Gln Glu Val Gln
        435                 440

<210> SEQ ID NO 90
<211> LENGTH: 1341
<212> TYPE: DNA
<213> ORGANISM: Ralstonia eutropha

<400> SEQUENCE: 90
atggccgact cacccaacaa cctcgctcac gaacatcctt cacttgaaca ctattggatg    60
```

-continued

```
ccttttaccg ccaatcgcca attcaaagcg agccctcgtt tactcgccca agctgaaggt    120
atgtattaca cagatatcaa tggcaacaag gtattagact ctacagcggg cttatggtgt    180
tgtaatgctg gccatggtcg ccgtgagatc agtgaagccg tcagcaaaca aattcggcag    240
atggattacg ctccctcctt ccaaatgggc catcccatcg cttttgaact ggccgaacgt    300
ttaaccgaac tcagcccaga aggactcaac aaagtattct ttaccaactc aggctctgag    360
tcggttgata ccgcgctaaa aatggctctt tgctaccata gagccaatgg ccaagcgtca    420
cgcacccgct ttattggccg tgaaatgggt taccatggcg taggatttgg tgggatctcg    480
gtgggtggtt taagcaataa ccgtaaagcc ttcagcggcc agctattgca aggcgtggat    540
cacctgcccc acaccttaga cattcaacat gccgcctttta gtcgtggctt accgagcctc    600
ggtgctgaaa agctgaggt attagaacaa ttagtcacac tccatggcgc cgaaaatatt    660
gccgccgtta ttgttgaacc catgtcaggt tctgcagggg taattttacc acctcaaggc    720
tacttaaaac gcttacgtga atcactaaa aaacacggca tcttattgat tttcgatgaa    780
gtcattaccg catttggccg tgtaggtgca gcattcgcca gccaacgttg gggcgttatt    840
ccagacataa tcaccacggc taaagccatt aataatggcg ccatccccat gggcgcagtg    900
tttgtacagg attatatcca cgatacttgc atgcaagggc caaccgaact gattgaattt    960
ttccacggtt atacctattc gggccaccca gtcgccgcag cagcagcact cgccacgctc   1020
tccatctacc aaaacgagca actgtttgag cgcagttttg agcttgagcg gtatttcgaa   1080
gaagccgttc atagcctcaa agggttaccg aatgtgattg atattcgcaa caccggatta   1140
gtcgcgggtt tccagctagc accgaatagc caaggtgttg gtaaacgcgg atacagcgtg   1200
ttcgagcatt gtttccatca aggcacactc gtgcgggcaa cgggcgatat tatcgccatg   1260
tccccaccac tcattgttga aaacatcag attgaccaaa tggtaaatag ccttagcgat   1320
gcaattcacg ccgttggatg a                                             1341
```

<210> SEQ ID NO 91
<211> LENGTH: 446
<212> TYPE: PRT
<213> ORGANISM: Shewanella oneidensis

<400> SEQUENCE: 91

```
Met Ala Asp Ser Pro Asn Asn Leu Ala His Glu His Pro Ser Leu Glu
1               5                   10                  15

His Tyr Trp Met Pro Phe Thr Ala Asn Arg Gln Phe Lys Ala Ser Pro
            20                  25                  30

Arg Leu Leu Ala Gln Ala Glu Gly Met Tyr Tyr Thr Asp Ile Asn Gly
        35                  40                  45

Asn Lys Val Leu Asp Ser Thr Ala Gly Leu Trp Cys Cys Asn Ala Gly
    50                  55                  60

His Gly Arg Arg Glu Ile Ser Glu Ala Val Ser Lys Gln Ile Arg Gln
65                  70                  75                  80

Met Asp Tyr Ala Pro Ser Phe Gln Met Gly His Pro Ile Ala Phe Glu
                85                  90                  95

Leu Ala Glu Arg Leu Thr Glu Leu Ser Pro Glu Gly Leu Asn Lys Val
            100                 105                 110

Phe Phe Thr Asn Ser Gly Ser Glu Ser Val Asp Thr Ala Leu Lys Met
        115                 120                 125

Ala Leu Cys Tyr His Arg Ala Asn Gly Gln Ala Ser Arg Thr Arg Phe
    130                 135                 140
```

Ile Gly Arg Glu Met Gly Tyr His Gly Val Gly Phe Gly Gly Ile Ser
145                 150                 155                 160

Val Gly Gly Leu Ser Asn Asn Arg Lys Ala Phe Ser Gly Gln Leu Leu
            165                 170                 175

Gln Gly Val Asp His Leu Pro His Thr Leu Asp Ile Gln His Ala Ala
        180                 185                 190

Phe Ser Arg Gly Leu Pro Ser Leu Gly Ala Glu Lys Ala Glu Val Leu
    195                 200                 205

Glu Gln Leu Val Thr Leu His Gly Ala Glu Asn Ile Ala Ala Val Ile
210                 215                 220

Val Glu Pro Met Ser Gly Ser Ala Gly Val Ile Leu Pro Pro Gln Gly
225                 230                 235                 240

Tyr Leu Lys Arg Leu Arg Glu Ile Thr Lys Lys His Gly Ile Leu Leu
            245                 250                 255

Ile Phe Asp Glu Val Ile Thr Ala Phe Gly Arg Val Gly Ala Ala Phe
        260                 265                 270

Ala Ser Gln Arg Trp Gly Val Ile Pro Asp Ile Ile Thr Thr Ala Lys
    275                 280                 285

Ala Ile Asn Asn Gly Ala Ile Pro Met Gly Ala Val Phe Val Gln Asp
290                 295                 300

Tyr Ile His Asp Thr Cys Met Gln Gly Pro Thr Glu Leu Ile Glu Phe
305                 310                 315                 320

Phe His Gly Tyr Thr Tyr Ser Gly His Pro Val Ala Ala Ala Ala Ala
            325                 330                 335

Leu Ala Thr Leu Ser Ile Tyr Gln Asn Glu Gln Leu Phe Glu Arg Ser
        340                 345                 350

Phe Glu Leu Glu Arg Tyr Phe Glu Glu Ala Val His Ser Leu Lys Gly
    355                 360                 365

Leu Pro Asn Val Ile Asp Ile Arg Asn Thr Gly Leu Val Ala Gly Phe
370                 375                 380

Gln Leu Ala Pro Asn Ser Gln Gly Val Gly Lys Arg Gly Tyr Ser Val
385                 390                 395                 400

Phe Glu His Cys Phe His Gln Gly Thr Leu Val Arg Ala Thr Gly Asp
            405                 410                 415

Ile Ile Ala Met Ser Pro Pro Leu Ile Val Glu Lys His Gln Ile Asp
        420                 425                 430

Gln Met Val Asn Ser Leu Ser Asp Ala Ile His Ala Val Gly
    435                 440                 445

<210> SEQ ID NO 92
<211> LENGTH: 1341
<212> TYPE: DNA
<213> ORGANISM: Shewanella oneidensis

<400> SEQUENCE: 92
atggccgact cacccaacaa cctcgctcac gaacatcctt cacttgaaca ctattggatg    60
ccttttaccg ccaatcgcca attcaaagcg agccctcgtt tactcgccca agctgaaggt   120
atgtattaca cagatatcaa tggcaacaag gtattagact ctacagcggg cttatggtgt   180
tgtaatgctg gccatggtcg ccgtgagatc agtgaagccg tcagcaaaca aattcggcag   240
atggattacg ctccctcctt ccaaatgggc catcccatcg cttttgaact ggccgaacgt   300
ttaaccgaac tcagcccaga aggactcaac aaagtattct ttaccaactc aggctctgag   360
tcggttgata ccgcgctaaa aatggctctt tgctaccata gagccaatgg ccaagcgtca   420

```
cgcacccgct ttattggccg tgaaatgggt taccatggcg taggatttgg tgggatctcg   480
gtgggtggtt taagcaataa ccgtaaagcc ttcagcggcc agctattgca aggcgtggat   540
cacctgcccc acaccttaga cattcaacat gccgccttta gtcgtggctt accgagcctc   600
ggtgctgaaa aagctgaggt attagaacaa ttagtcacac tccatggcgc cgaaaatatt   660
gccgccgtta ttgttgaacc catgtcaggt tctgcagggg taattttacc acctcaaggc   720
tacttaaaac gcttacgtga aatcactaaa aaacacggca tcttattgat tttcgatgaa   780
gtcattaccg catttggccg tgtaggtgca gcattcgcca gcaacgttg gggcgttatt   840 ccagacataa tcaccacggc taaagccatt aataatggcg ccatccccat gggcgcagtg   900
tttgtacagg attatatcca cgatacttgc atgcaagggc caaccgaact gattgaattt   960
ttccacggtt atacctattc gggccaccca gtcgccgcag cagcagcact cgccacgctc   1020
tccatctacc aaaacgagca actgtttgag cgcagttttg agcttgagcg gtatttcgaa   1080
gaagccgttc atagcctcaa agggttaccg aatgtgattg atattcgcaa caccggatta   1140
gtcgcgggtt tccagctagc accgaatagc caaggtgttg gtaaacgcgg atacagcgtg   1200
ttcgagcatt gtttccatca aggcacactc gtgcgggcaa cgggcgatat tatcgccatg   1260
tccccaccac tcattgttga aaacatcag attgaccaaa tggtaaatag ccttagcgat   1320
gcaattcacg ccgttggatg a                                             1341
```

<210> SEQ ID NO 93
<211> LENGTH: 448
<212> TYPE: PRT
<213> ORGANISM: Pseudomonas putida

<400> SEQUENCE: 93

```
Met Asn Met Pro Glu Thr Gly Pro Ala Gly Ile Ala Ser Gln Leu Lys
1               5                   10                  15

Leu Asp Ala His Trp Met Pro Tyr Thr Ala Asn Arg Asn Phe Gln Arg
            20                  25                  30

Asp Pro Arg Leu Ile Val Ala Ala Glu Gly Asn Tyr Leu Val Asp Asp
        35                  40                  45

His Gly Arg Lys Ile Phe Asp Ala Leu Ser Gly Leu Trp Thr Cys Gly
    50                  55                  60

Ala Gly His Thr Arg Lys Glu Ile Ala Asp Ala Val Thr Arg Gln Leu
65                  70                  75                  80

Ser Thr Leu Asp Tyr Ser Pro Ala Phe Gln Phe Gly His Pro Leu Ser
                85                  90                  95

Phe Gln Leu Ala Glu Lys Ile Ala Glu Leu Val Pro Gly Asn Leu Asn
            100                 105                 110

His Val Phe Tyr Thr Asn Ser Gly Ser Glu Cys Ala Asp Thr Ala Leu
        115                 120                 125

Lys Met Val Arg Ala Tyr Trp Arg Leu Lys Gly Gln Ala Thr Lys Thr
    130                 135                 140

Lys Ile Ile Gly Arg Ala Arg Gly Tyr His Gly Val Asn Ile Ala Gly
145                 150                 155                 160

Thr Ser Leu Gly Gly Val Asn Gly Asn Arg Lys Met Phe Gly Gln Leu
                165                 170                 175

Leu Asp Val Asp His Leu Pro His Thr Val Leu Pro Val Asn Ala Phe
            180                 185                 190

Ser Lys Gly Leu Pro Glu Glu Gly Gly Ile Ala Leu Ala Asp Glu Met
        195                 200                 205
```

Leu Lys Leu Ile Glu Leu His Asp Ala Ser Asn Ile Ala Ala Val Ile
    210                 215                 220

Val Glu Pro Leu Ala Gly Ser Ala Gly Val Leu Pro Pro Pro Lys Gly
225                 230                 235                 240

Tyr Leu Lys Arg Leu Arg Glu Ile Cys Thr Gln His Asn Ile Leu Leu
                245                 250                 255

Ile Phe Asp Glu Val Ile Thr Gly Phe Gly Arg Met Gly Ala Met Thr
            260                 265                 270

Gly Ser Glu Ala Phe Gly Val Thr Pro Asp Leu Met Cys Ile Ala Lys
        275                 280                 285

Gln Val Thr Asn Gly Ala Ile Pro Met Gly Ala Val Ile Ala Ser Ser
    290                 295                 300

Glu Ile Tyr Gln Thr Phe Met Asn Gln Pro Thr Pro Glu Tyr Ala Val
305                 310                 315                 320

Glu Phe Pro His Gly Tyr Thr Tyr Ser Ala His Pro Val Ala Cys Ala
                325                 330                 335

Ala Gly Leu Ala Ala Leu Asp Leu Leu Gln Lys Glu Asn Leu Val Gln
            340                 345                 350

Ser Ala Ala Glu Leu Ala Pro His Phe Glu Lys Leu Leu His Gly Val
        355                 360                 365

Lys Gly Thr Lys Asn Ile Val Asp Ile Arg Asn Tyr Gly Leu Ala Gly
    370                 375                 380

Ala Ile Gln Ile Ala Ala Arg Asp Gly Asp Ala Ile Val Arg Pro Tyr
385                 390                 395                 400

Glu Ala Ala Met Lys Leu Trp Lys Ala Gly Phe Tyr Val Arg Phe Gly
                405                 410                 415

Gly Asp Thr Leu Gln Phe Gly Pro Thr Phe Asn Thr Lys Pro Gln Glu
            420                 425                 430

Leu Asp Arg Leu Phe Asp Ala Val Gly Glu Thr Leu Asn Leu Ile Asp
        435                 440                 445

<210> SEQ ID NO 94
<211> LENGTH: 930
<212> TYPE: DNA
<213> ORGANISM: Pseudomonas putida

<400> SEQUENCE: 94

```
atgaccacga agaaagctga ttacatttgg ttcaatgggg agatggttcg ctgggaagac    60
gcgaaggtgc atgtgatgtc gcacgcgctg cactatggca cttcggtttt tgaaggcatc   120
cgttgctacg actcgcacaa aggaccggtt gtattccgcc atcgtgagca tatgcagcgt   180
ctgcatgact ccgccaaaat ctatcgcttc ccggtttcgc agagcattga tgagctgatg   240
gaagcttgtc gtgacgtgat ccgcaaaaac aatctcacca cgcctatat ccgtccgctg   300
atcttcgtcg gtgatgttgg catgggagta aacccgccag cgggatactc aaccgacgtg   360
attatcgctg ctttcccgtg gggagcgtat ctgggcgcag aagcgctgga gcagggcatc   420
gatgcgatgg tttcctcctg gaaccgcgca gcaccaaaca ccatcccgac ggcggcaaaa   480
gccggtggta actacctctc ttccctgctg gtgggtagcg aagcgcgccg ccacggttat   540
caggaaggta tcgcgctgga tgtgaacggt atatctctg aaggcgcagg cgaaaacctg   600
tttgaagtga agatggtgt gctgttcacc ccaccgttca cctcctccgc gctgccgggt   660
attaccgtg atgccatcat caaactggcg aaagagctgg aattgaagt acgtgagcag   720
gtgctgtcgc gcgaatccct gtacctggcg gatgaagtgt ttatgtccgg tacggcggca   780
```

```
gaaatcacgc cagtgcgcag cgtagacggt attcaggttg gcgaaggccg ttgtggcccg      840
gttaccaaac gcattcagca agccttcttc ggcctcttca ctggcgaaac cgaagataaa      900
tggggctggt tagatcaagt taatcaataa                                       930
```

<210> SEQ ID NO 95
<211> LENGTH: 566
<212> TYPE: PRT
<213> ORGANISM: Streptomyces cinnamonensis

<400> SEQUENCE: 95

| | | | | | | | | | | | | | | |
|---|---|---|---|---|---|---|---|---|---|---|---|---|---|---|
| Met | Asp | Ala | Asp | Ala | Ile | Glu | Glu | Gly | Arg | Arg | Trp | Gln | Ala | Arg |
| 1 | | | | 5 | | | | | 10 | | | | | 15 |
| Tyr | Asp | Lys | Ala | Arg | Lys | Arg | Asp | Ala | Asp | Phe | Thr | Thr | Leu | Ser | Gly |
| | | | 20 | | | | | 25 | | | | | 30 | | |
| Asp | Pro | Val | Asp | Pro | Val | Tyr | Gly | Pro | Arg | Pro | Gly | Asp | Thr | Tyr | Asp |
| | | 35 | | | | | 40 | | | | | 45 | | | |
| Gly | Phe | Glu | Arg | Ile | Gly | Trp | Pro | Gly | Glu | Tyr | Pro | Phe | Thr | Arg | Gly |
| | 50 | | | | | 55 | | | | | 60 | | | | |
| Leu | Tyr | Ala | Thr | Gly | Tyr | Arg | Gly | Arg | Thr | Trp | Thr | Ile | Arg | Gln | Phe |
| 65 | | | | | 70 | | | | | 75 | | | | | 80 |
| Ala | Gly | Phe | Gly | Asn | Ala | Glu | Gln | Thr | Asn | Glu | Arg | Tyr | Lys | Met | Ile |
| | | | | 85 | | | | | 90 | | | | | 95 | |
| Leu | Ala | Asn | Gly | Gly | Gly | Leu | Ser | Val | Ala | Phe | Asp | Met | Pro | Thr |
| | | | 100 | | | | | 105 | | | | | 110 | | |
| Leu | Met | Gly | Arg | Asp | Ser | Asp | Asp | Pro | Arg | Ser | Leu | Gly | Glu | Val | Gly |
| | | | 115 | | | | | 120 | | | | | 125 | | |
| His | Cys | Gly | Val | Ala | Ile | Asp | Ser | Ala | Ala | Asp | Met | Glu | Val | Leu | Phe |
| | 130 | | | | | 135 | | | | | 140 | | | | |
| Lys | Asp | Ile | Pro | Leu | Gly | Asp | Val | Thr | Thr | Ser | Met | Thr | Ile | Ser | Gly |
| 145 | | | | | 150 | | | | | 155 | | | | | 160 |
| Pro | Ala | Val | Pro | Val | Phe | Cys | Met | Tyr | Leu | Val | Ala | Ala | Glu | Arg | Gln |
| | | | | 165 | | | | | 170 | | | | | 175 | |
| Gly | Val | Asp | Pro | Ala | Val | Leu | Asn | Gly | Thr | Leu | Gln | Thr | Asp | Ile | Phe |
| | | | 180 | | | | | 185 | | | | | 190 | | |
| Lys | Glu | Tyr | Ile | Ala | Gln | Lys | Glu | Trp | Leu | Phe | Gln | Pro | Glu | Pro | His |
| | | 195 | | | | | 200 | | | | | 205 | | | |
| Leu | Arg | Leu | Ile | Gly | Asp | Leu | Met | Glu | His | Cys | Ala | Arg | Asp | Ile | Pro |
| | 210 | | | | | 215 | | | | | 220 | | | | |
| Ala | Tyr | Lys | Pro | Leu | Ser | Val | Ser | Gly | Tyr | His | Ile | Arg | Glu | Ala | Gly |
| 225 | | | | | 230 | | | | | 235 | | | | | 240 |
| Ala | Thr | Ala | Ala | Gln | Glu | Leu | Ala | Tyr | Thr | Leu | Ala | Asp | Gly | Phe | Gly |
| | | | | 245 | | | | | 250 | | | | | 255 | |
| Tyr | Val | Glu | Leu | Gly | Leu | Ser | Arg | Gly | Leu | Asp | Val | Asp | Val | Phe | Ala |
| | | | 260 | | | | | 265 | | | | | 270 | | |
| Pro | Gly | Leu | Ser | Phe | Phe | Phe | Asp | Ala | His | Val | Asp | Phe | Phe | Glu | Glu |
| | | 275 | | | | | 280 | | | | | 285 | | | |
| Ile | Ala | Lys | Phe | Arg | Ala | Ala | Arg | Ile | Trp | Ala | Arg | Trp | Leu | Arg |
| | 290 | | | | | 295 | | | | | 300 | | | | |
| Asp | Glu | Tyr | Gly | Ala | Lys | Thr | Glu | Lys | Ala | Gln | Trp | Leu | Arg | Phe | His |
| 305 | | | | | 310 | | | | | 315 | | | | | 320 |
| Thr | Gln | Thr | Ala | Gly | Val | Ser | Leu | Thr | Ala | Gln | Gln | Pro | Tyr | Asn | Asn |
| | | | | 325 | | | | | 330 | | | | | 335 | |
| Val | Val | Arg | Thr | Ala | Val | Glu | Ala | Leu | Ala | Ala | Val | Leu | Gly | Gly | Thr |
| | | | 340 | | | | | 345 | | | | | 350 | | |

Asn Ser Leu His Thr Asn Ala Leu Asp Glu Thr Leu Ala Leu Pro Ser
         355                 360                 365

Glu Gln Ala Ala Glu Ile Ala Leu Arg Thr Gln Gln Val Leu Met Glu
    370                 375                 380

Glu Thr Gly Val Ala Asn Val Ala Asp Pro Leu Gly Gly Ser Trp Tyr
385                 390                 395                 400

Ile Glu Gln Leu Thr Asp Arg Ile Glu Ala Asp Ala Glu Lys Ile Phe
            405                 410                 415

Glu Gln Ile Arg Glu Arg Gly Arg Ala Cys Pro Asp Gly Gln His
            420                 425                 430

Pro Ile Gly Pro Ile Thr Ser Gly Ile Leu Arg Gly Ile Glu Asp Gly
            435                 440                 445

Trp Phe Thr Gly Glu Ile Ala Glu Ser Ala Phe Gln Tyr Gln Arg Ser
        450                 455                 460

Leu Glu Lys Gly Asp Lys Arg Val Val Gly Val Asn Cys Leu Glu Gly
465                 470                 475                 480

Ser Val Thr Gly Asp Leu Glu Ile Leu Arg Val Ser His Glu Val Glu
                485                 490                 495

Arg Glu Gln Val Arg Glu Leu Ala Gly Arg Lys Gly Arg Asp Asp
            500                 505                 510

Ala Arg Val Arg Ala Ser Leu Asp Ala Met Leu Ala Ala Arg Asp
            515                 520                 525

Gly Ser Asn Met Ile Ala Pro Met Leu Glu Val Arg Ala Glu Ala
    530                 535                 540

Thr Leu Gly Glu Ile Cys Gly Val Leu Arg Asp Glu Trp Gly Val Tyr
545                 550                 555                 560

Val Glu Pro Pro Gly Phe
            565

<210> SEQ ID NO 96
<211> LENGTH: 4362
<212> TYPE: DNA
<213> ORGANISM: Streptomyces cinnamonensis

<400> SEQUENCE: 96

```
tgaggcgctg gatcgcctcg gagagcagct ggtaacggtc cgcgtggtac tcggccgggg      60
tgcagccgtc cacgatgtgc gggatcgcgt cgggctcgag gatcaccagg gcggggggcgt     120
cgccgatcgc gtcggcgaac gtgtccaccc agctccggta ggcctccgca ctggccgcgc     180
cgcccgcgga gtgctgaccg cagtcgcggt gcgggatgtt gtacgcgacg agtacggcgg     240
tgcggtcctc cttgaccgcg ccccgcgtcg ccttcgcgac gtcgggcgcc ggatcgtccc     300
cggccggcca cacggccatg gcccgttcgg agatgcgcct gagcgtctcg gcgtcctcgg     360
cgcggccctg ttcctcccac tgcctgacct ggcgcgcggc ggggctgtcg gggtcgaccc     420
agaaggtgcc ggcgggggc cggcgctcg cggtggcggg cttgcgcacg gccgcctcct      480
ccttcgtgcc gtcggacccc gggtctgagg aggagcagcc tgccgggagc ccgagggcgg     540
cgagggccgc gagtgccgtg aacgtgcgga gcagccggtg catccagccc ccttgggcga     600
tggtgacagt gacggtcagt cagcccggca atcgttacat aaaggactat tcaagctctt     660
gtgccacacc gcctccggtg ccgagcgcga accggcggg caccagagcc cgccgcggc      720
cgcggagccg tacgtacgac cgaattgcga cggggctg accaccatat gaccggcggg      780
taaggtcgat gccgtgccga agccgctcag cctcccctc gatcccatcg cccgcgccga     840
```

```
cgagctctgg aagcagcgct ggggatcggt cccggccatg ggcgcgatca cctcgatcat    900
gcggggcgcac cagatcctgc tcgccgaggt cgacgcggtc gtcaagccgt acggactgac    960
cttcgcgcgc tacgaggcgc tggtgctcct caccttctcg caggccggcg agttgccgat   1020
gtcgaagatc ggcgagcggc tcatggtgca cccgacctcg gtcacgaaca ccgtggaccg   1080
cctggtgaag tccggcctgg tcgacaagcg cccgaacccc aacgacggcc gcggcacgct   1140
cgcctccatc acgagaaagg gccgcgaggt cgtcgaggcg ccacccgcg agctgatggc   1200
gatggacttc gggctcgggg tgtacgacgc ggaggagtgc ggggagatct tcgcgatgct   1260
gcggcccctg cgggtggcgg cgcgcgattt cgaggagcag tagggcccgc ccggtgagaa   1320
gtgggatcgg gtcgtcccgg tacgggcggg ggcggcgaag atcgcgtgaa aagggcggtt   1380
acgctcgtag ccatgaaacg cagcgtgctg acccgctacc gggtgatggc ctacgtcacc   1440
gccgtcatgc tcctcatcct gtgcgcctgc atggtggcca agtacggctt cgacaagggc   1500
gagggtctga ccctcgtcgt gtcgcaggtg cacggcgtgc tctacatcat ctacctgatc   1560
ttcgccttcg acctgggctc caaggcgaag tggccgttcg gcaagctgct ctgggtgctg   1620
gtctcgggca cgatcccgac cgccgccttc ttcgtcgagc gcaaggtcgc ccgtgacgtc   1680
gagccgctga tcgccgacgg ctccccggtc accgcgaagg cgtaacccgc accgccacgg   1740
acaggtccgt ggcggttggc catcgacttt tactaggacg tcctagtaaa ttcgatggta   1800
tggacgctga cgcgatcgag gaaggccgcc gacgctggca ggcccgttac gacaaggccc   1860
gcaagcgcga cgcggacttc accacgctct ccggggaccc cgtcgacccc gtctacggcc   1920
cccgcccgg ggacacgtac gacgggttcg agcggatcgg ctggccgggg gagtaccct   1980
tcacccgcgg gctctacgcc accgggtacc gcggccgcac ctggaccatc gccagttcg   2040
ccggcttcgg caacgccgag cagacgaacg agcgctacaa gatgatcctg ccaacggcg   2100
gcggcggcct ctccgtcgcc ttcgacatgc cgaccctcat gggccgcgac tccgacgacc   2160
cgcgctcgct cggcgaggtc ggccactgcg gtgtcgccat cgactccgcc gccgacatgg   2220
aggtcctctt caaggacatc ccgctcggcg acgtcacgac gtccatgacc atcagcgggc   2280
ccgccgtgcc cgtcttctgc atgtaccctcg tcgcggccga cgccagggc gtcgacccgg   2340
ccgtcctcaa cggcacgctg cagaccgaca tcttcaagga gtacatcgcc cagaaggagt   2400
ggctcttcca gcccgagccg cacctgcgcc tcatcggcga cctgatggag cactgcgcgc   2460
gcgacatccc cgcgtacaag ccgctctcgg tctccggcta ccacatccgc gaggccgggg   2520
cgacggccgc gcaggagctc gcgtacaccc tcgcggacgg cttcgggtac gtggaactgg   2580
gcctctcgcg cggcctggac gtggacgtct tcgcgcccgg cctctccttc ttcttcgacg   2640
cgcacgtcga cttcttcgag gagatcgcga agttccgcgc gcacgccgc atctgggcgc   2700
gctggctccg ggacgagtac ggagcgaaga ccgagaaggc acagtggctg cgcttccaca   2760
cgcagaccgc gggggtctcg ctcacggccc agcagccgta caacaacgtg gtgcggacgg   2820
cggtggaggc cctcgccgcg gtgctcggcg gcacgaactc cctgcacacc aacgctctcg   2880
acgagaccct tgccctcccc agcgagcagg ccgcggagat cgcgctgcgc acccagcagg   2940
tgctgatgga ggagaccggc gtcgccaacg tcgcggaccc gctgggcggc tcctggtaca   3000
tcgagcagct caccgaccgc atcgaggccg acgccgagaa gatcttcgag cagatcaggg   3060
agcggggggcg gcgggcctgc cccgacgggc agcaccgat cggccgatc acctccggca   3120
tcctgcgcgc catcgaggac ggctggttca ccggcgagat cgccgagtcc gccttccagt   3180
accagcggtc cctggagaag ggcgacaagc gggtcgtcgg cgtcaactgc ctcgaaggct   3240
```

```
ccgtcaccgg cgacctggag atcctgcgcg tcagccacga ggtcgagcgc gagcaggtgc    3300
gggagcttgc ggggcgcaag gggcggcgtg acgatgcgcg ggtgcgggcc tcgctcgacg    3360
cgatgctcgc cgctgcgcgg gacgggtcga acatgattgc ccccatgctg gaggcggtgc    3420
gggccgaggc gaccctcggg gagatctgcg gggtgcttcg cgatgagtgg ggggtctacg    3480
tggagccgcc cgggttctga gggcgcgctc cctttgcctg cgggtctgct gtggctggtc    3540
gcgcagttcc ccgcacccct gaaagacccc ggcgctttcc cttcctggct cgcctcgtcg    3600
ctgtctgcgg ggccgtgggg gctggtcgcg cagttccccg cgccctgcc cgcacctgcg      3660 ccccgccgcc tgcatgccgc ccccaccctg acggggggcgt tcggggccca ccctgacggg    3720
tgcggtcggg gcgtgccggg gtcttttagg ggcgcgggga actgcgcgag caaccccccac   3780 ccacccgcag gtgcacgcgg agcggcggac gccccgcaga cggggggcaaa acggggcggag  3840 tgccccgcc cgccgggcgg cgcgaattcg taggtttaag gggcaggggt cagggcaggc     3900
gccgagccgt tcaaccgccc ccgtcccagg agaccccgtg acctcgaccg gccacgcccg    3960
caccgccgcc atcgccatcg gagccgccac cgccaccgtc ctcggcgcgc tgctggtcgg    4020
cggctccggc gaggtgagtg cgagcccgcc gcccgagccc aaggtccagg acgacttcga    4080
ctccctcggc cccgaggtgc gcgccgcgaa gctctccgac gggcggacgg cccactactc    4140
ggacacgggc gacaaggacg gcaagccggc cctgttcatc ggcggcaccg gcacgagcgc    4200
ccgcgcctcc cacatgaccg acttcttccg ctcgacgcgc gaggacctgg gcctgcgcct    4260
catctccgtg gagcgcaacg gcttcggcga caccgcgttc gacgagaagc tgggcaccgc    4320
cgacttcgcg aaggacgccc tcgaagtcct cgaccggctc gg                       4362
```

<210> SEQ ID NO 97
<211> LENGTH: 136
<212> TYPE: PRT
<213> ORGANISM: Streptomyces cinnamonensis

<400> SEQUENCE: 97

```
Met Gly Val Ala Ala Gly Pro Ile Arg Val Val Ala Lys Pro Gly
1               5                  10                  15

Leu Asp Gly His Asp Arg Gly Ala Lys Val Ile Ala Arg Ala Leu Arg
            20                  25                  30

Asp Ala Gly Met Glu Val Ile Tyr Thr Gly Leu His Gln Thr Pro Glu
        35                  40                  45

Gln Val Val Asp Thr Ala Ile Gln Glu Asp Ala Asp Ala Ile Gly Leu
    50                  55                  60

Ser Ile Leu Ser Gly Ala His Asn Thr Leu Phe Ala Arg Val Leu Glu
65                  70                  75                  80

Leu Leu Lys Glu Arg Asp Ala Glu Asp Ile Lys Val Phe Gly Gly Gly
                85                  90                  95

Ile Ile Pro Glu Ala Asp Ile Ala Pro Leu Lys Glu Lys Gly Val Ala
            100                 105                 110

Glu Ile Phe Thr Pro Gly Ala Thr Thr Thr Ser Ile Val Glu Trp Val
        115                 120                 125

Arg Gly Asn Val Arg Gln Ala Val
    130                 135
```

<210> SEQ ID NO 98
<211> LENGTH: 1643
<212> TYPE: DNA
<213> ORGANISM: Streptomyces cinnamonensis

<400> SEQUENCE: 98

```
gtcgacctcc cgtttggcgc acggaaggga ggctctgtcc cccgtgtgcc ctaggggggag      60
tcgtggtcga ggagtcggct gtgcgatggc gatcccggcc accgccctgc ggtgactccg     120
tgccccccgtt gcatcgccga tgcgcggtgt caccacgccg tgcggctgcc ggcgcggtgg     180
cccggcgtct cgttgcggct ccctcgcgc ctggtccgga tgcggagcgt gaaccccttgg    240
gttacgacg ggcgcgcagc gaacgtgtcc cacgtgtgat ttccccctcg ctctccaccg      300
cgaaactgcc gcttgcgcga tgctggggat aacgttcgtt cacttccccg gccggtgcgg     360
tgcgggtat ctgtgccggg acagactttg tcggtacga tatcggtaca tggaggcagt       420
gatgggtgtg gcagccgggc cgatccgcgt ggtggtcgcc aagccggggc tcgacgggca     480
cgatcgcggg gccaaggtga tcgcgcgggc gttgcgtgac gcgggtatgg aggtcatcta     540
caccgggctg caccagacgc ccgagcaggt ggtggacacc gcgatccagg aggacgccga     600
cgcgatcggc ctctccatcc tctccggagc gcacaaacg ctgttcgcgc gcgtgttgga      660
gctcttgaag gagcgggacg cggaggacat caaggtgttt ggtggcggca tcatcccgga    720
ggcggacatc gcgccgctga aggagaaggg cgtcgcggag atcttcacgc ccggggccac     780
caccacgtcg atcgtggagt gggttcgggg gaacgtgcga caggccgtct gaggcattcc     840
ccgtcgcccg tctgccgtgg tcggcgtcat atcggcggac atcgtctcgg tggacgtcat     900
ggcggcgggg ggagttcgtc gcgtatcgcc gcgcggaggc gcagggtggt gaccaggcgc     960
tggaacgctt ccgaccagta gctgcccgcg ccgggtgacg cgtcctccgc ttcgtcgggg    1020
accgcggtga gcgcttccag gcggaccgcc tcggccgggt ccagacagcg ttccgccagg    1080
cccatcactc cgctgaagct ccatgggtaa ctgcccgcgt cgcgcgcgat gttcagggcg    1140
tccaccacgg cccggccgag agggccggcc cagggcaccg cgcagacgcc gagcagttgg    1200
aacgcctccg acaggccgtg tgccgctatg aaccccgcca cccagtccgc gcgctcggcg    1260
gcaggcatgg aggcgagcag tttggcccgc tcggcgaggg acacggcgcc aggccccgcc    1320
gcgtcgggtg aggcggggc gccgagcagc gctctggacc aggcgacgtc acgctggcgt    1380
acggccgcgc ggcaccatgc ggcgtgcagt tcgccccgcc agtcgtcggc caccgggagc    1440
gccacgatct ccgccggggt gcggttgccg agccggggcg ccaggtggc gagcggggcc     1500
gattccacga gctggccgag ccaccaggag cgctcgcccc ggccggtggg gggcttcggg    1560
acgacgccgt cccgctccat gcccgcgtcg cactcgtgcg gcgcctcgac ggtgagggtc    1620
ggcgtgctcg atgtgtggtc gac                                           1643
```

<210> SEQ ID NO 99
<211> LENGTH: 566
<212> TYPE: PRT
<213> ORGANISM: Streptomyces coelicolor

<400> SEQUENCE: 99

```
Met Asp Ala His Ala Ile Glu Glu Gly Arg Leu Arg Trp Gln Ala Arg
1               5                   10                  15
Tyr Asp Ala Ala Arg Lys Arg Asp Ala Asp Phe Thr Thr Leu Ser Gly
            20                  25                  30
Asp Pro Val Glu Pro Val Tyr Gly Pro Arg Pro Gly Asp Glu Tyr Glu
        35                  40                  45
Gly Phe Glu Arg Ile Gly Trp Pro Gly Glu Tyr Pro Phe Thr Arg Gly
    50                  55                  60
```

```
Leu Tyr Pro Thr Gly Tyr Arg Gly Arg Thr Trp Thr Ile Arg Gln Phe
 65                  70                  75                  80

Ala Gly Phe Gly Asn Ala Glu Gln Thr Asn Glu Arg Tyr Lys Met Ile
                 85                  90                  95

Leu Arg Asn Gly Gly Gly Leu Ser Val Ala Phe Asp Met Pro Thr
                100                 105                 110

Leu Met Gly Arg Asp Ser Asp Pro Arg Ser Leu Gly Glu Val Gly
            115                 120                 125

His Cys Gly Val Ala Ile Asp Ser Ala Ala Asp Met Glu Val Leu Phe
    130                 135                 140

Lys Asp Ile Pro Leu Gly Asp Val Thr Thr Ser Met Thr Ile Ser Gly
145                 150                 155                 160

Pro Ala Val Pro Val Phe Cys Met Tyr Leu Val Ala Ala Glu Arg Gln
                165                 170                 175

Gly Val Asp Ala Ser Val Leu Asn Gly Thr Leu Gln Thr Asp Ile Phe
            180                 185                 190

Lys Glu Tyr Ile Ala Gln Lys Glu Trp Leu Phe Gln Pro Glu Pro His
            195                 200                 205

Leu Arg Leu Ile Gly Asp Leu Met Glu Tyr Cys Ala Ala Gly Ile Pro
210                 215                 220

Ala Tyr Lys Pro Leu Ser Val Ser Gly Tyr His Ile Arg Glu Ala Gly
225                 230                 235                 240

Ala Thr Ala Ala Gln Glu Leu Ala Tyr Thr Leu Ala Asp Gly Phe Gly
                245                 250                 255

Tyr Val Glu Leu Gly Leu Ser Arg Gly Leu Asp Val Asp Val Phe Ala
            260                 265                 270

Pro Gly Leu Ser Phe Phe Phe Asp Ala His Leu Asp Phe Phe Glu Glu
            275                 280                 285

Ile Ala Lys Phe Arg Ala Ala Arg Ile Trp Ala Arg Trp Met Arg
290                 295                 300

Asp Val Tyr Gly Ala Arg Thr Asp Lys Ala Gln Trp Leu Arg Phe His
305                 310                 315                 320

Thr Gln Thr Ala Gly Val Ser Leu Thr Ala Gln Gln Pro Tyr Asn Asn
                325                 330                 335

Val Val Arg Thr Ala Val Glu Ala Leu Ala Ala Val Leu Gly Gly Thr
            340                 345                 350

Asn Ser Leu His Thr Asn Ala Leu Asp Glu Thr Leu Ala Leu Pro Ser
            355                 360                 365

Glu Gln Ala Ala Glu Ile Ala Leu Arg Thr Gln Val Leu Met Glu
370                 375                 380

Glu Thr Gly Val Ala Asn Val Ala Asp Pro Leu Gly Gly Ser Trp Phe
385                 390                 395                 400

Ile Glu Gln Leu Thr Asp Arg Ile Glu Ala Asp Ala Glu Lys Ile Phe
                405                 410                 415

Glu Gln Ile Lys Glu Arg Gly Leu Arg Ala His Pro Asp Gly Gln His
            420                 425                 430

Pro Val Gly Pro Ile Thr Ser Gly Leu Leu Arg Gly Ile Glu Asp Gly
            435                 440                 445

Trp Phe Thr Gly Glu Ile Ala Glu Ser Ala Phe Arg Tyr Gln Gln Ser
            450                 455                 460

Leu Glu Lys Asp Asp Lys Lys Val Val Gly Val Asn Val His Thr Gly
465                 470                 475                 480

Ser Val Thr Gly Asp Leu Glu Ile Leu Arg Val Ser His Glu Val Glu
```

485                 490                 495
Arg Glu Gln Val Arg Val Leu Gly Glu Arg Lys Asp Ala Arg Asp Asp
                500                 505                 510

Ala Ala Val Arg Gly Ala Leu Asp Ala Met Leu Ala Ala Ala Arg Ser
            515                 520                 525

Gly Gly Asn Met Ile Gly Pro Met Leu Asp Ala Val Arg Ala Glu Ala
        530                 535                 540

Thr Leu Gly Glu Ile Cys Gly Val Leu Arg Asp Glu Trp Gly Val Tyr
545                 550                 555                 560

Thr Glu Pro Ala Gly Phe
                565

<210> SEQ ID NO 100
<211> LENGTH: 1701
<212> TYPE: DNA
<213> ORGANISM: Streptomyces coelicolor

<400> SEQUENCE: 100
atggacgctc atgccataga ggagggccgc cttcgctggc aggcccggta cgacgcggcg    60
cgcaagcgcg acgcggactt caccacgctc tccggagacc ccgtggagcc ggtgtacggg   120
ccccgccccg gggacgagta cgagggcttc gagcggatcg gctggccggg cgagtacccc   180
ttcacccgcg gcctgtatcc gaccgggtac cggggcgta cgtggaccat ccggcagttc   240
gccgggttcg gcaacgccga gcagaccaac gagcgctaca agatgatcct ccgcaacggc   300
ggcggcgggc tctcggtcgc cttcgacatg ccgaccctga tgggccgcga ctccgacgac   360
ccgcgctcgc tgggcgaggt cgggcactgc ggggtggcca tcgactcggc cgccgacatg   420
gaagtgctgt tcaaggacat cccgctcggg acgtgacga cctccatgac gatcagcggg   480
cccgccgtgc ccgtgttctg catgtaccgc gtcgccgccg agcgccaggg cgtcgacgca   540
tccgtgctca acggcacgct gcagaccgac atcttcaagg agtacatcgc ccagaaggag   600
tggctcttcc agcccgagcc ccacctccgg ctcatcggcg acctcatgga gtactgcgcg   660
gccggcatcc ccgcctacaa gccgctctcc gtctccggct accacatccg cgaggcgggc   720
gcgacggccg cgcaggagct ggcgtacacg ctcgccgacg gcttcggata cgtggagctg   780
ggcctcagcc gcgggctcga cgtggacgtc ttcgcgcccg gcctctcctt cttcttcgac   840
gcgcacctcg acttcttcga ggagatcgcc aagttccgcg cggcccgcag gatctgggcc   900
cgctggatgc gcgacgtgta cggcgcgcgg accgacaagg cccagtggct gcggttccac   960
acccagaccc ccggagtctc gctcaccgcg cagcagccgt acaacaacgt cgtacgcacc  1020
gcggtggagg cgctggcggc cgtgctcggc ggcaccaact ccctgcacac caacgcgctc  1080
gacgagaccc tcgccctgcc cagcgagcag gcgccgaga tcgccctgcg cacccagcag  1140
gtgctgatgg aggagaccgg cgtcgccaac gtcgccgacc cgctgggcgg ttcctggttc  1200
atcgagcagc tgaccgaccg catcgaggcc gacgccgaga gatcttcga gcagatcaag  1260 gagcgggggc tgcgcgccca ccccgacggg cagcacccc tcggaccgat cacctccggc  1320
ctgctgcgcg catcgaggga cggctggttc accggcgaga tcgccgagtc cgccttccgc  1380
taccagcagt ccttggagaa ggacgacaag aaggtggtcg cgtcaacgt ccacaccggc  1440 tccgtcaccg gcgacctgga gatcctgcgg gtcagccacg aggtcgagcg cgagcaggtg  1500
cgggtcctgg cgagcgcaa ggacgcccgg gacgacgccg ccgtgcgcgg cgccctggac  1560
gccatgctgg ccgcggcccg ctccggcggc aacatgatcg gccgatgct ggacgcggtg  1620

```
cgcgcggagg cgacgctggg cgagatctgc ggtgtgctgc gcgacgagtg ggggtgtac      1680 acggaaccgg cggggttctg a                                                1701
```

<210> SEQ ID NO 101
<211> LENGTH: 138
<212> TYPE: PRT
<213> ORGANISM: Streptomyces coelicolor

<400> SEQUENCE: 101

```
Met Gly Val Ala Ala Gly Pro Ile Arg Val Val Ala Lys Pro Gly
1               5                   10                  15

Leu Asp Gly His Asp Arg Gly Ala Lys Val Ile Ala Arg Ala Leu Arg
                20                  25                  30

Asp Ala Gly Met Glu Val Ile Tyr Thr Gly Leu His Gln Thr Pro Glu
            35                  40                  45

Gln Ile Val Asp Thr Ala Ile Gln Glu Asp Ala Asp Ala Ile Gly Leu
        50                  55                  60

Ser Ile Leu Ser Gly Ala His Asn Thr Leu Phe Ala Ala Val Ile Glu
65                  70                  75                  80

Leu Leu Arg Glu Arg Asp Ala Ala Asp Ile Leu Val Phe Gly Gly Gly
                85                  90                  95

Ile Ile Pro Glu Ala Asp Ile Ala Pro Leu Lys Glu Lys Gly Val Ala
            100                 105                 110

Glu Ile Phe Thr Pro Gly Ala Thr Ala Ser Ile Val Asp Trp Val
        115                 120                 125

Arg Ala Asn Val Arg Glu Pro Ala Gly Ala
    130                 135
```

<210> SEQ ID NO 102
<211> LENGTH: 417
<212> TYPE: DNA
<213> ORGANISM: Streptomyces coelicolor

<400> SEQUENCE: 102

```
atgggtgtgg cagccggtcc gatccgcgtg gtggtggcca agccgggggct cgacggccac      60 gatcgcgggg ccaaggtgat cgcgagggcc ctgcgtgacg ccggtatgga ggtgatctac     120
accgggctcc accagacgcc cgagcagatc gtcgacaccg cgatccagga ggacgccgac     180
gcgatcgggc tgtccatcct ctccggtgcg cacaacacgc tcttcgccgc cgtgatcgag     240
ctgctccggg agcgggacgc cgcggacatc ctggtcttcg gcggcgggat catccccgag     300
gcggacatcg ccccgctgaa ggagaagggc gtcgcggaga tcttcacgcc cggcgccacc     360
acggcgtcca tcgtggactg ggtccgggcg aacgtgcggg agcccgcggg agcatag       417
```

<210> SEQ ID NO 103
<211> LENGTH: 566
<212> TYPE: PRT
<213> ORGANISM: Streptomyces avermitilis

<400> SEQUENCE: 103

```
Met Asp Ala Asp Ala Ile Glu Glu Gly Arg Arg Arg Trp Gln Ala Arg
1               5                   10                  15

Tyr Asp Ala Ser Arg Lys Arg Glu Ala Asp Phe Thr Thr Leu Ser Gly
                20                  25                  30

Asp Pro Val Glu Pro Ala Tyr Gly Pro Arg Pro Gly Asp Ala Tyr Glu
            35                  40                  45

Gly Phe Glu Arg Ile Gly Trp Pro Gly Glu Tyr Pro Phe Thr Arg Gly
```

-continued

```
              50                  55                  60
Leu Tyr Pro Thr Gly Tyr Arg Gly Arg Thr Trp Thr Ile Arg Gln Phe
 65                  70                  75                  80

Ala Gly Phe Gly Asn Ala Glu Gln Thr Asn Glu Arg Tyr Lys Lys Ile
                 85                  90                  95

Leu Ala Asn Gly Gly Gly Leu Ser Val Ala Phe Asp Met Pro Thr
                100                 105                 110

Leu Met Gly Arg Asp Ser Asp Arg Arg Ala Leu Gly Glu Val Gly
                115                 120                 125

His Cys Gly Val Ala Ile Asp Ser Ala Ala Asp Met Glu Val Leu Phe
                130                 135                 140

Lys Asp Ile Pro Leu Gly Asp Val Thr Thr Ser Met Thr Ile Ser Gly
145                 150                 155                 160

Pro Ala Val Pro Val Phe Cys Met Tyr Leu Val Ala Ala Glu Arg Gln
                165                 170                 175

Gly Val Asp Pro Ser Val Leu Asn Gly Thr Leu Gln Thr Asp Ile Phe
                180                 185                 190

Lys Glu Tyr Ile Ala Gln Lys Glu Trp Leu Phe Gln Pro Glu Pro His
                195                 200                 205

Leu Arg Leu Ile Gly Asp Leu Met Glu His Cys Ala Ser Lys Ile Pro
210                 215                 220

Ala Tyr Lys Pro Leu Ser Val Ser Gly Tyr His Ile Arg Glu Ala Gly
225                 230                 235                 240

Ala Thr Ala Ala Gln Glu Leu Ala Tyr Thr Leu Ala Asp Gly Phe Gly
                245                 250                 255

Tyr Val Glu Leu Gly Leu Ser Arg Gly Leu Asp Val Asp Val Phe Ala
                260                 265                 270

Pro Gly Leu Ser Phe Phe Asp Ala His Val Asp Phe Phe Glu Glu
                275                 280                 285

Ile Ala Lys Phe Arg Ala Ala Arg Arg Ile Trp Ala Arg Trp Leu Arg
                290                 295                 300

Asp Val Tyr Gly Ala Lys Ser Glu Lys Ala Gln Trp Leu Arg Phe His
305                 310                 315                 320

Thr Gln Thr Ala Gly Val Ser Leu Thr Ala Gln Pro Tyr Asn Asn
                325                 330                 335

Val Val Arg Thr Ala Val Glu Ala Leu Ala Ala Val Leu Gly Gly Thr
                340                 345                 350

Asn Ser Leu His Thr Asn Ala Leu Asp Glu Thr Leu Ala Leu Pro Ser
                355                 360                 365

Glu Gln Ala Ala Glu Ile Ala Leu Arg Thr Gln Gln Val Leu Met Glu
                370                 375                 380

Glu Thr Gly Val Ala Asn Val Ala Asp Pro Leu Gly Gly Ser Trp Tyr
385                 390                 395                 400

Val Glu Gln Leu Thr Asp Arg Ile Glu Ala Asp Ala Glu Lys Ile Phe
                405                 410                 415

Glu Gln Ile Arg Glu Arg Gly Leu Arg Ala His Pro Asp Gly Arg His
                420                 425                 430

Pro Ile Gly Pro Ile Thr Ser Gly Ile Leu Arg Gly Ile Glu Asp Gly
                435                 440                 445

Trp Phe Thr Gly Glu Ile Ala Glu Ser Ala Phe Gln Tyr Gln Gln Ala
                450                 455                 460

Leu Glu Lys Gly Asp Lys Arg Val Val Gly Val Asn Val His His Gly
465                 470                 475                 480
```

```
Ser Val Thr Gly Asp Leu Glu Ile Leu Arg Val Ser His Glu Val Glu
            485                 490                 495

Arg Glu Gln Val Arg Val Leu Gly Glu Arg Lys Ser Gly Arg Asp Asp
        500                 505                 510

Thr Ala Val Thr Ala Ala Leu Asp Ala Met Leu Ala Ala Arg Asp
        515                 520                 525

Gly Ser Asn Met Ile Ala Pro Met Leu Asp Ala Val Arg Ala Glu Ala
        530                 535                 540

Thr Leu Gly Glu Ile Cys Asp Val Leu Arg Glu Trp Gly Val Tyr
545                 550                 555                 560

Thr Glu Pro Ala Gly Phe
            565

<210> SEQ ID NO 104
<211> LENGTH: 1701
<212> TYPE: DNA
<213> ORGANISM: Streptomyces avermitilis

<400> SEQUENCE: 104
tcagaaaccg gcgggctccg tgtagacccc ccactcctcc cggaggacat cgcagatctc      60
gcccagcgtg gcctccgcgc ggaccgcgtc cagcatcggg gcgatcatgt tcgacccgtc     120
gcgcgcggcg gcgagcatcg cgtccagggc gcggttacg gccgtgtcgt cgcgccccga      180
cttccgctcg cccagcaccc gcacctgctc gcgctccacc tcgtggctga cgcgcaggat     240
ctccaggtcg cccgtcacgg accgtggtg gacgttgacg ccgacgaccc gcttgtcgcc      300
cttctccagc gcctgctggt actggaaggc cgactcggcg atctccccgg tgaaccagcc     360
gtcctcgatg ccgcgcagga tgccggaggt gatgggcccg atcgggtgcc gcccgtccgg     420
gtgggcccgc agcccgcgct ccctgatctg ttcgaagatc ttctcggcgt cggcctcgat     480
ccggtcggtc agctgctcca cgtaccagga accgcccagc ggatcggcca cgttggcgac     540
gcccgtctcc tccatcagca cctgctgggt gcgcagggcg atctcggccg cctgctcgga     600
cggcagggcg agggtctcgt cgagggcgtt ggtgtgcagc gagttcgtcc gccgagcac      660 cgcggcgagg gcctccacgg ccgtccgtac gacgttgttg tacggctgct gcgcggtgag     720
cgagacgccc gcggtctggg tgtggaagcg cagccactgc gccttctccg acttcgcccc    780
gtacacgtcc cgcagccagc gcgcccagat gcgccgcgcc gcacggaact tggcgatctc     840
ctcgaagaag tcgacgtgcg cgtcgaagaa gaaggagagc ccgggcgcga acacgtccac     900
gtccaggccg cggctcagcc ccagctccac gtatccgaaa ccgtcggcga gggtgtacgc     960
cagctcctgg gcggccgtgg caccggcctc ccggatgtgg tacccggaga cggacagcgg    1020
cttgtacgcg gggatcttcg aggcgcagtg ctccatcagg tcgccgatga ccgcagatg     1080 gggctcgggc tggaagagcc actccttctg cgcgatgtac tccttgaaga tgtcggtctg    1140
gagggtgccg ttgaggacgg aggggtcgac gccctgccgc tcggccgcga ccaggtacat    1200
gcagaagacg ggcacggcgg gccgctgat cgtcatcgac gtcgtcacgt cacccagcgg     1260
gatgtccttg aacaggacct ccatgtcggc cgccgagtcg atcgcgaccc cgcagtgccc    1320
gacctcgccg agcgcgcggc ggtcgtcgga gtcgcgcccc atgagcgtcg gcatgtcgaa    1380
ggccacggac agcccaccgc cgccgttggc gaggatcttc ttgtagcgct cgttggtctg    1440
ctcggcgttg ccgaacccgg cgaactgccg gatggtccag gtccggcccc ggtagccggt    1500
cggatacaga ccgcgcgtga aggggtactc acccggccag ccgatccgct cgaaaccctc    1560
```

```
gtacgcgtcc ccgggccggg gcccgtacgc cggctccacg ggatcgccgg agagcgtggt   1620
gaaatcggcc tcgcgcttgc gtgaggcgtc gtagcgggcc tgccagcgtc ggcggccttc   1680
ctcgatggcg tcagcgtcca t                                              1701

<210> SEQ ID NO 105
<211> LENGTH: 138
<212> TYPE: PRT
<213> ORGANISM: Streptomyces avermitilis

<400> SEQUENCE: 105

Met Gly Val Ala Ala Gly Pro Ile Arg Val Val Ala Lys Pro Gly
1               5                   10                  15

Leu Asp Gly His Asp Arg Gly Ala Lys Val Ile Ala Arg Ala Leu Arg
            20                  25                  30

Asp Ala Gly Met Glu Val Ile Tyr Thr Gly Leu His Gln Thr Pro Glu
        35                  40                  45

Gln Ile Val Gly Thr Ala Ile Gln Glu Asp Ala Asp Ala Ile Gly Leu
    50                  55                  60

Ser Ile Leu Ser Gly Ala His Asn Thr Leu Phe Ala Ala Val Ile Asp
65                  70                  75                  80

Leu Leu Lys Glu Arg Asp Ala Glu Asp Ile Lys Val Phe Gly Gly Gly
                85                  90                  95

Ile Ile Pro Glu Ala Asp Ile Ala Pro Leu Lys Glu Lys Gly Val Ala
            100                 105                 110

Glu Ile Phe Thr Pro Gly Ala Thr Thr Ala Ser Ile Val Glu Trp Val
        115                 120                 125

Arg Ala Asn Val Arg Gln Pro Ala Gly Ala
    130                 135

<210> SEQ ID NO 106
<211> LENGTH: 1701
<212> TYPE: DNA
<213> ORGANISM: Streptomyces avermitilis

<400> SEQUENCE: 106
tcagaaaccg gcgggctccg tgtagacccc ccactcctcc ggaggacat cgcagatctc      60 gcccagcgtg gcctccgcgc ggaccgcgtc cagcatcggg gcgatcatgt tcgacccgtc    120
gcgcgcggcg gcgagcatcg cgtccagggc cgcggttacg gccgtgtcgt cgcgccccga    180
cttccgctcg cccagcaccc gcacctgctc gcgctccacc tcgtggctga cgcgcaggat    240
ctccaggtcg cccgtcacgg acccgtggtg gacgttgacg ccgacgaccc gcttgtcgcc    300
cttctccagc gcctgctggt actggaaggc cgactcggcg atctccccgg tgaaccagcc    360
gtcctcgatg ccgcgcagga tgccggaggt gatgggcccg atcgggtgcc gcccgtccgg    420
gtgggcccgc agcccgcgct ccctgatctg ttcgaagatc ttctcggcgt cggcctcgat    480
ccggtcggtc agctgctcca gtaccagga accgcccagc ggatcggcca cgttggcgac    540
gcccgtctcc tccatcagca cctgctgggt gcgcagggcg atctcggccg cctgctcgga    600
cggcagggcg agggtctcgt cgagggcgtt ggtgtgcagc gagttcgtcc gccgagcac     660 cgcggcgagg gcctccacgg ccgtccgtac gacgttgttg tacggctgct gcgcggtgag    720
cgagacgccc gcggtctggg tgtggaagcg cagccactgc gccttctccg acttcgcccc    780
gtacacgtcc cgcagccagc gcgcccagat gcgccgcgcc gcacggaact tggcgatctc    840
ctcgaagaag tcgacgtgcg cgtcgaagaa gaaggagagc ccgggcgcga acacgtccac    900
```

```
gtccaggccg cggctcagcc ccagctccac gtatccgaaa ccgtcggcga gggtgtacgc    960
cagctcctgg gcggccgtgg caccggcctc ccggatgtgg tacccggaga cggacagcgg   1020
cttgtacgcg gggatcttcg aggcgcagtg ctccatcagg tcgccgatga gccgcagatg   1080
gggctcgggc tggaagagcc actccttctg cgcgatgtac tccttgaaga tgtcggtctg   1140
gagggtgccg ttgaggacgg aggggtcgac gccctgccgc tcggccgcga ccaggtacat   1200
gcagaagacg ggcacggcgg gccgctgat  cgtcatcgac gtcgtcacgt cacccagcgg   1260
gatgtccttg aacaggacct ccatgtcggc cgccgagtcg atcgcgaccc cgcagtgccc   1320
gacctcgccg agcgcgcggc ggtcgtcgga gtcgcgcccc atgagcgtcg gcatgtcgaa   1380
ggccacggac agcccaccgc cgccgttggc gaggatcttc ttgtagcgct cgttggtctg   1440
ctcggcgttg ccgaacccgg cgaactgccg gatggtccag gtccggcccc ggtagccggt   1500
cggatacaga ccgcgcgtga aggggtactc acccggccag ccgatccgct cgaaaccctc   1560
gtacgcgtcc ccgggccggg gcccgtacgc cggctccacg ggatcgccgg agagcgtggt   1620
gaaatcggcc tcgcgcttgc gtgaggcgtc gtagcgggcc tgccagcgtc ggcggccttc   1680
ctcgatggcg tcagcgtcca t                                             1701
```

<210> SEQ ID NO 107
<211> LENGTH: 139
<212> TYPE: PRT
<213> ORGANISM: Saccharomyces cerevisiae

<400> SEQUENCE: 107

```
Met Ser Glu Ile Thr Leu Gly Lys Tyr Leu Phe Glu Arg Leu Lys Gln
1               5                   10                  15
Val Asn Val Asn Thr Val Phe Gly Leu Pro Gly Asp Phe Asn Leu Ser
            20                  25                  30
Leu Leu Asp Lys Ile Tyr Glu Val Glu Gly Met Arg Trp Ala Gly Asn
        35                  40                  45
Ala Asn Glu Leu Asn Ala Ala Tyr Ala Ala Asp Gly Tyr Ala Arg Ile
    50                  55                  60
Lys Gly Met Ser Cys Ile Ile Thr Thr Phe Gly Val Gly Glu Leu Ser
65                  70                  75                  80
Ala Leu Asn Gly Ile Ala Gly Ser Tyr Ala Glu His Val Gly Val Leu
                85                  90                  95
His Val Val Gly Val Pro Ser Ile Ser Ala Gln Ala Lys Gln Leu Leu
            100                 105                 110
Leu His His Thr Leu Gly Asn Gly Asp Phe Thr Val Phe His Arg Met
        115                 120                 125
Ser Ala Asn Ile Ser Glu Thr Thr Ala Met Ile
    130                 135
```

<210> SEQ ID NO 108
<211> LENGTH: 1689
<212> TYPE: DNA
<213> ORGANISM: Saccharomyces cerevisiae

<400> SEQUENCE: 108

```
atgtctgaaa ttactttggg taaatatttg ttcgaaagat aaagcaagt  caacgttaac    60
accgttttcg gtttgccagg tgacttcaac ttgtccttgt tggacaagat ctacgaagtt   120
gaaggtatga tgggctgg  taacgccaac gaattgaacg ctgcttacgc cgctgatggt   180
tacgctcgta tcaagggtat gtcttgtatc atcaccacct cggtgtcgg  tgaattgtct   240
```

```
gctttgaacg gtattgccgg ttcttacgct gaacacgtcg gtgttttgca cgttgttggt    300
gtcccatcca tctctgctca agctaagcaa ttgttgttgc accacacctt gggtaacggt    360
gacttcactg ttttccacag aatgtctgcc aacatttctg aaaccactgc tatgatcact    420
gacattgcta ccgccccagc tgaaattgac agatgtatca gaaccactta cgtcacccaa    480
agaccagtct acttaggttt gccagctaac ttggtcgact tgaacgtccc agctaagttg    540
ttgcaaactc caattgacat gtctttgaag ccaaacgatg ctgaatccga aaaggaagtc    600
attgacacca tcttggcttt ggtcaaggat gctaagaacc agttatcttg gctgatgct     660
tgttgttcca gacacgacgt caaggctgaa actaagaagt tgattgactt gactcaattc    720
ccagctttcg tcaccccaat gggtaagggt tccattgacg aacaacaccc aagatacggt    780
ggtgtttacg tcggtacctt gtccaagcca gaagttaagg aagccgttga atctgctgac    840
ttgattttgt ctgtcggtgc tttgttgtct gatttcaaca ccggttcttt ctcttactct    900
tacaagacca agaacattgt cgaattccac tccgaccaca tgaagatcag aaacgccact    960
ttcccaggtg tccaaatgaa attcgttttg caaaagttgt tgaccactat tgctgacgcc   1020
gctaagggtt acaagccagt tgctgtccca gctagaactc cagctaacgc tgctgtccca   1080
gcttctaccc cattgaagca agaatggatg tggaaccaat tgggtaactt cttgcaagaa   1140
ggtgatgttg tcattgctga aaccggtacc tccgctttcg gtatcaacca aaccactttc   1200
ccaaacaaca cctacggtat ctctcaagtc ttatggggtt ccattggttt caccactggt   1260
gctaccttgg gtgctgcttt cgctgctgaa gaaattgatc aaagaagag agttatctta   1320
ttcattggtg acggttcttt gcaattgact gttcaagaaa tctccaccat gatcagatgg   1380
ggcttgaagc atacttgtt cgtcttgaac aacgatggtt acaccattga aaagttgatt    1440
cacggtccaa aggctcaata caacgaaatt caaggttggg accacctatc cttgttgcca   1500
actttcggtg ctaaggacta tgaaacccac agagtcgcta ccaccggtga atgggacaag   1560
ttgacccaag acaagtcttt caacgacaac tctaagatca gaatgattga aatcatgttg   1620
ccagtcttcg atgctccaca aaacttggtt gaacaagcta agttgactgc tgctaccaac   1680
gctaagcaa                                                            1689

<210> SEQ ID NO 109
<211> LENGTH: 563
<212> TYPE: PRT
<213> ORGANISM: Saccharomyces cerevisiae

<400> SEQUENCE: 109

Met Ser Glu Ile Thr Leu Gly Lys Tyr Leu Phe Glu Arg Leu Ser Gln
1               5                   10                  15

Val Asn Cys Asn Thr Val Phe Gly Leu Pro Gly Asp Phe Asn Leu Ser
            20                  25                  30

Leu Leu Asp Lys Leu Tyr Glu Val Lys Gly Met Arg Trp Ala Gly Asn
        35                  40                  45

Ala Asn Glu Leu Asn Ala Ala Tyr Ala Ala Asp Gly Tyr Ala Arg Ile
    50                  55                  60

Lys Gly Met Ser Cys Ile Ile Thr Thr Phe Gly Val Gly Glu Leu Ser
65                  70                  75                  80

Ala Leu Asn Gly Ile Ala Gly Ser Tyr Ala Glu His Val Gly Val Leu
                85                  90                  95

His Val Val Gly Val Pro Ser Ile Ser Ser Gln Ala Lys Gln Leu Leu
            100                 105                 110
```

-continued

```
Leu His His Thr Leu Gly Asn Gly Asp Phe Thr Val Phe His Arg Met
        115                 120                 125
Ser Ala Asn Ile Ser Glu Thr Thr Ala Met Ile Thr Asp Ile Ala Asn
130                 135                 140
Ala Pro Ala Glu Ile Asp Arg Cys Ile Arg Thr Thr Tyr Thr Thr Gln
145                 150                 155                 160
Arg Pro Val Tyr Leu Gly Leu Pro Ala Asn Leu Val Asp Leu Asn Val
                165                 170                 175
Pro Ala Lys Leu Leu Glu Thr Pro Ile Asp Leu Ser Leu Lys Pro Asn
            180                 185                 190
Asp Ala Glu Ala Glu Ala Val Val Arg Thr Val Val Glu Leu Ile
        195                 200                 205
Lys Asp Ala Lys Asn Pro Val Ile Leu Ala Asp Ala Cys Ala Ser Arg
210                 215                 220
His Asp Val Lys Ala Glu Thr Lys Lys Leu Met Asp Leu Thr Gln Phe
225                 230                 235                 240
Pro Val Tyr Val Thr Pro Met Gly Lys Gly Ala Ile Asp Glu Gln His
                245                 250                 255
Pro Arg Tyr Gly Gly Val Tyr Val Gly Thr Leu Ser Arg Pro Glu Val
            260                 265                 270
Lys Lys Ala Val Glu Ser Ala Asp Leu Ile Leu Ser Ile Gly Ala Leu
        275                 280                 285
Leu Ser Asp Phe Asn Thr Gly Ser Phe Ser Tyr Ser Tyr Lys Thr Lys
        290                 295                 300
Asn Ile Val Glu Phe His Ser Asp His Ile Lys Ile Arg Asn Ala Thr
305                 310                 315                 320
Phe Pro Gly Val Gln Met Lys Phe Ala Leu Gln Lys Leu Leu Asp Ala
                325                 330                 335
Ile Pro Glu Val Val Lys Asp Tyr Lys Pro Val Ala Val Pro Ala Arg
            340                 345                 350
Val Pro Ile Thr Lys Ser Thr Pro Ala Asn Thr Pro Met Lys Gln Glu
        355                 360                 365
Trp Met Trp Asn His Leu Gly Asn Phe Leu Arg Glu Gly Asp Ile Val
370                 375                 380
Ile Ala Glu Thr Gly Thr Ser Ala Phe Gly Ile Asn Gln Thr Thr Phe
385                 390                 395                 400
Pro Thr Asp Val Tyr Ala Ile Val Gln Val Leu Trp Gly Ser Ile Gly
                405                 410                 415
Phe Thr Val Gly Ala Leu Leu Gly Ala Thr Met Ala Ala Glu Glu Leu
            420                 425                 430
Asp Pro Lys Lys Arg Val Ile Leu Phe Ile Gly Asp Gly Ser Leu Gln
        435                 440                 445
Leu Thr Val Gln Glu Ile Ser Thr Met Ile Arg Trp Gly Leu Lys Pro
        450                 455                 460
Tyr Ile Phe Val Leu Asn Asn Asn Gly Tyr Thr Ile Glu Lys Leu Ile
465                 470                 475                 480
His Gly Pro His Ala Glu Tyr Asn Glu Ile Gln Gly Trp Asp His Leu
                485                 490                 495
Ala Leu Leu Pro Thr Phe Gly Ala Arg Asn Tyr Glu Thr His Arg Val
            500                 505                 510
Ala Thr Thr Gly Glu Trp Glu Lys Leu Thr Gln Asp Lys Asp Phe Gln
        515                 520                 525
Asp Asn Ser Lys Ile Arg Met Ile Glu Val Met Leu Pro Val Phe Asp
```

Ala Pro Gln Asn Leu Val Lys Gln Ala Gln Leu Thr Ala Ala Thr Asn
545                 550                 555                 560

Ala Lys Gln

<210> SEQ ID NO 110
<211> LENGTH: 1689
<212> TYPE: DNA
<213> ORGANISM: Saccharomyces cerevisiae

<400> SEQUENCE: 110

| | | | | | |
|---|---|---|---|---|---|
| atgtctgaaa | taaccttagg | taaatatttta | tttgaaagat | tgagccaagt | caactgtaac | 60 |
| accgtcttcg | gtttgccagg | tgactttaac | ttgtctcttt | tggataagct | ttatgaagtc | 120 |
| aaaggtatga | gatgggctgg | taacgctaac | gaattgaacg | ctgcctatgc | tgctgatggt | 180 |
| tacgctcgta | tcaagggtat | gtcctgtatt | attaccacct | tcggtgttgg | tgaattgtct | 240 |
| gctttgaatg | gtattgccgg | ttcttacgct | gaacatgtcg | gtgttttgca | cgttgttggt | 300 |
| gttccatcca | tctcttctca | agctaagcaa | ttgttgttgc | atcataccct | gggtaacggt | 360 |
| gacttcactg | ttttccacag | aatgtctgcc | aacatttctg | aaaccactgc | catgatcact | 420 |
| gatattgcta | acgtccagc  | tgaaattgac | agatgtatca | gaaccaccta | cactacccaa | 480 |
| agaccagtct | acttgggttt | gccagctaac | ttggttgact | gaacgtccc  | agccaagtta | 540 |
| ttggaaactc | caattgactt | gtctttgaag | ccaaacgacg | ctgaagctga | agctgaagtt | 600 |
| gttagaactc | ttgttgaatt | gatcaaggat | gctaagaacc | cagttatctt | ggctgatgct | 660 |
| tgtgcttcta | gacatgatgt | caaggctgaa | actaagaagt | tgatggactt | gactcaattc | 720 |
| ccagtttacg | tcacccccaat | gggtaagggg | ctattgacg  | acaacaccc  | aagatacggt | 780 |
| ggtgtttacg | ttggtacctt | gtctagacca | gaagttaaga | aggctgtaga | atctgctgat | 840 |
| ttgatattgt | ctatcggtgc | tttgttgtct | gatttcaata | ccggttcttt | ctcttactcc | 900 |
| tacaagacca | aaaatatcgt | tgaattccac | tctgaccaca | tcaagatcag | aaacgccacc | 960 |
| ttcccaggtg | ttcaaatgaa | atttgccttg | caaaaattgt | tggatgctat | tccagaagtc | 1020 |
| gtcaaggact | acaaacctgt | tgctgtccca | gctagagttc | caattaccaa | gtctactcca | 1080 |
| gctaacactc | caatgaagca | agaatggatg | tggaaccatt | tgggtaactt | cttgagagaa | 1140 |
| ggtgatattg | ttattgctga | aaccggtact | tccgccttcg | gtattaacca | aactactttc | 1200 |
| ccaacagatg | tatacgctat | cgtccaagtc | ttgtgggggtt | ccattggttt | cacagtcggc | 1260 |
| gctctattgg | gtgctactat | ggccgctgaa | gaacttgatc | aaagaagag  | agttatttta | 1320 |
| ttcattggtg | acggttctct | acaattgact | gttcaagaaa | tctctaccat | gattagatgg | 1380 |
| ggtttgaagc | catacatttt | tgtcttgaat | aacaacggtt | acaccattga | aaaattgatt | 1440 |
| cacggtcctc | atgccgaata | taatgaaatt | caaggttggg | accacttggc | cttattgcca | 1500 |
| acttttggtg | ctagaaaacta | cgaaacccac | agagttgcta | ccactggtga | atgggaaaag | 1560 |
| ttgactcaag | acaaggactt | ccaagacaac | tctaagatta | gaatgattga | agttatgttg | 1620 |
| ccagtctttg | atgctccaca | aaacttggtt | aaacaagctc | aattgactgc | cgctactaac | 1680 |
| gctaaacaa | | | | | | 1689 |

<210> SEQ ID NO 111
<211> LENGTH: 533
<212> TYPE: PRT
<213> ORGANISM: Saccharomyces cerevisiae -continued

```
<400> SEQUENCE: 111

Met Ser Glu Ile Thr Leu Gly Lys Tyr Leu Phe Glu Arg Leu Lys Gln
1               5                   10                  15

Val Asn Val Asn Thr Ile Phe Gly Leu Pro Gly Asp Phe Asn Leu Ser
            20                  25                  30

Leu Leu Asp Lys Ile Tyr Glu Val Asp Gly Leu Arg Trp Ala Gly Asn
        35                  40                  45

Ala Asn Glu Leu Asn Ala Ala Tyr Ala Ala Asp Gly Tyr Ala Arg Ile
    50                  55                  60

Lys Gly Leu Ser Val Leu Val Thr Thr Phe Gly Val Gly Glu Leu Ser
65                  70                  75                  80

Ala Leu Asn Gly Ile Ala Gly Ser Tyr Ala Glu His Val Gly Val Leu
                85                  90                  95

His Val Val Gly Val Pro Ser Ile Ser Ala Gln Ala Lys Gln Leu Leu
            100                 105                 110

Leu His His Thr Leu Gly Asn Gly Asp Phe Thr Val Phe His Arg Met
        115                 120                 125

Ser Ala Asn Ile Ser Glu Thr Thr Ser Met Ile Thr Asp Ile Ala Thr
    130                 135                 140

Ala Pro Ser Glu Ile Asp Arg Leu Ile Arg Thr Thr Phe Ile Thr Gln
145                 150                 155                 160

Arg Pro Ser Tyr Leu Gly Leu Pro Ala Asn Leu Val Asp Leu Lys Val
                165                 170                 175

Pro Gly Ser Leu Leu Glu Lys Pro Ile Asp Leu Ser Leu Lys Pro Asn
            180                 185                 190

Asp Pro Glu Ala Glu Lys Glu Val Ile Asp Thr Val Leu Glu Leu Ile
        195                 200                 205

Gln Asn Ser Lys Asn Pro Val Ile Leu Ser Asp Ala Cys Ala Ser Arg
    210                 215                 220

His Asn Val Lys Lys Glu Thr Gln Lys Leu Ile Asp Leu Thr Gln Phe
225                 230                 235                 240

Pro Ala Phe Val Thr Pro Leu Gly Lys Gly Ser Ile Asp Glu Gln His
                245                 250                 255

Pro Arg Tyr Gly Gly Val Tyr Val Gly Thr Leu Ser Lys Gln Asp Val
            260                 265                 270

Lys Gln Ala Val Glu Ser Ala Asp Leu Ile Leu Ser Val Gly Ala Leu
        275                 280                 285

Leu Ser Asp Phe Asn Thr Gly Ser Phe Ser Tyr Ser Tyr Lys Thr Lys
    290                 295                 300

Asn Val Val Glu Phe His Ser Asp Tyr Val Lys Val Lys Asn Ala Thr
305                 310                 315                 320

Phe Leu Gly Val Gln Met Lys Phe Ala Leu Gln Asn Leu Leu Lys Val
                325                 330                 335

Ile Pro Asp Val Val Lys Gly Tyr Lys Ser Val Pro Val Pro Thr Lys
            340                 345                 350

Thr Pro Ala Asn Lys Gly Val Pro Ala Ser Thr Pro Leu Lys Gln Glu
        355                 360                 365

Trp Leu Trp Asn Glu Leu Ser Lys Phe Leu Gln Glu Gly Asp Val Ile
    370                 375                 380

Ile Ser Glu Thr Gly Thr Ser Ala Phe Gly Ile Asn Gln Thr Ile Phe
385                 390                 395                 400

Pro Lys Asp Ala Tyr Gly Ile Ser Gln Val Leu Trp Gly Ser Ile Gly
                405                 410                 415
```

```
Phe Thr Thr Gly Ala Thr Leu Gly Ala Ala Phe Ala Ala Glu Glu Ile
            420                 425                 430

Asp Pro Asn Lys Arg Val Ile Leu Phe Ile Gly Asp Gly Ser Leu Gln
        435                 440                 445

Leu Thr Val Gln Glu Ile Ser Thr Met Ile Arg Trp Gly Leu Lys Pro
    450                 455                 460

Tyr Leu Phe Val Leu Asn Asn Asp Gly Tyr Thr Ile Glu Lys Leu Ile
465                 470                 475                 480

His Gly Pro His Ala Glu Tyr Asn Glu Ile Gln Thr Trp Asp His Leu
                485                 490                 495

Ala Leu Leu Pro Ala Phe Gly Ala Lys Lys Tyr Glu Asn His Lys Ile
            500                 505                 510

Ala Thr Thr Gly Glu Trp Asp Ala Leu Thr Thr Asp Ser Glu Phe Gln
        515                 520                 525

Lys Asn Ser Val Ile
        530

<210> SEQ ID NO 112
<211> LENGTH: 1599
<212> TYPE: DNA
<213> ORGANISM: Saccharomyces cerevisiae

<400> SEQUENCE: 112
atgtctgaaa ttactcttgg aaaatactta tttgaaagat tgaagcaagt taatgttaac      60 accattttg ggctaccagg cgacttcaac ttgtccctat tggacaagat ttacgaggta      120
gatggattga gatgggctgg taatgcaaat gagctgaacg ccgcctatgc cgccgatggt     180
tacgcacgca tcaagggttt atctgtgctg gtaactactt tggcgtaggt gaattatcc     240 gccttgaatg gtattgcagg atcgtatgca gaacacgtcg gtgtactgca tgttgttggt    300
gtcccctcta tctccgctca ggctaagcaa ttgttgttgc atcatacctt gggtaacggt    360
gattttaccg ttttttcacag aatgtccgcc aatatctcag aaactacatc aatgattaca    420
gacattgcta cagcccccttc agaaatcgat aggttgatca ggacaacatt tataacacaa    480
aggcctagct acttggggtt gccagcgaat ttggtagatc taaaggttcc tggttctctt    540
ttggaaaaac cgattgatct atcattaaaa cctaacgatc ccgaagctga aaaggaagtt    600
attgataccg tactagaatt gatccagaat tcgaaaaacc ctgttatact atcggatgcc    660
tgtgcttcta ggcacaacgt taaaaagaa acccagaagt taattgattt gacgcaattc    720
ccagcttttg tgacacctct aggtaaaggg tcaatagatg aacagcatcc cagatatggc    780
ggtgtttatg tgggaacgct gtccaaacaa gacgtgaaac aggccgttga gtcggctgat    840
ttgatccttt cggtcggtgc tttgctctct gattttaaca caggttcgtt ttcctactcc    900
tacaagacta aaaatgtagt ggagtttcat tccgattacg taaaggtgaa gaacgctacg    960
ttcctcggtg tacaaatgaa atttgcacta caaaacttac tgaaggttat tcccgatgtt    1020
gttaagggct acaagagcgt tcccgtacca accaaaactc ccgcaaacaa aggtgtacct    1080
gctagcacgc ccttgaaaca agagtggttg tggaacgaat tgtccaaatt cttgcaagaa    1140
ggtgatgtta tcatttccga gaccggcacg tctgccttcg gtatcaatca aactatctt    1200 cctaaggacg cctacggtat ctcgcaggtg ttgtgggggt ccatcggttt tacaacagga    1260
gcaactttag gtgctgcctt tgccgctgag gagattgacc ccaacaagag agtcatctta    1320
ttcataggtg acgggtcttt gcagttaacc gtccaagaaa tctccaccat gatcagatgg    1380
```

```
gggttaaagc cgtatcttttt tgtccttaac aacgacggct acactatcga aaagctgatt    1440
catgggcctc acgcagagta caacgaaatc cagacctggg atcacctcgc cctgttgccc    1500
gcatttggtg cgaaaaagta cgaaaatcac aagatcgcca ctacgggtga gtgggatgcc    1560
ttaaccactg attcagagtt ccagaaaaac tcggtgatc                           1599
```

<210> SEQ ID NO 113
<211> LENGTH: 564
<212> TYPE: PRT
<213> ORGANISM: Candida glabrata

<400> SEQUENCE: 113

```
Met Ser Glu Ile Thr Leu Gly Arg Tyr Leu Phe Glu Arg Leu Asn Gln
1               5                   10                  15

Val Asp Val Lys Thr Ile Phe Gly Leu Pro Gly Asp Phe Asn Leu Ser
            20                  25                  30

Leu Leu Asp Lys Ile Tyr Glu Val Glu Gly Met Arg Trp Ala Gly Asn
        35                  40                  45

Ala Asn Glu Leu Asn Ala Ala Tyr Ala Ala Asp Gly Tyr Ala Arg Ile
    50                  55                  60

Lys Gly Met Ser Cys Ile Ile Thr Thr Phe Gly Val Gly Glu Leu Ser
65                  70                  75                  80

Ala Leu Asn Gly Ile Ala Gly Ser Tyr Ala Glu His Val Gly Val Leu
                85                  90                  95

His Val Val Gly Val Pro Ser Ile Ser Ser Gln Ala Lys Gln Leu Leu
            100                 105                 110

Leu His His Thr Leu Gly Asn Gly Asp Phe Thr Val Phe His Arg Met
        115                 120                 125

Ser Ala Asn Ile Ser Glu Thr Thr Ala Met Val Thr Asp Ile Ala Thr
    130                 135                 140

Ala Pro Ala Glu Ile Asp Arg Cys Ile Arg Thr Thr Tyr Ile Thr Gln
145                 150                 155                 160

Arg Pro Val Tyr Leu Gly Leu Pro Ala Asn Leu Val Asp Leu Lys Val
                165                 170                 175

Pro Ala Lys Leu Leu Glu Thr Pro Ile Asp Leu Ser Leu Lys Pro Asn
            180                 185                 190

Asp Pro Glu Ala Glu Thr Glu Val Val Asp Thr Val Leu Glu Leu Ile
        195                 200                 205

Lys Ala Ala Lys Asn Pro Val Ile Leu Ala Asp Ala Cys Ala Ser Arg
    210                 215                 220

His Asp Val Lys Ala Glu Thr Lys Lys Leu Ile Asp Ala Thr Gln Phe
225                 230                 235                 240

Pro Ser Phe Val Thr Pro Met Gly Lys Gly Ser Ile Asp Glu Gln His
                245                 250                 255

Pro Arg Phe Gly Gly Val Tyr Val Gly Thr Leu Ser Arg Pro Glu Val
            260                 265                 270

Lys Glu Ala Val Glu Ser Ala Asp Leu Ile Leu Ser Val Gly Ala Leu
        275                 280                 285

Leu Ser Asp Phe Asn Thr Gly Ser Phe Ser Tyr Ser Tyr Lys Thr Lys
    290                 295                 300

Asn Ile Val Glu Phe His Ser Asp Tyr Ile Lys Ile Arg Asn Ala Thr
305                 310                 315                 320

Phe Pro Gly Val Gln Met Lys Phe Ala Leu Gln Lys Leu Leu Asn Ala
                325                 330                 335
```

```
Val Pro Glu Ala Ile Lys Gly Tyr Lys Pro Val Pro Val Pro Ala Arg
            340                 345                 350

Val Pro Glu Asn Lys Ser Cys Asp Pro Ala Thr Pro Leu Lys Gln Glu
            355                 360                 365

Trp Met Trp Asn Gln Val Ser Lys Phe Leu Gln Glu Gly Asp Val Val
            370                 375             380

Ile Thr Glu Thr Gly Thr Ser Ala Phe Gly Ile Asn Gln Thr Pro Phe
385                 390                 395                 400

Pro Asn Asn Ala Tyr Gly Ile Ser Gln Val Leu Trp Gly Ser Ile Gly
                405                 410                 415

Phe Thr Thr Gly Ala Cys Leu Gly Ala Ala Phe Ala Ala Glu Glu Ile
            420                 425                 430

Asp Pro Lys Lys Arg Val Ile Leu Phe Ile Gly Asp Gly Ser Leu Gln
            435                 440                 445

Leu Thr Val Gln Glu Ile Ser Thr Met Ile Arg Trp Gly Leu Lys Pro
    450                 455                 460

Tyr Leu Phe Val Leu Asn Asn Asp Gly Tyr Thr Ile Glu Arg Leu Ile
465                 470                 475                 480

His Gly Glu Lys Ala Gly Tyr Asn Asp Ile Gln Asn Trp Asp His Leu
                485                 490                 495

Ala Leu Leu Pro Thr Phe Gly Ala Lys Asp Tyr Glu Asn His Arg Val
            500                 505                 510

Ala Thr Thr Gly Glu Trp Asp Lys Leu Thr Gln Asp Lys Glu Phe Asn
            515                 520                 525

Lys Asn Ser Lys Ile Arg Met Ile Glu Val Met Leu Pro Val Met Asp
    530                 535                 540

Ala Pro Thr Ser Leu Ile Glu Gln Ala Lys Leu Thr Ala Ser Ile Asn
545                 550                 555                 560

Ala Lys Gln Glu

<210> SEQ ID NO 114
<211> LENGTH: 1692
<212> TYPE: DNA
<213> ORGANISM: Candida glabrata

<400> SEQUENCE: 114
atgtctgaga ttactttggg tagatacttg ttcgagagat tgaaccaagt cgacgttaag      60
accatcttcg gtttgccagg tgacttcaac ttgtccctat ggacaagat  ctacgaagtt     120 gaaggtatga gatgggctgg taacgctaac gaattgaacg ctgcttacgc tgctgacggt     180
tacgctagaa tcaagggtat gtcctgtatc atcaccacct cggtgtcgg  tgaattgtct     240 gccttgaacg gtattgccgg ttcttacgct gaacacgtcg gtgtcttgca cgtcgtcggt     300
gtcccatcca tctcctctca agctaagcaa ttgttgttgc accacacctt gggtaacggt     360
gacttcactg tcttccacag aatgtccgct aacatctctg agaccaccgc tatggtcact     420
gacatcgcta ccgctccagc tgagatcgac agatgtatca gaaccaccta catcacccaa     480
agaccagtct acttgggtct accagctaac ttggtcgacc taaaggtccc agccaagctt     540
ttggaaaccc caattgactt gtccttgaag ccaaacgacc cagaagccga aactgaagtc     600
gttgacaccg tcttggaatt gatcaaggct gctaagaacc cagttatctt ggctgatgct     660
tgtgcttcca gacacgacgt caaggctgaa accaagaagt tgattgacgc cactcaattc     720
ccatccttcg ttaccccaat gggtaagggt tccatcgacg aacaacaccc aagattcggt     780
ggtgtctacg tcggtacctt gtccagacca gaagttaagg aagctgttga atccgctgac     840
```

```
ttgatcttgt ctgtcggtgc tttgttgtcc gatttcaaca ctggttcttt ctcttactct    900
tacaagacca agaacatcgt cgaattccac tctgactaca tcaagatcag aaacgctacc    960
ttcccaggtg tccaaatgaa gttcgctttg caaaagttgt tgaacgccgt cccagaagct    1020
atcaagggtt acaagccagt ccctgtccca gctagagtcc cagaaaacaa gtcctgtgac    1080
ccagctaccc cattgaagca agaatggatg tggaaccaag tttccaagtt cttgcaagaa    1140
ggtgatgttg ttatcactga aaccggtacc tccgcttttg gtatcaacca aaccccattc    1200
ccaaacaacg cttacggtat ctcccaagtt ctatggggtt ccatcggttt caccaccggt    1260
gcttgtttgg gtgccgcttt cgctgctgaa gaaatcgacc aaagaagag agttatcttg    1320 ttcattggtg acggttcttt gcaattgact gtccaagaaa tctccaccat gatcagatgg    1380
ggcttgaagc atacttgtt cgtcttgaac aacgacggtt acaccatcga agattgatt     1440 cacggtgaaa aggctggtta caacgacatc caaaactggg accacttggc tctattgcca    1500
accttcggtg ctaaggacta cgaaaaccac agagtcgcca ccaccggtga atgggacaag    1560
ttgacccaag acaaggaatt caacaagaac tccaagatca gaatgatcga agttatgttg    1620
ccagttatgg acgctccaac ttccttgatt gaacaagcta agttgaccgc ttccatcaac    1680
gctaagcaag aa                                                       1692

<210> SEQ ID NO 115
<211> LENGTH: 596
<212> TYPE: PRT
<213> ORGANISM: Pichia stipitis

<400> SEQUENCE: 115

Met Ala Glu Val Ser Leu Gly Arg Tyr Leu Phe Glu Arg Leu Tyr Gln
1               5                   10                  15

Leu Gln Val Gln Thr Ile Phe Gly Val Pro Gly Asp Phe Asn Leu Ser
            20                  25                  30

Leu Leu Asp Lys Ile Tyr Glu Val Glu Asp Ala His Gly Lys Asn Ser
        35                  40                  45

Phe Arg Trp Ala Gly Asn Ala Asn Glu Leu Asn Ala Ser Tyr Ala Ala
    50                  55                  60

Asp Gly Tyr Ser Arg Val Lys Arg Leu Gly Cys Leu Val Thr Thr Phe
65                  70                  75                  80

Gly Val Gly Glu Leu Ser Ala Leu Asn Gly Ile Ala Gly Ser Tyr Ala
                85                  90                  95

Glu His Val Gly Leu Leu His Val Gly Val Pro Ser Ile Ser Ser
            100                 105                 110

Gln Ala Lys Gln Leu Leu Leu His His Thr Leu Gly Asn Gly Asp Phe
        115                 120                 125

Thr Val Phe His Arg Met Ser Asn Asn Ile Ser Gln Thr Thr Ala Phe
    130                 135                 140

Ile Ser Asp Ile Asn Ser Ala Pro Ala Glu Ile Asp Arg Cys Ile Arg
145                 150                 155                 160

Glu Ala Tyr Val Lys Gln Arg Pro Val Tyr Ile Gly Leu Pro Ala Asn
                165                 170                 175

Leu Val Asp Leu Asn Val Pro Ala Ser Leu Leu Glu Ser Pro Ile Asn
            180                 185                 190

Leu Ser Leu Glu Lys Asn Asp Pro Glu Ala Gln Asp Glu Val Ile Asp
        195                 200                 205

Ser Val Leu Asp Leu Ile Lys Lys Ser Ser Asn Pro Ile Ile Leu Val
```

```
            210                 215                 220
Asp Ala Cys Ala Ser Arg His Asp Cys Lys Ala Glu Val Thr Gln Leu
225                 230                 235                 240

Ile Glu Gln Thr Gln Phe Pro Val Phe Val Thr Pro Met Gly Lys Gly
                245                 250                 255

Thr Val Asp Glu Gly Gly Val Asp Gly Glu Leu Leu Glu Asp Asp Pro
                260                 265                 270

His Leu Ile Ala Lys Val Ala Ala Arg Leu Ser Ala Gly Lys Asn Ala
            275                 280                 285

Ala Ser Arg Phe Gly Gly Val Tyr Val Gly Thr Leu Ser Lys Pro Glu
290                 295                 300

Val Lys Asp Ala Val Glu Ser Ala Asp Leu Ile Leu Ser Val Gly Ala
305                 310                 315                 320

Leu Leu Ser Asp Phe Asn Thr Gly Ser Phe Ser Tyr Ser Tyr Arg Thr
                325                 330                 335

Lys Asn Ile Val Glu Phe His Ser Asp Tyr Thr Lys Ile Arg Gln Ala
                340                 345                 350

Thr Phe Pro Gly Val Gln Met Lys Glu Ala Leu Gln Glu Leu Asn Lys
            355                 360                 365

Lys Val Ser Ser Ala Ala Ser His Tyr Glu Val Lys Pro Val Pro Lys
370                 375                 380

Ile Lys Leu Ala Asn Thr Pro Ala Thr Arg Glu Val Lys Leu Thr Gln
385                 390                 395                 400

Glu Trp Leu Trp Thr Arg Val Ser Ser Trp Phe Arg Glu Gly Asp Ile
                405                 410                 415

Ile Ile Thr Glu Thr Gly Thr Ser Ser Phe Gly Ile Val Gln Ser Arg
                420                 425                 430

Phe Pro Asn Asn Thr Ile Gly Ile Ser Gln Val Leu Trp Gly Ser Ile
            435                 440                 445

Gly Phe Ser Val Gly Ala Thr Leu Gly Ala Ala Met Ala Ala Gln Glu
450                 455                 460

Leu Asp Pro Asn Lys Arg Thr Ile Leu Phe Val Gly Asp Gly Ser Leu
465                 470                 475                 480

Gln Leu Thr Val Gln Glu Ile Ser Thr Ile Ile Arg Trp Gly Thr Thr
                485                 490                 495

Pro Tyr Leu Phe Val Leu Asn Asn Asp Gly Tyr Thr Ile Glu Arg Leu
            500                 505                 510

Ile His Gly Val Asn Ala Ser Tyr Asn Asp Ile Gln Pro Trp Gln Asn
            515                 520                 525

Leu Glu Ile Leu Pro Thr Phe Ser Ala Lys Asn Tyr Asp Ala Val Arg
530                 535                 540

Ile Ser Asn Ile Gly Glu Ala Glu Asp Ile Leu Lys Asp Lys Glu Phe
545                 550                 555                 560

Gly Lys Asn Ser Lys Ile Arg Leu Ile Glu Val Met Leu Pro Arg Leu
                565                 570                 575

Asp Ala Pro Ser Asn Leu Ala Lys Gln Ala Ala Ile Thr Ala Ala Thr
            580                 585                 590

Asn Ala Glu Ala
            595

<210> SEQ ID NO 116
<211> LENGTH: 1788
<212> TYPE: DNA
<213> ORGANISM: Pichia stipitis
```

<400> SEQUENCE: 116

```
atggctgaag tctcattagg aagatatctc ttcgagagat tgtaccaatt gcaagtgcag      60
accatcttcg gtgtccctgg tgatttcaac ttgtcgcttt tggacaagat ctacgaagtg     120
gaagatgccc atggcaagaa ttcgtttaga tgggctggta atgccaacga attgaatgca     180
tcgtacgctg ctgacggtta ctcgagagtc aagcgtttag ggtgtttggt cactaccttt     240
ggtgtcggtg aattgtctgc tttgaatggt attgccggtt cttatgccga acatgttggt     300
ttgcttcatg tcgtaggtgt tccatcgatt tcctcgcaag ctaagcaatt gttacttcac     360
cacactttgg gtaatggtga tttcactgtt ttccatagaa tgtccaacaa catttctcag     420
accacagcct ttatctccga tatcaactcg gctccagctg aaattgatag atgtatcaga     480
gaggcctacg tcaaacaaag accagtttat atcgggttac cagctaactt agttgatttg     540
aatgttccgg cctctttgct tgagtctcca atcaacttgt cgttggaaaa gaacgaccca     600
gaggctcaag atgaagtcat tgactctgtc ttagacttga tcaaaaagtc gctgaaccca     660
atcatcttgg tcgatgcctg tgcctcgaga catgactgta aggctgaagt tactcagttg     720
attgaacaaa cccaattccc agtatttgtc actccaatgg gtaaaggtac cgttgatgag     780
ggtggtgtag acggagaatt gttagaagat gatcctcatt tgattgccaa ggtcgctgct     840
aggttgtctg ctggcaagaa cgctgcctct agattcggag gtgtttatgt cggaaccttg     900
tcgaagcccg aagtcaagga cgctgtagag agtgcagatt tgattttgtc tgtcggtgcc     960
ctttgtctg atttcaacac tggttcattt tcctactcct acagaaccaa gaacatcgtc    1020
gaattccatt ctgattacac taagattaga caagccactt tcccaggtgt gcagatgaag    1080
gaagccttgc aagaattgaa caagaaagtt tcatctgctg ctagtcacta tgaagtcaag    1140
cctgtgccca agatcaagtt ggccaataca ccagccacca gagaagtcaa gttaactcag    1200
gaatggttgt ggaccagagt gtcttcgtgg ttcagagaag gtgatattat tatcaccgaa    1260
accggtacat cctccttcgg tatagttcaa tccagattcc caaacaacac catcggtatc    1320
tcccaagtat tgtggggttc tattggtttc tctgttggtg ccactttggg tgctgccatg    1380
gctgcccaag aactcgaccc taacaagaga accatcttgt tgttggaga tggttctttg    1440
caattgaccg ttcaggaaat ctccaccata atcagatggg gtaccacacc ttacctttc    1500
gtgttgaaca atgacggtta caccatcgag cgtttgatcc acggtgtaaa tgcctcatat    1560
aatgacatcc aaccatggca aaacttggaa atcttgccta ctttctcggc caagaactac    1620
gacgctgtga gaatctccaa catcggagaa gcagaagata tcttgaaaga caggaattc    1680
ggaaagaact ccaagattag attgatagaa gtcatgttac caagattgga tgcaccatct    1740
aaccttgcca acaagctgc cattacagct gccaccaacg ccgaagct                  1788
```

<210> SEQ ID NO 117
<211> LENGTH: 569
<212> TYPE: PRT
<213> ORGANISM: Pichia stipitis

<400> SEQUENCE: 117

```
Met Val Ser Thr Tyr Pro Glu Ser Glu Val Thr Leu Gly Arg Tyr Leu
1               5                   10                  15

Phe Glu Arg Leu His Gln Leu Lys Val Asp Thr Ile Phe Gly Leu Pro
                20                  25                  30

Gly Asp Phe Asn Leu Ser Leu Leu Asp Lys Val Tyr Glu Val Pro Asp
            35                  40                  45
```

```
Met Arg Trp Ala Gly Asn Ala Asn Glu Leu Asn Ala Ala Tyr Ala Ala
    50                  55                  60

Asp Gly Tyr Ser Arg Ile Lys Gly Leu Ser Cys Leu Val Thr Thr Phe
 65                  70                  75                  80

Gly Val Gly Glu Leu Ser Ala Leu Asn Gly Val Gly Gly Ala Tyr Ala
                 85                  90                  95

Glu His Val Gly Leu Leu His Val Val Gly Val Pro Ser Ile Ser Ser
                100                 105                 110

Gln Ala Lys Gln Leu Leu Leu His His Thr Leu Gly Asn Gly Asp Phe
            115                 120                 125

Thr Val Phe His Arg Met Ser Asn Ser Ile Ser Gln Thr Thr Ala Phe
            130                 135                 140

Leu Ser Asp Ile Ser Ile Ala Pro Gly Gln Ile Asp Arg Cys Ile Arg
145                 150                 155                 160

Glu Ala Tyr Val His Gln Arg Pro Val Tyr Val Gly Leu Pro Ala Asn
                165                 170                 175

Met Val Asp Leu Lys Val Pro Ser Ser Leu Leu Glu Thr Pro Ile Asp
            180                 185                 190

Leu Lys Leu Lys Gln Asn Asp Pro Glu Ala Gln Glu Val Val Glu Thr
            195                 200                 205

Val Leu Lys Leu Val Ser Gln Ala Thr Asn Pro Ile Ile Leu Val Asp
210                 215                 220

Ala Cys Ala Leu Arg His Asn Cys Lys Glu Glu Val Lys Gln Leu Val
225                 230                 235                 240

Asp Ala Thr Asn Phe Gln Val Phe Thr Thr Pro Met Gly Lys Ser Gly
                245                 250                 255

Ile Ser Glu Ser His Pro Arg Leu Gly Gly Val Tyr Val Gly Thr Met
                260                 265                 270

Ser Ser Pro Gln Val Lys Lys Ala Val Glu Asn Ala Asp Leu Ile Leu
            275                 280                 285

Ser Val Gly Ser Leu Leu Ser Asp Phe Asn Thr Gly Ser Phe Ser Tyr
            290                 295                 300

Ser Tyr Lys Thr Lys Asn Val Val Glu Phe His Ser Asp Tyr Met Lys
305                 310                 315                 320

Ile Arg Gln Ala Thr Phe Pro Gly Val Gln Met Lys Glu Ala Leu Gln
                325                 330                 335

Gln Leu Ile Lys Arg Val Ser Ser Tyr Ile Asn Pro Ser Tyr Ile Pro
            340                 345                 350

Thr Arg Val Pro Lys Arg Lys Gln Pro Leu Lys Ala Pro Ser Glu Ala
            355                 360                 365

Pro Leu Thr Gln Glu Tyr Leu Trp Ser Lys Val Ser Gly Trp Phe Arg
370                 375                 380

Glu Gly Asp Ile Ile Val Thr Glu Thr Gly Thr Ser Ala Phe Gly Ile
385                 390                 395                 400

Ile Gln Ser His Phe Pro Ser Asn Thr Ile Gly Ile Ser Gln Val Leu
                405                 410                 415

Trp Gly Ser Ile Gly Phe Thr Val Gly Ala Thr Val Gly Ala Ala Met
            420                 425                 430

Ala Ala Gln Glu Ile Asp Pro Ser Arg Arg Val Ile Leu Phe Val Gly
            435                 440                 445

Asp Gly Ser Leu Gln Leu Thr Val Gln Glu Ile Ser Thr Leu Cys Lys
450                 455                 460
```

```
Trp Asp Cys Asn Asn Thr Tyr Leu Tyr Val Leu Asn Asn Asp Gly Tyr
465                 470                 475                 480

Thr Ile Glu Arg Leu Ile His Gly Lys Ser Ala Ser Tyr Asn Asp Ile
            485                 490                 495

Gln Pro Trp Asn His Leu Ser Leu Leu Arg Leu Phe Asn Ala Lys Lys
                500                 505                 510

Tyr Gln Asn Val Arg Val Ser Thr Ala Gly Glu Leu Asp Ser Leu Phe
            515                 520                 525

Ser Asp Lys Lys Phe Ala Ser Pro Asp Arg Ile Arg Met Ile Glu Val
            530                 535                 540

Met Leu Ser Arg Leu Asp Ala Pro Ala Asn Leu Val Ala Gln Ala Lys
545                 550                 555                 560

Leu Ser Glu Arg Val Asn Leu Glu Asn
                565

<210> SEQ ID NO 118
<211> LENGTH: 1707
<212> TYPE: DNA
<213> ORGANISM: Pichia stipitis

<400> SEQUENCE: 118
atggtatcaa cctacccaga tcagaggtt actctaggaa ggtacctctt tgagcgactc     60
caccaattga agtggacac cattttcggc ttgccgggtg acttcaacct ttccttattg    120
gacaaagtgt atgaagttcc ggatatgagg tgggctggaa atgccaacga attgaatgct    180
gcctatgctg ccgatggtta ctccagaata aagggattgt cttgcttggt cacaactttt    240
ggtgttggtg aattgtctgc tttaaacgga gttggtggtg cctatgctga acacgtagga    300
cttctacatg tcgttggagt tccatccata tcgtcacagg ctaaacagtt gttgctccac    360 catacctgg gtaatggtga cttcactgtt tttcacagaa tgtccaatag catttctcaa    420
actacagcat ttctctcaga tatctctatt gcaccaggtc aaatagatag atgcatcaga    480
gaagcatatg ttcatcagag accagtttat gttggtttac cggcaaatat ggttgatctc    540
aaggttcctt ctagtctctt agaaactcca attgatttga aattgaaaca aaatgatcct    600
gaagctcaag aagttgttga acagtcctg aagttggtgt cccaagctac aaaccccatt    660
atcttggtag acgcttgtgc cctcagacac aattgcaaag aggaagtcaa acaattggtt    720
gatgccacta ttttcaagt ctttacaact ccaatgggta atctggtat ctccgaatct    780 catccaagat tgggcggtgt ctatgtcggg acaatgtcga gtcctcaagt caaaaaagcc    840
gttgaaaatg ccgatcttat actatctgtt ggttcgttgt tatcggactt caatacaggt    900
tcattttcat actcctacaa gacgaagaat gttgttgaat ccactctga ctatatgaaa    960 atcagacagg ccaccttccc aggagttcaa atgaaagaag ccttgcaaca gttgataaaa   1020
agggtctctt cttacatcaa tccaagctac attcctactc gagttcctaa aggaaacag   1080 ccattgaaag ctccatcaga agctcctttg acccaagaat atttgtggtc taaagtatcc   1140
ggctggttta gagagggtga tattatcgta accgaaactg gtacatctgc tttcggaatt   1200
attcaatccc attttcccag caacactatc ggtatatccc aagtcttgtg gggctcaatt   1260
ggtttcacag taggtgcaac agttggtgct gccatggcag cccaggaaat cgaccctagc   1320
aggagagtaa ttttgttcgt cggtgatggt tcattgcagt tgacggttca ggaaatctct   1380
acgttgtgta atgggattg taacaatact tatctttacg tgttgaacaa tgatggttac   1440
actatagaaa ggttgatcca cggcaaaagt gccagctaca acgatataca gccttggaac   1500
```

```
catttatcct tgcttcgctt attcaatgct aagaaatacc aaaatgtcag agtatcgact    1560
gctggagaat tggactcttt gttctctgat aagaaatttg cttctccaga taggataaga    1620
atgattgagg tgatgttatc gagattggat gcaccagcaa atcttgttgc tcaagcaaag    1680
ttgtctgaac gggtaaacct tgaaaat                                       1707
```

<210> SEQ ID NO 119
<211> LENGTH: 563
<212> TYPE: PRT
<213> ORGANISM: Kluyveromyces lactis

<400> SEQUENCE: 119

```
Met Ser Glu Ile Thr Leu Gly Arg Tyr Leu Phe Glu Arg Leu Lys Gln
1               5                   10                  15

Val Glu Val Gln Thr Ile Phe Gly Leu Pro Gly Asp Phe Asn Leu Ser
            20                  25                  30

Leu Leu Asp Asn Ile Tyr Glu Val Pro Gly Met Arg Trp Ala Gly Asn
        35                  40                  45

Ala Asn Glu Leu Asn Ala Ala Tyr Ala Ala Asp Gly Tyr Ala Arg Leu
    50                  55                  60

Lys Gly Met Ser Cys Ile Ile Thr Thr Phe Gly Val Gly Glu Leu Ser
65                  70                  75                  80

Ala Leu Asn Gly Ile Ala Gly Ser Tyr Ala Glu His Val Gly Val Leu
                85                  90                  95

His Val Val Gly Val Pro Ser Val Ser Ser Gln Ala Lys Gln Leu Leu
            100                 105                 110

Leu His His Thr Leu Gly Asn Gly Asp Phe Thr Val Phe His Arg Met
        115                 120                 125

Ser Ser Asn Ile Ser Glu Thr Thr Ala Met Ile Thr Asp Ile Asn Thr
    130                 135                 140

Ala Pro Ala Glu Ile Asp Arg Cys Ile Arg Thr Thr Tyr Val Ser Gln
145                 150                 155                 160

Arg Pro Val Tyr Leu Gly Leu Pro Ala Asn Leu Val Asp Leu Thr Val
                165                 170                 175

Pro Ala Ser Leu Leu Asp Thr Pro Ile Asp Leu Ser Leu Lys Pro Asn
            180                 185                 190

Asp Pro Glu Ala Glu Glu Val Ile Glu Asn Val Leu Gln Leu Ile
        195                 200                 205

Lys Glu Ala Lys Asn Pro Val Ile Leu Ala Asp Ala Cys Cys Ser Arg
    210                 215                 220

His Asp Ala Lys Ala Glu Thr Lys Lys Leu Ile Asp Leu Thr Gln Phe
225                 230                 235                 240

Pro Ala Phe Val Thr Pro Met Gly Lys Gly Ser Ile Asp Glu Lys His
                245                 250                 255

Pro Arg Phe Gly Gly Val Tyr Val Gly Thr Leu Ser Ser Pro Ala Val
            260                 265                 270

Lys Glu Ala Val Glu Ser Ala Asp Leu Val Leu Ser Val Gly Ala Leu
        275                 280                 285

Leu Ser Asp Phe Asn Thr Gly Ser Phe Ser Tyr Ser Tyr Lys Thr Lys
    290                 295                 300

Asn Ile Val Glu Phe His Ser Asp Tyr Thr Lys Ile Arg Ser Ala Thr
305                 310                 315                 320

Phe Pro Gly Val Gln Met Lys Phe Ala Leu Gln Lys Leu Leu Thr Lys
                325                 330                 335
```

```
Val Ala Asp Ala Ala Lys Gly Tyr Lys Pro Val Pro Val Pro Ser Glu
            340                 345                 350

Pro Glu His Asn Glu Ala Val Ala Asp Ser Thr Pro Leu Lys Gln Glu
        355                 360                 365

Trp Val Trp Thr Gln Val Gly Glu Phe Leu Arg Glu Gly Asp Val Val
    370                 375                 380

Ile Thr Glu Thr Gly Thr Ser Ala Phe Gly Ile Asn Gln Thr His Phe
385                 390                 395                 400

Pro Asn Asn Thr Tyr Gly Ile Ser Gln Val Leu Trp Gly Ser Ile Gly
                405                 410                 415

Phe Thr Thr Gly Ala Thr Leu Gly Ala Ala Phe Ala Ala Glu Glu Ile
            420                 425                 430

Asp Pro Lys Lys Arg Val Ile Leu Phe Ile Gly Asp Gly Ser Leu Gln
        435                 440                 445

Leu Thr Val Gln Glu Ile Ser Thr Met Ile Arg Trp Gly Leu Lys Pro
    450                 455                 460

Tyr Leu Phe Val Leu Asn Asn Asp Gly Tyr Thr Ile Glu Arg Leu Ile
465                 470                 475                 480

His Gly Glu Thr Ala Gln Tyr Asn Cys Ile Gln Asn Trp Gln His Leu
                485                 490                 495

Glu Leu Leu Pro Thr Phe Gly Ala Lys Asp Tyr Glu Ala Val Arg Val
            500                 505                 510

Ser Thr Thr Gly Glu Trp Asn Lys Leu Thr Thr Asp Glu Lys Phe Gln
        515                 520                 525

Asp Asn Thr Arg Ile Arg Leu Ile Glu Val Met Leu Pro Thr Met Asp
    530                 535                 540

Ala Pro Ser Asn Leu Val Lys Gln Ala Gln Leu Thr Ala Ala Thr Asn
545                 550                 555                 560

Ala Lys Asn

<210> SEQ ID NO 120
<211> LENGTH: 1689
<212> TYPE: DNA
<213> ORGANISM: Kluyveromyces lactis

<400> SEQUENCE: 120
atgtctgaaa ttacattagg tcgttacttg ttcgaaagat taaagcaagt cgaagttcaa      60
accatctttg gtctaccagg tgatttcaac ttgtccctat ggacaatat ctacgaagtc      120 ccaggtatga gatgggctgg taatgccaac gaattgaacg ctgcttacgc tgctgatggt      180
tacgccagat taagggtat gtcctgtatc atcaccacct tcggtgtcgg tgaattgtct      240
gctttgaacg gtattgccgg ttcttacgct gaacacgttg gtgtcttgca cgttgtcggt      300
gttccatccg tctcttctca agctaagcaa ttgttgttgc accacacctt gggtaacggt      360
gacttcactg ttttccacag aatgtcctcc aacatttctg aaaccactgc tatgatcacc      420
gatatcaaca ctgccccagc tgaaatcgac agatgtatca gaaccactta cgtttcccaa      480
agaccagtct acttgggttt gccagctaac ttggtcgact tgactgtccc agcttctttg      540
ttggacactc caattgattt gagcttgaag ccaaatgacc agaagccga agaagaagtc      600 atcgaaaacg tcttgcaact gatcaaggaa gctaagaacc cagttatctt ggctgatgct      660
tgttgttcca gacacgatgc caaggctgag accaagaagt tgatcgactt gactcaattc      720
ccagccttcg ttacccccaat gggtaagggt tccattgaca aaaagcaccc aagattcggt      780
ggtgtctacg tcggtaccct atcttctcca gctgtcaagg aagccgttga atctgctgac      840
```

```
ttggttctat cggtcggtgc tctattgtcc gatttcaaca ctggttcttt ctcttactct    900
tacaagacca agaacattgt cgaattccac tctgactaca ccaagatcag aagcgctacc    960
ttcccaggtg tccaaatgaa gttcgcttta caaaaattgt tgactaaggt tgccgatgct   1020
gctaagggtt acaagccagt tccagttcca tctgaaccag aacacaacga agctgtcgct   1080
gactccactc cattgaagca agaatgggtc tggactcaag tcggtgaatt cttgagagaa   1140
ggtgatgttg ttatcactga aaccggtacc tctgccttcg gtatcaacca aactcatttc   1200
ccaaacaaca catacggtat ctctcaagtt ttatggggtt ccattggttt caccactggt   1260
gctaccttgg gtgctgcctt cgctgccgaa gaaattgatc aaagaagag agttatctta   1320 ttcattggtg acggttcttt gcaattgact gttcaagaaa tctccaccat gatcagatgg   1380
ggcttgaagc atacttgtt cgtattgaac aacgacggtt acaccattga aagattgatt   1440
cacggtgaaa ccgctcaata caactgtatc caaaactggc aacacttgga attattgcca   1500
actttcggtg ccaaggacta cgaagctgtc agagtttcca ccactggtga atggaacaag   1560
ttgaccactg acgaaaagtt ccaagacaac accagaatca gattgatcga agttatgttg   1620
ccaactatgg atgctccatc taacttggtt aagcaagctc aattgactgc tgctaccaac   1680
gctaagaac                                                          1689
```

<210> SEQ ID NO 121
<211> LENGTH: 571
<212> TYPE: PRT
<213> ORGANISM: Yarrowia lipolytica

<400> SEQUENCE: 121

```
Met Ser Asp Ser Glu Pro Gln Met Val Asp Leu Gly Asp Tyr Leu Phe
1               5                   10                  15

Ala Arg Phe Lys Gln Leu Gly Val Asp Ser Val Phe Gly Val Pro Gly
                20                  25                  30

Asp Phe Asn Leu Thr Leu Leu Asp His Val Tyr Asn Val Asp Met Arg
            35                  40                  45

Trp Val Gly Asn Thr Asn Glu Leu Asn Ala Gly Tyr Ser Ala Asp Gly
        50                  55                  60

Tyr Ser Arg Val Lys Arg Leu Ala Cys Leu Val Thr Thr Phe Gly Val
65                  70                  75                  80

Gly Glu Leu Ser Ala Val Ala Val Ala Gly Ser Tyr Ala Glu His
                85                  90                  95

Val Gly Val Val His Val Gly Val Pro Ser Thr Ser Ala Glu Asn
                100                 105                 110

Lys His Leu Leu Leu His His Thr Leu Gly Asn Gly Asp Phe Arg Val
            115                 120                 125

Phe Ala Gln Met Ser Lys Leu Ile Ser Glu Tyr Thr His His Ile Glu
        130                 135                 140

Asp Pro Ser Glu Ala Ala Asp Val Ile Asp Thr Ala Ile Arg Ile Ala
145                 150                 155                 160

Tyr Thr His Gln Arg Pro Val Tyr Ile Ala Val Pro Ser Asn Phe Ser
                165                 170                 175

Glu Val Asp Ile Ala Asp Gln Ala Arg Leu Asp Thr Pro Leu Asp Leu
            180                 185                 190

Ser Leu Gln Pro Asn Asp Pro Glu Ser Gln Tyr Glu Val Ile Glu Glu
        195                 200                 205

Ile Cys Ser Arg Ile Lys Ala Ala Lys Lys Pro Val Ile Leu Val Asp
```

```
                         210                 215                 220
Ala Cys Ala Ser Arg Tyr Arg Cys Val Asp Glu Thr Lys Glu Leu Ala
225                 230                 235                 240

Lys Ile Thr Asn Phe Ala Tyr Phe Val Thr Pro Met Gly Lys Gly Ser
                245                 250                 255

Val Asp Glu Asp Thr Asp Arg Tyr Gly Thr Tyr Val Gly Ser Leu
            260                 265                 270

Thr Ala Pro Ala Thr Ala Glu Val Val Glu Thr Ala Asp Leu Ile Ile
            275                 280                 285

Ser Val Gly Ala Leu Leu Ser Asp Phe Asn Thr Gly Ser Phe Ser Tyr
290                 295                 300

Ser Tyr Ser Thr Lys Asn Val Val Glu Leu His Ser Asp His Val Lys
305                 310                 315                 320

Ile Lys Ser Ala Thr Tyr Asn Asn Val Gly Met Lys Met Leu Phe Pro
                325                 330                 335

Pro Leu Leu Glu Ala Val Lys Lys Leu Val Ala Glu Thr Pro Asp Phe
            340                 345                 350

Ala Ser Lys Ala Leu Ala Val Pro Asp Thr Thr Pro Lys Ile Pro Glu
            355                 360                 365

Val Pro Asp Asp His Ile Thr Thr Gln Ala Trp Leu Trp Gln Arg Leu
            370                 375                 380

Ser Tyr Phe Leu Arg Pro Thr Asp Ile Val Val Thr Glu Thr Gly Thr
385                 390                 395                 400

Ser Ser Phe Gly Ile Ile Gln Thr Lys Phe Pro His Asn Val Arg Gly
                405                 410                 415

Ile Ser Gln Val Leu Trp Gly Ser Ile Gly Tyr Ser Val Gly Ala Ala
            420                 425                 430

Cys Gly Ala Ser Ile Ala Ala Gln Glu Ile Asp Pro Gln Gln Arg Val
            435                 440                 445

Ile Leu Phe Val Gly Asp Gly Ser Leu Gln Leu Thr Val Thr Glu Ile
            450                 455                 460

Ser Cys Met Ile Arg Asn Asn Val Lys Pro Tyr Ile Phe Val Leu Asn
465                 470                 475                 480

Asn Asp Gly Tyr Thr Ile Glu Arg Leu Ile His Gly Glu Asn Ala Ser
                485                 490                 495

Tyr Asn Asp Val His Met Trp Lys Tyr Ser Lys Ile Leu Asp Thr Phe
            500                 505                 510

Asn Ala Lys Ala His Glu Ser Ile Val Asn Thr Lys Gly Glu Met
            515                 520                 525

Asp Ala Leu Phe Asp Asn Glu Glu Phe Ala Lys Pro Asp Lys Ile Arg
530                 535                 540

Leu Ile Glu Val Met Cys Asp Lys Met Asp Ala Pro Ala Ser Leu Ile
545                 550                 555                 560

Lys Gln Ala Glu Leu Ser Ala Lys Thr Asn Val
                565                 570

<210> SEQ ID NO 122
<211> LENGTH: 1713
<212> TYPE: DNA
<213> ORGANISM: Yarrowia lipolytica

<400> SEQUENCE: 122
atgagcgact ccgaacccca aatggtcgac ctgggcgact atctctttgc ccgattcaag    60
cagctaggcg tggactccgt ctttggagtg cccggcgact caacctcac cctgttggac   120
```

```
cacgtgtaca atgtcgacat gcggtgggtt gggaacacaa acgagctgaa tgccggctac      180
tcggccgacg gctactcccg ggtcaagcgg ctggcatgtc ttgtcaccac ctttggcgtg      240
ggagagctgt ctgccgtggc tgctgtggca ggctcgtacg ccgagcatgt gggcgtggtg      300
catgttgtgg gcgttcccag cacctctgct gagaacaagc atctgctgct gcaccacaca      360
ctcggtaacg gcgacttccg ggtctttgcc cagatgtcca aactcatctc cgagtacacc      420
caccatattg aggaccccag cgaggctgcc gacgtaatcg acaccgccat cgaatcgcc       480 tacacccacc agcggcccgt ttacattgct gtgccctcca acttctccga ggtcgatatt      540
gccgaccagg ctagactgga tacccccctg gacctttcgc tgcagcccaa cgaccccgag      600
agccagtacg aggtgattga ggagatttgc tcgcgtatca aggccgccaa gaagcccgtg      660
attctcgtcg acgcctgcgc ttcgcgatac agatgtgtgg acgagaccaa ggagctggcc      720
aagatcacca actttgccta ctttgtcact cccatgggta agggttctgt ggacgaggat      780
actgaccggt acgaggagaac atacgtcgga tcgctgactg ctcctgctac tgccgaggtg      840
gttgagacag ctgatctcat catctccgta ggagctcttc tgtcggactt caacaccggt      900
tccttctcgt actcctactc caccaaaaac gtggtggaat tgcattcgga ccacgtcaaa      960
atcaagtccg ccacctacaa caacgtcggc atgaaaatgc tgttcccgcc cctgctcgaa     1020
gccgtcaaga aactggttgc cgagacccct gactttgcat ccaaggctct ggctgttccc     1080
gacaccactc ccaagatccc cgaggtaccc gatgatcaca ttacgaccca ggcatggctg     1140
tggcagcgtc tcagttactt tctgaggccc accgacatcg tggtcaccga gaccggaacc     1200
tcgtcctttg gaatcatcca gaccaagttc ccccacaacg tccgaggtat ctcgcaggtg     1260
ctgtggggct ctattggata ctcggtggga gcagcctgtg gagcctccat tgctgcacag     1320
gagattgacc cccagcagcg agtgattctg tttgtgggcg acggctctct tcagctgacg     1380
gtgaccgaga tctcgtgcat gatccgcaac aacgtcaagc cgtacatttt tgtgctcaac     1440
aacgacggct acaccatcga gaggctcatt cacggcgaaa acgcctcgta caacgatgtg     1500
cacatgtgga agtactccaa gattctcgac acgttcaacg ccaaggccca cgagtcgatt     1560
gtggtcaaca ccaagggcga gatggacgct ctgttcgaca cgaagagtt tgccaagccc     1620 gacaagatcc ggctcattga ggtcatgtgc gacaagatgg acgcgcctgc ctcgttgatc     1680
aagcaggctg agctctctgc caagaccaac gtt                                  1713
```

<210> SEQ ID NO 123
<211> LENGTH: 571
<212> TYPE: PRT
<213> ORGANISM: Schizosaccharomyces pombe

<400> SEQUENCE: 123

Met Ser Gly Asp Ile Leu Val Gly Glu Tyr Leu Phe Lys Arg Leu Glu
1               5                   10                  15

Gln Leu Gly Val Lys Ser Ile Leu Gly Val Pro Gly Asp Phe Asn Leu
            20                  25                  30

Ala Leu Leu Asp Leu Ile Glu Lys Val Gly Asp Glu Lys Phe Arg Trp
        35                  40                  45

Val Gly Asn Thr Asn Glu Leu Asn Gly Ala Tyr Ala Ala Asp Gly Tyr
    50                  55                  60

Ala Arg Val Asn Gly Leu Ser Ala Ile Val Thr Thr Phe Gly Val Gly
65                  70                  75                  80

Glu Leu Ser Ala Ile Asn Gly Val Ala Gly Ser Tyr Ala Glu His Val

```
                    85                  90                  95
Pro Val Val His Ile Val Gly Met Pro Ser Thr Lys Val Gln Asp Thr
            100                 105                 110

Gly Ala Leu Leu His His Thr Leu Gly Asp Gly Asp Phe Arg Thr Phe
            115                 120                 125

Met Asp Met Phe Lys Lys Val Ser Ala Tyr Ser Ile Met Ile Asp Asn
        130                 135                 140

Gly Asn Asp Ala Ala Glu Lys Ile Asp Glu Ala Leu Ser Ile Cys Tyr
145                 150                 155                 160

Lys Lys Ala Arg Pro Val Tyr Ile Gly Ile Pro Ser Asp Ala Gly Tyr
                165                 170                 175

Phe Lys Ala Ser Ser Ser Asn Leu Gly Lys Arg Leu Lys Leu Glu Glu
                180                 185                 190

Asp Thr Asn Asp Pro Ala Val Glu Gln Glu Val Ile Asn His Ile Ser
            195                 200                 205

Glu Met Val Val Asn Ala Lys Lys Pro Val Ile Leu Ile Asp Ala Cys
        210                 215                 220

Ala Val Arg His Arg Val Val Pro Glu Val His Glu Leu Ile Lys Leu
225                 230                 235                 240

Thr His Phe Pro Thr Tyr Val Thr Pro Met Gly Lys Ser Ala Ile Asp
                245                 250                 255

Glu Thr Ser Gln Phe Phe Asp Gly Val Tyr Val Gly Ser Ile Ser Asp
            260                 265                 270

Pro Glu Val Lys Asp Arg Ile Glu Ser Thr Asp Leu Leu Leu Ser Ile
        275                 280                 285

Gly Ala Leu Lys Ser Asp Phe Asn Thr Gly Ser Phe Ser Tyr His Leu
        290                 295                 300

Ser Gln Lys Asn Ala Val Glu Phe His Ser Asp His Met Arg Ile Arg
305                 310                 315                 320

Tyr Ala Leu Tyr Pro Asn Val Ala Met Lys Tyr Ile Leu Arg Lys Leu
                325                 330                 335

Leu Lys Val Leu Asp Ala Ser Met Cys His Ser Lys Ala Ala Pro Thr
                340                 345                 350

Ile Gly Tyr Asn Ile Lys Pro Lys His Ala Glu Gly Tyr Ser Ser Asn
            355                 360                 365

Glu Ile Thr His Cys Trp Phe Trp Pro Lys Phe Ser Glu Phe Leu Lys
        370                 375                 380

Pro Arg Asp Val Leu Ile Thr Glu Thr Gly Thr Ala Asn Phe Gly Val
385                 390                 395                 400

Leu Asp Cys Arg Phe Pro Lys Asp Val Thr Ala Ile Ser Gln Val Leu
                405                 410                 415

Trp Gly Ser Ile Gly Tyr Ser Val Gly Ala Met Phe Gly Ala Val Leu
            420                 425                 430

Ala Val His Asp Ser Lys Glu Pro Asp Arg Arg Thr Ile Leu Val Val
        435                 440                 445

Gly Asp Gly Ser Leu Gln Leu Thr Ile Thr Glu Ile Ser Thr Cys Ile
        450                 455                 460

Arg His Asn Leu Lys Pro Ile Ile Phe Ile Ile Asn Asn Asp Gly Tyr
465                 470                 475                 480

Thr Ile Glu Arg Leu Ile His Gly Leu His Ala Ser Tyr Asn Glu Ile
                485                 490                 495

Asn Thr Lys Trp Gly Tyr Gln Gln Ile Pro Lys Phe Phe Gly Ala Ala
            500                 505                 510
```

Glu Asn His Phe Arg Thr Tyr Cys Val Lys Thr Pro Thr Asp Val Glu
        515                 520                 525

Lys Leu Phe Ser Asp Lys Glu Phe Ala Asn Ala Asp Val Ile Gln Val
        530                 535                 540

Val Glu Leu Val Met Pro Met Leu Asp Ala Pro Arg Val Leu Val Glu
545                 550                 555                 560

Gln Ala Lys Leu Thr Ser Lys Ile Asn Lys Gln
            565                 570

<210> SEQ ID NO 124
<211> LENGTH: 1713
<212> TYPE: DNA
<213> ORGANISM: Schizosaccharomyces pombe

<400> SEQUENCE: 124

| | |
|---|---:|
| atgagtgggg atattttagt cggtgaatat ctattcaaaa ggcttgaaca attaggggtc | 60 |
| aagtccattc ttggtgttcc aggagatttc aatttagctc tacttgactt aattgagaaa | 120 |
| gttggagatg agaaatttcg ttgggttggc ataccaatg agttgaatgg tgcttatgcc | 180 |
| gctgatggtt atgctcgtgt taatggtctt tcagccattg ttacaacgtt cggcgtggga | 240 |
| gagctttccg ctattaatgg agtggcaggt tcttatgcgg agcatgtccc agtagttcat | 300 |
| attgttggaa tgccttccac aaaggtgcaa gatactggag ctttgcttca tcatacttta | 360 |
| ggagatggag actttcgcac tttcatggat atgtttaaga agtttctgc ctacagtata | 420 |
| atgatcgata acgaaacga tgcagctgaa aagatcgatg aagccttgtc gatttgttat | 480 |
| aaaaaggcta ggcctgttta cattggtatt ccttctgatg ctggctactt caaagcatct | 540 |
| tcatcaaatc ttgggaaaag actaaagctc gaggaggata ctaacgatcc agcagttgag | 600 |
| caagaagtca tcaatcatat ctcggaaatg gttgtcaatg caaagaaacc agtgatttta | 660 |
| attgacgctt gtgctgtaag acatcgtgtc gttccagaag tacatgagct gattaaattg | 720 |
| acccatttcc ctacatatgt aactcccatg ggtaaatctg caattgacga aacttcgcaa | 780 |
| tttttttgacg gcgtttatgt tggttcaatt tcagatcctg aagttaaaga cagaattgaa | 840 |
| tccactgatc tgttgctatc catcggtgct ctcaaatcag actttaacac gggttccttc | 900 |
| tcttaccacc tcagccaaaa gaatgccgtt gagtttcatt cagaccacat gcgcattcga | 960 |
| tatgctcttt atccaaatgt agccatgaag tatattcttc gcaaactgtt gaaagtactt | 1020 |
| gatgcttcta tgtgtcattc caaggctgct cctaccattg ctacaacat caagcctaag | 1080 |
| catgcggaag atattcttc aacgagatt actcattgct ggttttggcc taaatttagt | 1140 |
| gaattttga gccccgaga tgttttgatc accgagactg gaactgcaaa ctttggtgtc | 1200 |
| cttgattgca ggtttccaaa ggatgtaaca gccatttccc aggtattatg gggatctatt | 1260 |
| ggatactccg ttggtgcaat gtttggtgct gttttggccg tccacgattc taaagagccc | 1320 |
| gatcgtcgta ccattcttgt agtaggtgat ggatccttac aactgacgat tacagagatt | 1380 |
| tcaacctgca ttcgccataa cctcaaacca attattttca taattaacaa cgacggttac | 1440 |
| accattgagc gtttaattca tggttttgcat gctagctata acgaaattaa cactaaatgg | 1500 |
| ggctaccaac agattcccaa gttttcgga gctgctgaaa accacttccg cacttactgt | 1560 |
| gttaaaactc ctactgacgt tgaaaagttg tttagcgaca aggagtttgc aaatgcagat | 1620 |
| gtcattcaag tagttgagct tgtaatgcct atgttggatg cacctcgtgt cctagttgag | 1680 |
| caagccaagt tgacgtctaa gatcaataag caa | 1713 |

<210> SEQ ID NO 125
<211> LENGTH: 563
<212> TYPE: PRT
<213> ORGANISM: Zygosaccharomyces rouxii

<400> SEQUENCE: 125

```
Met Ser Glu Ile Thr Leu Gly Arg Tyr Leu Phe Glu Arg Leu Lys Gln
1               5                   10                  15

Val Asp Thr Asn Thr Ile Phe Gly Val Pro Gly Asp Phe Asn Leu Ser
            20                  25                  30

Leu Leu Asp Lys Val Tyr Glu Val Gln Gly Leu Arg Trp Ala Gly Asn
        35                  40                  45

Ala Asn Glu Leu Asn Ala Ala Tyr Ala Ala Asp Gly Tyr Ala Arg Val
    50                  55                  60

Lys Gly Leu Ala Ala Leu Ile Thr Thr Phe Gly Val Gly Glu Leu Ser
65                  70                  75                  80

Ala Leu Asn Gly Ile Ala Gly Ser Tyr Ala Glu His Val Gly Val Leu
                85                  90                  95

His Ile Val Gly Val Pro Ser Val Ser Ser Gln Ala Lys Gln Leu Leu
            100                 105                 110

Leu His His Thr Leu Gly Asn Gly Asp Phe Thr Val Phe His Arg Met
        115                 120                 125

Ser Ala Asn Ile Ser Glu Thr Thr Ala Met Leu Thr Asp Ile Thr Ala
    130                 135                 140

Ala Pro Ala Glu Ile Asp Arg Cys Ile Arg Val Ala Tyr Val Asn Gln
145                 150                 155                 160

Arg Pro Val Tyr Leu Gly Leu Pro Ala Asn Leu Val Asp Gln Lys Val
                165                 170                 175

Pro Ala Ser Leu Leu Asn Thr Pro Ile Asp Leu Ser Leu Lys Glu Asn
            180                 185                 190

Asp Pro Glu Ala Glu Thr Glu Val Val Asp Thr Val Leu Glu Leu Ile
        195                 200                 205

Lys Glu Ala Lys Asn Pro Val Ile Leu Ala Asp Ala Cys Cys Ser Arg
    210                 215                 220

His Asp Val Lys Ala Glu Thr Lys Lys Leu Ile Asp Leu Thr Gln Phe
225                 230                 235                 240

Pro Ser Phe Val Thr Pro Met Gly Lys Gly Ser Ile Asp Glu Gln Asn
                245                 250                 255

Pro Arg Phe Gly Gly Val Tyr Val Gly Thr Leu Ser Ser Pro Glu Val
            260                 265                 270

Lys Glu Ala Val Glu Ser Ala Asp Leu Val Leu Ser Val Gly Ala Leu
        275                 280                 285

Leu Ser Asp Phe Asn Thr Gly Ser Phe Ser Tyr Ser Tyr Lys Thr Lys
    290                 295                 300

Asn Val Val Glu Phe His Ser Asp His Ile Lys Ile Arg Asn Ala Thr
305                 310                 315                 320

Phe Pro Gly Val Gln Met Lys Phe Val Leu Lys Lys Leu Leu Gln Ala
                325                 330                 335

Val Pro Glu Ala Val Lys Asn Tyr Lys Pro Gly Pro Val Pro Ala Pro
            340                 345                 350

Pro Ser Pro Asn Ala Glu Val Ala Asp Ser Thr Thr Leu Lys Gln Glu
        355                 360                 365

Trp Leu Trp Arg Gln Val Gly Ser Phe Leu Arg Glu Gly Asp Val Val
    370                 375                 380
```

Ile Thr Glu Thr Gly Thr Ser Ala Phe Gly Ile Asn Gln Thr His Phe
385                 390                 395                 400

Pro Asn Gln Thr Tyr Gly Ile Ser Gln Val Leu Trp Gly Ser Ile Gly
            405                 410                 415

Tyr Thr Thr Gly Ser Thr Leu Gly Ala Ala Phe Ala Ala Glu Glu Ile
        420                 425                 430

Asp Pro Lys Lys Arg Val Ile Leu Phe Ile Gly Asp Gly Ser Leu Gln
    435                 440                 445

Leu Thr Val Gln Glu Ile Ser Thr Met Ile Arg Trp Gly Leu Lys Pro
450                 455                 460

Tyr Leu Phe Val Leu Asn Asn Asp Gly Tyr Thr Ile Glu Arg Leu Ile
465                 470                 475                 480

His Gly Glu Thr Ala Glu Tyr Asn Cys Ile Gln Pro Trp Lys His Leu
                485                 490                 495

Glu Leu Leu Asn Thr Phe Gly Ala Lys Asp Tyr Glu Asn His Arg Val
            500                 505                 510

Ser Thr Val Gly Glu Trp Asn Lys Leu Thr Gln Asp Pro Lys Phe Asn
        515                 520                 525

Glu Asn Ser Arg Ile Arg Met Ile Glu Val Met Leu Glu Val Met Asp
    530                 535                 540

Ala Pro Ser Ser Leu Val Ala Gln Ala Gln Leu Thr Ala Ala Thr Asn
545                 550                 555                 560

Ala Lys Gln

<210> SEQ ID NO 126
<211> LENGTH: 1689
<212> TYPE: DNA
<213> ORGANISM: Zygosaccharomyces rouxii

<400> SEQUENCE: 126
atgtctgaaa ttactctagg tcgttacttg ttcgaaagat taaagcaagt tgacactaac      60
accatcttcg gtgttccagg tgacttcaac ttgtccttgt tggacaaggt ctacgaagtg     120
caaggtctaa gatgggctgg taacgctaac gaattgaacg ctgcctacgc tgctgacggt     180
tacgccagag ttaagggttt ggctgctttg atcaccacct tcggtgtcgg tgaattgtct     240
gctttgaacg gtattgcagg ttcttacgct gaacacgttg gtgttttgca cattgttggt     300
gttccatctg tctcttctca agctaagcaa ttgttgttgc accacacctt gggtaacggt     360
gacttcactg ttttccacag aatgtccgcc aacatctctg aaaccaccgc tatgttgacc     420
gacatcactg ctgctccagc tgaaattgac cgttgcatca gagttgctta cgtcaaccaa     480
agaccagtct acttgggtct accagctaac ttggttgacc aaaaggtccc agcttctttg     540
ttgaacactc caattgatct atctctaaag gagaacgacc cagaagctga accgaagtt      600
gttgacaccg ttttggaatt gatcaaggaa gctaagaacc cagttatctt ggctgatgct     660
tgctgctcca gacacgacgt caaggctgaa accaagaagt tgatcgactt gactcaattc     720
ccatctttcg ttactcctat gggtaagggt tccatcgacg aacaaaaccc aagattcggt     780
ggtgtctacg tcggtactct atccagccca gaagttaagg aagctgttga atctgctgac     840
ttggttctat ctgtcggtgc tctattgtcc gatttcaaca ctggttcttt ctcttactct     900
tacaagacca agaacgttgt tgaattccac tctgaccaca tcaagatcag aaacgctacc     960
ttcccaggtg ttcaaatgaa attcgttttg aagaaactat tgcaagctgt cccagaagct    1020
gtcaagaact acaagccagg tccagtccca gctccgccat ctccaaacgc tgaagttgct    1080

```
gactctacca ccttgaagca agaatggtta tggagacaag tcggtagctt cttgagagaa    1140
ggtgatgttg ttattaccga aactggtacc tctgctttcg gtatcaacca aactcacttc    1200
cctaaccaaa cttacggtat ctctcaagtc ttgtggggtt ctattggtta caccactggt    1260
tccactttgg gtgctgcctt cgctgctgaa gaaattgacc ctaagaagag agttatcttg    1320
ttcattggtg acggttctct acaattgacc gttcaagaaa tctccaccat gatcagatgg    1380
ggtctaaagc catacttgtt cgttttgaac aacgatggtt acaccattga agattgatt     1440 cacggtgaaa ccgctgaata caactgtatc caaccatgga agcacttgga attgttgaac    1500
accttcggtg ccaaggacta cgaaaaccac agagtctcca ctgtcggtga atggaacaag    1560
ttgactcaag atccaaaatt caacgaaaac tctagaatta gaatgatcga agttatgctt    1620
gaagtcatgg acgctccatc ttctttggtc gctcaagctc aattgaccgc tgctactaac    1680
gctaagcaa                                                            1689
```

<210> SEQ ID NO 127
<211> LENGTH: 267
<212> TYPE: PRT
<213> ORGANISM: Saccharomyces cerevisiae

<400> SEQUENCE: 127

```
Met Ser Gln Gly Arg Lys Ala Ala Glu Arg Leu Ala Lys Lys Thr Val
1               5                   10                  15

Leu Ile Thr Gly Ala Ser Ala Gly Ile Gly Lys Ala Thr Ala Leu Glu
            20                  25                  30

Tyr Leu Glu Ala Ser Asn Gly Asp Met Lys Leu Ile Leu Ala Ala Arg
        35                  40                  45

Arg Leu Glu Lys Leu Glu Glu Leu Lys Lys Thr Ile Asp Gln Glu Phe
    50                  55                  60

Pro Asn Ala Lys Val His Val Ala Gln Leu Asp Ile Thr Gln Ala Glu
65                  70                  75                  80

Lys Ile Lys Pro Phe Ile Glu Asn Leu Pro Gln Glu Phe Lys Asp Ile
                85                  90                  95

Asp Ile Leu Val Asn Asn Ala Gly Lys Ala Leu Gly Ser Asp Arg Val
            100                 105                 110

Gly Gln Ile Ala Thr Glu Asp Ile Gln Asp Val Phe Asp Thr Asn Val
        115                 120                 125

Thr Ala Leu Ile Asn Ile Thr Gln Ala Val Leu Pro Ile Phe Gln Ala
    130                 135                 140

Lys Asn Ser Gly Asp Ile Val Asn Leu Gly Ser Ile Ala Gly Arg Asp
145                 150                 155                 160

Ala Tyr Pro Thr Gly Ser Ile Tyr Cys Ala Ser Lys Phe Ala Val Gly
                165                 170                 175

Ala Phe Thr Asp Ser Leu Arg Lys Glu Leu Ile Asn Thr Lys Ile Arg
            180                 185                 190

Val Ile Leu Ile Ala Pro Gly Leu Val Glu Thr Glu Phe Ser Leu Val
        195                 200                 205

Arg Tyr Arg Gly Asn Glu Glu Gln Ala Lys Asn Val Tyr Lys Asp Thr
    210                 215                 220

Thr Pro Leu Met Ala Asp Asp Val Ala Asp Leu Ile Val Tyr Ala Thr
225                 230                 235                 240

Ser Arg Lys Gln Asn Thr Val Ile Ala Asp Thr Leu Ile Phe Pro Thr
                245                 250                 255
```

Asn Gln Ala Ser Pro His His Ile Phe Arg Gly
            260                 265

<210> SEQ ID NO 128
<211> LENGTH: 804
<212> TYPE: DNA
<213> ORGANISM: Saccharomyces cerevisiae

<400> SEQUENCE: 128

| | | | | | |
|---|---|---|---|---|---|
| atgtcccaag | gtagaaaagc | tgcagaaaga | ttggctaaga | agactgtcct | cattacaggt | 60 |
| gcatctgctg | gtattggtaa | ggcgaccgca | ttagagtact | tggaggcatc | caatggtgat | 120 |
| atgaaactga | tcttggctgc | tagaagatta | gaaaagctcg | aggaattgaa | gaagaccatt | 180 |
| gatcaagagt | ttccaaacgc | aaaagttcat | gtggcccagc | tggatatcac | tcaagcagaa | 240 |
| aaaatcaagc | ccttcattga | aaacttgcca | caagagttca | aggatattga | cattctggtg | 300 |
| aacaatgccg | gaaaggctct | tggcagtgac | cgtgtgggcc | agatcgcaac | ggaggatatc | 360 |
| caggacgtgt | ttgacaccaa | cgtcacggct | ttaatcaata | tcacacaagc | tgtactgccc | 420 |
| atattccaag | ccaagaattc | aggagatatt | gtaaatttgg | gttcaatcgc | tggcagagac | 480 |
| gcatacccaa | caggttctat | ctattgtgcc | tctaagtttg | ccgtgggggc | gttcactgat | 540 |
| agtttgagaa | aggagctcat | caacactaaa | attagagtca | ttctaattgc | accagggcta | 600 |
| gtcgagactg | aattttcact | agttagatac | agaggtaacg | aggaacaagc | caagaatgtt | 660 |
| tacaaggata | ctaccccatt | gatggctgat | gacgtggctg | atctgatcgt | ctatgcaact | 720 |
| tccagaaaac | aaaatactgt | aattgcagac | actttaatct | ttccaacaaa | ccaagcgtca | 780 |
| cctcatcata | tcttccgtgg | ataa | | | | 804 |